United States Patent
Mellstedt et al.

(10) Patent No.: US 11,008,318 B2
(45) Date of Patent: May 18, 2021

(54) 2-PHENYLIMIDAZO[4,5-B]PYRIDIN-7-AMINE DERIVATES USEFUL AS INHIBITORS OF MAMMALIAN TYROSINE KINASE ROR1 ACTIVITY

(71) Applicant: KANCERA AB, Solna (SE)

(72) Inventors: Håkan Mellstedt, Stockholm (SE); Styrbjörn Byström, Täby (SE); Jan Vågberg, Sollentuna (SE); Elisabeth Olsson, Sollentuna (SE)

(73) Assignee: KANCERA AB, Solna (SE)

( * ) Notice: Subject to any disclaimer, the term of this patent is extended or adjusted under 35 U.S.C. 154(b) by 0 days.

(21) Appl. No.: 16/314,708

(22) PCT Filed: Jul. 10, 2017

(86) PCT No.: PCT/EP2017/067262
§ 371 (c)(1),
(2) Date: Jan. 2, 2019

(87) PCT Pub. No.: WO2018/011138
PCT Pub. Date: Jan. 18, 2018

(65) Prior Publication Data
US 2020/0024272 A1     Jan. 23, 2020

(30) Foreign Application Priority Data
Jul. 11, 2016 (EP) .................... 16178928

(51) Int. Cl.
*C07D 471/04* (2006.01)
*A61P 25/28* (2006.01)

(52) U.S. Cl.
CPC ............ *C07D 471/04* (2013.01); *A61P 25/28* (2018.01)

(58) Field of Classification Search
CPC .................................................. C07D 471/04
See application file for complete search history.

(56) References Cited

U.S. PATENT DOCUMENTS

| | | | |
|---|---|---|---|
| 7,622,479 B2 | 11/2009 | Oda et al. | |
| 2014/0350011 A1 | 11/2014 | Breslin et al. | |

FOREIGN PATENT DOCUMENTS

| WO | 2003/045929 A1 | 5/2003 |
|---|---|---|
| WO | 2004/016270 A1 | 2/2004 |
| WO | 2004/016611 A1 | 2/2004 |
| WO | 2006/066913 A2 | 6/2006 |
| WO | 2006/066914 A2 | 6/2006 |
| WO | 2006/080821 A1 | 8/2006 |
| WO | 2006/125958 A1 | 11/2006 |
| WO | 2007/028135 A2 | 3/2007 |
| WO | 2007/072017 A2 | 6/2007 |
| WO | 2007/083978 A1 | 7/2007 |
| WO | 2008/121063 A1 | 10/2008 |
| WO | 2008/121064 A1 | 10/2008 |
| WO | 2009/001021 A1 | 12/2008 |
| WO | 2009/111277 A1 | 9/2009 |
| WO | 2011/066211 A1 | 6/2011 |
| WO | 2011/079902 A2 | 7/2011 |
| WO | 2013/116291 A1 | 8/2013 |
| WO | 2016/124553 A1 | 8/2016 |

OTHER PUBLICATIONS

International Search Report for corresponding International Application No. PCT/EP2017/067262 dated Oct. 16, 2017.
Written Opinion of the International Searching Authority for corresponding International Application No. PCT/EP2017/067262 dated Oct. 16, 2017.
Wang et al., "Discovery of azabenzimidazole derivatives as potent, selectrive inhibitors of TBK1/1KK kinases". Bioorganic & Medicinal Chemistry Letters, vol. 22, Jan. 14, 2012, pp. 2063-2069.
Borcherding et al., "ROR1, an embryonic protein with an emerging role in cancer biology", Protein Cell, vol. 5, No. 7, Jul. 1, 2014, pp. 496-502.
Balaian et al., "A Highly Selective Anti-ROR1 Monoclonal Antibody Inhibits Human Acute Myeloid Leukemia CD34+ Cell Survival and Self-Renewal", Blood Journal, 2012, Abstract 2560, 2 pages.
Bicocca et al, "Crosstalk between ROR1 and the Pre-B Receptor Promotes Survival of t(1;19) Acute Lymphoblastic Leukemia", Cancer Cell, vol. 22, Nov. 13, 2012, pp. 656-667.

(Continued)

*Primary Examiner* — Paul V Ward
(74) *Attorney, Agent, or Firm* — Renner, Otto, Boisselle & Sklar, LLP

(57) ABSTRACT

Compound of formula (I') or (I") or a pharmaceutically acceptable salt thereof. The compound is an inhibitor of mammalian kinase enzyme activity, including ROR1 tyrosine kinase activity and may be used in the treatment of disorders associated with such activity.

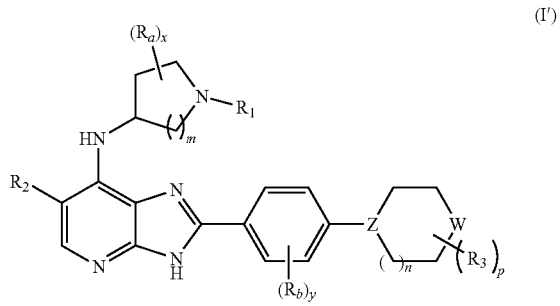

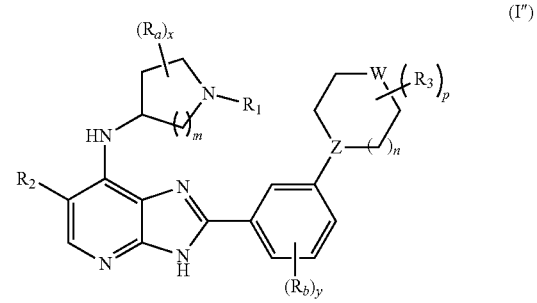

20 Claims, No Drawings

(56) References Cited

OTHER PUBLICATIONS

Chiorazzi et al., "Chronic Lymphocytic Leukemia", The New England Journal of Medicine, vol. 352, No. 8, Feb. 24, 2005, pp. 804-815.
Choudhury et al., "Silencing of ROR1 and FMOD with siRNA results in apoptosis of ClLL cells", British Journal of Haematology, vol. 151, Aug. 31, 2010, pp. 327-335.
Christodoulides et al., Adipogenesis and WNT signalling, Trends Endocrinol Metab., vol. 2, No. 1, Jan. 23, 2009, pp. 1-18.
Damle et al., "Ig V Gene Mutation Status and CD38 Expression as Novel Prognostic Indicators in Chronic Lymphocytic Leukemia", Blood, vol. 94, No. 6, Sep. 15, 1999, pp. 1840-1847.
Daneshmanesh et al., "Ror1, a cell surface receptor tyrosine kinase is expressed in chronic lymphocytic leukemia and may serve as a putative target for therapy", International Union Against Cancer, 2008, vol. 123, 2008, pp. 1190-1195.
Glass et al., "Agrin Acts via a MuSK Receptor Complex", Cell, vol. 85, May 17, 1996, pp. 513-523.
Hamblin et al., Blood, vol. 94, No. 6, Sep. 15, 1999, pp. 1848-1854.
Hojjat-Farsangi et al, "Inhibition of the Receptor Tyrosine Kinase ROR1 by Anti-ROR1 Monoclonal Antibodies and siRNA Induced Apoptosis of Melanoma Cells", PLoS One, vol. 8, Issue 4, e61167, Apr. 2013, pp. 1-10.
Klein et al., "Gene Expression Profiling of B Cell Chronic Lymphocytic Leukemia Reveals a Homogeneous Phenotype Related to Memory B Cells", Yhe Journal of Experimental Medicine, vol. 194, No. 11, Dec. 3, 2001, pp. 1625-1638.
Masiakowski et al., "A Novel Family of Cell Surface Receptors with Tyrosine Kinase-like Domain", The Journal of Biological Chemistry, vol. 67, No. 36, Dec. 25, 1992, pp. 6181-16190.
Reddy et al., "Human neural tissues express a truncated Ror1 receptor tyrosine kinase, lacking both extracellular and transmembrane domains", Oncogene, vol. 13, No. 7, Oct. 3, 1996, Abstract. 1 page.
Rosenwald et al., "Relation of Gene Expression Phenotype to Immunoglobulin Mutation Genotype in B Cell Chronic Lymphocytic Leukemia", The Journal of Experimental Medicine, vol. 194, No. 11, Dec. 3, 2001, pp. 1639-1647.
Sanchez-Solana et al., "Mouse Resistin Modulates Adipogenesis and Glucose Uptake in 3T3-L1 Preadipocytes Through the ROR1 Receptor", Molecular Endocrinology, vol. 26, No. 1, Jan. 2012, pp. 110-127.
Valenzuela et al., "Receptor Tyrosine Kinase Specific for the Skeletal Muscle Lineage: Expression in Embryonic Muscle, at the Neuromuscular Junction, and after Injury", Neuron, vol. 15, Sep. 1995, pp. 573-584.
Xiangming et al., "p-TsOH Catalyzed synthesis of 2-arylsubstituted benzimidazoles", ARKIVOC, vol. xiii, 2007, pp. 150-154.
Yadagiri et al., "Convenient Routes to Substituted Benzimidazoles and Imadazolo[4,5-b]Pyridines Using Nitrobenzene as Oxidant", Synthetic Communications, vol. 20, No. 7, 1990, pp. 955-963.
Yamaguchi et al., "NKX2-1/TITF1/TTF-1-Induced ROR1 s Required to Sustain EGFR Survival Signaling in Lung Adenocarcinoma", Cancer Cell, vol. 21, Mar. 20, 2012, pp. 348-361.
Yang et al., "A Versatile Method for the Synthesis of Benzimidazoles from o-Nitroanilines and Aldehydes in One Step via a Reductive Cyclization", Synthesis, No. 1, 2005, pp. 47-56.
Yoda et al., "Expression and Function of the Ror-Family Receptor Tyrosine Kinases During Development: Lessons from Genetic Analyses of Nematodes, Mice, and Humans", Journal of Receptors and Signal Transduction, vol. 23, No. 1, 2003, pp. 1-15.
Zhang et al., "ROR1 is Expressed in Human Breast Cancer and Associated with Enhanced Tumor-Cell Growth", PLoS ONE, vol. 7, Issue 3, e33127, Mar. 2012, pp. 1-12.
Zhang et al., "The Onco-Embryonic Antigen ROR1 s Expressed by a Variety of Human Cancers", The American Journal of Pathology, vol. 181, No. 6, Dec. 2012, pp. 1903-1910.
Bavetsias et al., "Imidazo[4,5-b]pyridine Derivatives as Inhibitors of Aurora Kinases: Lead Optimization Studies toward the Identification of an Orally Bioavailable Preclinical Development Candidate", Journal of Medicinal Chemistry, vol. 53, 2010, pp. 5213-5228.
Bavetsias et al., "Optimization of Imidazo[4,5-b]pyridine-Based Kinase Inhibitors: Identification of a Dual FLT3/Aurora Kinase Inhibitor as an Orally Bioavailable Preclinical Development Candidate for the Treatment of Acute Myeloid Leukemia", Journal of Medicinal Chemistry, vol. 55, 2012, pp. 8721-8734.

2-PHENYLIMIDAZO[4,5-B]PYRIDIN-7-AMINE DERIVATES USEFUL AS INHIBITORS OF MAMMALIAN TYROSINE KINASE ROR1 ACTIVITY

This application is a national phase of International Application No. PCT/EP2017/067262 filed Jul. 10, 2017, and claims priority to European Application No. 16178928.4 filed on Jul. 11, 2016, which is incorporated herein by reference.

FIELD OF THE INVENTION

The present invention relates to certain 2-phenylimidazo[4,5-b]pyridin-7-amine derivates that are useful as inhibitors of mammalian kinase enzyme activity, including ROR1 tyrosine kinase activity. The invention further relates to certain 2-phenylimidazo[4,5-b]pyridin-7-amine derivates for use in therapy, e.g. for the treatment of medical conditions in which the modulation of human kinase enzyme activity is beneficial. Examples of such a condition include various hyperproliferative diseases, e.g. hematological tumors such as chronic lymphocytic leukemia (CLL), acute myeloid leukemia (AML), acute lymphoblastic leukemia (ALL) or mantle cell lymphoma, and also solid tumors such as lung, ovarian, breast or pancreatic tumors. Other examples of such a condition include obesity-associated metabolic complications, autoimmune diseases and inflammatory conditions.

BACKGROUND OF THE INVENTION

Chronic lymphocytic leukemia (CLL) originates from B lymphocytes which differ in activation and maturation stage and are derived from antigen experienced B cells with different immunoglobulin heavy chain variable (IgVH) gene mutations (Chiorazzi N et al., *N. Engl. J. Med.,* 2005, 352, 804-15). Patients with mutated IgVH genes have a better prognosis compared to patients with unmutated genes (Damle R N et al., *Blood* 1999, 94, 1840-7; Hamblin T J et al., *Blood,* 1999, 94, 1848-54). Global gene expression profiling studies have revealed partly distinguishing but in general overlapping expression profiles in mutated and unmutated leukemic B cells, suggesting a common phenotype (Klein U et al., *J. Exp. Med.,* 2001, 194, 1625-38; Rosenwald A et al., *J. Exp. Med.,* 2001, 194, 1639-47).

Gene expression profiling studies showed a 43.8 fold increase of the orphan receptor tyrosine kinase (RTK) ROR1 in CLL cells (Klein U et al., *J. Exp. Med.,* 2001, 194, 1625-38). ROR1 is a member of the RTK family of orphan receptors related to muscle specific kinase (MUSK) and Trk neurotrophin receptors (Glass D J, et al., *Cell,* 1996, 85, 513-23; Masiakowski P et al., *J. Biol. Chem.,* 1992, 267, 26181-90; Valenzuela D M et al., *Neuron,* 1995, 15, 573-84). ROR receptors are cell surface receptors participating in signal transduction, cell-cell interaction, regulation of cell proliferation, differentiation, cell metabolism and survival (Masiakowski P et al., *Biol. Chem.,* 1992, 267, 26181-90; Yoda A et al., *J. Recept. Signal Transduct. Res.,* 2003, 23, 1-15). They are evolutionarily highly conserved between different species e.g. human, mouse, *Drosophila,* and *C. elegans,* suggesting important biological functions.

The human ROR1 gene has a coding region of 2814 bp with a predicted 937 amino acids sequence and 105 kDa protein size including an Ig-like domain, cysteine-rich domain, kringle domain, tyrosine kinase domain, and proline-rich domain (Yoda A et al., *J. Recept. Signal Transduct. Res.,* 2003, 23, 1-15). ROR1 is located on chromosomal region 1p31.3 (http://www.ensembl.org), a region where chromosomal aberrations are not frequently seen in hematological malignancies. The human ROR1 is expressed at the gene level in heart, lung, and kidney but less in placenta, pancreas and skeletal muscles (Reddy U R et al., *Oncogene,* 1996, 13, 1555-9). Importantly, there is an almost complete absence of ROR1 protein expression in normal human adult tissues and organs. ROR1 was originally cloned from a neuroblastoma cell line (Masiakowski P et al., *J. Biol. Chem.,* 1992, 267, 26181-90) and subsequently a shorter form lacking the entire extracellular domain but containing the transmembrane domain was isolated from a fetal brain library. Truncated ROR1 (t-Rorl) gene has been reported in fetal and adult human central nervous system, in human leukemias, lymphoma cell lines, and in a variety of human cancers derived from neuroectoderm (Reddy U R et al., *Oncogene,* 1996, 13, 1555-9). A shorter transcript from exons 1-7 including a short part of intron 7 has also been described with a predicted length of 393 amino acids and a molecular weight of 44 kDa (Ensembl ID; ENSG00000185483).

Gene profiling and protein expression studies of patients with chronic lymphocytic leukemia (CLL) has revealed increased expression of ROR1, while mature leucocytes from healthy donors do not express this protein (Danesh-Manesh, A H et al., *Int. J. Cancer,* 2008, 123, 1190-5). Silencing of ROR1 with siRNA in CLL cells resulted in apoptosis, while siRNA treatment of B cells from normal donors did not (Choudhury, A et al., *Brit. J. Haematol.,* 2010, 151, 327-35).

Acute myeloid leukemic (AML) stem cells (CD34$^+$) may potentially account for the resistance for many cytotoxic drugs. In an in vitro assay, a chimeric antibody against ROR1 (UC99961) inhibited in a dose-dependent manner colony formation of ROR1$^+$ AML stem cells but not ROR$^-$ AML cells and not normal CD34$^+$ stem cells. The results suggest that targeting ROR may represent an important component to eradicate malignant stem cells in AML and potentially also other refractory cancer-stem-cell-driven malignancies (Balaian L et al, *Blood*, ASH Annual Meeting) 2012, Abstract 2560). In acute lymphoblastic leukemia (ALL) ROR1 is up-regulated modulating in a counterbalancing manner with pre-BCR signaling pathways leading to activation of AKT, ERK and MEK. siRNA transfection induced impaired growth of ALL cells and apoptosis (Bicocca V et al, *Cancer Cell,* 22, 656-667, 2012).

Human breast cancer cells, but not normal breast epithelia cells also express ROR1. The intensity of ROR1 expression was higher in patients with hormone receptor negative tumors as well as in those with a low degree of cell differentiation, i.e. in patients with a poor prognosis. Silencing of ROR1 impaired the growth in vitro of human breast cancer cells and in immune-deficient mice. The results support the notion that ROR1 is of biological and clinical significance in breast cancer and may be a potential target for therapy (Zang S et al, *PLoS One,* 7(3): e31127, 2012).

In human lung adenocarcinoma cells ROR1 was overexpressed. The ROR1 kinase activity sustained a favorable prosurvival balance between the proliferative PI3K/AKT and apoptotic p38 signaling, partly through ROR1 kinase-dependent src activation as well as kinase-independent sustainment of EGFR/ERBB3 phosphorylation and PI3K activation. ROR1 knock-down effectively inhibited the growth of lung cancer cells in vitro and in vivo irrespective of EGFR status including those cells resistant to the EGFR tyrosine kinase inhibitor gefitinib. These data also indicate an important biological role of ROR1 in lung cancer and a structure for targeted therapy (Yamaguchi et al, *Cancer Cell*, 21, 348-361, 2012). Unexpectedly CLL cells showed an overexpression of ERBB2 and phosphorylation of src/PI3K, AKT/mTOR/CREB. The ROR1 tyrosine kinase inhibitors described in this work (see below) dephosphorylated ROR1/src/PI3K/AKT/mTOR/CREB which preceded apoptosis of CLL cells (own unpublished observations).

In another study, a number of solid tumor tissues (lung, ovarian, pancreatic) expressed ROR1 but not the normal cell counterpart. ROR1 expression was associated with high-grade histology and activation of AKT and CREB. Silencing of ROR1 using shRNA induced apoptosis of pancreatic and ovarian cancer cell lines and down regulation of the ROR1 protein as well as of activated AKT and CREB (Zhan S et al, *American Journal of Pathology*, 181:1903-1910, 2012).

Melanoma cells have been shown to express ROR1. ROR1 siRNA induced down regulation of ROR1 both at the mRNA and protein level, which preceded apoptosis. Targeting ROR1 of the melanoma cells by ROR1 directed monoclonal antibodies induced a significant apoptosis not requiring immune cells or complement. The degree of apoptosis induced by the antibodies varied between the cell lines (Hodjat-Farsangi M et al, *PLoS One*, 8, e61167, 2013). Furthermore, it has recently been shown that ROR1 plays an important role in adipogenesis and glucose homeostasis in 3T3-L1 cells (Sanchez-Solana, B, Laborda, J and Baladron, V, *Molecular Endocrinology* 26: 110-127, 2012). Hence, manipulating the WNT pathway, e.g. by modulation of ROR1, to alter adipose cellular makeup may constitute an attractive drug-development target to combat obesity-associated metabolic complications (Christodoulides, C, Lagathu, C, Sethi, J K and Vidal-Puig, A, *Trends Endocrinol. Metab.*, 2009 January; 20(1):16-24).

The above described data serve to illustrate the validity of modulating ROR1 activity for treatment of disorders and diseases that include not only chronic lymphocytic leukemia (CLL) but also other hematological malignancies as well as solid tumors and obesity-associated metabolic complications.

Antibody inhibitors of ROR1 have been described in the literature; e.g. PCT Int. Appl. WO2011079902. There are, however, no small molecule inhibitors of ROR1 known in the art. Substituted imidazo[4,5-b]pyridine compounds are well known in the art, e.g. PCT Int. Appl. WO2003045929, WO2004016270, WO2004016611, WO2006066913, WO2006066914, WO2006080821, WO2006125958, WO2007028135, WO2007072017, WO2007083978, WO2008121063, WO2008121064, WO2009001021, WO2009111277, WO2011066211, WO2013116291, Wang, T. et al. *Bioorg. Med. Chem. Lett.*, 2012, 22(5), 2063-2069, Bavetsias, V. et al. *J. Med. Chem.*, 2010, 53, 5213-5228 and Bavetsias, V. et al. *J. Med. Chem.*, 2012, 55, 8721-8734. However, it has not previously been shown that such compounds are capable of modulating ROR1 activity.

SUMMARY OF THE INVENTION

A first aspect is a compound of formula (I') or (I")

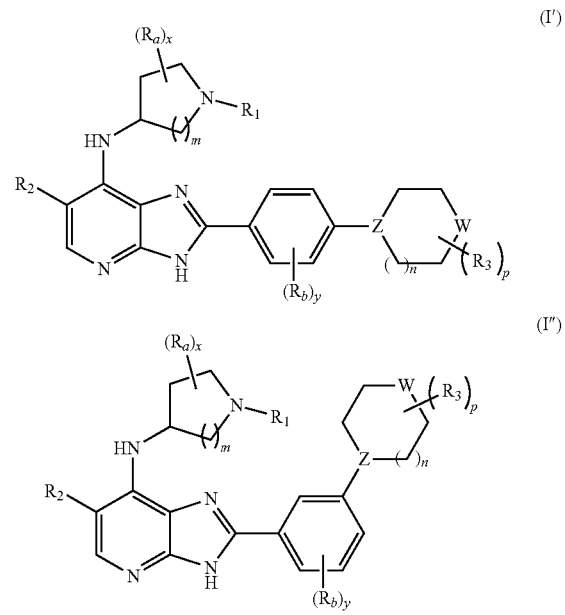

or a pharmaceutically acceptable salt thereof, wherein
x is an integer of from 0 to 4;
each $R_a$ is independently selected from C1-C3 alkyl;
m is 1 or 2;
$R_1$ is C1-C6 alkyl, C3-C6 cycloalkyl, C3-C6 cycloalkyl-C1-C6 alkyl, C1-C6 alkyl-C3-C6 cycloalkyl, C1-C6 alkoxy-C1-C6 alkyl, cyano-C1-C6 alkyl, or a moiety of formula (II)

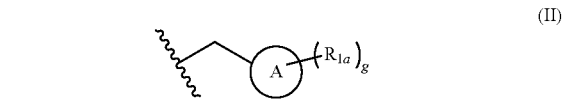

ring A is phenyl or 5- or 6-membered heteroaryl;
g is an integer of from 0 to 3;
each $R_{1a}$ is independently selected from C1-C6 alkyl, $R_{1b}O$, and $R_{1c}R_{1d}N$;
each $R_{1b}$ is independently selected from H and C1-C6 alkyl;
each $R_{1c}$ is independently selected from H and C1-C6 alkyl;
each $R_{1d}$ is independently selected from H and C1-C6 alkyl;
or two $R_{1a}$, attached to adjacent atoms of ring A form, together with the atoms to which they are attached, a 5- or 6-membered ring optionally containing one or more heteroatoms;
$R_2$ is Cl or Br;
p is an integer of from 0 to 3;
each $R_3$ is independently selected from C1-C6 alkyl;
y is an integer of from 0 to 3;
$R_b$ is selected from halogen, C1-C3 alkyl, and C1-C3 alkoxy;
Z is N or CH;
W is >Q-$R_4$, —O— or —N($R_5$)C(O)—;
Q is N or CH;

n is 1 or 2 when W is >Q-R$_4$ or —O—;
n is 0 or 1 when W is —N(R$_5$)C(O)—;
R$_4$ is C1-C6 alkyl, R$_{4a}$[O(CH$_2$)$_q$]$_r$—Y, R$_{4b}$S(O)$_2$, R$_{4c}$C(O), cyano-C1-C6 alkyl, or a moiety of formula (III)

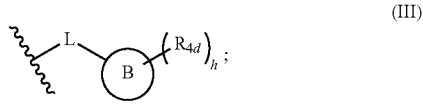

(III)

each q is independently selected from 1, 2, 3 and 4;
r is 1 or 2;
h is an integer of from 0 to 3;
Y is a direct bond or C(O);
L is a direct bond, C1-C4 alkylene, or -L$_1$-L$_2$-;
L$_1$ is a direct bond or C1-C4 alkylene;
L$_2$ is C(O) or NH;
R$_{4a}$ is H or C1-C6 alkyl;
R$_{4b}$ is C1-C6 alkyl;
R$_{4c}$ is C1-C6 alkyl;
R$_{4d}$ is C1-C6 alkyl;
ring B is selected from phenyl and 5- or 6-membered heteroaryl; R$_5$ is H, C1-C6 alkyl, R$_{5a}$[O(CH$_2$)$_u$]$_v$, or a moiety of formula (IV)

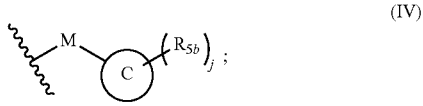

(IV)

R$_{5a}$ is H or C1-C6 alkyl;
each u is independently selected from 1, 2, 3 and 4;
v is 1 or 2;
M is a direct bond or C1-C4 alkylene;
ring C is selected from phenyl and 5- or 6-membered heteroaryl;
R$_{5b}$ is C1-C6 alkyl; and
j is an integer of from 0 to 3.

A further aspect is a compound of formula (I') or (I") for use in therapy.

A still further aspect is a compound of formula (I') or (I"), or a pharmaceutically acceptable salt thereof, for use as an inhibitor of tyrosine kinase ROR1 activity in a mammal; preferably a human.

A still further aspect is a pharmaceutical composition comprising a compound of formula ((I') or (I"), or a pharmaceutically acceptable salt thereof, and optionally a pharmaceutically acceptable excipient.

A still further aspect is a compound of formula (I') or (I"), or a pharmaceutically acceptable salt thereof, for use in the treatment of a condition or disorder in which the modulation of the activity of mammalian, e.g. human, tyrosine kinase ROR1 is beneficial, e.g. a malignant hyperproliferative disorder, an obesity-associated metabolic complication, an autoimmune disease or an inflammatory condition.

One aspect is a compound of formula (I') or (I"), or a pharmaceutically acceptable salt thereof, for use in the treatment of a malignant hyperproliferative disorder, an obesity-associated metabolic complication, an autoimmune disease or an inflammatory condition.

A further aspect is the use of a compound of formula (I') or (I") in the manufacturing of a medicament for use in the treatment of a condition or disorder in which the modulation of the activity of mammalian, e.g. human, tyrosine kinase ROR1 is beneficial, e.g. a malignant hyperproliferative disorder, an obesity-associated metabolic complication, an autoimmune disease or an inflammatory condition.

Examples of malignant hyperproliferative disorders include, but are not limited to, hematological tumors such as chronic lymphocytic leukemia (CLL), acute myeloid leukemia (AML), acute lymphoblastic leukemia (ALL) or mantle cell lymphoma, and also solid tumors such as lung, ovarian, breast or pancreatic tumors.

A further aspect is a method of treatment of a condition or disorder in which the modulation of the activity of mammalian, e.g. human, tyrosine kinase ROR1 is beneficial, e.g. a malignant hyperproliferative disorder, an obesity-associated metabolic complication, an autoimmune disease or an inflammatory condition, by administering a therapeutically effective amount of a compound of formula (I') or (I") to a mammal, preferably a human, in need of such treatment.

DETAILED DESCRIPTION OF THE INVENTION

Unless otherwise specified, any term used herein is to be given its conventional meaning. For example, the term "alkyl" either alone or as part of a radical, includes straight or branched chain alkyl of the general formula C$_n$H$_{2n+1}$.

The term "C1-C6 alkyl" refers to an alkyl moiety having 1, 2, 3, 4, 5 or 6 carbon atoms.

The term "alkylene" refers to a saturated bivalent radical derived from the corresponding alkane. For example, methylene is a C1 alkylene.

The term "C3-C6 cycloalkyl" refers to a cycloalkyl moiety having 3, 4, 5 or 6 carbon atoms in the ring, i.e. cyclopropyl, cyclobutyl, cyclopentyl or cyclohexyl.

The term "C3-C6 cycloalkyl-C1-C6 alkyl" refers to a C1-C6 alkyl substituted by a C3-C6 cycloalkyl. An example of such a moiety is cyclopropylmethyl of formula:

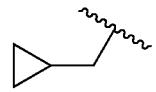

The term "C1-C6 alkyl-C3-C6 cycloalkyl" refers to a C3-C6 cycloalkyl substituted by a C1-C6 alkyl. An example of such a moiety is 4-methylcyclohexyl.

The term "C1-C6 alkoxy-C1-C6 alkyl" refers to a C1-C6 alkyl substituted by a C1-C6 alkoxy.

An example is 2-methoxyethyl, of formula:

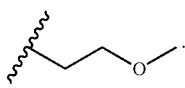 [SMILES: *CCOC]

The term "cyano-C1-C6 alkyl" refers to a C1-C6 alkyl substituted by a cyano group. An example is 2-cyanoethyl, of formula:

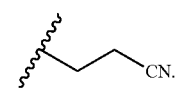 [SMILES: *CCC#N]

The term "direct bond" refers to a covalent bond between two moieties of a compound.

The term "heteroatom" preferably refers to N, O or S.

The term "5- or 6-membered heteroaryl" refers to a heteroaryl containing either 5 or 6 atoms in the ring.

The term "phenyl" refers to a moiety of formula

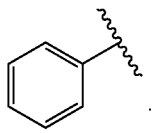 [SMILES: *c1ccccc1]

The term "benzyl" refers to a moiety of formula

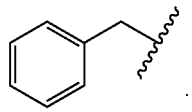

The term "halogen" refers to F, Cl, Br or I, in particular to F, Cl or Br.

The term "hydroxy" refers to a radical of the formula —OH.

A moiety of the type RO is a moiety of formula

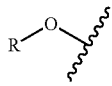

A moiety of the type $R[O(CH_2)_q]_r$ is a moiety of formula

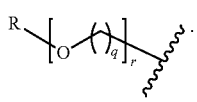

A moiety of the type $R[O(CH_2)_q]_r$—Y is a moiety of formula

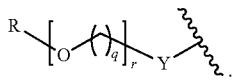

A moiety of the type NR is a moiety of formula

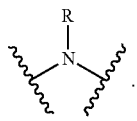

A moiety of the type NRC(O) is a moiety of formula

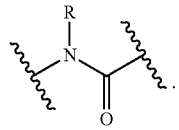

A moiety of the type $RS(O)_2$ is a moiety of formula

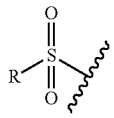

A moiety of the type N(R)(R') (which also may be written RR'N or NRR') is a moiety of formula

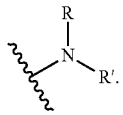

A moiety of the type RC(O) is a moiety of formula

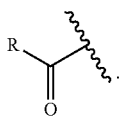

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "excipient" refers to pharmaceutically acceptable chemicals, such as known to those of ordinary skill in the art of pharmacy to aid the administration of the medicinal agent. It is a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

"Therapeutically effective amount" means an amount of a compound that, when administered to a subject for treating a disease state, is sufficient to effect such treatment for the disease state. The "therapeutically effective amount" will vary depending on the compound, the disease state being treated, the severity of the disease treated, the age and relative health of the subject, the route and form of administration, the judgment of the attending medical or veterinary practitioner, etc.

As used herein the terms "treatment" or "treating" is an approach for obtaining beneficial or desired results including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total) whether detectable or undetectable. The term can also mean prolonging survival as compared to expected survival without the treatment.

The term mammal refers to a human or any mammalian animal, e.g. a primate, a farm animal, a pet animal, or a laboratory animal. Examples of such animals are monkeys, cows, sheep, horses, pigs, dogs, cats, rabbits, mice, rats etc. Preferably, the mammal is a human.

The term "malignant hyperproliferative disorder" refers to any malignant growth or tumor caused by abnormal and uncontrolled cell division; it may spread to other parts of the body through the lymphatic system or the blood stream and includes both solid tumors and blood-borne tumors. Exemplary cancers include adrenocortical carcinoma, AIDS-related cancers, AIDS-related lymphoma, anal cancer, anorectal cancer, appendix cancer, childhood cerebellar astrocytoma, childhood cerebral astrocytoma, basal cell carcinoma, biliary cancer, extrahepatic bile duct cancer, intrahepatic bile duct cancer, urinary bladder cancer, bone and joint cancer, osteosarcoma and malignant fibrous histiocytoma, brain tumor, brain stem glioma, cerebellar astrocytoma, cerebral astrocytoma/malignant glioma, ependymoma, medulloblastoma, visual pathway and hypothalamic glioma, breast cancer, bronchial adenomas/carcinoids, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary syndrome, endometrial cancer, esophageal cancer, extracranial germ cell tumor, extragonadal germ cell tumor, eye cancer, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin's lymphoma, hypo pharyngeal cancer, ocular cancer, Kaposi's sarcoma, renal cancer, laryngeal cancer, acute lymphoblastic leukemia, acute myeloid leukemia, hairy cell leukemia, lip and oral cavity cancer, lung cancer, non-small cell lung cancer, small cell lung cancer, non-Hodgkin's lymphoma, primary central nervous system lymphoma, Waldenstrom's macroglobulinemia, intraocular (eye) melanoma, Merkel cell carcinoma, malignant mesothelioma, metastatic squamous neck cancer, cancer of the tongue, multiple endocrine neoplasia syndrome, myelodysplastic syndromes, myelodysplastic/myeloproliferative diseases, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rhabdomyosarcoma, salivary gland cancer, Ewing's sarcoma family of tumors, soft tissue sarcoma, uterine cancer, uterine sarcoma, skin cancer (non-melanoma), skin cancer (melanoma), small intestine cancer, squamous cell carcinoma, testicular cancer, throat cancer, thymoma, thymoma and thymic carcinoma, thyroid cancer, transitional cell cancer of the renal pelvis and ureter and other urinary organs, gestational trophoblastic tumor, urethral cancer, vaginal cancer, vulvar cancer, and Wilm's tumor.

The term "autoimmune disorder" refers to any disorder arising from an inappropriate immune response of the body against substances and tissues normally present in the body (autoimmunity). Such response may be restricted to certain organs or involve a particular tissue in different places. Exemplary autoimmune disorders are acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behcet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease (one of two types of idiopathic inflammatory bowel disease "IBD"), Cushing's Syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressiva, fibrosing alveolitis (or Idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis (aka gestational pemphigoid), Hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, Majeed syndrome, Ménière's disease, microscopic polyangiitis, mixed connective tissue disease, morphea, Mucha-Habermann disease (aka pityriasis lichenoides et varioliformis acuta), multiple sclerosis, myasthenia gravis, myositis, narcolepsy, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonage-Turner syndrome, pars planitis, pemphigus vulgaris, pernicious anaemia, perivenous encephalomyelitis, POEMS syndrome, polyarteritis *nodosa*, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome another form of APS, Schnitzler syndrome, Scleritis, Scleroderma, Serum Sickness, Sjögren's syndrome, spondyloarthropathy, stiff person syndrome, subacute bacterial endocarditis (SBE), Susac's syndrome, Sweet's syndrome, sympathetic ophthalmia, systemic lupus erythematosis, Takayasu's arteritis, temporal arteritis (also known as "giant cell arteritis"), thrombocytopenia, Tolosa-Hunt syndrome, transverse myelitis, ulcerative colitis (one of two types of idiopathic inflammatory bowel disease "IBD"), undifferentiated connective tissue disease different from mixed connective tissue disease, undifferentiated spondyloarthropathy, urticarial vasculitis, vasculitis, vitiligo, and Wegener's granulomatosis. The term "inflammatory disorder" refers to a pathological state associated with inflammation, typically caused by leukocyte infiltration. The inflammatory disorder may be acute or chronic. Exemplary inflammatory disorders include inflammatory skin diseases, including, without limitation, psoriasis and atopic dermatitis, systemic scleroderma and sclerosis, responses associated with inflammatory bowel disease (IBD) (such as Crohn's disease and ulcerative colitis), ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms, cerebral edema secondary to stroke, cranial trauma, hypovolemic shock, asphyxia, adult respiratory distress syndrome, acute-lung injury, Behcet's Disease, dermatomyositis, polymyositis, multiple sclerosis (MS), dermatitis, meningitis, encephalitis, uveitis, osteoarthritis, lupus nephritis, autoimmune diseases such as rheumatoid arthritis (RA), Sjögren's syndrome, vasculitis, diseases involving leukocyte diapedesis, central nervous system (CNS) inflammatory disorder, multiple organ injury syndrome secondary to septicemia or trauma, alcoholic hepatitis, bacterial pneumonia, antigen-antibody complex mediated diseases including glomerulonephritis, sepsis, sarcoidosis, immunopathologic responses to tissue or organ transplantation, inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis, etc.

The term "obesity-associated metabolic complication" refers generally to the metabolic complications due to obesity, often referred to as the metabolic syndrome, which syndrome is characterized by plasma lipid disorders (atherogenic dyslipidemia), raised blood pressure, elevated plasma glucose, and a prothrombotic state. Clinical consequences of the metabolic syndrome are e.g. coronary heart disease and stroke, type 2 diabetes and its complications, fatty liver, and cholesterol gallstones.

The compounds of formula (I') and (I") are positional isomers (regioisomers), which herein below will be represented by a common formula (I)

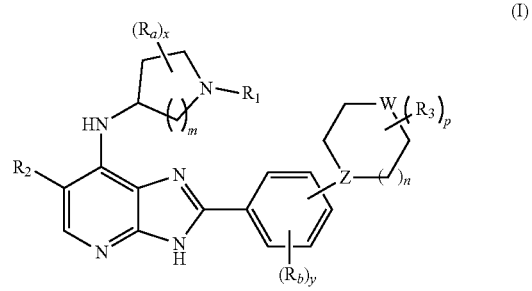

wherein ring containing Z and W is in either para position (formula (I')), or in meta position (formula (I")). Consequently, unless otherwise specified or apparent from the context, any reference to a compound of formula (I) is to be construed as referring equally to both regioisomers (I') and (I"). In some embodiments, however, the compound is as represented by formula (I'). In some further embodiments, the compound is as represented by formula (I").

It should be realized that three tautomers exist of the compound of formula (I). The compound of formula (I) should be construed as encompassing not only the 3H-imidazo[4,5-b]pyridine form, but also the tautomeric 1H-imidazo[4,5-b]pyridine form

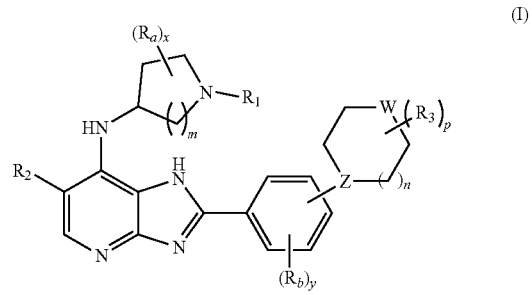

and the tautomeric 4H-imidazo[4,5-b]pyridine form

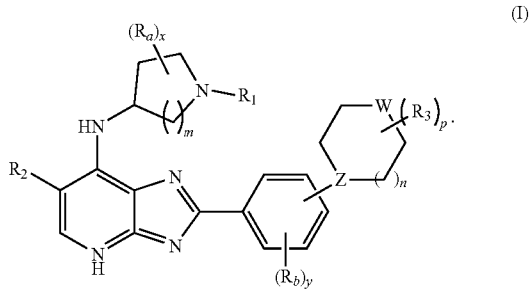

Therefore, any explicit reference to a 3H-imidazo[4,5-b] pyridine also encompasses the corresponding 1H-imidazo [4,5-b]pyridine and 4H-imidazo[4,5-b]pyridine tautomers. Furthermore, any reference to a compound of formula (I) is to be construed as referring equally to any of the below described embodiments thereof, unless otherwise specified or apparent from the context.

In a compound of formula (I), m is 1 or 2. In some embodiments, m is 1. In some further embodiments, m is 2, i.e. the compound of formula (I) may be represented by formula (Ia)

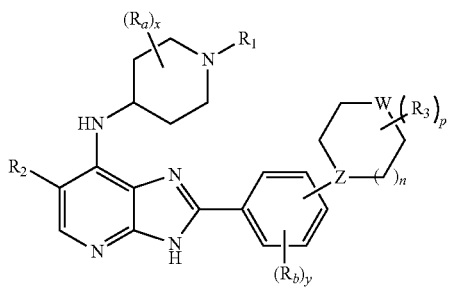

(Ia)

wherein $R_1$, $R_2$, each $R_3$, each $R_a$, each $R_b$, Z, W, n, p, x and y are as defined herein.

In a compound of formula (I), x is an integer selected from 0, 1, 2, 3, or 4, representing the number of moieties $R_a$. In some embodiments x is 0, 1 or 2. In some further embodiments, x is 0 or 1. In still further embodiments, x is 0 or 4. In some particular embodiments, x is 0. In some other particular embodiments, x is 4.

When x is different from 0, each moiety $R_a$ is selected from C1-C3 alkyl, e.g. from C1-C2 alkyl. In some embodiments, each moiety $R_a$ is methyl.

The moiety $R_1$ is C1-C6 alkyl, C3-C6 cycloalkyl, C3-C6 cycloalkyl-C1-C6 alkyl, C1-C6 alkyl-C3-C6 cycloalkyl, C1-C6 alkoxy-C1-C6 alkyl, cyano-C1-C6 alkyl, or a moiety of formula (II)

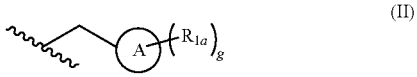

(II)

wherein ring A, $R_{1a}$ and g are as defined herein.

In some embodiments, $R_1$ is C1-C6 alkyl, C3-C6 cycloalkyl, C1-C6 alkyl-C3-C6 cycloalkyl, C1-C6 alkoxy-C1-C6 alkyl, cyano-C1-C6 alkyl, or a moiety of formula (II) as defined herein. In some further embodiments, $R_1$ is C1-C6 alkyl, C3-C6 cycloalkyl, C3-C6 cycloalkyl-C1-C6 alkyl, C1-C6 alkoxy-C1-C6 alkyl, cyano-C1-C6 alkyl, or a moiety of formula (II) as defined herein. In some further embodiments, $R_1$ is C1-C6 alkyl, C3-C6 cycloalkyl, C3-C6 cycloalkyl-C1-C6 alkyl, C1-C6 alkoxy-C1-C6 alkyl, or a moiety of formula (II) as defined herein. In some further embodiments, $R_1$ is C1-C6 alkyl, C3-C6 cycloalkyl, C3-C6 cycloalkyl-C1-C6 alkyl, cyano-C1-C6 alkyl, or a moiety of formula (II) as defined herein.

In some embodiments, $R_1$ is C1-C6 alkyl, C3-C6 cycloalkyl, C3-C6 cycloalkyl-C1-C6 alkyl, C1-C6 alkyl-C3-C6 cycloalkyl, cyano-C1-C6 alkyl, or a moiety of formula (II) as defined herein. In some further embodiments, $R_1$ is C1-C6 alkyl, C3-C6 cycloalkyl, C3-C6 cycloalkyl-C1-C6 alkyl, C1-C6 alkyl-C3-C6 cycloalkyl, or a moiety of formula (II) as defined herein.

In some embodiments, $R_1$ is C1-C6 alkyl, C3-C6 cycloalkyl, C3-C6 cycloalkyl-C1-C6 alkyl, C1-C6 alkyl-C3-C6 cycloalkyl, C1-C6 alkoxy-C1-C6 alkyl, or cyano-C1-C6 alkyl. In some further embodiments, $R_1$ is C1-C6 alkyl, C3-C6 cycloalkyl, C3-C6 cycloalkyl-C1-C6 alkyl, C1-C6 alkoxy-C1-C6 alkyl, or cyano-C1-C6 alkyl. In some further embodiments, $R_1$ is C1-C6 alkyl, C3-C6 cycloalkyl, C3-C6 cycloalkyl-C1-C6 alkyl, or cyano-C1-C6 alkyl.

In some embodiments, $R_1$ is C1-C6 alkyl, C3-C6 cycloalkyl, C3-C6 cycloalkyl-C1-C6 alkyl, or C1-C6 alkyl-C3-C6 cycloalkyl. In some further embodiments, $R_1$ is C1-C6 alkyl, C3-C6 cycloalkyl, or C3-C6 cycloalkyl-C1-C6 alkyl.

In some embodiments, $R_1$ is C1-C6 alkyl, C3-C6 cycloalkyl, or a moiety of formula (II) as defined herein. In some further embodiments, $R_1$ is C1-C6 alkyl or C3-C6 cycloalkyl, e.g. $R_1$ is C1-C5 alkyl or C3-C5 cycloalkyl; or $R_1$ is C1-C3 alkyl or C3-C4 cycloalkyl; or $R_1$ is C1-C3 alkyl or C3 cycloalkyl (i.e. cyclopropyl).

In some embodiments, $R_1$ is C1-C6 alkyl or a moiety of formula (II) as defined herein. In some further embodiments, $R_1$ is C1-C6 alkyl.

When $R_1$ is C1-C6 alkyl, it more particularly may be selected from C1-C5 alkyl, or from C1-C4 alkyl, or from C1-C3 alkyl; e.g. from methyl and ethyl. In some particular embodiments, $R_1$ is methyl, ethyl or isopropyl. In some other particular embodiments, $R_1$ is methyl. In some other particular embodiments, $R_1$ is ethyl.

When $R_1$ is C3-C6 cycloalkyl, it e.g. may be C3-C5 cycloalkyl, or C3-C4 cycloalkyl, e.g. cyclopropyl.

When $R_1$ is C3-C6 cycloalkyl-C1-C6 alkyl, it e.g. may be C3-C6 cycloalkyl-C1-C3 alkyl, such as C3-C6 cycloalkyl-C1-C2 alkyl, e.g. C3-C6 cycloalkyl-methyl. In some embodiments, when $R_1$ is C3-C6 cycloalkyl-C1-C6 alkyl, it more particularly is C3-C4 cycloalkyl-C1-C6 alkyl, or C3-C4 cycloalkyl-C1-C3 alkyl, such as C3-C4 cycloalkyl-C1-C2 alkyl, e.g. C3-C4 cycloalkyl-methyl. In some embodiments, when $R_1$ is C3-C6 cycloalkyl-C1-C6 alkyl, the C3-C6 cycloalkyl more particularly is cyclopropyl.

For the avoidance of doubt, it is noted that when $R_1$ is C3-C6 cycloalkyl-C1-C6 alkyl, $R_1$ is attached to the nitrogen containing ring of the compound of formula (I) through the alkyl moiety.

When $R_1$ is C1-C6 alkyl-C3-C6 cycloalkyl, it e.g. may be C1-C3 alkyl-C3-C6 cycloalkyl, e.g. methyl-C3-C6 cycloalkyl. For the avoidance of doubt, it is noted that when $R_1$ is C1-C6 alkyl-C3-C6 cycloalkyl, $R_1$ is attached to the nitrogen containing ring of the compound of formula (I) through the cycloalkyl moiety.

When $R_1$ is C1-C6 alkoxy-C1-C6 alkyl, it e.g. may be C1-C3 alkoxy-C1-C6 alkyl, such as methoxy-C1-C6 alkyl. In some embodiments, when $R_1$ is C1-C6 alkoxy-C1-C6 alkyl, it more particularly is C1-C6 alkoxy-C1-C3 alkyl, e.g. C1-C3 alkoxy-C1-C3 alkyl.

When $R_1$ is cyano-C1-C6 alkyl, it e.g. may be cyano-C1-C4 alkyl, or cyano-C1-C3 alkyl, such as cyano-C1-C2 alkyl.

In some embodiments, $R_1$ is a moiety of formula (II)

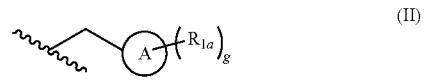

(II)

wherein ring A, $R_{1a}$ and g are as defined herein.

In the moiety of formula (II), ring A is phenyl, 5-membered heteroaryl, or 6-membered heteroaryl. In some embodiments, ring A is phenyl or 5-membered heteroaryl. In some further embodiments, ring A is 5- or 6-membered heteroaryl. In some embodiments, ring A is phenyl. In some further embodiments, ring A is 5-membered heteroaryl.

When ring A is 5- or 6-membered heteroaryl, the heteroarylic ring contains one or more heteroatoms, preferably independently selected from N, O and S, and at least one carbon atom. In some embodiments, the heteroarylic ring contains 1-4 heteroatoms, e.g. 1-3 heteroatoms, or 1-2 heteroatoms, or 1 heteroatom, said heteroatom(s) being independently selected from N, O and S. In some embodiments, when ring A is 5- or 6-membered heteroaryl, it more particularly is 5-membered heteroaryl containing 1-4, or 1-3, in particular 1 or 2 heteroatoms selected from N, O and S. In some embodiments, ring A is thienyl. In some further embodiments, ring A is pyrazolyl. In some embodiments, ring A is selected from phenyl, thienyl and pyrazolyl. e.g. phenyl, 2-thienyl, 3-thienyl, and pyrazol-4-yl, e.g. 1H-pyrazol-4-yl.

In the moiety of formula (II), g is an integer of from 0 to 4 indicating the number of moieties $R_{1a}$ attached to ring A. In some embodiments, g is an integer of from 0 to 3. In some further embodiments, g is an integer of from 0 to 2. In still further embodiments, g is an integer of from 1 to 4. In still further embodiments, g is an integer of from 1 to 3, e.g. g is 1 or 2. In some embodiments, g is 1.

In some embodiments, when ring A is phenyl, g is an integer of from 1 to 4, or from 1 to 3, e.g. g is 1 or 2, or g is 1; and when ring A is 5- or 6-membered heteroaryl, g is an integer of from 0 to 3, or from 0 to 2, e.g. g is 0 or 1, e.g. g is 0, or g is an integer of from 1 to 3, e.g. g is 3.

In some embodiments, ring A is phenyl and g is an integer of from 1 to 4, or from 1 to 3, e.g. g is 1 or 2, or g is 1; i.e. the moiety of formula (II) is as represented by formula (IIa)

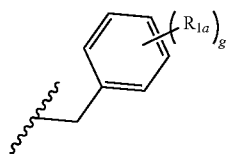

(IIa)

wherein $R_{1a}$ and g are as defined herein.

In some embodiments, the phenyl ring of the moiety of formula (IIa) is substituted in para position, i.e. said moiety more specifically is as represented by formula (IIb)

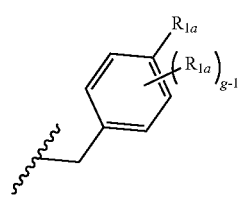

(IIb)

wherein $R_{1a}$ is as defined herein, and g is 1, 2 or 3, e.g. g is 1 or 2, or g is 1.

Thus, in some embodiments, the compound of the present invention may be represented by formula (Ib)

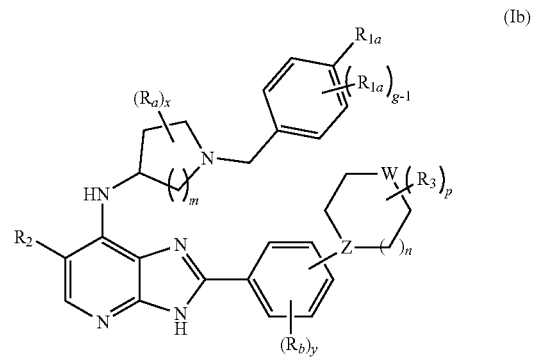

(Ib)

wherein each $R_{1a}$, $R_2$, each $R_3$, each $R_a$, each $R_b$, Z, W, m, n, p, x and y are as defined herein, and g is 1, 2 or 3, e.g. g is 1 or 2, or g is 1.

In some embodiments of a compound of formula (Ib), if g is 2, the further $R_1$, is in meta position on the phenyl ring (ring A). In some of these embodiments, the $R_{1a}$ in meta position and the $R_{1a}$ in para position, together with the atoms to which they are attached, form a 5- or 6-membered ring optionally containing one or more heteroatoms.

In some embodiments of a compound of formula (Ib), wherein g is 1, 2 or 3, e.g. g is 1 or 2, or g is 1, and one $R_{1a}$ is $R_{1b}O$, the compound is as represented by formula (Ib1)

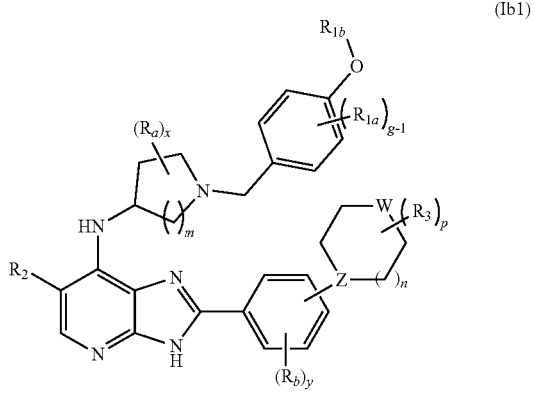

(Ib1)

wherein each $R_{1a}$, $R_{1b}$, $R_2$, each $R_3$, each $R_a$, each $R_b$, Z, W, m, n, p, x and y are as defined herein, e.g. $R_{1b}$ is C1-C3 alkyl, in particular methyl.

In some further embodiments, ring A is 5- or 6-membered heteroaryl, in particular 5-membered heteroaryl, and g is an integer of from 0 to 3. In some of these embodiments, g is an integer of from 0 to 2, e.g. 0 or 1, e.g. g is 0. In some other of these embodiments, g is an integer of from 1 to 3, e.g. g is 3.

In the moiety of formula (II), any $R_{1a}$, when present, is independently selected from C1-C6 alkyl, $R_{1b}O$, and $R_{1c}R_{1d}N$, and when g is at least 2, two $R_{1a}$, attached to adjacent atoms of ring A may form, together with the atoms to which they are attached, a 5- or 6-membered ring optionally containing one or more heteroatoms.

In some embodiments, each $R_{1a}$ is independently selected from C1-C6 alkyl, $R_{1b}O$, and $R_{1c}R_{1d}N$. In some embodiments, each $R_{1a}$ is independently selected from C1-C6 alkyl and $R_{1b}O$. In some embodiments, each $R_{1a}$ is $R_{1b}O$.

In some embodiments, each $R_{1a}$ is independently selected from C1-C6 alkyl and $R_{1b}O$, and when g is at least 2, two $R_{1a}$, attached to adjacent atoms of ring A may form, together with the atoms to which they are attached, a 5- or 6-membered ring optionally containing one or more heteroatoms.

In some embodiments, each $R_{1a}$ is $R_{1b}O$ and when g is at least 2, two $R_{1a}$, attached to adjacent atoms of ring A may form, together with the atoms to which they are attached, a 5- or 6-membered ring optionally containing one or more heteroatoms.

In some embodiments, g is at least 2, e.g. g is 2, and two $R_{1a}$, attached to adjacent atoms of ring A form, together with the atoms to which they are attached, a 5- or 6-membered ring optionally containing one or more heteroatoms.

When $R_{1a}$ is C1-C6 alkyl, it more particularly may be C1-C5 alkyl, or C1-C4 alkyl, or C1-C3 alkyl, e.g. methyl or ethyl, in particular methyl.

When two $R_{1a}$, attached to adjacent atoms of ring A, together with the atoms to which they are attached, form a 5- or 6-membered ring optionally containing one or more heteroatoms, said ring e.g. may be non-aromatic. In some embodiments, said ring is non-aromatic and contains one or two heteroatoms, e.g. one or two oxygen atoms. In some embodiments, when two $R_{1a}$, attached to adjacent atoms of ring A form, together with the atoms to which they are attached, a 5- or 6-membered ring optionally containing one or more heteroatoms, said ring is 5-membered and non-aromatic. In some embodiments, said ring is 5-membered, non-aromatic and contains one or two heteroatoms, e.g. one or two oxygen atoms. In some embodiments, said ring is non-aromatic and contains one heteroatom, e.g. one oxygen atom, e.g. said ring is 5-membered, non-aromatic and contains one heteroatom, e.g. one oxygen atom. For example, in some embodiments, when two $R_{1a}$, attached to adjacent atoms of ring A form, together with the atoms to which they are attached, a 5- or 6-membered ring optionally containing one or more heteroatoms, said two $R_{1a}$ form a diradical of formula

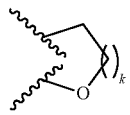

wherein k is 1 or 2; e.g. k is 1.

In some embodiments, when two $R_{1a}$, attached to adjacent atoms of ring A form, together with the atoms to which they are attached, a 5- or 6-membered ring optionally containing one or more heteroatoms, ring A is phenyl. In some of these embodiments, the moiety formula (II) more specifically is a moiety of formula (IIc)

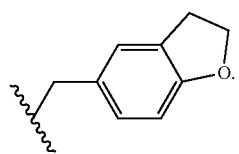

(IIc)

In any moiety $R_{1b}O$, $R_{1b}$ is independently selected from H and C1-C6 alkyl. In some embodiments, $R_{1b}$ is selected from H and C1-C5 alkyl, or from H and C1-C4 alkyl, or from H and C1-C3 alkyl, or from H and C1-C2 alkyl, or from H and methyl. In some embodiments, $R_{1b}$ is selected from C1-C6 alkyl, or from C1-C5 alkyl, or from C1-C4 alkyl, or from C1-C3 alkyl, or from C1-C2 alkyl, e.g. each $R_{1b}$ is methyl.

In any moiety $R_{1c}R_{1d}N$, $R_{1c}$ and $R_{1d}$ are independently selected from H and C1-C6 alkyl. In some embodiments, $R_{1c}$ is independently selected from H and C1-C5 alkyl, or from H and C1-C4 alkyl, or from H and C1-C3 alkyl, or from H and C1-C2 alkyl, or from H and methyl. In some further embodiments, $R_{1c}$ is selected from C1-C6 alkyl, or from C1-C5 alkyl, or from C1-C4 alkyl, or from C1-C3 alkyl, or from C1-C2 alkyl, e.g. $R_{1c}$ is methyl. Likewise, $R_{1d}$ is independently selected from H and C1-C6 alkyl. In some embodiments, $R_{1d}$ is independently selected from H and C1-C5 alkyl, or from H and C1-C4 alkyl, or from H and C1-C3 alkyl, or from H and C1-C2 alkyl, or from H and methyl. In some embodiments, $R_{1d}$ is selected from C1-C6 alkyl, or from C1-C5 alkyl, or from C1-C4 alkyl, or from C1-C3 alkyl, or from C1-C2 alkyl, e.g. $R_{1d}$ is methyl. In some embodiments, in any $R_{1c}R_{1d}N$, both $R_{1d}$ and $R_{1c}$ are C1-C6 alkyl, or both are C1-C5 alkyl, or both are C1-C4 alkyl, or both are C1-C3 alkyl, or both are C1-C2 alkyl, e.g. both are methyl.

In some embodiments, when ring A is 5- or 6-membered heteroaryl, $R_{1a}$ is C1-C6 alkyl, e.g. C1-C3 alkyl, such as methyl.

In some particular embodiments, $R_1$ is methyl, ethyl, isopropyl, n-propyl, cyclohexyl, cyclopropylmethyl, methoxyethyl, cyanomethyl, cyanoethyl, 4-methoxybenzyl, (1,3,5-trimethyl-1H-pyrazol-4-yl)methyl, thiophen-2-ylmethyl, 4-(dimethylamino)benzyl, 4-hydroxy-3-methoxybenzyl, (2,3-dihydrobenzofuran-6-yl)methyl, or thiophen-3-ylmethyl.

In a compound of formula (I), $R_2$ is Cl or Br. In some embodiments, $R_2$ is Cl. In some other embodiments, $R_2$ is Br.

In a compound of formula (I), each $R_3$ is independently selected from C1-C6 alkyl, e.g. from C1-C5 alkyl, or from C1-C4 alkyl, or from C1-C3 alkyl; e.g. $R_3$ is methyl or ethyl; in particular $R_3$ is methyl.

The number of moieties $R_3$, indicated by p, is from 0 to 3, e.g. from 0 to 2, e.g. p is 0 or 1. In some embodiments, p is 0. In some further embodiments, p is 1. For example, in some embodiments, when the ring containing Z and W is 7-membered, p is 0, and when the ring containing Z and W is 6-membered, p is 0, 1 or 2, e.g. p is 0 or 1.

In a compound of formula (I), y is an integer 0, 1, 2 or 3 indicating the number of moieties $R_b$. In some embodiments, y is 0, 1, or 2; e.g. y is 0 or 1. In some embodiments, y is 0. In some other embodiments, y is 1.

The moiety $R_b$ is selected from halogen, C1-C3 alkyl, and C1-C3 alkoxy, e.g. from F, methyl and methoxy. In some embodiments, $R_b$ is selected from halogen and C1-C3 alkoxy, e.g. from F and $CH_3O$. In some embodiments, $R_b$ is halogen, e.g. $R_b$ is F. In some embodiments, y is 1 and $R_b$ is selected from halogen and C1-C3 alkoxy, e.g. from F and $CH_3O$. In some embodiments, when y is 1 $R_b$ is F. In some further embodiments, when y is 1, $R_b$ is $CH_3O$.

In some particular embodiments, x and y are both 0, viz. both $R_a$ and $R_b$ are absent. In some other particular embodiments, x is 0, and y is 0 or 1. In some other embodiments, x is an integer of from 0 to 4, e.g. x is 0 or 4, and y is 0 or 1, e.g. y is 0.

In a compound of formula (I), Z is N or CH. In some embodiments, Z is CH. In some further embodiments, Z is N, i.e. compound of formula (I) is as represented by formula (Ic)

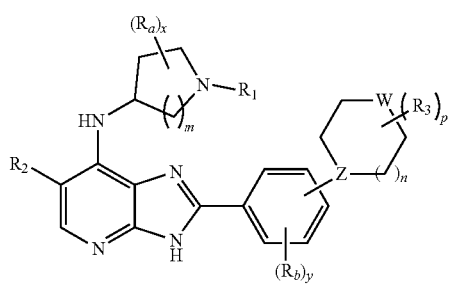

(Ic)

wherein $R_1$, $R_2$, each $R_3$, each $R_a$, each $R_b$, W, m, n, p, x and y are as defined herein.

In a compound of formula (I), W is $>Q\text{-}R_4$, —O— or —N($R_5$)C(O)—. In some embodiments, W is $>Q\text{-}R_4$ or —N($R_5$)C(O)—. In some further embodiments, W is $>Q\text{-}R_4$ or —O—. In still further embodiments, W is $>Q\text{-}R_4$.

In the moiety $>Q\text{-}R_4$, Q is N or CH. In some embodiments, Q is N. In some embodiments, therefore, W is $>N\text{-}R_4$, —O— or —N($R_5$)C(O)—.

In further embodiments, W is $>N\text{-}R_4$ or —N($R_5$)C(O)—.

In still further embodiments, W is $>N\text{-}R_4$ or —O—. In still further embodiments, W is $>Q\text{-}R_4$, viz. the compound of formula (I) may be represented by formula (Id)

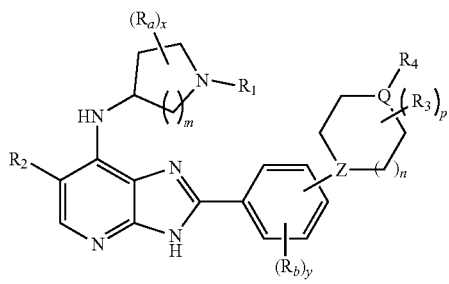

(Id)

wherein $R_1$, $R_2$, each $R_3$, $R_4$, each $R_a$, each $R_b$, Q, Z, m, n, p, x and y are as defined herein.

In some embodiments of a compound of formula (Id), Q is N, i.e. the compound may be represented by formula (Id1)

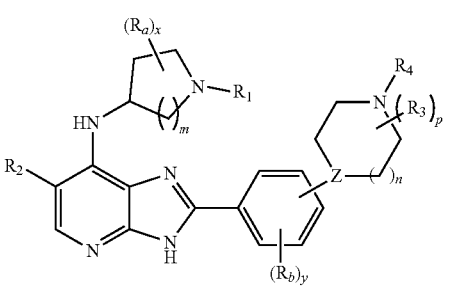

(Id1)

wherein $R_1$, $R_2$, each $R_3$, $R_4$, each $R_a$, each $R_b$, Z, m, n, p, x and y are as defined herein.

In some further embodiments of a compound of formula (Id), Q is CH, i.e. the compound may be represented by formula (Id2)

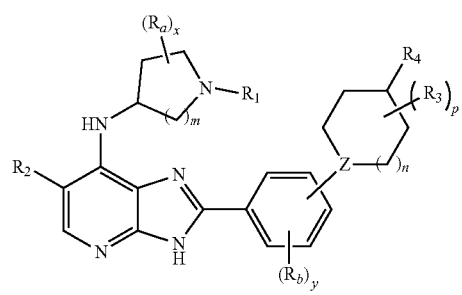

(Id2)

wherein $R_1$, $R_2$, each $R_3$, $R_4$, each $R_a$, each $R_b$, Z, m, n, p, x and y are as defined herein.

In some embodiments, when Q is CH, Z is N.

In some embodiments of a compound of formula (Id), $R_1$ is C1-C3 alkyl;
p is 0 or 1;
$R_3$ is C1-C3 alkyl;
$R_4$ is C1-C3 alkyl, $R_{4a}[O(CH_2)_q]_r$—Y, $R_{4b}S(O)_2$, $R_{4c}C(O)$ or a moiety of formula (III)

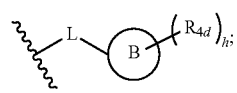

(III)

L is a direct bond or $CH_2$;
h is an integer of from 0 to 3;
$R_{4a}$ is H or C1-C3 alkyl;
$R_{4b}$ is C1-C3 alkyl;
$R_{4c}$ is C1-C3 alkyl;
$R_{4d}$ is C1-C3 alkyl; and
ring B is selected from phenyl and 5- or 6-membered heteroaryl, preferably ring B is 5- or 6-membered heteroaryl.

In still further embodiments of a compound of formula (Id),
$R_1$ is C1-C3 alkyl;
p is 0 or 1;
$R_3$ is C1-C3 alkyl;
$R_4$ is C1-C3 alkyl, $R_{4a}[O(CH_2)_q]_r$—Y, $R_{4b}S(O)_2$, or $R_{4c}C(O)$;
$R_{4a}$ is H or C1-C3 alkyl;
$R_{4b}$ is C1-C3 alkyl; and
$R_{4c}$ is C1-C3 alkyl.

In still further embodiments, W is —N($R_5$)C(O)—, i.e. the compound of formula (I) may be represented by formula (Ie)

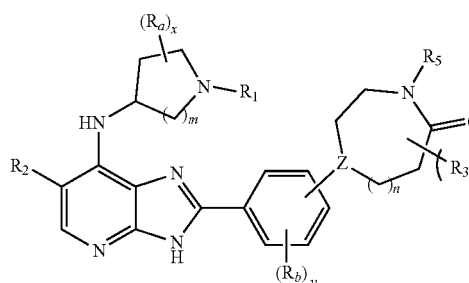

(Ie)

wherein $R_1$, $R_2$, each $R_3$, $R_5$, each $R_a$, each $R_b$, Z, m, n, p, x and y are as defined herein.

In some embodiments of a compound of formula (Ie), m is 2 and p is 0. In some further embodiments of a compound of formula (Ie), m is 2, p is 0 and n is 1, i.e. the compound is represented by formula (Ie1)

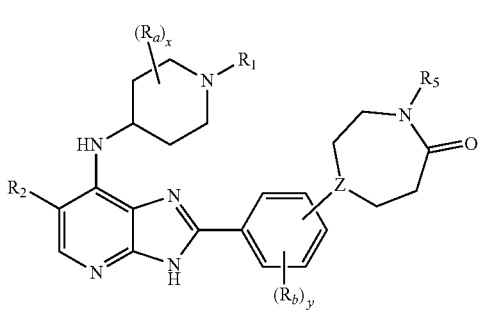

(Ie1)

wherein $R_1$, $R_2$, $R_5$, each $R_a$, each $R_b$, Z, x and y are as defined herein.

In some embodiments of a compound of formula (Ie) or (Ie1), Z is N. In some particular embodiments, the compound is as represented by formula (Ie2)

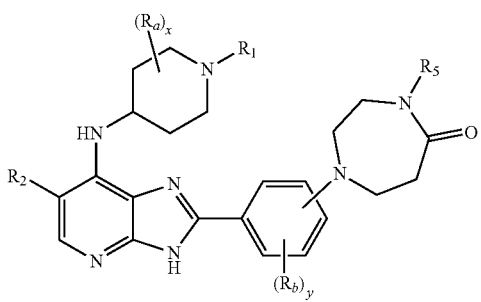

(Ie2)

wherein $R_1$, $R_2$, $R_5$, each $R_a$, each $R_b$, x and y are as defined herein.

In some other embodiments, the compound is as represented by formula (Ie3)

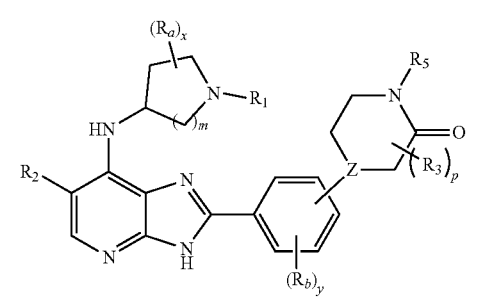

(Ie3)

wherein $R_1$, $R_2$, each $R_3$, $R_5$, each $R_a$, each $R_b$, Z, m, n, p, x and y are as defined herein.

In some embodiments of a compound of formula (Ie3), Z is N. In some further embodiments of a compound of formula (Ie3), Z is N, m is 2, and both p and y are 0. In some further embodiments of a compound of formula (Ie3), Z is N, m is 2, and p, x and y are 0.

In some particular embodiments of a compound of formula (Ie), (Ie1), (Ie2) or (Ie3), $R_5$ is H.

In some other embodiments of a compound of formula (Ie), e.g. in some embodiments of a compound of formula (Ie3), $R_5$ is C1-C6 alkyl, $R_{5a}[O(CH_2)_u]_v$, or a moiety of formula (IV)

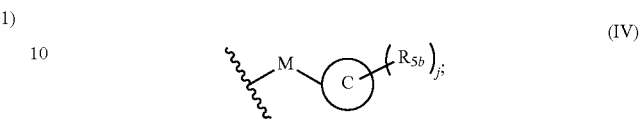

(IV)

wherein M, ring C, $R_{5b}$ and j are as defined herein; e.g. $R_5$ is C1-C6 alkyl or $R_{5a}[O(CH_2)_u]_v$; or $R_{5a}[O(CH_2)_u]_v$, or a moiety of formula (IV) as defined herein; or $R_5$ is $R_{5a}[O(CH_2)_u]_v$.

The ring containing W and Z is a 6- or 7-membered ring, i.e. n in formula (I) is an integer of from 0 to 2, wherein n is 1 or 2 when W is >Q-$R_4$ or —O—, and n is 0 or 1 when W is —N($R_5$)C(O)—.

In some embodiments, the ring containing W and Z is 6-membered, i.e. n in formula (I) is 1 when W is >Q-$R_4$ or —O—; and n is 0 when W is —N($R_5$)C(O)—. In some of these embodiments Q is N.

In some embodiments, the ring containing W and Z is 6-membered, and W is >Q-$R_4$ or —N($R_5$)C(O)—, i.e. n is 0 when W is —N($R_5$)C(O)— and n is 1 when W is >Q-$R_4$. In some of these embodiments Q is N.

In some further embodiments, the ring containing W and Z is 7-membered, i.e. n in formula (I) is 2 when W is >Q-$R_4$ or —O—; and n is 1 when W is —N($R_5$)C(O)—. In some of these embodiments Q is N.

In some embodiments, the ring containing W and Z is 7-membered, and W is >Q-$R_4$ or —N($R_5$)C(O)—, i.e. n is 1 when W is —N($R_5$)C(O)— and n is 2 when W is >Q-$R_4$. In some of these embodiments Q is N.

In some embodiments, n is 1 and W is >Q-$R_4$ or —O—. In some further embodiments, n is 2 and W is >Q-$R_4$ or —O—. In some of these embodiments Q is N.

In still further embodiments, W is >Q-$R_4$, —O— or —N($R_5$)C(O)—, wherein n is 1 or 2 when W is >Q-$R_4$; n is 1 when W is —O—; and n is 0 or 1 when W is —N($R_5$)C(O)—. In some of these embodiments Q is N.

In still further embodiments, W is >Q-$R_4$ or —O—, and n is 1 or 2 when W is >Q-$R_4$; and n is 1 when W is —O—.

In still further embodiments, W is —O— and n is 1.

In some embodiments, n is 1 and W is >Q-$R_4$, i.e. the compound is as represented by formula (Id), wherein n is 1. In some of these embodiments, Q is N.

In some further embodiments, n is 2 and W is >Q-$R_4$, i.e. the compound is a compound of formula (Id) wherein n is 2. In some of these embodiments, Q is N.

In some embodiments, W is >Q-$R_4$ or —N($R_5$)C(O)—; and n is 0 or 1 when W is —N($R_5$)C(O)—, and n is 1 when W is >Q-$R_4$. In some of these embodiments, Q is N.

In some further embodiments, W is >Q-$R_4$ or —N($R_5$)C(O)—; and n is 0 or 1 when W is —N($R_5$)C(O)—, and n is 2 when W is >Q-$R_4$. In some of these embodiments, Q is N.

In some further embodiments, W is >Q-$R_4$ or —N($R_5$)C(O)—; and n is 0 when W is —N($R_5$)C(O)—, and n is 1 or 2 when W is >Q-$R_4$. In some of these embodiments, Q is N.

In some further embodiments, W is >Q-$R_4$ or —N($R_5$)C(O)—, and n is 1 when W is —N($R_5$)C(O)— and n is 1 or 2 when W is >Q-$R_4$. In some of these embodiments, Q is N.

In the moiety >Q-$R_4$, $R_4$ is C1-C6 alkyl, $R_{4a}$[O($CH_2$)$_q$]$_r$—Y, $R_{4b}$S(O)$_2$, $R_{4c}$C(O), cyano-C1-C6 alkyl, or a moiety of formula (III)

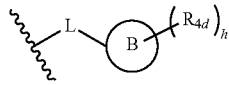

(III)

wherein L, ring B, each $R_{4d}$, and h are as defined herein.

In some embodiments, $R_4$ is C1-C6 alkyl, $R_{4a}$[O($CH_2$)$_q$]$_r$—Y, $R_{4b}$S(O)$_2$, or a moiety of formula (III) as defined herein. In some embodiments, $R_4$ is $R_{4a}$[O($CH_2$)$_q$]$_r$—Y, $R_{4b}$S(O)$_2$, $R_{4c}$C(O), or a moiety of formula (III) as defined herein. In some embodiments, $R_4$ is C1-C6 alkyl, $R_{4b}$S(O)$_2$, $R_{4c}$C(O), or a moiety of formula (III) as defined herein. In some embodiments, $R_4$ is C1-C6 alkyl, $R_{4a}$[O($CH_2$)$_q$]$_r$—Y, or a moiety of formula (III) as defined herein. In some further embodiments, $R_4$ is C1-C6 alkyl, $R_{4a}$[O($CH_2$)$_q$]$_r$—Y, $R_{4c}$C(O), or a moiety of formula (III) as defined herein. In some embodiments, $R_4$ is $R_{4a}$[O($CH_2$)$_q$]$_r$—Y, $R_{4c}$C(O), or a moiety of formula (III) as defined herein. In some embodiments, $R_4$ is $R_{4a}$[O($CH_2$)$_q$]$_r$—Y, $R_{4b}$S(O)$_2$, or a moiety of formula (III) as defined herein. In some embodiments, $R_4$ is $R_{4a}$[O($CH_2$)$_q$]$_r$—Y or a moiety of formula (III) as defined herein.

In some embodiments, $R_4$ is C1-C6 alkyl, $R_{4a}$[O($CH_2$)$_q$]$_r$—Y, $R_{4b}$S(O)$_2$ or $R_{4c}$C(O). In some embodiments, $R_4$ is C1-C6 alkyl, $R_{4a}$[O($CH_2$)$_q$]$_r$—Y, or $R_{4b}$S(O)$_2$. In some embodiments, $R_4$ is $R_{4a}$[O($CH_2$)$_q$]$_r$—Y, $R_{4b}$S(O)$_2$ or $R_{4c}$C(O). In some embodiments, $R_4$ is C1-C6 alkyl, $R_{4b}$S(O)$_2$ or $R_{4c}$C(O). In some embodiments, $R_4$ is C1-C6 alkyl, or $R_{4a}$[O($CH_2$)$_q$]$_r$—Y. In some further embodiments, $R_4$ is C1-C6 alkyl, $R_{4a}$[O($CH_2$)$_q$]$_r$—Y or $R_{4c}$C(O). In some embodiments, $R_4$ is $R_{4a}$[O($CH_2$)$_q$]$_r$—Y or $R_4$C(O). In some embodiments, $R_4$ is $R_{4a}$[O($CH_2$)$_q$]$_r$—Y or $R_{4b}$S(O)$_2$.

In some embodiments, when W is >Q-$R_4$, e.g. W is >N—$R_4$, $R_4$ is $R_{4a}$[O($CH_2$)$_q$]$_r$—Y.

In some embodiments, W is >Q-$R_4$ and $R_4$ is $R_{4a}$[O($CH_2$)$_q$]$_r$—Y, i.e. the compound of formula (I) may be represented by formula (If)

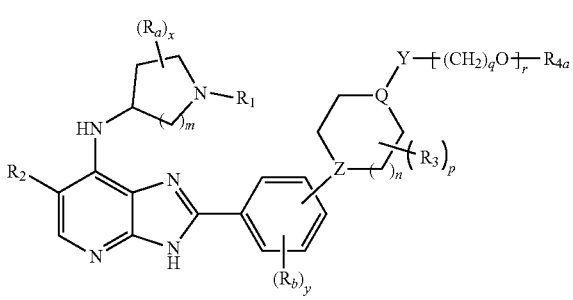

(If)

wherein $R_1$, $R_2$, each $R_3$, $R_{4a}$, each $R_a$, each $R_b$, Q, Y, Z, m, n, p, q, r, x and y are as defined herein.

In some embodiments of a compound of formula (If), Q is N, i.e. the compound may be represented by formula (If1)

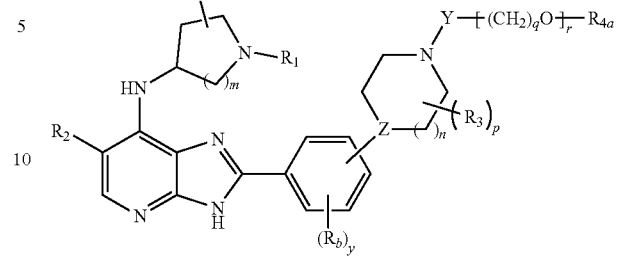

(If1)

wherein $R_1$, $R_2$, each $R_3$, $R_{4a}$, each $R_a$, each $R_b$, Y, Z, m, n, p, q, r, x and y are as defined herein.

In some embodiments of a compound of formula (If),
m is 1 or 2, preferably m is 2;
$R_1$ is C1-C6 alkyl, or a moiety of formula (II)

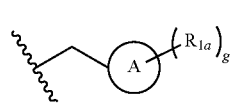

(II)

ring A is phenyl or 5- or 6-membered heteroaryl;
g is an integer of from 0 to 3;
each $R_{1a}$ is independently selected from C1-C3 alkyl, $R_{1b}$O, and $R_{1c}R_{1d}$N;
each $R_{1b}$ is independently selected from H, C1-C3 alkyl;
each $R_{1c}$ is independently selected from H and C1-C3 alkyl;
each $R_{1d}$ is independently selected from H and C1-C3 alkyl;
or two $R_{1a}$, attached to adjacent atoms of ring A form, together with the atoms to which they are attached, a 5- or 6-membered ring optionally containing one or more heteroatoms;
$R_2$ is Cl or Br, preferably $R_2$ is Br;
p is 0 or 1;
$R_3$ is C1-C3 alkyl;
Z is N or CH; preferably Z is N;
n is 1 or 2;
each q is independently selected from 2 and 3;
r is 1 or 2;
Y is a direct bond or C(O), preferably Y is a direct bond; and
$R_{4a}$ is H or C1-C3 alkyl.

In some further embodiments of a compound of formula (If), e.g. of formula (If1),
m is 1 or 2, preferably m is 2;
$R_1$ is C1-C6 alkyl, preferably $R_1$ is C1-C3 alkyl;
$R_2$ is Cl or Br, preferably $R_2$ is Br;
p is 0 or 1;
$R_3$ is C1-C3 alkyl; e.g. $R_3$ is methyl;
Z is N or CH; preferably Z is N;
n is 1 or 2, preferably n is 1;
each q is independently selected from 2 and 3;
r is 1 or 2;
Y is a direct bond or C(O), preferably Y is a direct bond; and
$R_{4a}$ is H or C1-C3 alkyl.

In some further embodiments of a compound of formula (If), e.g. of formula (If1), m is 2; $R_1$ is C1-C3 alkyl; p is 0 or 1; $R_3$ is methyl; Z is N; n is 1; each q is independently selected from 2 and 3; r is 1 or 2; Y is a direct bond; and $R_{4a}$ is H or C1-C3 alkyl.

In some further embodiments, when W is >Q-$R_4$, e.g. W is >N—$R_4$, $R_4$ is a moiety of formula (III)

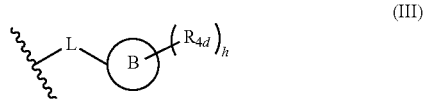

(III)

wherein L, ring B, h, and each $R_{4d}$ are as defined herein.

In some of embodiments, W is >Q-$R_4$ and $R_4$ is a moiety of formula (III), i.e. the compound of formula (I), may be represented by formula (Ig)

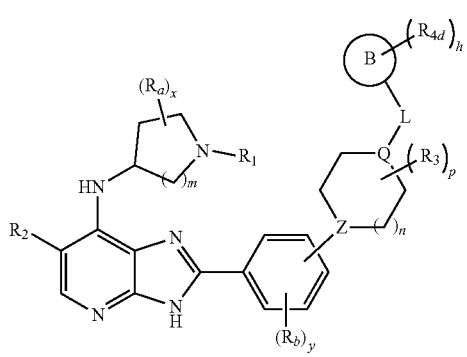

(Ig)

wherein $R_1$, $R_2$, each $R_3$, each $R_{4d}$, each $R_a$, each $R_b$, L, Q, Z, ring B, h, m, n, p, r, x and y are as defined herein.

In some embodiments of a compound of formula (Ig), Q is N, i.e. the compound is a compound of formula (Ig1)

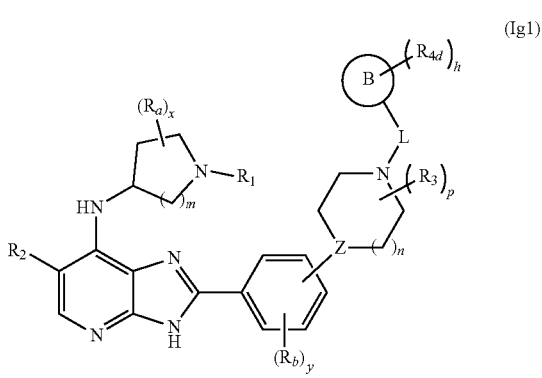

(Ig1)

wherein $R_1$, $R_2$, each $R_3$, each $R_{4d}$, each $R_a$, each $R_b$, L, Z, ring B, h, m, n, p, r, x and y are as defined herein.

In some particular embodiments of a compound of formula (Ig), $R_1$ is C1-C6 alkyl, in particular C1-C3 alkyl. In some other particular embodiments of a compound of formula (Ig), n is 1. In still further embodiments of a compound of formula (Ig), p is 0. In still further embodiments of a compound of formula (Ig), n is 1 and p is 0. In some embodiments of a compound of formula (Ig), $R_1$ is C1-C6 alkyl, in particular C1-C3 alkyl, n is 1, and p is 0. In some embodiments of a compound of formula (Ig), m is 2; e.g. m is 2, n is 1, and p is 0. In some embodiments of a compound of formula (Ig), m is 2, n is 1, p is 0, and $R_1$ is C1-C6 alkyl, in particular C1-C3 alkyl. In some embodiments of a compound of formula (Ig), m is 1; e.g. m is 1, n is 1, and p is 0. In some embodiments of a compound of formula (Ig), m is 1, n is 1, p is 0 and $R_1$ is C1-C6 alkyl, in particular C1-C3 alkyl.

In some embodiments of a compound of formula (Ig), L is methylene. In some of these embodiments, ring B is 5- or 6-membered heteroaryl, in particular 6-membered heteroaryl. In some further embodiments of a compound of formula (Ig), e.g. wherein ring B is 5- or 6-membered heteroaryl, in particular 6-membered heteroaryl, L is methylene, m is 2, n is 1, and p is 0. In some embodiments, L is methylene, m is 2, n is 1, p is 0, and $R_1$ is C1-C6 alkyl, e.g. C1-C3 alkyl. In still further embodiments, L is methylene, m is 1, n is 1, p is 0, and $R_1$ is C1-C6 alkyl, e.g. C1-C3 alkyl.

In some embodiments of a compound of formula (Ig), L is a direct bond. In some of these embodiments, ring B is phenyl or 6-membered heteroaryl, in particular 6-membered heteroaryl. For example, in some embodiments, e.g. wherein ring B is phenyl or 6-membered heteroaryl, in particular 6-membered heteroaryl, L is a direct bond, m is 2, n is 1, and p is 0.

In some further embodiments of a compound of formula (Ig), e.g. wherein ring B is phenyl or 6-membered heteroaryl, in particular 6-membered heteroaryl, L is a direct bond, m is 2, n is 1, p is 0, and $R_1$ is C1-C6 alkyl, e.g. C1-C3 alkyl. In still further embodiments wherein ring B is phenyl or 6-membered heteroaryl, ring B more particularly is phenyl.

When $R_4$ is C1-C6 alkyl, it more particularly may be C1-C5 alkyl, or C1-C4 alkyl, or C1-C3 alkyl, or C1-C2 alkyl, e.g. $CH_3$. In some embodiments, W is >Q-$R_4$ and $R_4$ is C1-C3 alkyl, e.g. methyl or ethyl, in particular methyl.

In the moiety $R_{4a}[O(CH_2)_q]_r$—Y, each q is independently selected from 1, 2, 3, and 4; r is 1 or 2, $R_{4a}$ is H or C1-C6 alkyl, and Y is a direct bond or C(O).

In some embodiments, Y is a direct bond, i.e. the moiety $R_{4a}[O(CH_2)_q]_r$—Y has the formula $R_{4a}[O(CH_2)_q]_r$—. In some further embodiments, Y is C(O), i.e. the moiety has the formula $R_{4a}[O(CH_2)_q]_rC(O)$.

In some embodiments, r is 2, i.e. the moiety $R_{4a}[O(CH_2)_q]_r$—Y has the formula $R_{4a}[O(CH_2)_q]_2$—Y. In some embodiments, when r is 2, each q is independently selected from 2 and 3. In some embodiments, when r is 2, each q is 2, or each q is 3. In some embodiments, when r is 2, each q is 2.

In some further embodiments, r is 1, i.e. the moiety is one having the formula $R_aO(CH_2)_q$—Y, wherein q is 1, 2, 3 or 4, e.g. q is 2, 3 or 4, or q is 2 or 3. In some embodiments, q is 3. In some embodiments, r is 1, and q is 1, 2, or 3. In some further embodiments, r is 1 and q is 3 or 4. In some particular embodiments, r is 1 and q is 3.

In some embodiments, each q is 2, i.e. the moiety is one having the formula $R_{4a}[O(CH_2)_2]_r$—Y, wherein r is 1 or 2.

In some embodiments, q is 2 and r is 1, i.e. the moiety has the formula $R_{4a}O(CH_2)$—Y. In some of these embodiments, Y is a direct bond, i.e. the moiety has the formula $R_{4a}O(CH_2)_2$—. In some other of these embodiments, Y is C(O), i.e. the moiety has the formula $R_{4a}O(CH_2)_2C(O)$—.

In some embodiments, when q is 2 and r is 2, Y is a direct bond, i.e. the moiety has the formula $R_{4a}O(CH_2)_2O(CH_2)_2$—.

In some embodiments, each q is 3, i.e. the moiety is one having the formula $R_{4a}[O(CH_2)_3]_r$—Y, where r is 1 or 2. In some of these embodiments, Y is a direct bond.

In some embodiments, when q is 3, r is 1, i.e. the moiety has the formula $R_{4a}O(CH_2)_3$—Y. In some of these embodiments, Y is a direct bond, i.e. the moiety has the formula $R_{4a}O(CH_2)_3$—.

In some further embodiments, q is 3 and r is 2, i.e. the moiety has the formula $R_{4a}[O(CH_2)_3]_2$—Y, i.e. $R_{4a}O(CH_2)_3O(CH_2)_3$—Y. In some of these embodiments, Y is a direct bond, i.e. the moiety has the formula $R_{4a}O(CH_2)_3O(CH_2)_3$—.

In some embodiments, each q is 4. In some embodiments, when q is 4, r is 1, i.e. the moiety has the formula $R_{4a}O(CH_2)_4$—Y. In some of these embodiments, Y is a direct bond, i.e. the moiety has the formula $R_{4a}O(CH_2)_4$—.

In some embodiments, each q is 1. In some embodiments, when q is 1, r is 1, i.e. the moiety has the formula $R_{4a}OCH_2$—Y. In some of these embodiments, Y is C(O), i.e. the moiety has the formula $R_{4a}OCH_2C(O)$—.

The moiety $R_{4a}$ is H or C1-C6 alkyl. In some embodiments, $R_{4a}$ is H or C1-C5 alkyl, e.g. $R_{4a}$ is H or C1-C4 alkyl, or $R_{4a}$ is H or C1-C3 alkyl, or $R_{4a}$ is H or C1-C2 alkyl, or $R_{4a}$ is H or methyl. In some further embodiments, $R_{4a}$ is C1-C6 alkyl, or $R_{4a}$ is C1-C5 alkyl, e.g. $R_{4a}$ is C1-C4 alkyl, or $R_{4a}$ is C1-C3 alkyl, or $R_{4a}$ is C1-C2 alkyl, or $R_{4a}$ is methyl. In some embodiments, $R_{4a}$ is H, methyl, ethyl, or isopropyl. In some embodiments, $R_{4a}$ is methyl, ethyl, or isopropyl, e.g. methyl or ethyl. In some embodiments, $R_{4a}$ is methyl. In some embodiments, $R_{4a}$ is ethyl. In some embodiments, $R_{4a}$ is isopropyl.

For example, in some embodiments, in the moiety of formula $R_{4a}[O(CH_2)_q]_r$—Y, $R_{4a}$ is H, methyl, ethyl, or isopropyl, in particular methyl, ethyl, or isopropyl; q is 2, 3 or 4, in particular q is 3; r is 1; and Y is a direct bond.

In the moiety $R_{4b}S(O)_2$, $R_{4b}$ is C1-C6 alkyl. In some embodiments, $R_{4b}$ is C1-C5 alkyl; e.g. $R_{4b}$ is C1-C4 alkyl; or $R_{4b}$ is C1-C3 alkyl; or $R_{4b}$ is C1-C2 alkyl; e.g. $R_{4b}$ is methyl.

In the moiety $R_{4c}C(O)$, $R_{4c}$ is C1-C6 alkyl. In some embodiments, $R_{4c}$ is C1-C5 alkyl; e.g. $R_{4c}$ is C1-C4 alkyl, e.g. $R_{4c}$ is methyl or tert-butyl; or $R_{4c}$ is C1-C3 alkyl; or $R_{4c}$ is C1-C2 alkyl; or $R_{4c}$ is methyl.

In the moiety of formula (III)

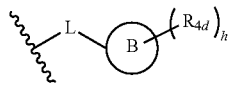

(III)

L is a direct bond, C1-C4 alkylene, or -$L_1$-$L_2$-;
$L_1$ is a direct bond or C1-C4 alkylene;
$L_2$ is C(O) or NH;
h is an integer of from 0 to 3,
$R_{4d}$ is C1-C6 alkyl, and
ring B is selected from phenyl and 5- or 6-membered heteroaryl.

In some embodiments, L is a direct bond or C1-C4 alkylene. In some further embodiments, L is C1-C4 alkylene or -$L_1$-$L_2$-. In still further embodiments, L is a direct bond or -$L_1$-$L_2$-.

When L is C1-C4 alkylene, L more particularly may be C1-C3 alkylene, or C1-C2 alkylene, or C1 alkylene, i.e. methylene. In some embodiments, when L is C2-C4 alkylene, the alkylene moiety is branched, e.g. it is ethylene or methylene substituted by one or two methyl groups; or methylene substituted by one or two methyl groups, or a methyl group and an ethyl group, or ethylene substituted by an ethyl group.

In some embodiments, L is a direct bond, i.e. the moiety of formula (III) is one having the formula (IIIa)

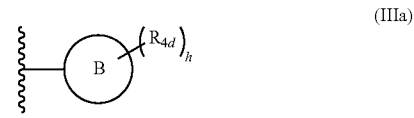

wherein h, $R_{4d}$, and ring B are as defined herein.

In some further embodiments, L is methylene, i.e. the moiety of formula (III) is one having the formula (IIIb)

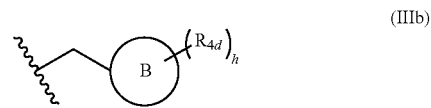

wherein h, $R_{4d}$, and ring B are as defined herein.

In the moiety -$L_1$-$L_2$-, $L_1$ is a direct bond or C1-C4 alkylene. In some embodiments, $L_1$ is a direct bond. In some other embodiments, $L_1$ is C1-C4 alkylene.

When $L_1$ is C1-C4 alkylene, it e.g. may be C2-C4 alkylene, or C2-C3 alkylene, in particular C2 alkylene, i.e. ethylene. In some embodiments, $L_2$ is ethylene, optionally substituted by one or 2 methyl groups, or by one ethyl group.

The moiety $L_2$ is NH or C(O). In some embodiments, $L_2$ is NH. In some further embodiments, $L_2$ is C(O).

In some embodiments, when L is -$L_1$-$L_2$-, $L_1$ is a direct bond and $L_2$ is C(O), or $L_1$ is C1-C4 alkylene and $L_2$ is NH.

In some embodiments, when L is -$L_1$-$L_2$-, the moiety of formula (III) more particularly has the formula (IIIc)

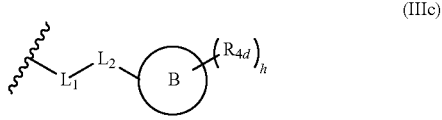

wherein $L_1$, $L_2$, ring B, $R_{4d}$ and h are as defined herein.

In some embodiments, L is a direct bond, $CH_2$, C(O), or —C2-C4 alkylene-NH—; e.g. a direct bond, $CH_2$, C(O), or —C2-C3 alkylene-NH—; or a direct bond, $CH_2$, C(O), or —$(CH_2)_2$NH—.

In the moiety of formula (III), h is an integer of from 0 to 3. In some embodiments, h is an integer of from 0 to 2. In some embodiments, h is 0 or 1. In some embodiments, h is 0. In still further embodiments, h is an integer of from 1 to 3, e.g. h is 1 or 2, or h is 1.

When h is 1, 2 or 3, each moiety $R_{4d}$ is independently selected from C1-C6 alkyl. In some embodiments, each $R_{4d}$ is selected from C1-C5 alkyl; e.g. each $R_{4d}$ is selected from C1-C4 alkyl; or each $R_{4d}$ is selected from C1-C3 alkyl; or each $R_{4d}$ is selected from C1-C2 alkyl; or each $R_{4d}$ is methyl. It should be realized that any $R_{4d}$ may be attached either to a carbon atom of ring B or to heteroatom of ring B, e.g. to a nitrogen atom of ring B.

Ring B is selected from phenyl and 5- or 6-membered heteroaryl. In some embodiments, ring B is phenyl. In some embodiments, ring B is 5- or 6-membered heteroaryl. In some embodiments, ring B is 5-membered heteroaryl. In some embodiments, ring B is 6-membered heteroaryl.

When ring B is 5- or 6-membered heteroaryl, said heteroaryl contains one or more heteroatoms in the ring, preferably selected from N, O and S. In some embodiments, the heteroaryl contains 1-4 heteroatoms, e.g. 1-3 heteroatoms or 1-2 heteroatoms, said heteroatoms being selected from N, O and S.

In some embodiments, when ring B is 5- or 6-membered heteroaryl, said heteroaryl contains one nitrogen atom (N) and optionally at least one further heteroatom selected from N, O and S. In some further embodiments, when ring B is 5-membered heteroaryl, said ring contains one O or one S and optionally also one or more N.

In some embodiments, when ring B is 5- or 6-membered heteroaryl, said heteroaryl may be selected from any of the rings

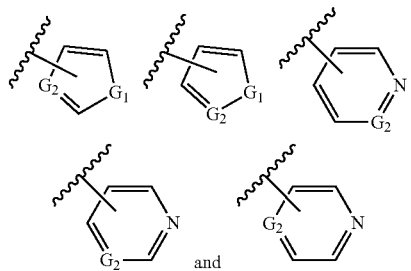

or, more particularly, from any of the rings

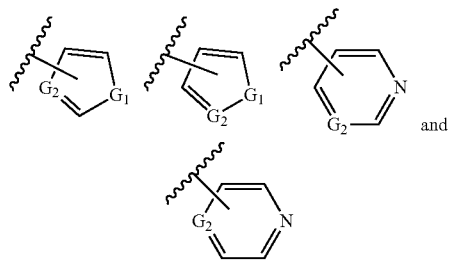

wherein $G_1$ is NH, O or S; e.g. $G_1$ is O or S; or $G_1$ is O or NH, or $G_1$ is NH, and when $G_1$ is NH, the hydrogen of the NH may be replaced by $R_{4d}$; and $G_2$ is N or CH, and when $G_2$ is CH, the hydrogen of the CH may be replaced by $R_{4d}$.

In some embodiments, when ring B is 6-membered heteroaryl, it more particularly is selected from any of the rings

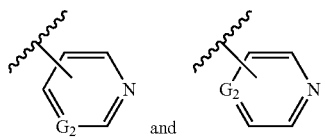

wherein $G_2$ is as defined herein above. In some of these embodiments, $G_2$ is CH. In some other of these embodiments, $G_2$ is N. In some embodiments, when ring B is 6-membered heteroaryl, it more particularly is

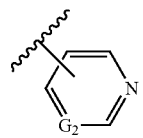

wherein $G_2$ is as defined herein above.

In some further embodiments, when ring B is 6-membered heteroaryl, it more particularly is

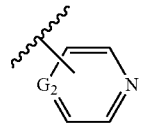

wherein $G_2$ is as defined herein above.

In some embodiments, when ring B is 5-membered heteroaryl, it more particularly is selected from any of the rings

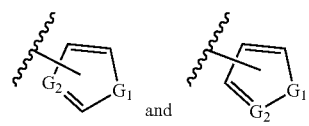

wherein $G_1$ and $G_2$ are as defined herein above, $G_1$ is NH, O or S; e.g. $G_1$ is O or S; or $G_1$ is O or NH, or $G_1$ is NH, and when $G_1$ is NH, the hydrogen of the NH may be replaced by $R_{4d}$; and $G_2$ is N. In some further embodiments, $G_1$ is O or S, e.g. $G_1$ is O, and $G_2$ is CH or $GR_{4d}$.

In some further embodiments, when ring B is 5-membered heteroaryl, it more particularly is

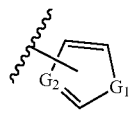

wherein $G_1$ and $G_2$ are as defined herein above.

In some further embodiments, when ring B is 5-membered heteroaryl, it more particularly is

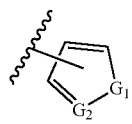

wherein $G_1$ and $G_2$ are as defined herein above.

In some particular embodiments of a compound of formula (I), ring B is 5- or 6-membered heteroaryl as defined herein above, and $R_1$ is C1-C6 alkyl or C3-C6 cycloalkyl, in particular C1-C3 alkyl or C3 cycloalkyl, e.g. $R_1$ is C1-C6 alkyl, or $R_1$ is C1-C3 alkyl.

In some other particular embodiments, ring B is 5- or 6-membered heteroaryl as defined herein above, $R_1$ is C1-C6 alkyl or C3-C6 cycloalkyl, in particular C1-C3 alkyl or C3 cycloalkyl, e.g. $R_1$ is C1-C6 alkyl, or $R_1$ is C1-C3 alkyl; and n is 1.

In some other particular embodiments, ring B is 6-membered heteroaryl as defined herein above, $R_1$ is C1-C6 alkyl or C3-C6 cycloalkyl, in particular C1-C3 alkyl or C3 cycloalkyl, e.g. $R_1$ is C1-C6 alkyl, or $R_1$ is C1-C3 alkyl; and n is 1. In some of these embodiments, L is a direct bond. In some other of these embodiments, L is methylene or C(O), e.g. L is methylene.

In some other particular embodiments, ring B is 5-membered heteroaryl as defined herein above, $R_1$ is C1-C6 alkyl or C3-C6 cycloalkyl, in particular C1-C3 alkyl or C3 cycloalkyl, e.g. $R_1$ is C1-C6 alkyl, or $R_1$ is C1-C3 alkyl; and n is 1.

In some other particular embodiments, ring B is 5-membered heteroaryl as defined herein above, $R_1$ is C1-C6 alkyl or C3-C6 cycloalkyl, in particular C1-C3 alkyl or C3 cycloalkyl, e.g. $R_1$ is C1-C6 alkyl, or $R_1$ is C1-C3 alkyl; n is 1; and L is C1-C4 alkylene or $L_1$-$L_2$, e.g. L is C1-C4 alkylene or $L_1$-$L_2$, $L_1$ is C1-C4 alkylene, and $L_2$ is C(O) or NH, in particular NH.

In some other particular embodiments, ring B is 5-membered heteroaryl as defined herein above, $R_1$ is C1-C6 alkyl or C3-C6 cycloalkyl, in particular C1-C3 alkyl or C3 cycloalkyl, e.g. $R_1$ is C1-C6 alkyl, or $R_1$ is C1-C3 alkyl; n is 1; and L is methylene.

In some embodiments of a compound of formula (I), $R_4$ is methyl, ethyl, 2-hydroxyethyl, 2-methoxyethyl, 2-ethoxyethyl, 2-isopropoxyethyl, 3-hydroxypropyl, 3-methoxypropyl, 2-(2-methoxyethoxy)ethyl, 4-methoxybutyl, 2-methoxyacetyl, 3-methoxypropanoyl, acetyl, pivaloyl, methylsulfonyl, cyanoethyl, 3-pyridinyl, 4-pyridinyl, pyrazin-2-yl, pyrazin-2-yl, benzyl, pyridin-2-ylmethyl, pyridin-3-ylmethyl pyridin-4-ylmethyl, (6-methylpyridin-2-yl)methyl, (6-methylpyridin-3-yl)methyl, (5-methylpyridin-2-yl)methyl, pyrimidin-5-ylmethyl, pyrazin-2-ylmethyl, furan-2-ylmethyl, (5-methylfuran-2-yl)methyl, furan-3-ylmethyl, 1,3-thiazol-2-ylmethyl, 1,3-thiazol-4-ylmethyl, 1,3-thiazol-5-ylmethyl, (3,5-dimethylisoxazol-4-yl)methyl, (1-methyl-1H-imidazol-2-yl)methyl, (1H-imidazol-4-yl)methyl, or 2-((1-methyl-1H-pyrazol-5-yl)amino)ethyl, pyridin-4-ylcarbonyl, pyridin-3-ylcarbonyl.

In the moiety —N($R_5$)C(O)—, $R_5$ is H, C1-C6 alkyl, $R_{5a}[O(CH_2)_u]_v$, or a moiety of formula (IV)

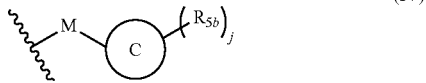

(IV)

wherein M, ring C, $R_{5b}$ and j are as defined herein.

In some embodiments, $R_5$ is H, C1-C6 alkyl, or $R_{5a}[O(CH_2)_u]_v$, e.g. $R_5$ is C1-C6 alkyl or $R_{5a}[O(CH_2)_u]_v$. In some embodiments, $R_5$ is H, $R_{5a}[O(CH_2)_u]_v$, or a moiety of formula (IV), e.g. $R_5$ is $R_{5a}[O(CH_2)_u]_v$ or a moiety of formula (IV). In some embodiments, $R_5$ is C1-C6 alkyl, $R_{5a}[O(CH_2)_u]_v$, or a moiety of formula (IV). In some embodiments, $R_5$ is H or C1-C6 alkyl. In some embodiments, $R_5$ is H or $R_{5a}[O(CH_2)_u]_v$, e.g. $R_5$ is $R_{5a}[O(CH_2)_u]_v$. In still further embodiments, $R_5$ is H.

When $R_5$ is C1-C6 alkyl, said alkyl in particular may be C1-C5 alkyl, or C1-C4 alkyl, or C1-C3 alkyl, or C1-C2 alkyl, e.g. methyl.

In some embodiments, $R_5$ is H or C1-C5 alkyl, e.g. $R_5$ is H or C1-C4 alkyl, or $R_5$ is H or C1-C3 alkyl, or $R_5$ is H or C1-C2 alkyl, or $R_5$ is H or methyl, or $R_5$ is H.

In the moiety $R_{5a}[O(CH_2)_u]_v$, $R_{5a}$ is H or C1-C6 alkyl, each u is independently selected from 1, 2, 3 and 4; and v is 1 or 2. In some embodiments, each u is 2 or 3, and v is 1 or 2. In some embodiments, each u is 2, i.e. the moiety has the formula $R_{5a}[O(CH_2)_2]_v$, wherein v is 1 or 2.

In some of the embodiments wherein u is 2, v is 1, i.e. the moiety $R_{5a}[O(CH_2)_u]_v$ has the formula $R_{5a}O(CH_2)_2$. In some other of the embodiments wherein u is 2, v is 2, i.e. the moiety $R_{5a}[O(CH_2)_u]_v$ has the formula $R_{5a}[O(CH_2)_2]_2$, i.e. $R_{5a}O(CH_2)_2O(CH_2)_2$.

In some embodiments, each u is 3, i.e. the moiety $R_{5a}[O(CH_2)_u]_v$ is one having the formula $R_{5a}[O(CH_2)_3]_v$, where v is 1 or 2. In some of the embodiments wherein u is 3, v is 1, i.e. the moiety $R_{5a}[O(CH_2)_u]_v$ has the formula $R_{5a}O(CH_2)_3$. In some other of the embodiments wherein u is 3, v is 2, i.e. the moiety $R_{5a}[O(CH_2)_u]_v$ has the formula $R_{5a}[O(CH_2)_3]_2$, i.e. $R_{5a}O(CH_2)_3O(CH_2)_3$.

In some embodiments, v is 1, i.e. the moiety is one having the formula $R_{5a}O(CH_2)_u$, wherein u is 1, 2, 3 or 4, e.g. u is 2, 3 or 4, in particular u is 2 or 3.

The moiety $R_{5a}$ is H or C1-C6 alkyl. In some embodiments, $R_{5a}$ is H or C1-C5 alkyl; e.g. $R_{5a}$ is H or C1-C4 alkyl; or $R_{5a}$ is H or C1-C3 alkyl; or $R_{5a}$ is H or C1-C2 alkyl; or $R_{5a}$ is H or methyl. In some further embodiments, $R_{5a}$ is C1-C6 alkyl, or $R_{5a}$ is C1-C5 alkyl; e.g. $R_{5a}$ is C1-C4 alkyl; or $R_{5a}$ is C1-C3 alkyl; or $R_{5a}$ is C1-C2 alkyl; or $R_{5a}$ is methyl. In some embodiments, $R_{5a}$ is H, methyl, ethyl, or isopropyl. In some embodiments, $R_{5a}$ is methyl, ethyl, or isopropyl. In some embodiments, $R_{5a}$ is methyl. In some embodiments, $R_{5a}$ is ethyl. In some embodiments, $R_{5a}$ is isopropyl.

In some particular embodiments, when $R_5$ is $R_{5a}[O(CH_2)_u]_v$, u is 2 or 3, v is 1, and $R_{5a}$ is H, methyl, ethyl, propyl, or isopropyl, in particular methyl, ethyl, propyl or isopropyl, more particularly methyl, ethyl, or isopropyl.

In some embodiments, $R_5$ is a moiety of formula (IV)

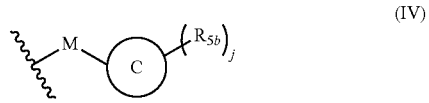

(IV)

wherein M, ring C, $R_{5b}$ and j are as defined herein.

In a moiety of formula (IV), M is a direct bond or C1-C4 alkylene; ring C is selected from phenyl and 5- or 6-membered heteroaryl, e.g. ring C is phenyl; $R_{5b}$ is C1-C6 alkyl, e.g. $R_{5b}$ is C1-C3 alkyl, or $R_{5b}$ is methyl; and j is an integer of from 0 to 3, e.g. j is 0, 1 or 2, or j is 0 or 1, or j is 0. In some embodiments, the moiety of formula (IV) is benzyl.

It should be realized that compounds of the invention may at the same time belong to more than one of the different embodiments referred to herein above and may thus at the same time be represented by more than one of the above formulas, unless otherwise indicated or apparent from the context, or unless the embodiments or formulas are mutually exclusive. Thus, in some embodiments, a compound of formula (Ia) also is a compound of formula (Ic), i.e. a compound as represented by formula (Ih)

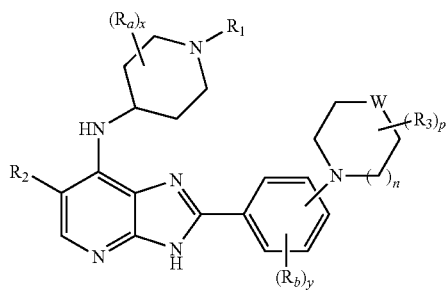

(Ih)

wherein $R_1$, $R_2$, each $R_3$, each $R_a$, each $R_b$, W, n, p, x, and y are as defined herein.

Likewise, in some embodiments, a compound of formula (Ia) also is a compound of formula (Id), i.e. a compound as represented by formula (Ij)

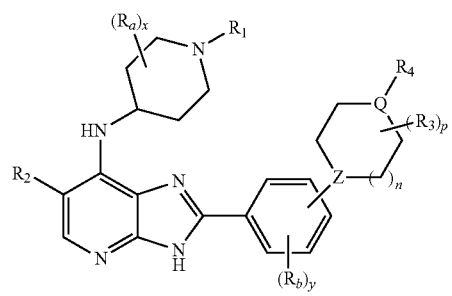

(Ij)

wherein $R_1$, $R_2$, each $R_3$, $R_4$, each $R_a$, each $R_b$, Q, Z, n, p, x, and y are as defined herein.

In still further embodiments, a compound of formula (Ij) also is a compound of formula (Ic), i.e. a compound as represented by formula (Ik)

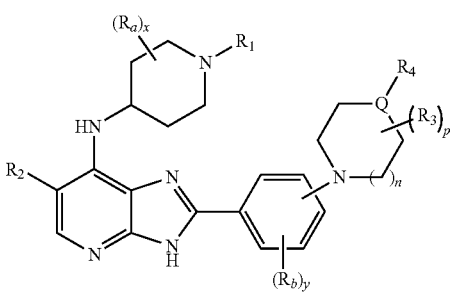

(Ik)

wherein $R_1$, $R_2$, each $R_3$, $R_4$, each $R_a$, each $R_b$, Q, n, p, x, and y are as defined herein.

In further embodiments, a compound of formula (Ia) also is a compound of formula (If), i.e. a compound as represented by formula (Im)

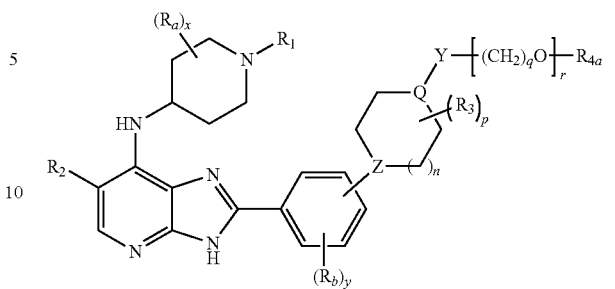

(Im)

wherein $R_1$, $R_2$, each $R_3$, $R_{4a}$, each $R_a$, each $R_b$, Q, Y, Z, n, p q, r, z and y are as defined herein.

In further embodiments, a compound of formula (Im) also is a compound of formula (Ic), i.e. a compound as represented by formula (In)

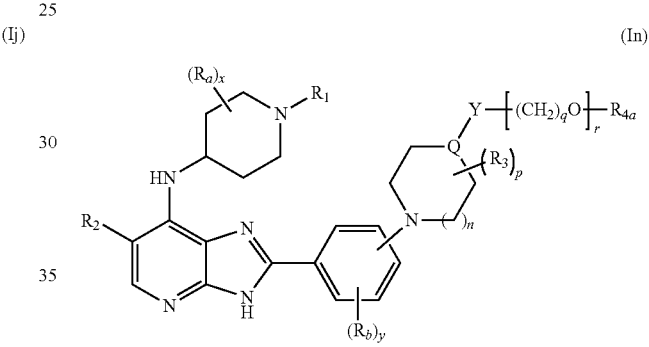

(In)

wherein $R_1$, $R_2$, each $R_3$, $R_{4a}$, each $R_a$, each $R_b$, Q, Y, n, p q, r, z and y are as defined herein.

In some embodiments of a compound of formula (In), Q is N, i.e. the compound is as represented by formula (In1)

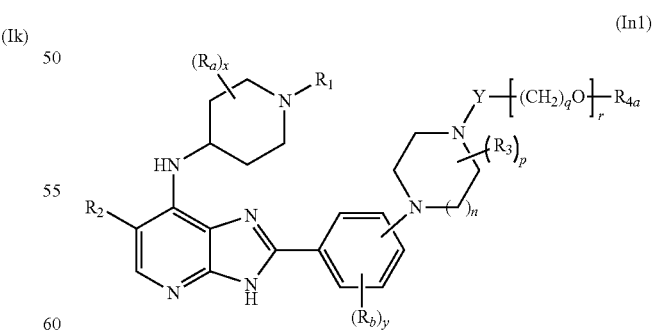

(In1)

wherein $R_1$, $R_2$, each $R_3$, $R_{4a}$, each $R_a$, each $R_b$, Y, n, p q, r, z and y are as defined herein.

In some further embodiments, a compound of formula (Ic) also is a compound of formula (Id), i.e. a compound as represented by formula (Io)

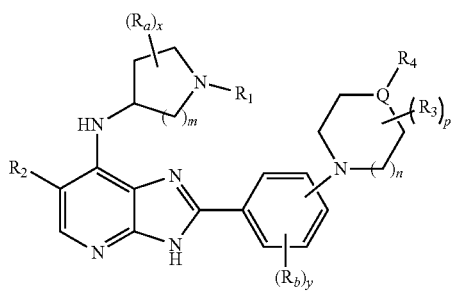

(Io)

wherein $R_1$, $R_2$, each $R_3$, $R_4$, each $R_a$, each $R_b$, Q, m, n, p, x and y are as defined herein.

In still further embodiments, a compound of formula (Io) also is a compound of formula (If), i.e. a compound as represented by formula (Ip)

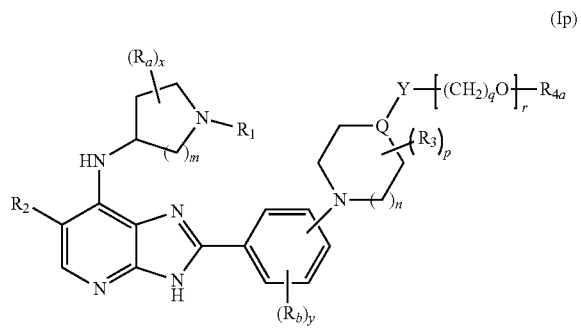

(Ip)

wherein $R_1$, $R_2$, each $R_3$, $R_{4a}$, each $R_a$, each $R_b$, Q, m, n, p, q, r, x and y are as defined herein.

In some embodiments of a compound of formula (If), (Im), (In), or (Ip), x is 0 and y is 0 or 1; or both x and y are 0.

In some further embodiments of a compound of formula (If), (Im), (In), or (Ip), x is 0 and y is 0 or 1, or both x and y are 0; and $R_1$ is C1-C6 alkyl, C3-C6 cycloalkyl, C3-C6 cycloalkyl-C1-C6 alkyl, C1-C6 alkyl-C3-C6 cycloalkyl, C1-C6 alkoxy-C1-C6 alkyl, or cyano-C1-C6 alkyl; in particular $R_1$ is C1-C6 alkyl, C3-C6 cycloalkyl, C3-C6 cycloalkyl-C1-C6 alkyl, C1-C6 alkoxy-C1-C6 alkyl, or cyano-C1-C6 alkyl; or $R_1$ is C1-C6 alkyl, C3-C6 cycloalkyl, C3-C6 cycloalkyl-C1-C6 alkyl; e.g. $R_1$ is C1-C6 alkyl.

In some further embodiments of a compound of formula (If), (Im), (In), or (Ip), x is 0; y is 0 or 1; and $R_1$ is C1-C6 alkyl, C3-C6 cycloalkyl, C3-C6 cycloalkyl-C1-C6 alkyl, C1-C6 alkyl-C3-C6 cycloalkyl, C1-C6 alkoxy-C1-C6 alkyl, or cyano-C1-C6 alkyl; in particular $R_1$ is C1-C6 alkyl, C3-C6 cycloalkyl, C3-C6 cycloalkyl-C1-C6 alkyl, C1-C6 alkoxy-C1-C6 alkyl, or cyano-C1-C6 alkyl; or $R_1$ is C1-C6 alkyl, C3-C6 cycloalkyl, C3-C6 cycloalkyl-C1-C6 alkyl; e.g. $R_1$ is C1-C6 alkyl.

In some embodiments, the compound of formula (I) more particularly is as represented by formula (If), or by formula (Im) or by formula (In), or by formula (Ip), wherein $R_1$ is C1-C6 alkyl, C3-C6 cycloalkyl, C3-C6 cycloalkyl-C1-C6 alkyl, C1-C6 alkyl-C3-C6 cycloalkyl, C1-C6 alkoxy-C1-C6 alkyl, cyano-C1-C6 alkyl; e.g. $R_1$ is C1-C6 alkyl, C3-C6 cycloalkyl, or C3-C6 cycloalkyl-C1-C6 alkyl; or $R_1$ is C1-C6 alkyl or C3-C6 cycloalkyl, in particular $R_1$ C1-C6 alkyl;

p is an integer of from 0 to 3; e.g. p is 0-2, or p is 0 or 1; in particular p is 0;

when p is not 0, each $R_3$ is independently selected from C1-C6 alkyl; e.g. each is methyl;

n is 1 or 2, e.g. n is 1;

each q is independently selected from 2 and 3, e.g. each q is 2, or each q is 3;

r is 1 or 2, e.g. r is 1; and $R_{4a}$ is H or C1-C6 alkyl, e.g. $R_{4a}$ is H or C1-C3 alkyl, in particular $R_{4a}$ is H, methyl, ethyl, or ispropyl.

In some embodiments, the compound of formula (I) more particularly is as represented by formula (If), or by formula (Im) or by formula (In), or by formula (Ip), wherein q is 2, 3 or 4, e.g. q is 2 or 3, in particular q is 3;

r is 1; and $R_{4a}$ is H or C1-C6 alkyl, e.g. $R_{4a}$ is H or C1-C3 alkyl, in particular $R_{4a}$ is H, methyl, ethyl, or ispropyl.

In some embodiments of a compound of formula (If), (Im), (In), or (Ip), Y is a direct bond. In some further embodiments of a compound of formula (If), (Im), (In), or (Ip), Y is C(O).

For example, in some embodiments, the compound of formula (I) more particularly is as represented by formula (If), or by formula (Im) or by formula (In), or by formula (Ip), wherein q is 2, 3 or 4, e.g. q is 2 or 3, in particular q is 3; r is 1; Y is a direct bond; and $R_{4a}$ is H or C1-C6 alkyl, e.g. $R_{4a}$ is H or C1-C3 alkyl, in particular $R_{4a}$ is H, methyl, ethyl, or ispropyl.

In some embodiments of a compound of formula (If), (Im), (In), or (Ip), $R_1$ is C1-C3 alkyl or C3 cycloalkyl, in particular C1-C3 alkyl; p is 0 or 1, in particular p is 0; $R_3$ is C1-C3 alkyl, e.g. methyl; n is 1 or 2, e.g. n is 1; each q is independently selected from 2 and 3; e.g. each q is 2; r is 1 or 2, e.g. r is 1; and $R_{4a}$ is H or C1-C3 alkyl, in particular $R_{4a}$ is H, methyl, ethyl, or ispropyl.

In some embodiments of a compound of formula (If), (Im), (In), or (Ip), $R_1$ is C1-C3 alkyl; n is 1; p is 0; q is 2; r is 1; and $R_{4a}$ is H or C1-C3 alkyl, in particular $R_{4a}$ is H, methyl, ethyl, or ispropyl.

In some embodiments of a compound of formula (If), (Im), (In), or (Ip), $R_1$ is methyl or ethyl; n is 1; p is 0; q is 2; r is 1; and $R_{4a}$ is H or C1-C3 alkyl, in particular $R_{4a}$ is H, methyl, ethyl, or ispropyl.

In some embodiments of a compound of formula (If), (Im), (In), or (Ip), $R_1$ is as defined herein; p is 0 or 1, in particular p is 0; $R_3$ is C1-C3 alkyl, e.g. methyl; n is 1 or 2, e.g. n is 1; each q is 2; r is 2; and $R_{4a}$ is H or C1-C3 alkyl, in particular $R_{4a}$ is H, methyl, ethyl, or ispropyl.

In some embodiments of a compound of formula (If), (Im), (In), or (Ip), $R_1$ is as defined herein, e.g. $R_1$ is C1-C6 alkyl, or C1-C3 alkyl; p is 0 or 1, in particular p is 0; $R_3$ is C1-C3 alkyl, e.g. methyl; n is 1 or 2, e.g. n is 1; q is 3; r is 1; and $R_{4a}$ is H or C1-C3 alkyl, in particular $R_{4a}$ is H, methyl, ethyl, or ispropyl.

In some embodiments of a compound of formula (If), (Im), (In), or (Ip), $R_1$ is C1-C6 alkyl, e.g. C1-C3 alkyl; p is 0 or 1, in particular p is 0; $R_3$ is C1-C3 alkyl, e.g. methyl; n is 1; q is 3; r is 1; and $R_{4a}$ is H or C1-C3 alkyl, in particular $R_{4a}$ is H, methyl, ethyl, or ispropyl.

In some embodiments of a compound of formula (If), (Im), (In), or (Ip), $R_1$ is C1-C3 alkyl; $R_2$ is Br; $R_3$ is C1-C3 alkyl, more preferably $R_3$ is methyl; Y is a direct bond; and p is 0 or 1, preferably p is 0.

In some embodiments of a compound of formula (If), (Im), (In), or (Ip), m is 2; $R_1$ is C1-C3 alkyl; $R_2$ is Br; $R_3$ is C1-C3 alkyl, preferably $R_3$ is methyl; Y is a direct bond; n is 1; p is 0 or 1; q is 2; and r is 1.

In some embodiments of a compound of formula (If), (Im), (In), or (Ip), m is 2; $R_1$ is C1-C3 alkyl; $R_2$ is Br; $R_3$ is C1-C3 alkyl, preferably $R_3$ is methyl; Y is a direct bond; n is 1; p is 0 or 1; preferably p is 0; q is 3; and r is 1.

In some embodiments of a compound of formula (If), (Im), (In), or (Ip), $R_1$ is C1-C6 alkyl, preferably $R_1$ is C1-C3 alkyl; $R_2$ is Cl or Br, preferably $R_2$ is Br; $R_3$ is C1-C3 alkyl, preferably $R_3$ is methyl; Y is a direct bond; n is 1 or 2, preferably n is 1; p is 0 or 1, preferably p is 0; each q is independently selected from 2 and 3, preferably each q is 2; and r is 1 or 2, preferably r is 1.

In some embodiments of a compound of formula (If), (Im), (In), or (Ip), $R_1$ is C1-C6 alkyl, preferably $R_1$ is C1-C3 alkyl; $R_2$ is Cl or Br, preferably $R_2$ is Br; Y is a direct bond; n is 1 or 2, preferably n is 1; p is 0; q is 3; and r is 1.

In some embodiments of a compound of formula (If), (Im), (In), or (Ip), $R_1$ is C1-C3 alkyl; $R_3$ is methyl; $R_{4a}$ is H or C1-C3 alkyl, in particular $R_{4a}$ is H, methyl, ethyl, or ispropyl; Y is a direct bond; n is 1; p is 0 or 1; q is 2; and r is 1.

In some embodiments of a compound of formula (If), (Im), (In), or (Ip), $R_1$ is C1-C3 alkyl; $R_{4a}$ is H or C1-C3 alkyl, in particular $R_{4a}$ is H, methyl, ethyl, or ispropyl; Y is a direct bond; n is 1; p is 0; q is 3; and r is 1.

In some embodiments, the compound is as represented by formula (Iq),

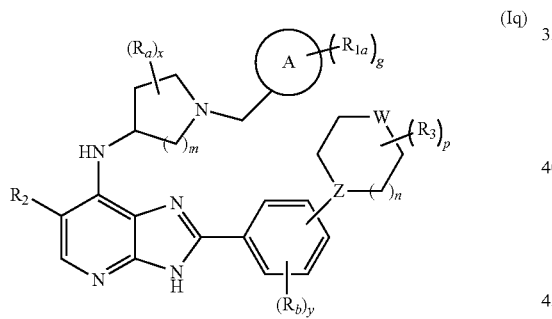

(Iq)

wherein ring A, each $R_{1a}$, $R_2$, each $R_3$, each $R_a$, each $R_b$, Z, W, g, m, n, p, x and y are as defined herein.

In some embodiments of a compound of formula (Iq), when W is >Q-$R_4$, e.g. W is >N—$R_4$, $R_4$ is C1-C6 alkyl, $R_{4a}[O(CH_2)_q]_r$—Y, $R_{4b}S(O)_2$, or $R_{4c}C(O)$. For example, in some embodiments of a compound of formula (Iq), W is >Q-$R_4$, or W is —N($R_5$)C(O)—, e.g. W is >N—$R_4$ or —N($R_5$)C(O)—, and when W is >Q-$R_4$ or >N—$R_4$, $R_4$ is C1-C6 alkyl, $R_{4a}[O(CH_2)_q]_r$—Y, $R_{4b}S(O)_2$, or $R_{4c}C(O)$.

In some embodiments of a compound of formula (Iq), W is >Q-$R_4$, and $R_4$ is C1-C6 alkyl, $R_{4a}[O(CH_2)_q]_r$—Y, $R_{4b}S(O)_2$, or $R_{4c}C(O)$. In some embodiments, W is >N—$R_4$, and $R_4$ is C1-C6 alkyl, $R_{4a}[O(CH_2)_q]_r$—Y, $R_{4b}S(O)_2$, or $R_{4c}C(O)$.

In some further embodiments of a compound of formula (Iq), the compound also is a compound as represented by formula (If), or by formula (Im) or by formula (In), or by formula (Ip).

In some embodiments, the compound is as represented by formula (Ir),

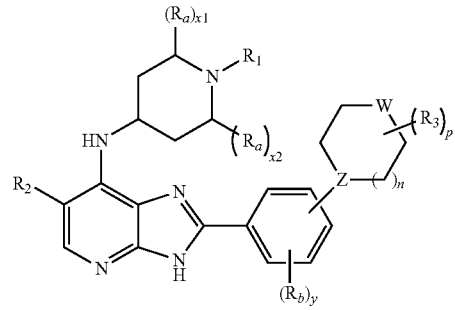

(Ir)

wherein $R_1$, $R_2$, each $R_3$, each $R_a$, each $R_b$, Z, W, n, p, and y are as defined herein, each one of x1 and x2 is an integer independently selected from 0, 1 and 2, x1 and x2 together indicating the total number of moieties $R_a$. In some embodiments, both x1 and x2 are 0. In some further embodiments, x1 and x2 are independently selected from 1 and 2, e.g. both are 2. In some embodiments, x1 and x2 are both 0, or x1 and x2 are both 2; e.g. x1 and x2 are both 0, or x1 and x2 are both 2 and each $R_a$ is methyl. In some embodiments, when either one or both of x1 and x2 are different from 0, $R_1$ is C1-C6 alkyl or C3-C6 cycloalkyl-C1-C6 alkyl, e.g. $R_1$ is C1-C6 alkyl, such as C1-C3 alkyl.

In some embodiments of a compound of formula (Ir), x is an integer of from 0 to 4, e.g. x is 0 or 4, and y is 0 or 1, e.g. y is 0.

In some embodiments, each $R_a$ is methyl and both x1 and x2 are 2, i.e. the compound is as represented by formula (Ir1)

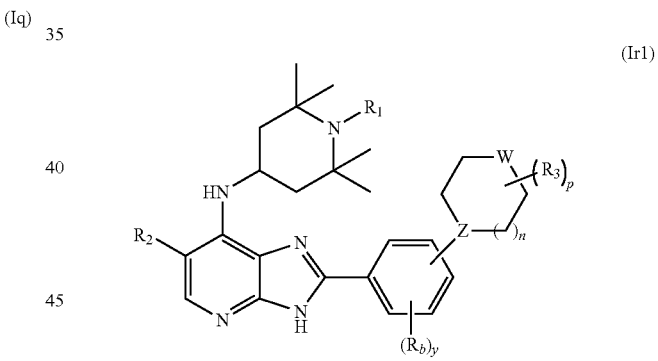

(Ir1)

wherein $R_1$, $R_2$, each $R_3$, each $R_b$, Z, W, n, p, and y are as defined herein.

In some embodiments, a compound of formula (Ir) is also a compound of any one of the formulas (Ic), (Id), (Id1), (Id2), (Ie), (If), (If), (Ig), (Ig1), (Io), or (Ip).

In some further embodiments of a compound of formula (I), m is 1 or 2, preferably m is 2;
$R_1$ is C1-C6 alkyl, or a moiety of formula (II)

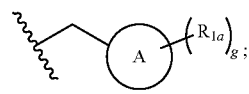

(II)

ring A is phenyl or 5- or 6-membered heteroaryl;
g is an integer of from 0 to 3;

each $R_{1a}$ is independently selected from C1-C3 alkyl, $R_{1b}O$, and $R_{1c}R_{1d}N$;
each $R_{1b}$ is independently selected from H, C1-C3 alkyl;
each $R_{1c}$ is independently selected from H and C1-C3 alkyl;
each $R_{1d}$ is independently selected from H and C1-C3 alkyl;
or two $R_{1a}$, attached to adjacent atoms of ring A, together with the atoms to which they are attached, form a 5- or 6-membered ring optionally containing one or more heteroatoms;
$R_2$ is Cl or Br;
p is 0 or 1;
$R_3$ is C1-C3 alkyl;
Z is N or CH; preferably Z is N;
W is >N—$R_4$, —O—, or —N($R_5$)C(O)—; preferably W is >N—$R_4$, or —N($R_5$)C(O)—;
n is 1 or 2 when W is >N—$R_4$ or —O—;
n is 0 or 1 when W is —N($R_5$)C(O)—;
$R_4$ is C1-C6 alkyl, $R_{4a}[O(CH_2)_q]_r$—Y, $R_{4b}S(O)_2$, $R_{4c}C(O)$ or a moiety of formula (III)

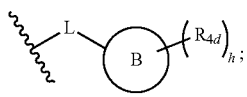

(III)

each q is independently selected from 2 and 3;
r is 1 or 2;
h is an integer of from 0 to 3;
L is a direct bond or methylene;
Y is a direct bond or C(O), preferably Y is a direct bond;
$R_{4a}$ is H or C1-C3 alkyl;
$R_{4b}$ is C1-C3 alkyl;
$R_{4c}$ is C1-C3 alkyl;
$R_{4d}$ is C1-C3 alkyl;
$R_5$ is H or C1-C3 alkyl; and
ring B is selected from phenyl and 5- or 6-membered heteroaryl, preferably ring B is 5- or 6-membered heteroaryl.

In still further embodiments of a compound of formula (I),
m is 1 or 2;
$R_1$ is C1-C3 alkyl;
$R_2$ is Cl or Br;
p is 0 or 1;
$R_3$ is C1-C3 alkyl;
Z is N or CH; preferably Z is N;
W is >N—$R_4$, —O— or —N($R_5$)C(O)—, preferably W is >N—$R_4$, or —N($R_5$)C(O)—;
n is 1 or 2 when W is >N—$R_4$ or —O—;
n is 0 or 1 when W is —N($R_5$)C(O)—;
$R_4$ is C1-C6 alkyl, $R_{4a}[O(CH_2)_q]_r$—Y, $R_{4b}S(O)_2$, $R_{4c}C(O)$ or a moiety of formula (III)

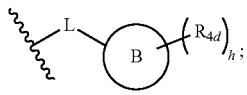

(III)

each q is independently selected from 2 and 3;
r is 1 or 2;
h is an integer of from 0 to 3;
L is a direct bond or methylene;
Y is a direct bond or C(O), preferably Y is a direct bond;

$R_{4a}$ is H or C1-C3 alkyl;
$R_{4b}$ is C1-C3 alkyl;
$R_{4c}$ is C1-C3 alkyl;
$R_{4d}$ is C1-C3 alkyl;
$R_5$ is H or C1-C3 alkyl; and
ring B is selected from phenyl and 5- or 6-membered heteroaryl, preferably ring B is 5- or 6-membered heteroaryl.

In still further embodiments of a compound of formula (I),
m is 1 or 2, preferably m is 2;
$R_1$ is C1-C3 alkyl;
$R_2$ is Cl or Br;
p is 0 or 1;
$R_3$ is C1-C3 alkyl;
Z is N or CH; preferably Z is N;
W is >N—$R_4$, or —N($R_5$)C(O)—;
n is 1 or 2 when W is >N—$R_4$;
n is 0 or 1 when W is —N($R_5$)C(O)—;
$R_4$ is C1-C6 alkyl, $R_{4a}[O(CH_2)_q]_r$—Y, $R_{4b}S(O)_2$, $R_{4c}C(O)$ or a moiety of formula (III)

(III)

each q is independently selected from 2 and 3;
r is 1 or 2;
L is a direct bond or methylene;
h is an integer of from 0 to 3;
Y is a direct bond or C(O), preferably Y is a direct bond;
$R_{4a}$ is H or C1-C3 alkyl;
$R_{4b}$ is C1-C3 alkyl;
$R_{4c}$ is C1-C3 alkyl;
$R_{4d}$ is C1-C3 alkyl;
$R_5$ is H or C1-C3 alkyl; and
ring B is selected from phenyl and 5- or 6-membered heteroaryl, preferably ring B is 5- or 6-membered heteroaryl.

In some of the above embodiments, x is 0, and y is 0 or 1. In some other of the above embodiments, x and y are both 0.

In some further embodiments of a compound of formula (I),
x is 0;
m is 1 or 2;
$R_1$ is C1-C6 alkyl, C3-C6 cycloalkyl, or a moiety of formula (II)

(II)

ring A is phenyl or 5- or 6-membered heteroaryl;
g is an integer of from 0 to 3;
each $R_{1a}$ is independently selected from C1-C6 alkyl, $R_{1b}O$, and $R_{1c}R_{1d}N$;
each $R_{1b}$ is independently selected from H and C1-C6 alkyl;
each $R_{1c}$ is independently selected from H and C1-C6 alkyl;
each $R_{1d}$ is independently selected from H and C1-C6 alkyl;

or two $R_{1a}$, attached to adjacent atoms of ring A form, together with the atoms to which they are attached, a 5- or 6-membered ring optionally containing one or more heteroatoms;

$R_2$ is Cl or Br;

p is an integer of from 0 to 3;

each $R_3$ is independently selected from C1-C6 alkyl;

y is 0;

Z is N or CH;

W is >N—$R_4$, —O— or —N($R_5$)C(O)—;

n is 1 or 2 when W is >N—$R_4$ or —O—;

n is 0 or 1 when W is —N($R_5$)C(O)—;

$R_4$ is C1-C6 alkyl, $R_{4a}[O(CH_2)_q]_r$—Y, $R_{4b}S(O)_2$, $R_{4c}C(O)$, or a moiety of formula (III)

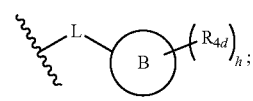
(III)

each q is independently selected from 2 and 3;

r is 1 or 2;

h is an integer of from 0 to 3;

Y is a direct bond or C(O);

L is a direct bond or methylene;

$R_{4a}$ is H or C1-C6 alkyl;

$R_{4b}$ is C1-C6 alkyl;

$R_{4c}$ is C1-C6 alkyl;

$R_{4d}$ is C1-C6 alkyl;

ring B is selected from phenyl and 5- or 6-membered heteroaryl;

$R_5$ is H, C1-C6 alkyl, or $R_{5a}[O(CH_2)_u]_v$;

$R_{5a}$ is H or C1-C6 alkyl;

u is 2 or 3; and v is 1 or 2.

As noted herein above, in some embodiments, x is 0. In such embodiments, the compound may be represented by formula (Is)

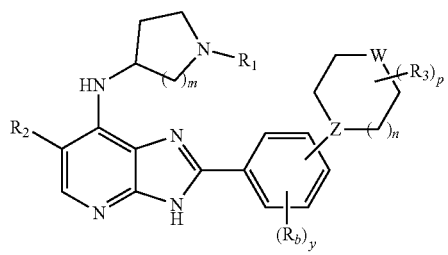
(Is)

wherein $R_1$, $R_2$, each $R_3$, each $R_b$, Z, W, m, n, p, and y are as defined herein.

In some embodiments of a compound of formula (I), e.g. of formula (Ir), (Ir1) or (Is), y is 0 or 1, e.g. y is 0. Thus, for example, in some embodiments, the compound may be represented by formula (Is1)

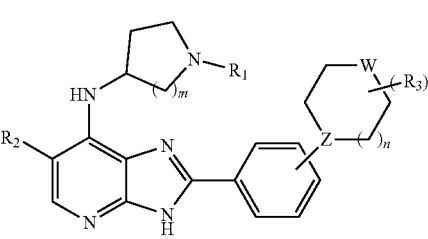
(Is1)

wherein $R_1$, $R_2$, each $R_3$, each $R_b$, Z, W, m, n, and p are as defined herein.

In some further embodiments, the compound is as represented by formula (It)

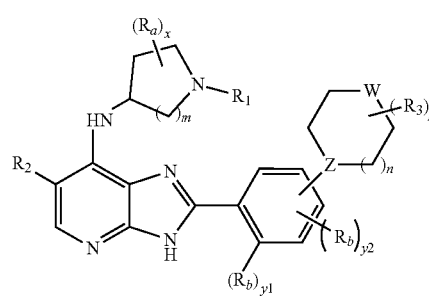
(It)

wherein $R_1$, $R_2$, each $R_3$, each $R_a$, each $R_b$, Z, W, m, n, p, and x are as defined herein, y1 is 0 or 1, and y2 is 0, 1, or 2; e.g. y2 is 0 or 1, or y2 is 0.

In some embodiments of a compound of formula (It), y2 is 0, i.e. the compound is as represented by formula (It1)

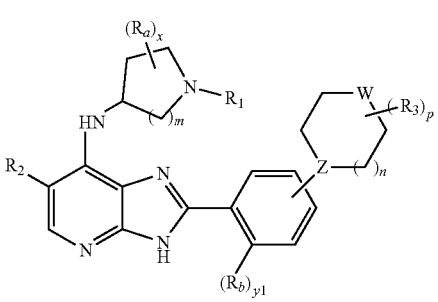
(It1)

wherein $R_1$, $R_2$, each $R_3$, each $R_a$, $R_b$, Z, W, m, n, p, x, and y1 are as defined herein. In some embodiments of a compound of formula (It1), y1 is 1.

In some embodiments, a compound of formula (It) is also a compound of formula (Ir), i.e. a compound as represented by formula (Iu)

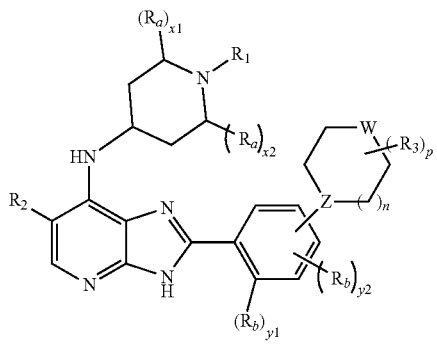

(Iu)

wherein R₁, R₂, each R₃, each Rₐ, each R_b, Z, W, n, p, x1, x2, y1 and y2 are as defined herein.

In some embodiments of a compound of formula (Iu), either both of y1 and y2 are 0, or one of y1 and y2 is 0, e.g. y2 is 0. In some further embodiments of a compound of formula (Iu), x1 and x2 are both 0, y1 is 0 or 1, and y2 is 0. In still further embodiments of a compound of formula (Iu), x1 and x2 are both 0 or both are 2.

In some further embodiments, the compound is as represented by formula (Iv)

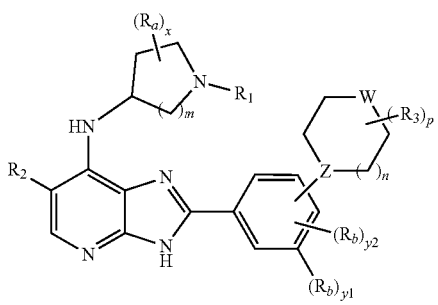

(Iv)

wherein R₁, R₂, each R₃, each Rₐ, each R_b, Z, W, m, n, p, and x are as defined herein, y1 is 0 or 1, and y2 is 0, 1, or 2; e.g. y2 is 0 or 1, or y2 is 0.

In some embodiments of a compound of formula (Iv), y2 is 0, i.e. the compound is as represented by formula (Iv1)

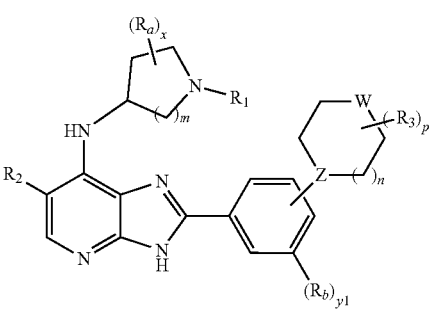

(Iv1)

wherein R₁, R₂, each R₃, each Rₐ, R_b, Z, W, m, n, p, x, and y1 are as defined herein. In some embodiments of a compound of formula (Iv1), y1 is 1.

In some embodiments, a compound of formula (Iv) is also a compound of formula (Ir), i.e. a compound as represented by formula (Ix)

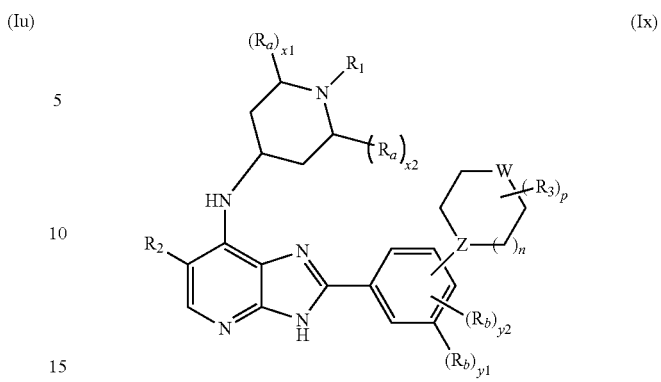

(Ix)

wherein R₁, R₂, each R₃, each Rₐ, each R_b, Z, W, n, p, x1, x2, y1 and y2 are as defined herein.

In some embodiments of a compound of formula (Ix), either both of y1 and y2 are 0, or one of y1 and y2 is 0, e.g. y2 is 0. In some further embodiments of a compound of formula (Ix), x1 and x2 are both 0, y1 is 0 or 1, and y2 is 0. In still further embodiments of a compound of formula (Iv), x1 and x2 are both 0, or both x1 and x2 are 2.

In some further embodiments of a compound formula (I), e.g. in some embodiments of a compound of formula (Ia), (Ib), (Ic), (Ih), (Iq), (Ir), (Ir1), (Is), (Is1), (It), (It1), (Iu), (Iv), (Iv1), or (Ix), W is >Q-R₄, or —N(R₅)C(O)—; R₄ is R_{4a}[O(CH₂)_q]_r—; and R₅ is R_{5a}[O(CH₂)_u]_v—.

In some particular embodiments of a compound of formula (I),
x is an integer of from 0 to 4; e.g. x is 0;
each Rₐ is methyl;
m is 1 or 2;
R₁ is methyl, ethyl, isopropyl, n-propyl, cyclohexyl, cyclopropylmethyl, methoxyethyl, cyanomethyl, cyanoethyl, 4-methoxybenzyl, (1,3,5-trimethyl-1H-pyrazol-4-yl)methyl, thiophen-2-ylmethyl, 4-(dimethylamino)benzyl, 4-hydroxy-3-methoxybenzyl, (2,3-dihydrobenzo furan-6-yl)methyl, thiophen-3-ylmethyl;
R₂ is Cl or Br;
p is 0 or 1;
R₃ is methyl;
y is 0 or 1; e.g. y is 0;
R_b is selected from F and methoxy;
Z is N or CH;
W is >Q-R₄, —O— or —N(R₅)C(O)—;
Q is N or CH;
n is 1 or 2 when W is >N—R₄ or —O—;
n is 0 or 1 when W is —N(R₅)C(O)—;
R⁴ is methyl, ethyl, 2-hydroxyethyl, 2-methoxyethyl, 2-ethoxyethyl, 2-isopropoxyethyl, 3-hydroxypropyl, 3-methoxypropyl, 2-(2-methoxyethoxy)ethyl, 4-methoxybutyl, 2-methoxyacetyl, 3-methoxypropanoyl, acetyl, pivaloyl, methylsulfonyl, cyanoethyl, 3-pyridinyl, 4-pyridinyl, pyrazin-2-yl, pyrazin-2-yl, benzyl, pyridin-2-ylmethyl, pyridin-3-ylmethyl pyridin-4-ylmethyl, (6-methylpyridin-2-yl)methyl, (6-methylpyridin-3-yl)methyl, (5-methylpyridin-2-yl)methyl, pyrimidin-5-ylmethyl, pyrazin-2-ylmethyl, furan-2-ylmethyl, (5-methylfuran-2-yl)methyl, furan-3-ylmethyl, 1,3-thiazol-2-ylmethyl, 1,3-thiazol-4-ylmethyl, 1,3-thiazol-5-ylmethyl, (3,5-dimethylisoxazol-4-yl)methyl, 1 (1-methyl-1H-imidazol-2-yl)methyl, (1H-imidazol-4-yl)methyl, 2-((1-methyl-1H-pyrazol-5-yl)amino)ethyl, pyridin-4-ylcarbonyl, or pyridin-3-ylcarbonyl; and $R_5$ is H, methyl, 2-methoxyethyl, 3-methoxypropyl, 2-ethoxyethyl, 2-isopropoxyethyl, or benzyl.

As noted herein above, in a compound of formula (I), the ring containing Z and W may be attached to the phenyl ring in either para or meta position, corresponding to a compound of formula (I') and (I"), respectively. It should be realized that this also applies to all of the above embodiments. Thus, in some embodiments the compound according to any of the above formulas (Ia) to (Ix), the ring containing Z and W is attached to the phenyl ring in para position. In some further embodiments, the compound according to any of the above formulas (Ia) to (Ix), the ring containing Z and W is attached to the phenyl ring in meta position.

It also should be realized that any reference herein to a compound of formula (I) implicitly also refers to a compound according to any of the embodiments thereof, e.g. as illustrated in any of the above formulas (Ia) to (Ix), unless otherwise indicated or apparent from the context.

The present invention includes pharmaceutical compositions comprising at least one compound according to formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration. For enteral, e.g. oral, administration, the compounds of the invention may be formulated in a wide variety of dosage forms.

The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant. Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propylparaben, and cholorobutanol.

For inhalation or nasal administration, suitable pharmaceutical formulations are as particles, aerosols, powders, mists or droplets, e.g. with an average size of about 10 μm in diameter or less. For example, compositions for inhalation may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery. The composition may be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation. Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient.

In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration.

The preferred manner of administration is generally oral using a convenient daily dosage regimen which can be adjusted according to the degree of affliction.

The compound of formula (I), as defined herein, or a pharmaceutically acceptable salt thereof, may be used in the treatment of a condition or disorder in which the modulation of the activity of mammalian, e.g. human, tyrosine kinase ROR1 is beneficial, e.g. a malignant hyperproliferative disorder, an obesity-associated metabolic complication, an autoimmune disorder or an inflammatory condition, as well as in a method for manufacturing a medicament in the treatment of such a disorder or condition.

In some embodiments, the compound of formula (I), or the pharmaceutically acceptable salt thereof, may be used in the treatment of a malignant hyperproliferative disorder or in a method for manufacturing a medicament in the treatment of such a disorder or condition.

In some embodiments, the compound of formula (I), as defined herein, or the pharmaceutically acceptable salt thereof, may be used in the treatment of an obesity-associated metabolic complication as well as in a method for manufacturing a medicament in the treatment of such a disorder or condition.

In some embodiments, the compound of formula (I), as defined herein, or the pharmaceutically acceptable salt thereof, may be used in the treatment of an autoimmune disorder as well as in a method for manufacturing a medicament in the treatment of such a disorder or condition.

In some embodiments, the compound of formula (I), as defined herein, or the pharmaceutically acceptable salt thereof, may be used in the treatment of an inflammatory disorder as well as in a method for manufacturing a medicament in the treatment of such a disorder or condition.

The compounds of formula (I) may be prepared by the person of ordinary skill in the art, using conventional methods of chemical synthesis.

The preparation of intermediates and compounds according to the present invention may in particular be illustrated by the following Schemes 1-5.

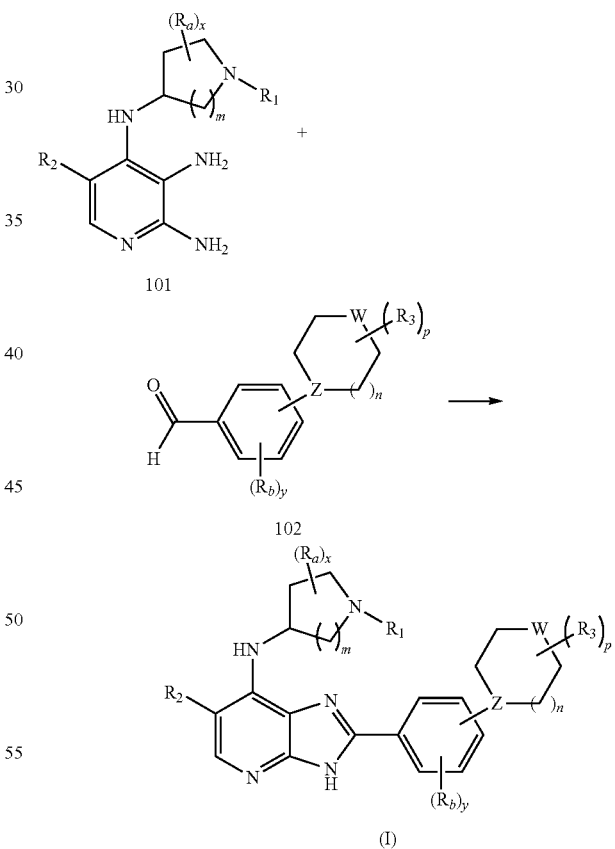

The compounds of formula (I) may for example be prepared according to the route shown in Scheme 1. Condensation of the 2,3-diaminopyridine 101 with an aldehyde 102 in the presence of an oxidant such as nitrobenzene at 150-160° C. results in the formation of imidazopyridine of formula (I) (Yadagiri, B and Lown, W J, *Synth. Communications*, 1990, 20(7), 955-963).

Alternatively, 101 and 102 can be transformed into the compound of formula (I) in the presence of air and p-toluenesulfonic acid in DMF at 80° C. (Xiangming, H, et al., *ARKIVOC*, 2007, xiii, 150-154).

Scheme 2

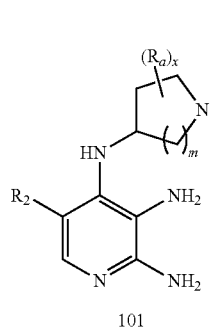

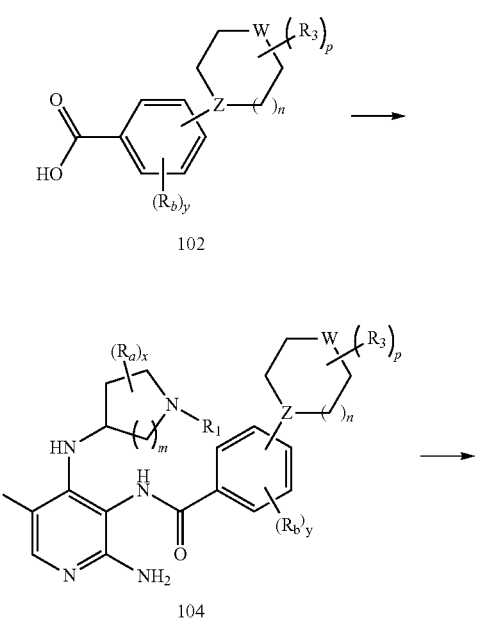

The synthesis of a compound of formula (I) can alternatively be achieved by the sequence shown in Scheme 2. Treatment of the 2,3-diaminopyridine 101 with an appropriate carboxylic acid 103 in the presence of a suitable coupling agent, such as 1-propanephosphonic acid cyclic anhydride or TBTU, gives the intermediate amide 104 which then is heated in acetic acid between 140-160° C. to yield the compound of formula (I).

Scheme 3

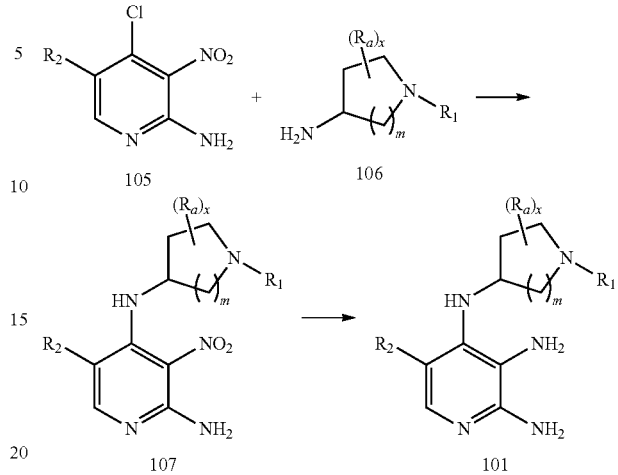

The requisite 2,3-diaminopyridines 101 can be prepared by the sequence outlined in Scheme 3. Treatment of the 4-chloro-3-nitro-2-aminopyridine 105 with an appropriate amine 106 in iso-propanol at elevated temperature generates the intermediate 107 via an aromatic nucleophilic substitution. Intermediate 107 is then easily reduced to the desired 2,3-diaminopyridine 101 by a suitable reducing agent, such as iron metal, zinc metal or SnCl$_2$ under acidic conditions.

Compounds of formula (I) may alternatively be prepared in one step starting from the intermediate 107 and performing the reduction and cyclization steps in a one-pot reaction as shown in Scheme 4. Formation of compounds of formula (I) from 107 and aldehyde 102 is then accomplished with sodium dithionite in ethanol and water at 60-70° C. (Yang, D, et al., *Synthesis*, 2005, 47-56).

Scheme 4

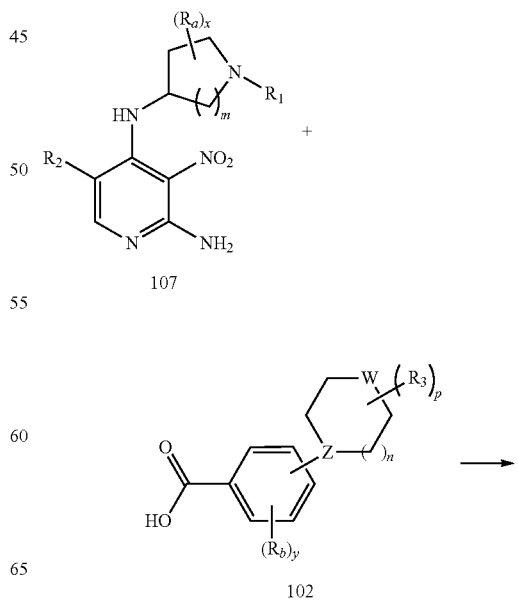

-continued

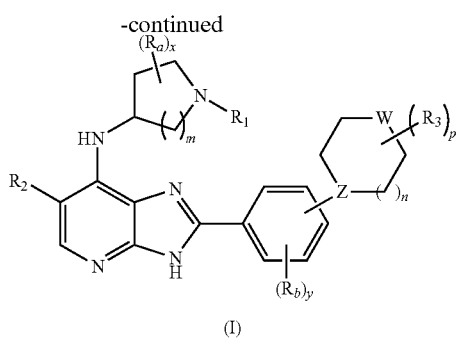

(I)

An alternative method of preparation of compounds of formula (I) is shown in Scheme 5. This method involves the introduction of the amine 106 in the last step via aromatic nucleophilic substitution of chloride in the imidazo[4,5-b]pyridine intermediate 108 at 120-160° C. in n-BuOH. (Wang, T, et al., *Bioorg. Med. Chem. Lett.*, 2012, 2063-2069). Intermediate 108 may be prepared by the method shown in Scheme 1.

Scheme 5

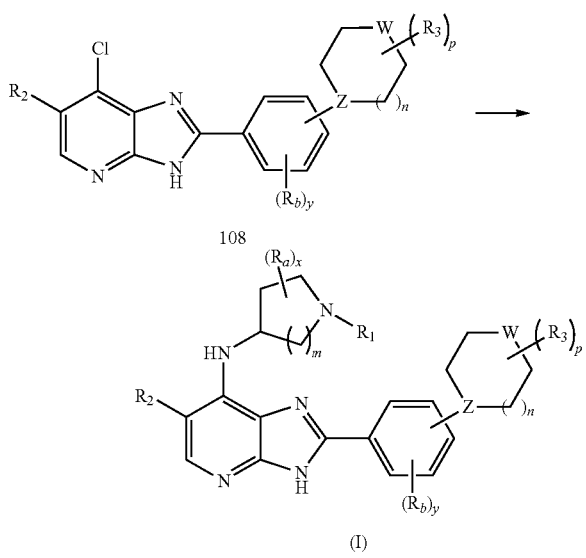

The necessary starting materials for preparation of the compounds of formula (I) are either commercially available, or may be prepared by methods known in the art.

The reactions described below in the experimental section may be carried out to give a compound of the invention in the form of a free base or as an acid addition salt. The term pharmaceutically acceptable salt of a compound refers to a salt that is pharmaceutically acceptable, as defined herein, and that possesses the desired pharmacological activity of the parent compound. A pharmaceutically acceptable acid addition salt may be obtained by dissolving the free base in a suitable organic solvent and treating the solution with an acid, in accordance with conventional procedures for preparation of acid addition salts from free bases.

Examples of addition salts include salts formed with inorganic acids, e.g. hydrochloric acid, hydrobromic acid, sulfuric acid, nitric acid, phosphoric acid; or formed with organic acids, e.g. acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethane-sulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, or trimethylacetic acid.

The compounds of formula (I) may possess one or more chiral carbon atoms, and may therefore be obtained in the form of optical isomers, e.g. as a pure enantiomer, or as a mixture of enantiomers (racemate) or as a mixture of diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes described herein may include, for example, solvents, reagents, catalysts, and protecting group and deprotecting group reagents. Examples of protecting groups are tert-butoxycarbonyl (Boc), benzyl, trityl (triphenylmethyl) and trimethylsilyl. The methods described above may also additionally include steps, either before or after the steps described specifically herein, to add or to remove suitable protecting groups in order to ultimately allow synthesis of the compounds. In addition, various synthetic steps may be performed in an alternate sequence or order to give the desired compounds. Synthetic chemistry transformations and protecting group methodologies are known in the art and include, for example, those described in R. C. Larock, *Comprehensive Organic Transformations*, VCH Publishers (1989); L. Fieser and M. Fieser, *Fieser and Fieser's Reagents for Organic Synthesis*, John Wiley and Sons (1994); L. A. Paquette, ed., *Encyclopedia of Reagents for Organic Synthesis*, John Wiley and Sons (1995); T. H. Greene and P. G. M. Wuts, *Protective Groups in Organic Synthesis*, $3^{rd}$ Ed., John Wiley and Sons (1999); and P. J. Kocieniski, Protecting Groups, Georg Thieme Verlag, (2000) and subsequent editions thereof.

The following abbreviations are used herein:
Boc tert-Butoxycarbonyl
DCE 1,2-Dichloroethane
DCM Dichloromethane
DIPEA N,N-diisopropylethylamine
DMF N,N-dimethylformamide
DMSO Dimethyl sulfoxide
ESI Electrospray ionization
EtOAc Ethyl acetate
EtOH Ethanol
HPLC High Performance Liquid Chromatography
i-PrOH iso-Propanol
MeOH Methanol
MS Mass Spectrometry
NBS N-Bromosuccinimide
NCS N-Chlorosuccinimide
NMR Nuclear Magnetic Resonance

EXAMPLES AND INTERMEDIATE COMPOUNDS

Experimental Methods $^1$H NMR and $^{13}$C NMR spectra were recorded on a Varian Inova 600 equipped with a triple resonance cold probe. All spectra were recorded using the residual solvent proton resonance as internal standard. Analytical HPLC was carried out on an Agilent Series 1100 system using either an ACE C8 (3 µm, 3.0×50 mm) column with 0.1% formic acid in MilliQ H₂O/CH₃CN as mobile phase (Acidic system) or a Gemini NX (3 μm 3.0×50 mm) column with 10 mM pH10 NH₄HCO₃/CH₃CN as mobile phase (Basic system). Electrospray mass spectrometry (ES-MS) was performed using an Agilent 1100 Series Liquid Chromatograph/Mass Selective Detector (MSD) to obtain the pseudo molecular [M+H]⁺ ion of the target molecules. Preparative HPLC was performed on a Gilson 306 HPLC system using either an Kinetex C18 (5 μm, 21×100 mm) column with 0.1% TFA in MilliQ H₂O/CH₃CN as mobile phase (Acidic system) or an Gemini NX (5 μm, 21×100 mm) column with 50 mM pH10 NH₄HCO₃/CH₃CN as mobile phase (Basic system). Fractions were collected based on the UV-signal at the maximum wavelength for the compound of interest. Preparative flash chromatography was performed on Merck silica gel 60 (230-400 mesh) or YMC gel 120 Å S-150 μm. Microwave reactions were performed with a Biotage Initiator instrument using 0.5-2 mL or 2-5 mL Biotage Process Vials fitted with aluminum caps and septa. The compounds were named using the software ACD Labs 10.0.

INTERMEDIATE 1

4,5-Dichloropyridin-2-amine

To a solution of 4-chloropyridine-2-amine (50.00 g, 0.389 mol) in EtOAc (400 mL) was added N-chloro succinimide (53.50 g, 0.401 mol) in one portion. The mixture was stirred over night (28 h) at room temperature, and was then filtered to remove precipitated succinimide. The filtrate was washed with aqueous 0.5M NaOH (8×50 mL), water (2×50 mL) and brine (2×50 mL). The organic phase was dried (Na₂SO₄), filtered and evaporated to furnish 59.4 g of crude light brown powder after vacuum drying. The dry isolated crude (with a purity of ca. 75% of the title compound) was slurried in hexane (800 mL) and stirred at reflux temperature for 15 min. The mixture was allowed to cool to 35° C. and was then filtered using a G3 glass frit filter. The filter cake was washed with hexane (ca. 200 mL) and dried on the filter to furnish 42.1 g (66%) of brown solid. The product was pure enough (96%) to be taken to the next step. ¹H NMR (600 MHz, DMSO-d₆) δ ppm 8.02 (s, 1H) 6.65 (s, 1H) 6.42 (s, 2H). MS: (ESI⁺) m/z 163, 165, 167 [M+H]⁺, di-chlorine isotopic pattern.

INTERMEDIATE 2

4,5-Dichloro-N-nitropyridine-2-amine 4,5-Dichloropyridin-2-amine (INTERMEDIATE 1, 45.2 g, 283.0 mmol) was added to 270 mL of ice cold conc. H₂SO₄, in small portions over ca 20 min. When dissolved, conc. HNO₃ (22 g) was added dropwise and the mixture was stirred at ca 5° C. for 3.5 h. LCMS indicated total conversion to expected product. The cold mixture was poured on crushed ice/water mixture (3 L), stirred for ca 5 min and then filtered. The solid was collected and slurried in ice cold water (500 mL) and filtered. The procedure was repeated until neutral pH. When semi dry on the filter, the solid was dissolved in EtOAc (ca. 3 L), washed with brine (ca. 100 mL) and the organic layer was dried with Na₂SO₄, filtered, and evaporated to furnish 46.2 g (78%) of 97% pure title product as beige-orange solid. ¹H NMR (600 MHz, CD₃OD) δ □D) δ (600 MHz, CDaporated to furnish 46.2⁺) m/z 208, 210, 212 [M+H]⁺, di-chlorine isotopic pattern.

INTERMEDIATE 3

4,5-Dichloro-3-nitropyridine-2-amine 4,5-Dichloro-N-nitropyridin-2-amine (INTERMEDIATE 2, 20.0 g, 96.2 mmol) was added to 200 mL of conc. H₂SO₄ at room temperature. After stirring at 40° C. for 2.5 h the mixture was cooled to below room temperature and poured onto crushed ice (2 L) while stirring. After the ice had melted, the volume was adjusted to ca. 2 L with ice cold water and the yellow precipitate was collected by filtration and washed with ice cold water until neutral pH (3×250 mL). The solid was allowed to semi-dry on the filter and was then dissolved in EtOAc (ca. 800 mL). The organic phase was washed with 0.25 M NaOH (3×30 mL), water (3×15 mL) and brine (15 mL), dried (Na₂SO₄), filtered and the solvent evaporated to furnish 11.7 g (59%) of 99% pure title product as yellow solid. ¹H NMR (600 MHz, CD₃OD) δ ppm 8.26 (s, 1H). MS: (ESI⁺) m/z 208, 210, 212 [M+H]⁺ chlorine isotopic pattern.

INTERMEDIATE 4

5-Bromo-4-chloropyridin-2-amine

The title product was prepared by the same procedure as the one used for 4,5-dichloropyridin-2-amine (INTERMEDIATE 1), with the exception that NCS was exchanged for NBS. ¹H NMR (600 MHz, CD₃OD) δ ppm 8.03 (s, 1H) 6.73 (s, 1H). MS (ESI⁺) m/z 207, 209, 211 [M+H]⁺ bromine-chlorine isotopic pattern.

INTERMEDIATE 5

5-Bromo-4-chloro-N-nitropyridine-2-amine

The title product was prepared by the same procedure as the one used for 4,5-dichloro-N-nitropyridine-2-amine (INTERMEDIATE 2). ¹H NMR (600 MHz, CDCl₃) δ ppm 8.49 (s, 1H) 8.06 (s, 1H). MS (ESI⁺) m/z 252, 254, 256 [M+H]⁺, bromine-chlorine isotopic pattern.

INTERMEDIATE 6

5-Bromo-4-chloro-3-nitropyridin-2-amine

The title product was prepared by the same procedure as the one used for 4,5-dichloro-3-nitropyridine-2-amine (INTERMEDIATE 3). ¹H NMR (600 MHz, CDCl₃) δ ppm 8.36 (s, 1H) 5.82 (br. s., 2H). MS (ESI⁺) m/z 252, 254, 256 [M+H]⁺, bromine-chlorine isotopic pattern.

INTERMEDIATE 7

1-(4-Methoxybenzyl)piperidin-4-amine

To a stirred mixture of 4-boc-aminopiperidine (1001 mg, 5.0 mmol) and 4-methoxy-benzaldehyde (681 mg, 5.0 mmol) in DCE (30 mL) was added NaBH(OAc)₃ (1696 mg, 8.0 mmol). The mixture was stirred at room temperature for 20 h. Sat. NaHCO₃ (10 mL) was added and the mixture was stirred for 10 min. The mixture was diluted with DCM (35 mL) and the phases were separated. The organic phase was washed with sat. NaHCO₃ (10 mL) and brine (8 mL), dried over Na₂SO₄ and concentrated in vacuo to yield 1.503 g (94%) of tert-butyl [1-(4-methoxybenzyl)piperidin-4-yl]carbamate as white solid. ¹H NMR (600 MHz, CD₃OD) δ ppm 7.22 (d, J=8.5 Hz, 2H) 6.87 (d, J=8.5 Hz, 2H) 3.78 (s, 3H) 3.45 (s, 2H) 3.32-3.35 (m, 0H) 2.84 (d, J=11.6 Hz, 2H) 2.09 (t, J=11.6 Hz, 2H) 1.83 (d, J=11.6 Hz, 2H) 1.44-1.51 (m, 2H) 1.42 (s, 9H). MS (ESI$^+$) m/z 321 [M+H]$^+$.

The product from the previous step was dissolved in dioxane (15 mL). Conc. HCl (2 mL, 25 mmol) was added and the reaction mixture was stirred at RT for 1.5 h. The mixture was evaporated to a small volume and water (10 mL) was added. The resulting aqueous phase was washed with EtOAc (15 mL). The pH of the aqueous phase was adjusted with 8M NaOH to approximately pH12, and then extracted with DCM (3×20 mL). The combined organic phases were washed with brine (5 mL) and dried over Na$_2$SO$_4$ and finally evaporated to yield 914 mg (88% over two steps) of pure title product as clear almost colorless oil. $^1$H NMR (600 MHz, CD$_3$OD) δ ppm 7.22 (d, J=8.9 Hz, 2H) 6.87 (d, J=8.5 Hz, 2H) 3.78 (s, 3H) 3.44 (s, 2H) 2.85 (d, J=12.2 Hz, 2H) 2.60 (tt, J=10.7, 4.3 Hz, 1H) 2.04 (td, J=11.9, 2.1 Hz, 2H) 1.79 (d, J=13.1 Hz, 2H) 1.39 (dq, J=12.1, 4.0 Hz, 2H). MS (ESI$^+$) m/z 221 [M+H]$^+$.

INTERMEDIATE 8

(3S)-1-(4-Methoxybenzyl)pyrrolidin-3-amine

The title product was prepared according to the procedure used for INTERMEDIATE 7, using (S)-3-boc-aminopyrrolidine instead of 4-boc-aminopiperidine. $^1$H NMR (600 MHz, CD$_3$OD) δ ppm 7.24 (d, J=8.9 Hz, 2H) 6.87 (d, J=8.9 Hz, 2H) 3.78 (s, 3H) 3.55 (s, 2H) 3.40-3.45 (m, 1H) 2.80 (dd, J=9.9, 6.9 Hz, 1H) 2.67 (td, J=8.9, 6.3 Hz, 1H) 2.54 (ddd, J=9.5, 8.2, 6.1 Hz, 1H) 2.27 (dd, J=9.8, 5.2 Hz, 1H) 2.15-2.22 (m, 1H) 1.47-1.54 (m, 1H). MS (ESI$^+$) m/z 207 [M+H]$^+$.

INTERMEDIATE 9

1-[4-(Dimethylamino)benzyl]piperidin-4-amine

The title product was prepared according to the procedure used for INTERMEDIATE 7, using 4-(dimethylamino)benzaldehyde instead of 4-methoxy-benzaldehyde. $^1$H NMR (600 MHz, CD$_3$OD) δ ppm 7.14 (d, J=8.5 Hz, 2H) 6.74 (d, J=8.9 Hz, 2H) 3.41 (s, 2H) 2.91 (s, 6H) 2.86 (d, J=12.2 Hz, 2H) 2.57-2.65 (m, 1H) 2.03 (td, J=11.8, 1.7 Hz, 2H) 1.77-1.83 (m, 2H) 1.40 (qd, J=12.0, 3.7 Hz, 2H). MS (ESI$^+$) m/z 234 [M+H]$^+$.

INTERMEDIATE 10

1-(2,3-Dihydro-1-benzofuran-5-ylmethyl)piperidin-4-amine

The title product was prepared according to the procedure used for INTERMEDIATE 7, using 2,3-dihydro-1-benzofuran-5-carbaldehyde instead of 4-methoxy-benzaldehyde. $^1$H NMR (600 MHz, CD$_3$OD) δ ppm 7.16 (s, 1H) 7.01 (dd, J=8.1, 1.7 Hz, 1H) 6.66 (d, J=7.9 Hz, 1H) 4.52 (t, J=8.7 Hz, 2H) 3.42 (s, 2H) 3.18 (t, J=8.7 Hz, 2H) 2.85 (d, J=12.2 Hz, 2H) 2.55-2.66 (m, 1H) 2.03 (t, J=11.9 Hz, 2H) 1.75-1.83 (m, 2H) 1.39 (qd, J=12.0, 3.8 Hz, 2H). MS (ESI$^+$) m/z 233 [M+H]$^+$.

INTERMEDIATE 11

1-(Thiophen-2-ylmethyl)piperidin-4-amine

The title product was prepared according to the procedure used for INTERMEDIATE 7, using thiophene-2-carbaldehyde instead of 4-methoxy-benzaldehyde. $^1$H NMR (600 MHz, CD$_3$OD) δ ppm 7.31 (dd, J=4.4, 2.0 Hz, 1H) 6.92-6.98 (m, 2H) 3.73 (s, 2H) 2.90 (d, J=12.2 Hz, 2H) 2.59 (tt, J=10.7, 4.3 Hz, 1H) 2.09 (td, J=11.9, 2.1 Hz, 2H) 1.77-1.85 (m, 2H) 1.41 (qd, J=12.0, 3.8 Hz, 2H). MS (ESI$^+$) m/z 197 [M+H]$^+$.

INTERMEDIATE 12

1-(Thiophen-3-ylmethyl)piperidin-4-amine

The title product was prepared according to the procedure used for INTERMEDIATE 7, using thiophene-3-carbaldehyde instead of 4-methoxy-benzaldehyde. $^1$H NMR (600 MHz, CD$_3$OD) δ ppm 7.36 (dd, J=4.93, 2.93 Hz, 1H) 7.24 (ddt, J=2.93, 1.28, 0.74 Hz, 1H) 7.09 (dd, J=4.93, 1.28 Hz, 1H) 3.56 (s, 2H) 2.85-2.92 (m, 2H) 2.65 (tt, J=10.83, 4.30 Hz, 1H) 2.07 (td, J=11.98, 2.14 Hz, 2H) 1.79-1.86 (m, 2H) 1.39-1.48 (m, 2H). MS (ESI$^+$) m/z 197 [M+H]$^+$.

INTERMEDIATE 13

4-[(4-Aminopiperidin-1-yl)methyl]-2-methoxyphenol

The title product was prepared according to the procedure used for INTERMEDIATE 7, using 4-hydroxy-3-methoxybenzaldehyde instead of 4-methoxy-benzaldehyde. $^1$H NMR (600 MHz, CD$_3$OD) δ ppm 6.93-6.95 (m, 1H) 6.74-6.76 (m, 2H) 3.85 (s, 3H) 3.53 (s, 2H) 3.10 (tt, J=11.52, 4.27 Hz, 1H) 2.98-3.05 (m, 2H) 2.19 (td, J=12.24, 2.36 Hz, 2H) 1.96-2.02 (m, 2H) 1.62-1.71 (m, 2H). MS (ESI$^+$) m/z 237 [M+H]$^+$.

INTERMEDIATE 14

1-[(1,3,5-Trimethyl-1H-pyrazol-4-yl)methyl]piperidin-4-amine

The title product was prepared according to the procedure used for INTERMEDIATE 7, using 1,3,5-trimethyl-1H-pyrazole-4-carbaldehyde instead of 4-methoxy-benzaldehyde. $^1$H NMR (600 MHz, DMSO-d$_6$) δ ppm 3.59 (s, 3H) 3.12 (s, 2H) 2.65 (d, J=11.6 Hz, 2H) 2.43-2.49 (m, 1H) 2.12 (s, 3H) 2.02 (s, 3H) 1.83 (t, J=10.7 Hz, 2H) 1.61 (d, J=12.2 Hz, 2H) 1.14 (qd, J=11.6, 2.6 Hz, 2H). MS (ESI$^+$) m/z 223 [M+H]$^+$.

INTERMEDIATE 15

1-Ethylpiperidin-4-amine

4-Boc-aminopiperidine (1.95 g, 9.7 mmol) and K$_2$CO$_3$ (2.02 g, 7.5 mmol) were suspended in CH$_3$CN (20 mL). The mixture was chilled in an ice-bath and iodoethane (1.67 g, 10.7 mmol) dissolved in CH$_3$CN (5 mL) was added dropwise. The mixture was slowly allowed to warm up to room temperature and was stirred for 18 h. The solids were filtered off and the solvent was evaporated. The residue was dissolved in EtOAc (50 mL) and the organic phase was washed with water (3×6 mL) and brine (6 mL), dried over Na$_2$SO$_4$ and evaporated to dryness to yield 1.975 g (89%) of tert-butyl(1-ethylpiperidin-4-yl)carbamate as white solid. $^1$H NMR (600 MHz, DMSO-d$_6$) δ ppm 6.73 (d, J=7.9 Hz, 1H) 3.08-3.24 (m, 1H) 2.77 (d, J=11.6 Hz, 2H) 2.26 (q, J=7.1 Hz, 2H) 1.83 (t, J=11.1 Hz, 2H) 1.66 (d, J=11.3 Hz, 2H) 1.37 (s, 9H) 1.33 (qd, J=11.9, 3.4 Hz, 2H) 0.96 (t, J=7.2 Hz, 3H). MS (ESI$^+$) m/z 229 [M+H]$^+$.

The tert-butyl (1-ethylpiperidin-4-yl)carbamate isolated in the previous step was dissolved in dioxane (15 mL) and conc. HCl (2.5 mL, 31.3 mmol) was added. The reaction mixture was stirred at 50° C. for 2.5 h. The solvent was evaporated and the residue was dissolved in MeOH and evaporated twice. The resulting solid was triturated twice with Et$_2$O and was then dried under vacuum overnight to yield 1.74 g (99.8%) of 1-ethylpiperidin-4-amine dihydrochloride as an off-white solid. $^1$H NMR (600 MHz, CD$_3$OD) δ ppm 3.67-3.73 (m, 2H) 3.50 (tt, J=12.2, 4.0 Hz, 1H) 3.21 (q, J=7.3 Hz, 2H) 3.10 (t, J=12.4 Hz, 2H) 2.30 (d, J=14.6 Hz, 2H) 2.03 (qd, J=13.1, 3.1 Hz, 2H) 1.38 (t, J=7.3 Hz, 3H). MS (ESI$^+$) m/z 129 [M+H]$^+$.

INTERMEDIATE 16

1-(1-Methylethyl)piperidin-4-amine

The title product was prepared according to the procedure used for INTERMEDIATE 15, using 2-bromo-propane instead of iodoethane. The product was isolated as the dihydrochloride salt. $^1$H NMR (600 MHz, CD$_3$OD) δ ppm 3.56-3.61 (m, 2H) 3.56 (spt, J=6.71 Hz, 1H) 3.49 (tt, J=12.10, 4.31 Hz, 1H) 3.19 (td, J=13.08, 2.20 Hz, 2H) 2.27-2.34 (m, 2H) 2.07 (dddd, J=14.08, 13.08, 12.10, 4.20 Hz, 2H) 1.39 (d, J=6.71 Hz, 6H). MS (ESI$^+$) m/z 143 [M+H]$^+$.

INTERMEDIATE 17
(3S)-1-Methylpyrrolidin-3-amine

The title product was prepared according to the procedure used for INTERMEDIATE 15, using (S)-3-boc-aminopyrrolidine instead of 4-boc-aminopiperidine, and iodomethane instead of iodoethane. The product was isolated as the dihydrochloride salt. $^1$H NMR (600 MHz, CD$_3$OD) δ ppm (two conformers) 4.17-4.29 (m, 1H) 4.05-4.18 (m, 2H) 3.85-3.95 (m, 1H) 3.74-3.86 (m, 2H) 3.53-3.63 (m, 1H) 3.40-3.51 (m, 1H) 3.18-3.30 (m, 2H) 3.06 (br. s., 3H) 3.00 (br. s., 3H) 2.65-2.78 (m, 1H) 2.48-2.62 (m, 1H) 2.25-2.37 (m, 1H) 2.16-2.28 (m, 1H). MS (ESI$^+$) m/z 101 [M+H]$^+$.

INTERMEDIATE 18

(3S)-1-Propylpyrrolidin-3-amine

The title product was prepared according to the procedure used for INTERMEDIATE 15, using (S)-3-boc-aminopyrrolidine instead of 4-boc-aminopiperidine, and iodopropane instead of iodoethane. The product was isolated as the dihydrochloride salt. $^1$H NMR (600 MHz, CD$_3$OD) δ ppm 3.39-4.32 (m, 4H) 3.16-3.31 (m, 3H) 2.45-2.79 (m, 1H) 2.15-2.35 (m, 1H) 1.76-1.85 (m, 2H) 1.05 (t, J=7.40 Hz, 3H). MS (ESI$^+$) m/z 129 [M+H]$^+$.

INTERMEDIATE 19

1-Propylpiperidin-4-amine

The title product was prepared according to the procedure used for INTERMEDIATE 15, using 1-iodopropane instead of iodoethane. The product was isolated as the dihydrochloride salt. $^1$H NMR (600 MHz, CD$_3$OD) δ ppm 3.67-3.73 (m, 2H) 3.49 (tt, J=12.00, 3.90 Hz, 1H) 3.12 (td, J=13.20, 2.50 Hz, 2H) 3.06-3.11 (m, 2H) 2.25-2.31 (m, 2H) 2.03 (dddd, J=13.70, 13.20, 12.00, 4.20 Hz, 2H) 1.77-1.85 (m, 2H) 1.02 (t, J=7.40 Hz, 3H). MS (ESI$^+$) m/z 143 [M+H]$^+$.

INTERMEDIATE 20

1-(2-Methoxyethyl)piperidin-4-amine

The title product was prepared according to the procedure used for INTERMEDIATE 15, using 2-bromoethyl methyl ether instead of iodoethane. The product was isolated as the dihydrochloride salt. $^1$H NMR (600 MHz, CD$_3$OD) δ ppm 3.74-3.78 (m, 2H) 3.72-3.77 (m, 2H) 3.46-3.53 (m, 1H) 3.41 (s, 3H) 3.35-3.38 (m, 2H) 3.20 (td, J=13.20, 2.29 Hz, 2H) 2.25-2.31 (m, 2H) 2.01-2.10 (m, 2H). MS (ESI$^+$) m/z 159 [M+H]$^+$.

INTERMEDIATE 21

1-Cyclohexylpiperidin-4-amine

The title product was prepared according to the procedure used for INTERMEDIATE 7, using cyclohexanone instead of 4-methoxy-benzaldehyde. $^1$H NMR (600 MHz, CD$_3$OD) δ ppm 2.90 (d, J=12.2 Hz, 2H) 2.55-2.61 (m, 1H) 2.25-2.34 (m, 3H) 1.91 (d, J=10.4 Hz, 2H) 1.79-1.86 (m, 4H) 1.65 (d, J=13.1 Hz, 1H) 1.38 (qd, J=11.9, 4.0 Hz, 2H) 1.19-1.33 (m, 4H) 1.09-1.18 (m, 1H). MS (ESI$^+$) m/z 183 [M+H]$^+$.

INTERMEDIATE 22

1-(Cyclopropylmethyl)piperidin-4-amine

The title product was prepared according to the procedure used for INTERMEDIATE 7, using cyclopropanecarbaldehyde instead of 4-methoxy-benzaldehyde. $^1$H NMR (600 MHz, CD$_3$OD) δ ppm 3.06 (d, J=11.3 Hz, 2H) 2.58-2.67 (m, 1H) 2.25 (d, J=6.7 Hz, 2H) 2.08 (t, J=11.4 Hz, 2H) 1.81-1.87 (m, 2H) 1.43 (qd, J=12.0, 3.7 Hz, 2H) 0.85-0.92 (m, 1H) 0.52-0.57 (m, 2H) 0.11-0.17 (m, 2H). MS (ESI$^+$) m/z 155 [M+H]$^+$.

INTERMEDIATE 23

(4-Aminopiperidin-1-yl)acetonitrile

The title product was prepared according to the procedure used for INTERMEDIATE 15, using bromoacetonitrile instead of iodoethane. The reaction was run at 75° C. for 17 h. The product was isolated as the dihydrochloride salt. $^1$H NMR (600 MHz, CD$_3$OD) δ ppm 4.39 (s, 2H) 3.61-3.68 (m, 2H) 3.46 (tt, J=11.80, 4.14 Hz, 1H) 3.19 (td, J=12.70, 2.52 Hz, 2H) 2.27-2.33 (m, 2H) 2.01 (dddd, J=13.80, 12.70, 11.80, 4.20 Hz, 2H). MS (ESI$^+$) m/z 140 [M+H]$^+$.

INTERMEDIATE 24

3-(4-Aminopiperidin-1-yl)propanenitrile

The title product was prepared according to the procedure used for INTERMEDIATE 15, using bromopropionitrile instead of iodoethane. The reaction was run at 75° C. for 18.5 h. The product was isolated as the dihydrochloride salt. $^1$H NMR (600 MHz, CD$_3$OD) δ ppm 3.69-3.82 (m, 2H) 3.46-3.60 (m, 3H) 3.19-3.30 (m, 2H) 3.14 (t, J=7.25 Hz, 2H) 2.27-2.34 (m, 2H) 2.02-2.14 (m, 2H). MS (ESI$^+$) m/z 154 [M+H]$^+$.

INTERMEDIATE 25

5-Chloro-$N^4$-[1-(4-methoxybenzyl)piperidin-4-yl]-3-nitropyridine-2,4-diamine

To a slurry of 4,5-dichloro-3-nitropyridine-2-amine (INTERMEDIATE 3, 3.71 g, 17.8 mmol) in i-PrOH (50 mL) was added 1-(4-methoxybenzyl)piperidin-4-amine (INTERMEDIATE 7, 4.00 g, 18.17 mmol) and DIPEA (5.7 mL). The mixture was stirred at 50° C. over night. The reaction was allowed to cool to room temperature and was centrifuged. The supernatant was separated and the yellow solid was sequentially washed with EtOAc (25 mL), MeOH (2×25 mL), EtOAc (30 mL) and then dried in vacuum to furnish 6.70 g (85%) of 99% pure title product as yellow powder. $^1$H NMR (600 MHz, DMSO-d$_6$) δ ppm 7.87 (s, 1H) 7.76 (d, J=6.41 Hz, 1H) 7.57 (br. s., 2H) 7.19 (d, J=8.55 Hz, 2H) 6.87 (d, J=8.85 Hz, 2H) 3.83 (br. s., 1H) 3.73 (s, 3H) 3.38 (s, 2H) 2.67 (d, J=9.46 Hz, 2H) 2.03 (t, J=10.38 Hz, 2H) 1.87 (dd, J=13.12, 3.36 Hz, 2H) 1.49-1.57 (m, 2H). MS (ESI$^+$) m/z 392, 394 [M+H]$^+$, chlorine isotopic pattern.

INTERMEDIATE 26

5-Bromo-$N^4$-[1-(4-methoxybenzyl)piperidin-4-yl]-3-nitropyridine-2,4-diamine

The title product was prepared according to the procedure used for INTERMEDIATE 25, using 5-bromo-4-chloro-3-nitropyridin-2-amine (INTERMEDIATE 6) instead of 4,5-dichloro-3-nitropyridine-2-amine. $^1$H NMR (600 MHz, DMSO-d$_6$) δ ppm 7.97 (s, 1H) 7.42 (s, 2H) 7.18 (d, J=8.55 Hz, 2H) 7.09 (d, 1H) 6.86 (d, 2H) 3.73 (s, 3H) 3.67 (br. s., 1H) 3.37 (s, 2H) 2.57-2.74 (m, 2H) 1.95-2.08 (m, 2H) 1.77-1.91 (m, 2H) 1.36-1.59 (m, 2H). MS (ESI$^+$) m/z 436, 438 [M+H]$^+$, bromine isotopic pattern.

INTERMEDIATE 27

5-Chloro-$N^4$-(1-methylpiperidin-4-yl)-3-nitropyridine-2,4-diamine

The title product was prepared according to the procedure used for INTERMEDIATE 25, using 1-methylpiperidin-4-amine instead of 1-(4-methoxybenzyl)piperidin-4-amine. $^1$H NMR (600 MHz, DMSO-d$_6$) δ ppm 7.88 (s, 1H) 7.75 (d, J=7.32 Hz, 1H) 7.57 (s, 2H) 3.72-3.85 (m, 1H) 2.56-2.67 (m, 2H) 2.14 (s, 3H) 1.99 (t, J=10.22 Hz, 2H) 1.86 (dd, J=12.82, 3.66 Hz, 2H) 1.54 (dq, 2H). MS (ESI$^+$) m/z 286 [M+H]$^+$.

INTERMEDIATE 28

5-Bromo-$N^4$-(1-methylpiperidin-4-yl)-3-nitropyridine-2,4-diamine

The title product was prepared according to the procedure used for INTERMEDIATE 25, using 5-bromo-4-chloro-3-nitropyridin-2-amine (INTERMEDIATE 6) instead of 4,5-dichloro-3-nitropyridine-2-amine and 1-methylpiperidin-4-amine instead of 1-(4-methoxybenzyl)piperidin-4-amine. $^1$H NMR (600 MHz, DMSO-d$_6$) δ ppm 8.02 (s, 1H) 7.45 (br. s., 2H) 6.93-7.14 (m, 1H) 3.68-3.93 (m, 1H) 3.33-3.46 (m, 2H) 2.88-3.11 (m, 2H) 2.70 (br. s., 3H) 2.06 (d, J=13.73 Hz, 2H) 1.70-1.93 (m, 2H). MS (ESI$^+$) m/z 330, 332 [M+H]$^+$, bromine isotopic pattern.

INTERMEDIATE 29

5-Bromo-$N^4$-(1-ethylpiperidin-4-yl)-3-nitropyridine-2,4-diamine

To a slurry of 5-bromo-4-chloro-3-nitropyridin-2-amine (INTERMEDIATE 6, 1010 mg, 4.0 mmol) in i-PrOH (15 mL) was added 1-ethylpiperidin-4-amine dihydrochloride (INTERMEDIATE 15, 805 mg, 4.0 mmol) and DIPEA (1.81 g, 14.0 mmol, 1.81 mL). The mixture was stirred at 50 for 19 h. The reaction was allowed to cool to room temperature, was centrifuged and the supernatant separated. The solid was slurried in EtOAc (200 mL) and washed with sat. Na$_2$CO$_3$ (2×20 mL). The phases were separated and the organic phase was washed with water (3×15 mL) and brine (15 mL), dried over Na$_2$SO$_4$, filtered and evaporated to yield 1.166 g (85%) of pure title product as bright yellow solid. $^1$H NMR (600 MHz, CD$_3$OD) δ ppm 7.93 (s, 1H) 3.99 (br. s., 1H) 2.87 (br. s., 2H) 2.45 (q, J=7.3 Hz, 2H) 2.17 (br. s., 2H) 2.00-2.09 (m, 2H) 1.60 (qd, J=11.2, 3.4 Hz, 2H) 1.11 (t, J=7.3 Hz, 3H). MS (ESI$^+$) m/z 344, 346 [M+H]$^+$.

INTERMEDIATE 30

5-Chloro-$N^4$-(1-ethylpiperidin-4-yl)-3-nitropyridine-2,4-diamine

The title product was prepared according to the procedure used for INTERMEDIATE 29, using 4,5-dichloro-3-nitropyridine-2-amine (INTERMEDIATE 3) instead of 5-bromo-4-chloro-3-nitropyridin-2-amine. $^1$H NMR (600 MHz, CD$_3$OD) δ ppm 7.81 (s, 1H) 4.15 (br. s., 1H) 2.89 (br. s., 2H) 2.46 (q, J=7.3 Hz, 2H) 2.19 (br. s., 2H) 2.03-2.10 (m, 2H) 1.62 (qd, J=11.2, 3.7 Hz, 2H) 1.11 (t, J=7.3 Hz, 3H). MS (ESI$^+$) m/z 300 [M+H]$^+$.

INTERMEDIATE 31

5-Bromo-3-nitro-$N^4$-(1-propylpiperidin-4-yl)pyridine-2,4-diamine

The title product was prepared according to the procedure used for INTERMEDIATE 25, using 5-bromo-4-chloro-3-nitropyridin-2-amine (INTERMEDIATE 6) instead of 4,5-dichloro-3-nitropyridine-2-amine and 1-(1-methylethyl)piperidin-4-amine dihydrochloride (INTERMEDIATE 16) instead of 1-(4-methoxybenzyl)piperidin-4-amine. $^1$H NMR (600 MHz, CD$_3$OD) δ ppm (major conformer) 8.01 (s, 1H) 4.14-4.27 (m, 1H) 3.45-3.60 (m, 3H) 3.08-3.21 (m, 2H) 2.32-2.43 (m, 2H) 1.76-1.90 (m, 2H) 1.37 (d, J=6.71 Hz, 6H). MS (ESI$^+$) m/z 358 [M+H]$^+$.

INTERMEDIATE 32

5-Chloro-$N^4$-[1-(1-methylethyl)piperidin-4-yl]-3-nitropyridine-2,4-diamine

The title product was prepared according to the procedure used for INTERMEDIATE 25, using 1-(1-methylethyl)piperidin-4-amine dihydrochloride (INTERMEDIATE 16) and 4,5-dichloro-3-nitropyridine-2-amine (INTERMEDIATE 3). $^1$H NMR (600 MHz, DMSO-d$_6$) δ ppm 7.83 (br. s., 1H) 3.51-4.01 (br. m, 1H) 2.61-2.71 (m, 3H) 2.16 (t, J=10.30 Hz, 2H) 1.70-1.94 (br. m, 2H) 1.34-1.53 (br. m, 2H) 0.93 (d, J=6.56 Hz, 6H). MS (ESI$^+$) m/z 314 [M+H]$^+$.

INTERMEDIATE 33

5-Chloro-3-nitro-N$^4$-{1-[(1,3,5-trimethyl-1H-pyrazol-4-yl)methyl]piperidin-4-yl}pyridine-2,4-diamine The title product was prepared according to the procedure used for INTERMEDIATE 25, using 4,5-dichloro-3-nitropyridine-2-amine (INTERMEDIATE 3) and 1-[(1,3,5-trimethyl-1H-pyrazol-4-yl)methyl]piperidin-4-amine (INTERMEDIATE 14). 1H NMR (600 MHz, DMSO-d$_6$) δ 7.87 (s, 1H) 7.72 (br. s., 1H) 7.55 (br. s., 2H) 3.79 (br. s., 1H) 3.60 (s, 3H) 3.16 (br. s., 2H) 2.65 (br. s., 2H) 2.13 (s, 3H) 2.04 (s, 3H) 1.97 (br. s., 2H) 1.85 (d, J=9.5 Hz, 2H) 1.48 (q, J=10.1 Hz, 2H). MS (ESI$^+$) m/z 394 [M+H]$^+$.

INTERMEDIATE 34

5-Chloro-3-nitro-N-[1-(thiophen-2-ylmethyl)piperidin-4-yl]pyridine-2,4-diamine

The title product was prepared according to the procedure used for INTERMEDIATE 25, using 1-(thiophen-2-ylmethyl)piperidin-4-amine (INTERMEDIATE 11) and 4,5-dichloro-3-nitropyridine-2-amine (INTERMEDIATE 3). $^1$H NMR (600 MHz, DMSO-d$_6$) δ ppm 7.87 (s, 1H) 7.73 (d, J=7.32 Hz, 1H) 7.56 (s, 2H) 7.41 (dd, J=4.88, 1.37 Hz, 1H) 6.93-6.97 (m, 2H) 3.76-3.86 (m, 1H) 3.67 (s, 2H) 2.68-2.79 (m, 2H) 2.10 (t, J=10.68 Hz, 2H) 1.84-1.91 (m, 2H) 1.50-1.60 (m, 2H). MS (ESI$^+$) m/z 368 [M+H]$^+$.

INTERMEDIATE 35

5-Chloro-3-nitro-N-[1-(thiophen-3-ylmethyl)piperidin-4-yl]pyridine-2,4-diamine

The title product was prepared according to the procedure used for INTERMEDIATE 25, using 1-(thiophen-3-ylmethyl)piperidin-4-amine (INTERMEDIATE 12) and 4,5-dichloro-3-nitropyridine-2-amine (INTERMEDIATE 3). $^1$H NMR (600 MHz, DMSO-d$_6$) δ ppm 7.87 (s, 1H) 7.76 (d, J=7.02 Hz, 1H) 7.57 (s, 2H) 7.47 (dd, J=4.94, 2.94 Hz, 1H) 7.27-7.30 (m, J=2.94, 1.24, 0.80, 0.80, 0.80 Hz, 1H) 7.02 (dd, J=4.94, 1.24 Hz, 1H) 3.76-3.87 (m, 1H) 3.46 (s, 2H) 2.62-2.75 (m, 2H) 2.05 (t, J=10.22 Hz, 2H) 1.84-1.91 (m, 2H) 1.49-1.59 (m, 2H). MS (ESI$^+$) m/z 368 [M+H]$^+$.

INTERMEDIATE 36

5-Chloro-N$^4$-{1-[4-(dimethylamino)benzyl]piperidin-4-yl}-3-nitropyridine-2,4-diamine The title product was prepared according to the procedure used for INTERMEDIATE 25, using 1-[4-(dimethylamino)benzyl]piperidin-4-amine (INTERMEDIATE 9) and 4,5-dichloro-3-nitropyridine-2-amine (INTERMEDIATE 3). $^1$H NMR (600 MHz, DMSO-d$_6$) δ ppm 7.87 (s, 1H) 7.76 (d, J=5.49 Hz, 1H) 7.57 (s, 2H) 7.04-7.09 (m, 2H) 6.64-6.68 (m, 2H) 3.76-3.87 (m, 1H) 3.32 (s, 2H) 2.86 (s, 6H) 2.60-2.73 (m, 2H) 1.94-2.07 (m, 2H) 1.82-1.90 (m, 2H) 1.46-1.57 (m, 2H). The methylene protons are not observed. Most likely they overlap with the DMSO peak. MS (ESI$^+$) m/z 405 [M+H]$^+$.

INTERMEDIATE 37

4-({4-[(2-Amino-5-chloro-3-nitropyridin-4-yl)amino]piperidin-1-yl}methyl)-2-methoxyphenol The title product was prepared according to the procedure used for INTERMEDIATE 25, using 4-[(4-aminopiperidin-1-yl)methyl]-2-methoxyphenol (INTERMEDIATE 13) and 4,5-dichloro-3-nitropyridine-2-amine (INTERMEDIATE 3). The work-up procedure was however different. The entire reaction mixture was evaporated and the crude solid was triturated with EtOAc once and MeOH three times. The resulting solid was dried in vacuum to yield approximately 70% pure title product, which was used in the next step without further purification. MS (ESI$^+$) m/z 408 [M+H]$^+$.

INTERMEDIATE 38

5-Chloro-N-[1-(2,3-dihydro-1-benzofuran-5-ylmethyl)piperidin-4-yl]-3-nitropyridine-2,4-diamine The title product was prepared according to the procedure used for INTERMEDIATE 25, using 1-(2,3-dihydro-1-benzofuran-5-ylmethyl)piperidin-4-amine (INTERMEDIATE 10) and 4,5-dichloro-3-nitropyridine-2-amine (INTERMEDIATE 3). $^1$H NMR (600 MHz, DMSO-d$_6$) δ ppm 7.87 (s, 1H) 7.76 (d, J=5.80 Hz, 1H) 7.57 (s, 2H) 7.13 (br. s., 1H) 6.96 (d, J=7.93 Hz, 1H) 6.67 (d, J=7.93 Hz, 1H) 4.49 (t, J=8.66 Hz, 2H) 3.76-3.89 (m, 1H) 3.35 (br. s., 2H) 3.14 (t, J=8.66 Hz, 2H) 2.62-2.73 (m, 2H) 1.96-2.11 (m, 2H) 1.82-1.91 (m, 2H) 1.47-1.59 (m, 2H). MS (ESI$^+$) m/z 404 [M+H]$^+$.

INTERMEDIATE 39

5-Chloro-N$^4$-[(3S)-1-methylpyrrolidin-3-yl]-3-nitropyridine-2,4-diamine

To a slurry of 4,5-dichloro-3-nitropyridin-2-amine (INTERMEDIATE 3, 1.20 g, 5.78 mmol) in i-PrOH (16 mL) was added (3S)-1-methylpyrrolidin-3-amine dihydrochloride (INTERMEDIATE 17, 1.00 g, 5.78 mmol) and DIPEA (2.48 g, 19.07 mmol, 3.5 mL). The mixture was stirred at 50° C. over night. The mixture was cooled to room temperature and filtered on a G3 glass filter. The solid material was washed with IPA (3×5 mL) and dried in vacuum. The solid was then dissolved in EtOAc (150 mL) and washed with aqueous sat. K$_2$CO$_3$ (2×8 mL), brine (8 mL) and dried (Na$_2$SO$_4$). The organic phase was filtered and the solvent evaporated to furnish 735 mg (53%) of 98% pure title product as yellow solid. $^1$H NMR (600 MHz, DMSO-d$_6$) δ ppm 8.13 (d, J=7.32 Hz, 1H) 7.86 (s, 1H) 7.59 (s, 2H) 4.38-4.49 (m, 1H) 2.71-2.77 (m, 1H) 2.60 (dd, J=9.92, 2.90 Hz, 1H) 2.52 (d, J=6.00 Hz, 1H) 2.25 (s, 3H) 2.17-2.24 (m, 2H) 1.68-1.73 (m, 1H). MS (ESI$^+$) m/z 272 [M+H]$^+$.

INTERMEDIATE 40

5-Bromo-N$^4$-[(3S)-1-methylpyrrolidin-3-yl]-3-nitropyridine-2,4-diamine

The title product was prepared according to the procedure used for INTERMEDIATE 39, using 5-bromo-4-chloro-3-nitropyridin-2-amine (INTERMEDIATE 6) instead of 4,5-dichloro-3-nitropyridine-2-amine. $^1$H NMR (600 MHz, DMSO-d$_6$) δ ppm 7.96 (s, 1H) 7.41 (s, 2H) 7.36-7.40 (m, 1H) 4.18-4.29 (m, 1H) 2.70-2.79 (m, 1H) 2.58 (dd, J=9.77, 2.75 Hz, 1H) 2.48 (d, J=6.10 Hz, 1H) 2.25 (s, 3H) 2.15-2.23 (m, 2H) 1.61-1.73 (m, 1H). MS (ESI$^+$) m/z 316 [M+H]$^+$.

INTERMEDIATE 41

5-Chloro-3-nitro-N$^4$-[(3S)-1-propylpyrrolidin-3-yl]pyridine-2,4-diamine

The title product was prepared according to the procedure used for INTERMEDIATE 25, using (3S)-1-propylpyrrolidin-3-amine dihydrochloride (INTERMEDIATE 18) instead of 1-(4-methoxybenzyl)piperidin-4-amine. MS (ESI+) m/z 300 [M+H]+.

INTERMEDIATE 42

5-chloro-$N^4$-[(3S)-1-(4-methoxybenzyl)pyrrolidin-3-yl]-3-nitropyridine-2,4-diamine The title product was prepared according to the procedure used for INTERMEDIATE 29, using 4,5-dichloro-3-nitropyridine-2-amine (INTERMEDIATE 3) and (3S)-1-(4-methoxybenzyl)pyrrolidin-3-amine (INTERMEDIATE 8). $^1$H NMR (600 MHz, CD$_3$OD) δ ppm 7.78 (s, 1H) 7.23-7.27 (m, 2H) 6.85-6.89 (m, 2H) 4.61-4.68 (m, 1H) 3.78 (s, 3H) 3.62 (d, J=12.67 Hz, 1H) 3.57 (d, J=12.67 Hz, 1H) 2.86-2.92 (m, 1H) 2.67-2.74 (m, 2H) 2.33-2.44 (m, 2H) 1.78-1.84 (m, 1H). MS (ESI+) m/z 378 [M+H]+.

INTERMEDIATE 43

5-Chloro-3-nitro-$N^4$-(1-propylpiperidin-4-yl)pyridine-2,4-diamine

The title product was prepared according to the procedure used for INTERMEDIATE 25, using 1-propylpiperidin-4-amine (INTERMEDIATE 19) and 4,5-dichloro-3-nitropyridine-2-amine (INTERMEDIATE 3). $^1$H NMR (600 MHz, CD$_3$OD) δ ppm 7.88 (s, 1H) 4.26-4.45 (br. m, 1H) 3.38-3.71 (br. m, 2H) 2.99-3.08 (m, 2H) 2.94-3.21 (br. m, 2H) 2.22-2.40 (br. m, 2H) 1.76-1.96 (br. m, 2H) 1.71-1.80 (m, 2H) 1.02 (t, J=7.40 Hz, 3H). MS (ESI+) m/z 314 [M+H]+.

INTERMEDIATE 44

5-Bromo-3-nitro-$N^4$-(1-propylpiperidin-4-yl)pyridine-2,4-diamine

The title product was prepared according to the procedure used for INTERMEDIATE 25, using 1-propylpiperidin-4-amine (INTERMEDIATE 19) and 5-bromo-4-chloro-3-nitropyridin-2-amine (INTERMEDIATE 6). $^1$H NMR (600 MHz, CD$_3$OD, two conformers) 6 ppm 8.00 (s, 2H) 4.10-4.29 (m, 2H) 3.49-3.73 (m, 4H) 2.85-3.24 (m, 8H) 2.26-2.40 (m, 2H) 2.21-2.28 (m, 2H) 1.92-2.03 (m, 2H) 1.77-1.94 (m, 2H) 1.73-1.81 (m, 4H) 1.03 (t, J=7.40 Hz, 3H) 1.02 (t, J=7.40 Hz, 3H). MS (ESI+) m/z 358, 360 [M+H]+.

INTERMEDIATE 45

5-Chloro-$N^4$-[1-(2-methoxyethyl)piperidin-4-yl]-3-nitropyridine-2,4-diamine

The title product was prepared according to the procedure used for INTERMEDIATE 25, using 1-(2-methoxyethyl)piperidin-4-amine (INTERMEDIATE 20) and 4,5-dichloro-3-nitropyridine-2-amine (INTERMEDIATE 3). $^1$H NMR (600 MHz, CD$_3$OD) δ ppm 7.89 (s, 1H) 4.29-4.38 (m, 1H) 3.69-3.76 (m, 2H) 3.62-3.71 (m, 2H) 3.42 (s, 3H) 3.31-3.37 (m, 2H) 3.10-3.20 (m, 2H) 2.30-2.40 (m, 2H) 1.77-1.93 (m, 2H). MS (ESI+) m/z 330 [M+H]+.

INTERMEDIATE 46

5-Chloro-$N^4$-(1-cyclohexylpiperidin-4-yl)-3-nitropyridine-2,4-diamine

The title product was prepared according to the procedure used for INTERMEDIATE 25, using 1-cyclohexylpiperidin-4-amine (INTERMEDIATE 21) and 4,5-dichloro-3-nitropyridine-2-amine (INTERMEDIATE 3). $^1$H NMR (600 MHz, DMSO-d$_6$) δ ppm 7.88 (s, 1H) 7.75 (d, J=8.09 Hz, 1H) 7.57 (s, 2H) 3.77-3.87 (m, 1H) 2.69-2.79 (m, 2H) 2.20-2.34 (m, 3H) 1.84-1.91 (m, 2H) 1.66-1.76 (m, 4H) 1.53-1.59 (m, 1H) 1.44-1.53 (m, 2H) 1.11-1.23 (m, 4H) 1.00-1.10 (m, 1H). MS (ESI+) m/z 354 [M+H]+.

INTERMEDIATE 47

5-Bromo-3-nitro-$N^4$-(1,2,2,6,6-pentamethylpiperidin-4-yl)pyridine-2,4-diamine

The title product was prepared according to the procedure used for INTERMEDIATE 25, using commercially available 4-amino-1,2,2,6,6-pentamethylpiperidine and 5-bromo-4-chloro-3-nitropyridin-2-amine (INTERMEDIATE 6). $^1$H NMR (600 MHz, DMSO-d$_6$) δ ppm 7.97 (s, 1H) 7.35 (s, 2H) 6.85 (d, J=6.87 Hz, 1H) 3.84-3.94 (m, 1H) 2.15 (s, 3H) 1.77 (dd, J=11.75, 2.44 Hz, 2H) 1.35 (t, J=11.75 Hz, 2H) 1.06 (s, 6H) 0.97 (s, 6H). MS (ESI+) m/z 386 [M+H]+.

INTERMEDIATE 48

5-Chloro-3-nitro-$N^4$-(1,2,2,6,6-pentamethylpiperidin-4-yl)pyridine-2,4-diamine The title product was prepared according to the procedure used for INTERMEDIATE 25, using commercially available 4-amino-1,2,2,6,6-pentamethylpiperidine and 4,5-dichloro-3-nitropyridine-2-amine (INTERMEDIATE 3). $^1$H NMR (600 MHz, DMSO-d$_6$) δ ppm 7.88 (s, 1H) 7.50 (br. s., 3H) 3.98-4.08 (m, 1H) 2.16 (br. s., 3H) 1.77-1.85 (m, 2H) 1.31-1.43 (m, 2H) 1.07 (br. s., 6H) 0.98 (br. s., 6H). MS (ESI+) m/z 342 [M+H]+.

INTERMEDIATE 49

5-Chloro-N-[1-(cyclopropylmethyl)piperidin-4-yl]-3-nitropyridine-2,4-diamine

The title product was prepared according to the procedure used for INTERMEDIATE 25, using 1-(cyclopropylmethyl)piperidin-4-amine (INTERMEDIATE 22) and 4,5-dichloro-3-nitropyridine-2-amine (INTERMEDIATE 3). $^1$H NMR (600 MHz, CD$_3$OD) δ ppm 7.81 (s, 1H) 4.15 (br. s., 1H) 3.01 (br. s., 2H) 2.29 (d, J=6.7 Hz, 2H) 2.25 (br. s., 2H) 2.04-2.11 (m, 2H) 1.60-1.70 (m, 2H) 0.85-0.93 (m, 1H) 0.53-0.58 (m, 2H) 0.13-0.17 (m, 2H). MS (ESI+) m/z 326 [M+H]+.

INTERMEDIATE 50

5-Bromo-N—[1-(cyclopropylmethyl)piperidin-4-yl]-3-nitropyridine-2,4-diamine

The title product was prepared according to the procedure used for INTERMEDIATE 25, using 1-(cyclopropylmethyl)piperidin-4-amine (INTERMEDIATE 22) and 5-bromo-4-chloro-3-nitropyridin-2-amine (INTERMEDIATE 6). $^1$H NMR (600 MHz, CD$_3$OD) δ ppm 7.94 (s, 1H) 3.98 (br. s., 1H) 3.00 (br. s., 2H) 2.29 (d, J=6.7 Hz, 2H) 2.23 (br. s., 2H) 2.02-2.08 (m, 2H) 1.58-1.67 (m, 2H) 0.84-0.93 (m, 1H) 0.50-0.60 (m, 2H) 0.10-0.20 (m, 2H). MS (ESI+) m/z 370, 372 [M+H]+.

INTERMEDIATE 51

{4-[(2-Amino-5-chloro-3-nitropyridin-4-yl)amino]piperidin-1-yl}acetonitrile

The title product was prepared according to the procedure used for INTERMEDIATE 25, using (4-aminopiperidin-1-yl)acetonitrile (INTERMEDIATE 23) and 4,5-dichloro-3-nitropyridine-2-amine (INTERMEDIATE 3). $^1$H NMR (600 MHz, DMSO-$d_6$) δ ppm 7.89 (s, 1H) 7.70 (d, J=7.48 Hz, 1H) 7.58 (s, 2H) 3.73-3.82 (m, 1H) 3.72 (s, 2H) 2.68-2.78 (m, 2H) 2.19-2.29 (m, 2H) 1.88-1.96 (m, 2H) 1.54-1.64 (m, 2H). MS (ESI$^+$) m/z 311 [M+H]$^+$.

INTERMEDIATE 52

{4-[(2-Amino-5-bromo-3-nitropyridin-4-yl)amino]piperidin-1-yl}acetonitrile

The title product was prepared according to the procedure used for INTERMEDIATE 25, using (4-aminopiperidin-1-yl)acetonitrile (INTERMEDIATE 23) and 5-bromo-4-chloro-3-nitropyridin-2-amine (INTERMEDIATE 6). $^1$H NMR (600 MHz, DMSO-$d_6$) δ ppm 7.98 (s, 1H) 7.45 (s, 2H) 7.13 (d, J=8.39 Hz, 1H) 3.72 (s, 2H) 3.60-3.69 (m, 1H) 2.69-2.77 (m, 2H) 2.18-2.26 (m, 2H) 1.86-1.94 (m, 2H) 1.53-1.63 (m, 2H). MS (ESI$^+$) m/z 355 [M+H]$^+$.

INTERMEDIATE 53

3-{4-[(2-Amino-5-chloro-3-nitropyridin-4-yl)amino]piperidin-1-yl}propanenitrile

The title product was prepared according to the procedure used for INTERMEDIATE 25, using 3-(4-aminopiperidin-1-yl)propanenitrile (INTERMEDIATE 24) and 4,5-dichloro-3-nitropyridine-2-amine (INTERMEDIATE 3). $^1$H NMR (600 MHz, DMSO-$d_6$) δ ppm 7.88 (s, 1H) 7.72 (d, J=8.85 Hz, 1H) 7.57 (s, 2H) 3.72-3.84 (m, 1H) 2.70-2.81 (m, 2H) 2.65 (dd, J=7.02, 6.41 Hz, 2H) 2.55 (dd, J=7.02, 6.41 Hz, 2H) 2.05-2.15 (m, 2H) 1.84-1.91 (m, 2H) 1.49-1.59 (m, 2H). MS (ESI$^+$) m/z 325 [M+H]$^+$.

INTERMEDIATE 54

3-{4-[(2-Amino-5-bromo-3-nitropyridin-4-yl)amino]piperidin-1-yl}propanenitrile

The title product was prepared according to the procedure used for INTERMEDIATE 25, using 3-(4-aminopiperidin-1-yl)propanenitrile (INTERMEDIATE 24) and 5-bromo-4-chloro-3-nitropyridin-2-amine (INTERMEDIATE 6). $^1$H NMR (600 MHz, DMSO-$d_6$) δ ppm 7.98 (s, 1H) 7.43 (s, 2H) 7.09 (d, J=8.54 Hz, 1H) 3.58-3.68 (m, 1H) 2.70-2.80 (m, 2H) 2.65 (dd, J=7.02, 6.41 Hz, 2H) 2.54 (dd, J=7.02, 6.41 Hz, 2H) 2.04-2.14 (m, 2H) 1.82-1.88 (m, 2H) 1.49-1.58 (m, 2H). MS (ESI$^+$) m/z 369 [M+H]$^+$.

INTERMEDIATE 55

4-[4-(2-Hydroxyethyl)piperazin-1-yl]benzaldehyde

To a stirred solution of 4-fluorobenzaldehyde (1.24 g, 10 mmol) in water (10 mL), 2-piperazin-1-ylethanol (1.95 g, 15 mmol) and potassium carbonate (2.76 g, 20 mmol) were added and the mixture was stirred at 100° C. for 12 h. The reaction mixture was allowed to cool down to room temperature and the formed precipitate was isolated by filtration. The filter cake was washed with water and dried in vacuum to afford 2.29 g (98%) of 99% pure title product as off-white solid. $^1$H NMR (600 MHz, DMSO-$d_6$) δ ppm 9.71 (s, 1H) 7.70 (d, J=9.2 Hz, 2H) 7.04 (d, J=9.2 Hz, 2H) 4.44 (br. s., 1H) 3.54 (t, J=5.6 Hz, 2H) 3.37 (t, J=5.2 Hz, 4H) 2.53 (t, J=5.2 Hz, 4H) 2.43 (t, J=6.3 Hz, 2H). MS (ESI$^+$) m/z 235 [M+H]$^+$.

INTERMEDIATE 56

4-[4-(2-Methoxyethyl)piperazin-1-yl]benzaldehyde

The title product was prepared according to the procedure used for INTERMEDIATE 55, using 1-(2-methoxyethyl)piperazine instead of 2-piperazin-1-ylethanol. The reaction mixture was extracted with DCM (2×30 mL) and the combined organic phases were washed with water (2×30 mL), dried over Na$_2$SO$_4$, and concentrated in vacuo to yield pure title product as light brown oil which solidified upon standing. $^1$H NMR (600 MHz, DMSO-$d_6$) δ ppm 9.71 (s, 1H) 7.70 (d, J=9.2 Hz, 2H) 7.04 (d, J=8.9 Hz, 2H) 3.47 (t, J=5.8 Hz, 2H) 3.37 (t, J=5.2 Hz, 4H) 3.24 (s, 3H) 2.53 (t, J=5.2 Hz, 4H) 2.52 (t, J=5.8 Hz, 2H). MS (ESI$^+$) m/z 249 [M+H]$^+$.

INTERMEDIATE 57

4-(4-Ethylpiperazin-1-yl)benzaldehyde

The title product was prepared according to the procedure used for INTERMEDIATE 56, using 1-ethylpiperazine instead of 1-(2-methoxyethyl)piperazine. $^1$H NMR (600 MHz, DMSO-$d_6$) δ ppm 9.71 (s, 1H) 7.70 (d, J=8.9 Hz, 2H) 7.04 (d, J=8.9 Hz, 2H) 3.38 (t, J=5.2 Hz, 4H) 2.47 (t, J=4.9 Hz, 4H) 2.36 (q, J=7.3 Hz, 2H) 1.03 (t, J=7.2 Hz, 3H). MS (ESI$^+$) m/z 219 [M+H]$^+$.

INTERMEDIATE 58

4-(4-Pyridin-4-ylpiperazin-1-yl)benzaldehyde

The title product was prepared according to the procedure used for INTERMEDIATE 56, using 1-pyridin-4-ylpiperazine instead of 1-(2-methoxyethyl)piperazine. $^1$H NMR (600 MHz, DMSO-$d_6$) δ ppm 9.73 (s, 1H) 8.18 (d, J=6.4 Hz, 2H) 7.74 (d, J=8.9 Hz, 2H) 7.07 (d, J=9.2 Hz, 2H) 6.84 (d, J=6.7 Hz, 2H) 3.55-3.59 (m, 4H) 3.48-3.53 (m, 4H). MS (ESI$^+$) m/z 268 [M+H]$^+$.

INTERMEDIATE 59

4-Morpholin-4-ylbenzaldehyde

The title product was prepared according to the procedure used for INTERMEDIATE 56, using morpholine instead of 1-(2-methoxyethyl)piperazine. $^1$H NMR (600 MHz, DMSO-$d_6$) δ ppm 9.74 (s, 1H) 7.73 (d, J=9.2 Hz, 2H) 7.06 (d, J=8.9 Hz, 2H) 3.73 (t, J=4.9 Hz, 4H) 3.34 (t, J=4.9 Hz, 4H). MS (ESI$^+$) m/z 192 [M+H]$^+$.

INTERMEDIATE 60

4-(4-Acetylpiperazin-1-yl)benzaldehyde

The title product was prepared according to the procedure used for INTERMEDIATE 56, using 1-acetylpiperazine instead of 1-(2-methoxyethyl)piperazine. The crude product was purified by trituration with i-PrOH followed by flash chromatography (silica, 0-2% MeOH in DCM). $^1$H NMR (600 MHz, DMSO-$d_6$) δ ppm 9.73 (s, 1H) 7.73 (d, J=8.9 Hz, 2H) 7.05 (d, J=8.9 Hz, 2H) 3.58 (dt, J=6.8, 3.5 Hz, 4H) 3.47 (t, J=5.5 Hz, 2H) 3.40 (t, J=5.5 Hz, 2H) 2.04 (s, 3H). MS (ESI$^+$) m/z 233 [M+H]$^+$.

INTERMEDIATE 61

4-(4-Methyl-1,4-diazepan-1-yl)benzaldehyde

The title product was prepared according to the procedure used for INTERMEDIATE 56, using 1-methyl-1,4-diazepane instead of 1-(2-methoxyethyl)piperazine. $^1$H NMR (600 MHz, DMSO-$d_6$) δ ppm 9.64 (s, 1H) 7.66 (d, J=8.9 Hz, 2H) 6.83 (d, J=8.9 Hz, 2H) 3.61 (t, J=4.9 Hz, 2H) 3.54 (t, J=6.3 Hz, 2H) 2.61 (t, J=4.9 Hz, 2H) 2.44 (t, J=5.5 Hz, 2H) 2.25 (s, 3H) 1.89 (ddd, J=11.7, 6.1, 6.0 Hz, 2H). MS (ESI$^+$) m/z 219 [M+H]$^+$.

INTERMEDIATE 62

4-(3-Oxopiperazin-1-yl)benzaldehyde

The title product was prepared according to the procedure used for INTERMEDIATE 56, using piperazin-2-one instead of 1-(2-methoxyethyl)piperazine. The crude product was purified by flash chromatography (silica, 2-3% MeOH in DCM). $^1$H NMR (600 MHz, DMSO-$d_6$) δ ppm 9.73 (s, 1H) 8.20 (br. s., 1H) 7.73 (d, J=8.9 Hz, 2H) 7.00 (d, J=8.9 Hz, 2H) 3.92 (s, 2H) 3.60 (dd, J=6.1, 4.6 Hz, 2H) 3.33 (dd, J=6.1, 4.6 Hz, 2H). MS (ESI$^+$) m/z 205 [M+H]$^+$.

INTERMEDIATE 63

1-(Methylsulfonyl)piperazine

Mesyl chloride (1.20 g, 10.5 mmol) in DCM (10 mL) was added drop-wise to a solution of boc-piperazine (1.86 g, 10 mmol) in DCM (35 mL) and Et$_3$N (2.02 g, 20 mmol, 2.79 mL). The mixture was stirred for 1.5 h at room temperature. The organic phase was washed with water (2×8 mL) and brine (8 mL), and dried over Na$_2$SO$_4$. The solvent was evaporated to yield 2.66 g (quant.) of tert-butyl 4-(methylsulfonyl)piperazine-1-carboxylate as white solid. $^1$H NMR (600 MHz, CD$_3$OD) δ ppm 3.53 (br. s., 4H) 3.18 (t, J=5.2 Hz, 4H) 2.84 (s, 3H) 1.47 (s, 9H). MS (ESI$^+$) m/z 165 [M+H-t-Boc]$^+$.

The crude tert-butyl 4-(methylsulfonyl)piperazine-1-carboxylate was dissolved in dioxane (20 mL) and conc. HCl (2 mL, 25 mmol) was added. The reaction mixture was stirred at room temperature for 3 h and then at 50° C. for one hour. The mixture was allowed to cool down to room temperature and the solvent was evaporated. The remaining solid was triturated with Et$_2$O and after removal of the supernatant the solid was dried in vacuum to yield 1.90 g (95%) of the title product as hydrochloride salt. $^1$H NMR (600 MHz, DMSO-$d_6$) δ ppm 9.31 (br. s., 1H) 3.36 (t, J=5.5 Hz, 4H) 3.18 (t, J=5.2 Hz, 4H) 2.99 (s, 3H). MS (ESI$^+$) m/z 165 [M+H]$^+$.

INTERMEDIATE 64

4-[4-(Methylsulfonyl)piperazin-1-yl]benzaldehyde

The title product was prepared according to the procedure used for INTERMEDIATE 56, using 1-(methylsulfonyl) piperazine hydrochloride (INTERMEDIATE 63) instead of 1-(2-methoxyethyl)piperazine and three equivalents of potassium carbonate instead of two. The crude product was purified by flash chromatography (silica, 40-60% EtOAc in n-hexane). $^1$H NMR (600 MHz, DMSO-$d_6$) δ ppm 9.74 (s, 1H) 7.74 (d, J=8.9 Hz, 2H) 7.10 (d, J=8.9 Hz, 2H) 3.53 (t, J=5.2 Hz, 4H) 3.23 (t, J=5.2 Hz, 4H) 2.92 (s, 3H). MS (ESI$^+$) m/z 269 [M+H]$^+$.

INTERMEDIATE 65

4-(5-Oxo-1,4-diazepan-1-yl)benzaldehyde

The title product was prepared according to the procedure used for INTERMEDIATE 56, using [1,4]diazepan-5-one instead of 1-(2-methoxyethyl)piperazine. The crude product was purified by flash chromatography (silica, 2-4% MeOH in DCM). $^1$H NMR (600 MHz, DMSO-$d_6$) δ ppm 9.69 (s, 1H) 7.71 (d, J=9.2 Hz, 2H) 7.62 (t, J=5.0 Hz, 1H) 6.98 (d, J=8.9 Hz, 2H) 3.71 (dt, J=5.5, 2.7 Hz, 2H) 3.65-3.69 (m, 2H) 3.22 (ddd, J=7.5, 5.5, 1.7 Hz, 2H) 2.53 (dt, J=5.5, 2.7 Hz, 2H). MS (ESI$^+$) m/z 219 [M+H]$^+$.

INTERMEDIATE 66

4-[4-(2-Ethoxyethyl)piperazin-1-yl]benzaldehyde

1-Boc-piperazine (1.86 g, 10.0 mmol), 2-bromoethyl ethyl ether (1.92 g, 12.5 mmol) and K$_2$CO$_3$ (2.07 g, 15.0 mmol) in CH$_3$CN (25 mL) were stirred at 70° C. for 19 h. The mixture was allowed to cool to room temperature. The solids were filtered off and the filtrate was diluted with EtOAc (60 mL). The organic phase was washed with water (6 mL) and brine (6 mL), dried over Na$_2$SO$_4$, and evaporated to yield 2.45 g (95%) of tert-butyl 4-(2-ethoxyethyl)piperazine-1-carboxylate. $^1$H NMR (600 MHz, DMSO-$d_6$) δ ppm 3.46 (t, J=6.0 Hz, 2H) 3.40 (q, J=7.0 Hz, 2H) 3.28 (br. s., 4H) 2.46 (t, J=6.0 Hz, 2H) 2.34 (t, J=5.2 Hz, 4H) 1.39 (s, 9H) 1.09 (t, J=7.0 Hz, 3H). MS (ESI$^+$) m/z 259 [M+H]$^+$.

The product was dissolved in dioxane (20 mL) and conc. HCl (3.2 mL, 40 mmol) was added. The mixture was stirred at room temperature for 1 h and then at 60° C. for 0.5 h. The reaction mixture was concentrated in vacuo to yield 2.10 g (96%) of 1-(2-ethoxyethyl)piperazine as the dihydrochloride salt. $^1$H NMR (600 MHz, CD$_3$OD) δ ppm 3.83-3.86 (m, 2H) 3.60 (q, J=7.0 Hz, 2H) 3.64 (br. s., 8H) 3.50-3.53 (m, 2H) 1.24 (t, J=7.0 Hz, 3H). MS (ESI$^+$) m/z 159 [M+H]$^+$.

To a stirred solution of 4-fluorobenzaldehyde (1.69 g, 13.6 mmol) in water (15 mL), 1-(2-ethoxyethyl)piperazine dihydrochloride (2.10 g, 9.08 mmol) and potassium carbonate (5.02 g, 36.3 mmol) were added and the mixture was stirred at 100° C. for 15 h. The reaction mixture was allowed to cool down to room temperature and was extracted with DCM (3×25 mL). The combined organic extracts were evaporated to yield 2.80 g of crude product which was purified by flash chromatography (silica, 2% MeOH in DCM). The pure fractions were combined and evaporated to yield 1.68 g (71%) of pure title product as slightly yellow oil. $^1$H NMR (600 MHz, DMSO-$d_6$) δ ppm 9.71 (s, 1H) 7.70 (d, J=8.9 Hz, 2H) 7.04 (d, J=8.9 Hz, 2H) 3.51 (t, J=6.0 Hz, 2H) 3.43 (q, J=7.0 Hz, 2H) 3.37 (t, J=5.2 Hz, 4H) 2.54 (t, J=5.2 Hz, 4H) 2.51 (t, J=6.0 Hz, 2H) 1.11 (t, J=7.0 Hz, 3H). MS (ESI$^+$) m/z 263 [M+H]$^+$.

INTERMEDIATE 67

4-[4-(2-Methoxyethyl)-1,4-diazepan-1-yl]benzaldehyde

The title product was prepared according to the procedure used for INTERMEDIATE 66, using 1-boc-homopiperazine instead of 1-boc-piperazine and 2-bromoethyl methyl ether instead of 2-bromoethyl ethyl ether.

tert-Butyl 4-(2-methoxyethyl)-1,4-diazepane-1-carboxylate: $^1$H NMR (600 MHz, DMSO-$d_6$) δ ppm 3.38 (t, J=6.0 Hz, 2H) 3.30-3.35 (m, 4H) 3.22 (s, 3H) 2.54-2.66 (m, 6H) 1.65-1.71 (m, 2H) 1.39 (s, 9H). MS (ESI$^+$) m/z 259 [M+H]$^+$.

1-(2-Methoxyethyl)-1,4-diazepane dihydrochloride: $^1$H NMR (600 MHz, CD$_3$OD) δ ppm 3.76 (t, J=4.9 Hz, 2H) 3.70 (br. s., 2H) 3.49 (t, J=5.2 Hz, 2H) 3.44-3.47 (m, 2H) 3.43 (s, 3H) 3.39-3.89 (m, 4H) 2.31 (ddd, J=10.5, 5.5, 5.3 Hz, 2H). MS (ESI$^+$) m/z 159 [M+H]$^+$. 4-[4-(2-Methoxyethyl)-1,4-diazepan-1-yl]benzaldehyde: $^1$H NMR (600 MHz, DMSO-$d_6$) δ ppm 9.64 (s, 1H) 7.66 (d, J=9.2 Hz, 2H) 6.83 (d, J=8.9 Hz, 2H) 3.58 (t, J=5.2 Hz, 2H) 3.55 (t, J=6.3 Hz, 2H) 3.38 (t, J=6.0 Hz, 2H) 3.21 (s, 3H) 2.77 (t, J=5.2 Hz, 2H) 2.62 (t, J=6.0 Hz, 2H) 2.56 (t, J=5.8 Hz, 2H) 1.84 (dt, J=11.8, 5.8 Hz, 2H). MS (ESI$^+$) m/z 263 [M+H]$^+$.

INTERMEDIATE 68

4-[4-(2-Ethoxyethyl)-1,4-diazepan-1-yl]benzaldehyde

The title product was prepared according to the procedure used for INTERMEDIATE 66, using 1-boc-homopiperazine instead of 1-boc-piperazine.

tert-Butyl 4-(2-ethoxyethyl)-1,4-diazepane-1-carboxylate: $^1$H NMR (600 MHz, CD$_3$OD) δ ppm 3.56 (t, J=5.3 Hz, 2H) 3.50 (q, J=7.0 Hz, 2H) 3.42-3.48 (m, 4H) 2.75-2.78 (m, 2H) 2.68-2.74 (m, 4H) 1.83 (sxt, J=6.0 Hz, 2H) 1.46 (s, 9H) 1.18 (t, J=7.0 Hz, 3H). MS (ESI$^+$) m/z 273 [M+H]$^+$.

1-(2-Ethoxyethyl)-1,4-diazepane dihydrochloride: $^1$H NMR (600 MHz, CD$_3$OD) δ ppm 3.93 (br. s., 1H) 3.82 (t, J=4.4 Hz, 2H) 3.77 (br. s., 2H) 3.73 (br. s., 2H) 3.60 (q, J=7.0 Hz, 2H) 3.50 (t, J=4.9 Hz, 2H) 3.48-3.50 (m, 2H) 3.38-3.47 (m, 2H) 2.30-2.36 (m, 2H) 1.24 (t, J=7.0 Hz, 3H). MS (ESI$^+$) m/z 173 [M+H]$^+$.

4-[4-(2-Ethoxyethyl)-1,4-diazepan-1-yl]benzaldehyde: $^1$H NMR (600 MHz, DMSO-$d_6$) δ ppm 9.64 (s, 1H) 7.66 (d, J=9.2 Hz, 2H) 6.82 (d, J=9.2 Hz, 2H) 3.58 (t, J=5.2 Hz, 2H) 3.55 (t, J=6.3 Hz, 2H) 3.42 (t, J=6.1 Hz, 2H) 3.38 (q, J=7.0 Hz, 2H) 2.78 (t, J=5.2 Hz, 2H) 2.61 (t, J=6.1 Hz, 2H) 2.57 (t, J=5.5 Hz, 2H) 1.84 (dt, J=11.8, 5.8 Hz, 2H) 1.07 (t, J=7.0 Hz, 3H). MS (ESI$^+$) m/z 277 [M+H]$^+$.

INTERMEDIATE 69

2-(1-Methylethoxy)ethyl methanesulfonate

To a stirred solution of 2-(1-methylethoxy)ethanol (2.83 g, 20 mmol) and triethylamine (4.05 g, 40 mmol, 5.58 mL) in DCM (30 mL) was added dropwise at ice-bath temperature a solution of mesyl chloride (2.52 g, 22 mmol, 1.1 eq) in DCM (10 mL). After stirring at room temperature for 1.5 h the organic phase was washed with water (2×8 mL) and brine (8 mL). The organic phase was dried over MgSO$_4$, filtered and the solvent was evaporated to yield 3.645 g (100%) of the title product as clear light amber liquid. $^1$H NMR (600 MHz, CD$_3$OD) δ ppm 4.31-4.34 (m, 2H) 3.69-3.71 (m, 2H) 3.67 (spt, J=6.1 Hz, 1H) 3.09 (s, 3H) 1.17 (d, J=6.4 Hz, 6H). MS (ESI$^+$) m/z 183 [M+H]$^+$.

INTERMEDIATE 70

4-{4-[2-(1-Methylethoxy)ethyl]piperazin-1-yl}benzaldehyde

The title product was prepared according to the procedure used for INTERMEDIATE 66, using 2-(1-methylethoxy)ethyl methanesulfonate (INTERMEDIATE 69) instead of 2-bromoethyl ethyl ether.

tert-Butyl 4-[2-(1-methylethoxy)ethyl]piperazine-1-carboxylate: $^1$H NMR (600 MHz, DMSO-$d_6$) δ ppm 3.51 (spt, J=6.1 Hz, 1H) 3.45 (t, J=6.1 Hz, 2H) 3.28 (br. s., 4H) 2.44 (t, J=6.1 Hz, 2H) 2.35 (t, J=5.2 Hz, 4H) 1.39 (s, 9H) 1.06 (d, J=6.1 Hz, 6H). MS (ESI$^+$) m/z 273 [M+H]$^+$.

1-[2-(1-Methylethoxy)ethyl]piperazine: $^1$H NMR (600 MHz, DMSO-$d_6$) δ ppm 3.50 (spt, J=6.0 Hz, 1H) 3.43 (t, J=6.3 Hz, 2H) 2.64 (t, J=4.9 Hz, 4H) 2.37 (t, J=6.3 Hz, 2H) 2.30 (br. s., 4H) 1.06 (d, J=5.8 Hz, 6H). MS (ESI$^+$) m/z 173 [M+H]$^+$.

4-{4-[2-(1-Methylethoxy)ethyl]piperazin-1-yl}benzaldehyde: $^1$H NMR (600 MHz, DMSO-$d_6$) δ ppm 9.71 (s, 1H) 7.70 (d, J=8.9 Hz, 2H) 7.04 (d, J=8.9 Hz, 2H) 3.54 (spt, J=6.1 Hz, 1H) 3.50 (t, J=6.0 Hz, 2H) 3.36 (t, J=5.2 Hz, 4H) 2.54 (t, J=4.9 Hz, 4H) 2.50 (t, J=5.9 Hz, 2H) 1.08 (d, J=6.1 Hz, 6H). MS (ESI$^+$) m/z 277 [M+H]$^+$.

INTERMEDIATE 71

4-{4-[2-(1-Methylethoxy)ethyl]-1,4-diazepan-1-yl}benzaldehyde

The title product was prepared according to the procedure used for INTERMEDIATE 66, using 1-boc-homopiperazine instead of 1-boc-piperazine and 2-(1-methylethoxy)ethyl methanesulfonate (INTERMEDIATE 69) instead of 2-bromoethyl ethyl ether.

tert-Butyl 4-[2-(1-methylethoxy)ethyl]-1,4-diazepane-1-carboxylate: $^1$H NMR (600 MHz, DMSO-$d_6$) δ ppm 3.51 (spt, J=6.1 Hz, 1H) 3.42 (t, J=6.1 Hz, 2H) 3.29-3.35 (m, 4H) 2.61-2.67 (m, 2H) 2.55-2.61 (m, 4H) 1.64-1.71 (m, 2H) 1.39 (s, 9H) 1.06 (d, J=6.1 Hz, 6H). MS (ESI$^+$) m/z 287 [M+H]$^+$.

1-[2-(1-Methylethoxy)ethyl]-1,4-diazepane: $^1$H NMR (600 MHz, CD$_3$OD) δ ppm 3.60 (spt, J=6.1 Hz, 1H) 3.57 (t, J=5.8 Hz, 2H) 2.91-2.96 (m, 4H) 2.79-2.83 (m, 4H) 2.73 (t, J=5.8 Hz, 2H) 1.80-1.86 (m, 2H) 1.15 (d, J=6.1 Hz, 6H). MS (ESI$^+$) m/z 187 [M+H]$^+$.

4-{4-[2-(1-Methylethoxy)ethyl]-1,4-diazepan-1-yl}benzaldehyde: $^1$H NMR (600 MHz, DMSO-$d_6$) δ ppm 9.64 (s, 1H) 7.65 (d, J=9.2 Hz, 2H) 6.82 (d, J=8.9 Hz, 2H) 3.58 (t, J=5.2 Hz, 2H) 3.55 (t, J=6.1 Hz, 2H) 3.49 (spt, J=6.1 Hz, 1H) 3.41 (t, J=6.3 Hz, 2H) 2.78 (t, J=5.2 Hz, 2H) 2.59 (t, J=6.3 Hz, 2H) 2.57 (t, J=5.5 Hz, 2H) 1.84 (quin, J=6.0 Hz, 2H) 1.05 (d, J=6.1 Hz, 6H). MS (ESI$^+$) m/z 291 [M+H]$^+$.

INTERMEDIATE 72

4-[4-(3-Methoxypropyl)piperazin-1-yl]benzaldehyde

The title product was prepared according to the procedure used for INTERMEDIATE 66, using 3-bromopropyl methyl ether instead of 2-bromoethyl ethyl ether.

tert-Butyl 4-(3-methoxypropyl)piperazine-1-carboxylate: $^1$H NMR (600 MHz, DMSO-$d_6$) δ ppm 3.32 (t, J=6.4 Hz, 2H) 3.28 (br. s., 4H) 3.20 (s, 3H) 2.30 (t, J=7.3 Hz, 2H) 2.27 (t, J=5.0 Hz, 4H) 1.64 (dt, J=14.9, 6.4 Hz, 2H) 1.39 (s, 9H). MS (ESI$^+$) m/z 259 [M+H]$^+$. 1-(3-Methoxypropyl)piperazine: $^1$H NMR (600 MHz, DMSO-$d_6$) δ ppm 3.31 (t, J=6.6 Hz, 2H) 3.20 (s, 3H) 2.67 (t, J=4.9 Hz, 4H) 2.26 (br. s., 4H) 2.24 (t, J=7.3 Hz, 2H) 1.62 (dt, J=14.6, 6.9 Hz, 2H). MS (ESI$^+$) m/z 159 [M+H]$^+$.

4-[4-(3-Methoxypropyl)piperazin-1-yl]benzaldehyde: $^1$H NMR (600 MHz, DMSO-$d_6$) δ ppm 9.71 (s, 1H) 7.70 (d, J=9.2 Hz, 2H) 7.04 (d, J=9.2 Hz, 2H) 3.37 (t, J=5.2 Hz, 4H) 3.36 (t, J=6.6 Hz, 2H) 3.22 (s, 3H) 2.47 (t, J=5.2 Hz, 4H) 2.35 (t, J=7.5 Hz, 2H) 1.69 (dt, J=14.6, 6.4 Hz, 2H). MS (ESI$^+$) m/z 263 [M+H]$^+$.

INTERMEDIATE 73

2-(2-Methoxyethoxy)ethyl methanesulfonate

To a stirred solution of diethyleneglycol monomethyl ether (2.4 g, 20 mmol) and triethylamine (4.05 g, 40 mmol, 5.5 mL) in DCM (30 mL) was added dropwise an ice-cold solution of mesyl chloride (2.52 g, 22 mmol, 1.1 eq.) in DCM (10 mL). The mixture was allowed to stir for 3 h at room temperature. The organic phase was washed with water (4×8 mL) and brine (10 mL) and dried over $Na_2SO_4$. The solvent was evaporated to furnish 3.71 g (94%) of product as clear light amber oil. $^1H$ NMR (600 MHz, DMSO-$d_6$) δ ppm 4.28-4.32 (m, 2H) 3.64-3.68 (m, 2H) 3.54-3.58 (m, 2H) 3.43-3.47 (m, 2H) 3.25 (s, 3H) 3.18 (s, 3H). MS (ESI$^+$) m/z 199 [M+H]$^+$.

INTERMEDIATE 74

4-{4-[2-(2-Methoxyethoxy)ethyl]piperazin-1-yl}benzaldehyde

The title product was prepared according to the procedure used for INTERMEDIATE 66, using 2-(2-methoxyethoxy)ethyl methanesulfonate (INTERMEDIATE 73) instead of 2-bromoethyl ethyl ether.

tert-Butyl 4-[2-(2-methoxyethoxy)ethyl]piperazine-1-carboxylate: MS (ESI$^+$) m/z 289 [M+H]$^+$.

1-[2-(2-Methoxyethoxy)ethyl]piperazine: MS (ESI$^+$) m/z 189 [M+H]$^+$.

4-{4-[2-(2-Methoxyethoxy)ethyl]piperazin-1-yl}benzaldehyde: $^1H$ NMR (600 MHz, DMSO-$d_6$) δ ppm 9.71 (s, 1H) 7.70 (d, J=9.16 Hz, 2H) 7.04 (d, J=8.85 Hz, 2H) 3.54 (t, J=5.95 Hz, 2H) 3.51 (t, J=4.80 Hz, 2H) 3.44 (t, J=4.80 Hz, 2H) 3.34-3.39 (m, 4H) 3.25 (s, 3H) 2.53-2.56 (m, 4H) 2.52 (t, J=5.95 Hz, 2H). MS (ESI$^+$) m/z 293 [M+H]$^+$.

INTERMEDIATE 75

4-(4-Pyrazin-2-ylpiperazin-1-yl)benzaldehyde

The title product was prepared according to the procedure used for INTERMEDIATE 56, using 2-piperazin-1-ylpyrazine instead of 1-(2-methoxyethyl)piperazine. $^1H$ NMR (600 MHz, DMSO-$d_6$) δ ppm 9.73 (s, 1H) 8.36 (d, J=1.2 Hz, 1H) 8.11 (dd, J=2.7, 1.5 Hz, 1H) 7.87 (d, J=2.7 Hz, 1H) 7.74 (d, J=8.9 Hz, 2H) 7.09 (d, J=8.9 Hz, 2H) 3.72-3.77 (m, 4H) 3.55-3.59 (m, 4H). MS (ESI$^+$) m/z 269 [M+H]$^+$.

INTERMEDIATE 76

4-[4-(Pyridin-2-ylmethyl)piperazin-1-yl]benzaldehyde

The title product was prepared according to the procedure used for INTERMEDIATE 56, using 1-(pyridin-2-ylmethyl)piperazine instead of 1-(2-methoxyethyl)piperazine. $^1H$ NMR (600 MHz, DMSO-$d_6$) δ ppm 9.71 (s, 1H) 8.51 (ddd, J=4.9, 1.8, 0.9 Hz, 1H) 7.78 (td, J=7.6, 1.8 Hz, 1H) 7.70 (d, J=8.9 Hz, 2H) 7.48 (d, J=7.9 Hz, 1H) 7.28 (ddd, J=7.3, 4.9, 1.2 Hz, 1 H) 7.04 (d, J=8.9 Hz, 2H) 3.65 (s, 2H) 3.40 (t, J=5.2 Hz, 4H) 2.55 (t, J=5.2 Hz, 4H). MS (ESI$^+$) m/z 282 [M+H]$^+$.

INTERMEDIATE 77

4-[4-(Pyridin-3-ylmethyl)piperazin-1-yl]benzaldehyde

The title product was prepared according to the procedure used for INTERMEDIATE 56, using 1-(pyridin-3-ylmethyl)piperazine instead of 1-(2-methoxyethyl)piperazine. The crude product was purified by flash chromatography (silica, 1-3% MeOH in DCM). $^1H$ NMR (600 MHz, DMSO-$d_6$) δ ppm 9.71 (s, 1H) 8.53 (d, J=1.5 Hz, 1H) 8.49 (dd, J=4.9, 1.8 Hz, 1H) 7.74 (dt, J=7.7, 1.9 Hz, 1H) 7.70 (d, J=8.9 Hz, 2H) 7.38 (ddd, J=7.6, 4.9, 0.6 Hz, 1H) 7.03 (d, J=8.9 Hz, 2H) 3.57 (s, 2H) 3.39 (t, J=4.9 Hz, 4H) 2.50 (t, J=4.9 Hz, 4H). MS (ESI$^+$) m/z 282 [M+H]$^+$.

INTERMEDIATE 78

4-[4-(Pyridin-4-ylmethyl)piperazin-1-yl]benzaldehyde

The title product was prepared according to the procedure used for INTERMEDIATE 56, using 1-(pyridin-4-ylmethyl)piperazine instead of 1-(2-methoxyethyl)piperazine. The crude product was purified by flash chromatography (silica, 3% MeOH in DCM). $^1H$ NMR (600 MHz, DMSO-$d_6$) δ ppm 9.71 (s, 1H) 8.51-8.54 (m, 2H) 7.71 (d, J=8.9 Hz, 2H) 7.36 (d, J=5.8 Hz, 2H) 7.04 (d, J=8.9 Hz, 2H) 3.57 (s, 2H) 3.41 (t, J=5.2 Hz, 4H) 2.51 (t, J=5.2 Hz, 4H). MS (ESI$^+$) m/z 282 [M+H]$^+$.

INTERMEDIATE 79

4-(4-Pyridin-3-ylpiperazin-1-yl)benzaldehyde

The title product was prepared according to the procedure used for INTERMEDIATE 56, using 1-pyridin-3-ylpiperazine instead of 1-(2-methoxyethyl)piperazine. The crude product was purified by trituration twice with MeOH. $^1H$ NMR (600 MHz, DMSO-$d_6$) δ ppm 9.74 (s, 1H) 8.36 (d, J=3.1 Hz, 1H) 8.03 (dd, J=4.3, 1.2 Hz, 1H) 7.74 (d, J=9.2 Hz, 2H) 7.38 (ddd, J=8.5, 3.1, 1.2 Hz, 1H) 7.24 (dd, J=8.5, 4.6 Hz, 1H) 7.12 (d, J=9.2 Hz, 2H) 3.57 (t, J=5.2 Hz, 4H) 3.36 (t, J=5.5 Hz, 4H). MS (ESI$^+$) m/z 268 [M+H]$^+$.

INTERMEDIATE 80

4-{4-[(6-Methylpyridin-2-yl)methyl]piperazin-1-yl}benzaldehyde

To a stirred mixture of N-boc-piperazine (931 mg, 5.0 mmol) and 6-methyl-2-pyridinecarboxaldehyde (606 mg, 5.0 mmol) in DCE (30 mL) was added NaBH(OAc)$_3$ (1.696 g, 8.0 mmol). The mixture was stirred at room temperature for 16 h. Sat. NaHCO$_3$ (10 mL) was added and the mixture was stirred for 10 min. The mixture was diluted with DCM (25 mL) and the phases were separated. The organic phase was washed with sat. NaHCO$_3$ (5 mL) and brine (5 mL), dried over Na$_2$SO$_4$ and concentrated in vacuo to yield 1.44 g (98%) of essentially pure tert-butyl 4-[(6-methylpyridin-2-yl)methyl]piperazine-1-carboxylate as clear almost colorless oil. $^1H$ NMR (600 MHz, DMSO-$d_6$) δ ppm 7.64 (t, J=7.6 Hz, 1H) 7.22 (d, J=7.6 Hz, 1H) 7.11 (d, J=7.6 Hz, 1H) 3.54 (s, 2H) 3.32 (t, J=5.2 Hz, 4H) 2.43 (s, 3H) 2.35 (t, J=5.2 Hz, 4H) 1.39 (s, 9H). MS (ESI$^+$) m/z 292 [M+H]$^+$.

To a solution of tert-butyl 4-[(6-methylpyridin-2-yl)methyl]piperazine-1-carboxylate (1.44 g, 4.92 mmol) in dioxane (20 mL) was added conc. HCl (2 mL, 25 mmol) and the mixture was stirred at room temperature for 1.5 h. The mixture was evaporated to a small volume and water (12 mL) was added and the resulting aqueous phase was washed with EtOAc (15 mL). The phases were separated and the pH of the aqueous phase was adjusted with 8M NaOH to ca. pH 12, and was then extracted with DCM (3×25 mL). The combined organic phases were washed with brine (5 mL) and dried over $Na_2SO_4$ and finally evaporated to yield 899 mg (95%) of pure 1-[(6-methylpyridin-2-yl)methyl]piperazine as clear almost colorless oil. $^1$H NMR (600 MHz, DMSO-$d_6$) δ ppm 7.62 (t, J=7.6 Hz, 1H) 7.21 (d, J=7.6 Hz, 1H) 7.09 (d, J=7.6 Hz, 1H) 3.48 (s, 2H) 2.68 (t, J=4.7 Hz, 4H) 2.42 (s, 3H) 2.32 (br. s., 4H). MS (ESI$^+$) m/z 192 [M+H]$^+$.

To a stirred mixture of p-fluorobenzaldehyde (712 mg, 5.74 mmol) and 1-[(6-methylpyridin-2-yl)methyl]piperazine (897 mg, 4.69 mmol) was added potassium carbonate (1.30 g, 9.38 mmol) dissolved in water (12 mL) and the mixture was stirred in a sealed tube at 100° C. for 24 h. The reaction mixture was allowed to cool to room temperature and DCM (35 mL) was added and the phases were separated. The aqueous phase was extracted with DCM (25 mL) and the combined organic phases were dried over $Na_2SO_4$ and evaporated to yield 1.44 g of 94% pure crude material as light brown oil. The crude product was purified by flash chromatography (silica, 2-4% MeOH in DCM). The pure fractions were pooled and evaporated to yield 1.06 g (76%) of >99% pure title product as clear slightly yellow oil. $^1$H NMR (600 MHz, DMSO-$d_6$) δ ppm 9.71 (s, 1H) 7.70 (d, J=8.9 Hz, 2H) 7.66 (t, J=7.6 Hz, 1 H) 7.27 (d, J=7.6 Hz, 1H) 7.13 (d, J=7.3 Hz, 1H) 7.04 (d, J=8.9 Hz, 2H) 3.60 (s, 2H) 3.40 (t, J=5.2 Hz, 4H) 2.55 (t, J=4.9 Hz, 4H) 2.45 (s, 3H). MS (ESI$^+$) m/z 296 [M+H]$^+$.

INTERMEDIATE 81

4-[4-(1,3-Thiazol-2-ylmethyl)piperazin-1-yl]benzaldehyde

The title product was prepared according to the procedure used for INTERMEDIATE 80, using 2-thiazolecarboxaldehyde instead of 6-methyl-2-pyridinecarboxaldehyde. tert-Butyl 4-(1,3-thiazol-2-ylmethyl)piperazine-1-carboxylate: $^1$H NMR (600 MHz, DMSO-$d_6$) δ ppm 7.72 (d, J=3.4 Hz, 1H) 7.66 (d, J=3.4 Hz, 1H) 3.85 (s, 2H) 3.33 (br. s., 4H) 2.44 (t, J=5.2 Hz, 4H) 1.39 (s, 9H). MS (ESI$^+$) m/z 284 [M+H]$^+$.
1-(1,3-Thiazol-2-ylmethyl)piperazine: $^1$H NMR (600 MHz, DMSO-$d_6$) δ ppm 7.70 (d, J=3.4 Hz, 1H) 7.64 (d, J=3.1 Hz, 1H) 3.77 (s, 2H) 2.70 (br. s., 4H) 2.40 (br. s., 4H). MS (ESI$^+$) m/z 184 [M+H]$^+$.
4-[4-(1,3-Thiazol-2-ylmethyl)piperazin-1-yl]benzaldehyde: $^1$H NMR (600 MHz, DMSO-$d_6$) δ ppm 9.72 (s, 1H) 7.74 (d, J=3.4 Hz, 1H) 7.71 (d, J=9.2 Hz, 2H) 7.68 (d, J=3.4 Hz, 1H) 7.05 (d, J=8.9 Hz, 2H) 3.91 (s, 2H) 3.42 (t, J=5.2 Hz, 4H) 2.63 (t, J=5.2 Hz, 4H). MS (ESI$^+$) m/z 288 [M+H]$^+$.

INTERMEDIATE 82

4-[4-(1H-Imidazol-4-ylmethyl)piperazin-1-yl]benzaldehyde

The title product was prepared according to the procedure used for INTERMEDIATE 80, using 1H-imidazole-4-carbaldehyde instead of 6-methyl-2-pyridinecarboxaldehyde. tert-Butyl 4-(1H-imidazol-4-ylmethyl)piperazine-1-carboxylate: MS (ESI$^+$) m/z 267 [M+H]$^+$. 1-(1H-Imidazol-4-ylmethyl)piperazine: The product was not isolated. The basic water phase was used directly in the next step. MS (ESI$^+$) m/z 167 [M+H]$^+$.
4-[4-(1H-Imidazol-4-ylmethyl)piperazin-1-yl]benzaldehyde: $^1$H NMR (600 MHz, DMSO-$d_6$) δ ppm 11.93 (br. s., 1H) 9.70 (s, 1H) 7.69 (d, J=9.2 Hz, 2H) 7.55 (d, J=1.2 Hz, 1H) 7.03 (d, J=8.9 Hz, 2H) 6.90 (br. s., 1H) 3.45 (s, 2H) 3.37 (t, J=5.2 Hz, 4H) 2.50 (t, J=5.2 Hz, 4H). MS (ESI$^+$) m/z 271 [M+H]$^+$.

INTERMEDIATE 83

4-{4-[(3,5-Dimethylisoxazol-4-yl)methyl]piperazin-1-yl}benzaldehyde

The title product was prepared according to the procedure used for INTERMEDIATE 80, using 3,5-dimethyl-4-isoxazolecarbaldehyde instead of 6-methyl-2-pyridinecarboxaldehyde. tert-Butyl 4-[(3,5-dimethylisoxazol-4-yl)methyl]piperazine-1-carboxylate: $^1$H NMR (600 MHz, DMSO-$d_6$) δ ppm 3.28 (br. s., 4H) 3.23 (s, 2H) 2.31 (s, 3H) 2.26 (t, J=4.9 Hz, 4H) 2.16 (s, 3H) 1.38 (s, 9H). MS (ESI$^+$) m/z 296 [M+H]$^+$.
1-[(3,5-Dimethylisoxazol-4-yl)methyl]piperazine: $^1$H NMR (600 MHz, DMSO-$d_6$) δ ppm 3.17 (s, 2H) 2.64 (t, J=4.4 Hz, 4H) 2.30 (s, 3H) 2.22 (br. s., 4H) 2.16 (s, 3H). MS (ESI$^+$) m/z 196 [M+H]$^+$.
4-{4-[(3,5-Dimethylisoxazol-4-yl)methyl]piperazin-1-yl}benzaldehyde: $^1$H NMR (600 MHz, DMSO-$d_6$) δ ppm 9.71 (s, 1H) 7.70 (d, J=8.9 Hz, 2H) 7.03 (d, J=8.9 Hz, 2H) 3.37 (t, J=5.2 Hz, 4H) 3.29 (s, 2H) 2.45 (t, J=4.9 Hz, 4H) 2.34 (s, 3H) 2.19 (s, 3H). MS (ESI$^+$) m/z 300 [M+H]$^+$.

INTERMEDIATE 84

4-[4-(Furan-2-ylmethyl)piperazin-1-yl]benzaldehyde

The title product was prepared according to the procedure used for INTERMEDIATE 80, using 2-furaldehyde instead of 6-methyl-2-pyridinecarboxaldehyde.
tert-Butyl 4-(furan-2-ylmethyl)piperazine-1-carboxylate: $^1$H NMR (600 MHz, DMSO-$d_6$) δ ppm 7.58 (d, J=1.8 Hz, 1H) 6.39 (dd, J=3.1, 1.8 Hz, 1H) 6.28 (d, J=3.1 Hz, 1H) 3.50 (s, 2H) 3.29 (br. s., 4H) 2.31 (t, J=5.2 Hz, 4H) 1.38 (s, 9H). MS (ESI$^+$) m/z 267 [M+H]$^+$. 1-(Furan-2-ylmethyl)piperazine: $^1$H NMR (600 MHz, CD$_3$OD) δ ppm 7.46 (dd, J=1.8, 0.6 Hz, 1H) 6.37 (dd, J=3.2, 2.0 Hz, 1H) 6.30 (dd, J=3.1, 0.6 Hz, 1H) 3.55 (s, 2H) 2.84 (t, J=5.0 Hz, 4H) 2.48 (br. s., 4H). MS (ESI$^+$) m/z 167 [M+H]$^+$.
4-[4-(Furan-2-ylmethyl)piperazin-1-yl]benzaldehyde: $^1$H NMR (600 MHz, DMSO-$d_6$) δ ppm 9.71 (s, 1H) 7.70 (d, J=8.9 Hz, 2H) 7.60 (dd, J=1.8, 0.9 Hz, 1H) 7.03 (d, J=8.9 Hz, 2H) 6.41 (dd, J=3.1, 1.8 Hz, 1H) 6.32 (d, J=3.4 Hz, 1H) 3.55 (s, 2H) 3.38 (t, J=5.2 Hz, 4H) 2.50 (t, J=5.2 Hz, 4H). MS (ESI$^+$) m/z 271 [M+H]$^+$.

INTERMEDIATE 85

4-{[4-(Pyrimidin-5-ylmethyl)piperazin-1-yl]methyl}benzaldehyde

The title product was prepared according to the procedure used for INTERMEDIATE 80, using pyrimidine-5-carbaldehyde instead of 6-methyl-2-pyridinecarboxaldehyde.
tert-Butyl 4-(pyrimidin-5-ylmethyl)piperazine-1-carboxylate: $^1$H NMR (600 MHz, DMSO-$d_6$) δ ppm 9.09 (s, 1H) 8.73 (s, 2H) 3.54 (s, 2H) 3.31 (br. s., 4H) 2.33 (t, J=5.2 Hz, 4H) 1.38 (s, 9H). MS (ESI$^+$) m/z 279 [M+H]$^+$.

5-(Piperazin-1-ylmethyl)pyrimidine: The product was not isolated. The basic water phase was used directly in the next step. MS (ESI$^+$) m/z 179 [M+H]$^+$.

4-{[4-(Pyrimidin-5-ylmethyl)piperazin-1-yl]methyl}benzaldehyde: $^1$H NMR (600 MHz, DMSO-d$_6$) δ ppm 9.71 (s, 1H) 9.11 (s, 1H) 8.77 (s, 2H) 7.70 (d, J=8.9 Hz, 2H) 7.04 (d, J=8.9 Hz, 2H) 3.60 (s, 2H) 3.40 (t, J=4.9 Hz, 4H) 2.52 (t, J=4.9 Hz, 4H). MS (ESI$^+$) m/z 283 [M+H]$^+$.

INTERMEDIATE 86

4-{4-[(6-Methylpyridin-3-yl)methyl]piperazin-1-yl}benzaldehyde

The title product was prepared according to the procedure used for INTERMEDIATE 80, using 6-methylnicotinaldehyde instead of 6-methyl-2-pyridinecarboxaldehyde.

tert-Butyl 4-[(6-methylpyridin-3-yl)methyl]piperazine-1-carboxylate: $^1$H NMR (600 MHz, DMSO-d$_6$) δ ppm 8.33 (d, J=2.1 Hz, 1H) 7.57 (dd, J=7.8, 2.3 Hz, 1H) 7.20 (d, J=7.9 Hz, 1H) 3.45 (s, 2H) 3.29 (br. s., 4H) 2.44 (s, 3H) 2.29 (t, J=5.2 Hz, 4H) 1.38 (s, 9H). MS (ESI$^+$) m/z 292 [M+H]$^+$.

1-[(6-Methylpyridin-3-yl)methyl]piperazine: H NMR (600 MHz, DMSO-d$_6$) δ ppm 8.31 (d, J=1.8 Hz, 1H) 7.56 (dd, J=7.8, 2.3 Hz, 1H) 7.19 (d, J=7.9 Hz, 1H) 3.39 (s, 2H) 2.65 (t, J=4.9 Hz, 4H) 2.43 (s, 3H) 2.25 (br. s., 4H). MS (ESI$^+$) m/z 192 [M+H]$^+$.

4-{4-[(6-Methylpyridin-3-yl)methyl]piperazin-1-yl}benzaldehyde: $^1$H NMR (600 MHz, DMSO-d$_6$) δ ppm 9.71 (s, 1H) 8.37 (d, J=2.1 Hz, 1H) 7.70 (d, J=8.9 Hz, 2H) 7.62 (dd, J=7.9, 2.4 Hz, 1H) 7.22 (d, J=7.9 Hz, 1H) 7.03 (d, J=8.9 Hz, 2H) 3.51 (s, 2H) 3.38 (t, J=5.2 Hz, 4H) 2.48 (t, J=4.9 Hz, 4H) 2.45 (s, 3H). MS (ESI$^+$) m/z 296 [M+H]$^+$.

INTERMEDIATE 87

4-[4-(Pyrazin-2-ylmethyl)piperazin-1-yl]benzaldehyde

The title product was prepared according to the procedure used for INTERMEDIATE 80, using pyrazine-2-carbaldehyde instead of 6-methyl-2-pyridinecarboxaldehyde.

tert-Butyl 4-(pyrazin-2-ylmethyl)piperazine-1-carboxylate: $^1$H NMR (600 MHz, DMSO-d$_6$) δ ppm 8.68 (d, J=1.5 Hz, 1H) 8.58 (dd, J=2.4, 1.5 Hz, 1H) 8.54 (d, J=2.4 Hz, 1H) 3.67 (s, 2H) 3.32 (br. s., 4H) 2.39 (t, J=4.9 Hz, 4H) 1.39 (s, 9H). MS (ESI$^+$) m/z 279 [M+H]$^+$.

2-(Piperazin-1-ylmethyl)pyrazine: $^1$H NMR (600 MHz, DMSO-d$_6$) δ ppm 8.66 (d, J=1.2 Hz, 1H) 8.57 (dd, J=2.4, 1.5 Hz, 1H) 8.52 (d, J=2.4 Hz, 1H) 3.61 (s, 2H) 2.69 (t, J=4.9 Hz, 4H) 2.34 (br. s., 4H). MS (ESI$^+$) m/z 179 [M+H]$^+$.

4-[4-(Pyrazin-2-ylmethyl)piperazin-1-yl]benzaldehyde: $^1$H NMR (600 MHz, DMSO-d$_6$) δ ppm 9.71 (s, 1H) 8.73 (d, J=1.5 Hz, 1H) 8.60 (dd, J=2.4, 1.5 Hz, 1H) 8.56 (d, J=2.4 Hz, 1H) 7.70 (d, J=9.2 Hz, 2H) 7.04 (d, J=8.9 Hz, 2H) 3.73 (s, 2H) 3.41 (t, J=5.2 Hz, 4H) 2.58 (t, J=4.9 Hz, 4H). MS (ESI$^+$) m/z 283 [M+H]$^+$.

INTERMEDIATE 88

4-[4-(Furan-2-ylmethyl)piperazin-1-yl]benzaldehyde

The title product was prepared according to the procedure used for INTERMEDIATE 80, using furan-2-carbaldehyde instead of 6-methyl-2-pyridinecarboxaldehyde.

tert-Butyl 4-(furan-2-ylmethyl)piperazine-1-carboxylate: $^1$H NMR (600 MHz, DMSO-d$_6$) δ ppm 7.58 (dd, J=1.8, 0.6 Hz, 1H) 6.39 (dd, J=3.1, 1.8 Hz, 1H) 6.28 (d, J=3.4 Hz, 1H) 3.50 (s, 2H) 3.29 (br. s., 4H) 2.31 (t, J=5.2 Hz, 4H) 1.38 (s, 9H). MS (ESI$^+$) m/z 267 [M+H]$^+$. 1-(Furan-2-ylmethyl)piperazine: $^1$H NMR (600 MHz, DMSO-d$_6$) δ ppm 7.57 (d, J=0.9 Hz, 1H) 6.38 (dd, J=2.9, 2.0 Hz, 1H) 6.25 (d, J=3.1 Hz, 1H) 3.43 (s, 2H) 2.67 (t, J=4.7 Hz, 4H) 2.29 (br. s., 4H). MS (ESI$^+$) m/z 167 [M+H]$^+$.

4-[4-(Furan-2-ylmethyl)piperazin-1-yl]benzaldehyde: $^1$H NMR (600 MHz, DMSO-d$_6$) δ ppm 9.70 (s, 1H) 7.69 (d, J=8.9 Hz, 2H) 7.60 (dd, J=1.8, 0.9 Hz, 1H) 7.03 (d, J=8.9 Hz, 2H) 6.41 (dd, J=3.1, 2.1 Hz, 1H) 6.31 (d, J=3.1 Hz, 1H) 3.55 (s, 2H) 3.38 (t, J=5.2 Hz, 4H) 2.50 (t, J=5.2 Hz, 4H). MS (ESI$^+$) m/z 271 [M+H]$^+$.

INTERMEDIATE 89

4-{4-[(5-Methylfuran-2-yl)methyl]piperazin-1-yl}benzaldehyde

The title product was prepared according to the procedure used for INTERMEDIATE 80, using 5-methylfuran-2-carbaldehyde instead of 6-methyl-2-pyridinecarboxaldehyde. tert-Butyl 4-[(5-methylfuran-2-yl)methyl]piperazine-1-carboxylate: $^1$H NMR (600 MHz, DMSO-d$_6$) δ ppm 6.13 (d, J=3.1 Hz, 1H) 5.98 (dd, J=2.9, 1.1 Hz, 1H) 3.41 (s, 2H) 3.29 (br. s., 4H) 2.30 (t, J=5.2 Hz, 4H) 2.22 (s, 3H) 1.38 (s, 9H). MS (ESI$^+$) m/z 281 [M+H]$^+$. 1-[(5-Methylfuran-2-yl)methyl]piperazine: $^1$H NMR (600 MHz, DMSO-d$_6$) δ ppm 6.10 (d, J=3.1 Hz, 1H) 5.96 (dd, J=3.0, 1.1 Hz, 1H) 3.34 (s, 2H) 2.66 (t, J=4.9 Hz, 4H) 2.28 (br. s., 4H) 2.22 (s, 3H). MS (ESI$^+$) m/z 181 [M+H]$^+$.

4-{4-[(5-Methylfuran-2-yl)methyl]piperazin-1-yl}benzaldehyde: $^1$H NMR (600 MHz, DMSO-d$_6$) δ ppm 9.71 (s, 1H) 7.70 (d, J=9.2 Hz, 2H) 7.03 (d, J=9.2 Hz, 2H) 6.16 (d, J=3.1 Hz, 1H) 5.99 (dd, J=2.7, 0.9 Hz, 1H) 3.47 (s, 2H) 3.38 (t, J=5.2 Hz, 4H) 2.50 (t, J=5.2 Hz, 4H) 2.23 (s, 3H). MS (ESI$^+$) m/z 285 [M+H]$^+$.

INTERMEDIATE 90

4-[4-(Furan-3-ylmethyl)piperazin-1-yl]benzaldehyde

The title product was prepared according to the procedure used for INTERMEDIATE 80, using furan-3-carbaldehyde instead of 6-methyl-2-pyridinecarboxaldehyde.

tert-Butyl 4-(furan-3-ylmethyl)piperazine-1-carboxylate: $^1$H NMR (600 MHz, DMSO-d$_6$) δ ppm 7.60 (t, J=1.5 Hz, 1H) 7.54-7.55 (m, 1H) 6.41 (dd, J=1.8, 0.9 Hz, 1H) 3.32 (s, 2H) 3.29 (br. s., 4H) 2.28 (t, J=5.2 Hz, 4H) 1.38 (s, 9H). MS (ESI$^+$) m/z 267 [M+H]$^+$. 1-(Furan-3-ylmethyl)piperazine: $^1$H NMR (600 MHz, DMSO-d$_6$) δ ppm 7.59 (t, J=1.7 Hz, 1H) 7.52 (d, J=0.9 Hz, 1H) 6.40 (d, J=0.9 Hz, 1H) 3.26 (s, 2H) 2.67 (t, J=4.9 Hz, 4H) 2.26 (br. s., 4H). MS (ESI$^+$) m/z 167 [M+H]$^+$.

4-[4-(Furan-3-ylmethyl)piperazin-1-yl]benzaldehyde: $^1$H NMR (600 MHz, DMSO-d$_6$) δ ppm 9.71 (s, 1H) 7.70 (d, J=8.9 Hz, 2H) 7.62 (t, J=1.5 Hz, 1H) 7.59 (s, 1H) 7.03 (d, J=8.9 Hz, 2H) 6.45 (d, J=0.9 Hz, 1H) 3.38 (t, J=4.9 Hz, 4H) 3.38 (s, 2H) 2.48 (t, J=4.9 Hz, 4H). MS (ESI$^+$) m/z 271 [M+H]$^+$.

INTERMEDIATE 91

4-[4-(1,3-Thiazol-4-ylmethyl)piperazin-1-yl]benzaldehyde

The title product was prepared according to the procedure used for INTERMEDIATE 80, using thiazole-4-carboxaldehyde instead of 6-methyl-2-pyridinecarboxaldehyde.

tert-Butyl 4-(1,3-thiazol-4-ylmethyl)piperazine-1-carboxylate: $^1$H NMR (600 MHz, DMSO-d$_6$) δ ppm 9.04 (d, J=2.1 Hz, 1H) 7.51 (d, J=2.1 Hz, 1H) 3.66 (s, 2H) 3.30 (t, J=4.9 Hz, 4H) 2.37 (t, J=4.9 Hz, 4H) 1.38 (s, 9H). MS (ESI$^+$) m/z 284 [M+H]$^+$.

1-(1,3-Thiazol-4-ylmethyl)piperazine: $^1$H NMR (600 MHz, DMSO-d$_6$) δ ppm 9.02 (d, J=2.1 Hz, 1H) 7.47 (d, J=2.1 Hz, 1H) 3.59 (s, 2H) 2.67 (t, J=4.9 Hz, 4H) 2.33 (br. s., 4H). MS (ESI$^+$) m/z 184 [M+H]$^+$.

4-[4-(1,3-Thiazol-4-ylmethyl)piperazin-1-yl]benzaldehyde: $^1$H NMR (600 MHz, DMSO-d$_6$) δ ppm 9.71 (s, 1H) 9.06 (d, J=2.1 Hz, 1H) 7.70 (d, J=8.9 Hz, 2H) 7.56 (d, J=2.1 Hz, 1H) 7.03 (d, J=9.2 Hz, 2H) 3.72 (s, 2H) 3.39 (t, J=5.2 Hz, 4H) 2.56 (t, J=5.2 Hz, 4H). MS (ESI$^+$) m/z 288 [M+H]$^+$.

INTERMEDIATE 92

4-[4-(1,3-Thiazol-5-ylmethyl)piperazin-1-yl]benzaldehyde

The title product was prepared according to the procedure used for INTERMEDIATE 80, using thiazole-5-carboxaldehyde instead of 6-methyl-2-pyridinecarboxaldehyde.

tert-Butyl 4-(1,3-thiazol-5-ylmethyl)piperazine-1-carboxylate: $^1$H NMR (600 MHz, DMSO-d$_6$) δ ppm 9.03 (s, 1H) 7.76 (s, 1H) 3.76 (s, 2H) 3.30 (br. s., 4H) 2.33 (t, J=4.9 Hz, 4H) 1.38 (s, 9H). MS (ESI$^+$) m/z 284 [M+H]$^+$.

1-(1,3-Thiazol-5-ylmethyl)piperazine: $^1$H NMR (600 MHz, DMSO-d$_6$) δ ppm 9.01 (s, 1H) 7.74 (s, 1H) 3.68 (s, 2H) 2.66 (t, J=4.9 Hz, 4H) 2.29 (br. s., 4H). MS (ESI$^+$) m/z 184 [M+H]$^+$.

4-[4-(1,3-Thiazol-5-ylmethyl)piperazin-1-yl]benzaldehyde: $^1$H NMR (600 MHz, DMSO-d$_6$) δ ppm 9.71 (s, 1H) 9.05 (d, J=0.6 Hz, 1H) 7.80 (d, J=0.6 Hz, 1H) 7.70 (d, J=8.9 Hz, 2H) 7.03 (d, J=8.9 Hz, 2H) 3.82 (s, 2H) 3.39 (t, J=5.2 Hz, 4H) 2.52 (t, J=5.2 Hz, 4H). MS (ESI$^+$) m/z 288 [M+H]$^+$.

INTERMEDIATE 93

4-{4-[(1-Methyl-1H-imidazol-2-yl)methyl]piperazin-1-yl}benzaldehyde

The title product was prepared according to the procedure used for INTERMEDIATE 80, using 1-methyl-1H-imidazole-2-carbaldehyde instead of 6-methyl-2-pyridinecarboxaldehyde. tert-Butyl 4-[(1-methyl-1H-imidazol-2-yl)methyl]piperazine-1-carboxylate: $^1$H NMR (600 MHz, DMSO-d$_6$) δ ppm 7.07 (d, J=1.2 Hz, 1H) 6.74 (d, J=1.2 Hz, 1H) 3.63 (s, 3H) 3.51 (s, 2H) 3.27 (br. s., 4H) 2.30 (t, J=4.9 Hz, 4H) 1.38 (s, 9H). MS (ESI$^+$) m/z 281 [M+H]$^+$.

1-[(1-Methyl-1H-imidazol-2-yl)methyl]piperazine: $^1$H NMR (600 MHz, DMSO-d$_6$) δ ppm 7.06 (d, J=1.2 Hz, 1H) 6.73 (d, J=1.2 Hz, 1H) 3.63 (s, 3H) 3.46 (s, 2H) 2.67 (t, J=4.9 Hz, 4H) 2.27 (br. s., 4H). MS (ESI$^+$) m/z 181 [M+H]$^+$.

4-{4-[(1-Methyl-1H-imidazol-2-yl)methyl]piperazin-1-yl}benzaldehyde: $^1$H NMR (600 MHz, DMSO-d$_6$) δ ppm 9.71 (s, 1H) 7.70 (d, J=8.9 Hz, 2H) 7.09 (d, J=0.9 Hz, 1H) 7.03 (d, J=8.9 Hz, 2H) 6.77 (d, J=1.2 Hz, 1H) 3.67 (s, 3H) 3.57 (s, 2H) 3.36 (t, J=4.9 Hz, 4H) 2.49 (t, J=5.2 Hz, 4H). MS (ESI$^+$) m/z 285 [M+H]$^+$.

INTERMEDIATE 94

4-{4-[(5-Methylpyridin-2-yl)methyl]piperazin-1-yl}benzaldehyde

The title product was prepared according to the procedure used for INTERMEDIATE 80, using 5-methylpyridine-2-carboxaldehyde instead of 6-methyl-2-pyridinecarboxaldehyde.

tert-Butyl 4-[(5-methylpyridin-2-yl)methyl]piperazine-1-carboxylate: $^1$H NMR (600 MHz, DMSO-d$_6$) δ ppm 8.32 (d, J=2.4 Hz, 1H) 7.57 (dd, J=7.8, 1.7 Hz, 1H) 7.31 (d, J=7.9 Hz, 1H) 3.55 (s, 2H) 3.30 (br. s., 4H) 2.34 (t, J=4.9 Hz, 4H) 2.27 (s, 3H) 1.38 (s, 9H). MS (ESI$^+$) m/z 292 [M+H]$^+$.

1-[(5-Methylpyridin-2-yl)methyl]piperazine: H NMR (600 MHz, DMSO-d$_6$) δ ppm 8.30 (dd, J=1.5, 0.9 Hz, 1H) 7.55 (dd, J=7.9, 1.8 Hz, 1H) 7.30 (d, J=7.9 Hz, 1H) 3.48 (s, 2H) 2.67 (t, J=4.9 Hz, 4H) 2.30 (br. s., 4H) 2.26 (s, 3H). MS (ESI$^+$) m/z 192 [M+H]$^+$.

4-{4-[(5-Methylpyridin-2-yl)methyl]piperazin-1-yl}benzaldehyde: $^1$H NMR (600 MHz, DMSO-d$_6$) δ ppm 9.71 (s, 1H) 8.34 (d, J=1.8 Hz, 1H) 7.70 (d, J=8.9 Hz, 2H) 7.59 (dd, J=7.9, 1.8 Hz, 1H) 7.36 (d, J=7.9 Hz, 1H) 7.03 (d, J=9.2 Hz, 2H) 3.60 (s, 2H) 3.39 (t, J=5.2 Hz, 4H) 2.53 (t, J=5.2 Hz, 4H) 2.28 (s, 3H). MS (ESI$^+$) m/z 296 [M+H]$^+$.

INTERMEDIATE 95

4-[4-(2-Methoxyethyl)-3-methylpiperazin-1-yl]benzaldehyde

The title product was prepared according to the procedure used for INTERMEDIATE 66, using N-1-boc-3-methylpiperazine instead of 1-boc-piperazine and 2-bromoethyl methyl ether instead of 2-bromoethyl ethyl ether.

tert-Butyl 4-(2-methoxyethyl)-3-methylpiperazine-1-carboxylate: $^1$H NMR (600 MHz, CD$_3$OD) δ ppm 3.67-3.75 (m, 1H) 3.64-3.71 (m, 1H) 3.54 (ddd, J=10.22, 6.80, 4.81 Hz, 1H) 3.50 (ddd, J=10.22, 5.95, 5.19 Hz, 1H) 3.33 (s, 3H) 3.09-3.18 (m, 1H) 2.89-2.96 (m, 1H) 2.87 (ddd, J=11.98, 4.12, 3.43 Hz, 1H) 2.72-2.91 (m, 1H) 2.51 (ddd, J=13.77, 5.95, 4.81 Hz, 1H) 2.41-2.48 (m, 1H) 2.28-2.36 (m, 1H) 1.45 (s, 9H) 1.06 (d, J=6.10 Hz, 3H). MS (ESI$^+$) m/z 259 [M+H]$^+$.

1-(2-Methoxyethyl)-2-methylpiperazine: $^1$H NMR (600 MHz, CD$_3$OD) δ ppm 3.54 (ddd, J=10.18, 6.81, 4.94 Hz, 1H) 3.51 (ddd, J=10.18, 5.93, 5.27 Hz, 1H) 3.33 (s, 3H) 2.97 (ddd, J=13.77, 6.83, 5.34 Hz, 1H) 2.88-2.93 (m, 2H) 2.85 (ddd, J=12.32, 2.78, 1.53 Hz, 1H) 2.77-2.83 (m, 1H) 2.45-2.52 (m, 2H) 2.38-2.45 (m, 1H) 2.36 (ddd, J=12.05, 11.14, 3.36 Hz, 1H) 1.05 (d, J=6.26 Hz, 3H). MS (ESI$^+$) m/z 159 [M+H]$^+$.

4-[4-(2-Methoxyethyl)-3-methylpiperazin-1-yl]benzaldehyde: $^1$H NMR (600 MHz, DMSO-d$_6$) δ ppm 9.70 (s, 1H) 7.67-7.71 (m, 2H) 7.01-7.06 (m, 2H) 3.67-3.73 (m, 2H) 3.40-3.47 (m, 2H) 3.24 (s, 3H) 3.03 (ddd, J=12.50, 10.40, 3.20 Hz, 1H) 2.92 (ddd, J=11.80, 3.60, 3.20 Hz, 1H) 2.86 (dt, J=13.54, 6.20 Hz, 1H) 2.73 (dd, J=12.51, 9.16 Hz, 1H) 2.45-2.50 (m, 1H) 2.42 (dt, J=13.54, 5.82 Hz, 1H) 2.38 (ddd, J=11.80, 10.40, 3.14 Hz, 1H) 1.05 (d, J=6.26 Hz, 3H). MS (ESI$^+$) m/z 263 [M+H]$^+$.

INTERMEDIATE 96

4-[3-Methyl-4-(pyridin-3-ylmethyl)piperazin-1-yl]benzaldehyde

The title product was prepared according to the procedure used for INTERMEDIATE 80, using 3-pyridinecarboxaldehyde instead of 6-methyl-2-pyridinecarboxaldehyde and N-1-boc-3-methylpiperazine instead of 1-boc-piperazine.

tert-Butyl 3-methyl-4-(pyridin-3-ylmethyl)piperazine-1-carboxylate: $^1$H NMR (600 MHz, CD$_3$OD) δ ppm 8.50 (ddt, J=2.19, 0.89, 0.65 Hz, 1H) 8.43 (dd, J=4.84, 1.66 Hz, 1H) 7.85 (dddt, J=7.84, 2.19, 1.66, 0.54, Hz, 1H) 7.42 (ddd, J=7.84, 4.91, 0.89 Hz, 1H) 4.03 (d, J=13.73 Hz, 1H)

3.66-3.74 (m, 1H) 3.57-3.68 (m, 1H) 3.34 (d, J=13.73 Hz, 1H) 3.13 (ddd, J=12.89, 9.61, 2.98 Hz, 1H) 2.76-3.08 (m, 1H) 2.60-2.68 (m, 1H) 2.44-2.52 (m, 1H) 2.10-2.18 (m, 1H) 1.45 (s, 9H) 1.16 (d, J=6.26 Hz, 3H). MS (ESI$^+$) m/z 292 [M+H]$^+$.

2-Methyl-1-(pyridin-3-ylmethyl)piperazine: $^1$H NMR (600 MHz, CD$_3$OD) δ ppm 8.50 (ddt, J=2.20, 0.91, 0.60 Hz, 1H) 8.43 (dd, J=4.89, 1.66 Hz, 1H) 7.84 (dddt, J=7.82, 2.20, 1.66, 0.51 Hz, 1H) 7.42 (ddd, J=7.82, 4.89, 0.91 Hz, 1H) 4.12 (d, J=13.73 Hz, 1H) 3.28 (d, J=13.73 Hz, 1H) 2.92 (ddd, J=12.52, 2.95, 1.37 Hz, 1H) 2.87 (dtd, J=12.57, 3.10, 1.30 Hz, 1H) 2.75 (ddd, J=12.60, 10.89, 3.10 Hz, 1H) 2.65 (dt, J=11.91, 3.10 Hz, 1H) 2.55 (dd, J=12.52, 9.72 Hz, 1H) 2.44 (dqd, J=9.72, 6.24, 2.95 Hz, 1H) 2.16 (ddd, J=11.89, 10.89, 3.10 Hz, 1H) 1.18 (d, J=6.24 Hz, 3H). MS (ESI$^+$) m/z 192 [M+H]$^+$.

4-[3-Methyl-4-(pyridin-3-ylmethyl)piperazin-1-yl]benzaldehyde: $^1$H NMR (600 MHz, DMSO-d$_6$) δ ppm 9.70 (s, 1H) 8.53 (d, J=2.00 Hz, 1H) 8.47 (dd, J=4.81, 1.68 Hz, 1H) 7.74 (ddd, J=7.77, 2.00, 1.68 Hz, 1H) 7.67-7.71 (m, 2H) 7.37 (ddd, J=7.77, 4.81, 0.61 Hz, 1H) 7.01-7.05 (m, 2H) 4.01 (d, J=13.73 Hz, 1H) 3.76 (ddd, J=12.55, 3.09, 1.59 Hz, 1H) 3.63-3.69 (m, 1H) 3.27 (d, J=13.73 Hz, 1H) 3.02 (ddd, J=12.55, 10.16, 3.09 Hz, 1H) 2.85 (dd, J=12.55, 8.97 Hz, 1H) 2.69 (ddd, J=11.76, 3.90, 3.09 Hz, 1H) 2.53 (dqd, J=8.97, 6.22, 3.09 Hz, 1H) 2.21 (ddd, J=11.67, 10.16, 3.09 Hz, 1H) 1.17 (d, J=6.22 Hz, 3H). MS (ESI$^+$) m/z 296 [M+H]$^+$.

INTERMEDIATE 97

4-[4-(3-Methoxypropyl)-3-methylpiperazin-1-yl]benzaldehyde

The title product was prepared according to the procedure used for INTERMEDIATE 66, using N-1-boc-3-methylpiperazine instead of 1-boc-piperazine and 3-bromopropyl methyl ether instead of 2-bromoethyl ethyl ether.

tert-Butyl 4-(3-methoxypropyl)-3-methylpiperazine-1-carboxylate: $^1$H NMR (600 MHz, CD$_3$OD) δ ppm 3.68-3.78 (m, 1H) 3.65-3.71 (m, 1H) 3.42 (t, J=6.18 Hz, 2H) 3.32 (s, 3H) 3.08-3.18 (m, 1H) 2.77-2.84 (m, 2H) 2.70-2.96 (m, 1H) 2.35-2.45 (m, 2H) 2.20-2.30 (m, 1H) 1.65-1.81 (m, 2H) 1.45 (s, 9H) 1.05 (d, J=6.26 Hz, 3H). MS (ESI$^+$) m/z 273 [M+H]$^+$.

1-(3-Methoxypropyl)-2-methylpiperazine: $^1$H NMR (600 MHz, CD$_3$OD) δ ppm 3.42 (t, J=6.18 Hz, 2H) 3.32 (s, 3H) 2.90 (dtd, J=12.40, 3.09, 1.53 Hz, 1H) 2.81-2.87 (m, J=14.10, 1.83, 1.50, 1.50 Hz, 3H) 2.79 (ddd, J=12.51, 11.00, 2.95 Hz, 1H) 2.45 (dd, J=12.47, 9.78 Hz, 1H) 2.39 (ddd, J=12.98, 10.42, 5.04 Hz, 1H) 2.33-2.39 (m, 1H) 2.27 (ddd, J=11.62, 11.00, 3.09 Hz, 1H) 1.74-1.82 (m, 1H) 1.66-1.74 (m, 1H) 1.05 (d, J=6.26 Hz, 3H). MS (ESI$^+$) m/z 173 [M+H]$^+$.

4-[4-(3-Methoxypropyl)-3-methylpiperazin-1-yl]benzaldehyde: $^1$H NMR (600 MHz, DMSO-d$_6$) δ ppm 9.70 (s, 1H) 7.67-7.71 (m, 2H) 7.01-7.06 (m, 2H) 3.67-3.74 (m, 2H) 3.35 (t, J=6.33 Hz, 2H) 3.22 (s, 3H) 3.03 (ddd, J=12.36, 10.38, 3.20 Hz, 1H) 2.87 (dt, J=11.60, 3.43 Hz, 1H) 2.70-2.78 (m, 2H) 2.40-2.46 (m, 1H) 2.21-2.29 (m, 2H) 1.57-1.71 (m, 2H) 1.04 (d, J=6.26 Hz, 3H). MS (ESI$^+$) m/z 277 [M+H]$^+$.

INTERMEDIATE 98

4-[3-Methyl-4-(1,3-thiazol-2-ylmethyl)piperazin-1-yl]benzaldehyde

The title product was prepared according to the procedure used for INTERMEDIATE 80, using 2-thiazolecarboxaldehyde instead of 6-methyl-2-pyridinecarboxaldehyde and N-1-boc-3-methylpiperazine instead of 1-boc-piperazine.

tert-Butyl 3-methyl-4-(1,3-thiazol-2-ylmethyl)piperazine-1-carboxylate: $^1$H NMR (600 MHz, CD$_3$OD) δ ppm 7.71 (d, J=3.36 Hz, 1H) 7.53 (d, J=3.36 Hz, 1H) 4.17 (d, J=15.56 Hz, 1H) 3.84 (d, J=15.56 Hz, 1H) 3.67-3.73 (m, 1H) 3.62-3.71 (m, 1H) 3.20 (ddd, J=12.55, 9.73, 2.75 Hz, 1H) 2.78-3.04 (m, 2H) 2.80 (dt, J=11.50, 3.81 Hz, 1H) 2.54-2.62 (m, 1H) 2.37 (ddd, J=11.44, 9.70, 3.36 Hz, 1H) 1.45 (s, 9H) 1.13 (d, J=6.41 Hz, 3H). MS (ESI$^+$) m/z 298 [M+H]$^+$.

2-Methyl-1-(1,3-thiazol-2-ylmethyl)piperazine: $^1$H NMR (600 MHz, CD$_3$OD) δ ppm 7.71 (d, J=3.36 Hz, 1H) 7.53 (d, J=3.36 Hz, 1H) 4.20 (d, J=15.50 Hz, 1H) 3.81 (d, J=15.50 Hz, 1H) 2.86-2.92 (m, 2H) 2.77-2.84 (m, 2H) 2.48-2.56 (m, 2H) 2.37-2.43 (m, 1H) 1.13 (d, J=5.95 Hz, 3H). MS (ESI$^+$) m/z 198 [M+H]$^+$.

4-[3-Methyl-4-(1,3-thiazol-2-ylmethyl)piperazin-1-yl]benzaldehyde: $^1$H NMR (600 MHz, DMSO-d$_6$) δ ppm 9.70 (s, 1H) 7.74 (d, J=3.30 Hz, 1H) 7.68-7.71 (m, 2H) 7.65 (d, J=3.30 Hz, 1H) 7.02-7.06 (m, 2H) 4.18 (d, J=15.48 Hz, 1H) 3.85 (d, J=15.48 Hz, 1H) 3.77 (ddd, J=12.63, 3.10, 1.70 Hz, 1H) 3.70-3.75 (m, 1H) 3.07 (ddd, J=12.66, 10.07, 3.05 Hz, 1H) 2.88 (dt, J=11.71, 3.45 Hz, 1H) 2.83 (dd, J=12.63, 9.10 Hz, 1H) 2.64 (dqd, J=9.10, 6.26, 3.10 Hz, 1H) 2.46 (ddd, J=11.71, 10.30, 3.13 Hz, 1H) 1.15 (d, J=6.26 Hz, 3H). MS (ESI$^+$) m/z 302 [M+H]$^+$.

INTERMEDIATE 99

4-[2-Methyl-4-(1,3-thiazol-2-ylmethyl)piperazin-1-yl]benzaldehyde

The title product was prepared according to the procedure used for INTERMEDIATE 80, using 2-thiazolecarboxaldehyde instead of 6-methyl-2-pyridinecarboxaldehyde and N-1-boc-2-methylpiperazine instead of 1-boc-piperazine. The last step was stirred at 100° C. for 5 days.

tert-Butyl 2-methyl-4-(1,3-thiazol-2-ylmethyl)piperazine-1-carboxylate: $^1$H NMR (600 MHz, CD$_3$OD) δ ppm 7.70 (d, J=3.36 Hz, 1H) 7.55 (d, J=3.36 Hz, 1H) 4.19-4.25 (m, 1H) 3.89 (d, J=15.11 Hz, 1H) 3.83 (dddd, J=13.27, 3.48, 1.98, 0.97 Hz, 1H) 3.80 (d, J=15.11 Hz, 1H) 3.16 (ddd, J=13.27, 12.25, 3.27 Hz, 1H) 2.87-2.92 (m, 1H) 2.74 (dt, J=11.24, 1.90 Hz, 1H) 2.32 (dd, J=11.24, 3.88 Hz, 1H) 2.19 (ddd, J=12.25, 11.24, 3.48 Hz, 1H) 1.46 (s, 9H) 1.29 (d, J=6.71 Hz, 3H). MS (ESI$^+$) m/z 298 [M+H]$^+$.

3-Methyl-1-(1,3-thiazol-2-ylmethyl)piperazine: $^1$H NMR (600 MHz, CD$_3$OD) δ ppm 7.71 (d, J=3.36 Hz, 1H) 7.55 (d, J=3.36 Hz, 1H) 3.83-3.90 (m, 2H) 2.91-2.96 (m, 1H) 2.80-2.89 (m, 4H) 2.17-2.25 (m, 1H) 1.89 (t, J=11.06 Hz, 1H) 1.04 (d, J=6.41 Hz, 3H). MS (ESI$^+$) m/z 198 [M+H]$^+$.

4-[2-methyl-4-(1,3-thiazol-2-ylmethyl)piperazin-1-yl]benzaldehyde. $^1$H NMR (600 MHz, CD$_3$OD) δ ppm 9.66 (s, 1H) 7.73-7.77 (m, 2H) 7.72 (d, J=3.36 Hz, 1H) 7.57 (d, J=3.36 Hz, 1H) 6.98-7.02 (m, 2H) 4.28-4.34 (m, 1H) 3.96 (d, J=14.95 Hz, 1H) 3.87 (d, J=14.95 Hz, 1H) 3.69-3.74 (m, 1H) 3.27 (ddd, J=12.52, 11.93, 3.56 Hz, 1H) 3.05-3.10 (m, 1H) 2.90 (dt, J=11.20, 2.19 Hz, 1H) 2.53 (dd, J=11.20, 3.59 Hz, 1H) 2.41 (ddd, J=11.93, 11.11, 3.51 Hz, 1H) 1.28 (d, J=6.71 Hz, 3H). MS (ESI$^+$) m/z 302 [M+H]$^+$.

INTERMEDIATE 100

4-[4-(2-Methoxyethyl)-2-methylpiperazin-1-yl]benzaldehyde

The title product was prepared according to the procedure used for INTERMEDIATE 66, using N-1-boc-2-methylpiperazine instead of 1-boc-piperazine and 2-bromoethyl methyl ether instead of 2-bromoethyl ethyl ether. The last step was stirred at 100° C. for 7 days.

tert-Butyl 4-(2-methoxyethyl)-2-methylpiperazine-1-carboxylate: $^1$H NMR (600 MHz, CD$_3$OD) δ ppm 4.13-4.20 (m, 1H) 3.77 (dddd, J=13.15, 3.51, 2.01, 1.04 Hz, 1H) 3.49-3.56 (m, 2H) 3.34 (s, 3H) 3.09 (ddd, J=13.15, 12.32, 3.37 Hz, 1H) 2.85 (dddd, J=11.40, 3.37, 2.01, 1.75 Hz, 1H) 2.77 (ddd, J=11.40, 1.87, 1.75 Hz, 1H) 2.55 (ddd, J=13.28, 6.10, 5.34 Hz, 1H) 2.49 (ddd, J=13.28, 5.80, 5.19 Hz, 1H) 2.15 (dd, J=11.40, 4.04 Hz, 1H) 1.99 (ddd, J=12.32, 11.40, 3.51 Hz, 1H) 1.45 (s, 9H) 1.24 (d, J=6.87 Hz, 3H). MS (ESI$^+$) m/z 259 [M+H]$^+$.

1-(2-Methoxyethyl)-3-methylpiperazine: $^1$H NMR (600 MHz, CD$_3$OD) δ ppm 3.53 (t, J=5.57 Hz, 2H) 3.33 (s, 3H) 2.89-2.93 (m, 1H) 2.80-2.88 (m, 4H) 2.56 (t, J=5.57 Hz, 2H) 2.04-2.10 (m, 1H) 1.75 (dd, J=11.50, 10.30 Hz, 1H) 1.04 (d, J=6.41 Hz, 3H). MS (ESI$^+$) m/z 159 [M+H]$^+$.

4-[4-(2-Methoxyethyl)-2-methylpiperazin-1-yl]benzaldehyde: $^1$H NMR (600 MHz, CD$_3$OD) δ ppm 9.66 (s, 1H) 7.72-7.76 (m, 2H) 6.96-7.00 (m, 2H) 4.23-4.30 (m, 1H) 3.66 (dddd, J=12.32, 3.52, 2.20, 0.83 Hz, 1H) 3.59 (ddd, J=10.31, 6.28, 5.08 Hz, 1H) 3.57 (ddd, J=10.31, 5.87, 5.08 Hz, 1H) 3.37 (s, 3H) 3.20 (td, J=12.32, 3.52 Hz, 1H) 3.03 (ddt, J=11.29, 3.52, 2.20 Hz, 1H) 2.93 (dt, J=11.29, 2.20 Hz, 1H) 2.62 (ddd, J=13.15, 6.28, 5.08 Hz, 1H) 2.55 (ddd, J=13.15, 5.87, 5.08 Hz, 1H) 2.37 (dd, J=11.29, 3.81 Hz, 1H) 2.22 (dd, J=12.32, 11.29, 3.62 Hz, 1H) 1.23 (d, J=6.71 Hz, 3H). MS (ESI$^+$) m/z 263 [M+H]$^+$.

INTERMEDIATE 101

4-(4-Benzylpiperazin-1-yl)benzaldehyde

The title product was prepared according to the procedure used for INTERMEDIATE 80, using benzaldehyde instead of 6-methyl-2-pyridinecarboxaldehyde.

tert-Butyl 4-benzylpiperazine-1-carboxylate: $^1$H NMR (600 MHz, CD$_3$OD) δ ppm 7.29-7.35 (m, 4H) 7.24-7.28 (m, 1H) 3.53 (s, 2H) 3.39-3.46 (m, 4H) 2.37-2.42 (m, 4H) 1.45 (s, 9H). MS (ESI$^+$) m/z 277 [M+H]$^+$.

1-Benzylpiperazine: $^1$H NMR (600 MHz, CD$_3$OD) δ ppm 7.29-7.34 (m, 4H) 7.24-7.28 (m, 1H) 3.51 (s, 2H) 2.84 (t, J=4.96 Hz, 4H) 2.32-2.60 (m, 4H). MS (ESI$^+$) m/z 177 [M+H]$^+$.

4-(4-Benzylpiperazin-1-yl)benzaldehyde: $^1$H NMR (600 MHz, CD$_3$OD) δ ppm 9.68 (s, 1H) 7.72-7.76 (m, 2H) 7.35-7.39 (m, 2H) 7.31-7.36 (m, 2H) 7.25-7.30 (m, 1H) 7.00-7.04 (m, 2H) 3.58 (s, 2H) 3.41-3.46 (m, 4H) 2.58-2.63 (m, 4H). MS (ESI$^+$) m/z 281 [M+H]$^+$.

INTERMEDIATE 102

4-[4-(3-Methoxypropyl)-2-methylpiperazin-1-yl]benzaldehyde

The title product was prepared according to the procedure used for INTERMEDIATE 66, using N-1-boc-2-methylpiperazine instead of 1-boc-piperazine and 3-bromopropyl methyl ether instead of 2-bromoethyl ethyl ether. The last step was stirred at 100° C. for 7 days.

tert-Butyl 4-(3-methoxypropyl)-2-methylpiperazine-1-carboxylate: $^1$H NMR (600 MHz, CD$_3$OD) δ ppm 4.15-4.21 (m, 1H) 3.78 (dddd, J=13.29, 3.51, 2.01, 0.99 Hz, 1H) 3.45 (t, J=6.36 Hz, 2H) 3.32 (s, 3H) 3.08 (ddd, J=13.29, 12.25, 3.32 Hz, 1H) 2.82 (dddd, J=11.34, 3.32, 2.01, 1.68 Hz, 1H) 2.74 (ddd, J=11.40, 1.90, 1.68 Hz, 1H) 2.41 (ddd, J=12.36, 8.29, 6.63 Hz, 1H) 2.33 (ddd, J=12.36, 8.24, 6.36 Hz, 1H) 2.07 (dd, J=11.40, 4.12 Hz, 1H) 1.91 (ddd, J=12.25, 11.34, 3.51 Hz, 1H) 1.69-1.80 (m, 2H) 1.45 (s, 9H) 1.23 (d, J=6.71 Hz, 3H). MS (ESI$^+$) m/z 273 [M+H]$^+$.

1-(3-Methoxypropyl)-3-methylpiperazine: $^1$H NMR (600 MHz, CD$_3$OD) δ ppm 3.42 (t, J=6.26 Hz, 2H) 3.32 (s, 3H) 2.90-2.95 (m, 1H) 2.78-2.87 (m, 4H) 2.39-2.45 (m, 2H) 1.97-2.04 (m, 1H) 1.74-1.81 (m, 2H) 1.69 (t, J=11.06 Hz, 1H) 1.05 (d, J=6.41 Hz, 3H). MS (ESI$^+$) m/z 173 [M+H]$^+$.

4-[4-(3-Methoxypropyl)-2-methylpiperazin-1-yl]benzaldehyde: H NMR (600 MHz, CD$_3$OD) δ ppm 9.66 (s, 1H) 7.72-7.76 (m, 2H) 6.96-7.00 (m, 2H) 4.25-4.31 (m, 1H) 3.67 (dddd, J=12.62, 3.59, 2.24, 0.90 Hz, 1H) 3.49 (dd, J=6.67, 6.42 Hz, 2H) 3.34 (s, 3H) 3.19 (ddd, J=12.62, 12.06, 3.55 Hz, 1H) 2.99 (ddt, J=11.23, 3.55, 2.24 Hz, 1H) 2.89 (dt, J=11.23, 2.24 Hz, 1H) 2.47 (ddd, J=12.22, 8.25, 6.67 Hz, 1H) 2.39 (ddd, J=12.22, 8.11, 6.42 Hz, 1H) 2.29 (dd, J=11.23, 3.89 Hz, 1H) 2.14 (ddd, J=12.06, 11.23, 3.59 Hz, 1H) 1.74-1.85 (m, 2H) 1.22 (d, J=6.71 Hz, 3H). MS (ESI$^+$) m/z 277 [M+H]$^+$.

INTERMEDIATE 103

4-[4-(2-Methoxyethyl)-3-oxopiperazin-1-yl]benzaldehyde

To a stirred mixture of 4-boc-piperazinone (2.00 g, 10.0 mmol) in DMF (25 mL) was added sodium hydride (95% dry, 505 mg, 20.0 mmol). The mixture was stirred at room temperature for 20 min and then 1-bromo-2-methoxyethane (2.78 g, 20.0 mmol) in DMF (5 mL) was added slowly and the reaction mixture was stirred at room temperature for 2 h. Ice-water (15 mL) was added and the mixture was extracted with DCM (2×50 mL). The combined extracts were washed with water (3×10 mL) and brine (10 mL), dried over MgSO$_4$ and concentrated in vacuo to yield 2.85 g of a clear, almost colorless oil. Purification by flash chromatography (silica, 1-2% MeOH in DCM) yielded 2.46 g (95%) of tert-butyl 4-(2-methoxyethyl)-3-oxopiperazine-1-carboxylate as a clear colorless oil. $^1$H NMR (600 MHz, CD$_3$OD) δ ppm 4.03 (s, 2H) 3.63 (br. s., 2H) 3.60 (dd, J=4.6, 1.2 Hz, 1H) 3.59 (dd, J=4.6, 0.6 Hz, 1H) 3.56 (dd, J=4.6, 0.9 Hz, 1H) 3.55 (dd, J=4.6, 1.2 Hz, 1H) 3.49 (t, J=5.5 Hz, 2H) 3.34 (s, 3H) 1.48 (s, 9H). MS (ESI$^+$) m/z 259 [M+H]$^+$.

The title product was prepared according to the procedure used for INTERMEDIATE 66 using the product from the previous step.

1-(2-Methoxyethyl)piperazin-2-one tris(trifluoroacetate): $^1$H NMR (600 MHz, CD$_3$OD) δ ppm 3.85 (s, 2H) 3.71-3.74 (m, 2H) 3.65 (t, J=5.2 Hz, 2H) 3.59 (d, J=5.2 Hz, 1H) 3.58 (dd, J=5.5, 0.6 Hz, 1H) 3.50-3.53 (m, 2H) 3.35 (s, 3H). MS (ESI$^+$) m/z 159 [M+H]$^+$.

4-[4-(2-Methoxyethyl)-3-oxopiperazin-1-yl]benzaldehyde: $^1$H NMR (600 MHz, DMSO-d$_6$) δ ppm 9.73 (s, 1H) 7.73 (d, J=8.9 Hz, 2H) 7.00 (d, J=8.9 Hz, 2H) 4.00 (s, 2H) 3.66 (t, J=5.9 Hz, 2H) 3.54 (td, J=5.2 Hz, 4H) 3.48 (t, J=5.5 Hz, 2H) 3.25 (s, 3H). MS (ESI$^+$) m/z 263 [M+H]$^+$.

INTERMEDIATE 104

4-[4-(Methoxyacetyl)piperazin-1-yl]benzaldehyde

Methoxyacetyl chloride (1.09 g, 10 mmol) was added dropwise at ice-bath temperature to a solution of boc-piperazine (1.86 g, 10 mmol) and DIPEA (2.59 g, 20 mmol, 3.48 mL) in DCM (25 mL). The reaction mixture was stirred for 50 min at ice-bath temperature and then 0.5 h at room temperature. DCM (10 mL) and water (10 mL) were added. The organic phase was washed with water (10 mL), 2M citric acid (2×10 mL) and brine (10 mL), dried over MgSO$_4$, filtered and evaporated to yield 1.95 g (75%) of tert-butyl 4-(methoxyacetyl)-piperazine-1-carboxylate as colorless oil. $^1$H NMR (600 MHz, CDCl$_3$) δ ppm 4.11 (s, 2H) 3.55-3.62 (m, 2H) 3.42 (s, 3H) 3.40-3.49 (m, 6H) 1.47 (s, 9H). MS (ESI$^+$) m/z 259 [M+H]$^+$.

The title product was prepared according to the procedure used for INTERMEDIATE 66 using the product from the previous step.

1-(Methoxyacetyl)piperazine trifluoroacetate: $^1$H NMR (600 MHz, CDCl$_3$) δ ppm 4.20 (s, 2H) 3.78-3.85 (m, 2H) 3.72-3.79 (m, 2H) 3.41 (s, 3H) 3.20-3.29 (m, 4H). MS (ESI$^+$) m/z 159 [M+H]$^+$.

4-[4-(Methoxyacetyl)piperazin-1-yl]benzaldehyde: $^1$H NMR (600 MHz, DMSO-d$_6$) δ ppm 9.73 (s, 1H) 7.71-7.75 (m, 2H) 7.03-7.07 (m, 2H) 4.13 (s, 2H) 3.56-3.61 (m, 2H) 3.52-3.57 (m, 2H) 3.43-3.47 (m, 2H) 3.40-3.45 (m, 2H) 3.30 (s, 3H). MS (ESI$^+$) m/z 263 [M+H]$^+$.

INTERMEDIATE 105

4-[4-(3-Methoxypropyl)-3-oxopiperazin-1-yl]benzaldehyde

The title product was prepared according to the procedure used for INTERMEDIATE 103 using 1-bromo-3-methoxypropane instead of 1-bromo-2-methoxyethane.

tert-Butyl 4-(3-methoxypropyl)-3-oxopiperazine-1-carboxylate: $^1$H NMR (600 MHz, CD$_3$OD) δ ppm 4.01 (br. s., 2H) 3.60-3.68 (m, 2H) 3.46-3.51 (m, 2H) 3.39-3.44 (m, 4H) 3.31 (s, 3H) 1.80-1.86 (m, 2H) 1.48 (s, 9H). MS (ESI$^+$) m/z 273 [M+H]

1-(3-Methoxypropyl)piperazin-2-one trifluoroacetate: $^1$H NMR (600 MHz, CD$_3$OD) δ ppm 3.83 (s, 2H) 3.61-3.65 (m, 2H) 3.50-3.54 (m, 4H) 3.44 (t, J=5.95 Hz, 2H) 3.33 (s, 3H) 1.82-1.89 (m, 2H). MS (ESI$^+$) m/z 173 [M+H]$^+$.

4-[4-(3-Methoxypropyl)-3-oxopiperazin-1-yl]benzaldehyde: $^1$H NMR (600 MHz, DMSO-d$_6$) δ ppm 9.73 (s, 1H) 7.71-7.75 (m, 2H) 6.98-7.02 (m, 2H) 3.98 (s, 2H) 3.64-3.69 (m, 2H) 3.45-3.50 (m, 2H) 3.37-3.43 (m, 2H) 3.30-3.33 (m, 2H) 3.21 (s, 3H) 1.70-1.77 (m, 2H). MS (ESI$^+$) m/z 277 [M+H]

INTERMEDIATE 106

4-[4-(2-Ethoxyethyl)-3-oxopiperazin-1-yl]benzaldehyde

The title product was prepared according to the procedure used for INTERMEDIATE 103 using 1-bromo-2-ethoxyethane instead of 1-bromo-2-methoxyethane.

tert-Butyl 4-(2-ethoxyethyl)-3-oxopiperazine-1-carboxylate: $^1$H NMR (600 MHz, CD$_3$OD) δ ppm 4.03 (s, 2H) 3.63 (br. s., 2H) 3.57-3.61 (m, 4H) 3.49-3.52 (m, 2H) 3.50 (q, J=7.0 Hz, 2H) 1.48 (s, 9H) 1.17 (t, J=7.0 Hz, 3H). MS (ESI$^+$) m/z 273 [M+H]$^+$.

1-(2-Ethoxyethyl)piperazin-2-one trifluoroacetate: $^1$H NMR (600 MHz, CD$_3$OD) δ ppm 3.85 (s, 2H) 3.74 (dd, J=6.1, 5.5 Hz, 2H) 3.61-3.66 (m, 4H) 3.50-3.53 (m, 2H) 3.52 (q, J=7.0 Hz, 2H) 1.18 (t, J=7.0 Hz, 3H). MS (ESI$^+$) m/z 173 [M+H]$^+$.

4-[4-(2-Ethoxyethyl)-3-oxopiperazin-1-yl]benzaldehyde: $^1$H NMR (600 MHz, DMSO-d$_6$) δ ppm 9.73 (s, 1H) 7.73 (d, J=8.9 Hz, 2H) 7.01 (d, J=8.9 Hz, 2H) 4.00 (s, 2H) 3.66 (dd, J=6.4, 4.3 Hz, 2H) 3.49-3.56 (m, 6H) 3.42 (q, J=7.0 Hz, 2H) 1.08 (t, J=6.9 Hz, 3H). MS (ESI$^+$) m/z 277 [M+H]$^+$.

INTERMEDIATE 107

4-[4-(2-Hydroxyethyl)piperidin-1-yl]benzaldehyde

The title product was prepared according to the last step of the procedure used for INTERMEDIATE 66 using 4-piperidine ethanol and 4-fluorobenzaldehyde. $^1$H NMR (600 MHz, CD$_3$OD) δ ppm 9.67 (s, 1H) 7.66-7.69 (m, 2H) 6.99-7.03 (m, 2H) 4.37 (t, J=5.11 Hz, 1H) 3.95-4.00 (m, 2H) 3.46 (td, J=6.61, 5.11 Hz, 2H) 2.87 (td, J=12.70, 2.52 Hz, 2H) 1.70-1.76 (m, 2H) 1.62-1.70 (m, 1H) 1.37 (q, J=6.61 Hz, 2H) 1.11-1.20 (m, J=12.70, 12.11, 12.11, 4.04 Hz, 2H). MS (ESI$^+$) m/z 234 [M+H]$^+$.

INTERMEDIATE 108

4-[4-(3-Hydroxypropyl)piperazin-1-yl]benzaldehyde

The title product was prepared according to the procedure used for INTERMEDIATE 66, using 3-bromo-1-propanol instead of 2-bromoethyl ethyl ether.

tert-Butyl 4-(3-hydroxypropyl)piperazine-1-carboxylate: $^1$H NMR (600 MHz, CD$_3$OD) δ ppm 4.42 (br. s., 1H) 3.42 (t, J=6.33 Hz, 2H) 3.24-3.31 (m, 4H) 2.29-2.34 (m, 2H) 2.24-2.30 (m, 4H) 1.52-1.59 (m, 2H) 1.39 (s, 9H). MS (ESI$^+$) m/z 245 [M+H]$^+$.

3-Piperazin-1-ylpropan-1-ol: $^1$H NMR (600 MHz, CD$_3$OD) δ ppm 3.61 (t, J=6.26 Hz, 2H) 2.84 (t, J=4.96 Hz, 4H) 2.44-2.48 (m, 2H) 2.34-2.60 (m, 4H) 1.70-1.77 (m, 2H). MS (ESI$^+$) m/z 145 [M+H]$^+$.

4-[4-(3-Hydroxypropyl)piperazin-1-yl]benzaldehyde: $^1$H NMR (600 MHz, CD$_3$OD) δ ppm 9.71 (s, 1H) 7.75-7.79 (m, 2H) 7.03-7.07 (m, 2H) 3.65 (t, J=6.26 Hz, 2H) 3.44-3.48 (m, 4H) 2.62-2.67 (m, 4H) 2.52-2.56 (m, 2H) 1.76-1.82 (m, 2H). MS (ESI$^+$) m/z 249 [M+H]$^+$.

INTERMEDIATE 109

4-{4-[2-(1-Methylethoxy)ethyl]-3-oxopiperazin-1-yl}benzaldehyde

The title product was prepared according to the procedure used for INTERMEDIATE 103 using 2-(1-methylethoxy)ethyl methanesulfonate (INTERMEDIATE 69) instead of 1-bromo-2-methoxyethane.

tert-Butyl 4-[2-(1-methylethoxy)ethyl]-3-oxopiperazine-1-carboxylate: $^1$H NMR (600 MHz, CD$_3$OD) δ ppm 4.03 (s, 2H) 3.62 (br. s., 2H) 3.59-3.61 (m, 2H) 3.59 (spt, J=6.1 Hz, 1H) 3.54-3.57 (m, 2H) 3.52 (t, J=5.5 Hz, 2H) 1.48 (s, 9H) 1.13 (d, J=6.1 Hz, 6H). MS (ESI$^+$) m/z 287 [M+H]$^+$.

1-[2-(1-Methylethoxy)ethyl]piperazin-2-one trifluoroacetate: $^1$H NMR (600 MHz, CD$_3$OD) δ ppm 3.85 (s, 2H) 3.75 (t, J=5.8 Hz, 2H) 3.60-3.65 (m, 5H) 3.51 (t, J=5.8 Hz, 2H) 1.15 (d, J=6.1 Hz, 6H). MS (ESI$^+$) m/z 187 [M+H]$^+$.

4-{4-[2-(1-Methylethoxy)ethyl]-3-oxopiperazin-1-yl}benzaldehyde: $^1$H NMR (600 MHz, DMSO-d$_6$) δ ppm 9.73 (s, 1H) 7.73 (d, J=8.9 Hz, 2H) 7.01 (d, J=8.9 Hz, 2H) 4.00 (s, 2H) 3.66 (dd, J=6.4, 4.3 Hz, 2H) 3.56 (dd, J=6.4, 4.3

Hz, 2H) 3.53 (spt, J=6.1 Hz, 1H) 3.50 (s, 4H) 1.05 (d, J=5.8 Hz, 6H). MS (ESI⁺) m/z 291 [M+H]

INTERMEDIATE 110

4-[4-(3-Methoxypropanoyl)piperazin-1-yl]benzaldehyde

The title product was prepared according to the procedure used for INTERMEDIATE 104 using 3-methoxypropanoyl chloride instead of methoxyacetyl chloride.

tert-Butyl 4-(3-methoxypropanoyl)piperazine-1-carboxylate: ¹H NMR (600 MHz, CD₃OD) δ ppm 3.66 (t, J=6.23 Hz, 2H) 3.53-3.60 (m, 4H) 3.43-3.49 (m, 2H) 3.37-3.44 (m, 2H) 3.33 (s, 3H) 2.66 (t, J=6.23 Hz, 2H) 1.47 (s, 9H). MS (ESI⁺) m/z 273 [M+H]⁺.

1-(3-Methoxypropanoyl)piperazine trifluoroacetate: ¹H NMR (600 MHz, CD₃OD) δ ppm 3.80-3.85 (m, 4H) 3.68 (t, J=6.10 Hz, 2H) 3.34 (s, 3H) 3.22-3.27 (m, 2H) 3.17-3.23 (m, 2H) 2.69 (t, J=6.03 Hz, 2H). MS (ESI⁺) m/z 173 [M+H]⁺.

4-[4-(3-Methoxypropanoyl)piperazin-1-yl]benzaldehyde: ¹H NMR (600 MHz, DMSO-d₆) δ ppm 9.73 (s, 1H) 7.71-7.75 (m, 2H) 7.02-7.06 (m, 2H) 3.58-3.64 (m, 4H) 3.57 (t, J=6.56 Hz, 2H) 3.43-3.48 (m, 2H) 3.37-3.42 (m, 2H) 3.23 (s, 3H) 2.61 (t, J=6.56 Hz, 2H). MS (ESI⁺) m/z 277 [M+H]

INTERMEDIATE 111

4-[4-(2-Methoxyethyl)piperidin-1-yl]benzaldehyde

Sodium hydride (202 mg, 8.0 mmol, 95%) was added in portions to a solution of tert-butyl-4-(2-hydroxyethyl) piperidine-1-carboxylate (917 mg, 4.0 mmol) in DMF (5 mL). The mixture was stirred at room temperature for 0.5 h and methyl iodide (1.14 g, 8.0 mmol) in DMF (3 mL) was added slowly. The reaction was quenched after 18 h by addition of water (10 mL), and the resulting aqueous phase was extracted with EtOAc (3×20 mL). The combined organic phases were washed with brine (2×5 mL), dried over MgSO₄, and concentrated in vacuo to yield 1.177 g of crude material as a light yellow oil. Purification by flash chromatography (silica, 10-20% EtOAc in n-hexane) yielded 912 mg (94%) of pure tert-butyl 4-(2-methoxyethyl)piperidine-1-carboxylate as a colorless oil. ¹H NMR (600 MHz, CD₃OD) δ ppm 4.04 (d, J=13.4 Hz, 2H) 3.45 (t, J=6.4 Hz, 2H) 3.31 (s, 3H) 2.73 (br. s., 2H) 1.69 (d, J=12.5 Hz, 2H) 1.54-1.64 (m, 1H) 1.51 (q, J=6.6 Hz, 2H) 1.45 (s, 9H) 1.07 (qd, J=12.2, 4.4 Hz, 2H). MS (ESI⁺) m/z 188 [M+H-t-Bu]+.

The title product was prepared according to the procedure used for INTERMEDIATE 66, using the intermediate described in the previous step.

4-(2-Methoxyethyl)piperidine hydrochloride: ¹H NMR (600 MHz, CD₃OD) δ ppm 3.46 (t, J=6.3 Hz, 2H) 3.37 (d, J=12.8 Hz, 2H) 3.32 (s, 3H) 2.97 (td, J=13.0, 3.1 Hz, 2H) 1.96 (d, J=14.3 Hz, 2H) 1.72-1.82 (m, 1H) 1.57 (q, J=6.4 Hz, 2H) 1.40 (qd, J=12.9, 3.6 Hz, 2H). MS (ESI⁺) m/z 144 [M+H]⁺.

4-[4-(2-Methoxyethyl)piperidin-1-yl]benzaldehyde: ¹H NMR (600 MHz, DMSO-d₆) δ ppm 9.68 (s, 1H) 7.67 (d, J=8.9 Hz, 2H) 7.01 (d, J=8.9 Hz, 2H) 3.98 (d, J=13.4 Hz, 2H) 3.37 (t, J=6.6 Hz, 2H) 3.22 (s, 3H) 2.87 (td, J=12.7, 2.4 Hz, 2H) 1.73 (d, J=12.5 Hz, 2H) 1.59-1.68 (m, 1H) 1.45 (q, J=6.6 Hz, 2H) 1.16 (qd, J=12.2, 4.0 Hz, 2H). MS (ESI⁺) m/z 248 [M+H]⁺.

INTERMEDIATE 112

4-[4-(2-Ethoxyethyl)piperidin-1-yl]benzaldehyde

The title product was prepared according to the procedure used for INTERMEDIATE 111, using ethyl iodide instead of methyl iodide.

tert-Butyl 4-(2-ethoxyethyl)piperidine-1-carboxylate: ¹H NMR (600 MHz, CD₃OD) δ ppm 4.04 (d, J=13.1 Hz, 2H) 3.49 (t, J=6.6 Hz, 2H) 3.48 (q, J=7.0 Hz, 2H) 2.74 (br. s., 2H) 1.69 (d, J=12.5 Hz, 2H) 1.56-1.66 (m, 1H) 1.51 (q, J=6.6 Hz, 2H) 1.45 (s, 9H) 1.17 (t, J=7.0 Hz, 3H) 1.08 (qd, J=12.2, 4.4 Hz, 2H). MS (ESI⁺) m/z 202 [M+H-t-Bu]

4-(2-Ethoxyethyl)piperidine hydrochloride: ¹H NMR (600 MHz, CD₃OD) δ ppm 3.51 (t, J=6.3 Hz, 2H) 3.48 (q, J=7.0 Hz, 2H) 3.37 (dt, J=12.9, 2.6 Hz, 2H) 2.97 (td, J=13.0, 3.1 Hz, 2H) 1.96 (d, J=14.3 Hz, 2H) 1.73-1.83 (m, 1H) 1.57 (q, J=6.4 Hz, 2H) 1.34-1.46 (m, 2H) 1.18 (t, J=7.0 Hz, 3H). MS (ESI⁺) m/z 158 [M+H]⁺.

4-[4-(2-Ethoxyethyl)piperidin-1-yl]benzaldehyde: ¹H NMR (600 MHz, DMSO-d₆) δ ppm 9.68 (s, 1H) 7.67 (d, J=9.2 Hz, 2H) 7.01 (d, J=9.2 Hz, 2H) 3.98 (d, J=13.1 Hz, 2H) 3.40 (t, J=6.7 Hz, 2H) 3.40 (q, J=7.0 Hz, 2H) 2.88 (td, J=12.7, 2.4 Hz, 2H) 1.73 (d, J=12.8 Hz, 2H) 1.59-1.69 (m, 1H) 1.45 (q, J=6.7 Hz, 2H) 1.16 (qd, J=12.2, 3.8 Hz, 2H) 1.10 (t, J=7.0 Hz, 3H). MS (ESI⁺) m/z 262 [M+H]⁺.

INTERMEDIATE 113

4-(4-Benzyl-3-oxopiperazin-1-yl)benzaldehyde

The title product was prepared according to the procedure used for INTERMEDIATE 103 using benzyl bromide instead of 1-bromo-2-methoxyethane.

tert-Butyl 4-benzyl-3-oxopiperazine-1-carboxylate: ¹H NMR (600 MHz, CD₃OD) δ ppm 7.32-7.37 (m, 2H) 7.26-7.31 (m, 1H) 7.26-7.29 (m, 2H) 4.63 (s, 2H) 4.12 (s, 2H) 3.56-3.65 (m, 2H) 3.31-3.33 (m, 2H) 1.47 (s, 9H). MS (ESI⁺) m/z 291 [M+H]⁺

1-Benzylpiperazin-2-one trifluoroacetate: ¹H NMR (600 MHz, CD₃OD) δ ppm 7.34-7.38 (m, 2H) 7.31-7.34 (m, 2H) 7.29-7.33 (m, 1H) 4.67 (s, 2H) 3.92 (s, 2H) 3.51-3.55 (m, 2H) 3.47-3.51 (m, 2H). MS (ESI⁺) m/z 191 [M+H]⁺.

4-(4-Benzyl-3-oxopiperazin-1-yl)benzaldehyde: ¹H NMR (600 MHz, DMSO-d₆) δ ppm 9.73 (s, 1H) 7.72-7.75 (m, 2H) 7.33-7.37 (m, 2H) 7.26-7.30 (m, 3H) 7.00-7.04 (m, 2H) 4.61 (s, 2H) 4.11 (s, 2H) 3.66-3.69 (m, 2H) 3.38-3.42 (m, 2H). MS (ESI⁺) m/z 295 [M+H]⁺.

INTERMEDIATE 114

4-(4-Methyl-3-oxopiperazin-1-yl)benzaldehyde

The title product was prepared according to the procedure used for INTERMEDIATE 103 using methyl iodide instead of 1-bromo-2-methoxyethane.

tert-Butyl 4-methyl-3-oxopiperazine-1-carboxylate: ¹H NMR (600 MHz, CD₃OD) δ ppm 4.01 (s, 2H) 3.61-3.69 (m, 2H) 3.37-3.42 (m, 2H) 2.98 (s, 3H) 1.47 (s, 9H). MS (ESI⁺) m/z 159 [M+H-t-Bu]+.

1-Methylpiperazin-2-one trifluoroacetate: ¹H NMR (600 MHz, CD₃OD) δ ppm 3.83 (s, 2H) 3.60-3.63 (m, 2H) 3.51-3.55 (m, 2H) 3.02 (s, 3H). MS (ESI⁺) m/z 115 [M+H]⁺.

4-(4-Methyl-3-oxopiperazin-1-yl)benzaldehyde: ¹H NMR (600 MHz, DMSO-d₆) δ ppm 9.73 (s, 1H) 7.72-7.75

(m, 2H) 7.01-7.05 (m, 2H) 3.98 (s, 2H) 3.67-3.72 (m, 2H) 3.44-3.48 (m, 2H) 2.91 (s, 3H). MS (ESI$^+$) m/z 219 [M+H]$^+$.

INTERMEDIATE 115

4-[4-(Pyridin-3-ylcarbonyl)piperazin-1-yl]benzaldehyde

The title product was prepared according to the procedure used for INTERMEDIATE 104 using pyridine-3-carbonyl chloride instead of methoxyacetyl chloride.

tert-Butyl 4-(pyridin-3-ylcarbonyl)piperazine-1-carboxylate: $^1$H NMR (600 MHz, CD$_3$OD) δ ppm 8.65 (dd, J=4.96, 1.67 Hz, 1H) 8.64 (dd, J=2.16, 0.93 Hz, 1H) 7.92 (ddd, J=7.88, 2.16, 1.67 Hz, 1H) 7.54 (ddd, J=7.88, 4.96, 0.93 Hz, 1H) 3.75 (br. s., 2H) 3.55 (br. s., 2H) 3.45 (br. s., 4H) 1.47 (s, 9H). MS (ESI$^+$) m/z 292 [M+H]$^+$.

1-(Pyridin-3-ylcarbonyl)piperazine bis(trifluoroacetate): $^1$H NMR (600 MHz, CD$_3$OD) δ ppm 8.70-8.76 (m, 2H) 8.05 (ddd, J=7.90, 2.15, 1.55 Hz, 1H) 7.63 (ddd, J=7.90, 5.03, 0.90 Hz, 1H) 3.53-4.24 (m, 4H) 3.33 (br. s., 4H). MS (ESI$^+$) m/z 192 [M+H]$^+$. 4-[4-(Pyridin-3-ylcarbonyl)piperazin-1-yl]benzaldehyde: $^1$H NMR (600 MHz, CD$_3$OD) δ ppm 9.72 (s, 1H) 8.69 (dd, J=2.14, 0.76 Hz, 1H) 8.67 (dd, J=5.04, 1.68 Hz, 1H) 7.97 (ddd, J=7.86, 2.14, 1.68 Hz, 1H) 7.76-7.81 (m, 2H) 7.56 (ddd, J=7.86, 5.04, 0.76 Hz, 1H) 7.05-7.09 (m, 2H) 3.93 (br. s., 2H) 3.53-3.72 (m, 4H) 3.48 (br. s., 2H). MS (ESI$^+$) m/z 296 [M+H]$^+$.

INTERMEDIATE 116

4-(4-{2-[(1-Methyl-1H-pyrazol-5-yl)amino]ethyl}piperazin-1-yl)benzaldehyde

The title product was prepared according to the procedure used for INTERMEDIATE 66, using N-(2-chloroethyl)-1-methyl-1H-pyrazol-5-amine instead of 2-bromoethyl ethyl ether. tert-Butyl 4-{2-[(1-methyl-1H-pyrazol-5-yl)amino]ethyl}piperazine-1-carboxylate: $^1$H NMR (600 MHz, CD$_3$OD) δ ppm 7.18 (d, J=2.1 Hz, 1H) 5.46 (d, J=1.8 Hz, 1H) 3.57 (s, 3H) 3.45 (br. s., 4H) 3.23 (t, J=6.7 Hz, 2H) 2.63 (t, J=6.6 Hz, 2H) 2.48 (t, J=5.0 Hz, 4H) 1.46 (s, 9H). MS (ESI$^+$) m/z 310 [M+H]$^+$.

1-Methyl-N-(2-piperazin-1-ylethyl)-1H-pyrazol-5-amine: $^1$H NMR (600 MHz, CD$_3$OD) δ ppm 7.18 (d, J=2.1 Hz, 1H) 5.46 (d, J=2.1 Hz, 1H) 3.57 (s, 3H) 3.22 (t, J=6.7 Hz, 2H) 2.87 (t, J=4.9 Hz, 4H) 2.61 (t, J=6.7 Hz, 2H) 2.52 (br. s., 4H). MS (ESI$^+$) m/z 210 [M+H]$^+$. 4-(4-{2-[(1-Methyl-1H-pyrazol-5-yl)amino]ethyl}piperazin-1-yl)benzaldehyde: $^1$H NMR (600 MHz, CD$_3$OD) δ ppm 9.69 (s, 1H) 7.76 (d, J=9.2 Hz, 2H) 7.19 (d, J=2.1 Hz, 1H) 7.04 (d, J=9.2 Hz, 2H) 5.49 (d, J=2.1 Hz, 1H) 3.58 (s, 3H) 3.47 (t, J=5.2 Hz, 4H) 3.27 (t, J=6.6 Hz, 2H) 2.66-2.71 (m, 6H). MS (ESI$^+$) m/z 314 [M+H]

INTERMEDIATE 117

4-[4-(Pyridin-4-ylcarbonyl)piperazin-1-yl]benzaldehyde

The title product was prepared according to the procedure used for INTERMEDIATE 104 using 4-pyridinoyl chloride hydrochloride instead of methoxyacetyl chloride.

tert-Butyl 4-(pyridin-4-ylcarbonyl)piperazine-1-carboxylate: $^1$H NMR (600 MHz, CD$_3$OD) δ ppm 8.65-8.68 (m, 2H) 7.45-7.48 (m, 2H) 3.70-3.78 (m, 2H) 3.51-3.60 (m, 2H) 3.40-3.48 (m, 2H) 3.34-3.40 (m, 2H) 1.47 (s, 9H). MS (ESI$^+$) m/z 292 [M+H]$^+$.

1-(Pyridin-4-ylcarbonyl)piperazine bis(trifluoroacetate): $^1$H NMR (600 MHz, CD$_3$OD) δ ppm 8.71-8.79 (m, 2H) 7.59-7.66 (m, 2H) 3.86-4.12 (m, 2H) 3.52-3.81 (m, 2H) 3.31-3.44 (m, 2H) 3.20-3.32 (m, 2H). MS (ESI$^+$) m/z 192 [M+H]$^+$ 4-[4-(Pyridin-4-ylcarbonyl)piperazin-1-yl]benzaldehyde: $^1$H NMR (600 MHz, DMSO-d$_6$) δ ppm 9.73 (s, 1H) 8.68-8.72 (m, 2H) 7.71-7.76 (m, 2H) 7.43-7.47 (m, 2H) 7.03-7.08 (m, 2H) 3.71-3.83 (m, 2H) 3.50-3.61 (m, 2H) 3.36-3.50 (m, 4H). MS (ESI$^+$) m/z 296 [M+H]$^+$.

INTERMEDIATE 118

3-[4-(4-Formylphenyl)piperazin-1-yl]propanenitrile

The title product was prepared according to the procedure used for INTERMEDIATE 66, using 3-bromopropionitrile instead of 2-bromoethyl ethyl ether.

tert-Butyl 4-(2-cyanoethyl)piperazine-1-carboxylate: $^1$H NMR (600 MHz, DMSO-d$_6$) δ ppm 3.30 (t, J=4.9 Hz, 4H) 2.67 (t, J=6.1 Hz, 2H) 2.57 (t, J=6.1 Hz, 2H) 2.36 (t, J=5.2 Hz, 4H) 1.39 (s, 9H). MS (ESI$^+$) m/z 184 [M+H-t-BuO]$^+$.

3-Piperazin-1-ylpropanenitrile: $^1$H NMR (600 MHz, CD$_3$OD) δ ppm 2.90 (t, J=5.0 Hz, 4H) 2.61-2.69 (m, 4H) 2.53 (br. s., 4H). MS (ESI$^+$) m/z 140 [M+H]$^+$ 3-[4-(4-Formylphenyl)piperazin-1-yl]propanenitrile: $^1$H NMR (600 MHz, DMSO-d$_6$) δ ppm 9.72 (s, 1H) 7.71 (d, J=9.2 Hz, 2H) 7.06 (d, J=9.2 Hz, 2H) 3.39 (t, J=5.2 Hz, 4H) 2.72 (t, J=6.4 Hz, 2H) 2.62 (t, J=6.7 Hz, 2H) 2.56 (t, J=5.2 Hz, 4H). MS (ESI$^+$) m/z 244 [M+H]$^+$.

INTERMEDIATE 119

4-[4-(4-Methoxybutyl)piperazin-1-yl]benzaldehyde

The title product was prepared according to the procedure used for INTERMEDIATE 66, using 2-bromobutyl methyl ether instead of 2-bromoethyl ethyl ether.

tert-Butyl 4-(4-methoxybutyl)piperazine-1-carboxylate: $^1$H NMR (600 MHz, DMSO-d$_6$) δ ppm 3.30 (t, J=6.4 Hz, 2H) 3.28 (br. s., 4H) 3.21 (s, 3H) 2.24-2.28 (m, 6H) 1.40-1.51 (m, 4H) 1.39 (s, 9H). MS (ESI$^+$) m/z 273 [M+H]$^+$.

1-(4-Methoxybutyl)piperazine: $^1$H NMR (600 MHz, CD$_3$OD) δ ppm 3.39-3.43 (m, 2H) 3.32 (s, 3H) 2.84 (t, J=4.9 Hz, 4H) 2.46 (br. s., 4H) 2.34-2.38 (m, 2H) 1.57 (dt, J=6.9, 3.4 Hz, 4H). MS (ESI$^+$) m/z 173 [M+H]$^+$.

4-[4-(4-Methoxybutyl)piperazin-1-yl]benzaldehyde: $^1$H NMR (600 MHz, DMSO-d$_6$) δ ppm 9.71 (s, 1H) 7.70 (d, J=8.9 Hz, 2H) 7.04 (d, J=8.9 Hz, 2H) 3.37 (t, J=5.2 Hz, 4H) 3.32 (t, J=6.1 Hz, 2H) 3.22 (s, 3H) 2.46 (t, J=5.2 Hz, 4H) 2.31 (t, J=7.0 Hz, 2H) 1.44-1.56 (m, 4H). MS (ESI$^+$) m/z 277 [M+H]$^+$.

INTERMEDIATE 120

4-[4-(2,2-Dimethylpropanoyl)piperazin-1-yl]benzaldehyde

The title product was prepared according to the procedure used for INTERMEDIATE 104 using pivaloyl chloride instead of methoxyacetyl chloride.

tert-Butyl 4-(2,2-dimethylpropanoyl)piperazine-1-carboxylate: $^1$H NMR (600 MHz, CD$_3$OD) δ ppm 3.60-3.67

(m, 4H) 3.39-3.47 (m, 4H) 1.47 (s, 9H) 1.28 (s, 9H). MS (ESI$^+$) m/z 215 [M+H-t-Bu]+.

1-(2,2-Dimethylpropanoyl)piperazine trifluoroacetate: $^1$H NMR (600 MHz, CD$_3$OD) δ ppm 3.87-3.92 (m, 4H) 3.21-3.25 (m, 4H) 1.29 (s, 9H). MS (ESI$^+$) m/z 171 [M+H]$^+$ 4-[4-(2,2-Dimethylpropanoyl)piperazin-1-yl]benzaldehyde: $^1$H NMR (600 MHz, DMSO-d$_6$) δ ppm 9.73 (s, 1H) 7.72-7.75 (m, 2H) 7.02-7.06 (m, 2H) 3.66-3.73 (m, 4H) 3.37-3.42 (m, 4H) 1.22 (s, 9H). MS (ESI$^+$) m/z 275 [M+H]

INTERMEDIATE 121

3-Fluoro-4-[4-(2-methoxyethyl)piperazin-1-yl]benzaldehyde

The title product was prepared according to the procedure used for INTERMEDIATE 55, using 1-(2-methoxyethyl)piperazine instead of 2-piperazin-1-ylethanol and 3,4-difluorobenzaldehyde instead of 4-fluorobenzaldehyde. After complete reaction the reaction mixture was extracted with DCM (2×30 mL) and the combined organic phases were concentrated in vacuo to yield a crude product, which was purified by flash chromatography (silica, 4% MeOH in DCM). $^1$H NMR (600 MHz, DMSO-d$_6$) δ ppm 9.81 (d, J=1.5 Hz, 1H) 7.67 (dd, J=8.2, 1.8 Hz, 1H) 7.58 (dd, J=13.7, 1.8 Hz, 1H) 7.16 (t, J=8.5 Hz, 1H) 3.46 (t, J=5.8 Hz, 2H) 3.24 (s, 3H) 3.20 (t, J=5.2 Hz, 4H) 2.57 (t, J=4.9 Hz, 4H) 2.52 (t, J=5.8 Hz, 2H). MS (ESI$^+$) m/z 267 [M+H]$^+$.

INTERMEDIATE 122

3-Methoxy-4-[4-(2-methoxyethyl)piperazin-1-yl]benzaldehyde

The title product was prepared according to the procedure used for INTERMEDIATE 121, using 4-fluoro-3-methoxybenzaldehyde instead of 3,4-difluorobenzaldehyde. $^1$H NMR (600 MHz, DMSO-d$_6$) δ ppm 9.81 (s, 1H) 7.48 (dd, J=8.1, 1.7 Hz, 1H) 7.35 (d, J=1.5 Hz, 1H) 7.02 (d, J=8.2 Hz, 1H) 3.85 (s, 3H) 3.46 (t, J=5.8 Hz, 2H) 3.24 (s, 3H) 3.13 (br. s., 4H) 2.56 (br. s., 4H) 2.52 (t, J=6.1 Hz, 2H). MS (ESI$^+$) m/z 279 [M+H]$^+$.

INTERMEDIATE 123

2-Fluoro-4-[4-(2-methoxyethyl)piperazin-1-yl]benzaldehyde

The title product was prepared according to the procedure used for INTERMEDIATE 121, using 2,4-difluorobenzaldehyde instead of 3,4-difluorobenzaldehyde. Two regioisomers were formed, i.e. the title product and 4-fluoro-2-[4-(2-methoxyethyl)piperazin-1-yl]benzaldehyde. The crude material was purified by flash chromatography (silica, 3% MeOH in DCM) to yield a mixture of isomers in the ratio of 77:23 in favor for the desired one. This material was taken to the next step without further purification. $^1$H NMR (600 MHz, DMSO-d$_6$) δ ppm 9.92 (s, 1H) 7.61 (t, J=8.9 Hz, 1H) 6.86 (dd, J=8.9, 2.1 Hz, 1H) 6.79 (dd, J=15.4, 2.3 Hz, 1H) 3.46 (t, J=5.8 Hz, 2H) 3.40 (t, J=5.2 Hz, 4H) 3.24 (s, 3H) 2.49-2.52 (m, 6H). MS (ESI$^+$) m/z 267 [M+H]$^+$.

4-Fluoro-2-[4-(2-methoxyethyl)piperazin-1-yl]benzaldehyde (minor isomer): $^1$H NMR (600 MHz, DMSO-d$_6$) δ ppm 10.05 (s, 1H) 7.76 (dd, J=8.9, 7.0 Hz, 1H) 7.00 (dd, J=11.6, 2.4 Hz, 1H) 6.94 (td, J=8.3, 2.0 Hz, 1H) 3.46 (t, J=5.8 Hz, 2H) 3.24 (s, 3H) 3.05 (t, J=4.9 Hz, 4H) 2.61 (br. s., 4H) 2.55 (t, J=5.8 Hz, 2H). MS (ESI$^+$) m/z 267 [M+H]$^+$

GENERAL PROCEDURE FOR THE SYNTHESIS OF COMPOUNDS OF FORMULA (I)

EXAMPLE 67

6-Chloro-2-{4-[4-(2-ethoxyethyl)piperazin-1-yl]phenyl}-N-(1-methylpiperidin-4-yl)-3H-imidazo[4,5-b]pyridin-7-amine 5-Chloro-N$^4$-(1-methylpiperidin-4-yl)-3-nitropyridine-2,4-diamine (INTERMEDIATE 21, 20.0 mg, 70 μmol) and 4-[4-(2-ethoxyethyl)piperazin-1-yl]benzaldehyde (INTERMEDIATE 41, 18.4 mg, 70 μmol) were slurried in EtOH (0.9 mL) and a freshly prepared aqueous solution of 0.7 M Na$_2$S$_2$O$_4$ (0.3 mL, 0.21 mmol, 3 eq.) was added. The mixture was stirred at 70° C. for 19 h. After cooling to room temperature the reaction mixture was evaporated and diluted with DMSO to about 1.5 mL, filtered and purified by preparatory RP-HPLC (basic method). The pure fractions were pooled and evaporated to yield 14.1 mg (40%) of pure title product as white solid. $^1$H NMR (600 MHz, DMSO-d$_6$) δ ppm 12.96 (br. s., 1H) 7.98 (d, J=8.9 Hz, 2H) 7.87 (s, 1H) 7.06 (d, J=9.2 Hz, 2H) 5.69 (d, J=9.2 Hz, 1H) 4.81-5.04 (m, 1H) 3.51 (t, J=6.0 Hz, 2H) 3.43 (q, J=7.0 Hz, 2H) 3.25 (t, J=5.2 Hz, 4H) 2.81 (d, J=11.3 Hz, 2H) 2.56 (t, J=4.9 Hz, 4H) 2.52 (t, J=6.0 Hz, 2H) 2.21 (s, 3H) 2.05 (td, J=11.3, 1.8 Hz, 2H) 1.97 (d, J=11.3 Hz, 2H) 1.66 (qd, J=11.6, 3.8 Hz, 2H) 1.11 (t, J=7.0 Hz, 3H. MS (ESI$^+$) m/z 498 [M+H]$^+$.

Examples of compounds of the invention are shown in Table 1.

TABLE 1

| Ex. | Chemical name | Structural formula |
|---|---|---|
| 1 | 6-Bromo-2-[4-(4-methylpiperazin-1-yl)phenyl]-N-(1-methylpiperidin-4-yl)-3H-imidazo[4,5-b]pyridin-7-amine | |

TABLE 1-continued

| Ex. | Chemical name | Structural formula |
|---|---|---|
| 2 | 6-Chloro-2-[4-(4-methylpiperazin-1-yl)phenyl]-N-(1-methylpiperidin-4-yl)-3H-imidazo[4,5-b]pyridin-7-amine | |
| 3 | 6-Chloro-N-[1-(4-methoxybenzyl)piperidin-4-yl]-2-[4-(4-methylpiperazin-1-yl)phenyl]-3H-imidazo[4,5-b]pyridin-7-amine | |
| 4 | 2-[4-(4-{6-Bromo-7-[(1-methylpiperidin-4-yl)amino]-3H-imidazo[4,5-b]pyridin-2-yl}phenyl)piperazin-1-yl]ethanol | |
| 5 | 2-[4-(4-{6-Chloro-7-[(1-methylpiperidin-4-yl)amino]-3H-imidazo[4,5-b]pyridin-2-yl}phenyl)piperazin-1-yl]ethanol | |
| 6 | 2-[4-(4-{6-Chloro-7-[(1-ethylpiperidin-4-yl)amino]-3H-imidazo[4,5-b]pyridin-2-yl}phenyl)piperazin-1-yl]ethanol | |
| 7 | 6-Bromo-2-{4-[4-(2-methoxyethyl)piperazin-1-yl]phenyl}-N-(1-methylpiperidin-4-yl)-3H-imidazo[4,5-b]pyridin-7-amine | |

TABLE 1-continued

| Ex. | Chemical name |
|---|---|
| 8 | 6-Chloro-2-{4-[4-(2-methoxyethyl)piperazin-1-yl]phenyl}-N-(1-methylpiperidin-4-yl)-3H-imidazo[4,5-b]pyridin-7-amine |
| 9 | 6-Chloro-N-(1-ethylpiperidin-4-yl)-2-{4-[4-(2-methoxyethyl)piperazin-1-yl]phenyl}-3H-imidazo[4,5-b]pyridin-7-amine |
| 10 | 6-Bromo-2-[4-(4-ethylpiperazin-1-yl)phenyl]-N-(1-methylpiperidin-4-yl)-3H-imidazo[4,5-b]pyridin-7-amine |
| 11 | 6-Chloro-2-[4-(4-ethylpiperazin-1-yl)phenyl]-N-(1-methylpiperidin-4-yl)-3H-imidazo[4,5-b]pyridin-7-amine |
| 12 | 6-Chloro-2-[4-(4-ethylpiperazin-1-yl)phenyl]-N-(1-ethylpiperidin-4-yl)-3H-imidazo[4,5-b]pyridin-7-amine |
| 13 | 2-{4-[4-(6-Chloro-7-{[1-(4-methoxybenzyl)piperidin-4-yl]amino}-3H-imidazo[4,5-b]pyridin-2-yl)phenyl]piperazin-1-yl}ethanol |

TABLE 1-continued

| Ex. | Chemical name |
|---|---|
| 14 | 6-Chloro-N-[1-(4-methoxybenzyl)piperidin-4-yl]-2-{4-[4-(2-methoxyethyl)piperazin-1-yl]phenyl}-3H-imidazo[4,5-b]pyridin-7-amine |
| 15 | 6-Chloro-2-[4-(4-ethylpiperazin-1-yl)phenyl]-N-[1-(4-methoxybenzyl)piperidin-4-yl]-3H-imidazo[4,5-b]pyridin-7-amine |
| 16 | 6-Bromo-N-(1-methylpiperidin-4-yl)-2-[4-(4-pyridin-4-ylpiperazin-1-yl)phenyl]-3H-imidazo[4,5-b]pyridin-7-amine |
| 17 | 6-Chloro-N-(1-methylpiperidin-4-yl)-2-[4-(4-pyridin-4-ylpiperazin-1-yl)phenyl]-3H-imidazo[4,5-b]pyridin-7-amine |
| 18 | 6-Chloro-N-[1-(1-methylethyl)piperidin-4-yl]-2-[4-(4-pyridin-4-ylpiperazin-1-yl)phenyl]-3H-imidazo[4,5-b]pyridin-7-amine |
| 19 | 6-Chloro-N-[1-(4-methoxybenzyl)piperidin-4-yl]-2-[4-(4-pyridin-4-ylpiperazin-1-yl)phenyl]-3H-imidazo[4,5-b]pyridin-7-amine |

TABLE 1-continued

| Ex. | Chemical name | Structural formula |
|---|---|---|
| 20 | 6-Bromo-N-[1-(1-methylethyl)piperidin-4-yl]-2-[4-(4-pyridin-4-ylpiperazin-1-yl)phenyl]-3H-imidazo[4,5-b]pyridin-7-amine | |
| 21 | 6-Bromo-2-[4-(4-methyl-1,4-diazepan-1-yl)phenyl]-N-(1-methylpiperidin-4-yl)-3H-imidazo[4,5-b]pyridin-7-amine | |
| 22 | 6-Chloro-2-[4-(4-methyl-1,4-diazepan-1-yl)phenyl]-N-(1-methylpiperidin-4-yl)-3H-imidazo[4,5-b]pyridin-7-amine | |
| 23 | 6-Chloro-2-[4-(4-methyl-1,4-diazepan-1-yl)phenyl]-N-[1-(1-methylethyl)piperidin-4-yl]-3H-imidazo[4,5-b]pyridin-7-amine | |
| 24 | 6-Bromo-2-[4-(4-methyl-1,4-diazepan-1-yl)phenyl]-N-[1-(1-methylethyl)piperidin-4-yl]-3H-imidazo[4,5-b]pyridin-7-amine | |
| 25 | 6-Chloro-N-[1-(4-methoxybenzyl)piperidin-4-yl]-2-[4-(4-methyl-1,4-diazepan-1-yl)phenyl]-3H-imidazo[4,5-b]pyridin-7-amine | |

TABLE 1-continued

| Ex. | Chemical name | Structural formula |
|---|---|---|
| 26 | 6-Bromo-N-(1-methylpiperidin-4-yl)-2-(4-morpholin-4-ylphenyl)-3H-imidazo[4,5-b]pyridin-7-amine | |
| 27 | 6-Chloro-N-(1-methylpiperidin-4-yl)-2-(4-morpholin-4-ylphenyl)-3H-imidazo[4,5-b]pyridin-7-amine | |
| 28 | 6-Chloro-N-[1-(1-methylethyl)piperidin-4-yl]-2-(4-morpholin-4-ylphenyl)-3H-imidazo[4,5-b]pyridin-7-amine | |
| 29 | 6-Bromo-N-[1-(1-methylethyl)piperidin-4-yl]-2-(4-morpholin-4-ylphenyl)-3H-imidazo[4,5-b]pyridin-7-amine | |
| 30 | 6-Chloro-N-[1-(4-methoxybenzyl)piperidin-4-yl]-2-(4-morpholin-4-ylphenyl)-3H-imidazo[4,5-b]pyridin-7-amine | |
| 31 | 2-[4-(4-Acetylpiperazin-1-yl)phenyl]-6-bromo-N-(1-methylpiperidin-4-yl)-3H-imidazo[4,5-b]pyridin-7-amine | |

TABLE 1-continued

| Ex. | Chemical name | Structural formula |
|---|---|---|
| 32 | 2-[4-(4-Acetylpiperazin-1-yl)phenyl]-6-chloro-N-(1-methylpiperidin-4-yl)-3H-imidazo[4,5-b]pyridin-7-amine | |
| 33 | 2-[4-(4-Acetylpiperazin-1-yl)phenyl]-6-chloro-N-[1-(1-methylethyl)piperidin-4-yl]-3H-imidazo[4,5-b]pyridin-7-amine | |
| 34 | 2-[4-(4-Acetylpiperazin-1-yl)phenyl]-6-bromo-N-[1-(1-methylethyl)piperidin-4-yl]-3H-imidazo[4,5-b]pyridin-7-amine | |
| 35 | 2-[4-(4-Acetylpiperazin-1-yl)phenyl]-6-chloro-N-[1-(4-methoxybenzyl)piperidin-4-yl]-3H-imidazo[4,5-b]pyridin-7-amine | |
| 36 | 4-(4-{6-Bromo-7-[(1-methylpiperidin-4-yl)amino]-3H-imidazo[4,5-b]pyridin-2-yl}phenyl)piperazin-2-one | |
| 37 | 4-(4-{6-Chloro-7-[(1-methylpiperidin-4-yl)amino]-3H-imidazo[4,5-b]pyridin-2-yl}phenyl)piperazin-2-one | |

TABLE 1-continued

| Ex. | Chemical name | Structural formula |
|---|---|---|
| 38 | 4-[4-(6-Chloro-7-{[1-(1-methylethyl)piperidin-4-yl]amino}-3H-imidazo[4,5-b]pyridin-2-yl)phenyl]piperazin-2-one | |
| 39 | 4-[4-(6-Chloro-7-{[1-(4-methoxybenzyl)piperidin-4-yl]amino}-3H-imidazo[4,5-b]pyridin-2-yl)phenyl]piperazin-2-one | |
| 40 | 6-Bromo-N-(1-methylpiperidin-4-yl)-2-{4-[4-(methylsulfonyl)piperazin-1-yl]phenyl}-3H-imidazo[4,5-b]pyridin-7-amine | |
| 41 | 6-Chloro-N-(1-methylpiperidin-4-yl)-2-{4-[4-(methylsulfonyl)piperazin-1-yl]phenyl}-3H-imidazo[4,5-b]pyridin-7-amine | |
| 42 | 6-Chloro-N-[1-(1-methylethyl)piperidin-4-yl]-2-{4-[4-(methylsulfonyl)piperazin-1-yl]phenyl}-3H-imidazo[4,5-b]pyridin-7-amine | |

TABLE 1-continued

| Ex. | Chemical name | Structural formula |
|---|---|---|
| 43 | 6-Bromo-N-[1-(1-methylethyl)piperidin-4-yl]-2-{4-[4-(methylsulfonyl)piperazin-1-yl]phenyl}-3H-imidazo[4,5-b]pyridin-7-amine | 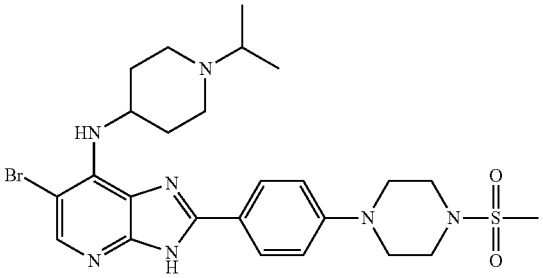 [SMILES: CC(C)N1CCC(Nc2c(Cl)cnc3[nH]c(-c4ccc(N5CCN(S(C)(=O)=O)CC5)cc4)nc23)CC1] |
| 44 | 6-Chloro-N-[1-(4-methoxybenzyl)piperidin-4-yl]-2-{4-[4-(methylsulfonyl)piperazin-1-yl]phenyl}-3H-imidazo[4,5-b]pyridin-7-amine | 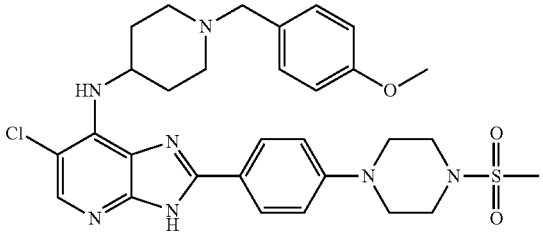 [SMILES: COc1ccc(CN2CCC(Nc3c(Cl)cnc4[nH]c(-c5ccc(N6CCN(S(C)(=O)=O)CC6)cc5)nc34)CC2)cc1] |
| 45 | 6-Chloro-N-(1-ethylpiperidin-4-yl)-2-{4-[4-(methylsulfonyl)piperazin-1-yl]phenyl}-3H-imidazo[4,5-b]pyridin-7-amine | 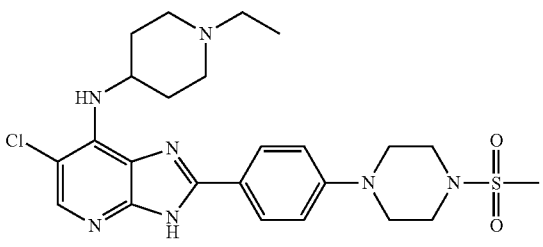 [SMILES: CCN1CCC(Nc2c(Cl)cnc3[nH]c(-c4ccc(N5CCN(S(C)(=O)=O)CC5)cc4)nc23)CC1] |
| 46 | 6-Bromo-N-(1-ethylpiperidin-4-yl)-2-{4-[4-(methylsulfonyl)piperazin-1-yl]phenyl}-3H-imidazo[4,5-b]pyridin-7-amine | 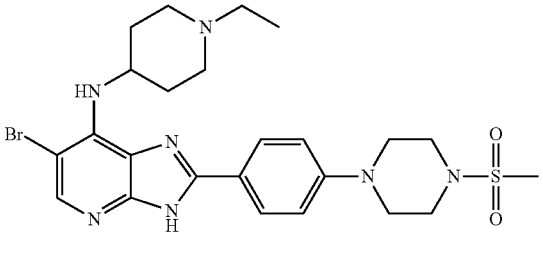 |
| 47 | 1-(4-{6-Bromo-7-[(1-methylpiperidin-4-yl)amino]-3H-imidazo[4,5-b]pyridin-2-yl}phenyl)-1,4-diazepan-5-one | 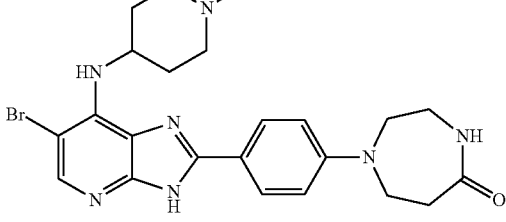 |
| 48 | 1-(4-{6-Chloro-7-[(1-methylpiperidin-4-yl)amino]-3H-imidazo[4,5-b]pyridin-2-yl}phenyl)-1,4-diazepan-5-one | 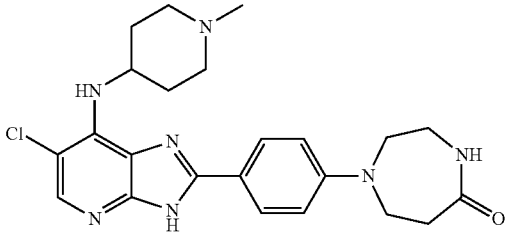 [SMILES: CN1CCC(Nc2c(Cl)cnc3[nH]c(-c4ccc(N5CCNC(=O)CC5)cc4)nc23)CC1] |

TABLE 1-continued

| Ex. | Chemical name | Structural formula |
|---|---|---|
| 49 | 1-[4-(6-Chloro-7-{[1-(1-methylethyl)piperidin-4-yl]amino}-3H-imidazo[4,5-b]pyridin-2-yl)phenyl]-1,4-diazepan-5-one | |
| 50 | 1-[4-(6-Bromo-7-{[1-(1-methylethyl)piperidin-4-yl]amino}-3H-imidazo[4,5-b]pyridin-2-yl)phenyl]-1,4-diazepan-5-one | |
| 51 | 1-[4-(6-Chloro-7-{[1-(4-methoxybenzyl)piperidin-4-yl]amino}-3H-imidazo[4,5-b]pyridin-2-yl)phenyl]-1,4-diazepan-5-one | |
| 52 | 1-(4-{6-Chloro-7-[(1-ethylpiperidin-4-yl)amino]-3H-imidazo[4,5-b]pyridin-2-yl}phenyl)-1,4-diazepan-5-one | |
| 53 | 1-(4-{6-Bromo-7-[(1-ethylpiperidin-4-yl)amino]-3H-imidazo[4,5-b]pyridin-2-yl}phenyl)-1,4-diazepan-5-one | |
| 54 | 1-{4-[6-Chloro-7-({1-[(1,3,5-trimethyl-1H-pyrazol-4-yl)methyl]piperidin-4-yl}amino)-3H-imidazo[4,5-b]pyridin-2-yl]phenyl}-1,4-diazepan-5-one | |

TABLE 1-continued

| Ex. | Chemical name | Structural formula |
| --- | --- | --- |
| 55 | 6-Chloro-2-[4-(4-methylpiperazin-1-yl)phenyl]-N-{1-[(1,3,5-trimethyl-1H-pyrazol-4-yl)methyl]piperidin-4-yl}-3H-imidazo[4,5-b]pyridin-7-amine | |
| 56 | 2-(4-{4-[6-Chloro-7-({1-[(1,3,5-trimethyl-1H-pyrazol-4-yl)methyl]piperidin-4-yl}amino)-3H-imidazo[4,5-b]pyridin-2-yl]phenyl}piperazin-1-yl)ethanol | |
| 57 | 6-Chloro-2-{4-[4-(2-methoxyethyl)piperazin-1-yl]phenyl}-N-{1-[(1,3,5-trimethyl-1H-pyrazol-4-yl)methyl]piperidin-4-yl}-3H-imidazo[4,5-b]pyridin-7-amine | |
| 58 | 6-Chloro-2-(4-morpholin-4-ylphenyl)-N-{1-[(1,3,5-trimethyl-1H-pyrazol-4-yl)methyl]piperidin-4-yl}-3H-imidazo[4,5-b]pyridin-7-amine | |
| 59 | 2-[4-(4-Acetylpiperazin-1-yl)phenyl]-6-chloro-N-{1-[(1,3,5-trimethyl-1H-pyrazol-4-yl)methyl]piperidin-4-yl}-3H-imidazo[4,5-b]pyridin-7-amine | |

TABLE 1-continued

| Ex. | Chemical name | Structural formula |
|---|---|---|
| 60 | 6-Chloro-2-{4-[4-(methylsulfonyl)piperazin-1-yl]phenyl}-N-{1-[(1,3,5-trimethyl-1H-pyrazol-4-yl)methyl]piperidin-4-yl}-3H-imidazo[4,5-b]pyridin-7-amine | |
| 61 | 6-Bromo-2-{4-[4-(2-methoxyethyl)-1,4-diazepan-1-yl]phenyl}-N-(1-methylpiperidin-4-yl)-3H-imidazo[4,5-b]pyridin-7-amine | |
| 62 | 6-Chloro-2-{4-[4-(2-methoxyethyl)-1,4-diazepan-1-yl]phenyl}-N-(1-methylpiperidin-4-yl)-3H-imidazo[4,5-b]pyridin-7-amine | |
| 63 | 6-Chloro-2-{4-[4-(2-methoxyethyl)-1,4-diazepan-1-yl]phenyl}-N-[1-(1-methylethyl)piperidin-4-yl]-3H-imidazo[4,5-b]pyridin-7-amine | |
| 64 | 6-Chloro-N-[1-(4-methoxybenzyl)piperidin-4-yl]-2-{4-[4-(2-methoxyethyl)-1,4-diazepan-1-yl]phenyl}-3H-imidazo[4,5-b]pyridin-7-amine | |
| 65 | 6-Chloro-N-(1-ethylpiperidin-4-yl)-2-{4-[4-(2-methoxyethyl)-1,4-diazepan-1-yl]phenyl}-3H-imidazo[4,5-b]pyridin-7-amine | |

TABLE 1-continued

| Ex. | Chemical name | Structural formula |
|---|---|---|
| 66 | 6-Bromo-2-{4-[4-(2-ethoxyethyl)piperazin-1-yl]phenyl}-N-(1-methylpiperidin-4-yl)-3H-imidazo[4,5-b]pyridin-7-amine | |
| 67 | 6-Chloro-2-{4-[4-(2-ethoxyethyl)piperazin-1-yl]phenyl}-N-(1-methylpiperidin-4-yl)-3H-imidazo[4,5-b]pyridin-7-amine | |
| 68 | 6-Chloro-2-{4-[4-(2-ethoxyethyl)piperazin-1-yl]phenyl}-N-[1-(1-methylethyl)piperidin-4-yl]-3H-imidazo[4,5-b]pyridin-7-amine | |
| 69 | 6-Chloro-2-{4-[4-(2-ethoxyethyl)piperazin-1-yl]phenyl}-N-[1-(4-methoxybenzyl)piperidin-4-yl]-3H-imidazo[4,5-b]pyridin-7-amine | |
| 70 | 6-Chloro-2-{4-[4-(2-ethoxyethyl)piperazin-1-yl]phenyl}-N-(1-ethylpiperidin-4-yl)-3H-imidazo[4,5-b]pyridin-7-amine | |
| 71 | 6-Bromo-2-{4-[4-(2-ethoxyethyl)-1,4-diazepan-1-yl]phenyl}-N-(1-methylpiperidin-4-yl)-3H-imidazo[4,5-b]pyridin-7-amine | |

TABLE 1-continued

| Ex. | Chemical name | Structural formula |
|---|---|---|
| 72 | 6-Chloro-2-{4-[4-(2-ethoxyethyl)-1,4-diazepan-1-yl]phenyl}-N-(1-methylpiperidin-4-yl)-3H-imidazo[4,5-b]pyridin-7-amine | |
| 73 | 6-Chloro-2-{4-[4-(2-ethoxyethyl)-1,4-diazepan-1-yl]phenyl}-N-[1-(1-methylethyl)piperidin-4-yl]-3H-imidazo[4,5-b]pyridin-7-amine | |
| 74 | 6-Chloro-2-{4-[4-(2-ethoxyethyl)-1,4-diazepan-1-yl]phenyl}-N-[1-(4-methoxybenzyl)piperidin-4-yl]-3H-imidazo[4,5-b]pyridin-7-amine | |
| 75 | 6-Chloro-2-{4-[4-(2-ethoxyethyl)-1,4-diazepan-1-yl]phenyl}-N-(1-ethylpiperidin-4-yl)-3H-imidazo[4,5-b]pyridin-7-amine | |
| 76 | 6-Bromo-2-(4-{4-[2-(1-methylethoxy)ethyl]piperazin-1-yl}phenyl)-N-(1-methylpiperidin-4-yl)-3H-imidazo[4,5-b]pyridin-7-amine | |

TABLE 1-continued

| Ex. | Chemical name | Structural formula |
|---|---|---|
| 77 | 6-Chloro-2-(4-{4-[2-(1-methylethoxy)ethyl]piperazin-1-yl}phenyl)-N-(1-methylpiperidin-4-yl)-3H-imidazo[4,5-b]pyridin-7-amine | |
| 78 | 6-Chloro-2-(4-{4-[2-(1-methylethoxy)ethyl]piperazin-1-yl}phenyl)-N-[1-(1-methylethyl)piperidin-4-yl]-3H-imidazo[4,5-b]pyridin-7-amine | |
| 79 | 6-Chloro-N-[1-(4-methoxybenzyl)piperidin-4-yl]-2-(4-{4-[2-(1-methylethoxy)ethyl]piperiazin-1-yl}phenyl)-3H-imidazo[4,5-b]pyridin-7-amine | |
| 80 | 6-Chloro-N-(1-ethylpiperidin-4-yl)-2-(4-{4-[2-(1-methylethoxy)ethyl]piperazin-1-yl}phenyl)-3H-imidazo[4,5-b]pyridin-7-amine | |
| 81 | 2-{4-[4-(6-Chloro-7-{[1-(thiophen-2-ylmethyl)piperidin-4-yl]amino}-3H-imidazo[4,5-b]pyridin-2-yl)phenyl]piperazin-1-yl}ethanol | |

TABLE 1-continued

| Ex. | Chemical name | Structural formula |
|---|---|---|
| 82 | 6-Chloro-2-{4-[4-(2-methoxyethyl)piperazin-1-yl]phenyl}-N-[1-(thiophen-2-ylmethyl)piperidin-4-yl]-3H-imidazo[4,5-b]pyridin-7-amine | |
| 83 | 6-Chloro-2-(4-morpholin-4-ylphenyl)-N-[1-(thiophen-2-ylmethyl)piperidin-4-yl]-3H-imidazo[4,5-b]pyridin-7-amine | |
| 84 | 6-Chloro-2-[4-(4-pyridin-4-ylpiperazin-1-yl)phenyl]-N-[1-(thiophen-2-ylmethyl)piperidin-4-yl]-3H-imidazo[4,5-b]pyridin-7-amine | |
| 85 | 6-Chloro-2-{4-[4-(2-ethoxyethyl)piperazin-1-yl]phenyl}-N-[1-(thiophen-2-ylmethyl)piperidin-4-yl]-3H-imidazo[4,5-b]pyridin-7-amine | |
| 86 | 6-Chloro-2-(4-{4-[2-(1-methylethoxy)ethyl]piperazin-1-yl}phenyl)-N-[1-(thiophen-2-ylmethyl)piperidin-4-yl]-3H-imidazo[4,5-b]pyridin-7-amine | |

TABLE 1-continued

| Ex. | Chemical name | Structural formula |
|---|---|---|
| 87 | 2-(4-{4-[6-Chloro-7-({1-[4-(dimethylamino)benzyl]piperidin-4-yl}amino)-3H-imidazo[4,5-b]pyridin-2-yl]phenyl}piperazin-1-yl)ethanol | |
| 88 | 6-Chloro-N-{1-[4-(dimethylamino)benzyl]piperidin-4-yl}-2-{4-[4-(2-methoxyethyl)piperazin-1-yl]phenyl}-3H-imidazo[4,5-b]pyridin-7-amine | |
| 89 | 6-Chloro-N-{1-[4-(dimethylamino)benzyl]piperidin-4-yl}-2-{4-[4-(2-methoxyethyl)piperazin-1-yl]phenyl}-3H-imidazo[4,5-b]pyridin-7-amine | |

TABLE 1-continued

| Ex. | Chemical name |
|---|---|
| 90 | 6-Chloro-N-{1-[4-(dimethylamino)benzyl]piperidin-4-yl}-2-(4-{4-[2-(1-methylethoxy)ethyl]piperazin-1-yl}phenyl)-3H-imidazo[4,5-b]pyridin-7-amine |
| 91 | 6-Bromo-2-(4-{4-[2-(1-methylethoxy)ethyl]-1,4-diazepan-1-yl}phenyl)-N-(1-methylpiperidin-4-yl)-3H-imidazo[4,5-b]pyridin-7-amine |
| 92 | 6-Chloro-2-(4-{4-[2-(1-methylethoxy)ethyl]-1,4-diazepan-1-yl}phenyl)-N-(1-methylpiperidin-4-yl)-3H-imidazo[4,5-b]pyridin-7-amine |
| 93 | 6-Chloro-2-(4-{4-[2-(1-methylethoxy)ethyl]-1,4-diazepan-1-yl}phenyl)-N-[1-(1-methylethyl)piperidin-4-yl]-3H-imidazo[4,5-b]pyridin-7-amine |
| 94 | 6-Chloro-N-[1-(4-methoxybenzyl)piperidin-4-yl]-2-(4-{4-[2-(1-methylethoxy)ethyl]-1,4-diazepan-1-yl}phenyl)-3H-imidazo[4,5-b]pyridin-7-amine |

TABLE 1-continued

| Ex. | Chemical name | Structural formula |
|---|---|---|
| 95 | 6-Bromo-N-(1-ethylpiperidin-4-yl)-2-(4-{4-[2-(1-methylethoxy)ethyl]-1,4-diazepan-1-yl}phenyl)-3H-imidazo[4,5-b]pyridin-7-amine | 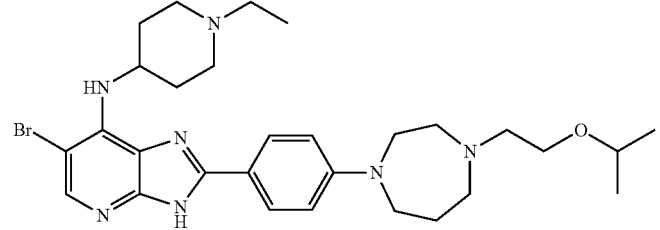 [SMILES: CCN1CCC(Nc2c(Cl)cnc3[nH]c(-c4ccc(N5CCCN(CCOC(C)C)CC5)cc4)nc23)CC1] |
| 96 | 6-Chloro-N-(1-ethylpiperidin-4-yl)-2-(4-{4-[2-(1-methylethoxy)ethyl]-1,4-diazepan-1-yl}phenyl)-3H-imidazo[4,5-b]pyridin-7-amine | 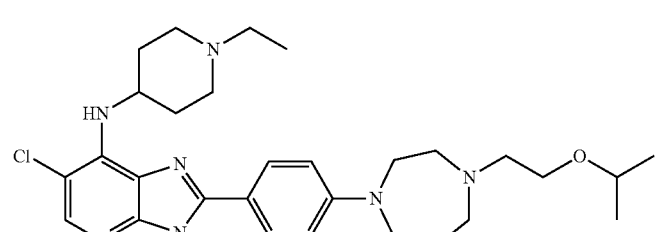 |
| 97 | 6-Chloro-N-(1-methylpiperidin-4-yl)-2-[4-(4-pyrazin-2-ylpiperazin-1-yl)phenyl]-3H-imidazo[4,5-b]pyridin-7-amine | 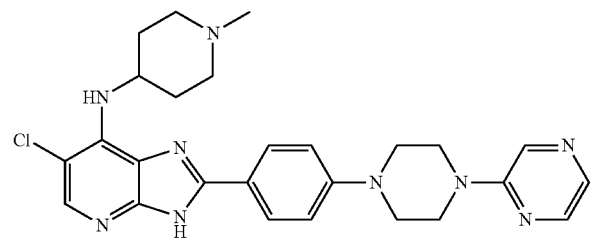 [SMILES: CN1CCC(Nc2c(Cl)cnc3[nH]c(-c4ccc(N5CCN(c6cnccn6)CC5)cc4)nc23)CC1] |
| 98 | 6-Chloro-N-(1-methylpiperidin-4-yl)-2-{4-[4-(pyridin-2-ylmethyl)piperazin-1-yl]phenyl}-3H-imidazo[4,5-b]pyridin-7-amine | 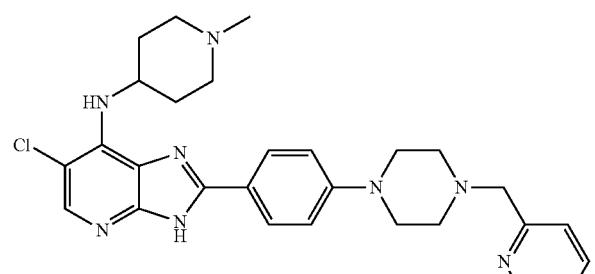 |
| 99 | 6-Chloro-N-(1-methylpiperidin-4-yl)-2-{4-[4-(pyridin-3-ylmethyl)piperazin-1-yl]phenyl}-3H-imidazo[4,5-b]pyridin-7-amine | 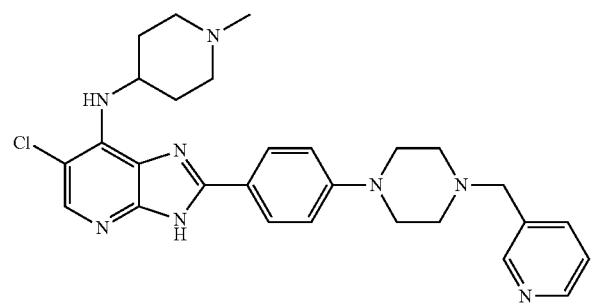 [SMILES: CN1CCC(Nc2c(Cl)cnc3[nH]c(-c4ccc(N5CCN(Cc6cccnc6)CC5)cc4)nc23)CC1] |

TABLE 1-continued

| Ex. | Chemical name | Structural formula |
|---|---|---|
| 100 | 6-Chloro-N-(1-methylpiperidin-4-yl)-2-{4-[4-(pyridin-4-ylmethyl)piperazin-1-yl]phenyl}-3H-imidazo[4,5-b]pyridin-7-amine | |
| 101 | 6-Chloro-N-(1-methylpiperidin-4-yl)-2-[4-(4-pyridin-3-ylpiperazin-1-yl)phenyl]-3H-imidazo[4,5-b]pyridin-7-amine | |
| 102 | 4-({4-[(6-Chloro-2-{4-[4-(2-hydroxyethyl)piperazin-1-yl]phenyl}-3H-imidazo[4,5-b]pyridin-7-yl)amino]piperidin-1-yl}methyl)-2-methoxyphenol | |
| 103 | 4-({4-[(6-Chloro-2-{4-[4-(2-methoxyethyl)piperazin-1-yl]phenyl}-3H-imidazo[4,5-b]pyridin-7-yl)amino]piperidin-1-yl}methyl)-2-methoxyphenol | |
| 104 | 2-{4-[4-(6-Chloro-7-{[1-(2,3-dihydro-1-benzofuran-5-ylmethyl)piperidin-4-yl]amino}-3H-imidazo[4,5-b]pyridin-2-yl)phenyl]piperazin-1-yl}ethanol | |
| 105 | 6-Chloro-N-[1-(2,3-dihydro-1-benzofuran-5-ylmethyl)piperidiin-4-yl]-2-{4-[4-(2-methoxyethyl)piperazin-1-yl]phenyl}-3H-imidazo[4,5-b]pyridin-7-amine | |

TABLE 1-continued

| Ex. | Chemical name |
|---|---|
| 106 | 6-Chloro-N-[1-(2,3-dihydro-1-benzofuran-5-ylmethyl)piperidin-4-yl]-2-{4-[4-(methylsulfonyl)piperazin-1-yl]phenyl}-3H-imidazo[4,5-b]pyridin-7-amine |
| 107 | 6-Chloro-N-[1-(2,3-dihydro-1-benzofuran-5-ylmethyl)piperidin-4-yl]-2-{4-[4-(2-ethoxyethyl)piperazin-1-yl]phenyl}-3H-imidazo[4,5-b]pyridin-7-amine |
| 108 | 6-Chloro-N-(1-methylpiperidin-4-yl)-2-{4-[4-(1,3-thiazol-2-ylmethyl)piperazin-1-yl]phenyl}-3H-imidazo[4,5-b]pyridin-7-amine |
| 109 | 6-Chloro-2-{4-[4-(1H-imidazol-4-ylmethyl)piperazin-1-yl]phenyl}-N-(1-methylpiperidin-4-yl)-3H-imidazo[4,5-b]pyridin-7-amine |
| 110 | 6-Chloro-N-(1-methylpiperidin-4-yl)-2-(4-{4-[(6-methylpyridin-2-yl)methyl]piperazin-1-yl}phenyl)-3H-imidazo[4,5-b]pyridin-7-amine |

TABLE 1-continued

| Ex. | Chemical name | Structural formula |
|---|---|---|
| 111 | 6-Bromo-N-(1-methylpiperidin-4-yl)-2-{4-[4-(pyridin-4-ylmethyl)piperain-1-yl]phenyl}-3H-imidazo[4,5-b]pyridin-7-amine | |
| 112 | 6-Bromo-N-(1-methylpiperidin-4-yl)-2-{4-[4-(1,3-thiazol-2-ylmethyl)piperazin-1-yl]phenyl}-3H-imidazo[4,5-b]pyridin-7-amine | |
| 113 | 6-Bromo-2-{4-[4-(1H-imidazol-4-ylmethyl)piperazin-1-yl]phenyl}-N-(1-methylpiperidin-4-yl)-3H-imidazo[4,5-b]pyridin-7-amine | |
| 114 | 6-Bromo-N-(1-methylpiperidin-4-yl)-2-(4-{4-[(6-methylpyridin-2-yl)methyl]piperazin-1-yl}phenyl)-3H-imidazo[4,5-b]pyridin-7-amine | |
| 115 | 6-Bromo-N-(1-methylpiperidin-4-yl)-2-{4-[4-(pyridin-2-ylmethyl)piperazin-1-yl]phenyl}-3H-imidazo[4,5-b]pyridin-7-amine | |

TABLE 1-continued

| Ex. | Chemical name |
|---|---|
| 116 | 6-Bromo-N-(1-methylpiperidin-4-yl)-2-{4-[4-(pyridin-3-ylmethyl)piperazin-1-yl]phenyl}-3H-imidazo[4,5-b]pyridin-7-amine |
| 117 | 6-Bromo-2-(4-{4-[(3,5-dimethylisoxazol-4-yl)methyl]piperazin-1-yl}phenyl)-N-(1-methylpiperidin-4-yl)-3H-imidazo[4,5-b]pyridin-7-amine |
| 118 | 6-Bromo-2-{4-[4-(furan-2-ylmethyl)piperazin-1-yl]phenyl}-N-(1-methylpiperidin-4-yl)-3H-imidazo[4,5-b]pyridin-7-amine |
| 119 | 6-Chloro-2-(4-{4-[(3,5-dimethylisoxazol-4-yl)methyl]piperazin-1-yl}phenyl)-N-(1-methylpiperidin-4-yl)-3H-imidazo[4,5-b]pyridin-7-amine |
| 120 | 6-Chloro-2-{4-[4-(furan-2-ylmethyl)piperazin-1-yl]phenyl}-N-(1-methylpiperidin-4-yl)-3H-imidazo[4,5-b]pyridin-7-amine |

TABLE 1-continued

| Ex. | Chemical name |
|---|---|
| 121 | 2-{4-[4-(6-Chloro-7-{[(3S)-1-methylpyrrolidin-3-yl]amino}-3H-imidazo[4,5-b]pyridin-2-yl)phenyl]piperazin-1-yl}ethanol |
| 122 | 6-Chloro-2-{4-[4-(2-methoxyethyl)piperazin-1-yl]phenyl}-N-[(3S)-1-methylpyrrolidin-3-yl]-3H-imidazo[4,5-b]pyridin-7-amine |
| 123 | 6-Chloro-2-{4-[4-(2-ethoxyethyl)piperazin-1-yl]phenyl}-N-[(3S)-1-methylpyrrolidin-3-yl]-3H-imidazo[4,5-b]pyridin-7-amine |
| 124 | 6-Chloro-N-[(3S)-1-methylpyrrolidin-3-yl]-2-{4-[4-(pyridin-2-ylmethyl)piperazin-1-yl]phenyl}-3H-imidazo[4,5-b]pyridin-7-amine |
| 125 | 6-Chloro-N-[(3S)-1-methylpyrrolidin-3-yl]-2-{4-[4-(pyridin-3-ylmethyl)piperazin-1-yl]phenyl}-3H-imidazo[4,5-b]pyridin-7-amine |

TABLE 1-continued

| Ex. | Chemical name | Structural formula |
|---|---|---|
| 126 | 6-Chloro-N-[(3S)-1-methylpyrrolidin-3-yl]-2-{4-[4-(pyridin-4-ylmethyl)piperazin-1-yl]phenyl}-3H-imidazo[4,5-b]pyridin-7-amine | |
| 127 | 2-{4-[4-(6-Chloro-7-{[(3S)-1-propylpyrrolidin-3-yl]amino}-3H-imidazo[4,5-b]pyridin-2-yl)phenyl]piperazin-1-yl}ethanol | |
| 128 | 6-Chloro-2-{4-[4-(2-methoxyethyl)piperazin-1-yl]phenyl}-N-[(3S)-1-propylpyrrolidin-3-yl]-3H-imidazo[4,5-b]pyridin-7-amine | |
| 129 | 6-Chloro-N-[(3S)-1-propylpyrrolidin-3-yl]-2-{4-[4-(pyridin-2-ylmethyl)piperazin-1-yl]phenyl}-3H-imidazo[4,5-b]pyridin-7-amine | |
| 130 | 6-Chloro-N-[(3S)-1-propylpyrrolidin-3-yl]-2-{4-[4-(pyridin-3-ylmethyl)piperazin-1-yl]phenyl}-3H-imidazo[4,5-b]pyridin-7-amine | |

TABLE 1-continued

| Ex. | Chemical name | Structural formula |
|---|---|---|
| 131 | 6-Chloro-N-[(3S)-1-propylpyrrolidin-3-yl]-2-{4-[4-(pyridin-4-ylmethyl)piperazin-1-yl]phenyl}-3H-imidazo[4,5-b]pyridin-7-amine | |
| 132 | 6-Chloro-N-(1-methylpiperidin-4-yl)-2-{4-[4-(pyrimidin-5-ylmethyl)piperazin-1-yl]phenyl}-3H-imidazo[4,5-b]pyridin-7-amine | |
| 133 | 6-Bromo-N-(1-methylpiperidin-4-yl)-2-{4-[4-(pyrimidin-5-ylmethyl)piperazin-1-yl]phenyl}-3H-imidazo[4,5-b]pyridin-7-amine | |
| 134 | 6-Chloro-N-(1-methylpiperidin-4-yl)-2-(4-{4-[(6-methylpyridin-3-yl)methyl]piperazin-1-yl}phenyl)-3H-imidazo[4,5-b]pyridin-7-amine | |
| 135 | 6-Bromo-N-(1-methylpiperidin-4-yl)-2-(4-{4-[(6-methylpyridin-3-yl)methyl]piperazin-1-yl}phenyl)-3H-imidazo[4,5-b]pyridin-7-amine | |

TABLE 1-continued

| Ex. | Chemical name | Structural formula |
|---|---|---|
| 136 | 6-Chloro-N-(1-ethylpiperidin-4-yl)-2-{4-[4-(pyridin-2-ylmethyl)piperazin-1-yl]phenyl}-3H-imidazo[4,5-b]pyridin-7-amine | 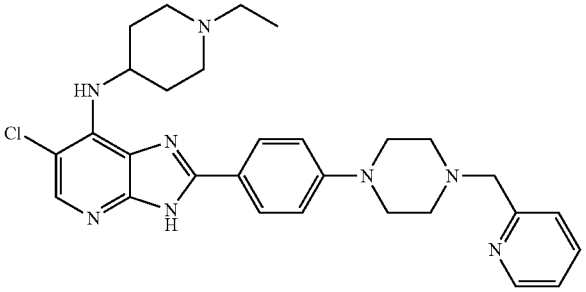 |
| 137 | 6-Chloro-N-(1-ethylpiperidin-4-yl)-2-{4-[4-(pyridin-3-ylmethyl)piperazin-1-yl]phenyl}-3H-imidazo[4,5-b]pyridin-7-amine | 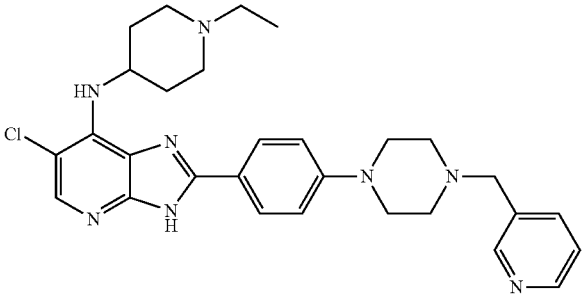 [SMILES: CCN1CCC(Nc2c(Cl)cnc3[nH]c(-c4ccc(N5CCN(Cc6cccnc6)CC5)cc4)nc23)CC1] |
| 138 | 6-Chloro-N-(1-ethylpiperidin-4-yl)-2-{4-[4-(pyridin-4-ylmethyl)piperazin-1-yl]phenyl}-3H-imidazo[4,5-b]pyridin-7-amine | 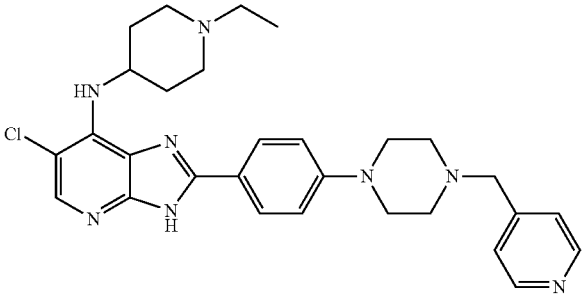 [SMILES: CCN1CCC(Nc2c(Cl)cnc3[nH]c(-c4ccc(N5CCN(Cc6ccncc6)CC5)cc4)nc23)CC1] |
| 139 | 6-Chloro-N-(1-ethylpiperidin-4-yl)-2-[4-(4-pyridin-3-ylpiperazin-1-yl)phenyl]-3H-imidazo[4,5-b]pyridin-7-amine | 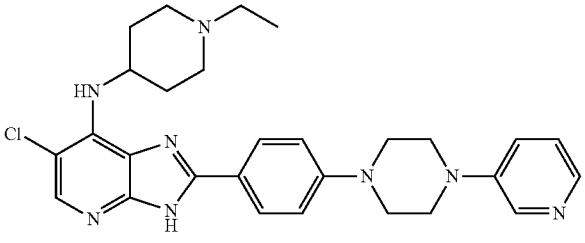 [SMILES: CCN1CCC(Nc2c(Cl)cnc3[nH]c(-c4ccc(N5CCN(c6cccnc6)CC5)cc4)nc23)CC1] |
| 140 | 6-Chloro-N-(1-ethylpiperidin-4-yl)-2-{4-[4-(1,3-thiazol-2-ylmethyl)piperazin-1-yl]phenyl}-3H-imidazo[4,5-b]pyridin-7-amine | 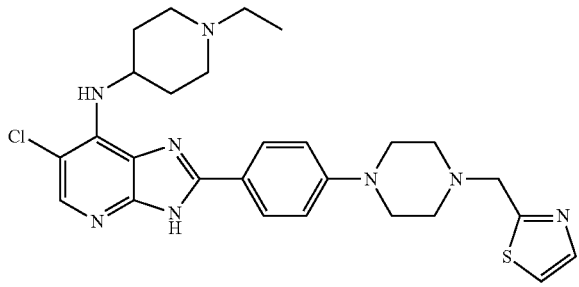 [SMILES: CCN1CCC(Nc2c(Cl)cnc3[nH]c(-c4ccc(N5CCN(Cc6nccs6)CC5)cc4)nc23)CC1] |

TABLE 1-continued

| Ex. | Chemical name | Structural formula |
|---|---|---|
| 141 | 6-Chloro-N-(1-ethylpiperidin-4-yl)-2-{4-[4-(1H-imidazol-4-ylmethyl)piperazin-1-yl]phenyl}-3H-imidazo[4,5-b]pyridin-7-amine | |
| 142 | 6-Chloro-N-(1-ethylpiperidin-4-yl)-2-(4-{4-[(6-methylpyridin-2-yl)methyl]piperazin-1-yl}phenyl)-3H-imidazo[4,5-b]pyridin-7-amine | |
| 143 | 6-Chloro-N-(1-methylpiperidin-4-yl)-2-{4-[4-(pyrazin-2-ylmethyl)piperazin-1-yl]phenyl}-3H-imidazo[4,5-b]pyridin-7-amine | |
| 144 | 6-Bromo-N-(1-methylpiperidin-4-yl)-2-{4-[4-(pyrazin-2-ylmethyl)piperazin-1-yl]phenyl}-3H-imidazo[4,5-b]pyridin-7-amine | |
| 145 | 2-{4-[4-(6-Chloro-7-{[(3S)-1-(4-methoxybenzyl)pyrrolidin-3-yl]amino}-3H-imidazo[4,5-b]pyridin-2-yl)phenyl]piperazin-1-yl}ethanol | |

TABLE 1-continued

| Ex. | Chemical name | Structural formula |
|---|---|---|
| 146 | 6-Chloro-N-[(3S)-1-(4-methoxybenzyl)pyrrolidin-3-yl]-2-{4-[4-(2-methoxyethyl)piperazin-1-yl]phenyl}-3H-imidazo[4,5-b]pyridin-7-amine | |
| 147 | 6-Chloro-N-[(3S)-1-(4-methoxybenzyl)pyrrolidin-3-yl]-2-{4-[4-(pyridin-3-ylmethyl)piperazin-1-yl]phenyl}-3H-imidazo[4,5-b]pyridin-7-amine | |
| 148 | 6-Chloro-2-{4-[4-(3-methoxypropyl)piperazin-1-yl]phenyl}-N-(1-methylpiperidin-4-yl)-3H-imidazo[4,5-b]pyridin-7-amine | |
| 149 | 6-Bromo-2-{4-[4-(3-methoxypropyl)piperazin-1-yl]phenyl}-N-(1-methylpiperidin-4-yl)-3H-imidazo[4,5-b]pyridin-7-amine | |
| 150 | 6-Bromo-N-[1-(1-methylethyl)piperidin-4-yl]-2-{4-[4-(pyridin-3-ylmethyl)piperazin-1-yl]phenyl}-3H-imidazo[4,5-b]pyridin-7-amine | |

TABLE 1-continued

| Ex. | Chemical name | Structural formula |
|---|---|---|
| 151 | 6-Bromo-N-[1-(1-methylethyl)piperidin-4-yl]-2-{4-[4-(pyridin-4-ylmethyl)piperazin-1-yl]phenyl}-3H-imidazo[4,5-b]pyridin-7-amine | |
| 152 | 6-Bromo-N-[1-(1-methylethyl)piperidin-4-yl]-2-[4-(4-pyridin-3-ylpiperazin-1-yl)phenyl]-3H-imidazo[4,5-b]pyridin-7-amine | |
| 153 | 6-Bromo-2-(4-{4-[(3,5-dimethylisoxazol-4-yl)methyl]piperazin-1-yl}phenyl)-N-[1-(1-methylethyl)piperidin-4-yl]-3H-imidazo[4,5-b]pyridin-7-amine | |
| 154 | 6-Bromo-2-{4-[4-(furan-2-ylmethyl)piperazin-1-yl]phenyl}-N-[1-(1-methylethyl)piperidin-4-yl]-3H-imidazo[4,5-b]pyridin-7-amine | |

TABLE 1-continued

| Ex. | Chemical name |
|---|---|
| 155 | 6-Bromo-N-[1-(1-methylethyl)piperidin-4-yl]-2-{4-[4-(pyrimidin-5-ylmethyl)piperazin-1-yl]phenyl}-3H-imidazo[4,5-b]pyridin-7-amine |
| 156 | 6-Bromo-2-{4-[4-(2-methoxyethyl)piperazin-1-yl]phenyl}-N-[(3S)-1-methylpyrrolidin-3-yl]-3H-imidazo[4,5-b]pyridin-7-amine |
| 157 | 6-Bromo-N-[(3S)-1-methylpyrrolidin-3-yl]-2-{4-[4-(pyrimidin-5-ylmethyl)piperazin-1-yl]phenyl}-3H-imidazo[4,5-b]pyridin-7-amine |
| 158 | 6-Bromo-N-[(3S)-1-methylpyrrolidin-3-yl]-2-{4-[4-(pyridin-2-ylmethyl)piperazin-1-yl]phenyl}-3H-imidazo[4,5-b]pyridin-7-amine |
| 159 | 6-Bromo-N-[(3S)-1-methylpyrrolidin-3-yl]-2-{4-[4-(pyridin-3-ylmethyl)piperazin-1-yl]phenyl}-3H-imidazo[4,5-b]pyridin-7-amine |

TABLE 1-continued

| Ex. | Chemical name |
|---|---|
| 160 | 6-Bromo-N-[(3S)-1-methylpyrrolidin-3-yl]-2-{4-[4-(pyridin-4-ylmethyl)piperazin-1-yl]phenyl}-3H-imidazo[4,5-b]pyridin-7-amine |
| 161 | 6-Bromo-N-[(3S)-1-methylpyrrolidin-3-yl]-2-[4-(4-pyridin-3-ylpiperazin-1-yl)phenyl]-3H-imidazo[4,5-b]pyridin-7-amine |
| 162 | 6-Bromo-N-[(3S)-1-methylpyrrolidin-3-yl]-2-[4-(4-pyrazin-2-ylpiperaizn-1-yl)phenyl]-3H-imidazo[4,5-b]pyridin-7-amine |
| 163 | 6-Chloro-2-(4-{4-[(3,5-dimethylisoxazol-4-yl)methyl]piperazin-1-yl}phenyl)-N-[1-(1-methylethyl)piperidin-4-yl]-3H-imidazo[4,5-b]pyridin-7-amine |
| 164 | 6-Chloro-2-{4-[4-(furan-2-ylmethyl)piperazin-1-yl]phenyl}-N-[1-(1-methylethyl)piperidin-4-yl]-3H-imidazo[4,5-b]pyridin-7-amine |

TABLE 1-continued

| Ex. | Chemical name | Structural formula |
|---|---|---|
| 165 | 6-Chloro-N-[1-(1-methylethyl)piperidin-4-yl]-2-{4-[4-(pyrimidin-5-ylmethyl)piperazin-1-yl]phenyl}-3H-imidazo[4,5-b]pyridin-7-amine | |
| 166 | 6-Chloro-N-[1-(1-methylethyl)piperidin-4-yl]-2-(4-{4-[(6-methylpyridin-3-yl)methyl]piperazin-1-yl}phenyl)-3H-imidazo[4,5-b]pyridin-7-amine | |
| 167 | 6-Chloro-N-[1-(1-methylethyl)piperidin-4-yl]-2-{4-[4-(pyrazin-2-ylmethyl)piperazin-1-yl]phenyl}-3H-imidazo[4,5-b]pyridin-7-amine | |
| 168 | 6-Chloro-N-[1-(1-methylethyl)piperidin-4-yl]-2-{4-[4-(pyridin-3-ylmethyl)piperazin-1-yl]phenyl}-3H-imidazo[4,5-b]pyridin-7-amine | |

TABLE 1-continued

| Ex. | Chemical name | Structural formula |
|---|---|---|
| 169 | 6-Bromo-N-(1-ethylpiperidin-4-yl)-2-{4-[4-(pyridin-2-ylmethyl)piperazin-1-yl]phenyl}-3H-imidazo[4,5-b]pyridin-7-amine | |
| 170 | 6-Bromo-N-(1-ethylpiperidin-4-yl)-2-(4-{4-[(6-methylpyridin-3-yl)methyl]piperazin-1-yl}phenyl)-3H-imidazo[4,5-b]pyridin-7-amine | |
| 171 | 6-Bromo-N-(1-ethylpiperidin-4-yl)-2-{4-[4-(1,3-thiazol-2-ylmethyl)piperazin-1-yl]phenyl}-3H-imidazo[4,5-b]pyridin-7-amine | |
| 172 | 6-Bromo-2-{4-[4-(2-ethoxyethyl)piperazin-1-yl]phenyl}-N-(1-ethylpiperidin-4-yl)-3H-imidazo[4,5-b]pyridin-7-amine | |
| 173 | 6-Bromo-N-(1-ethylpiperidin-4-yl)-2-{4-[4-(1H-imidazol-4-ylmethyl)piperazin-1-yl]phenyl}-3H-imidazo[4,5-b]pyridin-7-amine | |

TABLE 1-continued

| Ex. | Chemical name | Structural formula |
|---|---|---|
| 174 | 6-Bromo-N-(1-ethylpiperidin-4-yl)-2-{4-[4-(pyridin-3-ylmethyl)piperazin-1-yl]phenyl}-3H-imidazo[4,5-b]pyridin-7-amine | |
| 175 | 2-{4-[4-(6-Bromo-7-{[(3S)-1-methylpyrrolidin-3-yl]amino}-3H-imidazo[4,5-b]pyridin-2-yl)phenyl]piperazin-1-yl}ethanol | |
| 176 | 6-Bromo-N-[(3S)-1-methylpyrrolidin-3-yl]-2-{4-[4-(pyrazin-2-ylmethyl)piperazin-1-yl]phenyl}-3H-imidazo[4,5-b]pyridin-7-amine | |
| 177 | 6-Bromo-2-{4-[4-(furan-2-ylmethyl)piperazin-1-yl]phenyl}-N-[(3S)-1-methylpyrrolidin-3-yl]-3H-imidazo[4,5-b]pyridin-7-amine | |
| 178 | 6-Bromo-N-[(3S)-1-methylpyrrolidin-3-yl]-2-{4-[4-(1,3-thiazol-2-ylmethyl)piperazin-1-yl]phenyl}-3H-imidazo[4,5-b]pyridin-7-amine | |

TABLE 1-continued

| Ex. | Chemical name | Structural formula |
|---|---|---|
| 179 | 6-Bromo-2-{4-[4-(1H-imidazol-4-ylmethyl)piperazin-1-yl]phenyl}-N-[(3S)-1-methylpyrrolidin-3-yl]-3H-imidazo[4,5-b]pyridin-7-amine | |
| 180 | 6-Bromo-2-(4-{4-[(6-methylpyridin-3-yl)methyl]piperazin-1-yl}phenyl)-N-[(3S)-1-methylpyrrolidin-3-yl]-3H-imidazo[4,5-b]pyridin-7-amine | |
| 181 | 6-Bromo-2-(4-{4-[(6-methylpyridin-2-yl)methyl]piperazin-1-yl}phenyl)-N-[(3S)-1-methylpyrrolidin-3-yl]-3H-imidazo[4,5-b]pyridin-7-amine | |
| 182 | 6-Chloro-2-(4-{4-[(5-methylfuran-2-yl)methyl]piperazin-1-yl}phenyl)-N-(1-methylpiperidin-4-yl)-3H-imidazo[4,5-b]pyridin-7-amine | |
| 183 | 6-Bromo-2-(4-{4-[(5-methylfuran-2-yl)methyl]piperazin-1-yl}phenyl)-N-(1-methylpiperidin-4-yl)-3H-imidazo[4,5-b]pyridin-7-amine | |

TABLE 1-continued

| Ex. | Chemical name | Structural formula |
|---|---|---|
| 184 | 6-Chloro-2-{4-[4-(furan-3-ylmethyl)piperazin-1-yl]phenyl}-N-(1-methylpiperidin-4-yl)-3H-imidazo[4,5-b]pyridin-7-amine | |
| 185 | 6-Bromo-2-{4-[4-(furan-3-ylmethyl)piperazin-1-yl]phenyl}-N-(1-methylpiperidin-4-yl)-3H-imidazo[4,5-b]pyridin-7-amine | |
| 186 | 6-Chloro-2-(4-{4-[2-(2-methoxyethoxy)ethyl]piperazin-1-yl}phenyl)-N-(1-methylpiperidin-4-yl)-3H-imidazo[4,5-b]pyridin-7-amine | |
| 187 | 6-Bromo-2-(4-{4-[2-(2-methoxyethoxy)ethyl]piperazin-1-yl}phenyl)-N-(1-methylpiperidin-4-yl)-3H-imidazo[4,5-b]pyridin-7-amine | |
| 188 | 6-Chloro-N-(1-ethylpiperidin-4-yl)-2-(4-{4-[2-(2-methoxyethoxy)ethyl]piperazin-1-yl}phenyl)-3H-imidazo[4,5-b]pyridin-7-amine | |

TABLE 1-continued

| Ex. | Chemical name |
|---|---|
| 189 | 6-Chloro-2-(4-{4-[2-(2-methoxyethoxy)ethyl]piperazin-1-yl}phenyl)-N-[1-(1-methylethyl)piperidin-4-yl]-3H-imidazo[4,5-b]pyridin-7-amine |
| 190 | 6-Chloro-2-(4-{4-[2-(2-methoxyethoxy)ethyl]piperazin-1-yl}phenyl)-N-[(3S)-1-methylpyrrolidin-3-yl]-3H-imidazo[4,5-b]pyridin-7-amine |
| 191 | 6-Chloro-2-(4-{4-[2-(2-methoxyethoxy)ethyl]piperaizn-1-yl}phenyl)-N-[1-(thiophen-3-ylmethyl)piperidin-4-yl]-3H-imidazo[4,5-b]pyridin-7-amine |
| 192 | 6-Chloro-2-(4-{4-[2-(2-methoxyethoxy)ethyl]piperazin-1-yl}phenyl)-N-[1-(thiophen-2-ylmethyl)piperidin-4-yl]-3H-imidazo[4,5-b]pyridin-7-amine |
| 193 | 6-Chloro-N-(1-methylpiperidin-4-yl)-2-{4-[4-(1,3-thiazol-4-ylmethyl)piperazin-1-yl]phenyl}-3H-imidazo[4,5-b]pyridin-7-amine |

TABLE 1-continued

| Ex. | Chemical name | Structural formula |
|---|---|---|
| 194 | 6-Bromo-N-(1-methylpiperidin-4-yl)-2-{4-[4-(1,3-thiazol-4-ylmethyl)piperazin-1-yl]phenyl}-3H-imidazo[4,5-b]pyridin-7-amine | |
| 195 | 6-Chloro-N-(1-methylpiperidin-4-yl)-2-{4-[4-(1,3-thiaol-5-ylmethyl)piperazin-1-yl]phenyl}-3H-imidazo[4,5-b]pyridin-7-amine | |
| 196 | 6-Bromo-N-(1-methylpiperidin-4-yl)-2-{4-[4-(1,3-thiazol-5-ylmethyl)piperazin-1-yl]phenyl}-3H-imidazo[4,5-b]pyridin-7-amine | |
| 197 | 6-Chloro-N-(1-ethylpiperidin-4-yl)-2-{4-[4-(3-methoxypropyl)piperazin-1-yl]phenyl}-3H-imidazo[4,5-b]pyridin-7-amine | |
| 198 | 6-Bromo-N-(1-ethylpiperidin-4-yl)-2-{4-[4-(3-methoxypropyl)piperazin-1-yl]phenyl}-3-imidazo[4,5-b]pyridin-7-amine | |

TABLE 1-continued

| Ex. | Chemical name |
|---|---|
| 199 | 6-Chloro-2-{4-[4-(3-methoxypropyl)piperazin-1-yl]phenyl}-N-[1-(1-methylethyl)piperidin-4-yl]-3H-imidazo[4,5-b]pyridin-7-amine |
| 200 | 6-Bromo-2-{4-[4-(3-methoxypropyl)piperazin-1-yl]phenyl}-N-[1-(1-methylethyl)piperidin-4-yl]-3H-imidazo[4,5-b]pyridin-7-amine |
| 201 | 6-Chloro-2-{4-[4-(2-methoxyethyl)-3-methylpiperazin-1-yl]phenyl}-N-(1-methylpiperidin-4-yl)-3H-imidazo[4,5-b]pyridin-7-amine |
| 202 | 6-Bromo-2-{4-[4-(2-methoxyethyl)-3-methylpiperazin-1-yl]phenyl}-N-(1-methylpiperidin-4-yl)-3H-imidazo[4,5-b]pyridin-7-amine |
| 203 | 6-Chloro-N-(1-ethylpiperidin-4-yl)-2-{4-[4-(2-methoxyethyl)-3-methylpiperazin-1-yl]phenyl}-3H-imidazo[4,5-b]pyridin-7-amine |

TABLE 1-continued

| Ex. | Chemical name | Structural formula |
|---|---|---|
| 204 | 6-Chloro-N-(1-methylpiperidin-4-yl)-2-{4-[3-methyl-4-(pyridin-3-ylmethyl)piperazin-1-yl]phenyl}-3H-imidazo[4,5-b]pyridin-7-amine | |
| 205 | 6-Bromo-N-(1-methylpiperidin-4-yl)-2-{4-[3-methyl-4-(pyridin-3-ylmethyl)piperazin-1-yl]phenyl}-3H-imidazo[4,5-b]pyridin-7-amine | |
| 206 | 6-Bromo-N-(1-ethylpiperidin-4-yl)-2-{4-[3-methyl-4-(pyridin-3-ylmethyl)piperazin-1-yl]phenyl}-3H-imidazo[4,5-b]pyridin-7-amine | |
| 207 | 6-Chloro-2-(4-{4-[(1-methyl-1H-imidazol-2-yl)methyl]piperazin-1-yl}phenyl)-N-(1-methylpiperidin-4-yl)-3H-imidazo[4,5-b]pyridin-7-amine | |
| 208 | 6-Bromo-2-(4-{4-[(1-methyl-1H-imidazol-2-yl)methyl]piperazin-1-yl}phenyl)-N-(1-methylpiperidin-4-yl)-3H-imidazo[4,5-b]pyridin-7-amine | |

TABLE 1-continued

| Ex. | Chemical name | Structural formula |
|---|---|---|
| 209 | 6-Chloro-N-(1-ethylpiperidin-4-yl)-2-(4-{4-[(1-methyl-1H-imidazol-2-yl)methyl]piperazin-1-yl}phenyl)-3H-imidazo[4,5-b]pyridin-7-amine | |
| 210 | 6-Chloro-N-(1-methylpiperidin-4-yl)-2-(4-{4-[(5-methylpyridin-2-yl)methyl]piperazin-1-yl}phenyl)-3H-imidazo[4,5-b]pyridin-7-amine | |
| 211 | 6-Bromo-N-(1-methylpiperidin-4-yl)-2-(4-{4-[(5-methylpyridin-2-yl)methyl]piperazin-1-yl}phenyl)-3H-imidazo[4,5-b]pyridin-7-amine | |
| 212 | 6-Chloro-N-(1-ethylpiperidin-4-yl)-2-(4-{4-[(5-methylpyridin-2-yl)methyl]piperazin-1-yl}phenyl)-3H-imidazo[4,5-b]pyridin-7-amine | |

TABLE 1-continued

| Ex. | Chemical name | Structural formula |
|---|---|---|
| 213 | 6-Bromo-N-(1-ethylpiperidin-4-yl)-2-(4-{4-[(5-methylpyridin-2-yl)methyl]piperazin-1-yl}phenyl)-3H-imidazo[4,5-b]pyridin-7-amine | 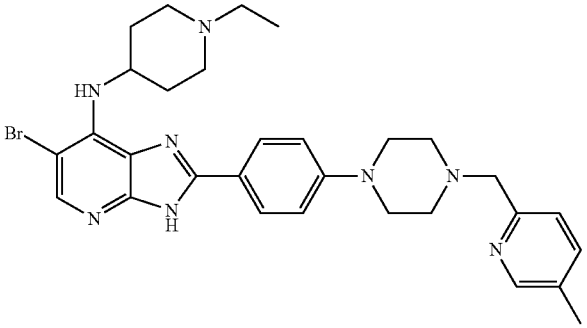 [SMILES: CCN1CCC(Nc2c(Cl)cnc3[nH]c(-c4ccc(N5CCN(Cc6ccc(C)cn6)CC5)cc4)nc23)CC1] |
| 214 | 6-Chloro-2-{4-[4-(3-methoxypropyl)-3-methylpiperazin-1-yl]phenyl}-N-(1-methylpiperidin-4-yl)-3H-imidazo[4,5-b]pyridin-7-amine | 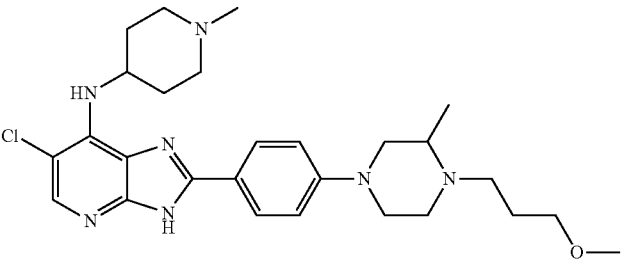 |
| 215 | 6-Bromo-2-{4-[4-(3-methoxypropyl)-3-methylpiperazin-1-yl]phenyl}-N-(1-methylpiperidin-4-yl)-3H-imidazo[4,5-b]pyridin-7-amine | 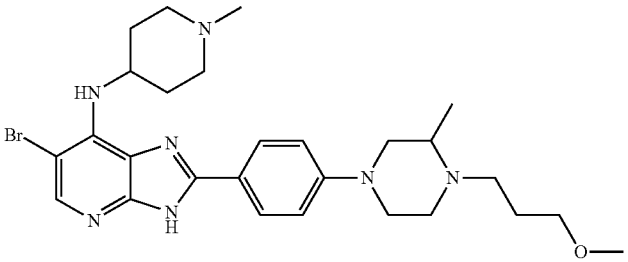 [SMILES: COCCCN1CCN(c2ccc(-c3nc4c(NC5CCN(C)CC5)c(Cl)cnc4[nH]3)cc2)CC1C] |
| 216 | 6-Bromo-N-(1-ethylpiperidin-4-yl)-2-{4-[4-(3-methoxypropyl)-3-methylpiperazin-1-yl]phenyl}-3H-imidazo[4,5-b]pyridin-7-amine | 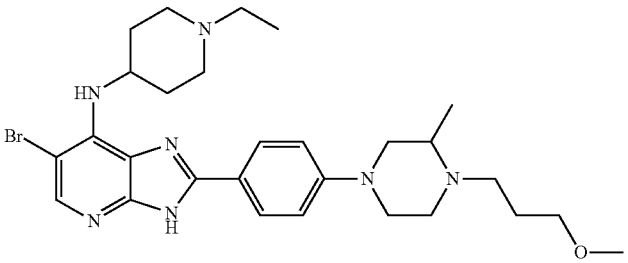 |
| 217 | 6-Chloro-N-(1-methylpiperidin-4-yl)-2-{4-[3-methyl-4-(1,3-thiazol-2-ylmethyl)piperazin-1-yl]phenyl}-3H-imidazo[4,5-b]pyridin-7-amine | 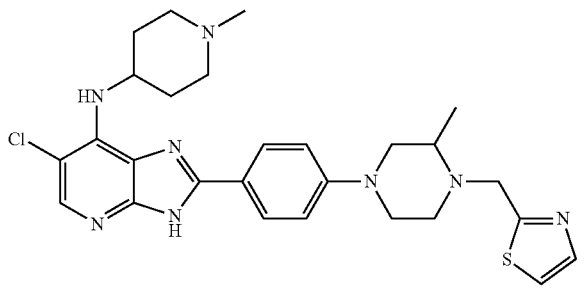 [SMILES: CC1CN(c2ccc(-c3nc4c(NC5CCN(C)CC5)c(Cl)cnc4[nH]3)cc2)CCN1Cc1nccs1] |

TABLE 1-continued

| Ex. | Chemical name | Structural formula |
|---|---|---|
| 218 | 6-Bromo-N-(1-methylpiperidin-4-yl)-2-{4-[3-methyl-4-(1,3-thiazol-2-ylmethyl)piperazin-1-yl]phenyl}-3H-imidazo[4,5-b]pyridin-7-amine | |
| 219 | 6-Chloro-N-(1-ethylpiperidin-4-yl)-2-{4-[3-methyl-4-(1,3-thiazol-2-ylmethyl)piperazin-1-yl]phenyl}-3H-imidazo[4,5-b]pyridin-7-amine | |
| 220 | 6-Chloro-N-(1-methylpiperidin-4-yl)-2-{4-[2-methyl-4-(1,3-thiazol-2-ylmethyl)piperazin-1-yl]phenyl}-3H-imidazo[4,5-b]pyridin-7-amine | |
| 221 | 6-Bromo-N-(1-methylpiperidin-4-yl)-2-{4-[2-methyl-4-(1,3-thiazol-2-ylmethyl)piperazin-1-yl]phenyl}-3H-imidazo[4,5-b]pyridin-7-amine | |
| 222 | 6-Chloro-2-{4-[4-(2-methoxyethyl)-2-methylpiperazin-1-yl]phenyl}-N-(1-methylpiperidin-4-yl)-3H-imidazo[4,5-b]pyridin-7-amine | |

TABLE 1-continued

| Ex. | Chemical name |
|---|---|
| 223 | 6-Bromo-2-{4-[4-(2-methoxyethyl)-2-methylpiperazin-1-yl]phenyl}-N-(1-methylpiperidin-4-yl)-3H-imidazo[4,5-b]pyridin-7-amine |
| 224 | 2-[4-(4-Benzylpiperazin-1-yl)phenyl]-6-chloro-N-(1-methylpiperidin-4-yl)-3H-imidazo[4,5-b]pyridin-7-amine |
| 225 | 2-[4-(4-Benzylpiperazin-1-yl)phenyl]-6-bromo-N-(1-methylpiperidin-4-yl)-3H-imidazo[4,5-b]pyridin-7-amine |
| 226 | 2-[4-(4-Benzylpiperazin-1-yl)phenyl]-6-chloro-N-(1-ethylpiperidin-4-yl)-3H-imidazo[4,5-b]pyridin-7-amine |
| 227 | 6-Chloro-2-{4-[4-(3-methoxypropyl)-2-methylpiperazin-1-yl]phenyl}-N-(1-methylpiperidin-4-yl)-3H-imidazo[4,5-b]pyridin-7-amine |

TABLE 1-continued

| Ex. | Chemical name |
|---|---|
| 228 | 6-Bromo-2-{4-[4-(3-methoxypropyl)-2-methylpiperazin-1-yl]phenyl}-N-(1-methylpiperidin-4-yl)-3H-imidazo[4,5-b]pyridin-7-amine |
| 229 | 6-Chloro-N-(1-ethylpiperidin-4-yl)-2-{4-[4-(3-methoxypropyl)-2-methylpiperazin-1-yl]phenyl}-3H-imidazo[4,5-b]pyridin-7-amine |
| 230 | 4-(4-{6-Chloro-7-[(1-methylpiperidin-4-yl)amino]-3H-imidazo[4,5-b]pyridin-2-yl}phenyl)-1-(2-methoxyethyl)piperazin-2-one |
| 231 | 4-(4-{6-Bromo-7-[(1-methylpiperidin-4-yl)amino]-3H-imidazo[4,5-b]pyridin-2-yl}phenyl)-1-(2-methoxyethyl)piperrazin-2-one |
| 232 | 4-(4-{6-Chloro-7-[(1-ethylpiperidin-4-yl)amino]-3H-imidazo[4,5-b]pyridin-2-yl}phenyl)-1-(2-methoxyethyl)piperazin-2-one |

TABLE 1-continued

| Ex. | Chemical name |
|---|---|
| 233 | 4-[4-(6-Chloro-7-{[1-(1-methylethyl)piperidin-4-yl]amino}-3H-imidazo[4,5-b]pyridin-2-yl)phenyl]-1-(2-methoxyethyl)piperazin-2-one |
| 234 | 4-[4-(6-Bromo-7-{[1-(1-methylethyl)piperidin-4-yl]amino}-3H-imidazo[4,5-b]pyridin-2-yl)phenyl]-1-(2-methoxyethyl)piperazin-2-one |
| 235 | 4-(4-{6-Bromo-7-[(1-ethylpiperidin-4-yl)amino]-3H-imidazo[4,5-b]pyridin-2-yl}phenyl)-1-(2-methoxyethyl)piperazin-2-one |
| 236 | 6-Chloro-2-{4-[4-(methoxyacetyl)piperazin-1-yl]phenyl}-N-(1-methylpiperidin-4-yl)-3H-imidazo[4,5-b]pyridin-7-amine |
| 237 | 6-Bromo-2-{4-[4-(methoxyacetyl)piperazin-1-yl]phenyl}-N-(1-methylpiperidin-4-yl)-3H-imidazo[4,5-b]pyridin-7-amine |

TABLE 1-continued

| Ex. | Chemical name |
|---|---|
| 238 | 6-Chloro-N-(1-ethylpiperidin-4-yl)-2-{4-[4-(methoxyacetyl)piperazin-1-yl]phenyl}-3H-imidazo[4,5-b]pyridin-7-amine |
| 239 | 6-Bromo-N-(1-ethylpiperidin-4-yl)-2-{4-[4-(methoxyacetyl)piperazin-1-yl]phenyl}-3H-imidazo[4,5-b]pyridin-7-amine |
| 240 | 6-Chloro-2-{4-[4-(methoxyacetyl)piperazin-1-yl]phenyl}-N-[1-(1-methylethyl)piperidin-4-yl]-3H-imidazo[4,5-b]pyridin-7-amine |
| 241 | 6-Bromo-2-{4-[4-(methoxyacetyl)piperazin-1-yl]phenyl}-N-[1-(1-methylethyl)piperidin-4-yl]-3H-imidazo[4,5-b]pyridin-7-amine |
| 242 | 4-(4-{6-Chloro-7-[(1-methylpiperidin-4-yl)amino]-3H-imidazo[4,5-b]pyridin-2-yl}phenyl)-1-(3-methoxypropyl)piperazin-2-one |

TABLE 1-continued

| Ex. | Chemical name |
|---|---|
| 243 | 4-(4-{6-Bromo-7-[(1-methylpiperidin-4-yl)amino]-3H-imidazo[4,5-b]pyridin-2-yl}phenyl)-1-(3-methoxypropyl)piperazin-2-one |
| 244 | 4-(4-{6-Chloro-7-[(1-ethylpiperidin-4-yl)amino]-3H-imidazo[4,5-b]pyridin-2-yl}phenyl)-1-(3-methoxypropyl)piperazin-2-one |
| 245 | 4-(4-{6-Bromo-7-[(1-ethylpiperidin-4-yl)amino]-3H-imidazo[4,5-b]pyridin-2-yl}phenyl)-1-(3-methoxypropyl)piperazin-2-one |
| 246 | 4-[4-(6-Chloro-7-{[1-(1-methylethyl)piperidin-4-yl]amino}-3H-imidazo[4,5-b]pyridin-2-yl)phenyl]-1-(3-methoxypropyl)piperazin-2-one |
| 247 | 4-[4-(6-Bromo-7-{[1-(1-methylethyl)piperidin-4-yl]amino}-3H-imidazo[4,5-b]pyridin-2-yl)phenyl]-1-(3-methoxypropyl)piperazin-2-one |

TABLE 1-continued

| Ex. | Chemical name | Structural formula |
|---|---|---|
| 248 | 4-(4-{6-Chloro-7-[(1-methylpiperidin-4-yl)amino]-3H-imidazo[4,5-b]pyridin-2-yl}phenyl)-1-(2-ethoxyethyl)piperazin-2-one | |
| 249 | 4-(4-{6-Bromo-7-[(1-methylpiperidin-4-yl)amino]-3H-imidazo[4,5-b]pyridin-2-yl}phenyl)-1-(2-ethoxyethyl)piperazin-2-one | |
| 250 | 4-(4-{6-Chloro-7-[(1-ethylpiperidin-4-yl)amino]-3H-imidazo[4,5-b]pyridin-2-yl}phenyl)-1-(2-ethoxyethyl)piperazin-2-one | |
| 251 | 4-(4-{6-Bromo-7-[(1-ethylpiperidin-4-yl)amino]-3H-imidazo[4,5-b]pyridin-2-yl}phenyl)-1-(2-ethoxyethyl)piperazin-2-one | |
| 252 | 4-[4-(6-Chloro-7-{[1-(1-methylethyl)piperidin-4-yl]amino}-3H-imidazo[4,5-b]pyridin-2-yl)phenyl]-1-(2-ethoxyethyl)piperazin-2-one | |

TABLE 1-continued

| Ex. | Chemical name | Structural formula |
|---|---|---|
| 253 | 4-[4-(6-Bromo-7-{[1-(1-methylethyl)piperidin-4-yl]amino}-3H-imidazo[4,5-b]pyridin-2-yl)phenyl]-1-(2-ethoxyethyl)piperazin-2-one | |
| 254 | 2-[1-(4-{6-Chloro-7-[(1-methylpiperidin-4-yl)amino]-3H-imidazo[4,5-b]pyridin-2-yl}phenyl)piperidin-4-yl]ethanol | |
| 255 | 2-[1-(4-{6-Bromo-7-[(1-methylpiperidin-4-yl)amino]-3H-imidazo[4,5-b]pyridin-2-yl}phenyl)piperidin-4-yl]ethanol | |
| 256 | 2-[1-(4-{6-Chloro-7-[(1-ethylpiperidin-4-yl)amino]-3H-imidazo[4,5-b]pyridin-2-yl}phenyl)piperidin-4-yl]ethanol | |
| 257 | 2-[1-(4-{6-Bromo-7-[(1-ethylpiperidin-4-yl)amino]-3H-imidazo[4,5-b]pyridin-2-yl}phenyl)piperidin-4-yl]ethanol | |
| 258 | 2-{1-[4-(6-Chloro-7-{[1-(1-methylethyl)piperidin-4-yl]amino}-3H-imidazo[4,5-b]pyridin-2-yl)phenyl]piperidin-4-yl}ethanol | |

TABLE 1-continued

| Ex. | Chemical name | Structural formula |
|---|---|---|
| 259 | 2-{1-[4-(6-Bromo-7-{[1-(1-methylethyl)piperidin-4-yl]amino}-3H-imidazo[4,5-b]pyridin-2-yl)phenyl]piperidin-4-yl}ethanol | |
| 260 | 4-[4-(6-Chloro-7-{1-(4-methoxybenzyl)piperidin-4-yl]amino}-3H-imidazo[4,5-b]pyridin-2-yl)phenyl]-1-(2-methoxyethyl)piperazin-2-one | |
| 261 | 4-[4-(6-Chloro-7-{[1-(4-methoxybenzyl)piperidin-4-yl]amino}-3H-imidazo[4,5-b]pyridin-2-yl)phenyl]-1-(2-ethoxyethyl)piperazin-2-one | |
| 262 | 6-Chloro-2-{4-[4-(methoxyacetyl)piperazin-1-yl]phenyl}-N-[1-(4-methoxybenzyl)piperidin-4-yl]-3H-imidazo[4,5-b]pyridin-7-amine | |
| 263 | 4-[4-(6-Chloro-7-{[1-(4-methoxybenzyl)piperidin-4-yl]amino}-3H-imidazo[4,5-b]pyridin-2-yl)phenyl]-1-(3-methoxypropyl)piperazin-2-one | |
| 264 | 2-{1-[4-(6-Chloro-7-{[1-(4-methoxybenzyl)piperidin-4-yl]amino}-3H-imidazo[4,5-b]pyridin-2-yl)phenyl]piperidin-4-yl}ethanol | |

TABLE 1-continued

| Ex. | Chemical name | Structural formula |
|---|---|---|
| 265 | 6-Chloro-2-{4-[4-(methoxyacetyl)piperazin-1-yl]phenyl}-N-[1-(thiophen-2-ylmethyl)piperidin-4-yl]-3H-imidazo[4,5-b]pyridin-7-amine | |
| 266 | 4-[4-(6-Chloro-7-{[1-(thiophen-2-ylmethyl)piperidin-4-yl]amino}-3H-imidazo[4,5-b]pyridin-2-yl)phenyl]-1-(3-methoxypropyl)piperazin-2-one | |
| 267 | 3-[4-(4-{6-Chloro-7-[(1-methylpiperidin-4-yl)amino]-3H-imidazo[4,5-b]pyridin-2-yl}phenyl)piperazin-1-yl]propan-1-ol | |
| 268 | 3-[4-(4-{6-Bromo-7-[(1-methylpiperidin-4-yl)amino]-3H-imidazo[4,5-b]pyridin-2-yl}phenyl)piperazin-1-yl]propan-1-ol | |
| 269 | 3-[4-(4-{6-Chloro-7-[(1-ethylpiperidin-4-yl)amino]-3H-imidazo[4,5-b]pyridin-2-yl}phenyl)piperazin-1-yl]propan-1-ol | |
| 270 | 4-(4-{6-Chloro-7-[(1-methylpiperidin-4-yl)amino]-3H-imidazo[4,5-b]pyridin-2-yl}phenyl)-1-[2-(1-methylethoxy)ethyl]piperazin-2-one | |

TABLE 1-continued

| Ex. | Chemical name | Structural formula |
|---|---|---|
| 271 | 4-(4-{6-Bromo-7-[(1-methylpiperidin-4-yl)amino]-3H-imidazo[4,5-b]pyridin-2-yl}phenyl)-1-[2-(1-methylethoxy)ethyl]piperazin-2-one | |
| 272 | 4-(4-{6-Chloro-7-[(1-ethylpiperidin-4-yl)amino]-3H-imidazo[4,5-b]pyridin-2-yl}phenyl)-1-[2-(1-methylethoxy)ethyl]piperazin-2-one | |
| 273 | 4-(4-{6-Bromo-7-[(1-ethylpiperidin-4-yl)amino]-3H-imidazo[4,5-b]pyridin-2-yl}phenyl)-1-[2-(1-methylethoxy)ethyl]piperazin-2-one | |
| 274 | 4-[4-(6-Chloro-7-{[1-(1-methylethyl)piperidin-4-yl]amino}-3H-imidazo[4,5-b]pyridin-2-yl)phenyl]-1-[2-(1-methylethoxy)ethyl]piperazin-2-one | |
| 275 | 4-[4-(6-Chloro-7-{[1-(4-methoxybenzyl)piperidin-4-yl]amino}-3H-imidazo[4,5-b]pyridin-2-yl)phenyl]-1-[2-(1-methylethoxy)ethyl]piperazin-2-one | |

TABLE 1-continued

| Ex. | Chemical name | Structural formula |
|---|---|---|
| 276 | 6-Chloro-2-{4-[4-(3-methoxypropanoyl)piperazin-1-yl]phenyl}-N-(1-methylpiperidin-4-yl)-3H-imidazo[4,5-b]pyridin-7-amine | |
| 277 | 6-Bromo-2-{4-[4-(3-methoxypropanoyl)piperazin-1-yl]phenyl}-N-(1-methylpiperidin-4-yl)-3H-imidazo[4,5-b]pyridin-7-amine | |
| 278 | 6-Chloro-N-(1-ethylpiperidin-4-yl)-2-{4-[4-(3-methoxypropanoyl)piperazin-1-yl]phenyl}-3H-imidazo[4,5-b]pyridin-7-amine | |
| 279 | 6-Bromo-N-(1-ethylpiperidin-4-yl)-2-{4-[4-(3-methoxypropanoyl)piperazin-1-yl]phenyl}-3H-imidazo[4,5-b]pyridin-7-amine | |
| 280 | 6-Chloro-N-[1-(4-methoxybenzyl)piperidin-4-yl]-2-{4-[4-(3-methoxypropanoyl)piperazin-1-yl]phenyl}-3H-imidazo[4,5-b]pyridin-7-amine | |
| 281 | 6-Chloro-2-{4-[4-(2-methoxyethyl)piperidin-1-yl]phenyl}-N-(1-methylpiperidin-4-yl)-3H-imidazo[4,5-b]pyridin-7-amine | |

TABLE 1-continued

| Ex. | Chemical name |
|---|---|
| 282 | 6-Bromo-2-{4-[4-(2-methoxyethyl)piperidin-1-yl]phenyl}-N-(1-methylpiperidin-4-yl)-3H-imidazo[4,5-b]pyridin-7-amine |
| 283 | 6-Chloro-N-(1-ethylpiperidin-4-yl)-2-{4-[4-(2-methoxyethyl)piperidin-1-yl]phenyl}-3H-imidazo[4,5-b]pyridin-7-amine |
| 284 | 6-Bromo-N-(1-ethylpiperidin-4-yl)-2-{4-[4-(2-methoxyethyl)piperidin-1-yl]phenyl}-3H-imidazo[4,5-b]pyridin-7-amine |
| 285 | 6-Chloro-2-{4-[4-(2-methoxyethyl)piperidin-1-yl]phenyl}-N-[1-(1-methylethyl)piperidin-4-yl]-3H-imidazo[4,5-b]pyridin-7-amine |
| 286 | 6-Chloro-2-{4-[4-(2-ethoxyethyl)piperidin-1-yl]phenyl}-N-(1-methylpiperidin-4-yl)-3H-imidazo[4,5-b]pyridin-7-amine |

TABLE 1-continued

| Ex. | Chemical name | Structural formula |
|---|---|---|
| 287 | 6-Bromo-2-{4-[4-(2-ethoxyethyl)piperidin-1-yl]phenyl}-N-(1-methylpiperidin-4-yl)-3H-imidazo[4,5-b]pyridin-7-amine | |
| 288 | 6-Chloro-N-(1-ethylpiperidin-4-yl)-2-{4-[4-(2-ethoxyethyl)piperidin-1-yl]phenyl}-3H-imidazo[4,5-b]pyridin-7-amine | |
| 289 | 6-Bromo-N-(1-ethylpiperidin-4-yl)-2-{4-[4-(2-ethoxyethyl)piperidin-1-yl]phenyl}-3H-imidazo[4,5-b]pyridin-7-amine | |
| 290 | 6-Chloro-2-{4-[4-(2-ethoxyethyl)piperidin-1-yl]phenyl}-N-[1-(1-methylethyl)piperidin-4-yl]-3H-imidazo[4,5-b]pyridin-7-amine | |
| 291 | 1-Benzyl-4-(4-{6-chloro-7-[(1-methylpiperidin-4-yl)amino]-3H-imidazo[4,5-b]pyridin-2-yl}phenyl)piperazin-2-one | |

TABLE 1-continued

| Ex. | Chemical name | Structural formula |
|---|---|---|
| 292 | 1-Benzyl-4-(4-{6-bromo-7-[(1-methylpiperidin-4-yl)amino]-3H-imidazo[4,5-b]pyridin-2-yl}phenyl)piperazin-2-one | |
| 293 | 1-Benzyl-4-(4-{6-chloro-7-[(1-ethylpiperidin-4-yl)amino]-3H-imidazo[4,5-b]pyridin-2-yl}phenyl)piperazin-2-one | |
| 294 | 1-Benzyl-4-(4-{6-bromo-7-[(1-ethylpiperidin-4-yl)amino]-3H-imidazo[4,5-b]pyridin-2-yl}phenyl)piperazin-2-one | |
| 295 | 1-Benzyl-4-[4-(6-chloro-7-{[1-(4-methoxybenzyl)piperidin-4-yl]amino}-3H-imidazo[4,5-b]pyridin-2-yl)phenyl]piperazin-2-one | |
| 296 | 4-(4-{6-Chloro-7-[(1-methylpiperidin-4-yl)amino]-3H-imidazo[4,5-b]pyridin-2-yl}phenyl)-1-methylpiperazin-2-one | |

TABLE 1-continued

| Ex. | Chemical name | Structural formula |
|---|---|---|
| 297 | 4-(4-{6-Bromo-7-[(1-methylpiperidin-4-yl)amino]-3H-imidazo[4,5-b]pyridin-2-yl}phenyl)-1-methylpiperazin-2-one | |
| 298 | 4-(4-{6-Chloro-7-[(1-ethylpiperidin-4-yl)amino]-3H-imidazo[4,5-b]pyridin-2-yl}phenyl)-1-methylpiperazin-2-one | |
| 299 | 4-(4-{6-Bromo-7-[(1-ethylpiperidin-4-yl)amino]-3H-imidazo[4,5-b]pyridin-2-yl}phenyl)-1-methylpiperazin-2-one | |
| 300 | 4-[4-(6-Chloro-7-{[1-(4-methoxybenzyl)piperidin-4-yl]amino}-3H-imidazo[4,5-b]pyridin-2-yl)phenyl]-1-methylpiperazin-2-one | |
| 301 | 6-Chloro-N-(1-methylpiperidin-4-yl)-2-{4-[4-(pyridin-3-ylcarbonyl)piperazin-1-yl]phenyl}-3H-imidazo[4,5-b]pyridin-7-amine | |
| 302 | 6-Bromo-N-(1-methylpiperidin-4-yl)-2-{4-[4-(pyridin-3-ylcarbonyl)piperazin-1-yl]phenyl}-3H-imidazo[4,5-b]pyridin-7-amine | |

TABLE 1-continued

| Ex. | Chemical name | Structural formula |
|---|---|---|
| 303 | 6-Chloro-N-(1-ethylpiperidin-4-yl)-2-{4-[4-(pyridin-3-ylcarbonyl)piperazin-1-yl]phenyl}-3H-imidazo[4,5-b]pyridin-7-amine | |
| 304 | 6-Bromo-N-(1-ethylpiperidin-4-yl)-2-{4-[4-(pyridin-3-ylcarbonyl)piperazin-1-yl]phenyl}-3H-imidazo[4,5-b]pyridin-7-amine | |
| 305 | 6-Chloro-N-[1-(4-methoxybenzyl)piperidin-4-yl]-2-{4-[4-(pyridin-3-ylcarbonyl)piperazin-1-yl]phenyl}-3H-imidazo[4,5-b]pyridin-7-amine | |
| 306 | 6-Chloro-2-{4-[4-(3-methoxypropyl)piperazin-1-yl]phenyl}-N-(1-propylpiperidin-4-yl)-3H-imidazo[4,5-b]pyridin-7-amine | |
| 307 | 6-Bromo-2-{4-[4-(3-methoxypropyl)piperazin-1-yl]phenyl}-N-(1-propylpiperidin-4-yl)-3H-imidazo[4,5-b]pyridin-7-amine | |
| 308 | 6-Chloro-N-[1-(2-methoxyethyl)piperidin-4-yl]-2-{4-[4-(3-methoxypropyl)piperazin-1-yl]phenyl}-3H-imidazo[4,5-b]pyridin-7-amine | |

TABLE 1-continued

| Ex. | Chemical name |
|---|---|
| 309 | 4-(4-{6-Chloro-7-[(1-propylpiperidin-4-yl)amino]-3H-imidazo[4,5-b]pyridin-2-yl}phenyl)-1-(2-ethoxyethyl)piperazin-2-one |
| 310 | 4-[4-(6-Chloro-7-{[1-(2-methoxyethyl)piperidin-4-yl]amino}-3H-imidazo[4,5-b]pyridin-2-yl)phenyl]-1-(2-ethoxyethyl)piperazin-2-one |
| 311 | 4-(4-{6-Chloro-7-[(1-cyclohexylpiperidin-4-yl)amino]-3H-imidazo[4,5-b]pyridin-2-yl}phenyl)-1-(2-methoxyethyl)piperain-2-one |
| 312 | 3-[4-(4-{6-Bromo-7-[(1-ethylpiperidin-4-yl)amino]-3H-imidazo[4,5-b]pyridin-2-yl}phenyl)piperazin-1-yl]propan-1-ol |
| 313 | 6-Chloro-N-(1-ethylpiperidin-4-yl)-2-{4-[4-(pyrazin-2-ylmethyl)piperazin-1-yl]phenyl}-3H-imidazo[4,5-b]pyridin-7-amine |

TABLE 1-continued

| Ex. | Chemical name | Structural formula |
|---|---|---|
| 314 | 6-Bromo-N-(1-ethylpiperidin-4-yl)-2-{4-[4-(pyrazin-2-ylmethyl)piperazin-1-yl]phenyl}-3H-imidazo[4,5-b]pyridin-7-amine | |
| 315 | 6-Chloro-N-[1-(4-methoxybenzyl)piperidin-4-yl]-2-{4-[4-(pyrazin-2-ylmethyl)piperazin-1-yl]phenyl}-3H-imidazo[4,5-b]pyridin-7-amine | |
| 316 | 6-Chloro-N-(1-ethylpiperidin-4-yl)-2-{4-[4-(1,3-thiazol-4-ylmethyl)piperazin-1-yl]phenyl}-3H-imidazo[4,5-b]pyridin-7-amine | |
| 317 | 6-Bromo-N-(1-ethylpiperidin-4-yl)-2-{4-[4-(1,3-thiazol-4-ylmethyl)piperazin-1-yl]phenyl}-3H-imidazo[4,5-b]pyridin-7-amine | |
| 318 | 6-Chloro-N-[1-(4-methoxybenzyl)piperidin-4-yl]-2-{4-[4-(1,3-thiazol-4-ylmethyl)piperazin-1-yl]phenyl}-3H-imidazo[4,5-b]pyridin-7-amine | |

TABLE 1-continued

| Ex. | Chemical name | Structural formula |
|---|---|---|
| 319 | 6-Chloro-N-[1-(4-methoxybenzyl)piperidin-4-yl]-2-{4-[4-(1,3-thiazol-5-ylmethyl)piperazin-1-yl]phenyl}-3H-imidazo[4,5-b]pyridin-7-amine | |
| 320 | 6-Chloro-N-(1-ethylpiperidin-4-yl)-2-{4-[4-(1,3-thiazol-5-ylmethyl)piperazin-1-yl]phenyl}-3H-imidazo[4,5-b]pyridin-7-amine | |
| 321 | 6-Bromo-N-(1-ethylpiperidin-4-yl)-2-{4-[4-(1,3-thiazol-5-ylmethyl)piperazin-1-yl]phenyl}-3H-imidazo[4,5-b]pyridin-7-amine | |
| 322 | 6-Chloro-N-(1-methylpiperidin-4-yl)-2-[4-(4-{2-[(1-methyl-1H-pyrazol-5-yl)amino]ethyl}piperazin-1-yl)phenyl]-3H-imidazo[4,5-b]pyridin-7-amine | |
| 323 | 6-Bromo-N-(1-methylpiperidin-4-yl)-2-[4-(4-{2-[(1-methyl-1H-pyrazol-5-yl)amino]ethyl}piperazin-1-yl)phenyl]-3H-imidazo[4,5-b]pyridin-7-amine | |

TABLE 1-continued

| Ex. | Chemical name | Structural formula |
|---|---|---|
| 324 | 6-Chloro-N-(1-ethylpiperidin-4-yl)-2-[4-(4-{2-[(1-methyl-1H-pyrazol-5-yl)amino]ethyl}piperazin-1-yl)phenyl]-3H-imidazo[4,5-b]pyridin-7-amine | 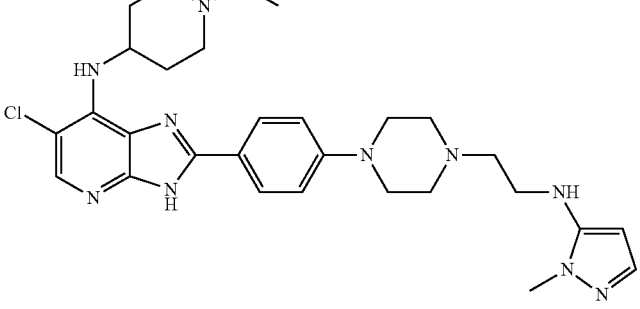 |
| 325 | 6-Bromo-N-(1-ethylpiperidin-4-yl)-2-[4-(4-{2-[(1-methyl-1H-pyrazol-5-yl)amino]ethyl}piperazin-1-yl)phenyl]-3H-imidazo[4,5-b]pyridin-7-amine | 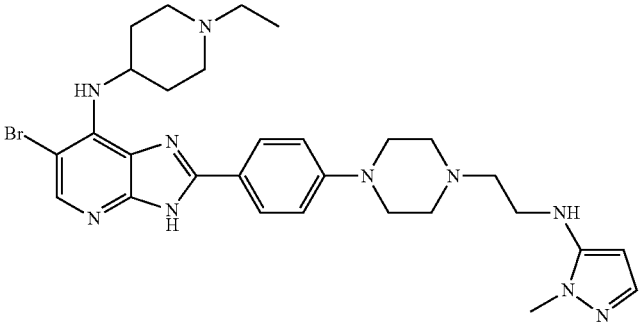 [SMILES: CCN1CCC(Nc2c(Cl)cnc3[nH]c(-c4ccc(N5CCN(CCNc6ccnn6C)CC5)cc4)nc23)CC1] |
| 326 | 6-Chloro-N-[1-(1-methylethyl)piperidin-4-yl]-2-[4-(4-{2-[(1-methyl-1H-pyrazol-5-yl)amino]ethyl}piperazin-1-yl)phenyl]-3H-imidazo[4,5-b]pyridin-7-amine | 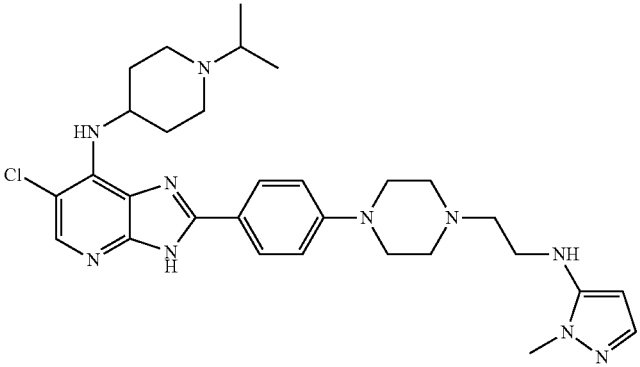 [SMILES: CC(C)N1CCC(Nc2c(Cl)cnc3[nH]c(-c4ccc(N5CCN(CCNc6ccnn6C)CC5)cc4)nc23)CC1] |
| 327 | 6-Chloro-N-[1-(4-methoxybenzyl)piperidin-4-yl]-2-[4-(4-{2-[(1-methyl-1H-pyrazol-5-yl)amino]ethyl}piperazin-1-yl)phenyl]-3H-imidazo[4,5-b]pyridin-7-amine | 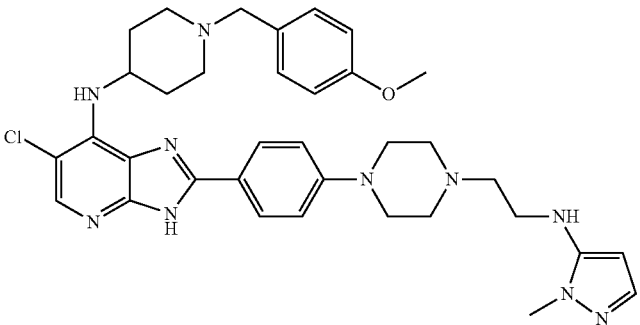 [SMILES: COc1ccc(CN2CCC(Nc3c(Cl)cnc4[nH]c(-c5ccc(N6CCN(CCNc7ccnn7C)CC6)cc5)nc34)CC2)cc1] |
| 328 | 6-Chloro-N-(1-methylpiperidin-4-yl)-2-{4-[4-(pyridin-4-ylcarbonyl)piperazin-1-yl]phenyl}-3H-imidazo[4,5-b]pyridin-7-amine | 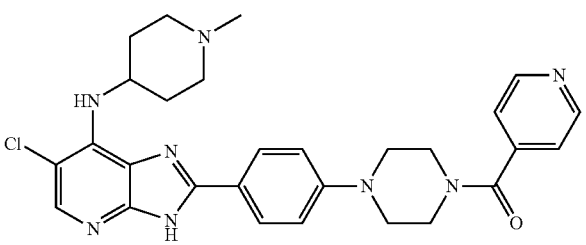 [SMILES: CN1CCC(Nc2c(Cl)cnc3[nH]c(-c4ccc(N5CCN(C(=O)c6ccncc6)CC5)cc4)nc23)CC1] |

TABLE 1-continued

| Ex. | Chemical name |
|---|---|
| 329 | 6-Bromo-N-(1-methylpiperidin-4-yl)-2-{4-[4-(pyridin-4-ylcarbonyl)piperazin-1-yl]phenyl}-3H-imidazo[4,5-b]pyridin-7-amine |
| 330 | 6-Chloro-N-(1-ethylpiperidin-4-yl)-2-{4-[4-(pyridin-4-ylcarbonyl)piperazin-1-yl]phenyl}-3H-imidazo[4,5-b]pyridin-7-amine |
| 331 | 6-Bromo-N-(1-ethylpiperidin-4-yl)-2-{4-[4-(pyridin-4-ylcarbonyl)piperazin-1-yl]phenyl}-3H-imidazo[4,5-b]pyridin-7-amine |
| 332 | 3-[4-(4-{6-Chloro-7-[(1-methylpiperidin-4-yl)amino]-3H-imidazo[4,5-b]pyridin-2-yl}phenyl)piperazin-1-yl]propanenitrile |
| 333 | 3-[4-(4-{6-Bromo-7-[(1-methylpiperidin-4-yl)amino]-3H-imidazo[4,5-b]pyridin-2-yl}phenyl)piperazin-1-yl]propanenitrile |
| 334 | 3-[4-(4-{6-Chloro-7-[(1-ethylpiperidin-4-yl)amino]-3H-imidazo[4,5-b]pyridin-2-yl}phenyl)piperazin-1-yl]propanenitrile |

TABLE 1-continued

| Ex. | Chemical name | Structural formula |
|---|---|---|
| 335 | 3-[4-(4-{6-Bromo-7-[(1-ethylpiperidin-4-yl)amino]-3H-imidazo[4,5-b]pyridin-2-yl}phenyl)piperazin-1-yl]propanenitrile | 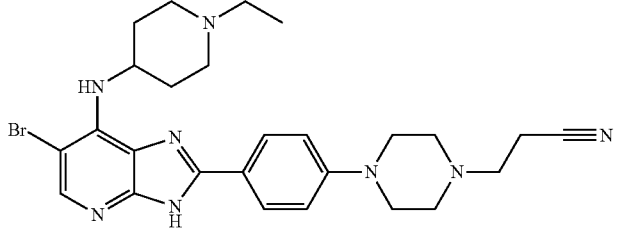 [SMILES: CCN1CCC(Nc2c(Cl)cnc3[nH]c(-c4ccc(N5CCN(CCC#N)CC5)cc4)nc23)CC1] |
| 336 | 3-{4-[4-(6-Chloro-7-{[1-(4-methoxybenzyl)piperidin-4-yl]amino}-3H-imidazo[4,5-b]pyridin-2-yl)phenyl]piperazin-1-yl}propanenitrile | 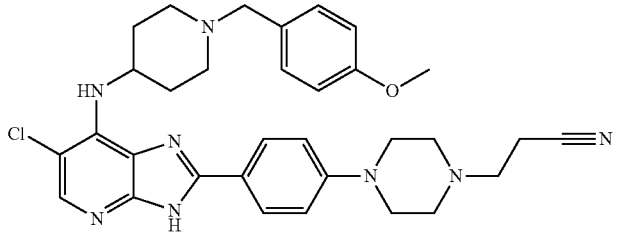 [SMILES: COc1ccc(CN2CCC(Nc3c(Cl)cnc4[nH]c(-c5ccc(N6CCN(CCC#N)CC6)cc5)nc34)CC2)cc1] |
| 337 | 3-{4-[4-(6-Bromo-7-{[1-(1-methylethyl)piperidin-4-yl]amino}-3H-imidazo[4,5-b]pyridin-2-yl)phenyl]piperazin-1-yl}propanenitrile | 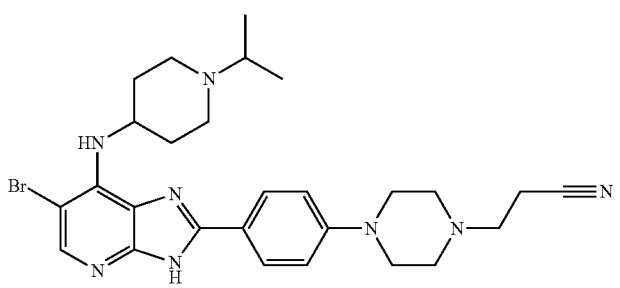 [SMILES: CC(C)N1CCC(Nc2c(Br)cnc3[nH]c(-c4ccc(N5CCN(CCC#N)CC5)cc4)nc23)CC1] |
| 338 | 6-Bromo-2-{4-[4-(3-methoxypropyl)piperazin-1-yl]phenyl}-N-(1,2,2,6,6-pentamethylpiperidin-4-yl)-3H-imidazo[4,5-b]pyridin-7-amine | 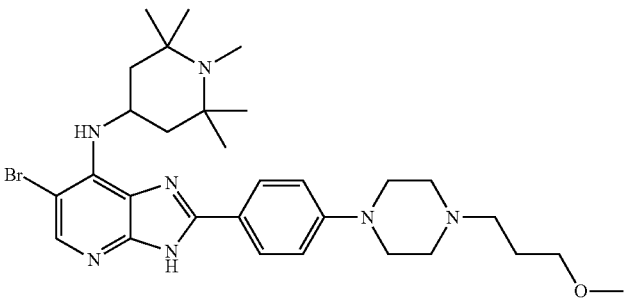 [SMILES: COCCCN1CCN(c2ccc(-c3nc4c(NC5CC(C)(C)N(C)C(C)(C)C5)c(Cl)cnc4[nH]3)cc2)CC1] |
| 339 | 6-Bromo-2-{4-[4-(2-methoxyethyl)piperazin-1-yl]phenyl}-N-(1,2,2,6,6-pentamethylpiperidin-4-yl)-3H-imidazo[4,5-b]pyridin-7-amine | 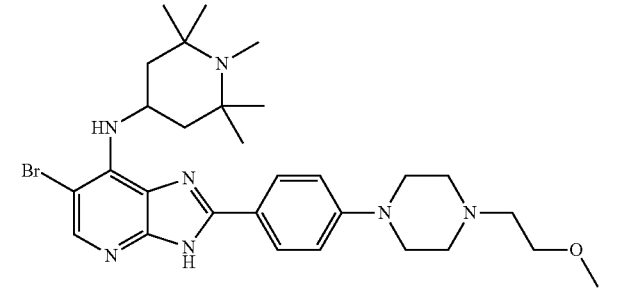 [SMILES: COCCN1CCN(c2ccc(-c3nc4c(NC5CC(C)(C)N(C)C(C)(C)C5)c(Cl)cnc4[nH]3)cc2)CC1] |

TABLE 1-continued

| Ex. | Chemical name |
|---|---|
| 340 | 6-Bromo-N-(1,2,2,6,6-pentamethylpiperidin-4-yl)-2-{4-[4-(pyridin-3-ylcarbonyl)piperazin-1-yl]phenyl}-3H-imidazo[4,5-b]pyridin-7-amine |
| 341 | 6-Bromo-2-[4-(4-{2-[(1-methyl-1H-pyrazol-5-yl)amino]ethyl}piperazin-1-yl)phenyl]-N-(1,2,2,6,6-pentamethylpiperidin-4-yl)-3H-imidazo[4,5-b]pyridin-7-amine |
| 342 | 4-(4-{6-Bromo-7-[(1,2,2,6,6-pentamethylpiperidin-4-yl)amino]-3H-imidazo[4,5-b]pyridin-2-yl}phenyl)-1-(2-ethoxyethyl)piperazin-2-one |
| 343 | 6-Chloro-2-{4-[4-(4-methoxybutyl)piperazin-1-yl]phenyl}-N-(1-methylpiperidin-4-yl)-3H-imidazo[4,5-b]pyridin-7-amine |
| 344 | 6-Bromo-2-{4-[4-(4-methoxybutyl)piperazin-1-yl]phenyl}-N-(1-methylpiperidin-4-yl)-3H-imidazo[4,5-b]pyridin-7-amine |

TABLE 1-continued

| Ex. | Chemical name | Structural formula |
|---|---|---|
| 345 | 6-Chloro-N-(1-ethylpiperidin-4-yl)-2-{4-[4-(4-methoxybutyl)piperazin-1-yl]phenyl}-3H-imidazo[4,5-b]pyridin-7-amine | |
| 346 | 6-Bromo-N-(1-ethylpiperidin-4-yl)-2-{4-[4-(4-methoxybutyl)piperazin-1-yl]phenyl}-3H-imidazo[4,5-b]pyridin-7-amine | |
| 347 | 6-Chloro-N-[1-(4-methoxybenzyl)piperidin-4-yl]-2-{4-[4-(4-methoxybutyl)piperazin-1-yl]phenyl}-3H-imidazo[4,5-b]pyridin-7-amine | |
| 348 | 6-Chloro-2-{4-[4-(3-methoxypropyl)piperazin-1-yl]phenyl}-N-(1,2,2,6,6-pentamethylpiperidin-4-yl)-3H-imidazo[4,5-b]pyridin-7-amine | |
| 349 | 6-Chloro-2-{4-[4-(2-methoxyethyl)piperazin-1-yl]phenyl}-N-(1,2,2,6,6-pentamethylpiperidin-4-yl)-3H-imidazo[4,5-b]pyridin-7-amine | |

TABLE 1-continued

| Ex. | Chemical name | Structural formula |
|---|---|---|
| 350 | 6-Chloro-N-(1,2,2,6,6-pentamethylpiperidin-4-yl)-2-{4-[4-(pyridin-3-ylcarbonyl)piperazin-1-yl]phenyl}-3H-imidazo[4,5-b]pyridin-7-amine | |
| 351 | 6-Chloro-2-[4-(4-{2-[(1-methyl-1H-pyrazol-5-yl)amino]ethyl}piperazin-1-yl)phenyl]-N-(1,2,2,6,6-pentamethylpiperidin-4-yl)-3H-imidazo[4,5-b]pyridin-7-amine | |
| 352 | 4-(4-{6-Chloro-7-[(1,2,2,6,6-pentamethylpiperidin-4-yl)amino]-3H-imidazo[4,5-b]pyridin-2-yl}phenyl)-1-(2-ethoxyethyl)piperazin-2-one | |
| 353 | 6-Chloro-N-[1-(cyclopropylmethyl)piperidin-4-yl]-2-[4-(4-{2-[(1-methyl-1H-pyrazol-5-yl)amino]ethyl}piperazin-1-yl)phenyl]-3H-imidazo[4,5-b]pyridin-7-amine | |
| 354 | 3-{4-[4-(6-Chloro-7-{[1-(cyclopropylmethyl)piperidin-4-yl]amino}-3H-imidazo[4,5-b]pyridin-2-yl)phenyl]piperazin-1-yl}propan-1-ol | |

TABLE 1-continued

| Ex. | Chemical name | Structural formula |
|-----|---------------|-------------------|
| 355 | 4-[4-(6-Chloro-7-{[1-(cyclopropylmethyl)piperidin-4-yl]amino}-3H-imidazo[4,5-b]pyridin-2-yl)phenyl]-1-(2-methoxyethyl)piperrazin-2-one | |
| 356 | 6-Chloro-N-[1-(cyclopropylmethyl)piperidin-4-yl]-2-{4-[4-(3-methoxypropyl)piperazin-1-yl]phenyl}-3H-imidazo[4,5-b]pyridin-7-amine | |
| 357 | 6-Chloro-N-[1-(cyclopropylmethyl)piperidin-4-yl]-2-{4-[4-(2-methoxyethyl)piperazin-1-yl]phenyl}-3H-imidazo[4,5-b]pyridin-7-amine | |
| 358 | 6-Chloro-N-[1-(cyclopropylmethyl)piperidin-4-yl]-2-{4-[4-(2-ethoxyethyl)piperazin-1-yl]phenyl}-3H-imidazo[4,5-b]pyridin-7-amine | |
| 359 | 6-Chloro-N-[1-(cyclopropylmethyl)piperidin-4-yl]-2-{4-[4-(pyridin-3-ylmethyl)piperazin-1-yl]phenyl}-3H-imidazo[4,5-b]pyridin-7-amine | |

TABLE 1-continued

| Ex. | Chemical name | Structural formula |
|---|---|---|
| 360 | 6-Chloro-N-[1-(cyclopropylmethyl)piperidin-4-yl]-2-{4-[4-(1,3-thiazol-2-ylmethyl)piperazin-1-yl]phenyl}-3H-imidazo[4,5-b]pyridin-7-amine | |
| 361 | 6-Chloro-2-{4-[4-(2,2-dimethylpropanoyl)piperazin-1-yl]phenyl}-N-(1-methylpiperidin-4-yl)-3H-imidazo[4,5-b]pyridin-7-amine | |
| 362 | 6-Bromo-2-{4-[4-(2,2-dimethylpropanoyl)piperazin-1-yl]phenyl}-N-(1-methylpiperidin-4-yl)-3H-imidazo[4,5-b]pyridin-7-amine | |
| 363 | 6-Bromo-2-{4-[4-(2,2-dimethylpropanoyl)piperazin-1-yl]phenyl}-N-(1-ethylpiperidin-4-yl)-3H-imidazo[4,5-b]pyridin-7-amine | |
| 364 | 6-Bromo-N-[1-(cyclopropylmethyl)piperidin-4-yl]-2-[4-(4-{2-[(1-methyl-1H-pyrazol-5-yl)amino]ethyl}piperazin-1-yl)phenyl]-3H-imidazo[4,5-b]pyridin-7-amine | |
| 365 | 3-{4-[4-(6-Bromo-7-{[1-(cyclopropylmethyl)piperidin-4-yl]amino}-3H-imidazo[4,5-b]pyridin-2-yl)phenyl]piperazin-1-yl}propan-1-ol | |

TABLE 1-continued

| Ex. | Chemical name |
|---|---|
| 366 | 4-[4-(6-Bromo-7-{[1-(cyclopropylmethyl)piperidin-4-yl]amino}-3H-imidazo[4,5-b]pyridin-2-yl)phenyl]-1-(2-methoxyethyl)piperazin-2-one |
| 367 | 6-Bromo-N-[1-(cyclopropylmethyl)piperidin-4-yl]-2-{4-[4-(3-methoxypropyl)piperazin-1-yl]phenyl}-3H-imidazo[4,5-b]pyridin-7-amine |
| 368 | 6-Bromo-N-[1-(cyclopropylmethyl)piperidin-4-yl]-2-{4-[4-(2-methoxyethyl)piperazin-1-yl]phenyl}-3H-imidazo[4,5-b]pyridin-7-amine |
| 369 | 6-Bromo-N-[1-(cyclopropylmethyl)piperidin-4-yl]-2-{4-[4-(2-ethoxyethyl)piperazin-1-yl]phenyl}-3H-imidazo[4,5-b]pyridin-7-amine |
| 370 | 6-Bromo-N-[1-(cyclopropylmethyl)piperidin-4-yl]-2-{4-[4-(pyridin-3-ylmethyl)piperazin-1-yl]phenyl}-3H-imidazo[4,5-b]pyridin-7-amine |

TABLE 1-continued

| Ex. | Chemical name |
|---|---|
| 371 | 6-Bromo-N-[1-(cyclopropylmethyl)piperidin-4-yl]-2-{4-[4-(1,3-thiazol-2-ylmethyl)piperazin-1-yl]phenyl}-3H-imidazo[4,5-b]pyridin-7-amine |
| 372 | 6-Chloro-2-{3-fluoro-4-[4-(2-methoxyethyl)piperazin-1-yl]phenyl}-N-(1-methylpiperidin-4-yl)-3H-imidazo[4,5-b]pyridin-7-amine |
| 373 | 6-Bromo-2-{3-fluoro-4-[4-(2-methoxyetthyl)piperazin-1-yl]phenyl}-N-(1-methylpiperidin-4-yl)-3H-imidazo[4,5-b]pyridin-7-amine |
| 374 | 6-Chloro-N-(1-ethylpiperidin-4-yl)-2-{3-fluoro-4-[4-(2-methoxyethyl)piperazin-1-yl]phenyl}-3H-imidazo[4,5-b]pyridin-7-amine |
| 375 | 6-Bromo-N-(1-ethylpiperidin-4-yl)-2-{3-fluoro-4-[4-(2-methoxyethyl)piperazin-1-yl]phenyl}-3H-imidazo[4,5-b]pyridin-7-amine |
| 376 | 6-Chloro-N-[1-(cyclopropylmethyl)piperidin-4-yl]-2-{3-fluoro-4-[4-(2-methoxyethyl)piperazin-1-yl]phenyl}-3H-imidazo[4,5-b]pyridin-7-amine |

TABLE 1-continued

| Ex. | Chemical name | Structural formula |
|---|---|---|
| 377 | 6-Bromo-N-[1-(cyclopropylmethyl)piperidin-4-yl]-2-{3-fluoro-4-[4-(2-methoxyethyl)piperazin-1-yl]phenyl}-3H-imidazo[4,5-b]pyridin-7-amine | |
| 378 | 6-Chloro-2-{3-fluoro-4-[4-(2-methoxyethyl)piperazin-1-yl]phenyl}-N-[1-(1-methylethyl)piperidin-4-yl]-3H-imidazo[4,5-b]pyridin-7-amine | |
| 379 | {4-[(6-Bromo-2-{4-[4-(2-methoxyethyl)piperazin-1-yl]phenyl}-3H-imidazo[4,5-b]pyridin-7-yl)amino]piperidin-1-yl}acetonitrile | |
| 380 | {4-[(6-Bromo-2-{3-fluoro-4-[4-(2-methoxyethyl)piperazin-1-yl]phenyl}-3H-imidazo[4,5-b]pyridin-7-yl)amino]piperidin-1-yl}acetonitrile | |
| 381 | 6-Chloro-2-{3-methoxy-4-[4-(2-methoxyethyl)piperazin-1-yl]phenyl}-N-(1-methylpiperidin-4-yl)-3H-imidazo[4,5-b]pyridin-7-amine | |

TABLE 1-continued

| Ex. | Chemical name | Structural formula |
|---|---|---|
| 382 | 6-Bromo-2-{3-methoxy-4-[4-(2-methoxyethyl)piperazin-1-yl]phenyl}-N-(1-methylpiperidin-4-yl)-3H-imidazo[4,5-b]pyridin-7-amine | |
| 383 | 6-Chloro-N-(1-ethylpiperidin-4-yl)-2-{3-methoxy-4-[4-(2-methoxyethyl)piperazin-1-yl]phenyl}-3H-imidazo[4,5-b]pyridin-7-amine | |
| 384 | 6-Bromo-N-(1-ethylpiperidin-4-yl)-2-{3-methoxy-4-[4-(2-methoxyethyl)piperazin-1-yl]phenyl}-3H-imidazo[4,5-b]pyridin-7-amine | |
| 385 | 6-Chloro-N-[1-(cyclopropylmethyl)piperidin-4-yl]-2-{3-methoxy-4-[4-(2-methoxyethyl)piperazin-1-yl]phenyl}-3H-imidazo[4,5-b]pyridin-7-amine | |
| 386 | 6-Bromo-N-[1-(cyclopropylmethyl)piperidin-4-yl]-2-{3-methoxy-4-[4-(2-methoxyethyl)piperazin-1-yl]phenyl}-3H-imidazo[4,5-b]pyridin-7-amine | |
| 387 | 6-Chloro-2-{3-methoxy-4-[4-(2-methoxyethyl)piperazin-1-yl]phenyl}-N-[1-(1-methylethyl)piperidin-4-yl]-3H-imidazo[4,5-b]pyridin-7-amine | |

TABLE 1-continued

| Ex. | Chemical name | Structural formula |
|---|---|---|
| 388 | 6-Chloro-2-{2-fluoro-4-[4-(2-methoxyethyl)piperazin-1-yl]phenyl}-N-(1-methylpiperidin-4-yl)-3H-imidazo[4,5-b]pyridin-7-amine | |
| 389 | 6-Bromo-2-{2-fluoro-4-[4-(2-methoxyethyl)piperazin-1-yl]phenyl}-N-(1-methylpiperidin-4-yl)-3H-imidazo[4,5-b]pyridin-7-amine | |
| 390 | 6-Chloro-N-(1-ethylpiperidin-4-yl)-2-{2-fluoro-4-[4-(2-methoxyethyl)piperazin-1-yl]phenyl}-3H-imidazo[4,5-b]pyridin-7-amine | |
| 391 | 6-Bromo-N-(1-ethylpiperidin-4-yl)-2-{2-fluoro-4-[4-(2-methoxyethyl)piperazin-1-yl]phenyl}-3H-imidazo[4,5-b]pyridin-7-amine | |
| 392 | 6-Chloro-N-[1-(cyclopropylmethyl)piperidin-4-yl]-2-{2-fluoro-4-[4-(2-methoxyethyl)piperazin-1-yl]phenyl}-3H-imidazo[4,5-b]pyridin-7-amine | |
| 393 | 6-Bromo-N-[1-(cyclopropylmethyl)piperidin-4-yl]-2-{2-fluoro-4-[4-(2-methoxyethyl)piperazin-1-yl]phenyl}-3H-imidazo[4,5-b]pyridin-7-amine | |

TABLE 1-continued

| Ex. | Chemical name |
|---|---|
| 394 | 6-Chloro-2-{2-fluoro-4-[4-(2-methoxyethyl)piperazin-1-yl]phenyl}-N-[1-(1-methylethyl)piperidin-4-yl]-3H-imidazo[4,5-b]pyridin-7-amine |
| 395 | 3-{4-[(6-Chloro-2-{4-[4-(3-methoxypropyl)piperazin-1-yl]phenyl}-3H-imidazo[4,5-b]pyridin-7-yl)amino]piperidin-1-yl}propanenitrile |
| 396 | 3-{4-[(6-Chloro-2-{4-[4-(2-methoxyethyl)piperazin-1-yl]phenyl}-3H-imidazo[4,5-b]pyridin-7-yl)amino]piperidin-1-yl}propanenitrile |
| 397 | 3-{4-[(6-Chloro-2-{4-[4-(4-methoxybutyl)piperazin-1-yl]phenyl}-3H-imidazo[4,5-b]pyridin-7-yl)amino]piperidin-1-yl}propanenitrile |
| 398 | 3-{4-[(6-Chloro-2-{4-[4-(2,2-dimethylpropanoyl)piperazin-1-yl]phenyl}-3H-imidazo[4,5-b]pyridin-7-yl)amino]piperidin-1-yl}propanenitrile |

TABLE 1-continued

| Ex. | Chemical name | Structural formula |
|---|---|---|
| 399 | 3-{4-[(6-Chloro-2-{4-[4-(3-hydroxypropyl)piperazin-1-yl]phenyl}-3H-imidazo[4,5-b]pyridin-7-yl)amino]piperidin-1-yl}propanenitrile | 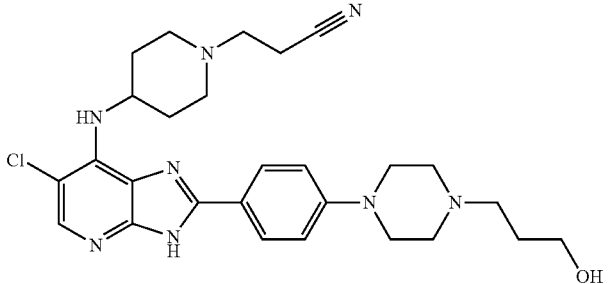 |
| 400 | 3-{4-[(6-Chloro-2-{4-[4-(2-ethoxyethyl)-3-oxopiperazin-1-yl]phenyl}-3H-imidazo[4,5-b]pyridin-7-yl)amino]piperidin-1-yl}propnaenitrile | 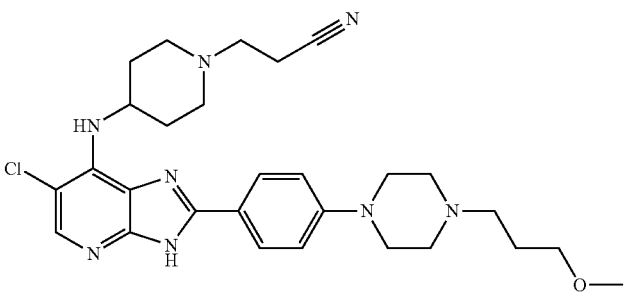 [SMILES: COCCCN1CCN(c2ccc(-c3nc4c(NC5CCN(CCC#N)CC5)c(Cl)cnc4[nH]3)cc2)CC1] |
| 401 | 3-{4-[(6-Chloro-2-{2-fluoro-4-[4-(2-methoxyethyl)piperazin-1-yl]phenyl}-3H-imidazo[4,5-b]pyridin-7-yl)amino]piperidin-1-yl}propanenitrile | 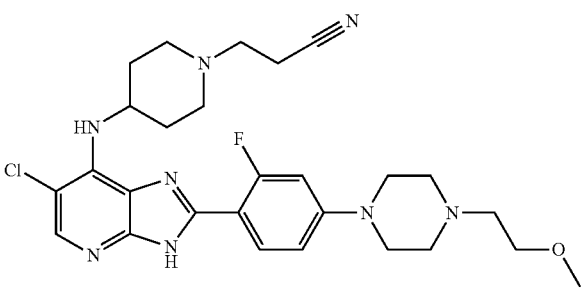 |
| 402 | 3-{4-[(6-Bromo-2-{4-[4-(2-methoxyethyl)piperazin-1-yl]phenyl}-3H-imidazo[4,5-b]pyridin-7-yl)amino]piperidin-1-yl}propanenitrile | 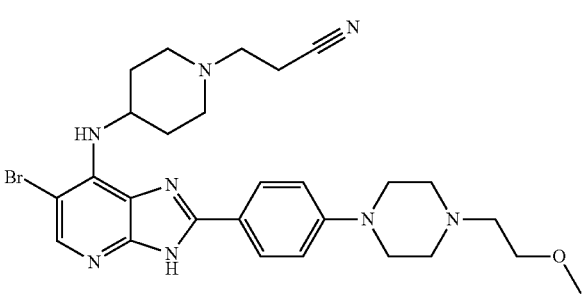 [SMILES: COCCN1CCN(c2ccc(-c3nc4c(NC5CCN(CCC#N)CC5)c(Cl)cnc4[nH]3)cc2)CC1] |
| 403 | 3-{4-[(6-Bromo-2-{4-[4-(4-methoxybutyl)piperazin-1-yl]phenyl}-3H-imidazo[4,5-b]pyridin-7-yl)amino]piperidin-1-yl}propanenitrile | 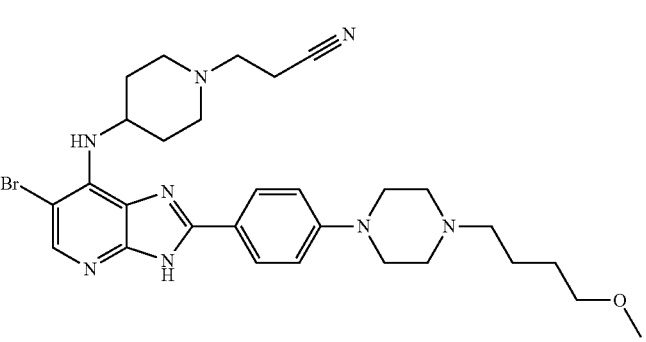 [SMILES: COCCCCN1CCN(c2ccc(-c3nc4c(NC5CCN(CCC#N)CC5)c(Cl)cnc4[nH]3)cc2)CC1] |

TABLE 1-continued

| Ex. | Chemical name | Structural formula |
|---|---|---|
| 404 | 3-{4-[(6-Bromo-2-{4-[4-(2,2-dimethylpropanoyl)piperazin-1-yl]phenyl}-3H-imidazo[4,5-b]pyridin-7-yl)amino]piperidin-1-yl}propanenitrile | |
| 405 | 3-{4-[(6-Bromo-2-{4-[4-(3-hydroxypropyl)piperazin-1-yl]phenyl}-3H-imidazo[4,5-b]pyridin-7-yl)amino]piperidin-1-yl}propanenitrile | |
| 406 | 3-{4-[(6-Bromo-2-{4-[4-(2-ethoxyethyl)-3-oxopiperrazin-1-yl]phenyl}-3H-imidazo[4,5-b]pyridin-7-yl)amino]piperidin-1-yl}propanenitrile | |
| 407 | 3-{4-[(6-Bromo-2-{2-fluoro-4-[4-(2-methoxyethyl)piperazin-1-yl]phenyl}-3H-imidazo[4,5-b]pyridin-7-yl)amino]piperidin-1-yl}propanenitrile | |
| 408 | 6-Chloro-N-[1-(cyclopropylmethyl)piperidin-4-yl]-2-{4-[4-(pyrazin-2-ylmethyl)pierazin-1-yl]phenyl}-3H-imidazo[4,5-b]pyridin-7-amine | |

TABLE 1-continued

| Ex. | Chemical name | Structural formula |
|---|---|---|
| 409 | 6-Chloro-N-[1-(cyclopropylmethyl)piperidin-4-yl]-2-{4-[4-(pyrimidin-5-ylmethyl)piperazin-1-yl]phenyl}-3H-imidazo[4,5-b]pyridin-7-amine | 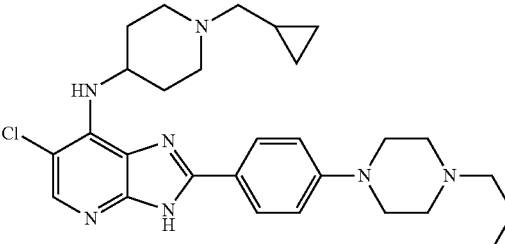 |
| 410 | 6-Chloro-N-[1-(cyclopropylmethyl)piperidin-4-yl]-2-{4-[4-(pyridin-4-ylmethyl)piperazin-1-yl]phenyl}-3H-imidazo[4,5-b]pyridin-7-amine | 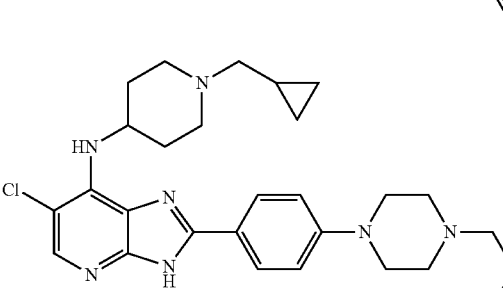 |

Analytical data of the above Examples are shown in Table 2, where the indicated MS data ([M+H]$^+$) were obtained by ESI.

TABLE 2

| Ex | m/z | $^1$H NMR (600 MHz, DMSO-d$_6$) δ ppm |
|---|---|---|
| 1 | 484 | 12.99 (br. s., 1 H) 7.97 (s, 1 H) 7.98 (d, J = 8.9 Hz, 2 H) 7.07 (d, J = 8.9 Hz, 2 H) 5.42 (d, J = 8.9 Hz, 1 H) 4.87-4.97 (m, 1 H) 3.26 (t, J = 5.2 Hz, 4 H) 2.79 (d, J = 11.3 Hz, 2 H) 2.45 (t, J = 4.9 Hz, 4 H) 2.23 (s, 3 H) 2.21 (s, 3 H) 2.08 (t, J = 10.8 Hz, 2 H) 1.99 (d, J = 10.4 Hz, 2 H) 1.65 (qd, J = 11.6, 3.1 Hz, 2 H). |
| 2 | 440 | 12.96 (br. s., 1 H) 7.98 (d, J = 8.9 Hz, 2 H) 7.88 (s, 1 H) 7.07 (d, J = 8.9 Hz, 2 H) 5.69 (d, J = 8.9 Hz, 1 H) 4.86-4.97 (m, 1 H) 3.26 (t, J = 5.2 Hz, 4 H) 2.81 (d, J = 11.9 Hz, 2 H) 2.45 (t, J = 4.9 Hz, 4 H) 2.23 (s, 3 H) 2.21 (s, 3 H) 2.05 (td, J = 11.3, 1.8 Hz, 2 H) 1.97 (d, J = 11.6 Hz, 2 H) 1.66 (qd, J = 11.6, 3.8 Hz, 2 H). |
| 3 | 546 | 12.96 (br. s., 1 H) 7.97 (d, J = 8.9 Hz, 2 H) 7.87 (s, 1 H) 7.23 (d, J = 8.9 Hz, 2 H) 7.06 (d, J = 9.2 Hz, 2 H) 6.89 (d, J = 8.5 Hz, 2 H) 5.70 (d, J = 8.9 Hz, 1 H) 4.89-5.04 (m, 1 H) 3.74 (s, 3 H) 3.44 (s, 2 H) 3.27 (t, J = 4.9 Hz, 4 H) 2.85 (d, J = 11.6 Hz, 2 H) 2.46 (t, J = 4.9 Hz, 4 H) 2.23 (s, 3 H) 2.10 (td, J = 11.6, 1.5 Hz, 2 H) 1.97 (d, J = 10.7 Hz, 2 H) 1.65 (qd, J = 11.6, 3.1 Hz, 2 H). |
| 4 | 514 | 7.97 (s, 1 H) 7.98 (d, J = 9.5 Hz, 2 H) 7.06 (d, J = 9.2 Hz, 2 H) 5.41 (d, J = 8.9 Hz, 1 H) 4.87-4.97 (m, 1 H) 4.44 (t, J = 5.3 Hz, 1 H) 3.54 (q, J = 6.1 Hz, 2 H) 3.26 (t, J = 5.2 Hz, 4 H) 2.79 (d, J = 11.6 Hz, 2 H) 2.56 (t, J = 5.2 Hz, 4 H) 2.44 (t, J = 6.3 Hz, 2 H) 2.21 (s, 3 H) 2.07 (t, J = 11.6 Hz, 2 H) 1.99 (d, J = 10.7 Hz, 2 H) 1.64 (qd, J = 11.5, 3.5 Hz, 2 H). |
| 5 | 470 | 12.96 (br. s., 1 H) 7.98 (d, J = 8.9 Hz, 2 H) 7.87 (s, 1 H) 7.06 (d, J = 9.2 Hz, 2 H) 5.69 (d, J = 8.9 Hz, 1 H) 4.83-4.98 (m, 1 H) 4.44 (t, J = 5.3 Hz, 1 H) 3.54 (q, J = 5.9 Hz, 2 H) 3.25 (t, J = 5.2 Hz, 4 H) 2.81 (d, J = 11.9 Hz, 2 H) 2.56 (t, J = 4.9 Hz, 4 H) 2.44 (t, J = 6.3 Hz, 2 H) 2.21 (s, 3 H) 2.05 (td, J = 11.9, 1.8 Hz, 2 H) 1.97 (d, J = 10.1 Hz, 2 H) 1.66 (qd, J = 11.7, 3.7 Hz, 2 H). |
| 6 | 484 | 12.96 (br. s., 1 H) 7.97 (d, J = 8.9 Hz, 2 H) 7.88 (s, 1 H) 7.06 (d, J = 9.2 Hz, 2 H) 5.68 (d, J = 8.5 Hz, 1 H) 4.88-4.99 (m, 1 H) 4.44 (t, J = 5.3 Hz, 1 H) 3.54 (q, J = 5.8 Hz, 2 H) 3.26 (t, J = 5.2 Hz, 4 H) 2.92 (d, J = 11.3 Hz, 2 H) 2.56 (t, J = 4.9 Hz, 4 H) 2.44 (t, J = 6.3 Hz, 2 H) 2.36 (q, J = 7.0 Hz, 2 H) 2.03 (t, J = 11.9 Hz, 2 H) 1.99 (d, J = 11.3 Hz, 2 H) 1.64 (qd, J = 11.6, 3.4 Hz, 2 H) 1.03 (t, J = 7.2 Hz, 3 H). |
| 7 | 528 | 12.99 (br. s., 1 H) 7.98 (d, J = 8.9 Hz, 2 H) 7.97 (s, 1 H) 7.06 (d, J = 8.9 Hz, 2 H) 5.40 (d, J = 8.9 Hz, 1 H) 4.87-4.98 (m, 1 H) 3.48 (t, J = 5.8 Hz, 2 H) 3.25 (s, 3 H) 3.25 (t, J = 5.0 Hz, 4 H) 2.79 (d, J = 11.6 Hz, 2 H) 2.56 (t, J = 4.9 Hz, 4 H) 2.52 (t, J = 5.6 Hz, 2 H) 2.21 (s, 3 H) 2.07 (t, J = 10.7 Hz, 2 H) 1.99 (d, J = 10.7 Hz, 2 H) 1.64 (qd, J = 11.4, 3.5 Hz, 2 H). |
| 8 | 484 | 12.95 (br. s., 1 H) 7.98 (d, J = 8.9 Hz, 2 H) 7.87 (s, 1 H) 7.06 (d, J = 9.2 Hz, 2 H) 5.69 (d, J = 8.5 Hz, 1 H) 4.86-4.97 (m, 1 H) 3.48 (t, J = 5.8 Hz, 2 H) 3.25 (s, 3 H) 3.25 (t, J = 5.1 Hz, 4 H) 2.81 (d, J = 11.6 Hz, 2 H) 2.56 (t, J = 4.9 Hz, 4 H) 2.52 (t, |

TABLE 2-continued

| Ex | m/z | ¹H NMR (600 MHz, DMSO-d$_6$) δ ppm |
|---|---|---|
| | | J = 5.8 Hz, 2 H) 2.21 (s, 3 H) 2.05 (td, J = 11.6, 1.8 Hz, 2 H) 1.97 (d, J = 11.6 Hz, 2 H) 1.66 (qd, J = 11.7, 3.7 Hz, 2 H). |
| 9 | 498 | 7.98 (d, J = 9.2 Hz, 2 H) 7.87 (s, 1 H) 7.05 (d, J = 8.9 Hz, 2 H) 5.66 (d, J = 8.9 Hz, 1 H) 4.87-5.01 (m, 1 H) 3.48 (t, J = 5.8 Hz, 2 H) 3.25 (s, 3 H) 3.25 (t, J = 4.9 Hz, 4 H) 2.92 (d, J = 11.3 Hz, 2 H) 2.56 (t, J = 4.9 Hz, 4 H) 2.52 (t, J = 5.8 Hz, 2 H) 2.35 (q, J = 7.2 Hz, 2 H) 2.03 (t, J = 11.9 Hz, 2 H) 1.99 (d, J = 11.6 Hz, 2 H) 1.63 (qd, J = 11.6, 3.5 Hz, 2 H) 1.03 (t, J = 7.2 Hz, 3 H). |
| 10 | 498 | 12.98 (br. s., 1 H) 7.98 (d, J = 8.9 Hz, 2 H) 7.97 (s, 1 H) 7.06 (d, J = 9.2 Hz, 2 H) 5.40 (d, J = 8.9 Hz, 1 H) 4.86-5.01 (m, 1 H) 3.26 (t, J = 5.2 Hz, 4 H) 2.79 (d, J = 11.9 Hz, 2 H) 2.50 (t, J = 5.2 Hz, 4 H) 2.37 (q, J = 7.0 Hz, 2 H) 2.21 (s, 3 H) 2.07 (t, J = 10.8 Hz, 2 H) 1.99 (d, J = 12.2 Hz, 2 H) 1.64 (qd, J = 11.4, 3.7 Hz, 2 H) 1.04 (t, J = 7.2 Hz, 3 H). |
| 11 | 454 | 12.95 (br. s., 1 H) 7.98 (d, J = 8.9 Hz, 2 H) 7.87 (s, 1 H) 7.06 (d, J = 8.9 Hz, 2 H) 5.68 (d, J = 8.9 Hz, 1 H) 4.86-4.98 (m, 1 H) 3.26 (t, J = 5.2 Hz, 4 H) 2.81 (d, J = 11.9 Hz, 2 H) 2.50 (t, J = 5.2 Hz, 4 H) 2.37 (q, J = 7.2 Hz, 2 H) 2.21 (s, 3 H) 2.05 (td, J = 11.6, 1.5 Hz, 2 H) 1.97 (d, J = 10.4 Hz, 2 H) 1.66 (qd, J = 11.7, 3.7 Hz, 2 H) 1.04 (t, J = 7.2 Hz, 3 H). |
| 12 | 468 | 12.96 (br. s., 1 H) 7.98 (d, J = 8.8 Hz, 2 H) 7.87 (s, 1 H) 7.06 (d, J = 9.2 Hz, 2 H) 5.66 (d, J = 8.5 Hz, 1 H) 4.88-4.99 (m, 1 H) 3.26 (t, J = 5.2 Hz, 4 H) 2.92 (d, J = 11.3 Hz, 2 H) 2.50 (t, J = 5.2 Hz, 4 H) 2.37 (q, J = 7.2 Hz, 2 H) 2.36 (q, J = 7.3 Hz, 2 H) 2.03 (t, J = 11.7 Hz, 2 H) 1.99 (d, J = 11.0 Hz, 2 H) 1.63 (qd, J = 11.5, 3.5 Hz, 2 H) 1.04 (t, J = 7.6 Hz, 3 H) 1.03 (t, J = 7.2 Hz, 3 H). |
| 13 | 576 | 7.97 (d, J = 8.9 Hz, 2 H) 7.87 (s, 1 H) 7.23 (d, J = 8.5 Hz, 2 H) 7.06 (d, J = 8.9 Hz, 2 H) 6.89 (d, J = 8.9 Hz, 2 H) 5.70 (d, J = 8.9 Hz, 1 H) 4.91-5.00 (m, 1 H) 4.44 (t, J = 5.3 Hz, 1 H) 3.74 (s, 3 H) 3.55 (q, J = 6.1 Hz, 2 H) 3.44 (s, 2 H) 3.26 (t, J = 5.2 Hz, 4 H) 2.85 (d, J = 11.3 Hz, 2 H) 2.57 (t, J = 4.9 Hz, 4 H) 2.45 (t, J = 6.1 Hz, 2 H) 2.10 (t, J = 10.8 Hz, 2 H) 1.97 (d, J = 11.0 Hz, 2 H) 1.65 (qd, J = 11.6, 3.7 Hz, 2 H). |
| 14 | 590 | 7.97 (d, J = 8.9 Hz, 2 H) 7.87 (s, 1 H) 7.23 (d, J = 8.9 Hz, 2 H) 7.05 (d, J = 9.2 Hz, 2 H) 6.89 (d, J = 8.5 Hz, 2 H) 5.68 (d, J = 8.5 Hz, 1 H) 4.91-5.02 (m, 1 H) 3.74 (s, 3 H) 3.48 (t, J = 5.8 Hz, 2 H) 3.44 (s, 2 H) 3.26 (s, 3 H) 3.26 (t, J = 5.1 Hz, 4 H) 2.85 (d, J = 11.6 Hz, 2 H) 2.57 (t, J = 4.9 Hz, 4 H) 2.53 (t, J = 5.8 Hz, 2 H) 2.10 (t, J = 10.5 Hz, 2 H) 1.97 (d, J = 10.4 Hz, 2 H) 1.64 (qd, J = 11.7, 2.9 Hz, 2 H). |
| 15 | 560 | 12.96 (br. s., 1 H) 7.97 (d, J = 8.9 Hz, 2 H) 7.87 (s, 1 H) 7.23 (d, J = 8.5 Hz, 2 H) 7.06 (d, J = 9.2 Hz, 2 H) 6.89 (d, J = 8.9 Hz, 2 H) 5.70 (d, J = 8.9 Hz, 1 H) 4.91-5.01 (m, 1 H) 3.74 (s, 3 H) 3.44 (s, 2 H) 3.27 (t, J = 5.2 Hz, 4 H) 2.85 (d, J = 11.3 Hz, 2 H) 2.51 (t, J = 5.0 Hz, 4 H) 2.38 (q, J = 7.2 Hz, 2 H) 2.10 (t, J = 10.8 Hz, 2 H) 1.97 (d, J = 11.6 Hz, 2 H) 1.65 (qd, J = 11.6, 3.2 Hz, 2 H) 1.05 (t, J = 7.3 Hz, 3 H). |
| 16 | 547 | 12.99 (br. s., 1 H) 8.19 (d, J = 6.7 Hz, 2 H) 8.02 (d, J = 8.9 Hz, 2 H) 7.98 (s, 1 H) 7.13 (d, J = 9.2 Hz, 2 H) 6.89 (d, J = 6.4 Hz, 2 H) 5.42 (d, J = 8.5 Hz, 1 H) 4.87-4.99 (m, 1 H) 3.48-3.52 (m, 4 H) 3.41-3.46 (m, 4 H) 2.80 (d, J = 11.6 Hz, 2 H) 2.21 (s, 3 H) 2.08 (t, J = 11.6 Hz, 2 H) 1.99 (d, J = 10.4 Hz, 2 H) 1.65 (qd, J = 11.5, 3.8 Hz, 2 H). |
| 17 | 503 | 12.99 (br. s., 1 H) 8.19 (d, J = 6.4 Hz, 2 H) 8.02 (d, J = 8.9 Hz, 2 H) 7.88 (s, 1 H) 7.13 (d, J = 8.9 Hz, 2 H) 6.89 (d, J = 6.4 Hz, 2 H) 5.70 (d, J = 8.9 Hz, 1 H) 4.85-5.01 (m, 1 H) 3.47-3.53 (m, 4 H) 3.40-3.45 (m, 4 H) 2.82 (d, J = 11.6 Hz, 2 H) 2.21 (s, 3 H) 2.06 (td, J = 11.3, 2.1 Hz, 2 H) 1.97 (d, J = 11.0 Hz, 2 H) 1.67 (qd, J = 11.6, 4.0 Hz, 2 H). |
| 18 | 531 | 12.99 (br. s., 1 H) 8.19 (d, J = 6.4 Hz, 2 H) 8.01 (d, J = 8.9 Hz, 2 H) 7.88 (s, 1 H) 7.13 (d, J = 9.2 Hz, 2 H) 6.88 (d, J = 6.4 Hz, 2 H) 5.64 (d, J = 8.5 Hz, 1 H) 4.84-4.96 (m, 1 H) 3.47-3.52 (m, 4 H) 3.41-3.45 (m, 4 H) 2.85 (d, J = 11.9 Hz, 2 H) 2.72 (spt, J = 6.6 Hz, 1 H) 2.28 (td, J = 11.3, 2.1 Hz, 2 H) 2.01 (d, J = 10.7 Hz, 2 H) 1.60 (qd, J = 11.5, 3.5 Hz, 2 H) 1.01 (d, J = 6.4 Hz, 6 H). |
| 19 | 609 | 12.99 (br. s., 1 H) 8.20 (d, J = 6.4 Hz, 2 H) 8.01 (d, J = 8.8 Hz, 2 H) 7.87 (s, 1 H) 7.24 (d, J = 8.5 Hz, 2 H) 7.13 (d, J = 8.9 Hz, 2 H) 6.90 (d, J = 8.5 Hz, 2 H) 6.89 (d, J = 6.4 Hz, 2 H) 5.70 (d, J = 9.5 Hz, 1 H) 4.91-5.03 (m, 1 H) 3.74 (s, 3 H) 3.48-3.53 (m, 4 H) 3.44 (s, 2 H) 3.42-3.45 (m, 4 H) 2.86 (d, J = 11.3 Hz, 2 H) 2.11 (t, J = 10.8 Hz, 2 H) 1.98 (d, J = 10.7 Hz, 2 H) 1.65 (qd, J = 11.7, 2.9 Hz, 2 H). |
| 20 | 575 | 13.01 (br. s., 1 H) 8.19 (d, J = 6.4 Hz, 2 H) 8.01 (d, J = 8.9 Hz, 2 H) 7.98 (s, 1 H) 7.13 (d, J = 8.9 Hz, 2 H) 6.88 (d, J = 6.7 Hz, 2 H) 5.37 (d, J = 8.9 Hz, 1 H) 4.85-5.01 (m, 1 H) 3.47-3.54 (m, 4 H) 3.40-3.45 (m, 4 H) 2.84 (d, J = 11.9 Hz, 2 H) 2.73 (spt, J = 6.6 Hz, 1 H) 2.29 (td, J = 11.3, 1.8 Hz, 2 H) 2.03 (d, J = 10.1 Hz, 2 H) 1.58 (qd, J = 11.4, 3.4 Hz, 2 H) 1.01 (d, J = 6.7 Hz, 6 H). |
| 21 | 498 | 12.88 (br. s., 1 H) 7.95 (s, 1 H) 7.93 (d, J = 9.2 Hz, 2 H) 6.82 (d, J = 9.2 Hz, 2 H) 5.36 (d, J = 8.9 Hz, 1 H) 4.87-4.97 (m, 1 H) 3.58 (t, J = 5.2 Hz, 2 H) 3.51 (t, J = 6.4 Hz, 2 H) 2.80 (d, J = 11.6 Hz, 2 H) 2.62 (t, J = 4.9 Hz, 2 H) 2.44 (t, J = 5.5 Hz, 2 H) 2.26 (s, 3 H) 2.21 (s, 3 H) 2.08 (td, J = 11.6, 1.5 Hz, 2 H) 1.99 (d, J = 10.7 Hz, 2 H) 1.90 (ddd, J = 11.5, 6.1, 5.9 Hz, 2 H) 1.64 (qd, J = 11.5, 3.5 Hz, 2 H). |
| 22 | 454 | 12.85 (br. s., 1 H) 7.93 (d, J = 8.9 Hz, 2 H) 7.85 (s, 1 H) 6.82 (d, J = 8.9 Hz, 2 H) 5.63 (d, J = 8.9 Hz, 1 H) 4.84-5.02 (m, 1 H) 3.58 (t, J = 4.9 Hz, 2 H) 3.51 (t, J = 6.3 Hz, 2 H) 2.81 (d, J = 11.3 Hz, 2 H) 2.62 (t, J = 4.9 Hz, 2 H) 2.44 (t, J = 5.5 Hz, 2 H) 2.26 (s, 3 H) 2.21 (s, 3 H) 2.05 (td, J = 11.3, 1.8 Hz, 2 H) 1.97 (d, J = 10.7 Hz, 2 H) 1.90 (quin, J = 5.9 Hz, 2 H) 1.66 (qd, J = 11.6, 3.7 Hz, 2 H). |
| 23 | 482 | 12.85 (br. s., 1 H) 7.93 (d, J = 8.9 Hz, 2 H) 7.85 (s, 1 H) 6.82 (d, J = 8.9 Hz, 2 H) 5.58 (d, J = 8.9 Hz, 1 H) 4.84-4.95 (m, 1 H) 3.58 (t, J = 4.9 Hz, 2 H) 3.51 (t, J = 6.3 Hz, 2 H) 2.85 (d, J = 11.6 Hz, 2 H) 2.72 (spt, J = 6.6 Hz, 1 H) 2.62 (t, J = 4.9 Hz, 2 H) 2.44 (t, J = 5.8 Hz, 2 H) 2.27 (td, J = 11.6, 1.8 Hz, 2 H) 2.26 (s, 3 H) 2.01 (d, J = 11.6 Hz, 2 H) 1.90 (ddd, J = 11.5, 6.1, 5.9 Hz, 2 H) 1.59 (qd, J = 11.5, 3.5 Hz, 2 H) 1.01 (d, J = 6.4 Hz, 6 H). |

TABLE 2-continued

| Ex | m/z | $^1$H NMR (600 MHz, DMSO-$d_6$) δ ppm |
|---|---|---|
| 24 | 526 | 12.88 (br. s., 1 H) 7.95 (s, 1 H) 7.93 (d, J = 9.2 Hz, 2 H) 6.82 (d, J = 8.9 Hz, 2 H) 5.30 (d, J = 8.9 Hz, 1 H) 4.84-4.95 (m, 1 H) 3.58 (t, J = 4.9 Hz, 2 H) 3.51 (t, J = 6.3 Hz, 2 H) 2.83 (d, J = 11.9 Hz, 2 H) 2.72 (spt, J = 6.6 Hz, 1 H) 2.62 (t, J = 4.9 Hz, 2 H) 2.44 (t, J = 5.5 Hz, 2 H) 2.28 (td, J = 11.3, 2.1 Hz, 2 H) 2.26 (s, 3 H) 2.03 (d, J = 11.0 Hz, 2 H) 1.90 (ddd, J = 11.5, 6.1, 5.9 Hz, 2 H) 1.57 (qd, J = 11.4, 3.7 Hz, 2 H) 1.01 (d, J = 6.4 Hz, 6 H). |
| 25 | 560 | 12.85 (s, 1 H) 7.92 (d, J = 8.9 Hz, 2 H) 7.85 (s, 1 H) 7.24 (d, J = 8.9 Hz, 2 H) 6.89 (d, J = 8.9 Hz, 2 H) 6.82 (d, J = 9.2 Hz, 2 H) 5.65 (d, J = 8.9 Hz, 1 H) 4.90-5.02 (m, 1 H) 3.74 (s, 3 H) 3.59 (t, J = 5.2 Hz, 2 H) 3.52 (t, J = 6.3 Hz, 2 H) 3.44 (s, 2 H) 2.86 (d, J = 11.9 Hz, 2 H) 2.63 (t, J = 4.9 Hz, 2 H) 2.45 (t, J = 5.5 Hz, 2 H) 2.27 (s, 3 H) 2.10 (td, J = 11.0, 1.5 Hz, 2 H) 1.97 (d, J = 10.4 Hz, 2 H) 1.91 (ddd, J = 11.7, 6.1, 6.0 Hz, 2 H) 1.64 (qd, J = 11.7, 3.4 Hz, 2 H). |
| 26 | 471 | 13.01 (br. s., 1 H) 8.00 (d, J = 8.9 Hz, 2 H) 7.98 (s, 1 H) 7.08 (d, J = 9.2 Hz, 2 H) 5.42 (d, J = 8.9 Hz, 1 H) 4.87-4.99 (m, 1 H) 3.75 (t, J = 4.9 Hz, 4 H) 3.23 (t, J = 4.9 Hz, 4 H) 2.79 (d, J = 11.3 Hz, 2 H) 2.21 (s, 3 H) 2.08 (d, J = 10.8 Hz, 2 H) 1.99 (d, J = 11.0 Hz, 2 H) 1.65 (qd, J = 11.4, 3.7 Hz, 2 H). |
| 27 | 427 | 12.98 (br. s., 1 H) 8.00 (d, J = 9.2 Hz, 2 H) 7.88 (s, 1 H) 7.08 (d, J = 8.9 Hz, 2 H) 5.70 (d, J = 8.9 Hz, 1 H) 4.86-4.98 (m, 1 H) 3.75 (t, J = 5.2 Hz, 4 H) 3.23 (t, J = 4.9 Hz, 4 H) 2.81 (d, J = 11.6 Hz, 2 H) 2.21 (s, 3 H) 2.05 (td, J = 11.9, 2.1 Hz, 2 H) 1.97 (d, J = 10.1 Hz, 2 H) 1.67 (qd, J = 11.7, 3.4 Hz, 2 H). |
| 28 | 455 | 12.98 (br. s., 1 H) 8.00 (d, J = 9.2 Hz, 2 H) 7.88 (s, 1 H) 7.08 (d, J = 9.2 Hz, 2 H) 5.64 (d, J = 9.2 Hz, 1 H) 4.85-4.95 (m, 1 H) 3.75 (t, J = 5.2 Hz, 4 H) 3.23 (t, J = 4.9 Hz, 4 H) 2.85 (d, J = 11.6 Hz, 2 H) 2.72 (spt, J = 6.5 Hz, 1 H) 2.27 (td, J = 11.6, 2.1 Hz, 2 H) 2.00 (d, J = 9.8 Hz, 2 H) 1.60 (qd, J = 11.5, 3.8 Hz, 2 H) 1.01 (d, J = 6.7 Hz, 6 H). |
| 29 | 499 | 13.01 (br. s., 1 H) 8.00 (d, J = 9.2 Hz, 2 H) 7.98 (s, 1 H) 7.08 (d, J = 8.9 Hz, 2 H) 5.37 (d, J = 8.9 Hz, 1 H) 4.85-4.97 (m, 1 H) 3.75 (t, J = 4.9 Hz, 4 H) 3.23 (t, J = 4.6 Hz, 4 H) 2.83 (d, J = 11.6 Hz, 2 H) 2.72 (spt, J = 6.6 Hz, 1 H) 2.29 (td, J = 11.3, 2.1 Hz, 2 H) 2.02 (d, J = 11.0 Hz, 2 H) 1.58 (qd, J = 11.3, 3.8 Hz, 2 H) 1.01 (d, J = 6.4 Hz, 6 H). |
| 30 | 609 | 12.98 (br. s., 1 H) 7.99 (d, J = 8.9 Hz, 2 H) 7.87 (s, 1 H) 7.23 (d, J = 8.9 Hz, 2 H) 7.08 (d, J = 9.2 Hz, 2 H) 6.89 (d, J = 8.5 Hz, 2 H) 5.70 (d, J = 8.5 Hz, 1 H) 4.91-5.02 (m, 1 H) 3.76 (t, J = 4.9 Hz, 4 H) 3.74 (s, 3 H) 3.44 (s, 2 H) 3.24 (t, J = 4.9 Hz, 4 H) 2.85 (d, J = 11.6 Hz, 2 H) 2.10 (t, J = 10.8 Hz, 2 H) 1.97 (d, J = 10.7 Hz, 2 H) 1.65 (qd, J = 11.7, 3.7 Hz, 2 H). |
| 31 | 512 | 13.01 (br. s., 1 H) 8.00 (d, J = 8.8 Hz, 2 H) 7.98 (s, 1 H) 7.09 (d, J = 9.2 Hz, 2 H) 5.42 (d, J = 8.9 Hz, 1 H) 4.87-4.98 (m, 1 H) 3.55-3.62 (m, 4 H) 3.32 (t, J = 5.2 Hz, 2 H) 3.25 (t, J = 5.2 Hz, 2 H) 2.80 (d, J = 11.6 Hz, 2 H) 2.21 (s, 3 H) 2.08 (t, J = 11.3 Hz, 2 H) 2.05 (s, 3 H) 1.99 (d, J = 10.7 Hz, 2 H) 1.65 (qd, J = 11.4, 3.7 Hz, 2 H). |
| 32 | 468 | 12.99 (br. s., 1 H) 8.00 (d, J = 8.8 Hz, 2 H) 7.88 (s, 1 H) 7.10 (d, J = 9.2 Hz, 2 H) 5.71 (d, J = 8.9 Hz, 1 H) 4.86-4.97 (m, 1 H) 3.55-3.63 (m, 4 H) 3.32 (t, J = 5.5 Hz, 2 H) 3.25 (t, J = 5.5 Hz, 2 H) 2.81 (d, J = 11.3 Hz, 2 H) 2.21 (s, 3 H) 2.05 (s, 3 H) 2.05 (t, J = 10.8 Hz, 2 H) 1.97 (d, J = 10.7 Hz, 2 H) 1.67 (qd, J = 11.7, 3.7 Hz, 2 H). |
| 33 | 496 | 12.99 (br. s., 1 H) 8.00 (d, J = 8.9 Hz, 2 H) 7.88 (s, 1 H) 7.09 (d, J = 9.2 Hz, 2 H) 5.66 (d, J = 9.2 Hz, 1 H) 4.85-4.95 (m, 1 H) 3.56-3.62 (m, 4 H) 3.32 (t, J = 5.5 Hz, 2 H) 3.25 (t, J = 5.5 Hz, 2 H) 2.85 (d, J = 11.6 Hz, 2 H) 2.72 (spt, J = 6.6 Hz, 1 H) 2.27 (td, J = 11.4, 1.5 Hz, 2 H) 2.05 (s, 3 H) 2.01 (d, J = 11.0 Hz, 2 H) 1.60 (qd, J = 11.5, 3.8 Hz, 2 H) 1.01 (d, J = 6.7 Hz, 6 H). |
| 34 | 540 | 13.02 (br. s., 1 H) 8.00 (d, J = 8.9 Hz, 2 H) 7.98 (s, 1 H) 7.09 (d, J = 9.2 Hz, 2 H) 5.37 (d, J = 8.9 Hz, 1 H) 4.85-4.97 (m, 1 H) 3.55-3.62 (m, 4 H) 3.32 (t, J = 5.5 Hz, 2 H) 3.25 (t, J = 5.5 Hz, 2 H) 2.83 (d, J = 11.6 Hz, 2 H) 2.72 (spt, J = 6.5 Hz, 1 H) 2.29 (td, J = 11.3, 1.8 Hz, 2 H) 2.05 (s, 3 H) 2.02 (d, J = 10.7 Hz, 2 H) 1.58 (qd, J = 11.3, 3.5 Hz, 2 H) 1.01 (d, J = 6.7 Hz, 6 H). |
| 35 | 574 | 12.99 (br. s., 1 H) 7.99 (d, J = 8.9 Hz, 2 H) 7.87 (s, 1 H) 7.24 (d, J = 8.5 Hz, 2 H) 7.09 (d, J = 8.9 Hz, 2 H) 6.90 (d, J = 8.9 Hz, 2 H) 5.70 (d, J = 8.5 Hz, 1 H) 4.90-5.02 (m, 1 H) 3.74 (s, 3 H) 3.56-3.63 (m, 4 H) 3.44 (s, 2 H) 3.33 (t, J = 5.2 Hz, 2 H) 3.26 (t, J = 5.2 Hz, 2 H) 2.86 (d, J = 11.6 Hz, 2 H) 2.10 (t, J = 10.8 Hz, 2 H) 2.06 (s, 3 H) 1.98 (d, J = 10.4 Hz, 2 H) 1.65 (qd, J = 11.6, 3.1 Hz, 2 H). |
| 36 | 484 | 12.99 (br. s., 1 H) 8.11 (br. s., 1 H) 8.01 (d, J = 8.9 Hz, 2 H) 7.97 (s, 1 H) 7.05 (d, J = 8.9 Hz, 2 H) 5.41 (d, J = 8.9 Hz, 1 H) 4.87-4.98 (m, 1 H) 3.84 (s, 2 H) 3.53 (dd, J = 5.9, 4.7 Hz, 2 H) 3.33-3.35 (m, 2 H) 2.80 (d, J = 11.6 Hz, 2 H) 2.21 (s, 3 H) 2.08 (t, J = 11.6 Hz, 2 H) 1.99 (d, J = 9.5 Hz, 2 H) 1.65 (qd, J = 11.5, 3.7 Hz, 2 H). |
| 37 | 440 | 12.97 (br. s., 1 H) 8.11 (br. s., 1 H) 8.01 (d, J = 9.2 Hz, 2 H) 7.88 (s, 1 H) 7.05 (d, J = 9.2 Hz, 2 H) 5.70 (d, J = 8.9 Hz, 1 H) 4.87-4.98 (m, 1 H) 3.84 (s, 2 H) 3.53 (dd, J = 5.9, 4.7 Hz, 2 H) 3.32-3.35 (m, 2 H) 2.81 (d, J = 11.6 Hz, 2 H) 2.21 (s, 3 H) 2.06 (td, J = 11.6, 1.8 Hz, 2 H) 1.97 (d, J = 9.8 Hz, 2 H) 1.67 (qd, J = 11.6, 3.5 Hz, 2 H). |
| 38 | 468 | 12.97 (br. s., 1 H) 8.11 (br. s., 1 H) 8.00 (d, J = 8.9 Hz, 2 H) 7.88 (s, 1 H) 7.04 (d, J = 8.9 Hz, 2 H) 5.65 (d, J = 8.9 Hz, 1 H) 4.85-4.96 (m, 1 H) 3.84 (s, 2 H) 3.53 (dd, J = 5.9, 4.7 Hz, 2 H) 3.32-3.35 (m, 2 H) 2.85 (d, J = 11.9 Hz, 2 H) 2.72 (spt, J = 6.6 Hz, 1 H) 2.28 (td, J = 11.6, 1.8 Hz, 2 H) 2.01 (d, J = 10.4 Hz, 2 H) 1.60 (qd, J = 11.4, 3.5 Hz, 2 H) 1.01 (d, J = 6.4 Hz, 6 H). |
| 39 | 546 | 12.97 (br. s., 1 H) 8.12 (br. s., 1 H) 8.00 (d, J = 8.9 Hz, 2 H) 7.87 (s, 1 H) 7.24 (d, J = 8.9 Hz, 2 H) 7.04 (d, J = 9.2 Hz, 2 H) 6.90 (d, J = 8.5 Hz, 2 H) 5.69 (d, J = 7.9 Hz, 1 H) 4.92-5.01 (m, 1 H) 3.85 (s, 2 H) 3.74 (s, 3 H) 3.53 (dd, J = 5.9, 4.7 Hz, 2 H) 3.44 (s, 2 H) 3.33-3.36 (m, 2 H) 2.86 (d, J = 11.6 Hz, 2 H) 2.11 (t, J = 11.0 Hz, 2 H) 1.98 (d, J = 11.3 Hz, 2 H) 1.65 (qd, J = 11.6, 3.5 Hz, 2 H). |
| 40 | 548 | 13.03 (br. s., 1 H) 8.01 (d, J = 8.9 Hz, 2 H) 7.98 (s, 1 H) 7.13 (d, J = 9.2 Hz, 2 H) 5.44 (d, J = 8.9 Hz, 1 H) 4.88-4.98 (m, 1 H) 3.40 (t, J = 5.5 Hz, 4 H) 3.25 (t, J = 4.9 Hz, |

TABLE 2-continued

| Ex | m/z | ¹H NMR (600 MHz, DMSO-d$_6$) δ ppm |
|---|---|---|
| | | 4 H) 2.93 (s, 3 H) 2.80 (d, J = 11.3 Hz, 2 H) 2.21 (s, 3 H) 2.07 (td, J = 11.6, 2.1 Hz, 2 H) 1.99 (d, J = 11.3 Hz, 2 H) 1.65 (qd, J = 11.5, 3.8 Hz, 2 H). |
| 41 | 504 | 13.00 (br. s., 1 H) 8.01 (d, J = 9.2 Hz, 2 H) 7.88 (s, 1 H) 7.13 (d, J = 9.2 Hz, 2 H) 5.72 (d, J = 8.9 Hz, 1 H) 4.86-4.98 (m, 1 H) 3.40 (t, J = 5.5 Hz, 4 H) 3.25 (t, J = 5.2 Hz, 4 H) 2.93 (s, 3 H) 2.82 (d, J = 11.6 Hz, 2 H) 2.21 (s, 3 H) 2.05 (td, J = 11.6, 1.5 Hz, 2 H) 1.97 (d, J = 11.3 Hz, 2 H) 1.67 (qd, J = 11.6, 3.8 Hz, 2 H). |
| 42 | 532 | 13.00 (br. s., 1 H) 8.01 (d, J = 9.2 Hz, 2 H) 7.89 (s, 1 H) 7.12 (d, J = 9.2 Hz, 2 H) 5.67 (d, J = 8.9 Hz, 1 H) 4.85-4.95 (m, 1 H) 3.40 (t, J = 5.5 Hz, 4 H) 3.25 (t, J = 5.2 Hz, 4 H) 2.93 (s, 3 H) 2.85 (d, J = 11.6 Hz, 2 H) 2.72 (spt, J = 6.5 Hz, 1 H) 2.27 (td, J = 11.4, 1.8 Hz, 2 H) 2.01 (d, J = 10.4 Hz, 2 H) 1.60 (qd, J = 11.4, 3.4 Hz, 2 H) 1.01 (d, J = 6.7 Hz, 6 H). |
| 43 | 576 | 13.03 (br. s., 1 H) 8.01 (d, J = 8.9 Hz, 2 H) 7.98 (s, 1 H) 7.12 (d, J = 8.9 Hz, 2 H) 5.39 (d, J = 8.9 Hz, 1 H) 4.85-4.98 (m, 1 H) 3.40 (t, J = 5.5 Hz, 4 H) 3.25 (t, J = 5.2 Hz, 4 H) 2.93 (s, 3 H) 2.84 (d, J = 11.9 Hz, 2 H) 2.72 (spt, J = 6.6 Hz, 1 H) 2.29 (td, J = 11.4, 2.0 Hz, 2 H) 2.02 (d, J = 10.4 Hz, 2 H) 1.58 (qd, J = 11.3, 3.7 Hz, 2 H) 1.01 (d, J = 6.4 Hz, 6 H). |
| 44 | 610 | 13.00 (br. s., 1 H) 8.00 (d, J = 9.2 Hz, 2 H) 7.88 (s, 1 H) 7.24 (d, J = 8.5 Hz, 2 H) 7.12 (d, J = 9.2 Hz, 2 H) 6.90 (d, J = 8.5 Hz, 2 H) 5.73 (d, J = 8.9 Hz, 1 H) 4.91-5.02 (m, 1 H) 3.74 (s, 3 H) 3.44 (s, 2 H) 3.41 (t, J = 5.5 Hz, 4 H) 3.26 (t, J = 4.9 Hz, 4 H) 2.94 (s, 3 H) 2.86 (d, J = 11.3 Hz, 2 H) 2.10 (td, J = 11.0, 1.5 Hz, 2 H) 1.98 (d, J = 11.3 Hz, 2 H) 1.65 (qd, J = 11.7, 3.7 Hz, 2 H). |
| 45 | 518 | 13.01 (s, 1 H) 8.01 (d, J = 9.2 Hz, 2 H) 7.89 (s, 1 H) 7.13 (d, J = 8.8 Hz, 2 H) 5.72 (d, J = 8.9 Hz, 1 H) 4.88-4.99 (m, 1 H) 3.40 (t, J = 5.2 Hz, 4 H) 3.25 (t, J = 5.2 Hz, 4 H) 2.93 (s, 3 H) 2.93 (d, J = 10.7 Hz, 2 H) 2.36 (q, J = 7.0 Hz, 2 H) 2.04 (t, J = 12.2 Hz, 2 H) 2.00 (d, J = 11.6 Hz, 2 H) 1.64 (qd, J = 11.6, 3.5 Hz, 2 H) 1.03 (t, J = 7.2 Hz, 3 H). |
| 46 | 562 | 13.03 (br. s., 1 H) 8.01 (d, J = 9.2 Hz, 2 H) 7.98 (s, 1 H) 7.13 (d, J = 8.9 Hz, 2 H) 5.43 (d, J = 8.5 Hz, 1 H) 4.89-4.99 (m, 1 H) 3.40 (t, J = 5.2 Hz, 4 H) 3.25 (t, J = 5.2 Hz, 4 H) 2.93 (s, 3 H) 2.90 (d, J = 11.0 Hz, 2 H) 2.36 (q, J = 7.1 Hz, 2 H) 2.06 (t, J = 12.1 Hz, 2 H) 2.02 (d, J = 11.0 Hz, 2 H) 1.62 (qd, J = 11.4, 3.5 Hz, 2 H) 1.03 (t, J = 7.2 Hz, 3 H). |
| 47 | 498 | 12.97 (br. s., 1 H) 7.98 (d, J = 9.2 Hz, 2 H) 7.97 (s, 1 H) 7.61 (t, J = 5.3 Hz, 1 H) 7.00 (d, J = 8.9 Hz, 2 H) 5.41 (d, J = 8.9 Hz, 1 H) 4.86-4.98 (m, 1 H) 3.64-3.68 (m, 2 H) 3.60-3.64 (m, 2 H) 3.18-3.24 (m, 2 H) 2.80 (d, J = 11.3 Hz, 2 H) 2.51-2.55 (m, 2 H) 2.21 (s, 3 H) 2.07 (t, J = 11.4 Hz, 2 H) 2.00 (d, J = 10.7 Hz, 2 H) 1.64 (qd, J = 11.5, 3.7 Hz, 2 H). |
| 48 | 454 | 12.95 (s, 1 H) 7.98 (d, J = 9.2 Hz, 2 H) 7.87 (s, 1 H) 7.61 (t, J = 5.5 Hz, 1 H) 7.00 (d, J = 9.2 Hz, 2 H) 5.69 (d, J = 8.9 Hz, 1 H) 4.87-4.95 (m, 1 H) 3.64-3.69 (m, 2 H) 3.60-3.64 (m, 2 H) 3.18-3.23 (m, 2 H) 2.82 (d, J = 11.6 Hz, 2 H) 2.51-2.55 (m, 2 H) 2.21 (s, 3 H) 2.05 (td, J = 11.6, 1.5 Hz, 2 H) 1.97 (d, J = 11.6 Hz, 2 H) 1.66 (qd, J = 11.6, 3.7 Hz, 2 H). |
| 49 | 482 | 12.94 (br. s., 1 H) 7.98 (d, J = 9.2 Hz, 2 H) 7.87 (s, 1 H) 7.61 (t, J = 5.3 Hz, 1 H) 6.99 (d, J = 8.9 Hz, 2 H) 5.63 (d, J = 8.9 Hz, 1 H) 4.84-4.94 (m, 1 H) 3.64-3.69 (m, 2 H) 3.60-3.64 (m, 2 H) 3.19-3.22 (m, 2 H) 2.85 (d, J = 11.6 Hz, 2 H) 2.72 (spt, J = 6.5 Hz, 1 H) 2.51-2.55 (m, 2 H) 2.26 (td, J = 11.6, 1.8 Hz, 2 H) 2.01 (d, J = 9.8 Hz, 2 H) 1.60 (qd, J = 11.5, 3.7 Hz, 2 H) 1.01 (d, J = 6.4 Hz, 6 H). |
| 50 | 526 | 12.97 (s, 1 H) 7.97 (s, 1 H) 7.98 (d, J = 8.9 Hz, 2 H) 7.61 (t, J = 5.5 Hz, 1 H) 7.00 (d, J = 8.9 Hz, 2 H) 5.35 (d, J = 8.9 Hz, 1 H) 4.85-4.95 (m, 1 H) 3.64-3.68 (m, 2 H) 3.60-3.64 (m, 2 H) 3.18-3.24 (m, 2 H) 2.84 (d, J = 11.6 Hz, 2 H) 2.72 (spt, J = 6.6 Hz, 1 H) 2.51-2.55 (m, 2 H) 2.28 (td, J = 11.0, 1.5 Hz, 2 H) 2.03 (d, J = 11.6 Hz, 2 H) 1.58 (qd, J = 11.4, 3.5 Hz, 2 H) 1.01 (d, J = 6.4 Hz, 6 H). |
| 51 | 560 | 12.94 (br. s., 1 H) 7.97 (d, J = 8.9 Hz, 2 H) 7.86 (s, 1 H) 7.62 (t, J = 5.3 Hz, 1 H) 7.24 (d, J = 8.5 Hz, 2 H) 7.00 (d, J = 8.9 Hz, 2 H) 6.89 (d, J = 8.5 Hz, 1 H) 5.69 (d, J = 8.5 Hz, 1 H) 4.91-5.01 (m, 1 H) 3.74 (s, 3 H) 3.65-3.69 (m, 2 H) 3.61-3.65 (m, 2 H) 3.44 (s, 2 H) 3.19-3.24 (m, 2 H) 2.86 (d, J = 11.3 Hz, 2 H) 2.52-2.56 (m, 2 H) 2.10 (t, J = 11.0 Hz, 2 H) 1.98 (d, J = 11.3 Hz, 2 H) 1.65 (qd, J = 11.7, 3.7 Hz, 2 H). |
| 52 | 468 | 12.94 (br. s., 1 H) 7.98 (d, J = 8.9 Hz, 2 H) 7.87 (s, 1 H) 7.61 (t, J = 5.5 Hz, 1 H) 7.00 (d, J = 8.9 Hz, 2 H) 5.67 (d, J = 8.9 Hz, 1 H) 4.87-4.98 (m, 1 H) 3.64-3.68 (m, 2 H) 3.59-3.64 (m, 2 H) 3.18-3.23 (m, 2 H) 2.93 (d, J = 11.6 Hz, 2 H) 2.51-2.55 (m, 2 H) 2.35 (q, J = 7.2 Hz, 2 H) 2.03 (t, J = 11.6 Hz, 2 H) 2.00 (br. s., J = 11.0 Hz, 2 H) 1.64 (qd, J = 11.8, 3.8 Hz, 2 H) 1.03 (t, J = 7.2 Hz, 3 H). |
| 53 | 512 | 12.97 (br. s., 1 H) 7.98 (d, J = 8.9 Hz, 2 H) 7.96 (s, 1 H) 7.61 (t, J = 5.3 Hz, 1 H) 7.00 (d, J = 9.2 Hz, 2 H) 5.39 (d, J = 8.5 Hz, 1 H) 4.89-4.99 (m, 1 H) 3.64-3.69 (m, 2 H) 3.60-3.64 (m, 2 H) 3.18-3.23 (m, 2 H) 2.91 (d, J = 11.3 Hz, 2 H) 2.51-2.55 (m, 2 H) 2.36 (q, J = 7.3 Hz, 2 H) 2.05 (t, J = 11.6 Hz, 2 H) 2.02 (d, J = 11.4 Hz, 2 H) 1.62 (qd, J = 11.3, 4.0 Hz, 2 H) 1.03 (t, J = 7.2 Hz, 3 H). |
| 54 | 562 | 12.93 (br. s., 1 H) 7.99 (d, J = 8.9 Hz, 2 H) 7.86 (s, 1 H) 7.61 (t, J = 5.5 Hz, 1 H) 7.00 (d, J = 8.9 Hz, 2 H) 5.67 (d, J = 8.5 Hz, 1 H) 4.89-5.01 (m, 1 H) 3.64-3.70 (m, 2 H) 3.62-3.64 (m, 2 H) 3.62 (s, 3 H) 3.22 (s, 2 H) 3.20-3.21 (m, 2 H) 2.84 (d, J = 11.3 Hz, 2 H) 2.52-2.57 (m, 2 H) 2.17 (s, 3 H) 2.08 (s, 3 H) 2.05 (t, J = 10.8 Hz, 2 H) 1.96 (d, J = 10.1 Hz, 2 H) 1.60 (qd, J = 11.7, 3.7 Hz, 2 H). |
| 55 | 548 | 12.96 (br. s., 1 H) 7.98 (d, J = 8.9 Hz, 2 H) 7.87 (s, 1 H) 7.06 (d, J = 9.2 Hz, 2 H) 5.68 (d, J = 8.5 Hz, 1 H) 4.89-5.02 (m, 1 H) 3.62 (s, 3 H) 3.27 (t, J = 5.2 Hz, 4 H) 3.22 (s, 2 H) 2.83 (d, J = 11.3 Hz, 2 H) 2.46 (t, J = 4.9 Hz, 4 H) 2.23 (s, 3 H) 2.17 (s, 3 H) 2.08 (s, 3 H) 2.05 (t, J = 11.6 Hz, 2 H) 1.96 (d, J = 10.4 Hz, 2 H) 1.60 (qd, J = 11.7, 3.5 Hz, 2 H). |
| 56 | 578 | 12.95 (br. s., 1 H) 7.98 (d, J = 8.9 Hz, 2 H) 7.87 (s, 1 H) 7.06 (d, J = 8.9 Hz, 2 H) 5.69 (d, J = 8.9 Hz, 1 H) 4.87-5.01 (m, 1 H) 4.44 (t, J = 5.3 Hz, 1 H) 3.61 (s, 3 H) 3.55 (q, J = 6.1 Hz, 2 H) 3.26 (t, J = 5.2 Hz, 4 H) 3.22 (s, 2 H) 2.83 (d, J = 11.3 Hz, 2 |

TABLE 2-continued

| Ex | m/z | ¹H NMR (600 MHz, DMSO-d$_6$) δ ppm |
|---|---|---|
| | | H) 2.57 (t, J = 4.6 Hz, 4 H) 2.44 (t, J = 6.3 Hz, 2 H) 2.17 (s, 3 H) 2.08 (s, 3 H) 2.05 (t, J = 10.8 Hz, 2 H) 1.96 (d, J = 11.0 Hz, 2 H) 1.60 (qd, J = 11.6, 3.5 Hz, 2 H). |
| 57 | 592 | 12.94 (br. s., 1 H) 7.98 (d, J = 9.2 Hz, 2 H) 7.86 (s, 1 H) 7.06 (d, J = 9.2 Hz, 2 H) 5.68 (d, J = 8.9 Hz, 1 H) 4.88-5.03 (m, 1 H) 3.62 (s, 3 H) 3.48 (t, J = 5.8 Hz, 2 H) 3.26 (s, 3 H) 3.26 (t, J = 4.9 Hz, 4 H) 3.22 (s, 2 H) 2.83 (d, J = 11.6 Hz, 2 H) 2.57 (t, J = 4.9 Hz, 4 H) 2.53 (t, J = 5.8 Hz, 2 H) 2.17 (s, 3 H) 2.08 (s, 3 H) 2.05 (t, J = 11.0 Hz, 2 H) 1.96 (d, J = 10.7 Hz, 2 H) 1.60 (qd, J = 11.7, 3.8 Hz, 2 H). |
| 58 | 535 | 12.97 (br. s., 1 H) 8.00 (d, J = 8.9 Hz, 2 H) 7.87 (s, 1 H) 7.08 (d, J = 9.2 Hz, 2 H) 5.69 (d, J = 8.9 Hz, 1 H) 4.89-5.00 (m, 1 H) 3.76 (t, J = 5.2 Hz, 4 H) 3.61 (s, 3 H) 3.24 (t, J = 4.9 Hz, 4 H) 3.22 (s, 2 H) 2.84 (d, J = 11.3 Hz, 2 H) 2.17 (s, 3 H) 2.08 (s, 3 H) 2.05 (t, J = 10.7 Hz, 2 H) 1.96 (d, J = 9.8 Hz, 2 H) 1.60 (qd, J = 11.6, 3.5 Hz, 2 H). |
| 59 | 576 | 12.98 (br. s., 1 H) 8.00 (d, J = 9.2 Hz, 2 H) 7.87 (s, 1 H) 7.09 (d, J = 8.9 Hz, 2 H) 5.70 (d, J = 8.9 Hz, 1 H) 4.90-5.01 (m, 1 H) 3.62 (s, 3 H) 3.58-3.61 (m, 4 H) 3.32-3.35 (m, 2 H) 3.23-3.28 (m, 2 H) 3.22 (s, 2 H) 2.84 (d, J = 11.3 Hz, 2 H) 2.17 (s, 3 H) 2.08 (s, 3 H) 2.06 (s, 3 H) 2.05 (t, J = 11.6 Hz, 2 H) 1.96 (d, J = 11.9 Hz, 2 H) 1.60 (qd, J = 11.7, 3.4 Hz, 2 H). |
| 60 | 612 | 12.99 (br. s., 1 H) 8.02 (d, J = 9.2 Hz, 2 H) 7.87 (s, 1 H) 7.12 (d, J = 8.9 Hz, 2 H) 5.70 (d, J = 8.2 Hz, 1 H) 4.89-5.02 (m, 1 H) 3.62 (s, 3 H) 3.41 (t, J = 5.5 Hz, 2 H) 3.26 (t, J = 5.2 Hz, 4 H) 3.22 (s, 2 H) 2.93 (s, 3 H) 2.84 (d, J = 11.0 Hz, 2 H) 2.17 (s, 3 H) 2.08 (s, 3 H) 2.05 (t, J = 11.0 Hz, 2 H) 1.96 (d, J = 11.6 Hz, 2 H) 1.60 (qd, J = 11.6, 2.7 Hz, 2 H). |
| 61 | 542 | 12.87 (br. s., 1 H) 7.95 (s, 1 H) 7.93 (d, J = 8.9 Hz, 2 H) 6.82 (d, J = 9.2 Hz, 2 H) 5.36 (d, J = 8.9 Hz, 1 H) 4.87-4.97 (m, 1 H) 3.56 (t, J = 5.2 Hz, 2 H) 3.52 (t, J = 6.3 Hz, 2 H) 3.39 (t, J = 6.0 Hz, 2 H) 3.22 (s, 3 H) 2.80 (d, J = 11.5 Hz, 2 H) 2.77 (t, J = 4.9 Hz, 2 H) 2.63 (t, J = 6.0 Hz, 2 H) 2.57 (t, J = 5.8 Hz, 2 H) 2.21 (s, 3 H) 2.07 (t, J = 11.6 Hz, 2 H) 1.99 (d, J = 10.4 Hz, 2 H) 1.86 (quin, J = 5.8 Hz, 2 H) 1.64 (qd, J = 11.5, 3.7 Hz, 2 H). |
| 62 | 498 | 12.85 (br. s., 1 H) 7.93 (d, J = 8.9 Hz, 2 H) 7.85 (s, 1 H) 6.82 (d, J = 9.2 Hz, 2 H) 5.64 (d, J = 8.9 Hz, 1 H) 4.86-4.97 (m, 1 H) 3.56 (t, J = 5.2 Hz, 2 H) 3.52 (t, J = 6.3 Hz, 2 H) 3.39 (t, J = 6.0 Hz, 2 H) 3.22 (s, 3 H) 2.81 (d, J = 11.6 Hz, 2 H) 2.77 (t, J = 4.9 Hz, 2 H) 2.63 (t, J = 6.0 Hz, 2 H) 2.57 (t, J = 5.8 Hz, 2 H) 2.21 (s, 3 H) 2.06 (td, J = 11.3, 1.8 Hz, 2 H) 1.97 (d, J = 9.8 Hz, 2 H) 1.86 (quin, J = 5.9 Hz, 2 H) 1.66 (qd, J = 11.6, 3.4 Hz, 2 H). |
| 63 | 526 | 12.84 (br. s., 1 H) 7.93 (d, J = 8.9 Hz, 2 H) 7.85 (s, 1 H) 6.82 (d, J = 9.2 Hz, 2 H) 5.56 (d, J = 8.9 Hz, 1 H) 4.84-4.95 (m, 1 H) 3.55 (t, J = 4.9 Hz, 2 H) 3.52 (t, J = 6.1 Hz, 2 H) 3.39 (t, J = 6.0 Hz, 2 H) 3.22 (s, 3 H) 2.85 (d, J = 11.9 Hz, 2 H) 2.77 (t, J = 4.9 Hz, 2 H) 2.72 (spt, J = 6.5 Hz, 1 H) 2.63 (t, J = 6.0 Hz, 2 H) 2.57 (t, J = 6.1 Hz, 2 H) 2.27 (td, J = 11.6, 1.5 Hz, 2 H) 2.01 (d, J = 10.7 Hz, 2 H) 1.86 (quin, J = 5.9 Hz, 2 H) 1.59 (qd, J = 11.5, 3.5 Hz, 2 H) 1.01 (d, J = 6.7 Hz, 6 H). |
| 64 | 604 | 12.85 (br. s., 1 H) 7.92 (d, J = 8.9 Hz, 2 H) 7.84 (s, 1 H) 7.24 (d, J = 8.5 Hz, 2 H) 6.89 (d, J = 8.9 Hz, 2 H) 6.82 (d, J = 9.2 Hz, 2 H) 5.63 (d, J = 7.6 Hz, 1 H) 4.88-5.03 (m, 1 H) 3.74 (s, 3 H) 3.56 (t, J = 5.2 Hz, 2 H) 3.53 (t, J = 6.3 Hz, 2 H) 3.44 (s, 2 H) 3.40 (t, J = 6.0 Hz, 2 H) 3.22 (s, 3 H) 2.85 (d, J = 11.6 Hz, 2 H) 2.78 (t, J = 5.2 Hz, 2 H) 2.63 (t, J = 6.0 Hz, 2 H) 2.57 (t, J = 5.8 Hz, 2 H) 2.10 (t, J = 11.7 Hz, 2 H) 1.97 (d, J = 9.8 Hz, 2 H) 1.87 (quin, J = 5.9 Hz, 2 H) 1.64 (qd, J = 11.7, 3.4 Hz, 2 H). |
| 65 | 512 | 12.85 (br. s., 1 H) 7.93 (d, J = 8.9 Hz, 2 H) 7.85 (s, 1 H) 6.82 (d, J = 8.9 Hz, 2 H) 5.63 (d, J = 8.9 Hz, 1 H) 4.88-5.00 (m, 1 H) 3.55 (t, J = 5.2 Hz, 2 H) 3.52 (t, J = 6.1 Hz, 2 H) 3.39 (t, J = 6.0 Hz, 2 H) 3.22 (s, 3 H) 2.92 (d, J = 11.3 Hz, 2 H) 2.77 (t, J = 5.2 Hz, 2 H) 2.63 (t, J = 6.0 Hz, 2 H) 2.57 (t, J = 5.8 Hz, 2 H) 2.36 (q, J = 7.3 Hz, 2 H) 2.03 (t, J = 11.6 Hz, 2 H) 2.00 (d, J = 11.3 Hz, 2 H) 1.86 (quin, J = 5.9 Hz, 2 H) 1.63 (qd, J = 11.5, 3.7 Hz, 2 H) 1.03 (t, J = 7.2 Hz, 3 H). |
| 66 | 542 | 12.98 (br. s., 1 H) 7.98 (d, J = 9.2 Hz, 2 H) 7.96 (s, 1 H) 7.06 (d, J = 9.2 Hz, 2 H) 5.41 (d, J = 8.9 Hz, 1 H) 4.86-4.98 (m, 1 H) 3.51 (t, J = 5.8 Hz, 2 H) 3.43 (q, J = 7.0 Hz, 2 H) 3.25 (t, J = 5.2 Hz, 4 H) 2.79 (d, J = 11.3 Hz, 2 H) 2.56 (t, J = 4.9 Hz, 4 H) 2.52 (t, J = 6.0 Hz, 2 H) 2.21 (s, 3 H) 2.07 (t, J = 11.6 Hz, 2 H) 1.99 (d, J = 12.2 Hz, 2 H) 1.64 (qd, J = 11.3, 3.1 Hz, 2 H) 1.11 (t, J = 7.0 Hz, 3 H). |
| 67 | 498 | 12.96 (br. s., 1 H) 7.98 (d, J = 8.9 Hz, 2 H) 7.87 (s, 1 H) 7.06 (d, J = 9.2 Hz, 2 H) 5.69 (d, J = 9.2 Hz, 1 H) 4.81-5.04 (m, 1 H) 3.51 (t, J = 6.0 Hz, 2 H) 3.43 (q, J = 7.0 Hz, 2 H) 3.25 (t, J = 5.2 Hz, 4 H) 2.81 (d, J = 11.3 Hz, 2 H) 2.56 (t, J = 4.9 Hz, 4 H) 2.52 (t, J = 6.0 Hz, 2 H) 2.21 (s, 3 H) 2.05 (td, J = 11.3, 1.8 Hz, 2 H) 1.97 (d, J = 11.3 Hz, 2 H) 1.66 (qd, J = 11.6, 3.8 Hz, 2 H) 1.11 (t, J = 7.0 Hz, 3 H). |
| 68 | 526 | 12.95 (br. s., 1 H) 7.97 (d, J = 8.9 Hz, 2 H) 7.87 (s, 1 H) 7.05 (d, J = 9.2 Hz, 2 H) 5.63 (d, J = 8.5 Hz, 1 H) 4.82-4.98 (m, 1 H) 3.51 (t, J = 6.0 Hz, 2 H) 3.43 (q, J = 7.0 Hz, 2 H) 3.25 (t, J = 5.2 Hz, 4 H) 2.84 (d, J = 11.6 Hz, 2 H) 2.72 (spt, J = 6.5 Hz, 1 H) 2.56 (t, J = 4.9 Hz, 4 H) 2.52 (t, J = 6.0 Hz, 2 H) 2.27 (td, J = 11.5, 2.0 Hz, 2 H) 2.00 (d, J = 10.1 Hz, 2 H) 1.59 (qd, J = 11.5, 3.7 Hz, 2 H) 1.11 (t, J = 7.0 Hz, 3 H) 1.01 (d, J = 6.4 Hz, 6 H). |
| 69 | 604 | 12.96 (br. s., 1 H) 7.97 (d, J = 8.9 Hz, 2 H) 7.87 (s, 1 H) 7.23 (d, J = 8.5 Hz, 2 H) 7.06 (d, J = 9.2 Hz, 2 H) 6.89 (d, J = 8.5 Hz, 2 H) 5.70 (d, J = 8.9 Hz, 1 H) 4.91-5.01 (m, 1 H) 3.74 (s, 3 H) 3.52 (t, J = 6.0 Hz, 2 H) 3.44 (s, 2 H) 3.44 (q, J = 7.0 Hz, 2 H) 3.26 (t, J = 5.2 Hz, 4 H) 2.85 (d, J = 11.3 Hz, 2 H) 2.57 (t, J = 5.2 Hz, 4 H) 2.53 (t, J = 6.0 Hz, 2 H) 2.10 (td, J = 10.8, 1.2 Hz, 2 H) 1.97 (d, J = 9.5 Hz, 2 H) 1.65 (qd, J = 11.7, 3.5 Hz, 2 H) 1.12 (t, J = 7.0 Hz, 3 H). |
| 70 | 512 | 12.95 (br. s., 1 H) 7.97 (d, J = 9.2 Hz, 2 H) 7.87 (s, 1 H) 7.05 (d, J = 9.2 Hz, 2 H) 5.67 (d, J = 9.2 Hz, 1 H) 4.85-5.05 (m, 1 H) 3.51 (t, J = 6.0 Hz, 2 H) 3.43 (q, J = 7.0 Hz, 2 H) 3.25 (t, J = 5.2 Hz, 4 H) 2.92 (d, J = 11.3 Hz, 2 H) 2.56 (t, J = 4.9 Hz, 4 H) 2.52 (t, J = 6.0 Hz, 2 H) 2.35 (q, J = 7.2 Hz, 2 H) 2.03 (t, J = 11.9 Hz, 2 H) 1.99 (d, |

TABLE 2-continued

| Ex | m/z | ¹H NMR (600 MHz, DMSO-d₆) δ ppm |
|---|---|---|
| | | J = 11.6 Hz, 2 H) 1.63 (qd, J = 11.5, 3.5 Hz, 2 H) 1.11 (t, J = 7.0 Hz, 3 H) 1.03 (t, J = 7.2 Hz, 3 H). |
| 71 | 556 | 12.88 (br. s., 1 H) 7.95 (s, 1 H) 7.93 (d, J = 8.9 Hz, 2 H) 6.82 (d, J = 8.9 Hz, 2 H) 5.36 (d, J = 8.9 Hz, 1 H) 4.87-4.98 (m, 1 H) 3.56 (t, J = 5.2 Hz, 2 H) 3.52 (t, J = 6.3 Hz, 2 H) 3.43 (t, J = 6.1 Hz, 2 H) 3.39 (q, J = 6.8 Hz, 2 H) 2.75-2.84 (m, 4 H) 2.62 (t, J = 6.1 Hz, 2 H) 2.57 (t, J = 5.8 Hz, 2 H) 2.21 (s, 3 H) 2.08 (t, J = 10.8 Hz, 2 H) 1.99 (d, J = 10.1 Hz, 2 H) 1.86 (quin, J = 5.8 Hz, 2 H) 1.64 (qd, J = 11.4, 3.5 Hz, 2 H) 1.08 (t, J = 7.0 Hz, 3 H). |
| 72 | 512 | 12.85 (s, 1 H) 7.93 (d, J = 9.2 Hz, 2 H) 7.85 (s, 1 H) 6.82 (d, J = 8.9 Hz, 2 H) 5.64 (d, J = 8.9 Hz, 1 H) 4.83-4.99 (m, 1 H) 3.56 (t, J = 4.9 Hz, 2 H) 3.52 (t, J = 6.3 Hz, 2 H) 3.43 (t, J = 6.1 Hz, 2 H) 3.39 (q, J = 7.0 Hz, 2 H) 2.81 (t, J = 11.6 Hz, 2 H) 2.78 (t, J = 5.2 Hz, 2 H) 2.62 (t, J = 6.3 Hz, 2 H) 2.57 (t, J = 5.8 Hz, 2 H) 2.21 (s, 3 H) 2.06 (td, J = 11.3, 1.8 Hz, 2 H) 1.97 (d, J = 10.4 Hz, 2 H) 1.86 (quin, J = 5.8 Hz, 2 H) 1.66 (qd, J = 11.7, 3.8 Hz, 2 H) 1.08 (t, J = 6.9 Hz, 3 H). |
| 73 | 540 | 12.85 (s, 1 H) 7.93 (d, J = 8.9 Hz, 2 H) 7.85 (s, 1 H) 6.82 (d, J = 9.2 Hz, 2 H) 5.58 (d, J = 8.9 Hz, 1 H) 4.84-4.95 (m, 1 H) 3.55 (t, J = 5.2 Hz, 2 H) 3.52 (t, J = 6.1 Hz, 2 H) 3.43 (t, J = 6.1 Hz, 2 H) 3.39 (q, J = 7.0 Hz, 2 H) 2.85 (d, J = 11.3 Hz, 2 H) 2.78 (t, J = 4.9 Hz, 2 H) 2.72 (spt, J = 6.5 Hz, 1 H) 2.62 (t, J = 6.1 Hz, 2 H) 2.57 (t, J = 5.5 Hz, 2 H) 2.27 (t, J = 11.0 Hz, 2 H) 2.01 (d, J = 10.7 Hz, 2 H) 1.86 (quin, J = 5.9 Hz, 2 H) 1.59 (qd, J = 11.5, 3.7 Hz, 2 H) 1.08 (t, J = 7.0 Hz, 3 H) 1.01 (d, J = 6.7 Hz, 6 H). |
| 74 | 618 | 12.85 (s, 1 H) 7.92 (d, J = 9.2 Hz, 2 H) 7.85 (s, 1 H) 7.24 (d, J = 8.5 Hz, 2 H) 6.89 (d, J = 8.9 Hz, 2 H) 6.82 (d, J = 9.2 Hz, 2 H) 5.65 (d, J = 8.9 Hz, 1 H) 4.90-5.02 (m, 1 H) 3.74 (s, 3 H) 3.56 (t, J = 4.9 Hz, 2 H) 3.53 (t, J = 6.3 Hz, 2 H) 3.44 (s, 2 H) 3.43 (t, J = 6.1 Hz, 2 H) 3.40 (q, J = 7.0 Hz, 2 H) 2.86 (d, J = 11.3 Hz, 2 H) 2.79 (t, J = 4.9 Hz, 2 H) 2.63 (t, J = 6.1 Hz, 2 H) 2.58 (t, J = 5.8 Hz, 2 H) 2.11 (t, J = 11.1 Hz, 2 H) 1.97 (d, J = 9.8 Hz, 2 H) 1.87 (quin, J = 5.9 Hz, 2 H) 1.64 (qd, J = 11.7, 3.8 Hz, 2 H) 1.08 (t, J = 7.0 Hz, 3 H). |
| 75 | 526 | 12.85 (s, 1 H) 7.93 (d, J = 8.9 Hz, 2 H) 7.85 (s, 1 H) 6.82 (d, J = 9.2 Hz, 2 H) 5.63 (d, J = 8.9 Hz, 1 H) 4.88-4.98 (m, 1 H) 3.55 (t, J = 5.2 Hz, 2 H) 3.52 (t, J = 6.3 Hz, 2 H) 3.43 (t, J = 6.1 Hz, 2 H) 3.39 (q, J = 7.0 Hz, 2 H) 2.93 (d, J = 11.3 Hz, 2 H) 2.78 (t, J = 5.2 Hz, 2 H) 2.62 (t, J = 6.1 Hz, 2 H) 2.57 (t, J = 5.8 Hz, 2 H) 2.36 (q, J = 7.3 Hz, 2 H) 2.04 (t, J = 11.9 Hz, 2 H) 2.00 (d, J = 11.6 Hz, 2 H) 1.86 (quin, J = 5.9 Hz, 2 H) 1.63 (qd, J = 11.7, 3.7 Hz, 2 H) 1.08 (t, J = 7.0 Hz, 3 H) 1.03 (t, J = 7.2 Hz, 3 H). |
| 76 | 556 | 12.99 (br. s., 1 H) 7.97 (s, 1 H) 7.98 (d, J = 8.5 Hz, 2 H) 7.06 (d, J = 9.2 Hz, 2 H) 5.41 (d, J = 8.9 Hz, 1 H) 4.87-4.97 (m, 1 H) 3.54 (spt, J = 6.1 Hz, 1 H) 3.51 (t, J = 6.1 Hz, 2 H) 3.25 (t, J = 5.2 Hz, 4 H) 2.79 (d, J = 11.3 Hz, 2 H) 2.57 (t, J = 4.9 Hz, 2 H) 2.51 (t, J = 6.1 Hz, 2 H) 2.21 (s, 3 H) 2.07 (td, J = 11.4, 1.5 Hz, 2 H) 1.99 (d, J = 11.0 Hz, 2 H) 1.65 (qd, J = 11.4, 3.7 Hz, 2 H) 1.09 (d, J = 6.1 Hz, 6 H). |
| 77 | 512 | 12.96 (br. s., 1 H) 7.98 (d, J = 8.9 Hz, 2 H) 7.87 (s, 1 H) 7.06 (d, J = 9.2 Hz, 2 H) 5.69 (d, J = 8.9 Hz, 1 H) 4.85-4.97 (m, 1 H) 3.54 (spt, J = 6.1 Hz, 1 H) 3.51 (t, J = 6.1 Hz, 2 H) 3.25 (t, J = 5.2 Hz, 4 H) 2.81 (d, J = 11.6 Hz, 2 H) 2.57 (t, J = 4.9 Hz, 4 H) 2.50 (t, J = 6.1 Hz, 2 H) 2.21 (s, 3 H) 2.05 (td, J = 11.6, 1.8 Hz, 2 H) 1.97 (d, J = 11.3 Hz, 2 H) 1.66 (qd, J = 11.6, 3.7 Hz, 2 H) 1.09 (d, J = 6.1 Hz, 6 H). |
| 78 | 540 | 12.96 (s, 1 H) 7.97 (d, J = 8.9 Hz, 2 H) 7.88 (s, 1 H) 7.06 (d, J = 9.2 Hz, 2 H) 5.64 (d, J = 8.9 Hz, 1 H) 4.85-4.95 (m, 1 H) 3.54 (spt, J = 6.1 Hz, 1 H) 3.51 (t, J = 6.1 Hz, 2 H) 3.25 (t, J = 5.2 Hz, 4 H) 2.85 (d, J = 11.9 Hz, 2 H) 2.72 (spt, J = 6.5 Hz, 1 H) 2.57 (t, J = 5.2 Hz, 4 H) 2.50 (t, J = 6.1 Hz, 2 H) 2.27 (td, J = 11.3, 1.8 Hz, 2 H) 2.00 (d, J = 10.7 Hz, 2 H) 1.60 (qd, J = 11.6, 3.7 Hz, 2 H) 1.09 (d, J = 6.1 Hz, 6 H) 1.01 (d, J = 6.7 Hz, 6 H). |
| 79 | 618 | 12.95 (br. s., 1 H) 7.96 (d, J = 9.2 Hz, 2 H) 7.87 (s, 1 H) 7.23 (d, J = 8.9 Hz, 2 H) 7.05 (d, J = 9.2 Hz, 2 H) 6.89 (d, J = 8.9 Hz, 2 H) 5.69 (d, J = 8.2 Hz, 1 H) 4.88-5.05 (m, 1 H) 3.74 (s, 3 H) 3.55 (spt, J = 6.1 Hz, 1 H) 3.52 (t, J = 6.0 Hz, 2 H) 3.44 (s, 2 H) 3.26 (t, J = 5.2 Hz, 4 H) 2.85 (d, J = 11.9 Hz, 2 H) 2.58 (t, J = 4.9 Hz, 4 H) 2.51 (t, J = 6.1 Hz, 2 H) 2.10 (t, J = 10.8 Hz, 2 H) 1.97 (d, J = 9.2 Hz, 2 H) 1.64 (qd, J = 11.6, 3.7 Hz, 2 H) 1.09 (d, J = 6.1 Hz, 6 H). |
| 80 | 526 | 12.96 (br. s., 1 H) 7.97 (d, J = 8.9 Hz, 2 H) 7.88 (s, 1 H) 7.06 (d, J = 9.2 Hz, 2 H) 5.68 (d, J = 8.9 Hz, 1 H) 4.87-5.00 (m, 1 H) 3.54 (spt, J = 6.1 Hz, 1 H) 3.51 (t, J = 6.1 Hz, 2 H) 3.25 (t, J = 5.2 Hz, 4 H) 2.92 (d, J = 11.3 Hz, 2 H) 2.57 (t, J = 5.2 Hz, 4 H) 2.50 (t, J = 6.1 Hz, 2 H) 2.36 (q, J = 7.3 Hz, 2 H) 2.03 (t, J = 11.7 Hz, 2 H) 1.99 (d, J = 11.6 Hz, 2 H) 1.64 (qd, J = 11.4, 3.5 Hz, 2 H) 1.09 (d, J = 6.1 Hz, 6 H) 1.03 (t, J = 7.2 Hz, 3 H). |
| 81 | 552 | 12.96 (br. s., 1 H) 7.95-7.99 (m, 2 H) 7.87 (s, 1 H) 7.44 (dd, J = 4.88, 1.53 Hz, 1 H) 7.03-7.08 (m, 2 H) 6.96-7.00 (m, 2 H) 5.74 (d, J = 8.70 Hz, 1 H) 4.93-5.01 (m, 1 H) 4.44 (t, J = 5.34 Hz, 1 H) 3.73 (s, 2 H) 3.55 (td, J = 6.24, 5.34 Hz, 2 H) 3.24-3.28 (m, 4 H) 2.90-2.96 (m, 2 H) 2.54-2.59 (m, 4 H) 2.44 (t, J = 6.24 Hz, 2 H) 2.16 (td, J = 11.60, 1.70 Hz, 2 H) 1.95-2.02 (m, 2 H) 1.67 (dtd, J = 11.83, 11.60, 3.81 Hz, 2 H). |
| 82 | 566 | 12.96 (br. s., 1 H) 7.95-7.99 (m, 2 H) 7.87 (s, 1 H) 7.44 (dd, J = 4.73, 1.53 Hz, 1 H) 7.03-7.08 (m, 2 H) 6.96-7.00 (m, 2 H) 5.74 (d, J = 8.70 Hz, 1 H) 4.93-5.01 (m, 1 H) 3.73 (s, 2 H) 3.48 (t, J = 5.80 Hz, 2 H) 3.26 (s, 3 H) 3.23-3.28 (m, 4 H) 2.90-2.96 (m, 2 H) 2.54-2.60 (m, 4 H) 2.53 (t, J = 5.80 Hz, 2 H) 2.16 (td, J = 11.71, 1.75 Hz, 2 H) 1.96-2.02 (m, 2 H) 1.63-1.72 (m, 2 H). |
| 83 | 509 | 12.98 (br. s., 1 H) 7.97-8.01 (m, 2 H) 7.87 (s, 1 H) 7.44 (dd, J = 4.73, 1.68 Hz, 1 H) 7.05-7.10 (m, 2 H) 6.96-7.00 (m, 2 H) 5.74 (d, J = 8.55 Hz, 1 H) 4.93-5.02 (m, 1 H) 3.74-3.78 (m, 4 H) 3.73 (s, 2 H) 3.21-3.27 (m, 4 H) 2.90-2.97 (m, 2 H) 2.17 (td, J = 11.70, 1.53 Hz, 2 H) 1.96-2.02 (m, 2 H) 1.68 (qd, J = 11.70, 3.59 Hz, 2 H). |

TABLE 2-continued

| Ex | m/z | $^1$H NMR (600 MHz, DMSO-$d_6$) δ ppm |
|---|---|---|
| 84 | 585 | 12.98 (br. s., 1 H) 8.18-8.21 (m, 2 H) 7.99-8.03 (m, 2 H) 7.88 (s, 1 H) 7.44 (dd, J = 4.73, 1.53 Hz, 1 H) 7.10-7.14 (m, 2 H) 6.97-7.00 (m, 2 H) 6.87-6.91 (m, 2 H) 5.75 (d, J = 8.70 Hz, 1 H) 4.93-5.02 (m, 1 H) 3.73 (s, 2 H) 3.48-3.53 (m, 4 H) 3.41-3.45 (m, 4 H) 2.91-2.97 (m, 2 H) 2.17 (td, J = 11.65, 1.53 Hz, 2 H) 1.96-2.03 (m, 2 H) 1.68 (dtd, J = 11.94, 11.65, 3.51 Hz, 2 H). |
| 85 | 580 | 12.95 (br. s., 1 H) 7.94-7.99 (m, 2 H) 7.87 (s, 1 H) 7.44 (dd, J = 4.73, 1.53 Hz, 1 H) 7.03-7.08 (m, 2 H) 6.95-7.00 (m, 2 H) 5.74 (d, J = 8.70 Hz, 1 H) 4.93-5.01 (m, 1 H) 3.73 (s, 2 H) 3.52 (t, J = 5.95 Hz, 2 H) 3.44 (q, J = 7.02 Hz, 2 H) 3.23-3.28 (m, 4 H) 2.90-2.96 (m, 2 H) 2.55-2.60 (m, 4 H) 2.53 (t, J = 5.95 Hz, 2 H) 2.16 (td, J = 11.70, 1.75 Hz, 2 H) 1.95-2.03 (m, 2 H) 1.68 (qd, J = 11.70, 3.81 Hz, 2 H) 1.12 (t, J = 7.02 Hz, 3 H). |
| 86 | 594 | 12.96 (br. s., 1 H) 7.95-7.99 (m, 2 H) 7.87 (s, 1 H) 7.44 (dd, J = 4.81, 1.60 Hz, 1 H) 7.03-7.07 (m, 2 H) 6.96-7.00 (m, 2 H) 5.74 (d, J = 8.85 Hz, 1 H) 4.93-5.01 (m, 1 H) 3.73 (s, 2 H) 3.55 (spt, J = 6.10 Hz, 1 H) 3.51 (t, J = 6.03 Hz, 2 H) 3.23-3.28 (m, 4 H) 2.90-2.96 (m, 2 H) 2.54-2.60 (m, 4 H) 2.51 (t, J = 6.03 Hz, 2 H) 2.16 (td, J = 11.64, 1.53 Hz, 2 H) 1.95-2.02 (m, 2 H) 1.68 (dtd, J = 11.98, 11.64, 3.81 Hz, 2 H) 1.09 (d, J = 6.10 Hz, 6 H). |
| 87 | 589 | 12.96 (br. s., 1 H) 7.95-7.99 (m, 2 H) 7.86 (s, 1 H) 7.10-7.15 (m, 2 H) 7.03-7.08 (m, 2 H) 6.67-6.71 (m, 2 H) 5.68 (br. s., 1 H) 4.91-4.99 (m, 1 H) 4.44 (t, J = 5.42 Hz, 1 H) 3.55 (td, J = 6.18, 5.42 Hz, 2 H) 3.38 (s, 2 H) 3.24-3.28 (m, 4 H) 2.87 (s, 6 H) 2.82-2.89 (m, 2 H) 2.54-2.59 (m, 4 H) 2.45 (t, J = 6.18 Hz, 2 H) 2.04-2.11 (m, 2 H) 1.94-2.00 (m, 2 H) 1.58-1.68 (m, 2H). |
| 88 | 603 | 12.96 (s, 1 H) 7.94-7.99 (m, 2 H) 7.87 (s, 1 H) 7.10-7.14 (m, 2 H) 7.04-7.08 (m, 2 H) 6.67-6.71 (m, 2 H) 5.69 (d, J = 9.16 Hz, 1 H) 4.91-4.99 (m, 1 H) 3.48 (t, J = 5.75 Hz, 2 H) 3.38 (s, 2 H) 3.26 (s, 3 H) 3.24-3.28 (m, 4 H) 2.87 (s, 6 H) 2.83-2.88 (m, 2 H) 2.55-2.59 (m, 4 H) 2.53 (t, J = 5.75 Hz, 2 H) 2.03-2.11 (m, 2 H) 1.93-2.00 (m, 2 H) 1.59-1.68 (m, 2 H). |
| 89 | 617 | 12.96 (s, 1 H) 7.94-7.99 (m, 2 H) 7.87 (s, 1 H) 7.10-7.14 (m, 2 H) 7.04-7.08 (m, 2 H) 6.67-6.71 (m, 2 H) 5.69 (d, J = 9.16 Hz, 1 H) 4.91-4.99 (m, 1 H) 3.48 (t, J = 5.75 Hz, 2 H) 3.38 (s, 2 H) 3.26 (s, 3 H) 3.24-3.28 (m, 4 H) 2.87 (s, 6 H) 2.83-2.88 (m, 2 H) 2.55-2.59 (m, 4 H) 2.53 (t, J = 5.75 Hz, 2 H) 2.03-2.11 (m, 2 H) 1.93-2.00 (m, 2 H) 1.59-1.68 (m, 2 H). |
| 90 | 631 | 12.96 (br. s., 1 H) 7.95-7.98 (m, 2 H) 7.87 (s, 1 H) 7.10-7.14 (m, 2 H) 7.03-7.08 (m, 2 H) 6.67-6.71 (m, 2 H) 5.69 (d, J = 8.54 Hz, 1 H) 4.90-4.99 (m, 1 H) 3.55 (spt, J = 6.10 Hz, 1 H) 3.52 (t, J = 6.03 Hz, 2 H) 3.38 (s, 2 H) 3.23-3.28 (m, 4 H) 2.87 (s, 6 H) 2.82-2.88 (m, 2 H) 2.55-2.60 (m, 4 H) 2.51 (t, J = 6.03 Hz, 2 H) 2.04-2.11 (m, 2 H) 1.93-2.00 (m, 2 H) 1.63 (qd, J = 11.57, 2.98 Hz, 2 H) 1.09 (d, J = 6.10 Hz, 6 H). |
| 91 | 570 | 12.88 (s, 1 H) 7.95 (s, 1 H) 7.93 (d, J = 8.9 Hz, 2 H) 6.82 (d, J = 9.2 Hz, 2 H) 5.36 (d, J = 8.9 Hz, 1 H) 4.88-4.97 (m, 1 H) 3.55 (t, J = 5.2 Hz, 2 H) 3.53 (t, J = 6.3 Hz, 2 H) 3.50 (spt, J = 6.1 Hz, 1 H) 3.42 (t, J = 6.1 Hz, 2 H) 2.76-2.83 (m, 4 H) 2.60 (t, J = 6.1 Hz, 2 H) 2.58 (t, J = 6.1 Hz, 2 H) 2.21 (s, 3 H) 2.07 (t, J = 11.7 Hz, 2 H) 1.99 (d, J = 11.6 Hz, 2 H) 1.86 (quin, J = 5.8 Hz, 2 H) 1.64 (qd, J = 11.5, 3.7 Hz, 2 H) 1.05 (d, J = 6.1 Hz, 6 H). |
| 92 | 526 | 12.85 (br. s., 1 H) 7.93 (d, J = 9.2 Hz, 2 H) 7.85 (s, 1 H) 6.82 (d, J = 8.9 Hz, 2 H) 5.64 (d, J = 8.9 Hz, 1 H) 4.87-4.96 (m, 1 H) 3.55 (t, J = 4.9 Hz, 2 H) 3.52 (t, J = 6.3 Hz, 2 H) 3.50 (spt, J = 6.1 Hz, 1 H) 3.42 (t, J = 6.3 Hz, 2 H) 2.81 (d, J = 11.6 Hz, 2 H) 2.78 (t, J = 5.2 Hz, 2 H) 2.60 (t, J = 6.1 Hz, 2 H) 2.58 (t, J = 5.8 Hz, 2 H) 2.21 (s, 3 H) 2.05 (td, J = 11.5, 1.7 Hz, 2 H) 1.97 (d, J = 12.5 Hz, 2 H) 1.86 (quin, J = 5.8 Hz, 2 H) 1.66 (qd, J = 11.7, 3.7 Hz, 2 H) 1.05 (d, J = 6.1 Hz, 6 H). |
| 93 | 554 | 12.85 (s, 1 H) 7.92 (d, J = 9.2 Hz, 2 H) 7.85 (s, 1 H) 6.81 (d, J = 9.2 Hz, 2 H) 5.58 (d, J = 8.9 Hz, 1 H) 4.84-4.95 (m, 1 H) 3.55 (t, J = 5.2 Hz, 2 H) 3.52 (t, J = 6.4 Hz, 2 H) 3.50 (spt, J = 6.1 Hz, 1 H) 3.42 (t, J = 6.1 Hz, 2 H) 2.85 (d, J = 11.6 Hz, 2 H) 2.78 (t, J = 4.9 Hz, 2 H) 2.72 (spt, J = 6.5 Hz, 1 H) 2.60 (t, J = 6.3 Hz, 2 H) 2.58 (t, J = 5.8 Hz, 2 H) 2.27 (td, J = 11.5, 1.7 Hz, 2 H) 2.01 (d, J = 9.2 Hz, 2 H) 1.85 (quin, J = 5.9 Hz, 2 H) 1.59 (qd, J = 11.6, 3.7 Hz, 2 H) 1.05 (d, J = 6.1 Hz, 6 H) 1.01 (d, J = 6.7 Hz, 6 H). |
| 94 | 632 | 12.85 (s, 1 H) 7.92 (d, J = 9.2 Hz, 2 H) 7.85 (s, 1 H) 7.24 (d, J = 8.5 Hz, 2 H) 6.89 (d, J = 8.5 Hz, 2 H) 6.82 (d, J = 8.9 Hz, 2 H) 5.64 (d, J = 8.9 Hz, 1 H) 4.91-5.01 (m, 1 H) 3.74 (s, 3 H) 3.56 (t, J = 5.2 Hz, 2 H) 3.53 (t, J = 6.1 Hz, 2 H) 3.51 (spt, J = 6.1 Hz, 1 H) 3.44 (s, 2 H) 3.43 (t, J = 6.1 Hz, 2 H) 2.86 (d, J = 11.9 Hz, 2 H) 2.80 (t, J = 4.9 Hz, 2 H) 2.61 (t, J = 6.3 Hz, 2 H) 2.58 (t, J = 5.8 Hz, 2 H) 2.10 (t, J = 10.8 Hz, 2 H) 1.97 (d, J = 10.7 Hz, 2 H) 1.87 (quin, J = 5.8 Hz, 2 H) 1.64 (qd, J = 11.6, 3.5 Hz, 2 H) 1.06 (d, J = 6.1 Hz, 6 H). |
| 95 | 584 | 12.88 (s, 1 H) 7.95 (s, 1 H) 7.93 (d, J = 8.9 Hz, 2 H) 6.82 (d, J = 9.2 Hz, 2 H) 5.35 (d, J = 8.9 Hz, 1 H) 4.89-4.99 (m, 1 H) 3.55 (t, J = 5.2 Hz, 2 H) 3.52 (t, J = 6.4 Hz, 2 H) 3.50 (spt, J = 6.1 Hz, 1 H) 3.42 (t, J = 6.1 Hz, 2 H) 2.90 (d, J = 11.0 Hz, 2 H) 2.78 (t, J = 4.9 Hz, 2 H) 2.60 (t, J = 6.3 Hz, 2 H) 2.57 (t, J = 5.2 Hz, 2 H) 2.36 (q, J = 7.3 Hz, 2 H) 2.06 (t, J = 11.9 Hz, 2 H) 2.02 (d, J = 11.0 Hz, 2 H) 1.85 (quin, J = 5.8 Hz, 2 H) 1.61 (qd, J = 11.4, 3.5 Hz, 2 H) 1.05 (d, J = 6.1 Hz, 6 H) 1.03 (t, J = 7.2 Hz, 3 H). |
| 96 | 540 | 12.85 (s, 1 H) 7.93 (d, J = 8.9 Hz, 2 H) 7.85 (s, 1 H) 6.82 (d, J = 9.2 Hz, 2 H) 5.63 (d, J = 8.9 Hz, 1 H) 4.88-4.99 (m, 1 H) 3.55 (t, J = 5.2 Hz, 2 H) 3.52 (t, J = 6.1 Hz, 2 H) 3.50 (spt, J = 6.1 Hz, 1 H) 3.42 (t, J = 6.3 Hz, 2 H) 2.93 (d, J = 11.0 Hz, 2 H) 2.78 (t, J = 4.9 Hz, 2 H) 2.60 (t, J = 6.1 Hz, 2 H) 2.57 (t, J = 5.8 Hz, 2 H) 2.36 (q, J = 7.0 Hz, 2 H) 2.04 (t, J = 12.3 Hz, 2 H) 2.00 (d, J = 13.1 Hz, 2 H) 1.85 (quin, J = 5.8 Hz, 2 H) 1.63 (qd, J = 11.5, 3.7 Hz, 2 H) 1.05 (d, J = 6.1 Hz, 6 H) 1.03 (t, J = 7.2 Hz, 3 H). |
| 97 | 504 | 8.40 (d, J = 1.5 Hz, 1 H) 8.12 (dd, J = 2.6, 1.4 Hz, 1 H) 8.02 (d, J = 8.9 Hz, 2 H) 7.88 (s, 1 H) 7.87 (d, J = 2.7 Hz, 1 H) 7.14 (d, J = 9.2 Hz, 2 H) 5.69 (d, J = 9.5 Hz, 1 H) 4.87-4.98 (m, 1 H) 3.74 (t, J = 5.5 Hz, 4 H) 3.42 (t, J = 5.2 Hz, 4 H) 2.82 (d, J = 11.9 Hz, |

TABLE 2-continued

| Ex | m/z | ¹H NMR (600 MHz, DMSO-d$_6$) δ ppm |
|---|---|---|
| | | 2 H) 2.21 (s, 3 H) 2.06 (td, J = 11.7, 2.1 Hz, 2 H) 1.97 (d, J = 11.6 Hz, 2 H) 1.67 (qd, J = 11.6, 3.5 Hz, 2 H). |
| 98 | 517 | 12.97 (s, 1 H) 8.51 (dq, J = 4.9, 0.9 Hz, 1 H) 7.98 (d, J = 8.9 Hz, 2 H) 7.88 (s, 1 H) 7.79 (td, J = 7.6, 1.8 Hz, 1 H) 7.48 (d, J = 7.6 Hz, 1 H) 7.28 (ddd, J = 7.5, 5.0, 0.9 Hz, 1 H) 7.06 (d, J = 8.9 Hz, 2 H) 5.70 (d, J = 8.9 Hz, 1 H) 4.87-4.96 (m, 1 H) 3.66 (s, 2 H) 3.29 (t, J = 4.6 Hz, 4 H) 2.81 (d, J = 11.3 Hz, 2 H) 2.58 (t, J = 4.9 Hz, 4 H) 2.20 (s, 3 H) 2.05 (t, J = 10.8 Hz, 2 H) 1.97 (d, J = 11.3 Hz, 2 H) 1.66 (qd, J = 11.7, 3.8 Hz, 2 H). |
| 99 | 517 | 12.94 (br. s., 1 H) 8.54 (d, J = 1.8 Hz, 1 H) 8.49 (dd, J = 4.9, 1.5 Hz, 1 H) 7.98 (d, J = 9.2 Hz, 2 H) 7.87 (s, 1 H) 7.75 (dt, J = 7.9, 1.8 Hz, 1 H) 7.38 (ddd, J = 7.6, 4.9, 0.6 Hz, 1 H) 7.06 (d, J = 8.9 Hz, 2 H) 5.69 (d, J = 8.5 Hz, 1 H) 4.87-4.96 (m, 1 H) 3.57 (s, 2 H) 3.28 (t, J = 5.2 Hz, 4 H) 2.81 (d, J = 11.6 Hz, 2 H) 2.53 (t, J = 5.2 Hz, 4 H) 2.20 (s, 3 H) 2.05 (td, J = 11.6, 1.8 Hz, 2 H) 1.97 (d, J = 10.4 Hz, 2 H) 1.66 (qd, J = 11.7, 3.8 Hz, 2 H). |
| 100 | 517 | 12.97 (br. s., 1 H) 8.51-8.55 (m, 2 H) 7.98 (d, J = 8.9 Hz, 2 H) 7.88 (s, 1 H) 7.37 (d, J = 5.8 Hz, 2 H) 7.07 (d, J = 9.2 Hz, 2 H) 5.71 (d, J = 8.9 Hz, 1 H) 4.87-4.96 (m, 1 H) 3.58 (s, 2 H) 3.30 (t, J = 4.9 Hz, 4 H) 2.81 (d, J = 11.3 Hz, 2 H) 2.54 (t, J = 4.9 Hz, 4 H) 2.21 (s, 3 H) 2.06 (t, J = 11.1 Hz, 2 H) 1.97 (d, J = 11.3 Hz, 2 H) 1.67 (qd, J = 11.6, 3.7 Hz, 2 H). |
| 101 | 503 | 12.86 (br. s., 1 H) 8.38 (d, J = 2.7 Hz, 1 H) 8.03 (dd, J = 4.3, 1.2 Hz, 1 H) 8.02 (d, J = 8.9 Hz, 2 H) 7.88 (s, 1 H) 7.40 (ddd, J = 8.5, 3.1, 1.2 Hz, 1 H) 7.25 (dd, J = 8.2, 4.6 Hz, 1 H) 7.15 (d, J = 9.2 Hz, 2 H) 5.69 (d, J = 8.5 Hz, 1 H) 4.88-4.97 (m, 1 H) 3.45 (dd, J = 6.4, 4.0 Hz, 4 H) 3.36 (dd, J = 6.3, 4.1 Hz, 4 H) 2.82 (d, J = 11.9 Hz, 2 H) 2.21 (s, 3 H) 2.06 (td, J = 11.5, 1.7 Hz, 2 H) 1.98 (d, J = 11.3 Hz, 2 H) 1.67 (qd, J = 11.6, 3.8 Hz, 2 H). |
| 102 | 592 | 12.96 (br. s., 1 H) 8.80 (s, 1 H) 7.94-7.99 (m, 2 H) 7.87 (s, 1 H) 7.03-7.08 (m, 2 H) 6.87 (d, J = 1.53 Hz, 1 H) 6.71 (d, J = 7.93 Hz, 1 H) 6.69 (dd, J = 7.93, 1.53 Hz, 1 H) 5.71 (d, J = 9.31 Hz, 1 H) 4.92-5.01 (m, 1 H) 4.44 (t, J = 5.34 Hz, 1 H) 3.76 (s, 3 H) 3.55 (td, J = 6.26, 5.34 Hz, 2 H) 3.40 (s, 2 H) 3.23-3.29 (m, 4 H) 2.84-2.90 (m, 2 H) 2.53-2.60 (m, 4 H) 2.45 (t, J = 6.26 Hz, 2 H) 2.05-2.14 (m, 2 H) 1.94-2.01 (m, 2 H) 1.66 (qd, J = 11.65, 3.20 Hz, 2 H). |
| 103 | 606 | 12.96 (br. s., 1 H) 8.80 (s, 1 H) 7.94-7.99 (m, 2 H) 7.87 (s, 1 H) 7.03-7.08 (m, 2 H) 6.87 (d, J = 1.50 Hz, 1 H) 6.72 (d, J = 7.93 Hz, 1 H) 6.69 (dd, J = 7.93, 1.50 Hz, 1 H) 5.71 (d, J = 8.85 Hz, 1 H) 4.92-5.00 (m, 1 H) 3.76 (s, 3 H) 3.48 (t, J = 5.80 Hz, 2 H) 3.40 (s, 2 H) 3.26 (s, 3 H) 3.23-3.28 (m, 4 H) 2.84-2.90 (m, 2 H) 2.55-2.59 (m, 4 H) 2.53 (t, J = 5.80 Hz, 2 H) 2.06-2.13 (m, 2 H) 1.94-2.01 (m, 2 H) 1.66 (dtd, J = 11.98, 11.71, 3.51 Hz, 2 H). |
| 104 | 588 | 12.96 (s, 1 H) 7.95-7.99 (m, 2 H) 7.87 (s, 1 H) 7.16-7.19 (m, 1 H) 7.03-7.08 (m, 2 H) 7.01 (dd, J = 8.09, 1.50 Hz, 1 H) 6.70 (d, J = 8.09 Hz, 1 H) 5.69 (d, J = 8.70 Hz, 1 H) 4.92-5.00 (m, 1 H) 4.50 (t, J = 8.70 Hz, 2 H) 4.44 (t, J = 5.34 Hz, 1 H) 3.55 (td, J = 6.18, 5.34 Hz, 2 H) 3.41 (s, 2 H) 3.24-3.29 (m, 4 H) 3.16 (t, J = 8.70 Hz, 2 H) 2.83-2.89 (m, 2 H) 2.53-2.60 (m, 4 H) 2.45 (t, J = 6.18 Hz, 2 H) 2.06-2.13 (m, 2 H) 1.94-2.01 (m, 2 H) 1.64 (qd, J = 11.70, 3.66 Hz, 2 H). |
| 105 | 602 | 12.96 (br. s., 1 H) 7.95-7.99 (m, 2 H) 7.87 (s, 1 H) 7.16-7.19 (m, 1 H) 7.03-7.08 (m, 2 H) 7.01 (dd, J = 8.09, 1.50 Hz, 1 H) 6.70 (d, J = 8.09 Hz, 1 H) 5.68 (d, J = 8.70 Hz, 1 H) 4.92-5.00 (m, 1 H) 4.50 (t, J = 8.70 Hz, 2 H) 3.48 (t, J = 5.80 Hz, 2 H) 3.41 (s, 2 H) 3.26 (s, 3 H) 3.23-3.28 (m, 4 H) 3.16 (t, J = 8.70 Hz, 2 H) 2.83-2.89 (m, 2 H) 2.55-2.59 (m, 4 H) 2.53 (t, J = 5.80 Hz, 2 H) 2.06-2.13 (m, 2 H) 1.93-2.01 (m, 2 H) 1.64 (dtd, J = 11.94, 11.62, 3.13 Hz, 2 H). |
| 106 | 622 | 13.01 (s, 1 H) 7.99-8.03 (m, 2 H) 7.88 (s, 1 H) 7.17-7.19 (m, 1 H) 7.10-7.15 (m, 2 H) 7.01 (dd, J = 8.09, 1.50 Hz, 1 H) 6.70 (d, J = 8.09 Hz, 1 H) 5.71 (d, J = 9.00 Hz, 1 H) 4.92-5.00 (m, 1 H) 4.50 (t, J = 8.70 Hz, 2 H) 3.41 (s, 2 H) 3.38-3.44 (m, 4 H) 3.23-3.28 (m, 4 H) 3.16 (t, J = 8.70 Hz, 2 H) 2.94 (s, 3 H) 2.83-2.90 (m, 2 H) 2.05-2.14 (m, 2 H) 1.94-2.01 (m, 2 H) 1.65 (dtd, J = 11.86, 11.62, 3.66 Hz, 2 H). |
| 107 | 616 | 12.96 (s, 1 H) 7.95-8.00 (m, 2 H) 7.87 (s, 1 H) 7.16-7.19 (m, 1 H) 7.04-7.08 (m, 2 H) 7.01 (dd, J = 8.09, 1.50 Hz, 1 H) 6.70 (d, J = 8.09 Hz, 1 H) 5.69 (d, J = 8.85 Hz, 1 H) 4.91-5.01 (m, 1 H) 4.50 (t, J = 8.70 Hz, 2 H) 3.52 (t, J = 5.90 Hz, 2 H) 3.44 (q, J = 7.02 Hz, 2 H) 3.41 (s, 2 H) 3.23-3.28 (m, 4 H) 3.16 (t, J = 8.70 Hz, 2 H) 2.83-2.89 (m, 2 H) 2.55-2.60 (m, 4 H) 2.53 (t, J = 5.90 Hz, 2 H) 2.06-2.13 (m, 2 H) 1.94-2.01 (m, 2 H) 1.59-1.69 (m, 2 H) 1.12 (t, J = 7.02 Hz, 3 H). |
| 108 | 523 | 12.97 (br. s., 1 H) 7.98 (d, J = 8.9 Hz, 2 H) 7.88 (s, 1 H) 7.74 (d, J = 3.4 Hz, 1 H) 7.69 (d, J = 3.4 Hz, 1 H) 7.07 (d, J = 9.2 Hz, 2 H) 5.71 (d, J = 8.9 Hz, 1 H) 4.86-4.97 (m, 1 H) 3.91 (s, 2 H) 3.31 (t, J = 5.5 Hz, 4 H) 2.81 (d, J = 11.6 Hz, 2 H) 2.66 (t, J = 4.9 Hz, 4 H) 2.20 (s, 3 H) 2.05 (t, J = 10.8 Hz, 2 H) 1.97 (d, J = 10.1 Hz, 2 H) 1.66 (qd, J = 11.7, 3.7 Hz, 2 H). |
| 109 | 506 | Mixture of conformers, major conformer: 12.96 (br. s., 1 H) 11.88 (br. s., 1 H) 7.97 (d, J = 8.5 Hz, 2 H) 7.87 (s, 1 H) 7.55 (s, 1 H) 7.05 (d, J = 8.2 Hz, 2 H) 6.99 (s, 1 H) 5.69 (d, J = 8.9 Hz, 1 H) 4.85-4.98 (m, 1 H) 3.43 (s, 2 H) 3.21-3.29 (m, 4 H) 2.81 (d, J = 11.6 Hz, 2 H) 2.52-2.56 (m, 4 H) 2.20 (s, 3 H) 2.05 (t, J = 11.1 Hz, 2 H) 1.97 (d, J = 10.7 Hz, 2 H) 1.66 (qd, J = 11.6, 3.5 Hz, 2 H). |
| 110 | 531 | 12.96 (br. s., 1 H) 7.98 (d, J = 8.9 Hz, 2 H) 7.87 (s, 1 H) 7.66 (t, J = 7.6 Hz, 1 H) 7.27 (d, J = 7.6 Hz, 1 H) 7.13 (d, J = 7.3 Hz, 1 H) 7.06 (d, J = 8.9 Hz, 2 H) 5.69 (d, J = 8.9 Hz, 1 H) 4.85-4.97 (m, 1 H) 3.61 (s, 2 H) 3.29 (t, J = 4.6 Hz, 4 H) 2.81 (d, J = 11.9 Hz, 2 H) 2.57 (t, J = 4.9 Hz, 4 H) 2.45 (s, 3 H) 2.20 (s, 3 H) 2.05 (t, J = 10.8 Hz, 2 H) 1.97 (d, J = 10.7 Hz, 2 H) 1.66 (qd, J = 11.6, 3.7 Hz, 2 H). |
| 111 | 561 | 12.98 (br. s., 1 H) 8.53 (d, J = 6.1 Hz, 2 H) 7.98 (d, J = 8.9 Hz, 2 H) 7.97 (s, 1 H) 7.37 (d, J = 5.8 Hz, 2 H) 7.06 (d, J = 9.2 Hz, 2 H) 5.41 (d, J = 8.9 Hz, 1 H) |

TABLE 2-continued

| Ex | m/z | $^1$H NMR (600 MHz, DMSO-$d_6$) δ ppm |
|---|---|---|
| | | 4.87-4.97 (m, 1 H) 3.58 (s, 2 H) 3.30 (t, J = 4.9 Hz, 4 H) 2.79 (d, J = 11.3 Hz, 2 H) 2.54 (t, J = 4.9 Hz, 4 H) 2.20 (s, 3 H) 2.07 (t, J = 11.0 Hz, 2 H) 1.99 (d, J = 10.1 Hz, 2 H) 1.64 (qd, J = 11.4, 3.5 Hz, 2 H). |
| 112 | 567 | 13.00 (br. s., 1 H) 7.99 (d, J = 8.9 Hz, 2 H) 7.97 (s, 1 H) 7.74 (d, J = 3.4 Hz, 1 H) 7.69 (d, J = 3.4 Hz, 1 H) 7.08 (d, J = 9.2 Hz, 2 H) 5.42 (d, J = 8.9 Hz, 1 H) 4.87-4.97 (m, 1 H) 3.91 (s, 2 H) 3.31 (t, J = 4.9 Hz, 4 H) 2.79 (d, J = 11.3 Hz, 2 H) 2.66 (t, J = 4.9 Hz, 4 H) 2.21 (s, 3 H) 2.07 (t, J = 10.7 Hz, 2 H) 1.99 (d, J = 10.4 Hz, 2 H) 1.65 (dq, J = 11.5, 3.5 Hz, 2 H). |
| 113 | 550 | mixture of conformers, major conformer: 12.98 (br. s., 1 H) 11.88 (br. s., 1 H) 7.97 (s, 1 H) 7.97 (d, J = 8.9 Hz, 2 H) 7.55 (s, 1 H) 7.05 (d, J = 8.9 Hz, 2 H) 6.99 (s, 1 H) 5.41 (d, J = 8.5 Hz, 1 H) 4.87-4.98 (m, 1 H) 3.43 (s, 2 H) 3.22-3.26 (m, 4 H) 2.79 (d, J = 11.3 Hz, 2 H) 2.54 (t, J = 4.4 Hz, 4 H) 2.21 (s, 3 H) 2.07 (t, J = 11.3 Hz, 2 H) 1.99 (d, J = 11.3 Hz, 2 H) 1.64 (qd, J = 11.5, 3.5 Hz, 2 H). |
| 114 | 575 | 13.00 (s, 1 H) 7.98 (d, J = 9.2 Hz, 2 H) 7.97 (s, 1 H) 7.66 (t, J = 7.8 Hz, 1 H) 7.27 (d, J = 7.6 Hz, 1 H) 7.13 (d, J = 7.6 Hz, 1 H) 7.06 (d, J = 9.2 Hz, 2 H) 5.42 (d, J = 8.9 Hz, 1 H) 4.87-4.98 (m, 1 H) 3.61 (s, 2 H) 3.29 (t, J = 4.9 Hz, 4 H) 2.79 (d, J = 11.3 Hz, 2 H) 2.58 (t, J = 4.9 Hz, 4 H) 2.45 (s, 3 H) 2.20 (s, 3 H) 2.07 (td, J = 11.3, 1.8 Hz, 2 H) 1.99 (d, J = 11.0 Hz, 2 H) 1.64 (qd, J = 11.4, 3.7 Hz, 2 H). |
| 115 | 561 | 13.00 (s, 1 H) 8.51 (dq, J = 4.9, 0.8 Hz, 1 H) 7.97 (s, 1 H) 7.98 (d, J = 9.2 Hz, 2 H) 7.79 (td, J = 7.6, 1.8 Hz, 1 H) 7.49 (d, J = 7.6 Hz, 1 H) 7.28 (ddd, J = 7.5, 4.9, 1.1 Hz, 1 H) 7.06 (d, J = 9.2 Hz, 2 H) 5.42 (d, J = 8.5 Hz, 1 H) 4.86-4.97 (m, 1 H) 3.66 (s, 2 H) 3.29 (t, J = 4.9 Hz, 4 H) 2.79 (d, J = 11.3 Hz, 2 H) 2.58 (t, J = 4.9 Hz, 4 H) 2.21 (s, 3 H) 2.07 (t, J = 10.8 Hz, 2 H) 1.99 (d, J = 12.2 Hz, 2 H) 1.64 (qd, J = 11.5, 3.8 Hz, 2 H). |
| 116 | 561 | 13.00 (s, 1 H) 8.54 (d, J = 1.5 Hz, 1 H) 8.49 (dd, J = 4.7, 1.7 Hz, 1 H) 7.97 (s, 1 H) 7.98 (d, J = 8.5 Hz, 2 H) 7.75 (dt, J = 7.7, 1.9 Hz, 1 H) 7.38 (ddd, J = 7.6, 4.9, 0.6 Hz, 1 H) 7.06 (d, J = 9.2 Hz, 2 H) 5.42 (d, J = 8.9 Hz, 1 H) 4.87-4.96 (m, 1 H) 3.57 (s, 2 H) 3.28 (t, J = 4.9 Hz, 4 H) 2.79 (d, J = 11.3 Hz, 2 H) 2.53 (t, J = 4.9 Hz, 4 H) 2.20 (s, 3 H) 2.07 (t, J = 10.5 Hz, 2 H) 1.99 (d, J = 10.1 Hz, 2 H) 1.64 (qd, J = 11.4, 3.5 Hz, 2 H). |
| 117 | 579 | 13.00 (s, 1 H) 7.97 (s, 1 H) 7.98 (d, J = 8.9 Hz, 2 H) 7.05 (d, J = 9.2 Hz, 2 H) 5.42 (d, J = 8.9 Hz, 1 H) 4.87-4.97 (m, 1 H) 3.30 (s, 2 H) 3.25 (t, J = 5.2 Hz, 4 H) 2.80 (d, J = 11.6 Hz, 2 H) 2.48 (t, J = 4.9 Hz, 4 H) 2.35 (s, 3 H) 2.21 (s, 3 H) 2.20 (s, 3 H) 2.08 (t, J = 11.4 Hz, 2 H) 1.99 (d, J = 11.0 Hz, 2 H) 1.65 (qd, J = 11.4, 3.7 Hz, 2 H). |
| 118 | 550 | 12.99 (s, 1 H) 7.97 (s, 1 H) 7.97 (d, J = 8.9 Hz, 2 H) 7.61 (dd, J = 1.8, 0.9 Hz, 1 H) 7.05 (d, J = 8.9 Hz, 2 H) 6.42 (dd, J = 3.1, 1.8 Hz, 1 H) 6.32 (d, J = 2.4 Hz, 1 H) 5.42 (d, J = 8.9 Hz, 1 H) 4.87-4.97 (m, 1 H) 3.56 (s, 2 H) 3.26 (t, J = 4.9 Hz, 4 H) 2.79 (d, J = 11.3 Hz, 2 H) 2.53 (t, J = 4.9 Hz, 4 H) 2.21 (s, 3 H) 2.07 (t, J = 11.1 Hz, 2 H) 1.99 (d, J = 10.4 Hz, 2 H) 1.64 (qd, J = 11.5, 3.5 Hz, 2 H). |
| 119 | 535 | 12.97 (s, 1 H) 7.97 (d, J = 8.9 Hz, 2 H) 7.88 (s, 1 H) 7.05 (d, J = 9.2 Hz, 2 H) 5.70 (d, J = 8.5 Hz, 1 H) 4.87-4.96 (m, 1 H) 3.30 (s, 2 H) 3.25 (t, J = 4.9 Hz, 4 H) 2.81 (d, J = 11.6 Hz, 2 H) 2.48 (t, J = 4.9 Hz, 4 H) 2.35 (s, 3 H) 2.21 (s, 3 H) 2.20 (s, 3 H) 2.05 (td, J = 11.6, 1.8 Hz, 2 H) 1.97 (d, J = 11.0 Hz, 2 H) 1.66 (qd, J = 11.6, 3.5 Hz, 2 H). |
| 120 | 506 | 12.97 (s, 1 H) 7.97 (d, J = 9.2 Hz, 2 H) 7.88 (s, 1 H) 7.61 (dd, J = 1.8, 0.9 Hz, 1 H) 7.05 (d, J = 9.2 Hz, 2 H) 6.42 (dd, J = 3.1, 1.8 Hz, 1 H) 6.32 (d, J = 3.1 Hz, 1 H) 5.70 (d, J = 8.9 Hz, 1 H) 4.86-4.97 (m, 1 H) 3.56 (s, 2 H) 3.26 (t, J = 4.9 Hz, 4 H) 2.81 (d, J = 11.6 Hz, 2 H) 2.53 (t, J = 4.9 Hz, 4 H) 2.20 (s, 3 H) 2.05 (td, J = 11.6, 1.8 Hz, 2 H) 1.97 (d, J = 9.5 Hz, 2 H) 1.66 (qd, J = 11.7, 3.8 Hz, 2 H). |
| 121 | 456 | 13.00 (s, 1 H) 7.96-8.01 (m, 2 H) 7.90 (s, 1 H) 7.02-7.07 (m, 2 H) 5.70 (d, J = 8.54 Hz, 1 H) 5.52-5.60 (m, 1 H) 4.43 (t, J = 5.34 Hz, 1 H) 3.54 (td, J = 6.26, 5.34 Hz, 2 H) 3.21-3.28 (m, 4 H) 2.70-2.77 (m, 2 H) 2.58 (dd, J = 9.61, 4.12 Hz, 1 H) 2.54-2.58 (m, 4 H) 2.44 (t, J = 6.26 Hz, 2 H) 2.31-2.40 (m, 2 H) 2.27 (s, 3 H) 1.75-1.84 (m, 1 H). |
| 122 | 470 | 13.00 (s, 1 H) 7.96-8.01 (m, 2 H) 7.90 (s, 1 H) 7.02-7.08 (m, 2 H) 5.70 (d, J = 8.70 Hz, 1 H) 5.52-5.59 (m, 1 H) 3.48 (t, J = 5.80 Hz, 2 H) 3.25 (s, 3 H) 3.20-3.28 (m, 4 H) 2.70-2.77 (m, 2 H) 2.58 (dd, J = 9.92, 4.12 Hz, 1 H) 2.55-2.58 (m, 4 H) 2.53 (t, J = 5.80 Hz, 2 H) 2.31-2.40 (m, 2 H) 2.27 (s, 3 H) 1.75-1.83 (m, 1 H). |
| 123 | 484 | 13.00 (s, 1 H) 7.96-8.01 (m, 2 H) 7.90 (s, 1 H) 7.02-7.07 (m, 2 H) 5.70 (d, J = 8.70 Hz, 1 H) 5.52-5.60 (m, 1 H) 3.51 (t, J = 5.95 Hz, 2 H) 3.43 (q, J = 7.00 Hz, 2 H) 3.21-3.27 (m, 4 H) 2.74 (dd, J = 9.50, 6.41 Hz, 1 H) 2.70-2.75 (m, 1 H) 2.58 (dd, J = 9.50, 4.27 Hz, 1 H) 2.56-2.59 (m, 4 H) 2.53 (t, J = 5.95 Hz, 2 H) 2.31-2.40 (m, 2 H) 2.27 (s, 3 H) 1.75-1.83 (m, 1 H) 1.11 (t, J = 7.00 Hz, 3 H). |
| 124 | 503 | 13.01 (s, 1 H) 8.51 (ddd, J = 4.86, 1.84, 0.92 Hz, 1 H) 7.96-8.01 (m, 2 H) 7.90 (s, 1 H) 7.79 (ddd, J = 7.82, 7.47, 1.84 Hz, 1 H) 7.49 (ddd, J = 7.82, 1.18, 0.92 Hz, 1 H) 7.28 (ddd, J = 7.47, 4.86, 1.18 Hz, 1 H) 7.03-7.07 (m, 2 H) 5.70 (d, J = 8.70 Hz, 1 H) 5.52-5.59 (m, 1 H) 3.67 (s, 2 H) 3.25-3.31 (m, 4 H) 2.70-2.77 (m, 2 H) 2.56-2.61 (m, 5 H) 2.31-2.40 (m, 2 H) 2.27 (s, 3 H) 1.76-1.83 (m, 1 H). |
| 125 | 503 | 13.01 (s, 1 H) 8.54 (d, J = 2.20, 0.87 Hz, 1 H) 8.49 (dd, J = 4.77, 1.72 Hz, 1 H) 7.96-8.00 (m, 2 H) 7.90 (s, 1 H) 7.75 (ddd, J = 7.77, 2.20, 1.72 Hz, 1 H) 7.38 (ddd, J = 7.77, 4.77, 0.87 Hz, 1 H) 7.02-7.07 (m, 2 H) 5.70 (d, J = 8.70 Hz, 1 H) 5.52-5.59 (m, 1 H) 3.58 (s, 2 H) 3.25-3.29 (m, 4 H) 2.74 (dd, J = 9.31, 6.71 Hz, 1 H) 2.70-2.75 (m, 1 H) 2.58 (dd, J = 9.31, 3.97 Hz, 1 H) 2.51-2.56 (m, 4 H) 2.30-2.40 (m, 2 H) 2.27 (s, 3 H) 1.76-1.83 (m, 1 H). |

TABLE 2-continued

| Ex | m/z | ¹H NMR (600 MHz, DMSO-d$_6$) δ ppm |
|---|---|---|
| 126 | 503 | 13.01 (s, 1 H) 8.51-8.55 (m, 2 H) 7.97-8.01 (m, 2 H) 7.90 (s, 1 H) 7.35-7.39 (m, 2 H) 7.03-7.08 (m, 2 H) 5.71 (d, J = 8.70 Hz, 1 H) 5.52-5.59 (m, 1 H) 3.59 (s, 2 H) 3.27-3.31 (m, 4 H) 2.74 (dd, J = 9.46, 6.71 Hz, 1 H) 2.70-2.75 (m, 1 H) 2.58 (dd, J = 9.46, 3.97 Hz, 1 H) 2.52-2.57 (m, 4 H) 2.31-2.40 (m, 2 H) 2.27 (s, 3 H) 1.75-1.83 (m, 1 H). |
| 127 | 484 | 13.00 (s, 1 H) 7.96-8.01 (m, 2 H) 7.90 (s, 1 H) 7.02-7.07 (m, 2 H) 5.70 (d, 1 H) 5.50-5.57 (m, 1 H) 4.43 (t, J = 5.34 Hz, 1 H) 3.54 (td, J = 6.26, 5.34 Hz, 2 H) 3.21-3.28 (m, 4 H) 2.79 (dd, J = 9.45, 6.49 Hz, 1 H) 2.75 (td, J = 8.54, 6.52 Hz, 1 H) 2.59 (dd, J = 9.45, 4.35 Hz, 1 H) 2.54-2.58 (m, 4 H) 2.44 (t, J = 6.26 Hz, 2 H) 2.41 (td, J = 8.55, 6.71 Hz, 1 H) 2.38 (t, J = 7.35 Hz, 1 H) 2.37 (t, J = 7.35 Hz, 1 H) 2.28-2.35 (m, 1 H) 1.75-1.82 (m, 1 H) 1.45 (sxt, J = 7.35 Hz, 2 H) 0.88 (t, J = 7.35 Hz, 3 H). |
| 128 | 498 | 13.00 (s, 1 H) 7.96-8.01 (m, 2 H) 7.90 (s, 1 H) 7.02-7.06 (m, 2 H) 5.70 (d, J = 8.70 Hz, 1 H) 5.50-5.57 (m, 1 H) 3.48 (t, J = 5.80 Hz, 2 H) 3.25 (s, 3 H) 3.22-3.27 (m, 4 H) 2.79 (dd, J = 9.44, 6.51 Hz, 1 H) 2.75 (td, J = 8.65, 5.10 Hz, 1 H) 2.59 (dd, J = 9.44, 4.34 Hz, 1 H) 2.55-2.58 (m, 4 H) 2.53 (t, J = 5.80 Hz, 2 H) 2.41 (td, J = 8.65, 6.78 Hz, 1 H) 2.37 (t, J = 7.40 Hz, 1 H) 2.37 (t, J = 7.40 Hz, 1 H) 2.28-2.35 (m, 1 H) 1.75-1.82 (m, 1 H) 1.45 (sxt, J = 7.40 Hz, 2 H) 0.88 (t, J = 7.40 Hz, 3 H). |
| 129 | 531 | 13.01 (s, 1 H) 8.51 (ddd, J = 4.85, 1.79, 0.94 Hz, 1 H) 7.96-8.01 (m, 2 H) 7.90 (s, 1 H) 7.79 (ddd, J = 7.82, 7.50, 1.79 Hz, 1 H) 7.49 (ddd, J = 7.82, 1.14, 0.94 Hz, 1 H) 7.28 (ddd, J = 7.50, 4.85, 1.14 Hz, 1 H) 7.03-7.07 (m, 2 H) 5.70 (d, J = 8.85 Hz, 1 H) 5.50-5.57 (m, 1 H) 3.67 (s, 2 H) 3.26-3.30 (m, 4 H) 2.79 (dd, J = 9.40, 6.54 Hz, 1 H) 2.75 (td, J = 8.57, 5.16 Hz, 1 H) 2.56-2.61 (m, 5 H) 2.41 (td, J = 8.57, 6.43 Hz, 1 H) 2.37 (t, J = 7.40 Hz, 1 H) 2.37 (t, J = 7.40 Hz, 1 H) 2.27-2.35 (m, 1 H) 1.75-1.82 (m, 1 H) 1.45 (sxt, J = 7.40 Hz, 2 H) 0.88 (t, J = 7.40 Hz, 3 H). |
| 130 | 531 | 13.01 (s, 1 H) 8.54 (dd, J = 2.00, 0.71 Hz, 1 H) 8.49 (dd, J = 4.78, 1.67 Hz, 1 H) 7.96-8.01 (m, 2 H) 7.90 (s, 1 H) 7.75 (ddd, J = 7.81, 2.00, 1.67 Hz, 1 H) 7.38 (ddd, J = 7.81, 4.78, 0.71 Hz, 1 H) 7.02-7.07 (m, 2 H) 5.70 (d, J = 8.54 Hz, 1 H) 5.50-5.57 (m, 1 H) 3.58 (s, 2 H) 3.25-3.29 (m, 4 H) 2.79 (dd, J = 9.39, 6.54 Hz, 1 H) 2.75 (td, J = 8.45, 5.07 Hz, 1 H) 2.59 (dd, J = 9.39, 4.27 Hz, 1 H) 2.51-2.55 (m, 4 H) 2.41 (td, J = 8.45, 6.54 Hz, 1 H) 2.37 (t, J = 7.40 Hz, 1 H) 2.36 (t, J = 7.40 Hz, 1 H) 2.27-2.35 (m, 1 H) 1.75-1.82 (m, 1 H) 1.45 (sxt, J = 7.40 Hz, 2 H) 0.88 (t, J = 7.40 Hz, 3 H). |
| 131 | 531 | 13.01 (s, 1 H) 8.51-8.55 (m, 2 H) 7.96-8.01 (m, 2 H) 7.90 (s, 1 H) 7.36-7.39 (m, 2 H) 7.02-7.07 (m, 2 H) 5.70 (d, J = 8.70 Hz, 1 H) 5.50-5.57 (m, 1 H) 3.58 (s, 2 H) 3.27-3.31 (m, 4 H) 2.79 (dd, J = 9.45, 6.53 Hz, 1 H) 2.75 (td, J = 8.55, 5.06 Hz, 1 H) 2.59 (dd, J = 9.45, 4.30 Hz, 1 H) 2.52-2.57 (m, 4 H) 2.41 (td, J = 8.55, 6.59 Hz, 1 H) 2.37 (t, J = 7.40 Hz, 1 H) 2.37 (t, J = 7.40 Hz, 1 H) 2.28-2.35 (m, 1 H) 1.75-1.82 (m, 1 H) 1.45 (sxt, J = 7.40 Hz, 2 H) 0.88 (t, J = 7.40 Hz, 3 H). |
| 132 | 518 | 12.97 (s, 1 H) 9.12 (s, 1 H) 8.78 (s, 2 H) 7.98 (d, J = 8.9 Hz, 2 H) 7.88 (s, 1 H) 7.06 (d, J = 8.9 Hz, 2 H) 5.70 (d, J = 8.9 Hz, 1 H) 4.86-4.96 (m, 1 H) 3.61 (s, 2 H) 3.29 (t, J = 4.9 Hz, 4 H) 2.81 (d, J = 11.6 Hz, 2 H) 2.55 (t, J = 4.9 Hz, 4 H) 2.20 (s, 3 H) 2.05 (t, J = 10.8 Hz, 2 H) 1.97 (d, J = 11.3 Hz, 2 H) 1.66 (qd, J = 11.6, 3.5 Hz, 2 H). |
| 133 | 562 | 13.00 (br. s., 1 H) 9.12 (s, 1 H) 8.78 (s, 2 H) 7.97 (s, 1 H) 7.98 (d, J = 8.9 Hz, 2 H) 7.06 (d, J = 8.9 Hz, 2 H) 5.42 (d, J = 8.9 Hz, 1 H) 4.87-4.97 (m, 1 H) 3.61 (s, 2 H) 3.29 (t, J = 5.2 Hz, 4 H) 2.79 (d, J = 11.3 Hz, 2 H) 2.55 (t, J = 4.9 Hz, 4 H) 2.20 (s, 3 H) 2.07 (td, J = 11.6, 1.8 Hz, 2 H) 1.99 (d, J = 10.4 Hz, 2 H) 1.64 (qd, J = 11.5, 3.8 Hz, 2H). |
| 134 | 531 | 12.97 (br. s., 1 H) 8.38 (d, J = 1.8 Hz, 1 H) 7.97 (d, J = 8.9 Hz, 2 H) 7.87 (s, 1 H) 7.62 (dd, J = 7.9, 2.4 Hz, 1 H) 7.23 (d, J = 7.9 Hz, 1 H) 7.05 (d, J = 9.2 Hz, 2 H) 5.70 (d, J = 8.9 Hz, 1 H) 4.86-4.96 (m, 1 H) 3.52 (s, 2 H) 3.27 (t, J = 5.2 Hz, 4 H) 2.81 (d, J = 11.3 Hz, 2 H) 2.51 (t, J = 4.9 Hz, 4 H) 2.45 (s, 3 H) 2.20 (s, 3 H) 2.05 (td, J = 11.5, 1.7 Hz, 2 H) 1.97 (d, J = 11.0 Hz, 2 H) 1.66 (qd, J = 11.7, 3.5 Hz, 2 H). |
| 135 | 575 | 13.00 (s, 1 H) 8.38 (d, J = 2.1 Hz, 1 H) 7.97 (s, 1 H) 7.98 (d, J = 8.9 Hz, 2 H) 7.62 (dd, J = 7.9, 2.4 Hz, 1 H) 7.23 (d, J = 7.9 Hz, 1 H) 7.05 (d, J = 9.2 Hz, 2 H) 5.42 (d, J = 8.9 Hz, 1 H) 4.87-4.97 (m, 1 H) 3.52 (s, 2 H) 3.26 (t, J = 5.2 Hz, 4 H) 2.79 (d, J = 11.3 Hz, 2 H) 2.50 (t, J = 5.2 Hz, 4 H) 2.45 (s, 3 H) 2.20 (s, 3 H) 2.07 (t, J = 10.8 Hz, 2 H) 1.99 (d, J = 11.0 Hz, 2 H) 1.64 (qd, J = 11.5, 3.4 Hz, 2 H). |
| 136 | 531 | 12.97 (s, 1 H) 8.51 (ddd, J = 4.88, 1.83, 0.91 Hz, 1 H) 7.95-8.00 (m, 2 H) 7.88 (s, 1 H) 7.79 (ddd, J = 7.84, 7.47, 1.83 Hz, 1 H) 7.48 (ddd, J = 7.84, 1.16, 0.91 Hz, 1 H) 7.28 (ddd, J = 7.47, 4.88, 1.16 Hz, 1 H) 7.03-7.09 (m, 2 H) 5.70 (d, J = 7.93 Hz, 1 H) 4.88-4.98 (m, 1 H) 3.66 (s, 2 H) 3.27-3.31 (m, 4 H) 2.86-2.99 (m, 2 H) 2.54-2.61 (m, 4 H) 2.30-2.42 (m, 2 H) 1.99-2.10 (m, 2 H) 1.97-2.04 (m, 2 H) 1.59-1.69 (m, 2 H) 1.03 (t, J = 7.02 Hz, 3 H). |
| 137 | 531 | 12.97 (s, 1 H) 8.54 (dd, J = 2.19, 0.84 Hz, 1 H) 8.49 (dd, J = 4.80, 1.68 Hz, 1 H) 7.95-8.00 (m, 2 H) 7.88 (s, 1 H) 7.75 (ddd, J = 7.77, 2.19, 1.68 Hz, 1 H) 7.38 (ddd, J = 7.77, 4.80, 0.84 Hz, 1 H) 7.03-7.08 (m, 2 H) 5.70 (d, J = 8.54 Hz, 1 H) 4.88-4.97 (m, 1 H) 3.57 (s, 2 H) 3.26-3.29 (m, 4 H) 2.88-2.98 (m, 2 H) 2.51-2.55 (m, 4 H) 2.30-2.41 (m, 2 H) 1.98-2.12 (m, 2 H) 1.96-2.03 (m, 2 H) 1.60-1.69 (m, 2 H) 1.03 (t, J = 7.25 Hz, 3 H). |
| 138 | 531 | 12.97 (s, 1 H) 8.51-8.55 (m, 2 H) 7.95-8.00 (m, 2 H) 7.88 (s, 1 H) 7.35-7.39 (m, 2 H) 7.04-7.09 (m, 2 H) 5.69 (d, J = 8.85 Hz, 1 H) 4.89-4.97 (m, 1 H) 3.58 (s, 2 H) 3.27-3.31 (m, 4 H) 2.89-2.95 (m, 2 H) 2.51-2.56 (m, 4 H) 2.35 (q, J = 7.17 Hz, 2 H) 1.99-2.08 (m, 2 H) 1.96-2.03 (m, 2 H) 1.64 (dtd, J = 11.64, 11.50, 3.66 Hz, 2 H) 1.02 (t, J = 7.17 Hz, 3 H). |
| 139 | 517 | 13.00 (s, 1 H) 8.38 (dd, J = 3.04, 0.57 Hz, 1 H) 8.03 (dd, J = 4.52, 1.30 Hz, 1 H) 8.00-8.03 (m, 2 H) 7.89 (s, 1 H) 7.40 (ddd, J = 8.50, 3.04, 1.30 Hz, 1 H) 7.25 (ddd, J = 8.50, 4.52, 0.57 Hz, 1 H) 7.13-7.17 (m, 2 H) 5.70 (d, J = 8.85 Hz, 1 H) 4.90-4.98 (m, 1 H) 3.42-3.47 (m, 4 H) 3.34-3.39 (m, 4 H) 2.90-2.96 (m, 2 H) |

TABLE 2-continued

| Ex | m/z | ¹H NMR (600 MHz, DMSO-$d_6$) δ ppm |
|---|---|---|
| | | 2.36 (q, J = 7.17 Hz, 2 H) 2.01-2.07 (m, 2 H) 1.97-2.03 (m, 2 H) 1.64 (dtd, J = 11.75, 11.56, 3.89 Hz, 2 H) 1.03 (t, J = 7.17 Hz, 3 H). |
| 140 | 537 | 12.97 (s, 1 H) 7.96-8.01 (m, 2 H) 7.88 (s, 1 H) 7.74 (d, J = 3.36 Hz, 1 H) 7.69 (d, J = 3.36 Hz, 1 H) 7.05-7.09 (m, 2 H) 5.70 (d, J = 8.70 Hz, 1 H) 4.89-4.97 (m, 1 H) 3.91 (s, 2 H) 3.28-3.31 (m, 4 H) 2.89-2.96 (m, 2 H) 2.63-2.68 (m, 4 H) 2.36 (q, J = 7.17 Hz, 2 H) 2.00-2.07 (m, 2 H) 1.96-2.03 (m, 2 H) 1.64 (qd, J = 11.57, 3.43 Hz, 2 H) 1.03 (t, J = 7.17 Hz, 3 H). |
| 141 | 520 | Broad peaks observed. For the imidazole ring two broad double peaks are observed from NH and one CH. 12.97 (s, 1 H) 12.03 (br. s., 0.5 H) 11.88 (br. s., 0.5 H) 7.95-7.99 (m, 2 H) 7.88 (s, 1 H) 7.55 (d, J = 0.92 Hz, 1 H) 7.02-7.08 (m, 2 H) 6.98 (br. s., 0.5 H) 6.80 (br. s., 0.5 H) 5.70 (d, J = 8.85 Hz, 1 H) 4.88-4.98 (m, 1 H) 3.45 (br. s., 2 H) 3.21-3.29 (m, 4 H) 2.87-3.00 (m, 2 H) 2.50-2.56 (m, 4 H) 2.31-2.42 (m, 2 H) 2.00-2.11 (m, 2 H) 1.97-2.03 (m, 2 H) 1.59-1.69 (m, 2 H) 1.03 (t, J = 7.17 Hz, 3 H). |
| 142 | 545 | 12.97 (s, 1 H) 7.95-8.00 (m, 2 H) 7.88 (s, 1 H) 7.66 (t, J = 7.63 Hz, 1 H) 7.27 (d, J = 7.63 Hz, 1 H) 7.13 (d, J = 7.63 Hz, 1 H) 7.03-7.08 (m, 2 H) 5.69 (d, 1 H) 4.88-4.97 (m, 1 H) 3.61 (s, 2 H) 3.26-3.31 (m, 4 H) 2.88-2.96 (m, 2 H) 2.53-2.61 (m, 4 H) 2.45 (s, 3 H) 2.35 (q, J = 7.17 Hz, 2 H) 2.00-2.07 (m, 2 H) 1.95-2.02 (m, 2 H) 1.64 (dtd, J = 11.83, 11.52, 3.43 Hz, 2 H) 1.02 (t, J = 7.17 Hz, 3 H). |
| 143 | 518 | 12.97 (s, 1 H) 8.73 (d, J = 1.5 Hz, 1 H) 8.61 (dd, J = 2.7, 1.5 Hz, 1 H) 8.56 (d, J = 2.7 Hz, 1 H) 7.98 (d, J = 9.2 Hz, 2 H) 7.88 (s, 1 H) 7.06 (d, J = 8.9 Hz, 2 H) 5.70 (d, J = 8.9 Hz, 1 H) 4.87-4.96 (m, 1 H) 3.74 (s, 2 H) 3.29 (t, J = 4.9 Hz, 4 H) 2.81 (d, J = 11.6 Hz, 2 H) 2.60 (t, J = 4.9 Hz, 4 H) 2.20 (s, 3 H) 2.05 (td, J = 11.5, 1.4 Hz, 2 H) 1.97 (d, J = 10.1 Hz, 2 H) 1.66 (qd, J = 11.6, 3.8 Hz, 2 H). |
| 144 | 562 | 13.00 (s, 1 H) 8.73 (d, J = 1.5 Hz, 1 H) 8.61 (dd, J = 2.4, 1.5 Hz, 1 H) 8.56 (d, J = 2.7 Hz, 1 H) 7.97 (s, 1 H) 7.98 (d, J = 9.2 Hz, 2 H) 7.07 (d, J = 9.2 Hz, 2 H) 5.42 (d, J = 8.9 Hz, 1 H) 4.86-4.97 (m, 1 H) 3.74 (s, 2 H) 3.29 (t, J = 4.9 Hz, 4 H) 2.79 (d, J = 11.6 Hz, 2 H) 2.60 (t, J = 4.9 Hz, 4 H) 2.21 (s, 3 H) 2.07 (t, J = 11.3 Hz, 2 H) 1.99 (d, J = 11.6 Hz, 2 H) 1.65 (qd, J = 11.5, 3.8 Hz, 2 H). |
| 145 | 562 | 12.98 (s, 1 H) 7.93-7.97 (m, 2 H) 7.89 (s, 1 H) 7.22-7.26 (m, 2 H) 7.02-7.06 (m, 2 H) 6.84-6.88 (m, 2 H) 5.75 (d, J = 8.55 Hz, 1 H) 5.47-5.54 (m, 1 H) 4.44 (t, J = 5.34 Hz, 1 H) 3.71 (s, 3 H) 3.57 (d, J = 12.82 Hz, 1 H) 3.55 (td, J = 6.26, 5.34 Hz, 2 H) 3.52 (d, J = 12.82 Hz, 1 H) 3.22-3.28 (m, 4 H) 2.88 (dd, J = 9.31, 6.56 Hz, 1 H) 2.73 (td, J = 8.58, 5.57 Hz, 1 H) 2.54-2.60 (m, 4 H) 2.49-2.52 (m, 1 H) 2.46-2.50 (m, 1 H) 2.45 (t, J = 6.26 Hz, 2 H) 2.30-2.37 (m, 1 H) 1.79-1.86 (m, 1 H). |
| 146 | 576 | 12.99 (s, 1 H) 7.93-7.97 (m, 2 H) 7.89 (s, 1 H) 7.22-7.26 (m, 2 H) 7.02-7.06 (m, 2 H) 6.84-6.88 (m, 2 H) 5.75 (d, J = 8.39 Hz, 1 H) 5.47-5.53 (m, 1 H) 3.71 (s, 3 H) 3.57 (d, J = 12.82 Hz, 1 H) 3.52 (d, J = 12.82 Hz, 1 H) 3.48 (t, J = 5.80 Hz, 2 H) 3.26 (s, 3 H) 3.23-3.27 (m, 4 H) 2.88 (dd, J = 9.38, 6.64 Hz, 1 H) 2.73 (td, J = 8.55, 5.34 Hz, 1 H) 2.55-2.60 (m, 4 H) 2.53 (t, J = 5.80 Hz, 2 H) 2.50-2.53 (m, 1 H) 2.48 (td, J = 8.55, 6.15 Hz, 1 H) 2.29-2.37 (m, 1 H) 1.79-1.86 (m, 1 H). |
| 147 | 609 | 12.99 (s, 1 H) 8.54 (dd, J = 2.11, 0.86 Hz, 1 H) 8.49 (dd, J = 4.83, 1.68 Hz, 1 H) 7.93-7.97 (m, 2 H) 7.89 (s, 1 H) 7.76 (ddd, J = 7.83, 2.11, 1.68 Hz, 1 H) 7.38 (ddd, J = 7.83, 4.83, 0.68 Hz, 1 H) 7.22-7.25 (m, 2 H) 7.02-7.06 (m, 2 H) 6.84-6.87 (m, 2 H) 5.75 (d, J = 8.55 Hz, 1 H) 5.46-5.54 (m, 1 H) 3.70 (s, 3 H) 3.58 (s, 2 H) 3.56 (d, J = 12.82 Hz, 1 H) 3.52 (d, J = 12.82 Hz, 1 H) 3.25-3.29 (m, 4 H) 2.87 (dd, J = 9.23, 6.49 Hz, 1 H) 2.73 (td, J = 8.62, 5.65 Hz, 1 H) 2.52-2.56 (m, 4 H) 2.50-2.54 (m, 1 H) 2.48 (td, J = 8.62, 6.71 Hz, 1 H) 2.30-2.37 (m, 1 H) 1.79-1.86 (m, 1 H). |
| 148 | 498 | 12.96 (br. s., 1 H) 7.98 (d, J = 9.2 Hz, 2 H) 7.88 (s, 1 H) 7.06 (d, J = 9.2 Hz, 2 H) 5.70 (d, J = 8.5 Hz, 1 H) 4.86-4.97 (m, 1 H) 3.36 (t, J = 6.4 Hz, 2 H) 3.26 (t, J = 5.2 Hz, 4 H) 3.23 (s, 3 H) 2.81 (d, J = 11.3 Hz, 2 H) 2.49 (t, J = 5.2 Hz, 4 H) 2.36 (t, J = 7.6 Hz, 2 H) 2.21 (s, 3 H) 2.05 (td, J = 11.5, 1.7 Hz, 2 H) 1.97 (d, J = 10.4 Hz, 2 H) 1.69 (dt, J = 14.3, 6.7 Hz, 2 H) 1.66 (qd, J = 11.9, 3.4 Hz, 2 H). |
| 149 | 542 | 12.99 (s, 1 H) 7.97 (s, 1 H) 7.98 (d, J = 8.9 Hz, 2 H) 7.06 (d, J = 8.9 Hz, 2 H) 5.42 (d, J = 8.9 Hz, 1 H) 4.87-4.99 (m, 1 H) 3.36 (t, J = 6.4 Hz, 2 H) 3.26 (t, J = 5.2 Hz, 4 H) 3.23 (s, 3 H) 2.79 (d, J = 11.6 Hz, 2 H) 2.49 (t, J = 5.2 Hz, 4 H) 2.36 (t, J = 7.3 Hz, 2 H) 2.21 (s, 3 H) 2.08 (t, J = 11.0 Hz, 2 H) 1.99 (d, J = 11.9 Hz, 2 H) 1.70 (dt, J = 14.6, 6.7 Hz, 2 H) 1.65 (qd, J = 11.4, 3.2 Hz, 2 H). |
| 150 | 589 | 13.00 (s, 1 H) 8.54 (dd, J = 2.22, 0.77 Hz, 1 H) 8.49 (dd, J = 4.80, 1.69 Hz, 1 H) 7.97 (s, 1 H) 7.95-7.99 (m, 2 H) 7.75 (ddd, J = 7.74, 2.22, 1.69 Hz, 1 H) 7.38 (ddd, J = 7.74, 4.80, 0.77 Hz, 1 H) 7.03-7.08 (m, 2 H) 5.37 (d, J = 9.00 Hz, 1 H) 4.86-4.94 (m, 1 H) 3.58 (s, 2 H) 3.26-3.30 (m, 4 H) 2.79-2.87 (m, 2 H) 2.72 (spt, J = 6.56 Hz, 1 H) 2.50-2.55 (m, 4 H) 2.24-2.33 (m, 2 H) 1.98-2.05 (m, 2 H) 1.58 (qd, J = 11.19, 3.05 Hz, 2 H) 1.01 (d, J = 6.56 Hz, 6 H). |
| 151 | 589 | 13.00 (s, 1 H) 8.51-8.55 (m, 2 H) 7.97 (s, 1 H) 7.96-8.00 (m, 2 H) 7.35-7.39 (m, 2 H) 7.04-7.08 (m, 2 H) 5.37 (d, J = 8.85 Hz, 1 H) 4.86-4.94 (m, 1 H) 3.58 (s, 2 H) 3.28-3.31 (m, 4 H) 2.79-2.87 (m, 2 H) 2.72 (spt, J = 6.56 Hz, 1 H) 2.51-2.56 (m, 4 H) 2.24-2.33 (m, 2 H) 1.99-2.05 (m, 2 H) 1.53-1.63 (m, 2 H) 1.00 (d, J = 6.56 Hz, 6 H). |
| 152 | 575 | 13.03 (s, 1 H) 8.38 (d, J = 3.00 Hz, 1 H) 8.03 (dd, J = 4.57, 1.30 Hz, 1 H) 8.00-8.03 (m, 2 H) 7.98 (s, 1 H) 7.40 (ddd, J = 8.51, 3.00, 1.30 Hz, 1 H) 7.25 (ddd, J = 8.51, 4.57, 0.66 Hz, 1 H) 7.13-7.17 (m, 2 H) 5.38 (d, J = 8.85 Hz, 1 H) 4.88-4.95 (m, 1 H) 3.42-3.48 (m, 4 H) 3.34-3.39 (m, 4 H) 2.81-2.87 (m, 2 H) 2.73 (spt, J = 6.56 Hz, 1 H) 2.30 (td, J = 11.41, 2.06 Hz, 2 H) 2.00-2.06 (m, 2 H) 1.54-1.63 (m, J = 11.41, 11.41, 11.22, 3.51 Hz, 2 H) 1.01 (d, J = 6.56 Hz, 6 H). |
| 153 | 607 | 12.99 (s, 1 H) 7.97 (s, 1 H) 7.95-7.99 (m, 2 H) 7.03-7.07 (m, 2 H) 5.36 (d, J = 9.00 Hz, 1 H) 4.86-4.95 (m, 1 H) 3.30 (s, 2 H) 3.22-3.28 (m, 4 H) |

TABLE 2-continued

| Ex | m/z | ¹H NMR (600 MHz, DMSO-d$_6$) δ ppm |
|---|---|---|
|  |  | 2.80-2.86 (m, 2 H) 2.72 (spt, J = 6.56 Hz, 1 H) 2.46-2.49 (m, 4 H) 2.35 (s, 3 H) 2.28 (td, J = 11.52, 2.14 Hz, 2 H) 2.20 (s, 3 H) 1.99-2.06 (m, 2 H) 1.53-1.63 (m, 2 H) 1.00 (d, J = 6.56 Hz, 6 H). |
| 154 | 578 | 12.99 (s, 1 H) 7.97 (s, 1 H) 7.95-7.99 (m, 2 H) 7.61 (dd, J = 1.84, 0.70 Hz, 1 H) 7.03-7.07 (m, 2 H) 6.42 (dd, J = 3.20, 1.84 Hz, 1 H) 6.32 (dq, J = 3.20, 0.70 Hz, 1 H) 5.37 (d, J = 8.85 Hz, 1 H) 4.86-4.94 (m, 1 H) 3.56 (s, 2 H) 3.23-3.29 (m, 4 H) 2.80-2.87 (m, 2 H) 2.72 (spt, J = 6.56 Hz, 1 H) 2.51-2.55 (m, 4 H) 2.25-2.32 (m, 2 H) 1.99-2.05 (m, 2 H) 1.58 (qd, J = 11.39, 3.66 Hz, 2 H) 1.01 (d, J = 6.56 Hz, 6 H). |
| 155 | 590 | 13.00 (s, 1 H) 9.12 (s, 1 H) 8.78 (s, 2 H) 7.97 (s, 1 H) 7.96-8.00 (m, 2 H) 7.04-7.08 (m, 2 H) 5.37 (d, J = 8.85 Hz, 1 H) 4.86-4.94 (m, 1 H) 3.61 (s, 2 H) 3.27-3.30 (m, 4 H) 2.80-2.87 (m, 2 H) 2.72 (spt, J = 6.56 Hz, 1 H) 2.52-2.57 (m, 4 H) 2.25-2.33 (m, 2 H) 1.99-2.05 (m, 2 H) 1.58 (qd, J = 11.32, 3.74 Hz, 2 H) 1.00 (d, J = 6.56 Hz, 6 H). |
| 156 | 514 | 13.03 (s, 1 H) 7.99 (d, J = 8.85 Hz, 2 H) 7.05 (d, J = 9.16 Hz, 2 H) 5.53-5.61 (m, 1 H) 5.47 (d, J = 8.55 Hz, 1 H) 3.48 (t, J = 5.80 Hz, 2 H) 3.25 (s, 3 H) 3.20-3.25 (m, 4 H) 2.77 (td, J = 8.16, 3.81 Hz, 1 H) 2.71 (dd, J = 9.46, 6.41 Hz, 1 H) 2.60 (dd, 1 H) 2.57 (t, J = 4.88 Hz, 4 H) 2.53 (t, J = 5.80 Hz, 2 H) 2.30-2.41 (m, 2 H) 2.28 (s, 3 H) 1.70-1.80 (m, 1 H). |
| 157 | 548 | 13.03 (s, 1 H) 9.12 (s, 1 H) 8.78 (s, 2 H) 7.99 (s, 1 H) 7.99 (d, J = 8.85 Hz, 2 H) 7.05 (d, J = 8.85 Hz, 2 H) 5.53-5.61 (m, 1 H) 5.48 (d, J = 8.85 Hz, 1 H) 3.61 (s, 2 H) 3.26-3.30 (m, 4 H) 2.74-2.80 (m, 1 H) 2.71 (dd, J = 9.46, 7.02 Hz, 1 H) 2.58-2.63 (m, 1 H) 2.53-2.58 (m, 4 H) 2.51-2.53 (m, 1 H) 2.30-2.41 (m, 2 H) 2.28 (s, 3 H) 1.71-1.79 (m, 1 H). |
| 158 | 547 | 13.03 (s, 1 H) 8.51 (d, J = 4.27 Hz, 1 H) 7.99 (s, 1 H) 7.99 (d, J = 8.85 Hz, 2 H) 7.79 (td, J = 7.55, 1.68 Hz, 1 H) 7.49 (d, J = 7.93 Hz, 1 H) 7.28 (dd, J = 6.87, 5.34 Hz, 1 H) 7.05 (d, J = 8.85 Hz, 2 H) 5.52-5.62 (m, 1 H) 5.47 (d, J = 8.85 Hz, 1 H) 3.67 (s, 2 H) 3.26-3.30 (m, 4 H) 2.74-2.80 (m, 1 H) 2.68-2.74 (m, 1 H) 2.60-2.65 (m, 1 H) 2.55-2.60 (m, 4 H) 2.31-2.41 (m, 2 H) 2.28 (s, 3 H) 1.71-1.79 (m, 1 H). |
| 159 | 547 | 13.03 (s, 1 H) 8.54 (d, J = 1.53 Hz, 1 H) 8.49 (dd, J = 4.73, 1.68 Hz, 1 H) 7.99 (s, 1 H) 7.99 (d, J = 8.85 Hz, 2 H) 7.75 (dt, J = 7.86, 1.87 Hz, 1 H) 7.38 (d, J = 7.78, 4.73 Hz, 1 H) 7.04 (d, J = 9.16 Hz, 2 H) 5.53-5.61 (m, 1 H) 5.47 (d, J = 8.85 Hz, 1 H) 3.58 (s, 2 H) 3.25-3.29 (m, 4 H) 2.76 (td, J = 8.24, 3.97 Hz, 1 H) 2.70 (dd, J = 9.46, 6.10 Hz, 1 H) 2.60 (dd, J = 9.46, 3.36 Hz, 1 H) 2.51-2.56 (m, 4 H) 2.29-2.41 (m, J = 8.39, 4.20, 4.20, 3.97 Hz, 2 H) 2.28 (s, 3 H) 1.69-1.79 (m, 1 H). |
| 160 | 547 | 13.03 (s, 1 H) 8.53 (d, J = 6.10 Hz, 2 H) 7.99 (s, 1 H) 7.99 (d, J = 8.85 Hz, 2 H) 7.37 (d, J = 6.10 Hz, 2 H) 7.05 (d, J = 8.85 Hz, 2 H) 5.53-5.61 (m, 1 H) 5.47 (d, J = 8.85 Hz, 1 H) 3.59 (s, 2 H) 3.29 (t, J = 4.88 Hz, 4 H) 2.73-2.79 (m, 1 H) 2.68-2.73 (m, 1 H) 2.61 (dd, J = 9.31, 3.20 Hz, 1 H) 2.52-2.56 (m, 4 H) 2.30-2.41 (m, 2 H) 2.28 (s, 3 H) 1.71-1.78 (m, 1 H). |
| 161 | 533 | 13.06 (s, 1 H) 8.38 (d, J = 2.75 Hz, 1 H) 8.03 (d, J = 1.22 Hz, 1 H) 8.03 (d, J = 8.85 Hz, 2 H) 8.00 (s, 1 H) 7.40 (ddd, J = 8.55, 3.05, 1.22 Hz, 1 H) 7.25 (dd, J = 8.39, 4.73 Hz, 1 H) 7.14 (d, J = 9.16 Hz, 2 H) 5.55-5.62 (m, J = 8.55, 8.55, 5.80, 3.05 Hz, 1 H) 5.49 (d, J = 8.54 Hz, 1 H) 3.41-3.47 (m, 4 H) 3.34-3.39 (m, 4 H) 2.75-2.81 (m, 1 H) 2.69-2.75 (m, 1 H) 2.59-2.64 (m, 1 H) 2.31-2.42 (m, 2 H) 2.29 (s, 3 H) 1.73-1.79 (m, 1 H). |
| 162 | 534 | 13.06 (s, 1 H) 8.40 (d, J = 1.53 Hz, 1 H) 8.12 (dd, J = 2.44, 1.53 Hz, 1 H) 8.03 (d, J = 8.85 Hz, 2 H) 8.00 (s, 1 H) 7.87 (d, J = 2.44 Hz, 1 H) 7.13 (d, J = 8.85 Hz, 2 H) 5.55-5.61 (m, J = 5.98, 5.98, 5.98, 5.72, 1.98 Hz, 1 H) 5.49 (d, J = 8.55 Hz, 1 H) 3.72-3.77 (m, 4 H) 3.38-3.44 (m, 4 H) 2.75-2.81 (m, 1 H) 2.69-2.75 (m, 1 H) 2.59-2.64 (m, 1 H) 2.31-2.42 (m, 2 H) 2.29 (s, 3 H) 1.71-1.80 (m, 1 H). |
| 163 | 563 | 12.97 (s, 1 H) 7.95-8.00 (m, 2 H) 7.88 (s, 1 H) 7.03-7.07 (m, 2 H) 5.64 (d, J = 8.85 Hz, 1 H) 4.89 (br. s., 1 H) 3.30 (s, 2 H) 3.21-3.29 (m, 4 H) 2.80-2.89 (m, 2 H) 2.72 (spt, J = 6.57, 6.33 Hz, 1 H) 2.45-2.50 (m, 4 H) 2.35 (s, 3 H) 2.23-2.31 (m, 2 H) 2.20 (s, 3 H) 1.97-2.04 (m, 2 H) 1.60 (dtd, J = 11.71,11.54, 3.36 Hz, 2 H) 1.01 (d, J = 6.56 Hz, 6 H). |
| 164 | 534 | 12.96 (s, 1 H) 7.95-7.99 (m, 2 H) 7.88 (s, 1 H) 7.61 (dd, J = 1.83, 0.76 Hz, 1 H) 7.02-7.07 (m, 2 H) 6.42 (dd, J = 3.13, 1.83 Hz, 1 H) 6.32 (dq, J = 3.13, 0.76 Hz, 1 H) 5.64 (d, J = 8.85 Hz, 1 H) 4.85-4.93 (m, 1 H) 3.56 (s, 2 H) 3.23-3.29 (m, 4 H) 2.81-2.87 (m, 2 H) 2.72 (spt, J = 6.56 Hz, 1 H) 2.50-2.56 (m, 4 H) 2.27 (td, J = 11.56, 1.91 Hz, 2 H) 1.97-2.03 (m, 2 H) 1.60 (tdd, J = 11.56, 11.25, 3.43 Hz, 2 H) 1.00 (d, J = 6.56 Hz, 6 H). |
| 165 | 546 | 12.97 (br. s., 1 H) 9.12 (s, 1 H) 8.78 (s, 2 H) 7.95-8.00 (m, 2 H) 7.88 (s, 1 H) 7.03-7.09 (m, 2 H) 5.64 (d, J = 9.00 Hz, 1 H) 4.85-4.94 (m, 1 H) 3.61 (s, 2 H) 3.25-3.31 (m, 4 H) 2.81-2.87 (m, 2 H) 2.72 (spt, J = 6.56 Hz, 1 H) 2.52-2.57 (m, 4 H) 2.27 (td, J = 11.60, 1.83 Hz, 2 H) 1.97-2.03 (m, 2 H) 1.60 (dtd, J = 11.60, 11.54, 3.81 Hz, 2 H) 1.00 (d, J = 6.56 Hz, 6 H). |
| 166 | 559 | 12.97 (s, 1 H) 8.38 (d, J = 2.14 Hz, 1 H) 7.94-8.00 (m, 2 H) 7.88 (s, 1 H) 7.62 (dd, J = 7.93, 2.14 Hz, 1 H) 7.23 (d, J = 7.93 Hz, 1 H) 7.02-7.08 (m, 2 H) 5.64 (d, J = 8.85 Hz, 1 H) 4.84-4.94 (m, 1 H) 3.52 (s, 2 H) 3.24-3.29 (m, 4 H) 2.81-2.87 (m, 2 H) 2.72 (spt, J = 6.59 Hz, 1 H) 2.49-2.53 (m, 4 H) 2.45 (s, 3 H) 2.26 (td, J = 11.50, 1.83 Hz, 2 H) 1.96-2.04 (m, 2 H) 1.60 (qd, J = 11.50, 3.81 Hz, 2 H) 1.00 (d, J = 6.56 Hz, 6 H). |
| 167 | 546 | 12.97 (s, 1 H) 8.73 (d, J = 1.60 Hz, 1 H) 8.61 (dd, J = 2.52, 1.60 Hz, 1 H) 8.56 (d, J = 2.52 Hz, 1 H) 7.95-8.00 (m, 2 H) 7.88 (s, 1 H) 7.03-7.09 (m, 2 H) 5.65 (d, J = 8.85 Hz, 1 H) 4.85-4.94 (m, 1 H) 3.74 (s, 2 H) 3.28-3.31 (m, 4 H) |

TABLE 2-continued

| Ex | m/z | $^1$H NMR (600 MHz, DMSO-d$_6$) δ ppm |
|---|---|---|
| | | 2.81-2.87 (m, 2 H) 2.72 (spt, J = 6.56 Hz, 1 H) 2.57-2.63 (m, 4 H) 2.27 (td, J = 11.47, 1.98 Hz, 2 H) 1.97-2.03 (m, 2 H) 1.60 (qd, J = 11.47, 3.59 Hz, 2 H) 1.00 (d, J = 6.56 Hz, 6 H). |
| 168 | 545 | 12.97 (s, 1 H) 8.54 (dd, J = 2.20, 0.83 Hz, 1 H) 8.49 (dd, J = 4.77, 1.68 Hz, 1 H) 7.95-7.99 (m, 2 H) 7.88 (s, 1 H) 7.75 (ddd, J = 7.77, 2.20, 1.68 Hz, 1 H) 7.38 (ddd, J = 7.77, 4.77, 0.83 Hz, 1 H) 7.03-7.08 (m, 2 H) 5.64 (d, J = 8.70 Hz, 1 H) 4.85-4.94 (m, 1 H) 3.57 (s, 2 H) 3.24-3.30 (m, 4 H) 2.82-2.87 (m, 2 H) 2.72 (spt, J = 6.56 Hz, 1 H) 2.50-2.55 (m, 4 H) 2.27 (td, J = 11.44, 1.60 Hz, 2 H) 1.97-2.03 (m, 2 H) 1.60 (dtd, J = 11.67, 11.44, 3.74 Hz, 2 H) 1.00 (d, J = 6.56 Hz, 6 H). |
| 169 | 575 | 13.00 (s, 1 H) 8.54 (dd, J = 2.23, 0.81 Hz, 1 H) 8.49 (dd, J = 4.78, 1.70 Hz, 1 H) 7.97 (s, 1 H) 7.96-8.00 (m, 2 H) 7.75 (ddd, J = 7.75, 2.23, 1.70 Hz, 1 H) 7.38 (ddd, J = 7.75, 4.78, 0.81 Hz, 1 H) 7.04-7.08 (m, 2 H) 5.40 (d, J = 9.00 Hz, 1 H) 4.89-4.98 (m, 1 H) 3.57 (s, 2 H) 3.26-3.29 (m, 4 H) 2.87-2.93 (m, 2 H) 2.50-2.55 (m, 4 H) 2.35 (q, J = 7.17 Hz, 2 H) 2.02-2.09 (m, 2 H) 1.98-2.04 (m, 2 H) 1.62 (dtd, J = 11.67, 11.41, 3.51 Hz, 2 H) 1.02 (t, J = 7.17 Hz, 3 H). |
| 170 | 589 | 12.99 (br. s., 1 H) 8.38 (d, J = 2.23 Hz, 1 H) 7.97 (s, 1 H) 7.95-7.99 (m, 2 H) 7.62 (dd, J = 7.93, 2.29 Hz, 1 H) 7.23 (d, J = 7.93 Hz, 1 H) 7.03-7.07 (m, 2 H) 5.40 (d, J = 8.70 Hz, 1 H) 4.89-4.98 (m, 1 H) 3.52 (s, 2 H) 3.24-3.29 (m, 4 H) 2.86-2.93 (m, 2 H) 2.49-2.53 (m, 4 H) 2.45 (s, 3 H) 2.35 (q, J = 7.17 Hz, 2 H) 2.02-2.09 (m, 2 H) 1.98-2.04 (m, 2 H) 1.62 (m, J = 11.60, 11.37, 3.66 Hz, 2 H) 1.02 (t, J = 7.17 Hz, 3 H). |
| 171 | 581 | 13.00 (br. s., 1 H) 7.97 (s, 1 H) 7.96-8.00 (m, 2 H) 7.74 (d, J = 3.30 Hz, 1 H) 7.69 (d, J = 3.30 Hz, 1 H) 7.05-7.09 (m, 2 H) 5.41 (d, J = 8.70 Hz, 1 H) 4.90-4.98 (m, 1 H) 3.91 (s, 2 H) 3.29-3.32 (m, 4 H) 2.87-2.93 (m, 2 H) 2.63-2.68 (m, 4 H) 2.36 (q, J = 7.17 Hz, 2 H) 2.03-2.09 (m, 2 H) 1.99-2.04 (m, 2 H) 1.62 (dtd, J = 11.67, 11.37, 3.43 Hz, 2 H) 1.02 (t, J = 7.17 Hz, 3 H). |
| 172 | 556 | 12.99 (s, 1 H) 7.97 (s, 1 H) 7.95-8.00 (m, 2 H) 7.04-7.08 (m, 2 H) 5.41 (d, J = 8.85 Hz, 1 H) 4.90-4.98 (m, 1 H) 3.51 (t, J = 5.95 Hz, 2 H) 3.43 (q, J = 7.02 Hz, 2 H) 3.22-3.28 (m, 4 H) 2.87-2.93 (m, 2 H) 2.54-2.59 (m, 4 H) 2.52 (t, J = 5.95 Hz, 2 H) 2.36 (q, J = 7.17 Hz, 2 H) 2.03-2.10 (m, 2 H) 1.98-2.04 (m, 2 H) 1.62 (qd, J = 11.39, 3.81 Hz, 2 H) 1.11 (t, J = 7.02 Hz, 3 H) 1.03 (t, J = 7.17 Hz, 3 H). |
| 173 | 564 | Two tautomers observed, molar ratio 1:0.7. Chemical shifts for both: 12.99 (br. s., 2 H) 12.03 (br. s., 1 H) 11.88 (br. s., 1 H) 7.97 (s, 2 H) 7.94-8.00 (m, 4 H) 7.55 (s, 2 H) 7.04-7.08 (m, 2 H) 7.02-7.06 (m, 2 H) 6.99 (s, 1 H) 6.78 (s, 1 H) 5.40 (d, J = 8.70 Hz, 2 H) 4.89-4.97 (m, 2 H) 3.50 (s, 2 H) 3.43 (s, 2 H) 3.21-3.29 (m, 8 H) 2.86-2.93 (m, 4 H) 2.52-2.57 (m, 8 H) 2.35 (q, J = 7.17 Hz, 4 H) 2.02-2.09 (m, 4 H) 1.98-2.04 (m, 4 H) 1.62 (qd, J = 11.32, 3.43 Hz, 4 H) 1.02 (t, J = 7.17 Hz, 6H). |
| 174 | 575 | 13.00 (s, 1 H) 8.51 (ddd, J = 4.92, 1.87, 0.92 Hz, 1 H) 7.97 (s, 1 H) 7.96-8.00 (m, 2 H) 7.79 (ddd, J = 7.80, 7.47, 1.87 Hz, 1 H) 7.48 (ddd, J = 7.80, 1.20, 0.92 Hz, 1 H) 7.28 (ddd, J = 7.47, 4.92, 1.20 Hz, 1 H) 7.04-7.08 (m, 2 H) 5.41 (d, J = 8.85 Hz, 1 H) 4.89-4.98 (m, 1 H) 3.66 (s, 2 H) 3.27-3.31 (m, 4 H) 2.87-2.93 (m, 2 H) 2.55-2.61 (m, 4 H) 2.35 (q, J = 7.17 Hz, 2 H) 2.02-2.09 (m, 2 H) 1.98-2.04 (m, 2 H) 1.62 (dtd, J = 11.67, 11.41, 3.51 Hz, 2 H) 1.02 (t, J = 7.17 Hz, 3 H). |
| 175 | 500 | 13.03 (s, 1 H) 7.99 (s, 1 H) 7.99 (d, J = 8.85 Hz, 2 H) 7.05 (d, J = 9.16 Hz, 2 H) 5.53-5.62 (m, 1 H) 5.47 (d, J = 8.55 Hz, 1 H) 4.43 (t, J = 5.34 Hz, 1 H) 3.54 (q, J = 6.10 Hz, 2 H) 3.21-3.28 (m, 4 H) 2.73-2.81 (m, 1 H) 2.71 (dd, J = 9.46, 6.41 Hz, 1 H) 2.61 (dd, J = 9.77, 3.36 Hz, 1 H) 2.53-2.58 (m, 4 H) 2.44 (t, J = 6.26 Hz, 2 H) 2.30-2.41 (m, 2 H) 2.28 (s, 3 H) 1.70-1.79 (m, 1 H). |
| 176 | 548 | 13.03 (s, 1 H) 8.73 (s, 1 H) 8.61 (d, J = 1.53 Hz, 1 H) 8.56 (d, J = 2.14 Hz, 1 H) 7.99 (br. s., 1 H) 7.99 (d, J = 8.55 Hz, 2 H) 7.05 (d, J = 8.85 Hz, 2 H) 5.53-5.61 (m, 1 H) 5.47 (d, J = 8.55 Hz, 1 H) 3.74 (s, 2 H) 3.24-3.30 (m, 4 H) 2.73-2.79 (m, 1 H) 2.67-2.72 (m, 1 H) 2.57-2.64 (m, 5 H) 2.30-2.42 (m, 2 H) 2.28 (s, 3 H) 1.70-1.79 (m, 1 H). |
| 177 | 536 | 13.03 (s, 1 H) 7.99 (s, 1 H) 7.98 (d, J = 8.85 Hz, 2 H) 7.61 (d, J = 1.53 Hz, 1 H) 7.04 (d, J = 9.16 Hz, 2 H) 6.42 (dd, J = 3.05, 2.14 Hz, 1 H) 6.32 (d, J = 3.05 Hz, 1 H) 5.53-5.60 (m, 1 H) 5.48 (d, J = 8.85 Hz, 1 H) 3.56 (s, 2 H) 3.22-3.28 (m, 4 H) 2.74-2.81 (m, 1 H) 2.68-2.74 (m, 1 H) 2.58-2.64 (m, 1 H) 2.52-2.56 (m, 4 H) 2.31-2.41 (m, 2 H) 2.29 (s, 3 H) 1.69-1.79 (m, 1 H). |
| 178 | 553 | 13.04 (s, 1 H) 7.99 (s, 1 H) 7.99 (d, J = 8.85 Hz, 2 H) 7.74 (d, J = 3.36 Hz, 1 H) 7.69 (d, J = 3.36 Hz, 1 H) 7.06 (d, J = 8.85 Hz, 2 H) 5.53-5.62 (m, 1 H) 5.48 (d, J = 8.55 Hz, 1 H) 3.92 (s, 2 H) 3.27-3.31 (m, 4 H) 2.75-2.81 (m, 1 H) 2.72 (dd, J = 9.00, 6.56 Hz, 1 H) 2.64-2.69 (m, 4 H) 2.58-2.64 (m, 1 H) 2.31-2.41 (m, 2 H) 2.29 (s, 3 H) 1.69-1.80 (m, 1 H). |
| 179 | 536 | 13.02 (s, 1 H) 12.03 (br. s., 1 H) 11.87 (br. s., 1 H) 7.99 (s, 1 H) 7.98 (d, J = 8.85 Hz, 2 H) 7.55 (s, 1 H) 7.04 (d, J = 8.85 Hz, 2 H) 6.98 (br. s., 1 H) 6.79 (br. s., 1 H) 5.53-5.61 (m, 1 H) 5.47 (d, J = 7.93 Hz, 1 H) 3.39-3.54 (m, 2 H) 3.14-3.28 (m, 4 H) 2.74-2.82 (m, 1 H) 2.71 (dd, J = 10.22, 5.95 Hz, 1 H) 2.58-2.64 (m, 1 H) 2.51-2.58 (m, 4 H) 2.31-2.41 (m, 2 H) 2.29 (s, 3 H) 1.69-1.80 (m, 1 H). |
| 180 | 561 | 13.03 (s, 1 H) 8.38 (d, J = 2.14 Hz, 1 H) 7.99 (s, 1 H) 7.98 (d, J = 8.85 Hz, 2 H) 7.62 (dd, J = 7.78, 2.29 Hz, 1 H) 7.23 (d, J = 7.93 Hz, 1 H) 7.04 (d, J = 9.16 Hz, 2 H) 5.52-5.61 (m, 1 H) 5.47 (d, J = 8.55 Hz, 1 H) 3.52 (s, 2 H) 3.21-3.28 (m, 4 H) 2.77 (td, J = 8.16, 3.81 Hz, 1 H) 2.70 (dd, J = 9.31, 6.26 Hz, 1 H) 2.60 (dd, J = 9.61, 3.51 Hz, 1 H) 2.51-2.54 (m, 4 H) 2.45 (s, 3 H) 2.29-2.41 (m, 2 H) 2.28 (s, 3 H) 1.70-1.79 (m, 1 H). |
| 181 | 561 | 13.03 (s, 1 H) 7.99 (s, 1 H) 7.99 (d, J = 8.85 Hz, 2 H) 7.66 (t, J = 7.63 Hz, 1 H) 7.28 (d, J = 7.63 Hz, 1 H) 7.13 (d, J = 7.63 Hz, 1 H) 7.05 (d, J = 8.85 Hz, 2 H) 5.53-5.61 (m, 1 H) 5.48 (d, J = 8.85 Hz, 1 H) 3.61 (s, 2 H) 3.25-3.30 (m, 4 H) 2.74-2.80 (m, |

TABLE 2-continued

| Ex | m/z | ¹H NMR (600 MHz, DMSO-d$_6$) δ ppm |
|---|---|---|
| | | 1 H) 2.68-2.74 (m, 1 H) 2.60-2.65 (m, 1 H) 2.55-2.59 (m, 4 H) 2.45 (s, 3 H) 2.31-2.39 (m, 2 H) 2.29 (s, 3 H) 1.71-1.79 (m, 1 H). |
| 182 | 520 | 12.98 (s, 1 H) 7.97 (d, J = 8.9 Hz, 2 H) 7.88 (s, 1 H) 7.05 (d, J = 8.9 Hz, 2 H) 6.17 (d, J = 3.1 Hz, 1 H) 6.00 (dd, J = 3.1, 0.9 Hz, 1 H) 5.73 (d, J = 8.9 Hz, 1 H) 4.86-4.97 (m, 1 H) 3.47 (s, 2 H) 3.26 (t, J = 5.2 Hz, 4 H) 2.83 (d, J = 9.8 Hz, 2 H) 2.52 (t, J = 5.2 Hz, 4 H) 2.24 (s, 3 H) 2.22 (s, 3 H) 2.08 (br. s., 2 H) 1.97 (d, J = 11.3 Hz, 2 H) 1.67 (qd, J = 11.7, 3.5 Hz, 2 H). |
| 183 | 564 | 13.01 (s, 1 H) 7.97 (s, 1 H) 7.97 (d, J = 8.9 Hz, 2 H) 7.05 (d, J = 9.2 Hz, 2 H) 6.17 (d, J = 2.7 Hz, 1 H) 6.00 (dd, J = 2.9, 1.1 Hz, 1 H) 5.44 (d, J = 8.9 Hz, 1 H) 4.86-4.98 (m, 1 H) 3.47 (s, 2 H) 3.26 (t, J = 5.2 Hz, 4 H) 2.80 (d, J = 11.0 Hz, 2 H) 2.52 (t, J = 5.2 Hz, 4 H) 2.24 (s, 3 H) 2.21 (s, 3 H) 2.07 (t, J = 11.0 Hz, 2 H) 1.98 (d, J = 11.0 Hz, 2 H) 1.65 (qd, J = 11.4, 3.4 Hz, 2 H). |
| 184 | 506 | 12.98 (s, 1 H) 7.97 (d, J = 8.9 Hz, 2 H) 7.88 (s, 1 H) 7.63 (t, J = 1.7 Hz, 1 H) 7.60 (s, 1 H) 7.06 (d, J = 9.2 Hz, 2 H) 6.46 (d, J = 0.9 Hz, 1 H) 5.73 (d, J = 8.9 Hz, 1 H) 4.86-4.97 (m, 1 H) 3.38 (s, 2 H) 3.26 (t, J = 5.2 Hz, 4 H) 2.83 (d, J = 11.0 Hz, 2 H) 2.50 (t, J = 5.2 Hz, 4 H, concealed by the solvent residual peak) 2.22 (s, 3 H) 2.07 (t, J = 10.4 Hz, 2 H) 1.97 (d, J = 11.3 Hz, 2 H) 1.67 (qd, J = 11.6, 3.5 Hz, 2 H). |
| 185 | 550 | 13.01 (s, 1 H) 7.97 (s, 1 H) 7.98 (d, J = 8.9 Hz, 2 H) 7.63 (t, J = 1.7 Hz, 1 H) 7.60 (d, J = 0.6 Hz, 1 H) 7.06 (d, J = 9.2 Hz, 2 H) 6.46 (d, J = 0.9 Hz, 1 H) 5.44 (d, J = 8.9 Hz, 1 H) 4.87-4.98 (m, 1 H) 3.38 (s, 2 H) 3.26 (t, J = 5.2 Hz, 4 H) 2.81 (d, J = 10.7 Hz, 2 H) 2.50 (t, J = 5.2 Hz, 4 H, concealed by the solvent residual peak) 2.21 (s, 3 H) 2.08 (t, J = 11.0 Hz, 2 H) 1.99 (d, J = 11.9 Hz, 2 H) 1.65 (qd, J = 11.5, 3.5 Hz, 2 H). |
| 186 | 528 | 12.96 (s, 1 H) 7.98 (d, J = 9.16 Hz, 2 H) 7.88 (s, 1 H) 7.06 (d, J = 9.16 Hz, 2 H) 5.70 (d, J = 8.85 Hz, 1 H) 4.85-4.96 (m, 1 H) 3.55 (t, J = 5.95 Hz, 2 H) 3.52 (t, J = 4.88 Hz, 2 H) 3.44 (t, J = 4.88 Hz, 2 H) 3.25 (s, 3 H) 3.22-3.28 (m, 4 H) 2.78-2.85 (m, 2 H) 2.55-2.59 (m, 4 H) 2.53 (t, J = 5.95 Hz, 2 H) 2.21 (s, 3 H) 2.05 (dt, J = 11.50, 2.00 Hz, 2 H) 1.94-2.00 (m, 2 H) 1.66 (dq, J = 11.75, 11.60, 3.81 Hz, 2 H). |
| 187 | 572 | 12.99 (s, 1 H) 7.98 (d, J = 8.85 Hz, 2 H) 7.97 (s, 1 H) 7.06 (d, J = 8.85 Hz, 2 H) 5.42 (d, J = 8.85 Hz, 1 H) 4.85-4.97 (m, 1 H) 3.55 (t, J = 5.95 Hz, 2 H) 3.52 (t, J = 4.80 Hz, 2 H) 3.44 (t, J = 4.88 Hz, 2 H) 3.25 (s, 3 H) 3.21-3.28 (m, 4 H) 2.76-2.83 (m, 2 H) 2.54-2.59 (m, 4 H) 2.53 (t, J = 5.95 Hz, 2 H) 2.21 (s, 3 H) 2.08 (td, J = 11.44, 1.53 Hz, 2 H) 1.96-2.02 (m, 2 H) 1.65 (dq, J = 11.60, 11.44, 3.66 Hz, 2 H). |
| 188 | 542 | 12.97 (s, 1 H) 7.97 (d, J = 9.16 Hz, 2 H) 7.88 (s, 1 H) 7.06 (d, J = 9.16 Hz, 2 H) 5.69 (d, J = 8.55 Hz, 1 H) 4.88-4.98 (m, 1 H) 3.55 (t, J = 5.95 Hz, 2 H) 3.52 (t, J = 4.80 Hz, 2 H) 3.44 (t, J = 4.80 Hz, 2 H) 3.25 (s, 3 H) 3.21-3.28 (m, 4 H) 2.89-2.96 (m, 2 H) 2.55-2.59 (m, 4 H) 2.53 (t, J = 5.95 Hz, 2 H) 2.36 (q, J = 6.82 Hz, 2 H) 1.94-2.09 (m, 4 H) 1.64 (qd, J = 11.70, 3.66 Hz, 2 H) 1.03 (t, J = 7.17 Hz, 3 H). |
| 189 | 556 | 12.96 (s, 1 H) 7.97 (d, J = 9.16 Hz, 2 H) 7.88 (s, 1 H) 7.06 (d, J = 8.85 Hz, 2 H) 5.65 (d, J = 8.24 Hz, 1 H) 4.84-4.95 (m, 1 H) 3.55 (t, J = 5.95 Hz, 2 H) 3.52 (t, J = 4.80 Hz, 2 H) 3.44 (t, J = 4.80 Hz, 2 H) 3.25 (s, 3 H) 3.20-3.28 (m, 4 H) 2.81-2.89 (m, 2 H) 2.69-2.77 (m, 1 H) 2.54-2.59 (m, 4 H) 2.53 (t, J = 5.95 Hz, 2 H) 2.24-2.33 (m, 2 H) 1.97-2.04 (m, 2 H) 1.60 (qd, J = 11.39, 3.05 Hz, 2 H) 1.01 (d, J = 6.41 Hz, 6H). |
| 190 | 514 | 13.00 (br. s., 1 H) 7.98 (d, J = 9.16 Hz, 2 H) 7.90 (s, 1 H) 7.05 (d, J = 8.85 Hz, 2 H) 5.70 (d, J = 8.55 Hz, 1 H) 5.52-5.60 (m, 1 H) 3.55 (t, J = 5.80 Hz, 2 H) 3.49-3.53 (m, 2 H) 3.42-3.47 (m, 2 H) 3.25 (s, 3 H) 3.21-3.27 (m, 4 H) 2.69-2.77 (m, 2 H) 2.55-2.61 (m, 5 H) 2.53 (t, J = 5.95 Hz, 2 H) 2.30-2.41 (m, 2 H) 2.27 (s, 3 H) 1.75-1.84 (m, 1 H). |
| 191 | 610 | 12.96 (br. s., 1 H) 7.97 (d, J = 8.85 Hz, 2 H) 7.87 (s, 1 H) 7.49 (dd, J = 4.88, 3.05 Hz, 1 H) 7.32 (dd, J = 3.05, 1.22 Hz, 1 H) 7.07 (dd, J = 5.04, 1.07 Hz, 1 H) 7.06 (d, J = 9.16 Hz, 2 H) 5.71 (d, J = 8.85 Hz, 1 H) 4.89-4.99 (m, 1 H) 3.56 (t, J = 5.80 Hz, 2 H) 3.50-3.54 (m, 4 H) 3.43-3.47 (m, 2 H) 3.26 (s, 3 H) 3.23-3.28 (m, 4 H) 2.85-2.91 (m, 2 H) 2.55-2.60 (m, 4 H) 2.53 (t, J = 5.95 Hz, 2 H) 2.11 (td, J = 11.98, 2.29 Hz, 2 H) 1.94-2.01 (m, 2 H) 1.60-1.70 (m, J = 11.83, 11.64, 11.64, 3.66 Hz, 2H). |
| 192 | 610 | 12.96 (br. s., 1 H) 7.97 (d, J = 8.85 Hz, 2 H) 7.87 (s, 1 H) 7.44 (dd, J = 4.88, 1.53 Hz, 1 H) 7.05 (d, J = 9.16 Hz, 2 H) 6.96-6.99 (m, 2 H) 5.75 (d, J = 9.16 Hz, 1 H) 4.93-5.01 (m, J = 15.14, 15.14, 4.50, 4.27 Hz, 1 H) 3.73 (s, 2 H) 3.56 (t, J = 5.80 Hz, 2 H) 3.50-3.54 (m, 2 H) 3.42-3.47 (m, 2 H) 3.26 (s, 3 H) 3.23-3.28 (m, 4 H) 2.90-2.96 (m, 2 H) 2.55-2.59 (m, 4 H) 2.53 (t, J = 5.95 Hz, 2 H) 2.16 (td, J = 11.52, 1.68 Hz, 2 H) 1.95-2.01 (m, 2 H) 1.63-1.72 (m, J = 11.98, 11.79, 11.79, 4.12 Hz, 2 H). |
| 193 | 523 | 12.96 (br. s., 1 H) 9.06 (d, J = 2.1 Hz, 1 H) 7.97 (d, J = 8.9 Hz, 2 H) 7.87 (s, 1 H) 7.56 (d, J = 2.1 Hz, 1 H) 7.06 (d, J = 8.9 Hz, 2 H) 5.70 (d, J = 8.9 Hz, 1 H) 4.85-4.98 (m, 1 H) 3.73 (s, 2 H) 3.28 (t, J = 5.2 Hz, 4 H) 2.81 (d, J = 11.6 Hz, 2 H) 2.59 (t, J = 4.6 Hz, 4 H) 2.20 (s, 3 H) 2.05 (td, J = 11.9, 1.8 Hz, 2 H) 1.97 (d, J = 11.6 Hz, 2 H) 1.66 (qd, J = 11.6, 3.7 Hz, 2 H). |
| 194 | 567 | 12.99 (br. s., 1 H) 9.06 (d, J = 1.8 Hz, 1 H) 7.97 (s, 1 H) 7.98 (d, J = 8.9 Hz, 2 H) 7.56 (d, J = 1.8 Hz, 1 H) 7.06 (d, J = 9.2 Hz, 2 H) 5.42 (d, J = 8.9 Hz, 1 H) 4.87-4.96 (m, 1 H) 3.73 (s, 2 H) 3.28 (t, J = 5.2 Hz, 4 H) 2.79 (d, J = 11.0 Hz, 2 H) 2.59 (t, J = 4.9 Hz, 4 H) 2.20 (s, 3 H) 2.07 (td, J = 11.6, 1.5 Hz, 2 H) 1.99 (d, J = 9.5 Hz, 2 H) 1.64 (qd, J = 11.6, 3.7 Hz, 2 H). |
| 195 | 523 | 12.97 (br. s., 1 H) 9.05 (d, J = 0.9 Hz, 1 H) 7.98 (d, J = 8.9 Hz, 2 H) 7.88 (s, 1 H) 7.81 (d, J = 0.9 Hz, 1 H) 7.06 (d, J = 9.2 Hz, 2 H) 5.70 (d, J = 8.5 Hz, 1 H) 4.85-4.97 (m, 1 H) 3.82 (s, 2 H) 3.27 (t, J = 5.2 Hz, 4 H) 2.81 (d, J = 11.6 Hz, 2 H) 2.55 (t, J = 4.9 Hz, 4 H) 2.20 (s, 3 H) 2.05 (td, J = 11.6, 1.8 Hz, 2 H) 1.97 (d, J = 9.8 Hz, 2 H) 1.66 (qd, J = 11.6, 3.8 Hz, 2 H). |
| 196 | 567 | 13.00 (br. s., 1 H) 9.05 (d, J = 0.6 Hz, 1 H) 7.97 (s, 1 H) 7.98 (d, J = 8.8 Hz, 2 H) 7.81 (d, J = 0.6 Hz, 1 H) 7.06 (d, J = 9.2 Hz, 2 H) 5.42 (d, J = 8.9 Hz, 1 H) |

TABLE 2-continued

| Ex | m/z | $^1$H NMR (600 MHz, DMSO-$d_6$) δ ppm |
|---|---|---|
| | | 4.87-4.97 (m, 1 H) 3.82 (s, 2 H) 3.28 (t, J = 5.2 Hz, 4 H) 2.79 (d, J = 11.3 Hz, 2 H) 2.55 (t, J = 4.9 Hz, 4 H) 2.20 (s, 3 H) 2.07 (td, J = 11.4, 1.5 Hz, 2 H) 1.99 (d, J = 11.6 Hz, 2 H) 1.64 (qd, J = 11.5, 3.8 Hz, 2 H). |
| 197 | 512 | 12.97 (s, 1 H) 7.97 (d, J = 9.2 Hz, 2 H) 7.88 (s, 1 H) 7.06 (d, J = 9.2 Hz, 2 H) 5.70 (d, J = 8.5 Hz, 1 H) 4.88-4.98 (m, 1 H) 3.36 (t, J = 6.4 Hz, 2 H) 3.26 (t, J = 5.2 Hz, 4 H) 3.23 (s, 3 H) 2.93 (d, J = 10.4 Hz, 2 H) 2.49 (t, J = 5.2 Hz, 4 H) 2.36 (t, J = 6.4 Hz, 2 H) 2.36 (t, J = 7.2 Hz, 2 H) 2.04 (br. s., 2 H) 2.00 (d, J = 11.9 Hz, 2 H) 1.69 (dt, J = 14.6, 6.4 Hz, 2 H) 1.64 (qd, J = 11.6, 3.1 Hz, 2 H) 1.03 (t, J = 7.2 Hz, 3 H). |
| 198 | 556 | 13.00 (s, 1 H) 7.97 (s, 1 H) 7.98 (d, J = 9.2 Hz, 2 H) 7.06 (d, J = 9.2 Hz, 2 H) 5.41 (d, J = 8.9 Hz, 1 H) 4.89-4.99 (m, 1 H) 3.36 (t, J = 6.4 Hz, 2 H) 3.26 (t, J = 5.2 Hz, 4 H) 3.23 (s, 3 H) 2.90 (d, J = 10.7 Hz, 2 H) 2.36 (t, J = 5.2 Hz, 4 H) 2.36 (t, J = 7.2 Hz, 2 H) 2.36 (t, J = 6.4 Hz, 2 H) 2.06 (t, J = 11.1 Hz, 2 H) 2.01 (d, J = 11.0 Hz, 2 H) 1.69 (dt, J = 14.3, 6.7 Hz, 2 H) 1.62 (qd, J = 11.4, 3.5 Hz, 2 H) 1.03 (t, J = 7.2 Hz, 3 H). |
| 199 | 526 | 12.96 (s, 1 H) 7.97 (d, J = 9.2 Hz, 2 H) 7.88 (s, 1 H) 7.06 (d, J = 9.2 Hz, 2 H) 5.65 (d, J = 8.9 Hz, 1 H) 4.84-4.95 (m, 1 H) 3.36 (t, J = 6.4 Hz, 2 H) 3.26 (t, J = 5.2 Hz, 4 H) 3.23 (s, 3 H) 2.85 (d, J = 11.6 Hz, 2 H) 2.72 (spt, J = 6.6 Hz, 1 H) 2.49 (t, J = 5.2 Hz, 4 H) 2.36 (t, J = 7.6 Hz, 2 H) 2.27 (t, J = 11.0 Hz, 2 H) 2.00 (d, J = 9.5 Hz, 2 H) 1.69 (dt, J = 14.6, 6.4 Hz, 2 H) 1.60 (qd, J = 11.5, 3.8 Hz, 2 H) 1.01 (d, J = 6.7 Hz, 6 H). |
| 200 | 570 | 12.99 (s, 1 H) 7.97 (s, 1 H) 7.98 (d, J = 8.9 Hz, 2 H) 7.06 (d, J = 9.2 Hz, 2 H) 5.37 (d, J = 8.9 Hz, 1 H) 4.86-4.96 (m, 1 H) 3.36 (t, J = 6.4 Hz, 2 H) 3.26 (t, J = 5.2 Hz, 4 H) 3.23 (s, 3 H) 2.84 (d, J = 11.9 Hz, 2 H) 2.73 (spt, J = 6.1 Hz, 1 H) 2.49 (br. s., J = 5.2, 5.2 Hz, 4 H) 2.36 (t, J = 7.6 Hz, 2 H) 2.29 (t, J = 11.0 Hz, 2 H) 2.02 (d, J = 10.4 Hz, 2 H) 1.69 (dt, J = 14.6, 6.4 Hz, 2 H) 1.58 (qd, J = 11.0, 2.7 Hz, 2 H) 1.01 (d, J = 6.7 Hz, 6H). |
| 201 | 498 | 12.96 (br. s., 1 H) 7.95-7.99 (m, 2 H) 7.87 (s, 1 H) 7.04-7.08 (m, 2 H) 5.71 (d, J = 9.00 Hz, 1 H) 4.87-4.95 (m, 1 H) 3.57-3.63 (m, 2 H) 3.41-3.49 (m, 2 H) 3.25 (s, 3 H) 2.93 (dt, J = 11.41, 3.22 Hz, 1 H) 2.84-2.91 (m, 2 H) 2.79-2.85 (m, 2 H) 2.58 (dd, J = 11.90, 9.31 Hz, 1 H) 2.50-2.53 (m, 1 H) 2.38-2.45 (m, 2 H) 2.21 (s, 3 H) 2.05 (td, J = 11.67, 1.83 Hz, 2 H) 1.94-2.00 (m, 2 H) 1.66 (dtd, J = 11.86, 11.69, 3.66 Hz, 2 H) 1.07 (d, J = 6.15 Hz, 3 H). |
| 202 | 542 | 12.99 (br. s., 1 H) 7.97 (s, 1 H) 7.95-7.99 (m, 2 H) 7.03-7.08 (m, 2 H) 5.42 (d, J = 8.55 Hz, 1 H) 4.88-4.96 (m, 1 H) 3.57-3.64 (m, 2 H) 3.42-3.49 (m, 2 H) 3.25 (s, 3 H) 2.93 (dt, J = 11.33, 3.26 Hz, 1 H) 2.84-2.91 (m, 2 H) 2.76-2.83 (m, 2 H) 2.58 (dd, J = 11.98, 9.23 Hz, 1 H) 2.50-2.54 (m, 1 H) 2.38-2.44 (m, 2 H) 2.21 (s, 3 H) 2.03-2.11 (m, 2 H) 1.95-2.02 (m, 2 H) 1.65 (qd, J = 11.47, 3.59 Hz, 2 H) 1.07 (d, J = 6.10 Hz, 3 H). |
| 203 | 512 | 12.96 (br. s., 1 H) 7.95-7.99 (m, 2 H) 7.87 (s, 1 H) 7.03-7.07 (m, 2 H) 5.70 (d, J = 8.55 Hz, 1 H) 4.88-4.97 (m, 1 H) 3.57-3.63 (m, 2 H) 3.42-3.49 (m, 2 H) 3.25 (s, 3 H) 2.84-2.96 (m, 5 H) 2.58 (dd, J = 11.90, 9.31 Hz, 1 H) 2.50-2.54 (m, 1 H) 2.38-2.45 (m, 2 H) 2.35 (q, J = 7.17 Hz, 2 H) 1.99-2.07 (m, 2 H) 1.97-2.02 (m, 2 H) 1.64 (dtd, J = 11.83, 11.52, 3.74 Hz, 2 H) 1.07 (d, J = 6.10 Hz, 3 H) 1.03 (t, J = 7.17 Hz, 3 H). |
| 204 | 531 | 12.93 (br. s., 1 H) 8.54 (d, J = 2.11 Hz, 1 H) 8.47 (dd, J = 4.75, 1.68 Hz, 1 H) 7.95-7.99 (m, 2 H) 7.87 (s, 1 H) 7.75 (ddd, J = 7.70, 2.11, 1.68 Hz, 1 H) 7.37 (ddd, J = 7.70, 4.75, 0.78 Hz, 1 H) 7.03-7.07 (m, 2 H) 5.69 (d, J = 8.85 Hz, 1 H) 4.87-4.95 (m, 1 H) 4.04 (d, J = 13.73 Hz, 1 H) 3.63-3.69 (m, 1 H) 3.53-3.59 (m, 1 H) 3.26 (d, J = 13.73 Hz, 1 H) 2.83-2.91 (m, 1 H) 2.77-2.84 (m, 2 H) 2.66-2.73 (m, 2 H) 2.52-2.59 (m, 1 H) 2.21-2.27 (m, 1 H) 2.20 (s, 3 H) 2.01-2.07 (m, 2 H) 1.93-2.00 (m, 2 H) 1.66 (qd, J = 11.75, 3.36 Hz, 2 H) 1.19 (d, J = 6.10 Hz, 3 H). |
| 205 | 575 | 12.98 (br. s., 1 H) 8.54 (d, J = 2.15 Hz, 1 H) 8.47 (dd, J = 4.77, 1.69 Hz, 1 H) 7.96 (s, 1 H) 7.95-7.99 (m, 2 H) 7.75 (ddd, J = 7.73, 2.15, 1.69 Hz, 1 H) 7.37 (ddd, J = 7.73, 4.77, 0.81 Hz, 1 H) 7.03-7.08 (m, 2 H) 5.41 (d, J = 8.54 Hz, 1 H) 4.87-4.96 (m, 1 H) 4.04 (d, J = 13.73 Hz, 1 H) 3.64-3.69 (m, 1 H) 3.53-3.59 (m, 1 H) 3.26 (d, J = 13.73 Hz, 1 H) 2.84-2.91 (m, 1 H) 2.75-2.84 (m, 2 H) 2.66-2.74 (m, 2 H) 2.52-2.58 (m, 1 H) 2.24 (td, J = 10.70, 3.20 Hz, 1 H) 2.20 (s, 3 H) 2.02-2.10 (m, 2 H) 1.95-2.02 (m, 2 H) 1.64 (qd, J = 11.39, 3.51 Hz, 2 H) 1.19 (d, J = 6.10 Hz, 3 H). |
| 206 | 589 | 12.98 (br. s., 1 H) 8.54 (d, J = 2.09 Hz, 1 H) 8.47 (dd, J = 4.77, 1.69 Hz, 1 H) 7.96 (s, 1 H) 7.95-7.99 (m, 2 H) 7.75 (ddd, J = 7.73, 2.09, 1.69 Hz, 1 H) 7.37 (ddd, J = 7.73, 4.77, 0.87 Hz, 1 H) 7.02-7.08 (m, 2 H) 5.40 (d, J = 8.24 Hz, 1 H) 4.89-4.98 (m, 1 H) 4.04 (d, J = 13.58 Hz, 1 H) 3.64-3.69 (m, 1 H) 3.53-3.59 (m, 1 H) 3.26 (d, J = 13.58 Hz, 1 H) 2.83-2.94 (m, 3 H) 2.67-2.73 (m, 2 H) 2.52-2.58 (m, 1 H) 2.35 (q, J = 7.17 Hz, 2 H) 2.24 (td, J = 10.87, 2.98 Hz, 1 H) 2.01-2.09 (m, 2 H) 1.98-2.04 (m, 2 H) 1.61 (dtd, J = 11.67, 11.41, 3.36 Hz, 2 H) 1.19 (d, J = 6.10 Hz, 3 H) 1.02 (t, J = 7.17 Hz, 3 H). |
| 207 | 520 | 12.97 (br. s., 1 H) 7.97 (d, J = 9.2 Hz, 2 H) 7.88 (s, 1 H) 7.10 (d, J = 1.2 Hz, 1 H) 7.05 (d, J = 8.9 Hz, 2 H) 6.77 (d, J = 1.2 Hz, 1 H) 5.70 (d, J = 8.9 Hz, 1 H) 4.86-4.97 (m, 1 H) 3.67 (s, 3 H) 3.58 (s, 2 H) 3.25 (t, J = 5.2 Hz, 4 H) 2.81 (d, J = 11.6 Hz, 2 H) 2.51 (t, J = 4.9 Hz, 4 H) 2.20 (s, 3 H) 2.05 (t, J = 11.0 Hz, 2 H) 1.97 (d, J = 10.7 Hz, 2 H) 1.66 (qd, J = 11.7, 3.8 Hz, 2 H). |
| 208 | 564 | 12.99 (br. s., 1 H) 7.97 (s, 1 H) 7.98 (d, J = 8.9 Hz, 2 H) 7.10 (d, J = 1.2 Hz, 1 H) 7.06 (d, J = 8.9 Hz, 2 H) 6.77 (d, J = 1.2 Hz, 1 H) 5.42 (d, J = 9.2 Hz, 1 H) 4.87-4.97 (m, 1 H) 3.67 (s, 3 H) 3.58 (s, 2 H) 3.25 (t, J = 5.2 Hz, 4 H) 2.79 (d, J = 11.6 Hz, 2 H) 2.51 (t, J = 5.2 Hz, 4 H) 2.20 (s, 3 H) 2.07 (t, J = 10.8 Hz, 2 H) 1.99 (d, J = 10.1 Hz, 2 H) 1.64 (qd, J = 11.5, 3.7 Hz, 2 H). |
| 209 | 534 | 12.97 (br. s., 1 H) 7.97 (d, J = 8.9 Hz, 2 H) 7.88 (s, 1 H) 7.10 (d, J = 1.2 Hz, 1 H) 7.05 (d, J = 9.2 Hz, 2 H) 6.77 (d, J = 1.2 Hz, 1 H) 5.69 (d, J = 9.2 Hz, 1 H) |

TABLE 2-continued

| Ex | m/z | ¹H NMR (600 MHz, DMSO-d$_6$) δ ppm |
|---|---|---|
|  |  | 4.87-5.00 (m, 1 H) 3.67 (s, 3 H) 3.58 (s, 2 H) 3.24 (t, J = 4.9 Hz, 4 H) 2.92 (d, J = 11.3 Hz, 2 H) 2.51 (t, J = 5.2 Hz, 4 H) 2.35 (q, J = 7.1 Hz, 2 H) 2.03 (t, J = 11.6 Hz, 2 H) 1.99 (d, J = 12.5 Hz, 2 H) 1.63 (qd, J = 11.5, 3.5 Hz, 2 H) 1.02 (t, J = 7.2 Hz, 3 H). |
| 210 | 531 | 12.96 (br. s., 1 H) 8.34 (d, J = 2.1 Hz, 1 H) 7.98 (d, J = 8.9 Hz, 2 H) 7.87 (s, 1 H) 7.59 (dd, J = 7.9, 1.5 Hz, 1 H) 7.36 (d, J = 7.9 Hz, 1 H) 7.06 (d, J = 8.9 Hz, 2 H) 5.70 (d, J = 8.5 Hz, 1 H) 4.84-4.98 (m, 1 H) 3.61 (s, 2 H) 3.28 (t, J = 4.6 Hz, 4 H) 2.81 (d, J = 11.3 Hz, 2 H) 2.56 (t, J = 4.9 Hz, 4 H) 2.28 (s, 3 H) 2.20 (s, 3 H) 2.05 (t, J = 10.7 Hz, 2 H) 1.97 (d, J = 10.7 Hz, 2 H) 1.66 (qd, J = 11.7, 3.5 Hz, 2 H). |
| 211 | 575 | 13.00 (s, 1 H) 8.34 (d, J = 2.1 Hz, 1 H) 7.97 (s, 1 H) 7.98 (d, J = 7.9 Hz, 2 H) 7.59 (dd, J = 7.9, 1.5 Hz, 1 H) 7.36 (d, J = 7.9 Hz, 1 H) 7.06 (d, J = 9.2 Hz, 2 H) 5.42 (d, J = 8.9 Hz, 1 H) 4.87-4.96 (m, 1 H) 3.61 (s, 2 H) 3.28 (t, J = 4.6 Hz, 4 H) 2.79 (d, J = 11.6 Hz, 2 H) 2.56 (t, J = 4.6 Hz, 4 H) 2.28 (s, 3 H) 2.21 (s, 3 H) 2.07 (t, J = 11.9 Hz, 2 H) 1.99 (d, J = 11.6 Hz, 2 H) 1.64 (qd, J = 11.4, 3.7 Hz, 2 H). |
| 212 | 545 | 12.97 (br. s., 1 H) 8.34 (d, J = 2.1 Hz, 1 H) 7.97 (d, J = 9.2 Hz, 2 H) 7.88 (s, 1 H) 7.59 (dd, J = 7.9, 1.5 Hz, 1 H) 7.36 (d, J = 7.9 Hz, 1 H) 7.05 (d, J = 8.9 Hz, 2 H) 5.69 (d, J = 8.9 Hz, 1 H) 4.87-4.98 (m, 1 H) 3.61 (s, 2 H) 3.27 (t, J = 5.2 Hz, 4 H) 2.92 (d, J = 11.3 Hz, 2 H) 2.56 (t, J = 4.9 Hz, 4 H) 2.35 (q, J = 7.3 Hz, 2 H) 2.28 (s, 3 H) 2.03 (t, J = 11.6 Hz, 2 H) 1.99 (d, J = 12.8 Hz, 2 H) 1.63 (qd, J = 11.5, 3.4 Hz, 2 H) 1.02 (t, J = 7.2 Hz, 3 H). |
| 213 | 589 | 13.00 (s, 1 H) 8.34 (d, J = 2.1 Hz, 1 H) 7.97 (s, 1 H) 7.97 (d, J = 8.9 Hz, 2 H) 7.59 (dd, J = 7.9, 1.5 Hz, 1 H) 7.36 (d, J = 7.9 Hz, 1 H) 7.06 (d, J = 9.2 Hz, 2 H) 5.41 (d, J = 8.9 Hz, 1 H) 4.89-4.99 (m, 1 H) 3.61 (s, 2 H) 3.28 (t, J = 5.2 Hz, 4 H) 2.90 (d, J = 11.0 Hz, 2 H) 2.56 (t, J = 4.9 Hz, 4 H) 2.36 (q, J = 7.2 Hz, 2 H) 2.28 (s, 3 H) 2.06 (t, J = 11.6 Hz, 2 H) 2.01 (d, J = 11.6 Hz, 2 H) 1.62 (qd, J = 11.4, 3.5 Hz, 2 H) 1.02 (t, J = 7.2 Hz, 3 H). |
| 214 | 512 | 12.95 (br. s., 1 H) 7.95-8.00 (m, 2 H) 7.87 (s, 1 H) 7.03-7.08 (m, 2 H) 5.70 (d, J = 8.85 Hz, 1 H) 4.87-4.95 (m, 1 H) 3.58-3.64 (m, 2 H) 3.35 (t, J = 6.49 Hz, 2 H) 3.23 (s, 3 H) 2.85-2.92 (m, 2 H) 2.78-2.85 (m, 2 H) 2.77 (ddd, J = 12.82, 8.77, 6.79 Hz, 1 H) 2.59 (dd, J = 12.05, 9.31 Hz, 1 H) 2.41-2.48 (m, 1 H) 2.27-2.33 (m, 1 H) 2.24 (ddd, J = 13.08, 8.43, 5.19 Hz, 1 H) 2.21 (s, 3 H) 2.05 (td, J = 11.60, 1.53 Hz, 2 H) 1.94-2.00 (m, 2 H) 1.59-1.72 (m, 4 H) 1.05 (d, J = 6.10 Hz, 3 H). |
| 215 | 556 | 12.98 (br. s., 1 H) 7.97 (s, 1 H) 7.95-7.99 (m, 2 H) 7.03-7.08 (m, 2 H) 5.42 (d, J = 8.70 Hz, 1 H) 4.87-4.96 (m, 1 H) 3.57-3.64 (m, 2 H) 3.35 (t, J = 6.41 Hz, 2 H) 3.23 (s, 3 H) 2.85-2.93 (m, 2 H) 2.77-2.83 (m, 2 H) 2.77 (ddd, J = 12.82, 8.70, 6.71 Hz, 1 H) 2.59 (dd, J = 12.21, 9.31 Hz, 1 H) 2.41-2.48 (m, 1 H) 2.27-2.33 (m, 1 H) 2.24 (ddd, J = 13.16, 8.43, 5.26 Hz, 1 H) 2.21 (s, 3 H) 2.03-2.11 (m, 2 H) 1.96-2.02 (m, 2 H) 1.59-1.72 (m, 4 H) 1.05 (d, J = 6.10 Hz, 3 H). |
| 216 | 570 | 12.98 (s, 1 H) 7.97 (s, 1 H) 7.95-7.99 (m, 2 H) 7.03-7.08 (m, 2 H) 5.41 (d, J = 8.85 Hz, 1 H) 4.89-4.97 (m, 1 H) 3.58-3.63 (m, 2 H) 3.35 (t, J = 6.49 Hz, 2 H) 3.23 (s, 3 H) 2.86-2.94 (m, 4 H) 2.77 (ddd, J = 12.78, 8.74, 6.87 Hz, 1 H) 2.59 (dd, J = 11.75, 9.16 Hz, 1 H) 2.42-2.48 (m, 1 H) 2.36 (q, J = 7.17 Hz, 2 H) 2.27-2.32 (m, 1 H) 2.24 (ddd, J = 13.01, 8.35, 5.19 Hz, 1 H) 2.03-2.09 (m, 2 H) 1.98-2.05 (m, 2 H) 1.58-1.72 (m, 4 H) 1.05 (d, J = 6.26 Hz, 3 H) 1.03 (t, J = 7.17 Hz, 3 H). |
| 217 | 537 | 12.96 (br. s., 1 H) 7.96-8.00 (m, 2 H) 7.87 (s, 1 H) 7.74 (d, J = 3.36 Hz, 1 H) 7.65 (d, J = 3.36 Hz, 1 H) 7.05-7.09 (m, 2 H) 5.71 (d, J = 8.85 Hz, 1 H) 4.87-4.95 (m, 1 H) 4.19 (d, J = 15.41 Hz, 1 H) 3.84 (d, J = 15.41 Hz, 1 H) 3.65-3.70 (m, 1 H) 3.60-3.65 (m, 1 H) 2.91-2.97 (m, 1 H) 2.88 (dt, J = 11.60, 3.28 Hz, 1 H) 2.79-2.84 (m, 2 H) 2.63-2.72 (m, 2 H) 2.47-2.53 (m, 1 H) 2.20 (s, 3 H) 2.05 (td, J = 11.62, 1.83 Hz, 2 H) 1.94-2.00 (m, 2 H) 1.66 (qd, J = 11.62, 3.43 Hz, 2 H) 1.17 (d, J = 5.80 Hz, 3H). |
| 218 | 581 | 12.99 (br. s., 1 H) 7.97 (s, 1 H) 7.95-8.00 (m, 2 H) 7.74 (d, J = 3.36 Hz, 1 H) 7.65 (d, J = 3.36 Hz, 1 H) 7.04-7.10 (m, 2 H) 5.42 (d, J = 8.55 Hz, 1 H) 4.87-4.96 (m, 1 H) 4.19 (d, J = 15.41 Hz, 1 H) 3.84 (d, J = 15.41 Hz, 1 H) 3.65-3.70 (m, 1 H) 3.59-3.65 (m, 1 H) 2.91-2.97 (m, 1 H) 2.88 (ddd, J = 11.60, 3.28, 3.13 Hz, 1 H) 2.75-2.84 (m, 2 H) 2.63-2.73 (m, 2 H) 2.47-2.53 (m, 1 H) 2.21 (s, 3 H) 2.03-2.11 (m, 2 H) 1.95-2.02 (m, 2 H) 1.64 (dtd, J = 11.60, 11.48, 3.74 Hz, 2 H) 1.17 (d, J = 5.80 Hz, 3 H). |
| 219 | 551 | 12.96 (s, 1 H) 7.95-8.00 (m, 2 H) 7.88 (s, 1 H) 7.74 (d, J = 3.36 Hz, 1 H) 7.65 (d, J = 3.36 Hz, 1 H) 7.03-7.09 (m, 2 H) 5.70 (d, J = 8.70 Hz, 1 H) 4.88-4.97 (m, 1 H) 4.19 (d, J = 15.41 Hz, 1 H) 3.84 (d, J = 15.41 Hz, 1 H) 3.65-3.70 (m, 1 H) 3.59-3.65 (m, 1 H) 2.90-2.97 (m, 3 H) 2.88 (ddd, J = 11.37, 3.20, 2.98 Hz, 1 H) 2.63-2.72 (m, 2 H) 2.47-2.54 (m, 1 H) 2.35 (q, J = 7.17 Hz, 2 H) 2.00-2.07 (m, 2 H) 1.96-2.02 (m, 2 H) 1.64 (dtd, J = 11.60, 11.48, 3.74 Hz, 2 H) 1.17 (d, J = 5.80 Hz, 3 H) 1.03 (t, J = 7.17 Hz, 3 H). |
| 220 | 537 | 12.95 (s, 1 H) 7.96-8.00 (m, 2 H) 7.87 (s, 1 H) 7.74 (d, J = 3.36 Hz, 1 H) 7.68 (d, J = 3.36 Hz, 1 H) 6.99-7.04 (m, 2 H) 5.69 (d, J = 8.70 Hz, 1 H) 4.87-4.96 (m, 1 H) 4.18-4.24 (m, 1 H) 3.95 (d, J = 14.95 Hz, 1 H) 3.82 (d, J = 14.95 Hz, 1 H) 3.51-3.57 (m, 1 H) 3.07 (td, J = 11.94, 3.28 Hz, 1 H) 2.99-3.04 (m, 1 H) 2.77-2.84 (m, 3 H) 2.46 (dd, J = 11.06, 3.43 Hz, 1 H) 2.36 (td, J = 11.37, 3.36 Hz, 1 H) 2.21 (s, 3 H) 2.01-2.09 (m, 2 H) 1.94-2.00 (m, 2 H) 1.66 (dtd, J = 11.75, 11.64, 3.59 Hz, 2 H) 1.13 (d, J = 6.56 Hz, 3 H). |
| 221 | 581 | 12.97 (br. s., 1 H) 7.97-8.00 (m, 2 H) 7.97 (s, 1 H) 7.74 (d, J = 3.36 Hz, 1 H) 7.68 (d, J = 3.36 Hz, 1 H) 6.99-7.04 (m, 2 H) 5.41 (d, J = 8.85 Hz, 1 H) 4.88-4.96 (m, 1 H) 4.18-4.24 (m, 1 H) 3.95 (d, J = 14.95 Hz, 1 H) 3.82 (d, J = 14.95 Hz, 1 H) 3.52-3.57 (m, 1 H) 3.07 (td, J = 11.90, 3.36 Hz, 1 H) 2.99-3.04 (m, 1 H) 2.76-2.83 (m, 3 H) 2.46 (dd, J = 10.91, 3.43 Hz, 1 H) 2.36 (td, J = 11.33, 3.43 Hz, 1 H) 2.21 (s, 3 H) 2.04-2.11 (m, 2H) 1.96-2.02 (m, 2 H) 1.64 (qd, J = 11.50, 3.66 Hz, 2H) 1.13 (d, J = 6.41 Hz, 3 H). |

TABLE 2-continued

| Ex | m/z | ¹H NMR (600 MHz, DMSO-d$_6$) δ ppm |
|---|---|---|
| 222 | 498 | 12.93 (br. s., 1 H) 7.95-7.99 (m, 2 H) 7.87 (s, 1 H) 6.97-7.02 (m, 2 H) 5.67 (d, J = 8.70 Hz, 1 H) 4.87-4.95 (m, 1 H) 4.12-4.18 (m, 1 H) 3.48 (t, J = 5.80 Hz, 2 H) 3.44-3.48 (m, 1 H) 3.27 (s, 3 H) 2.99 (td, J = 11.75, 3.51 Hz, 1 H) 2.92-2.98 (m, 1 H) 2.77-2.84 (m, 3 H) 2.45-2.55 (m, 2 H) 2.31 (dd, J = 10.83, 3.36 Hz, 1 H) 2.21 (s, 3 H) 2.14 (td, J = 11.25, 3.28 Hz, 1 H) 2.02-2.09 (m, 2 H) 1.93-2.00 (m, 2 H) 1.66 (qd, J = 11.60, 3.51 Hz, 2 H) 1.07 (d, J = 6.56 Hz, 3 H). |
| 223 | 542 | 12.95 (br. s., 1 H) 7.95-8.00 (m, 2 H) 7.95 (s, 1 H) 6.97-7.02 (m, 2 H) 5.36 (d, J = 7.78 Hz, 1 H) 4.88-4.97 (m, 1 H) 4.12-4.18 (m, 1 H) 3.48 (t, J = 5.87 Hz, 2 H) 3.43-3.48 (m, 1 H) 3.27 (s, 3 H) 2.99 (td, J = 11.83, 3.36 Hz, 1 H) 2.92-2.97 (m, 1 H) 2.75-2.84 (m, 3 H) 2.45-2.54 (m, 2 H) 2.31 (dd, J = 11.14, 3.36 Hz, 1 H) 2.21 (s, 3 H) 2.14 (td, J = 11.33, 3.43 Hz, 1 H) 2.04-2.11 (m, 2 H) 1.95-2.03 (m, 2 H) 1.64 (qd, J = 11.39, 3.66 Hz, 2 H) 1.07 (d, J = 6.56 Hz, 3 H). |
| 224 | 516 | 12.96 (br. s., 1 H) 7.95-7.99 (m, 2 H) 7.87 (s, 1 H) 7.32-7.37 (m, 4 H) 7.24-7.30 (m, 1 H) 7.03-7.08 (m, 2 H) 5.70 (d, J = 8.85 Hz, 1 H) 4.87-4.95 (m, 1 H) 3.53 (s, 2 H) 3.25-3.30 (m, 4 H) 2.78-2.84 (m, 2 H) 2.50-2.54 (m, 4 H) 2.20 (s, 3 H) 2.05 (td, J = 11.65, 1.98 Hz, 2 H) 1.93-2.00 (m, 2 H) 1.66 (qd, J = 11.65, 3.66 Hz, 2 H). |
| 225 | 560 | 12.98 (br. s., 1 H) 7.97 (s, 1 H) 7.95-8.00 (m, 2 H) 7.32-7.37 (m, 4 H) 7.25-7.30 (m, 1 H) 7.03-7.08 (m, 2 H) 5.41 (d, J = 8.70 Hz, 1 H) 4.87-4.96 (m, 1 H) 3.53 (s, 2 H) 3.24-3.30 (m, 4 H) 2.75-2.83 (m, 2 H) 2.50-2.53 (m, 4 H) 2.20 (s, 3 H) 2.07 (td, J = 11.63, 1.45 Hz, 2 H) 1.95-2.02 (m, 2 H) 1.64 (qd, J = 11.63, 3.51 Hz, 2 H). |
| 226 | 530 | 12.96 (br. s., 1 H) 7.95-7.99 (m, 2 H) 7.87 (s, 1 H) 7.32-7.37 (m, 4 H) 7.25-7.29 (m, 1 H) 7.03-7.08 (m, 2 H) 5.68 (d, J = 9.00 Hz, 1 H) 4.88-4.97 (m, 1 H) 3.53 (s, 2 H) 3.25-3.29 (m, 4 H) 2.89-2.95 (m, 2 H) 2.49-2.53 (m, 4 H) 2.35 (q, J = 7.17 Hz, 2 H) 2.03 (td, J = 11.83, 1.83 Hz, 2 H) 1.96-2.02 (m, 2 H) 1.63 (dtd, J = 11.83, 11.56, 3.51 Hz, 2 H) 1.02 (t, J = 7.17 Hz, 3 H). |
| 227 | 512 | 12.92 (br. s., 1 H) 7.95-7.99 (m, 2 H) 7.87 (s, 1 H) 6.97-7.02 (m, 2 H) 5.67 (d, J = 8.85 Hz, 1 H) 4.87-4.96 (m, 1 H) 4.13-4.20 (m, 1 H) 3.44-3.51 (m, 1 H) 3.38 (t, J = 6.49 Hz, 2 H) 3.23 (s, 3 H) 2.99 (td, J = 11.94, 3.59 Hz, 1 H) 2.88-2.93 (m, 1 H) 2.78-2.84 (m, 2 H) 2.77 (dt, J = 10.91, 1.98 Hz, 1 H) 2.37 (dt, J = 12.10, 7.40 Hz, 1 H) 2.30 (dt, J = 12.10, 7.02 Hz, 1 H) 2.21 (s, 3 H) 2.18-2.22 (m, 1 H) 2.01-2.09 (m, 3 H) 1.94-2.00 (m, 2 H) 1.61-1.74 (m, 4 H) 1.07 (d, J = 6.41 Hz, 3 H). |
| 228 | 556 | 12.95 (br. s., 1 H) 7.96 (s, 1 H) 7.96-7.99 (m, 2 H) 6.97-7.02 (m, 2 H) 5.39 (d, J = 8.85 Hz, 1 H) 4.88-4.97 (m, 1 H) 4.13-4.20 (m, 1 H) 3.44-3.51 (m, 1 H) 3.38 (t, J = 6.41 Hz, 2 H) 3.23 (s, 3 H) 2.99 (td, J = 12.02, 3.28 Hz, 1 H) 2.88-2.94 (m, 1 H) 2.74-2.83 (m, 3 H) 2.37 (dt, J = 12.21, 7.40 Hz, 1 H) 2.30 (dt, J = 12.21, 6.94 Hz, 1 H) 2.21 (s, 3 H) 2.17-2.22 (m, 1 H) 2.02-2.11 (m, 3 H) 1.96-2.02 (m, 2H) 1.66-1.73 (m, 2 H) 1.64 (tdd, J = 11.75, 11.37, 3.43 Hz, 2 H) 1.07 (d, J = 6.56 Hz, 3 H). |
| 229 | 526 | 12.93 (br. s., 1 H) 7.94-7.99 (m, 2 H) 7.87 (s, 1 H) 6.97-7.02 (m, 2 H) 5.66 (d, J = 8.54 Hz, 1 H) 4.89-4.97 (m, 1 H) 4.13-4.20 (m, 1 H) 3.44-3.50 (m, 1 H) 3.38 (t, J = 6.41 Hz, 2 H) 3.23 (s, 3 H) 2.99 (td, J = 11.90, 3.20 Hz, 1 H) 2.87-2.95 (m, 3 H) 2.75-2.79 (m, 1 H) 2.34-2.40 (m, 1 H) 2.36 (q, J = 7.17 Hz, 2 H) 2.30 (dt, J = 12.13, 7.06 Hz, 1 H) 2.20 (dd, J = 10.99, 3.36 Hz, 1 H) 2.00-2.08 (m, 3 H) 1.96-2.02 (m, 2 H) 1.66-1.72 (m, 2 H) 1.63 (dtd, J = 11.90, 11.37, 3.28 Hz, 2 H) 1.07 (d, J = 6.56 Hz, 3 H) 1.03 (t, J = 7.17 Hz, 3 H). |
| 230 | 498 | 12.98 (s, 1 H) 8.01 (d, J = 8.9 Hz, 2 H) 7.88 (s, 1 H) 7.06 (d, J = 9.2 Hz, 2 H) 5.71 (d, J = 8.9 Hz, 1 H) 4.87-4.97 (m, 1 H) 3.91 (s, 2 H) 3.57-3.61 (m, 2 H) 3.53 (ddd, J = 9.8, 5.3, 5.0 Hz, 4 H) 3.47-3.51 (m, 2 H) 3.25 (s, 3 H) 2.82 (d, J = 11.3 Hz, 2 H) 2.21 (s, 3 H) 2.07 (t, J = 11.0 Hz, 2 H) 1.97 (d, J = 10.7 Hz, 2 H) 1.67 (qd, J = 11.6, 3.8 Hz, 2 H). |
| 231 | 542 | 13.01 (s, 1 H) 8.01 (d, J = 9.2 Hz, 2 H) 7.98 (s, 1 H) 7.06 (d, J = 9.2 Hz, 2 H) 5.43 (d, J = 8.9 Hz, 1 H) 4.87-4.99 (m, 1 H) 3.91 (s, 2 H) 3.57-3.61 (m, 2 H) 3.53 (ddd, J = 9.9, 5.2, 5.0 Hz, 4 H) 3.47-3.51 (m, 2 H) 3.26 (s, 3 H) 2.80 (d, J = 11.0 Hz, 2 H) 2.22 (s, 3 H) 2.09 (t, J = 10.8 Hz, 2 H) 1.99 (d, J = 11.3 Hz, 2 H) 1.65 (qd, J = 11.4, 3.7 Hz, 2 H). |
| 232 | 512 | 12.99 (s, 1 H) 8.01 (d, J = 8.9 Hz, 2 H) 7.88 (s, 1 H) 7.06 (d, J = 8.9 Hz, 2 H) 5.70 (d, J = 8.9 Hz, 1 H) 4.88-4.99 (m, 1 H) 3.91 (s, 2 H) 3.56-3.61 (m, 2 H) 3.51-3.56 (m, 4 H) 3.47-3.51 (m, 2 H) 3.26 (s, 3 H) 2.93 (d, J = 11.3 Hz, 2 H) 2.36 (q, J = 7.0 Hz, 2 H) 2.04 (t, J = 11.9 Hz, 2 H) 2.00 (d, J = 11.6 Hz, 2 H) 1.64 (qd, J = 11.6, 3.4 Hz, 2 H) 1.03 (t, J = 7.2 Hz, 3 H). |
| 233 | 526 | 12.98 (s, 1 H) 8.00 (d, J = 8.9 Hz, 2 H) 7.88 (s, 1 H) 7.06 (d, J = 8.9 Hz, 2 H) 5.65 (d, J = 8.5 Hz, 1 H) 4.85-4.95 (m, 1 H) 3.91 (s, 2 H) 3.56-3.61 (m, 2 H) 3.51-3.56 (m, 4 H) 3.47-3.51 (m, 2 H) 3.26 (s, 3 H) 2.85 (d, J = 11.6 Hz, 2 H) 2.73 (spt, J = 6.6 Hz, 1 H) 2.28 (td, J = 11.3, 1.8 Hz, 2 H) 2.01 (d, J = 10.4 Hz, 2 H) 1.60 (qd, J = 11.6, 3.8 Hz, 2 H) 1.01 (d, J = 6.4 Hz, 6 H). |
| 234 | 570 | 13.01 (s, 1 H) 8.01 (d, J = 8.9 Hz, 2 H) 7.98 (s, 1 H) 7.06 (d, J = 9.2 Hz, 2 H) 5.38 (d, J = 8.9 Hz, 1 H) 4.86-4.96 (m, 1 H) 3.91 (s, 2 H) 3.57-3.61 (m, 2 H) 3.51-3.56 (m, 4 H) 3.47-3.51 (m, 2 H) 3.26 (s, 3 H) 2.84 (d, J = 11.3 Hz, 2 H) 2.73 (spt, J = 6.6 Hz, 1 H) 2.29 (td, J = 11.3, 1.8 Hz, 2 H) 2.02 (d, J = 11.3 Hz, 2 H) 1.58 (qd, J = 11.3, 3.8 Hz, 2 H) 1.01 (d, J = 6.4 Hz, 6 H). |
| 235 | 556 | 13.01 (s, 1 H) 8.01 (d, J = 9.2 Hz, 2 H) 7.98 (s, 1 H) 7.06 (d, J = 9.2 Hz, 2 H) 5.42 (d, J = 8.9 Hz, 1 H) 4.89-4.99 (m, 1 H) 3.91 (s, 2 H) 3.56-3.61 (m, 2 H) 3.51-3.56 (m, 4 H) 3.47-3.50 (m, 2 H) 3.25 (s, 3 H) 2.91 (d, J = 11.3 Hz, 2 H) 2.37 (q, J = 7.3 Hz, 2 H) 2.07 (t, J = 10.5 Hz, 2 H) 2.02 (d, J = 12.8 Hz, 2 H) 1.63 (qd, J = 11.4, 3.5 Hz, 2 H) 1.03 (t, J = 7.2 Hz, 3 H). |

TABLE 2-continued

| Ex | m/z | ¹H NMR (600 MHz, DMSO-d₆) δ ppm |
|---|---|---|
| 236 | 498 | 12.99 (br. s., 1 H) 7.98-8.02 (m, 2 H) 7.88 (s, 1 H) 7.07-7.12 (m, 2 H) 5.71 (d, J = 8.85 Hz, 1 H) 4.87-4.96 (m, 1 H) 4.14 (s, 2 H) 3.57-3.63 (m, 2 H) 3.52-3.58 (m, 2 H) 3.31 (s, 3 H) 3.29-3.33 (m, 2 H) 3.25-3.30 (m, 2 H) 2.78-2.84 (m, 2 H) 2.21 (s, 3 H) 2.02-2.09 (m, 2 H) 1.94-2.00 (m, 2 H) 1.67 (qd, J = 11.72, 3.59 Hz, 2 H). |
| 237 | 542 | 13.02 (br. s., 1 H) 7.98-8.02 (m, 2 H) 7.98 (s, 1 H) 7.07-7.12 (m, 2 H) 5.43 (d, J = 8.70 Hz, 1 H) 4.88-4.96 (m, 1 H) 4.14 (s, 2 H) 3.57-3.63 (m, 2 H) 3.51-3.58 (m, 2 H) 3.31 (s, 3 H) 3.29-3.33 (m, 2 H) 3.25-3.30 (m, 2 H) 2.76-2.83 (m, 2 H) 2.21 (s, 3 H) 2.08 (td, J = 11.67, 1.75 Hz, 2 H) 1.96-2.02 (m, 2 H) 1.65 (dtd, J = 11.67, 11.44, 3.59 Hz, 2 H). |
| 238 | 512 | 12.99 (br. s., 1 H) 7.97-8.02 (m, 2 H) 7.88 (s, 1 H) 7.07-7.12 (m, 2 H) 5.70 (d, J = 8.85 Hz, 1 H) 4.89-4.97 (m, 1 H) 4.14 (s, 2 H) 3.57-3.63 (m, 2 H) 3.52-3.57 (m, 2 H) 3.31 (s, 3 H) 3.29-3.33 (m, 2 H) 3.24-3.30 (m, 2 H) 2.89-2.95 (m, 2 H) 2.36 (q, J = 7.17 Hz, 2 H) 2.01-2.07 (m, 2 H) 1.96-2.02 (m, 2 H) 1.64 (qd, J = 11.65, 3.51 Hz, 2 H) 1.03 (t, J = 7.17 Hz, 3 H). |
| 239 | 556 | 13.02 (br. s., 1 H) 7.98-8.02 (m, 2 H) 7.98 (s, 1 H) 7.07-7.12 (m, 2 H) 5.42 (d, J = 8.70 Hz, 1 H) 4.90-4.98 (m, 1 H) 4.14 (s, 2 H) 3.57-3.63 (m, 2 H) 3.51-3.57 (m, 2 H) 3.31 (s, 3 H) 3.29-3.33 (m, 2 H) 3.25-3.30 (m, 2 H) 2.87-2.93 (m, 2 H) 2.36 (q, J = 7.17 Hz, 2 H) 2.08 (td, J = 11.67, 1.75 Hz, 2 H) 1.98-2.04 (m, 2 H) 1.62 (qd, J = 11.50, 3.51 Hz, 2 H) 1.03 (t, J = 7.17 Hz, 3 H). |
| 240 | 526 | 12.98 (br. s., 1 H) 7.97-8.03 (m, 2 H) 7.88 (s, 1 H) 7.06-7.12 (m, 2 H) 5.65 (d, J = 8.85 Hz, 1 H) 4.85-4.94 (m, 1 H) 4.14 (s, 2 H) 3.57-3.63 (m, 2 H) 3.51-3.57 (m, 2 H) 3.31 (s, 3 H) 3.29-3.33 (m, 2 H) 3.25-3.30 (m, 2 H) 2.81-2.88 (m, 2 H) 2.72 (spt, J = 6.56 Hz, 1 H) 2.27 (td, J = 11.50, 1.68 Hz, 2 H) 1.97-2.04 (m, 2 H) 1.60 (dtd, J = 11.63, 11.50, 3.66 Hz, 2 H) 1.01 (d, J = 6.56 Hz, 6 H). |
| 241 | 570 | 13.01 (br. s., 1 H) 7.98-8.02 (m, 2 H) 7.98 (s, 1 H) 7.07-7.12 (m, 2 H) 5.38 (d, J = 8.85 Hz, 1 H) 4.86-4.95 (m, 1 H) 4.14 (s, 2 H) 3.57-3.63 (m, 2 H) 3.51-3.58 (m, 2 H) 3.30 (s, 3 H) 3.29-3.33 (m, 2 H) 3.24-3.30 (m, 2 H) 2.80-2.87 (m, 2 H) 2.72 (spt, J = 6.56 Hz, 1 H) 2.29 (td, J = 11.37, 1.75 Hz, 2 H) 1.99-2.05 (m, 2 H) 1.58 (qd, J = 11.37, 3.74 Hz, 2 H) 1.01 (d, J = 6.56 Hz, 6 H). |
| 242 | 512 | 12.98 (br. s., 1 H) 7.98-8.03 (m, 2 H) 7.88 (s, 1 H) 7.03-7.09 (m, 2 H) 5.71 (d, J = 8.70 Hz, 1 H) 4.87-4.96 (m, 1 H) 3.90 (s, 2 H) 3.57-3.63 (m, 2 H) 3.44-3.48 (m, 2 H) 3.38-3.42 (m, 2 H) 3.30-3.33 (m, 2 H) 3.22 (s, 3 H) 2.79-2.84 (m, 2 H) 2.21 (s, 3 H) 2.06 (td, J = 11.64, 1.75 Hz, 2 H) 1.94-2.00 (m, 2 H) 1.71-1.78 (m, 2 H) 1.67 (dtd, J = 11.83, 11.64, 3.74 Hz, 2 H). |
| 243 | 556 | 13.00 (br. s., 1 H) 7.99-8.03 (m, 2 H) 7.97 (s, 1 H) 7.03-7.09 (m, 2 H) 5.42 (d, J = 8.85 Hz, 1 H) 4.88-4.96 (m, 1 H) 3.90 (s, 2 H) 3.58-3.63 (m, 2 H) 3.44-3.48 (m, 2 H) 3.37-3.43 (m, 2 H) 3.30-3.33 (m, 2 H) 3.22 (s, 3 H) 2.77-2.83 (m, 2 H) 2.21 (s, 3 H) 2.05-2.11 (m, 2 H) 1.96-2.02 (m, 2 H) 1.71-1.78 (m, 2 H) 1.65 (dtd, J = 11.75, 11.48, 3.59 Hz, 2 H). |
| 244 | 526 | 12.97 (br. s., 1 H) 7.98-8.03 (m, 2 H) 7.88 (s, 1 H) 7.03-7.08 (m, 2 H) 5.69 (d, J = 8.70 Hz, 1 H) 4.89-4.97 (m, 1 H) 3.89 (s, 2 H) 3.58-3.63 (m, 2 H) 3.44-3.48 (m, 2 H) 3.37-3.42 (m, 2 H) 3.30-3.32 (m, 2 H) 3.22 (s, 3 H) 2.89-2.96 (m, 2 H) 2.36 (q, J = 7.17 Hz, 2 H) 2.01-2.07 (m, 2 H) 1.96-2.02 (m, 2 H) 1.71-1.77 (m, 2 H) 1.60-1.69 (m, 2 H) 1.03 (t, J = 7.17 Hz, 3 H). |
| 245 | 570 | 13.00 (br. s., 1 H) 7.98-8.03 (m, 2 H) 7.98 (s, 1 H) 7.03-7.08 (m, 2 H) 5.41 (d, J = 8.85 Hz, 1 H) 4.90-4.98 (m, 1 H) 3.90 (s, 2 H) 3.58-3.62 (m, 2 H) 3.44-3.48 (m, 2 H) 3.38-3.42 (m, 2 H) 3.30-3.33 (m, 2 H) 3.22 (s, 3 H) 2.87-2.93 (m, 2 H) 2.36 (q, J = 7.17 Hz, 2 H) 2.03-2.10 (m, 2 H) 1.99-2.04 (m, 2 H) 1.71-1.78 (m, 2 H) 1.62 (qd, J = 11.37, 3.66 Hz, 2 H) 1.03 (t, J = 7.17 Hz, 3 H). |
| 246 | 540 | 12.97 (br. s., 1 H) 7.98-8.03 (m, 2 H) 7.88 (s, 1 H) 7.03-7.08 (m, 2 H) 5.65 (d, J = 8.85 Hz, 1 H) 4.86-4.94 (m, 1 H) 3.90 (s, 2 H) 3.58-3.63 (m, 2 H) 3.44-3.48 (m, 2 H) 3.37-3.42 (m, 2 H) 3.30-3.33 (m, 2 H) 3.22 (s, 3 H) 2.81-2.88 (m, 2 H) 2.72 (spt, J = 6.53 Hz, 1 H) 2.28 (td, J = 11.62, 1.83 Hz, 2 H) 1.98-2.04 (m, 2 H) 1.71-1.78 (m, 2 H) 1.60 (qd, J = 11.62, 3.74 Hz, 2 H) 1.01 (d, J = 6.56 Hz, 6 H). |
| 247 | 584 | 13.00 (br. s., 1 H) 7.98-8.03 (m, 2 H) 7.97 (s, 1 H) 7.04-7.08 (m, 2 H) 5.37 (d, J = 8.70 Hz, 1 H) 4.87-4.95 (m, 1 H) 3.90 (s, 2 H) 3.58-3.62 (m, 2 H) 3.44-3.48 (m, 2 H) 3.38-3.42 (m, 2 H) 3.30-3.33 (m, 2 H) 3.22 (s, 3 H) 2.81-2.86 (m, 2 H) 2.73 (spt, J = 6.56 Hz, 1 H) 2.29 (td, J = 11.40, 1.91 Hz, 2 H) 1.99-2.05 (m, 2 H) 1.71-1.77 (m, 2 H) 1.58 (qd, J = 11.40, 3.66 Hz, 2 H) 1.01 (d, J = 6.56 Hz, 6 H). |
| 248 | 512 | 12.98 (s, 1 H) 8.01 (d, J = 8.9 Hz, 2 H) 7.88 (s, 1 H) 7.06 (d, J = 9.2 Hz, 2 H) 5.72 (d, J = 8.9 Hz, 1 H) 4.86-4.98 (m, 1 H) 3.91 (s, 2 H) 3.56-3.62 (m, 2 H) 3.49-3.56 (m, 6 H) 3.43 (q, J = 6.9 Hz, 2 H) 2.82 (d, J = 11.6 Hz, 2 H) 2.22 (s, 3 H) 2.07 (t, J = 11.3 Hz, 2 H) 1.97 (d, J = 10.4 Hz, 2 H) 1.67 (qd, J = 11.6, 3.5 Hz, 2 H) 1.09 (t, J = 7.0 Hz, 3 H). |
| 249 | 556 | 13.01 (s, 1 H) 8.01 (d, J = 9.2 Hz, 2 H) 7.98 (s, 1 H) 7.06 (d, J = 9.2 Hz, 2 H) 5.43 (d, J = 8.9 Hz, 1 H) 4.87-4.98 (m, 1 H) 3.91 (s, 2 H) 3.57-3.62 (m, 2 H) 3.49-3.56 (m, 6 H) 3.43 (q, J = 7.0 Hz, 2 H) 2.80 (d, J = 11.3 Hz, 2 H) 2.21 (s, 3 H) 2.08 (t, J = 11.0 Hz, 2 H) 1.99 (d, J = 10.1 Hz, 2 H) 1.65 (qd, J = 11.5, 3.8 Hz, 2 H) 1.09 (t, J = 7.0 Hz, 3 H). |
| 250 | 526 | 12.98 (s, 1 H) 8.01 (d, J = 8.8 Hz, 2 H) 7.88 (s, 1 H) 7.06 (d, J = 9.2 Hz, 2 H) 5.70 (d, J = 8.9 Hz, 1 H) 4.89-4.98 (m, 1 H) 3.91 (s, 2 H) 3.56-3.62 (m, 2 H) 3.49-3.56 (m, 6 H) 3.43 (q, J = 7.0 Hz, 2 H) 2.93 (d, J = 10.7 Hz, 2 H) 2.33-2.42 (m, 2 H) 2.03-2.10 (m, 2 H) 2.00 (d, J = 11.9 Hz, 2 H) 1.65 (qd, J = 11.7, 3.5 Hz, 2 H) 1.09 (t, J = 6.9 Hz, 3 H) 1.03 (t, J = 7.2 Hz, 3 H). |
| 251 | 570 | 13.01 (s, 1 H) 8.01 (d, J = 8.9 Hz, 2 H) 7.98 (s, 1 H) 7.06 (d, J = 8.9 Hz, 2 H) 5.42 (d, J = 8.9 Hz, 1 H) 4.89-5.00 (m, 1 H) 3.91 (s, 2 H) 3.57-3.61 (m, 2 H) 3.49-3.56 (m, 6 H) 3.43 (q, J = 7.0 Hz, 2 H) 2.91 (d, J = 11.3 Hz, 2 H) 2.37 (q, J = 7.3 Hz, 2 H) |

TABLE 2-continued

| Ex | m/z | $^1$H NMR (600 MHz, DMSO-$d_6$) δ ppm |
|---|---|---|
| | | 2.07 (t, J = 11.6 Hz, 2 H) 2.02 (d, J = 11.3 Hz, 2 H) 1.62 (qd, J = 11.5, 3.7 Hz, 2 H) 1.09 (t, J = 6.9 Hz, 3 H) 1.03 (t, J = 7.3 Hz, 3 H). |
| 252 | 540 | 12.98 (s, 1 H) 8.00 (d, J = 8.9 Hz, 2 H) 7.88 (s, 1 H) 7.06 (d, J = 9.2 Hz, 2 H) 5.66 (d, J = 8.9 Hz, 1 H) 4.83-4.96 (m, 1 H) 3.91 (s, 2 H) 3.57-3.62 (m, 2 H) 3.49-3.56 (m, 6 H) 3.43 (q, J = 7.0 Hz, 2 H) 2.85 (d, J = 11.6 Hz, 2 H) 2.73 (spt, J = 6.7 Hz, 1 H) 2.28 (t, J = 10.8 Hz, 2 H) 2.01 (d, J = 10.1 Hz, 2 H) 1.60 (qd, J = 11.5, 3.8 Hz, 2 H) 1.09 (t, J = 7.0 Hz, 3 H) 1.01 (d, J = 6.7 Hz, 6 H). |
| 253 | 584 | 13.01 (s, 1 H) 8.01 (d, J = 8.8 Hz, 2 H) 7.98 (s, 1 H) 7.06 (d, J = 9.2 Hz, 2 H) 5.38 (d, J = 8.9 Hz, 1 H) 4.83-4.99 (m, 1 H) 3.91 (s, 2 H) 3.56-3.63 (m, 2 H) 3.49-3.57 (m, 6 H) 3.43 (q, J = 7.0 Hz, 2 H) 2.84 (d, J = 11.0 Hz, 2 H) 2.73 (spt, J = 6.4 Hz, 1 H) 2.30 (t, J = 11.0 Hz, 2 H) 2.03 (d, J = 10.4 Hz, 2 H) 1.59 (qd, J = 11.0, 2.8 Hz, 2 H) 1.09 (t, J = 6.9 Hz, 3 H) 1.01 (d, J = 6.4 Hz, 6 H). |
| 254 | 469 | 12.93 (s, 1 H) 7.93-7.98 (m, 2 H) 7.87 (s, 1 H) 7.02-7.07 (m, 2 H) 5.68 (d, J = 9.00 Hz, 1 H) 4.87-4.95 (m, 1 H) 4.37 (t, J = 5.16 Hz, 1 H) 3.82-3.89 (m, 2 H) 3.47 (td, J = 6.64, 5.16 Hz, 2 H) 2.78-2.85 (m, 2 H) 2.75 (td, J = 12.36, 2.37 Hz, 2 H) 2.21 (s, 3 H) 2.02-2.09 (m, 2 H) 1.94-2.00 (m, 2 H) 1.70-1.76 (m, 2 H) 1.66 (dtd, J = 11.98, 11.71, 3.81 Hz, 2 H) 1.55-1.64 (m, 1 H) 1.39 (q, J = 6.64 Hz, 2 H) 1.21 (dtd, J = 12.36, 12.21, 3.66 Hz, 2 H). |
| 255 | 513 | 12.96 (s, 1 H) 7.97 (s, 1 H) 7.94-7.98 (m, 2 H) 7.02-7.07 (m, 2 H) 5.40 (d, J = 8.85 Hz, 1 H) 4.87-4.96 (m, 1 H) 4.37 (t, J = 5.18 Hz, 1 H) 3.82-3.89 (m, 2 H) 3.47 (td, J = 6.63, 5.18 Hz, 2 H) 2.76-2.83 (m, 2 H) 2.75 (td, J = 12.40, 2.44 Hz, 2 H) 2.21 (s, 3 H) 2.03-2.12 (m, 2 H) 1.96-2.02 (m, 2 H) 1.70-1.77 (m, 2 H) 1.64 (qd, J = 11.55, 3.66 Hz, 2 H) 1.56-1.64 (m, 1 H) 1.39 (q, J = 6.63 Hz, 2 H) 1.21 (qd, J = 12.40, 3.66 Hz, 2 H). |
| 256 | 483 | 12.93 (s, 1 H) 7.93-7.98 (m, 2 H) 7.87 (s, 1 H) 7.02-7.06 (m, 2 H) 5.67 (d, J = 8.85 Hz, 1 H) 4.89-4.97 (m, 1 H) 4.37 (t, J = 5.13 Hz, 1 H) 3.82-3.89 (m, 2 H) 3.47 (td, J = 6.57, 5.13 Hz, 2 H) 2.88-2.96 (m, 2 H) 2.74 (t, J = 12.30, 2.14 Hz, 2 H) 2.36 (q, J = 7.17 Hz, 2 H) 2.00-2.07 (m, 2 H) 1.96-2.03 (m, 2 H) 1.70-1.76 (m, 2 H) 1.63 (qd, J = 11.50, 3.28 Hz, 2 H) 1.56-1.64 (m, 1 H) 1.39 (q, J = 6.57 Hz, 2 H) 1.21 (qd, J = 12.30, 3.97 Hz, 2 H) 1.03 (t, J = 7.17 Hz, 3 H). |
| 257 | 527 | 12.96 (s, 1 H) 7.97 (s, 1 H) 7.94-7.98 (m, 2 H) 7.02-7.07 (m, 2 H) 5.39 (d, J = 8.70 Hz, 1 H) 4.90-4.98 (m, 1 H) 4.37 (t, J = 5.11 Hz, 1 H) 3.83-3.88 (m, 2 H) 3.47 (td, J = 6.68, 5.16 Hz, 2 H) 2.86-2.94 (m, 2 H) 2.75 (td, J = 12.30, 2.21 Hz, 2 H) 2.36 (q, J = 7.17 Hz, 2 H) 2.02-2.10 (m, 2 H) 1.98-2.04 (m, 2 H) 1.70-1.76 (m, 2 H) 1.62 (qd, J = 11.40, 3.80 Hz, 2 H) 1.56-1.62 (m, 1 H) 1.39 (q, J = 6.68 Hz, 2 H) 1.21 (qd, J = 12.30, 3.97 Hz, 2 H) 1.03 (t, J = 7.17 Hz, 3 H). |
| 258 | 497 | 12.93 (br. s., 1 H) 7.93-7.98 (m, 2 H) 7.87 (s, 1 H) 7.01-7.06 (m, 2 H) 5.63 (d, J = 8.85 Hz, 1 H) 4.85-4.93 (m, 1 H) 4.37 (t, J = 5.16 Hz, 1 H) 3.82-3.88 (m, 2 H) 3.47 (td, J = 6.61, 5.16 Hz, 2 H) 2.82-2.87 (m, 2 H) 2.74 (td, J = 12.36, 1.98 Hz, 2 H) 2.72 (spt, J = 6.56 Hz, 1 H) 2.27 (td, J = 11.47, 1.75 Hz, 2 H) 1.97-2.03 (m, 2 H) 1.70-1.76 (m, 2 H) 1.60 (qd, J = 11.47, 3.59 Hz, 2H) 1.55-1.64 (m, 1 H) 1.39 (q, J = 6.61 Hz, 2 H) 1.21 (qd, J = 12.36, 3.89 Hz, 2 H) 1.01 (d, J = 6.56 Hz, 6 H). |
| 259 | 541 | 12.96 (br. s., 1 H) 7.97 (s, 1 H) 7.93-7.98 (m, 2 H) 7.02-7.06 (m, 2 H) 5.35 (d, J = 8.85 Hz, 1 H) 4.86-4.94 (m, 1 H) 4.37 (t, J = 5.19 Hz, 1 H) 3.82-3.89 (m, 2 H) 3.47 (td, J = 6.67, 5.19 Hz, 2 H) 2.80-2.86 (m, 2 H) 2.74 (td, J = 12.20, 2.29 Hz, 2 H) 2.72 (spt, J = 6.56 Hz, 1 H) 2.29 (td, J = 11.41, 1.98 Hz, 2 H) 1.99-2.06 (m, 2 H) 1.70-1.77 (m, 2 H) 1.57-1.64 (m, 1 H) 1.58 (dtd, J = 11.90, 11.41, 3.66 Hz, 2 H) 1.39 (q, J = 6.67 Hz, 2 H) 1.21 (qd, J = 12.20, 4.27 Hz, 2 H) 1.01 (d, J = 6.56 Hz, 6 H). |
| 260 | 604 | 12.98 (s, 1 H) 8.00 (d, J = 9.2 Hz, 2 H) 7.87 (s, 1 H) 7.24 (d, J = 8.5 Hz, 2 H) 7.05 (d, J = 9.2 Hz, 2 H) 6.90 (d, J = 8.5 Hz, 2 H) 5.71 (d, J = 8.9 Hz, 1 H) 4.91-5.01 (m, 1 H) 3.92 (s, 2 H) 3.74 (s, 3 H) 3.58-3.61 (m, 2 H) 3.52-3.56 (m, 4 H) 3.48-3.51 (m, 2 H) 3.44 (s, 2 H) 3.26 (s, 3 H) 2.86 (d, J = 11.6 Hz, 2 H) 2.11 (t, J = 10.8 Hz, 2 H) 1.97 (d, J = 9.5 Hz, 2 H) 1.65 (qd, J = 11.6, 3.7 Hz, 2 H). |
| 261 | 618 | 12.98 (s, 1 H) 8.00 (d, J = 8.9 Hz, 2 H) 7.88 (s, 1 H) 7.24 (d, J = 8.5 Hz, 2 H) 7.05 (d, J = 9.2 Hz, 2 H) 6.90 (d, J = 8.5 Hz, 2 H) 5.71 (d, J = 8.9 Hz, 1 H) 4.91-5.01 (m, 1 H) 3.92 (s, 2 H) 3.74 (s, 3 H) 3.57-3.62 (m, 2 H) 3.50-3.57 (m, 6 H) 3.44 (s, 2 H) 3.43 (q, J = 7.0 Hz, 2 H) 2.86 (d, J = 11.6 Hz, 2 H) 2.11 (t, J = 10.8 Hz, 2 H) 1.97 (d, J = 9.2 Hz, 2 H) 1.65 (qd, J = 11.7, 3.4 Hz, 2 H) 1.09 (t, J = 6.9 Hz, 3 H). |
| 262 | 604 | 12.99 (br. s., 1 H) 7.97-8.01 (m, 2 H) 7.88 (s, 1 H) 7.22-7.26 (m, 2 H) 7.07-7.12 (m, 2 H) 6.87-6.92 (m, 2 H) 5.72 (d, J = 8.85 Hz, 1 H) 4.92-5.00 (m, 1 H) 4.15 (s, 2 H) 3.74 (s, 3 H) 3.58-3.64 (m, 2 H) 3.53-3.58 (m, 2 H) 3.44 (s, 2 H) 3.30-3.33 (m, 2 H) 3.31 (s, 3 H) 3.27-3.31 (m, 2 H) 2.83-2.89 (m, 2 H) 2.06-2.14 (m, 2 H) 1.94-2.01 (m, 2 H) 1.65 (dtd, J = 11.94, 11.73, 3.66 Hz, 2 H). |
| 263 | 618 | 12.98 (br. s., 1 H) 7.97-8.02 (m, 2 H) 7.87 (s, 1 H) 7.22-7.26 (m, 2 H) 7.03-7.08 (m, 2 H) 6.88-6.92 (m, 2 H) 5.71 (d, J = 8.85 Hz, 1 H) 4.92-5.00 (m, 1 H) 3.91 (s, 2 H) 3.74 (s, 3 H) 3.59-3.63 (m, 2 H) 3.45-3.49 (m, 2 H) 3.44 (s, 2 H) 3.38-3.43 (m, 2 H) 3.30-3.33 (m, 2 H) 3.22 (s, 3 H) 2.82-2.89 (m, 2 H) 2.10 (td, J = 11.60, 1.68 Hz, 2 H) 1.94-2.01 (m, 2 H) 1.72-1.78 (m, 2 H) 1.65 (qd, J = 11.60, 3.51 Hz, 2 H). |
| 264 | 575 | 12.93 (br. s., 1 H) 7.92-7.97 (m, 2 H) 7.86 (s, 1 H) 7.21-7.26 (m, 2 H) 7.02-7.06 (m, 2 H) 6.87-6.91 (m, 2 H) 5.69 (d, J = 9.00 Hz, 1 H) 4.91-5.00 (m, 1 H) 4.38 (t, J = 5.18 Hz, 1 H) 3.83-3.89 (m, 2 H) 3.74 (s, 3 H) 3.48 (td, J = 6.64, 5.18 Hz, 2 H) 3.44 (s, 2 H) 2.82-2.88 (m, 2 H) 2.75 (td, J = 12.30, 2.29 Hz, 2 H) 2.10 (td, J = 11.60, 1.75 Hz, 2 H) 1.94-2.00 (m, 2 H) 1.71-1.78 (m, 2 H) 1.64 (qd, J = 11.60, 3.42 Hz, 2 H) 1.56-1.64 (m, 1 H) 1.40 (q, J = 6.64 Hz, 2 H) 1.22 (qd, J = 12.30, 3.89 Hz, 2 H). |
| 265 | 580 | 12.95 (br. s., 1 H) 7.97-8.02 (m, 2 H) 7.87 (s, 1 H) 7.44 (dd, J = 4.73, 1.68 Hz, 1 H) 7.06-7.11 (m, 2 H) 6.97-7.00 (m, 2 H) 5.73 (d, J = 8.24 Hz, 1 H) |

TABLE 2-continued

| Ex | m/z | ¹H NMR (600 MHz, DMSO-d$_6$) δ ppm |
|---|---|---|
| | | 4.93-5.01 (m, 1 H) 4.14 (s, 2 H) 3.73 (s, 2 H) 3.58-3.63 (m, 2 H) 3.52-3.58 (m, 2 H) 3.31 (s, 3 H) 3.29-3.32 (m, 2 H) 3.25-3.31 (m, 2 H) 2.90-2.96 (m, 2 H) 2.17 (td, J = 11.70, 1.68 Hz, 2 H) 1.96-2.02 (m, 2 H) 1.67 (dtd, J = 11.94, 11.70, 3.66 Hz, 2 H). |
| 266 | 594 | 12.95 (br. s., 1 H) 7.97-8.03 (m, 2 H) 7.87 (s, 1 H) 7.44 (dd, J = 4.88, 1.53 Hz, 1 H) 7.02-7.07 (m, 2 H) 6.96-7.00 (m, 2 H) 5.75 (d, J = 9.00 Hz, 1 H) 4.92-5.01 (m, 1 H) 3.90 (s, 2 H) 3.73 (s, 2 H) 3.58-3.63 (m, 2 H) 3.45-3.49 (m, 2 H) 3.38-3.43 (m, 2 H) 3.30-3.33 (m, 2 H) 3.22 (s, 3 H) 2.90-2.96 (m, 2 H) 2.17 (td, J = 11.75, 1.91 Hz, 2H) 1.96-2.02 (m, 2H) 1.72-1.78 (m, 2 H) 1.68 (dtd, J = 11.75, 11.29, 3.60 Hz, 2 H). |
| 267 | 484 | 12.96 (br. s., 1 H) 7.96-8.00 (m, 2 H) 7.88 (s, 1 H) 7.04-7.08 (m, 2 H) 5.70 (d, J = 8.85 Hz, 1 H) 4.87-4.95 (m, 1 H) 4.45 (t, J = 4.65 Hz, 1 H) 3.43-3.49 (m, 2 H) 3.23-3.28 (m, 4 H) 2.77-2.85 (m, 2 H) 2.48-2.50 (m, 4 H) 2.38 (t, J = 7.25 Hz, 2 H) 2.21 (s, 3 H) 2.05 (td, J = 11.60, 1.68 Hz, 2 H) 1.94-2.00 (m, 2 H) 1.66 (qd, J = 11.60, 3.50 Hz, 2 H) 1.58-1.65 (m, 2H). |
| 268 | 528 | 12.99 (s, 1 H) 7.97 (s, 1 H) 7.96-8.00 (m, 2 H) 7.03-7.09 (m, 2 H) 5.42 (d, J = 8.70 Hz, 1 H) 4.88-4.96 (m, 1 H) 4.44 (br. s., 1 H) 3.46 (t, J = 5.87 Hz, 2 H) 3.24-3.28 (m, 4 H) 2.75-2.83 (m, 2 H) 2.47-2.50 (m, 4 H) 2.38 (t, J = 7.25 Hz, 2 H) 2.21 (s, 3 H) 2.04-2.12 (m, 2 H) 1.96-2.02 (m, 2 H) 1.65 (qd, J = 11.60, 3.66 Hz, 2 H) 1.59-1.65 (m, 2 H). |
| 269 | 498 | 12.97 (br. s., 1 H) 7.95-8.00 (m, 2 H) 7.88 (s, 1 H) 7.03-7.09 (m, 2 H) 5.69 (d, J = 9.00 Hz, 1 H) 4.89-4.97 (m, 1 H) 4.44 (br. s., 1 H) 3.43-3.49 (m, 2 H) 3.22-3.28 (m, 4 H) 2.88-2.96 (m, 2 H) 2.48-2.51 (m, 4 H) 2.36-2.41 (m, 2 H) 2.36 (q, J = 7.17 Hz, 2 H) 1.99-2.07 (m, 2 H) 1.96-2.03 (m, 2 H) 1.58-1.68 (m, 4 H) 1.03 (t, J = 7.17 Hz, 3 H). |
| 270 | 526 | 12.98 (br. s., 1 H) 8.01 (d, J = 9.2 Hz, 2 H) 7.88 (s, 1 H) 7.06 (d, J = 8.9 Hz, 2 H) 5.71 (d, J = 8.9 Hz, 1 H) 4.85-4.98 (m, 1 H) 3.91 (s, 2 H) 3.57-3.61 (m, 2 H) 3.53-3.56 (m, 2 H) 3.52 (spt, J = 6.1 Hz, 1 H) 3.49-3.51 (m, 4 H) 2.81 (d, J = 11.6 Hz, 2 H) 2.21 (s, 3 H) 2.06 (td, J = 11.3, 1.8 Hz, 2 H) 1.97 (d, J = 10.7 Hz, 2 H) 1.67 (qd, J = 11.6, 3.7 Hz, 2 H) 1.06 (d, J = 6.1 Hz, 6 H). |
| 271 | 570 | 13.01 (s, 1 H) 8.01 (d, J = 8.9 Hz, 2 H) 7.98 (s, 1 H) 7.06 (d, J = 9.2 Hz, 2 H) 5.43 (d, J = 8.9 Hz, 1 H) 4.87-4.97 (m, 1 H) 3.91 (s, 2 H) 3.58-3.61 (m, 2 H) 3.53-3.57 (m, 2 H) 3.52 (spt, J = 6.1 Hz, 1 H) 3.47-3.51 (m, 4 H) 2.80 (d, J = 11.0 Hz, 2 H) 2.21 (s, 3 H) 2.08 (t, J = 10.8 Hz, 2 H) 1.99 (d, J = 10.4 Hz, 2 H) 1.65 (qd, J = 11.4, 3.7 Hz, 2 H) 1.06 (d, J = 6.1 Hz, 6 H). |
| 272 | 540 | 12.98 (s, 1 H) 8.00 (d, J = 9.2 Hz, 2 H) 7.88 (s, 1 H) 7.06 (d, J = 9.2 Hz, 2 H) 5.70 (d, J = 8.9 Hz, 1 H) 4.88-4.98 (m, 1 H) 3.91 (s, 2 H) 3.57-3.61 (m, 2 H) 3.53-3.56 (m, 2 H) 3.52 (spt, J = 6.1 Hz, 1 H) 3.47-3.51 (m, 4 H) 2.93 (d, J = 11.3 Hz, 2 H) 2.36 (q, J = 7.1 Hz, 2 H) 2.04 (t, J = 11.6 Hz, 2 H) 2.00 (d, J = 11.3 Hz, 2 H) 1.64 (qd, J = 11.6, 3.5 Hz, 2 H) 1.06 (d, J = 6.1 Hz, 6 H) 1.03 (t, J = 7.2 Hz, 3 H). |
| 273 | 584 | 13.01 (s, 1 H) 8.01 (d, J = 8.9 Hz, 2 H) 7.98 (s, 1 H) 7.06 (d, J = 9.2 Hz, 2 H) 5.42 (d, J = 8.9 Hz, 1 H) 4.89-4.99 (m, 1 H) 3.91 (s, 2 H) 3.57-3.61 (m, 2 H) 3.53-3.57 (m, 2 H) 3.52 (spt, J = 6.1 Hz, 1 H) 3.47-3.51 (m, 4 H) 2.91 (d, J = 10.7 Hz, 2 H) 2.37 (q, J = 7.2 Hz, 2 H) 2.07 (t, J = 11.1 Hz, 2 H) 2.02 (d, J = 11.6 Hz, 2 H) 1.62 (qd, J = 11.4, 3.2 Hz, 2 H) 1.06 (d, J = 5.8 Hz, 6 H) 1.03 (t, J = 7.3 Hz, 3 H). |
| 274 | 554 | 12.98 (s, 1 H) 8.00 (d, J = 8.8 Hz, 2 H) 7.88 (s, 1 H) 7.06 (d, J = 8.9 Hz, 2 H) 5.65 (d, J = 8.9 Hz, 1 H) 4.84-4.95 (m, 1 H) 3.91 (s, 2 H) 3.57-3.62 (m, 2 H) 3.53-3.57 (m, 2 H) 3.52 (spt, J = 5.8 Hz, 1 H) 3.47-3.51 (m, 4 H) 2.85 (d, J = 11.6 Hz, 2 H) 2.72 (spt, J = 6.5 Hz, 1 H) 2.28 (td, J = 11.4, 1.8 Hz, 2 H) 2.01 (d, J = 9.5 Hz, 2 H) 1.60 (qd, J = 11.6, 3.7 Hz, 2 H) 1.06 (d, J = 6.1 Hz, 6 H) 1.01 (d, J = 6.7 Hz, 6 H). |
| 275 | 632 | 12.98 (s, 1 H) 8.00 (d, J = 9.2 Hz, 2 H) 7.88 (s, 1 H) 7.24 (d, J = 8.9 Hz, 2 H) 7.05 (d, J = 9.2 Hz, 2 H) 6.90 (d, J = 8.9 Hz, 2 H) 5.71 (d, J = 9.2 Hz, 1 H) 4.91-5.01 (m, 1 H) 3.92 (s, 2 H) 3.74 (s, 3 H) 3.58-3.62 (m, 2 H) 3.55-3.57 (m, 2 H) 3.54 (spt, J = 6.1 Hz, 1 H) 3.48-3.52 (m, 4 H) 3.44 (s, 2 H) 2.86 (d, J = 11.6 Hz, 2 H) 2.11 (t, J = 11.1 Hz, 2 H) 1.97 (d, J = 10.1 Hz, 2 H) 1.65 (qd, J = 11.7, 3.5 Hz, 2 H) 1.07 (d, J = 6.1 Hz, 6 H). |
| 276 | 512 | 12.99 (br. s., 1 H) 7.98-8.02 (m, 2 H) 7.88 (s, 1 H) 7.07-7.12 (m, 2 H) 5.71 (d, J = 8.85 Hz, 1 H) 4.87-4.95 (m, 1 H) 3.59-3.64 (m, 4 H) 3.57 (t, J = 6.60 Hz, 2 H) 3.30-3.32 (m, 2 H) 3.23-3.28 (m, 2 H) 3.23 (s, 3 H) 2.78-2.85 (m, 2 H) 2.62 (t, J = 6.60 Hz, 2 H) 2.21 (s, 3 H) 2.06 (td, J = 11.70, 1.98 Hz, 2 H) 1.93-2.01 (m, 2 H) 1.67 (dtd, J = 11.90, 11.71, 3.74 Hz, 2 H). |
| 277 | 556 | 13.02 (s, 1 H) 7.98-8.02 (m, 2 H) 7.98 (s, 1 H) 7.07-7.12 (m, 2 H) 5.43 (d, J = 9.00 Hz, 1 H) 4.88-4.96 (m, 1 H) 3.59-3.64 (m, 4 H) 3.57 (t, J = 6.56 Hz, 2 H) 3.29-3.32 (m, 2 H) 3.23-3.28 (m, 2 H) 3.23 (s, 3 H) 2.77-2.83 (m, 2 H) 2.62 (t, J = 6.56 Hz, 2 H) 2.21 (s, 3 H) 2.03-2.12 (m, 2 H) 1.96-2.02 (m, 2 H) 1.65 (qd, J = 11.50, 3.51 Hz, 2 H). |
| 278 | 526 | 12.98 (br. s., 1 H) 7.97-8.02 (m, 2 H) 7.88 (s, 1 H) 7.06-7.12 (m, 2 H) 5.69 (d, J = 8.70 Hz, 1 H) 4.89-4.97 (m, 1 H) 3.59-3.64 (m, 4 H) 3.57 (t, J = 6.56 Hz, 2 H) 3.29-3.32 (m, 2 H) 3.23-3.27 (m, 2 H) 3.23 (s, 3 H) 2.89-2.95 (m, 2 H) 2.62 (t, J = 6.56 Hz, 2 H) 2.36 (q, J = 7.17 Hz, 2 H) 2.00-2.07 (m, 2 H) 1.96-2.03 (m, 2 H) 1.64 (dtd, J = 11.79, 11.54, 3.43 Hz, 2 H) 1.03 (t, J = 7.17 Hz, 3 H). |
| 279 | 570 | 13.01 (br. s., 1 H) 7.98-8.02 (m, 2 H) 7.98 (s, 1 H) 7.07-7.11 (m, 2 H) 5.41 (d, J = 8.54 Hz, 1 H) 4.90-4.98 (m, 1 H) 3.58-3.64 (m, 4 H) 3.57 (t, J = 6.56 Hz, 2 H) 3.29-3.32 (m, 2 H) 3.23-3.28 (m, 2 H) 3.23 (s, 3 H) 2.87-2.93 (m, 2 H) 2.62 (t, J = 6.56 Hz, 2 H) 2.36 (q, J = 7.17 Hz, 2 H) 2.03-2.10 (m, 2 H) 1.98-2.04 (m, 2 H) 1.62 (dtd, J = 11.67, 11.44, 3.59 Hz, 2 H) 1.03 (t, J = 7.17 Hz, 3 H). |
| 280 | 618 | 12.98 (br. s., 1 H) 7.97-8.01 (m, 2 H) 7.87 (s, 1 H) 7.22-7.26 (m, 2 H) 7.06-7.11 (m, 2 H) 6.88-6.91 (m, 2 H) 5.70 (d, J = 8.85 Hz, 1 H) 4.92-5.01 (m, 1 H) |

TABLE 2-continued

| Ex | m/z | $^1$H NMR (600 MHz, DMSO-d$_6$) δ ppm |
|---|---|---|
| | | 3.74 (s, 3 H) 3.60-3.65 (m, 4 H) 3.58 (t, J = 6.56 Hz, 2 H) 3.44 (s, 2 H) 3.30-3.32 (m, 2 H) 3.24-3.28 (m, 2 H) 3.24 (s, 3 H) 2.82-2.89 (m, 2 H) 2.63 (t, J = 6.56 Hz, 2 H) 2.10 (td, J = 11.60, 1.75 Hz, 2 H) 1.94-2.01 (m, 2 H) 1.65 (qd, J = 11.60, 3.36 Hz, 2 H). |
| 281 | 483 | 12.93 (br. s., 1 H) 7.96 (d, J = 9.2 Hz, 2 H) 7.87 (s, 1 H) 7.04 (d, J = 9.2 Hz, 2 H) 5.68 (d, J = 8.9 Hz, 1 H) 4.85-4.98 (m, 1 H) 3.85 (d, J = 12.8 Hz, 2 H) 3.38 (t, J = 6.6 Hz, 2 H) 3.23 (s, 3 H) 2.81 (d, J = 11.6 Hz, 2 H) 2.74 (td, J = 12.4, 2.3 Hz, 2 H) 2.21 (s, 3 H) 2.05 (td, J = 11.6, 1.8 Hz, 2 H) 1.97 (d, J = 10.7 Hz, 2 H) 1.73 (d, J = 11.3 Hz, 2 H) 1.66 (qd, J = 11.7, 3.7 Hz, 2 H) 1.52-1.61 (m, 1 H) 1.46 (q, J = 6.5 Hz, 2 H) 1.22 (qd, J = 12.2, 3.8 Hz, 2 H). |
| 282 | 527 | 12.96 (br. s., 1 H) 7.96 (s, 1 H) 7.96 (d, J = 8.9 Hz, 2 H) 7.04 (d, J = 9.2 Hz, 2 H) 5.40 (d, J = 8.9 Hz, 1 H) 4.88-4.97 (m, 1 H) 3.86 (d, J = 12.8 Hz, 2 H) 3.38 (t, J = 6.4 Hz, 2 H) 3.23 (s, 3 H) 2.79 (d, J = 11.6 Hz, 2 H) 2.74 (td, J = 12.4, 2.4 Hz, 2 H) 2.21 (s, 3 H) 2.07 (td, J = 11.5, 1.7 Hz, 2 H) 1.99 (d, J = 11.6 Hz, 2 H) 1.73 (d, J = 11.6 Hz, 2 H) 1.64 (qd, J = 11.5, 3.8 Hz, 2 H) 1.52-1.60 (m, 1 H) 1.47 (q, J = 6.6 Hz, 2 H) 1.22 (qd, J = 12.2, 4.0 Hz, 2 H). |
| 283 | 497 | 12.94 (br. s., 1 H) 7.96 (d, J = 8.9 Hz, 2 H) 7.87 (s, 1 H) 7.04 (d, J = 8.9 Hz, 2 H) 5.66 (d, J = 8.9 Hz, 1 H) 4.87-4.98 (m, 1 H) 3.85 (d, J = 12.5 Hz, 2 H) 3.38 (t, J = 6.6 Hz, 2 H) 3.23 (s, 3 H) 2.92 (d, J = 11.3 Hz, 2 H) 2.74 (td, J = 12.5, 2.4 Hz, 2 H) 2.36 (q, J = 7.2 Hz, 2 H) 2.03 (t, J = 11.9 Hz, 2 H) 1.99 (d, J = 11.3 Hz, 2 H) 1.73 (d, J = 11.3 Hz, 2 H) 1.63 (qd, J = 11.6, 3.8 Hz, 2 H) 1.52-1.60 (m, 1 H) 1.46 (q, J = 6.6 Hz, 2 H) 1.22 (qd, J = 12.2, 3.8 Hz, 2 H) 1.03 (t, J = 7.2 Hz, 3 H). |
| 284 | 541 | 12.96 (br. s., 1 H) 7.97 (s, 1 H) 7.96 (d, J = 9.2 Hz, 2 H) 7.04 (d, J = 9.2 Hz, 2 H) 5.38 (d, J = 8.9 Hz, 1 H) 4.89-4.99 (m, 1 H) 3.85 (d, J = 12.5 Hz, 2 H) 3.38 (t, J = 6.4 Hz, 2 H) 3.23 (s, 3 H) 2.90 (d, J = 11.3 Hz, 2 H) 2.74 (td, J = 12.5, 2.4 Hz, 2 H) 2.36 (q, J = 7.2 Hz, 2 H) 2.06 (t, J = 11.6 Hz, 2 H) 2.01 (d, J = 10.7 Hz, 2 H) 1.73 (d, J = 11.0 Hz, 2 H) 1.61 (qd, J = 11.6, 3.5 Hz, 2 H) 1.52-1.58 (m, 1 H) 1.46 (q, J = 6.6 Hz, 2 H) 1.22 (qd, J = 11.9, 3.0 Hz, 2 H) 1.03 (t, J = 7.2 Hz, 3 H). |
| 285 | 511 | 12.93 (s, 1 H) 7.95 (d, J = 8.9 Hz, 2 H) 7.87 (s, 1 H) 7.04 (d, J = 9.2 Hz, 2 H) 5.63 (d, J = 8.9 Hz, 1 H) 4.82-4.98 (m, 1 H) 3.85 (d, J = 12.8 Hz, 1 H) 3.38 (t, J = 6.6 Hz, 2 H) 3.23 (s, 3 H) 2.84 (d, J = 11.6 Hz, 2 H) 2.74 (td, J = 13.1, 2.1 Hz, 2 H) 2.72 (spt, J = 6.4 Hz, 1 H) 2.27 (td, J = 11.5, 2.0 Hz, 2 H) 2.00 (d, J = 9.2 Hz, 2 H) 1.73 (d, J = 11.3 Hz, 2 H) 1.60 (qd, J = 11.7, 3.4 Hz, 2 H) 1.52-1.58 (m, 1 H) 1.47 (q, J = 6.6 Hz, 2 H) 1.22 (qd, J = 12.1, 3.2 Hz, 2 H) 1.01 (d, J = 6.4 Hz, 6 H). |
| 286 | 497 | 12.93 (br. s., 1 H) 7.96 (d, J = 8.9 Hz, 2 H) 7.87 (s, 1 H) 7.04 (d, J = 9.2 Hz, 2 H) 5.68 (d, J = 8.9 Hz, 1 H) 4.86-4.97 (m, 1 H) 3.85 (d, J = 12.8 Hz, 2 H) 3.42 (t, J = 6.6 Hz, 2 H) 3.40 (q, J = 7.0 Hz, 2 H) 2.81 (d, J = 11.9 Hz, 2 H) 2.75 (td, J = 12.4, 2.3 Hz, 2 H) 2.21 (s, 3 H) 2.05 (td, J = 11.6, 1.8 Hz, 2 H) 1.97 (d, J = 12.2 Hz, 2 H) 1.73 (d, J = 11.3 Hz, 2 H) 1.66 (qd, J = 11.7, 3.7 Hz, 2 H) 1.53-1.61 (m, 1 H) 1.46 (q, J = 6.7 Hz, 2 H) 1.22 (qd, J = 12.2, 4.0 Hz, 2 H) 1.10 (t, J = 7.0 Hz, 3 H). |
| 287 | 541 | 12.96 (br. s., 1 H) 7.96 (s, 1 H) 7.96 (d, J = 9.2 Hz, 2 H) 7.04 (d, J = 9.2 Hz, 2 H) 5.40 (d, J = 8.9 Hz, 1 H) 4.88-4.97 (m, 1 H) 3.86 (d, J = 12.8 Hz, 2 H) 3.42 (t, J = 6.6 Hz, 2 H) 3.40 (q, J = 6.7 Hz, 2 H) 2.79 (d, J = 11.3 Hz, 2 H) 2.75 (td, J = 12.6, 2.3 Hz, 2 H) 2.21 (s, 3 H) 2.07 (t, J = 10.7 Hz, 2 H) 1.99 (d, J = 12.8 Hz, 2 H) 1.73 (d, J = 11.3 Hz, 2 H) 1.64 (qd, J = 11.6, 3.1 Hz, 2 H) 1.53-1.60 (m, 1 H) 1.46 (q, J = 6.7 Hz, 2 H) 1.22 (qd, J = 12.1, 3.7 Hz, 2 H) 1.10 (t, J = 7.0 Hz, 3 H). |
| 288 | 511 | 12.93 (s, 1 H) 7.95 (d, J = 8.9 Hz, 2 H) 7.87 (s, 1 H) 7.04 (d, J = 8.9 Hz, 2 H) 5.67 (d, J = 8.9 Hz, 1 H) 4.88-4.98 (m, 1 H) 3.85 (d, J = 12.8 Hz, 2 H) 3.42 (t, J = 6.6 Hz, 2 H) 3.40 (q, J = 7.0 Hz, 2 H) 2.92 (d, J = 11.3 Hz, 2 H) 2.75 (td, J = 12.4, 2.0 Hz, 2 H) 2.36 (q, J = 7.1 Hz, 2 H) 2.04 (t, J = 11.7 Hz, 2 H) 1.99 (d, J = 12.2 Hz, 2 H) 1.73 (d, J = 11.3 Hz, 2 H) 1.64 (qd, J = 11.6, 3.7 Hz, 2 H) 1.53-1.60 (m, 1 H) 1.46 (q, J = 6.6 Hz, 2 H) 1.22 (qd, J = 12.2, 3.7 Hz, 2 H) 1.10 (t, J = 7.0 Hz, 3 H) 1.03 (t, J = 7.2 Hz, 3 H). |
| 289 | 555 | 12.96 (br. s., 1 H) 7.97 (s, 1 H) 7.96 (d, J = 9.2 Hz, 2 H) 7.04 (d, J = 9.2 Hz, 2 H) 5.39 (d, J = 8.9 Hz, 1 H) 4.89-4.99 (m, 1 H) 3.85 (d, J = 12.8 Hz, 2 H) 3.42 (t, J = 6.6 Hz, 2 H) 3.40 (q, J = 7.0 Hz, 2 H) 2.90 (d, J = 11.3 Hz, 2 H) 2.75 (td, J = 12.4, 2.1 Hz, 2 H) 2.36 (q, J = 7.0 Hz, 2 H) 2.06 (t, J = 11.6 Hz, 2 H) 2.01 (d, J = 11.9 Hz, 2 H) 1.73 (d, J = 11.6 Hz, 2 H) 1.62 (qd, J = 11.3, 3.4 Hz, 2 H) 1.53-1.58 (m, 1 H) 1.46 (q, J = 6.5 Hz, 2 H) 1.22 (qd, J = 12.2, 3.8 Hz, 2 H) 1.10 (t, J = 7.0 Hz, 3 H) 1.03 (t, J = 7.2 Hz, 3 H). |
| 290 | 525 | 12.93 (br. s., 1 H) 7.95 (d, J = 8.9 Hz, 2 H) 7.87 (s, 1 H) 7.04 (d, J = 9.2 Hz, 2 H) 5.62 (d, J = 8.9 Hz, 1 H) 4.84-4.94 (m, 1 H) 3.85 (d, J = 12.5 Hz, 2 H) 3.42 (t, J = 6.6 Hz, 2 H) 3.40 (q, J = 7.0 Hz, 2 H) 2.84 (d, J = 11.6 Hz, 2 H) 2.74 (td, J = 12.8, 2.4 Hz, 2 H) 2.72 (spt, J = 6.4 Hz, 1 H) 2.27 (td, J = 11.4, 1.5 Hz, 2 H) 2.00 (d, J = 9.8 Hz, 2 H) 1.73 (d, J = 11.3 Hz, 2 H) 1.60 (qd, J = 11.4, 3.5 Hz, 2 H) 1.53-1.56 (m, 1 H) 1.46 (q, J = 6.5 Hz, 2 H) 1.22 (qd, J = 12.2, 3.8 Hz, 2 H) 1.10 (t, J = 7.0 Hz, 3 H) 1.01 (d, J = 6.7 Hz, 6 H). |
| 291 | 530 | 12.99 (br. s., 1 H) 7.99-8.03 (m, 2 H) 7.88 (s, 1 H) 7.32-7.37 (m, 2 H) 7.26-7.30 (m, 3 H) 7.05-7.10 (m, 2 H) 5.71 (d, J = 8.85 Hz, 1 H) 4.87-4.96 (m, 1 H) 4.61 (s, 2 H) 4.02 (s, 2 H) 3.58-3.63 (m, 2 H) 3.36-3.41 (m, 2 H) 2.78-2.85 (m, 2 H) 2.21 (s, 3 H) 2.06 (td, J = 11.67, 1.91 Hz, 2 H) 1.94-2.00 (m, 2 H) 1.67 (dtd, J = 11.83, 11.67, 3.74 Hz, 2 H). |
| 292 | 574 | 13.02 (br. s., 1 H) 7.99-8.03 (m, 2 H) 7.98 (s, 1 H) 7.32-7.37 (m, 2 H) 7.26-7.30 (m, 3 H) 7.05-7.10 (m, 2 H) 5.42 (d, J = 8.85 Hz, 1 H) 4.88-4.97 (m, 1 H) 4.61 (s, 2 H) 4.02 (s, 2 H) 3.58-3.63 (m, 2 H) 3.36-3.41 (m, 2 H) 2.76-2.84 (m, 2 H) 2.21 (s, 3 H) 2.04-2.12 (m, 2 H) 1.95-2.03 (m, 2 H) 1.65 (qd, J = 11.60, 3.36 Hz, 2 H). |

TABLE 2-continued

| Ex | m/z | ¹H NMR (600 MHz, DMSO-d$_6$) δ ppm |
|---|---|---|
| 293 | 544 | 12.99 (br. s., 1 H) 7.98-8.03 (m, 2 H) 7.88 (s, 1 H) 7.32-7.37 (m, 2 H) 7.26-7.30 (m, 3 H) 7.04-7.10 (m, 2 H) 5.70 (d, J = 8.85 Hz, 1 H) 4.89-4.97 (m, 1 H) 4.61 (s, 2 H) 4.01 (s, 2 H) 3.58-3.63 (m, 2 H) 3.36-3.41 (m, 2 H) 2.88-2.96 (m, 2 H) 2.36 (q, J = 7.17 Hz, 2 H) 2.00-2.07 (m, 2 H) 1.97-2.02 (m, 2 H) 1.64 (dtd, J = 11.75, 11.56, 3.74 Hz, 2 H) 1.03 (t, J = 7.17 Hz, 3 H). |
| 294 | 588 | 13.01 (br. s., 1 H) 7.98-8.03 (m, 2 H) 7.98 (s, 1 H) 7.32-7.37 (m, 2 H) 7.25-7.30 (m, 3 H) 7.04-7.10 (m, 2 H) 5.41 (d, J = 9.00 Hz, 1 H) 4.89-4.99 (m, 1 H) 4.61 (s, 2 H) 4.02 (s, 2 H) 3.58-3.63 (m, 2 H) 3.36-3.41 (m, 2 H) 2.87-2.93 (m, 2 H) 2.36 (q, J = 7.17 Hz, 2 H) 2.03-2.10 (m, 2 H) 1.98-2.04 (m, 2 H) 1.62 (qd, J = 11.34, 3.36 Hz, 2 H) 1.03 (t, J = 7.17 Hz, 3 H). |
| 295 | 636 | 12.98 (br. s., 1 H) 7.98-8.02 (m, 2 H) 7.87 (s, 1 H) 7.33-7.38 (m, 2 H) 7.26-7.31 (m, 3 H) 7.21-7.26 (m, 2 H) 7.05-7.09 (m, 2 H) 6.87-6.92 (m, 2 H) 5.71 (d, J = 9.00 Hz, 1 H) 4.92-5.00 (m, 1 H) 4.62 (s, 2 H) 4.02 (s, 2 H) 3.74 (s, 3 H) 3.58-3.64 (m, 2 H) 3.44 (s, 2 H) 3.37-3.42 (m, 2 H) 2.81-2.89 (m, 2 H) 2.06-2.15 (m, 2 H) 1.93-2.01 (m, 2 H) 1.65 (qd, J = 11.67, 3.28 Hz, 2 H). |
| 296 | 454 | 12.95-13.02 (m, 1 H) 7.98-8.03 (m, 2 H) 7.88 (s, 1 H) 7.05-7.10 (m, 2 H) 5.71 (d, J = 8.85 Hz, 1 H) 4.87-4.96 (m, 1 H) 3.89 (s, 2 H) 3.59-3.64 (m, 2 H) 3.43-3.47 (m, 2 H) 2.91 (s, 3 H) 2.78-2.85 (m, 2 H) 2.21 (s, 3 H) 2.02-2.10 (m, 2 H) 1.94-2.00 (m, 2 H) 1.67 (dtd, J = 11.79, 11.65, 3.51 Hz, 2 H). |
| 297 | 498 | 13.01 (s, 1 H) 7.99-8.03 (m, 2 H) 7.98 (s, 1 H) 7.05-7.10 (m, 2 H) 5.43 (d, J = 8.70 Hz, 1 H) 4.88-4.96 (m, 1 H) 3.89 (s, 2 H) 3.59-3.64 (m, 2 H) 3.43-3.48 (m, 2 H) 2.91 (s, 3 H) 2.76-2.83 (m, 2 H) 2.21 (s, 3 H) 2.04-2.12 (m, 2 H) 1.96-2.02 (m, 2 H) 1.65 (qd, J = 11.44, 3.51 Hz, 2 H). |
| 298 | 468 | 12.98 (br. s., 1 H) 7.98-8.03 (m, 2 H) 7.88 (s, 1 H) 7.05-7.09 (m, 2 H) 5.70 (d, J = 8.85 Hz, 1 H) 4.89-4.97 (m, 1 H) 3.89 (s, 2 H) 3.60-3.63 (m, 2 H) 3.43-3.47 (m, 2 H) 2.91 (s, 3 H) 2.89-2.95 (m, 2 H) 2.36 (q, J = 7.17 Hz, 2 H) 2.04 (td, J = 11.83, 1.98 Hz, 2 H) 1.96-2.03 (m, 2 H) 1.64 (dtd, J = 11.83, 11.60, 3.59 Hz, 2 H) 1.03 (t, J = 7.17 Hz, 3 H). |
| 299 | 512 | 13.01 (br. s., 1 H) 7.99-8.03 (m, 2 H) 7.98 (s, 1 H) 7.05-7.10 (m, 2 H) 5.41 (d, J = 8.85 Hz, 1 H) 4.89-4.98 (m, 1 H) 3.89 (s, 2 H) 3.59-3.63 (m, 2 H) 3.43-3.48 (m, 2 H) 2.91 (s, 3 H) 2.87-2.93 (m, 2 H) 2.36 (q, J = 7.17 Hz, 2 H) 2.03-2.10 (m, 2 H) 1.98-2.04 (m, 2 H) 1.62 (qd, J = 11.55, 3.50 Hz, 2 H) 1.03 (t, J = 7.17 Hz, 3 H). |
| 300 | 560 | 12.98 (br. s., 1 H) 7.98-8.02 (m, 2 H) 7.87 (s, 1 H) 7.22-7.26 (m, 2 H) 7.05-7.09 (m, 2 H) 6.88-6.92 (m, 2 H) 5.70 (d, J = 8.85 Hz, 1 H) 4.92-5.00 (m, 1 H) 3.90 (s, 2 H) 3.74 (s, 3 H) 3.60-3.64 (m, 2 H) 3.45-3.48 (m, 2 H) 3.44 (s, 2 H) 2.92 (s, 3 H) 2.82-2.89 (m, 2 H) 2.10 (td, J = 11.67, 1.30 Hz, 2 H) 1.94-2.01 (m, 2 H) 1.60-1.69 (m, J = 11.90, 11.67, 11.67, 3.66 Hz, 2 H). |
| 301 | 531 | 12.99 (br. s., 1 H) 8.68 (dd, J = 4.88, 1.67 Hz, 1 H) 8.67 (dd, J = 2.15, 0.76 Hz, 1 H) 7.99-8.03 (m, 2 H) 7.90 (ddd, J = 7.78, 2.15, 1.67 Hz, 1 H) 7.88 (s, 1 H) 7.51 (ddd, J = 7.78, 4.88, 0.76 Hz, 1 H) 7.08-7.13 (m, 2 H) 5.71 (d, J = 8.54 Hz, 1 H) 4.87-4.95 (m, 1 H) 3.79 (br. m., 2 H) 3.50 (br. m., 2 H) 3.41 (br. m., 2 H) 3.32 (br. m., 2 H) 2.77-2.85 (m, 2 H) 2.20 (s, 3 H) 2.05 (td, J = 11.60, 1.60 Hz, 2 H) 1.93-2.00 (m, 2 H) 1.67 (dtd, J = 11.83, 11.60, 3.81 Hz, 2 H). |
| 302 | 575 | 13.02 (br. s., 1 H) 8.68 (dd, J = 4.88, 1.68 Hz, 1 H) 8.67 (dd, J = 2.17, 0.76 Hz, 1 H) 7.99-8.03 (m, 2 H) 7.98 (s, 1 H) 7.90 (ddd, J = 7.81, 2.17, 1.68 Hz, 1 H) 7.51 (ddd, J = 7.81, 4.88, 0.76 Hz, 1 H) 7.08-7.13 (m, 2 H) 5.43 (d, J = 8.54 Hz, 1 H) 4.88-4.96 (m, 1 H) 3.79 (br. m., 2 H) 3.50 (br. m., 2 H) 3.41 (br. m., 2 H) 3.34 (br. m., 2 H) 2.76-2.83 (m, 2 H) 2.21 (s, 3 H) 2.04-2.11 (m, 2 H) 1.96-2.02 (m, 2 H) 1.65 (dtd J = 11.60, 11.44, 3.20 Hz, 2 H). |
| 303 | 545 | 12.99 (br. s., 1 H) 8.68 (dd, J = 4.88, 1.68 Hz, 1 H) 8.67 (dd, J = 2.15, 0.90 Hz, 1 H) 7.98-8.03 (m, 2 H) 7.90 (ddd, J = 7.78, 2.15, 1.68 Hz, 1 H) 7.88 (s, 1 H) 7.51 (ddd, J = 7.78, 4.88, 0.76 Hz, 1 H) 7.07-7.12 (m, 2 H) 5.70 (d, J = 8.85 Hz, 1 H) 4.89-4.98 (m, 1 H) 3.80 (br. m., 2 H) 3.49 (br. m., 2 H) 3.41 (br. m., 2 H) 3.32 (br. m., 2 H) 2.89-2.96 (m, 2 H) 2.35 (q, J = 7.27 Hz, 2 H) 2.00-2.07 (m, 2 H) 1.96-2.03 (m, 2 H) 1.64 (qd, J = 11.60, 3.20 Hz, 2 H) 1.02 (t, J = 7.17 Hz, 3 H). |
| 304 | 589 | 13.02 (br. s., 1 H) 8.68 (dd, J = 4.88, 1.71 Hz, 1 H) 8.67 (dd, J = 2.19, 0.91 Hz, 1 H) 7.99-8.03 (m, 2 H) 7.98 (s, 1 H) 7.90 (ddd, J = 7.78, 2.19, 1.71 Hz, 1 H) 7.51 (ddd, J = 7.78, 4.88, 0.91 Hz, 1 H) 7.08-7.13 (m, 2 H) 5.42 (d, J = 8.85 Hz, 1 H) 4.90-4.98 (m, 1 H) 3.80 (br. m., 2 H) 3.49 (br. m., 2 H) 3.41 (br. m., 2 H) 3.32 (br. m., 2 H) 2.86-2.94 (m, 2 H) 2.36 (q, J = 7.17 Hz, 2 H) 2.03-2.10 (m, 2 H) 1.98-2.05 (m, 2 H) 1.62 (qd, J = 11.50, 3.50 Hz, 2 H) 1.02 (t, J = 7.17 Hz, 3 H). |
| 305 | 637 | 12.99 (br. s., 1 H) 8.68 (dd, J = 4.92, 1.70 Hz, 1 H) 8.68 (dd, J = 2.15, 0.93 Hz, 1 H) 7.97-8.02 (m, 2 H) 7.90 (ddd, J = 7.82, 2.15, 1.70 Hz, 1 H) 7.88 (s, 1 H) 7.52 (ddd, J = 7.82, 4.92, 0.93 Hz, 1 H) 7.21-7.25 (m, 2 H) 7.07-7.12 (m, 2 H) 6.87-6.91 (m, 2 H) 5.72 (d, J = 9.31 Hz, 1 H) 4.92-5.00 (m, 1 H) 3.80 (br. m., 2 H) 3.74 (s, 3 H) 3.50 (br. m., 2 H) 3.44 (s, 2 H) 3.42 (br. m., 2 H) 3.32 (br. m., 2 H) 2.82-2.89 (m, 2 H) 2.06-2.14 (m, 2 H) 1.94-2.01 (m, 2 H) 1.65 (qd, J = 11.60, 3.50 Hz, 2 H). |
| 306 | 526 | 12.96 (br. s., 1 H) 7.95-8.00 (m, 2 H) 7.88 (s, 1 H) 7.03-7.08 (m, 2 H) 5.68 (d, J = 8.85 Hz, 1 H) 4.89-4.97 (m, 1 H) 3.36 (t, J = 6.40 Hz, 2 H) 3.23-3.28 (m, 4 H) 3.23 (s, 3 H) 2.87-2.94 (m, 2 H) 2.48-2.51 (m, 4 H) 2.34-2.39 (m, 2 H) 2.24-2.30 (m, 2 H) 2.04 (td, J = 11.60, 1.98 Hz, 2 H) 1.95-2.01 (m, 2 H) 1.66-1.73 (m, 2 H) 1.64 (qd, J = 11.60, 3.28 Hz, 2 H) 1.42-1.50 (m, 2 H) 0.87 (t, J = 7.40 Hz, 3 H). |
| 307 | 570 | 12.99 (br. s., 1 H) 7.97 (s, 1 H) 7.96-7.99 (m, 2 H) 7.03-7.08 (m, 2 H) 5.40 (d, J = 8.85 Hz, 1 H) 4.90-4.98 (m, 1 H) 3.36 (t, J = 6.41 Hz, 2 H) 3.23-3.28 (m, 4 H) 3.23 (s, 3 H) 2.84-2.91 (m, 2 H) 2.48-2.50 (m, 4 H) 2.34-2.39 (m, 2 H) 2.24-2.29 (m, 2 H) 2.03-2.11 (m, 2 H) 1.97-2.03 (m, 2 H) 1.66-1.73 (m, 2 H) 1.62 (dtd, J = 11.60, 11.48, 3.28 Hz, 2 H) 1.42-1.50 (m, 2 H) 0.87 (t, J = 7.32 Hz, 3 H). |

TABLE 2-continued

| Ex | m/z | $^1$H NMR (600 MHz, DMSO-$d_6$) δ ppm |
|---|---|---|
| 308 | 542 | 12.96 (br. s., 1 H) 7.95-8.00 (m, 2 H) 7.88 (s, 1 H) 7.03-7.08 (m, 2 H) 5.70 (d, J = 8.70 Hz, 1 H) 4.88-4.97 (m, 1 H) 3.45 (t, J = 5.87 Hz, 2 H) 3.36 (t, J = 6.49 Hz, 2 H) 3.25 (s, 3 H) 3.23-3.28 (m, 4 H) 3.23 (s, 3 H) 2.90-2.96 (m, 2 H) 2.49-2.52 (m, 2 H) 2.48-2.51 (m, 4 H) 2.34-2.39 (m, 2 H) 2.14 (td, J = 11.70, 2.06 Hz, 2 H) 1.94-2.00 (m, 2 H) 1.66-1.73 (m, 2 H) 1.64 (qd, J = 11.70, 3.50 Hz, 2 H). |
| 309 | 540 | 12.98 (br. s., 1 H) 7.98-8.03 (m, 2 H) 7.88 (s, 1 H) 7.03-7.08 (m, 2 H) 5.69 (d, J = 8.55 Hz, 1 H) 4.89-4.98 (m, 1 H) 3.91 (s, 2 H) 3.57-3.61 (m, 2 H) 3.49-3.56 (m, 6 H) 3.43 (q, J = 7.02 Hz, 2 H) 2.88-2.93 (m, 2 H) 2.25-2.29 (m, 2 H) 2.05 (td, J = 11.70, 1.98 Hz, 2 H) 1.96-2.02 (m, 2 H) 1.64 (dtd, J = 11.94, 11.70, 3.51 Hz, 2 H) 1.46 (sxt, J = 7.39 Hz, 2 H) 1.09 (t, J = 7.02 Hz, 3 H) 0.87 (t, J = 7.40 Hz, 3 H). |
| 310 | 556 | 12.98 (br. s., 1 H) 7.98-8.03 (m, 2 H) 7.88 (s, 1 H) 7.03-7.08 (m, 2 H) 5.71 (d, J = 8.85 Hz, 1 H) 4.88-4.97 (m, 1 H) 3.91 (s, 2 H) 3.56-3.61 (m, 2 H) 3.49-3.57 (m, 6 H) 3.45 (t, J = 5.87 Hz, 2 H) 3.43 (q, J = 7.02 Hz, 2 H) 3.25 (s, 3 H) 2.91-2.97 (m, 2 H) 2.49-2.53 (m, 2 H) 2.14 (td, J = 11.70, 1.83 Hz, 2 H) 1.94-2.01 (m, 2 H) 1.65 (qd, J = 11.70, 3.66 Hz, 2 H) 1.09 (t, J = 7.02 Hz, 3 H). |
| 311 | 566 | 12.95 (br. s., 1 H) 7.98-8.02 (m, 2 H) 7.86 (s, 1 H) 7.03-7.08 (m, 2 H) 5.54-5.65 (m, 1 H) 4.84-4.94 (m, 1 H) 3.91 (s, 2 H) 3.56-3.61 (m, 2 H) 3.51-3.56 (m, 4 H) 3.47-3.51 (m, 2 H) 3.26 (s, 3 H) 2.85-2.92 (m, 2 H) 2.36 (td, J = 11.48, 1.60 Hz, 2 H) 2.26-2.33 (m, 1 H) 1.97-2.04 (m, 2 H) 1.72-1.82 (m, 4 H) 1.54-1.63 (m, 3 H) 1.17-1.29 (m, 4 H) 1.04-1.14 (m, 1 H). |
| 312 | 542 | 12.93 (br. s., 1 H) 7.96-8.00 (m, 2 H) 7.96 (s, 1 H) 7.02-7.08 (m, 2 H) 5.30-5.41 (m, 1 H) 4.90-4.99 (m, 1 H) 4.44 (t, J = 5.04 Hz, 1 H) 3.46 (td, J = 6.30, 5.04 Hz, 2 H) 3.22-3.29 (m, 4 H) 2.85-2.94 (m, 2 H) 2.48-2.51 (m, 4 H) 2.38 (t, J = 7.25 Hz, 2 H) 2.36 (q, J = 7.17 Hz, 2 H) 2.06 (td, J = 11.44, 2.14 Hz, 2 H) 1.98-2.04 (m, 2 H) 1.57-1.65 (m, 4 H) 1.03 (t, J = 7.17 Hz, 3 H). |
| 313 | 532 | 12.96 (br. s., 1 H) 8.73 (d, J = 1.5 Hz, 1 H) 8.61 (dd, J = 2.7, 1.5 Hz, 1 H) 8.56 (d, J = 2.4 Hz, 1 H) 7.98 (d, J = 8.9 Hz, 2 H) 7.88 (s, 1 H) 7.06 (d, J = 8.9 Hz, 2 H) 5.69 (d, J = 8.9 Hz, 1 H) 4.88-4.98 (m, 1 H) 3.74 (s, 2 H) 3.29 (t, J = 4.9 Hz, 4 H) 2.92 (d, J = 11.6 Hz, 2 H) 2.60 (t, J = 4.9 Hz, 4 H) 2.35 (q, J = 7.3 Hz, 2 H) 2.03 (t, J = 11.6 Hz, 2 H) 1.99 (d, J = 12.2 Hz, 2 H) 1.63 (qd, J = 11.5, 3.4 Hz, 2 H) 1.02 (t, J = 7.2 Hz, 3H). |
| 314 | 576 | 13.00 (br. s., 1 H) 8.73 (d, J = 1.2 Hz, 1 H) 8.61 (dd, J = 2.4, 1.5 Hz, 1 H) 8.56 (d, J = 2.7 Hz, 1 H) 7.97 (s, 1 H) 7.98 (d, J = 9.2 Hz, 2 H) 7.06 (d, J = 9.2 Hz, 2 H) 5.40 (d, J = 8.9 Hz, 1 H) 4.89-5.00 (m, 1 H) 3.74 (s, 2 H) 3.30 (t, J = 4.9 Hz, 4 H) 2.90 (d, J = 11.0 Hz, 2 H) 2.60 (t, J = 4.9 Hz, 4 H) 2.35 (q, J = 7.0 Hz, 2 H) 2.05 (t, J = 11.6 Hz, 2 H) 2.01 (d, J = 11.3 Hz, 2 H) 1.62 (qd, J = 11.4, 3.5 Hz, 2 H) 1.02 (t, J = 7.2 Hz, 3H). |
| 315 | 624 | 12.96 (br. s., 1 H) 8.74 (d, J = 1.5 Hz, 1 H) 8.61 (dd, J = 2.7, 1.5 Hz, 1 H) 8.57 (d, J = 2.4 Hz, 1 H) 7.97 (d, J = 8.9 Hz, 2 H) 7.87 (s, 1 H) 7.23 (d, J = 8.9 Hz, 2 H) 7.06 (d, J = 9.2 Hz, 2 H) 6.89 (d, J = 8.9 Hz, 2 H) 5.70 (d, J = 8.9 Hz, 1 H) 4.91-5.02 (m, 1 H) 3.75 (s, 2 H) 3.74 (s, 3 H) 3.44 (s, 2 H) 3.30 (t, J = 4.9 Hz, 4 H) 2.85 (d, J = 11.3 Hz, 2 H) 2.61 (t, J = 4.9 Hz, 4 H) 2.10 (t, J = 10.8 Hz, 2 H) 1.97 (d, J = 11.6 Hz, 2 H) 1.65 (qd, J = 11.6, 3.4 Hz, 2 H). |
| 316 | 537 | 12.96 (s, 1 H) 9.06 (d, J = 1.8 Hz, 1 H) 7.97 (d, J = 8.9 Hz, 2 H) 7.88 (s, 1 H) 7.56 (d, J = 1.8 Hz, 1 H) 7.05 (d, J = 9.2 Hz, 2 H) 5.69 (d, J = 8.9 Hz, 1 H) 4.87-4.99 (m, 1 H) 3.73 (s, 2 H) 3.28 (t, J = 5.2 Hz, 4 H) 2.92 (d, J = 11.3 Hz, 2 H) 2.59 (t, J = 4.9 Hz, 4 H) 2.35 (q, J = 7.0 Hz, 2 H) 2.03 (t, J = 11.9 Hz, 2 H) 1.99 (d, J = 11.6 Hz, 2 H) 1.63 (qd, J = 11.6, 3.7 Hz, 2 H) 1.02 (t, J = 7.2 Hz, 3 H). |
| 317 | 581 | 12.99 (br. s., 1 H) 9.06 (d, J = 1.8 Hz, 1 H) 7.97 (s, 1 H) 7.97 (d, J = 8.9 Hz, 2 H) 7.56 (d, J = 1.8 Hz, 1 H) 7.06 (d, J = 9.2 Hz, 2 H) 5.40 (d, J = 8.9 Hz, 1 H) 4.89-4.98 (m, 1 H) 3.73 (s, 2 H) 3.28 (t, J = 5.2 Hz, 4 H) 2.90 (d, J = 11.3 Hz, 2 H) 2.59 (t, J = 4.9 Hz, 4 H) 2.35 (q, J = 7.2 Hz, 2 H) 2.05 (t, J = 11.6 Hz, 2 H) 2.01 (d, J = 11.6 Hz, 2 H) 1.62 (qd, J = 11.4, 3.5 Hz, 2 H) 1.02 (t, J = 7.2 Hz, 3 H). |
| 318 | 629 | 12.96 (br. s., 1 H) 9.07 (d, J = 2.1 Hz, 1 H) 7.96 (d, J = 9.2 Hz, 2 H) 7.87 (s, 1 H) 7.57 (d, J = 2.1 Hz, 1 H) 7.23 (d, J = 8.5 Hz, 2 H) 7.05 (d, J = 8.9 Hz, 2 H) 6.89 (d, J = 8.5 Hz, 2 H) 5.69 (d, J = 8.5 Hz, 1 H) 4.90-5.02 (m, 1 H) 3.74 (s, 3 H) 3.73 (s, 2 H) 3.44 (s, 2 H) 3.29 (t, J = 4.9 Hz, 4 H) 2.85 (d, J = 11.6 Hz, 2 H) 2.60 (t, J = 4.9 Hz, 4 H) 2.10 (t, J = 10.8 Hz, 2 H) 1.97 (d, J = 10.1 Hz, 2 H) 1.64 (qd, J = 11.6, 3.2 Hz, 2 H). |
| 319 | 629 | 12.96 (br. s., 1 H) 9.05 (d, J = 0.6 Hz, 1 H) 7.97 (d, J = 8.9 Hz, 2 H) 7.87 (s, 1 H) 7.81 (d, J = 0.6 Hz, 1 H) 7.23 (d, J = 8.5 Hz, 2 H) 7.05 (d, J = 8.9 Hz, 2 H) 6.89 (d, J = 8.9 Hz, 2 H) 5.70 (d, J = 9.2 Hz, 1 H) 4.91-5.01 (m, 1 H) 3.83 (s, 2 H) 3.74 (s, 3 H) 3.43 (s, 2 H) 3.28 (t, J = 4.9 Hz, 4 H) 2.85 (d, J = 11.3 Hz, 2 H) 2.56 (t, J = 4.9 Hz, 4 H) 2.10 (t, J = 10.8 Hz, 2 H) 1.97 (d, J = 10.4 Hz, 2 H) 1.64 (qd, J = 11.6, 3.2 Hz, 2 H). |
| 320 | 537 | 12.97 (s, 1 H) 9.05 (d, J = 0.6 Hz, 1 H) 7.97 (d, J = 9.2 Hz, 2 H) 7.88 (s, 1 H) 7.81 (d, J = 0.6 Hz, 1 H) 7.06 (d, J = 8.9 Hz, 2 H) 5.69 (d, J = 8.9 Hz, 1 H) 4.87-4.98 (m, 1 H) 3.82 (s, 2 H) 3.27 (t, J = 5.2 Hz, 4 H) 2.92 (d, J = 11.3 Hz, 2 H) 2.55 (t, J = 4.9 Hz, 4 H) 2.35 (q, J = 7.0 Hz, 2 H) 2.03 (t, J = 11.9 Hz, 2 H) 1.99 (d, J = 12.2 Hz, 2 H) 1.63 (qd, J = 11.6, 3.7 Hz, 2 H) 1.02 (t, J = 7.2 Hz, 3 H). |
| 321 | 581 | 13.00 (br. s., 1 H) 9.05 (d, J = 0.6 Hz, 1 H) 7.97 (s, 1 H) 7.97 (d, J = 8.9 Hz, 2 H) 7.81 (d, J = 0.6 Hz, 1 H) 7.06 (d, J = 9.2 Hz, 2 H) 5.40 (d, J = 8.9 Hz, 1 H) 4.89-4.99 (m, 1 H) 3.82 (s, 2 H) 3.27 (t, J = 5.2 Hz, 4 H) 2.90 (d, J = 11.0 Hz, 2 H) 2.55 (t, J = 4.6 Hz, 4 H) 2.35 (q, J = 7.3 Hz, 2 H) 2.05 (t, J = 11.7 Hz, 2 H) 2.01 (d, J = 10.7 Hz, 2 H) 1.62 (qd, J = 11.5, 3.5 Hz, 2 H) 1.02 (t, J = 7.2 Hz, 3 H). |
| 322 | 549 | 7.98 (d, J = 8.9 Hz, 2 H) 7.88 (s, 1 H) 7.08 (d, J = 1.8 Hz, 1 H) 7.07 (d, J = 8.5 Hz, 2 H) 5.70 (d, J = 8.9 Hz, 1 H) 5.37 (d, J = 1.8 Hz, 1 H) 5.25 (t, J = 5.8 Hz, 1 H) 4.87-4.97 (m, 1 H) 3.51 (s, 3 H) 3.28 (t, J = 4.6 Hz, 4 H) 3.12 (q, J = 6.7 Hz, 2 H) 2.81 (d, |

TABLE 2-continued

| Ex | m/z | $^1$H NMR (600 MHz, DMSO-$d_6$) δ ppm |
|---|---|---|
| | | J = 11.9 Hz, 2 H) 2.58 (t, J = 5.8 Hz, 4 H) 2.56 (t, J = 6.7 Hz, 2 H) 2.21 (s, 3 H) 2.05 (td, J = 11.6, 2.1 Hz, 2 H) 1.97 (d, J = 11.9 Hz, 2 H) 1.66 (qd, J = 11.7, 3.7 Hz, 2 H). |
| 323 | 593 | 12.99 (br. s., 1 H) 7.99 (d, J = 9.2 Hz, 2 H) 7.97 (s, 1 H) 7.07 (d, J = 1.8 Hz, 1 H) 7.07 (d, J = 8.2 Hz, 2 H) 5.41 (d, J = 8.9 Hz, 1 H) 5.37 (d, J = 1.8 Hz, 1 H) 5.25 (t, J = 5.8 Hz, 1 H) 4.88-4.97 (m, 1 H) 3.51 (s, 3 H) 3.28 (t, J = 4.6 Hz, 4 H) 3.12 (q, J = 6.7 Hz, 2 H) 2.79 (d, J = 11.3 Hz, 2 H) 2.58 (t, J = 5.8 Hz, 4 H) 2.56 (t, J = 6.7 Hz, 2 H) 2.21 (s, 3 H) 2.07 (td, J = 11.5, 1.8 Hz, 2 H) 1.99 (d, J = 10.7 Hz, 2 H) 1.64 (qd, J = 11.4, 3.7 Hz, 2 H). |
| 324 | 563 | 12.97 (s, 1 H) 7.98 (d, J = 8.8 Hz, 2 H) 7.88 (s, 1 H) 7.07 (d, J = 1.8 Hz, 1 H) 7.07 (d, J = 8.9 Hz, 2 H) 5.69 (d, J = 8.9 Hz, 1 H) 5.37 (d, J = 1.8 Hz, 1 H) 5.25 (t, J = 5.8 Hz, 1 H) 4.88-4.99 (m, 1 H) 3.51 (s, 3 H) 3.28 (t, J = 4.9 Hz, 4 H) 3.12 (q, J = 6.7 Hz, 2 H) 2.92 (d, J = 11.6 Hz, 2 H) 2.58 (t, J = 5.8 Hz, 4 H) 2.56 (t, J = 6.7 Hz, 2 H) 2.36 (q, J = 7.3 Hz, 2 H) 2.03 (t, J = 11.9 Hz, 2 H) 1.99 (d, J = 11.9 Hz, 2 H) 1.64 (qd, J = 11.6, 3.7 Hz, 2 H) 1.03 (t, J = 7.2 Hz, 3 H). |
| 325 | 607 | 13.00 (br. s., 1 H) 7.98 (d, J = 8.9 Hz, 2 H) 7.97 (s, 1 H) 7.07 (d, J = 1.8 Hz, 1 H) 7.07 (d, J = 8.9 Hz, 2 H) 5.40 (d, J = 8.9 Hz, 1 H) 5.37 (d, J = 1.8 Hz, 1 H) 5.25 (t, J = 5.8 Hz, 1 H) 4.89-4.99 (m, 1 H) 3.51 (s, 3 H) 3.28 (t, J = 4.6 Hz, 4 H) 3.12 (q, J = 6.7 Hz, 2 H) 2.90 (d, J = 11.3 Hz, 2 H) 2.58 (t, J = 5.8 Hz, 4 H) 2.56 (t, J = 6.7 Hz, 2 H) 2.36 (q, J = 7.2 Hz, 2 H) 2.06 (t, J = 11.6 Hz, 2 H) 2.01 (d, J = 10.7 Hz, 2 H) 1.62 (qd, J = 11.4, 3.5 Hz, 2 H) 1.03 (t, J = 7.2 Hz, 3 H). |
| 326 | 577 | 12.97 (br. s., 1 H) 7.98 (d, J = 9.2 Hz, 2 H) 7.87 (s, 1 H) 7.07 (d, J = 1.8 Hz, 1 H) 7.07 (d, J = 9.2 Hz, 2 H) 5.63 (d, J = 8.9 Hz, 1 H) 5.37 (d, J = 1.8 Hz, 1 H) 5.25 (t, J = 5.8 Hz, 1 H) 4.84-4.97 (m, 1 H) 3.51 (s, 3 H) 3.28 (t, J = 4.6 Hz, 4 H) 3.12 (q, J = 6.7 Hz, 2 H) 2.85 (d, J = 11.6 Hz, 2 H) 2.72 (spt, J = 6.5 Hz, 1 H) 2.58 (t, J = 4.9 Hz, 4 H) 2.56 (t, J = 6.7 Hz, 2 H) 2.27 (td, J = 11.4, 1.7 Hz, 2 H) 2.01 (d, J = 10.1 Hz, 2 H) 1.60 (qd, J = 11.4, 3.5 Hz, 2 H) 1.01 (d, J = 6.4 Hz, 6 H). |
| 327 | 655 | 12.96 (br. s., 1 H) 7.97 (d, J = 8.9 Hz, 2 H) 7.87 (s, 1 H) 7.23 (d, J = 8.5 Hz, 2 H) 7.08 (d, J = 1.8 Hz, 1 H) 7.06 (d, J = 8.9 Hz, 2 H) 6.89 (d, J = 8.9 Hz, 2 H) 5.68 (d, J = 8.2 Hz, 1 H) 5.38 (d, J = 1.8 Hz, 1 H) 5.26 (t, J = 5.6 Hz, 1 H) 4.91-5.01 (m, 1 H) 3.74 (s, 3 H) 3.51 (s, 3 H) 3.44 (s, 2 H) 3.29 (t, J = 4.3 Hz, 4 H) 3.13 (q, J = 6.7 Hz, 2 H) 2.85 (d, J = 11.6 Hz, 2 H) 2.59 (t, J = 4.6 Hz, 4 H) 2.57 (t, J = 7.3 Hz, 2 H) 2.10 (td, J = 11.5, 1.8 Hz, 2 H) 1.97 (d, J = 9.8 Hz, 2 H) 1.64 (qd, J = 11.7, 2.9 Hz, 2 H). |
| 328 | 531 | 13.00 (s, 1 H) 8.68-8.72 (m, 2 H) 7.98-8.03 (m, 2 H) 7.88 (s, 1 H) 7.43-7.46 (m, 2 H) 7.07-7.12 (m, 2 H) 5.73 (d, J = 8.70 Hz, 1 H) 4.87-4.96 (m, 1 H) 3.74-3.82 (m, 2 H) 3.37-3.47 (m, 4 H) 3.27-3.32 (m, 2 H) 2.79-2.87 (m, 2 H) 2.22 (s, 3 H) 2.02-2.14 (m, 2 H) 1.94-2.01 (m, 2 H) 1.67 (qd, J = 11.62, 3.28 Hz, 2 H). |
| 329 | 575 | 13.03 (s, 1 H) 8.68-8.72 (m, 2 H) 7.98-8.03 (m, 2 H) 7.98 (s, 1 H) 7.43-7.47 (m, 2 H) 7.07-7.13 (m, 2 H) 5.45 (d, J = 8.70 Hz, 1 H) 4.88-4.97 (m, 1 H) 3.75-3.81 (m, 2 H) 3.38-3.46 (m, 4 H) 3.27-3.32 (m, 2 H) 2.75-2.88 (m, 2 H) 2.23 (br. s., 3 H) 2.04-2.18 (m, 2 H) 1.96-2.04 (m, 2 H) 1.66 (dtd, J = 11.56, 11.39, 3.51 Hz, 2 H). |
| 330 | 545 | 13.00 (s, 1 H) 8.68-8.72 (m, 2 H) 7.98-8.03 (m, 2 H) 7.89 (s, 1 H) 7.43-7.47 (m, 2 H) 7.06-7.12 (m, 2 H) 5.72 (d, J = 7.63 Hz, 1 H) 4.88-4.98 (m, 1 H) 3.75-3.82 (m, 2 H) 3.38-3.45 (m, 4 H) 3.27-3.32 (m, 2 H) 2.86-3.00 (m, 2 H) 2.29-2.43 (m, 2 H) 1.97-2.10 (m, 2 H) 1.96-2.04 (m, 2 H) 1.59-1.70 (m, 2 H) 1.03 (t, J = 7.17 Hz, 3 H). |
| 331 | 589 | 13.03 (s, 1 H) 8.68-8.72 (m, 2 H) 7.98-8.03 (m, 2 H) 7.98 (s, 1 H) 7.43-7.46 (m, 2 H) 7.07-7.13 (m, 2 H) 5.43 (d, J = 8.70 Hz, 1 H) 4.89-4.99 (m, 1 H) 3.73-3.83 (m, 2 H) 3.37-3.47 (m, 4 H) 3.27-3.32 (m, 2 H) 2.83-2.98 (m, 2 H) 2.29-2.43 (m, 2 H) 2.00-2.14 (m, 2 H) 1.98-2.06 (m, 2 H) 1.57-1.69 (m, 2 H) 1.03 (t, J = 7.17 Hz, 3 H). |
| 332 | 479 | 12.98 (br. s., 1 H) 7.96-8.00 (m, 2 H) 7.87 (s, 1 H) 7.06-7.10 (m, 2 H) 5.73 (d, J = 8.39 Hz, 1 H) 4.87-4.95 (m, 1 H) 3.25-3.30 (m, 4 H) 2.78-2.85 (m, 2 H) 2.73 (t, J = 6.71 Hz, 2 H) 2.62 (t, J = 6.71 Hz, 2 H) 2.55-2.60 (m, 4 H) 2.20 (s, 3 H) 2.04 (td, J = 11.64, 1.60 Hz, 2 H) 1.93-2.00 (m, 2 H) 1.66 (dtd, J = 11.83, 11.64, 3.66 Hz, 2 H). |
| 333 | 523 | 13.00 (br. s., 1 H) 7.97 (s, 1 H) 7.96-8.00 (m, 2 H) 7.05-7.11 (m, 2 H) 5.44 (d, J = 8.70 Hz, 1 H) 4.88-4.96 (m, 1 H) 3.25-3.30 (m, 4 H) 2.76-2.83 (m, 2 H) 2.73 (t, J = 6.64 Hz, 2 H) 2.62 (t, J = 6.64 Hz, 2 H) 2.55-2.60 (m, 4 H) 2.20 (s, 3 H) 2.02-2.11 (m, 2 H) 1.95-2.01 (m, 2 H) 1.65 (qd, J = 11.55, 3.51 Hz, 2 H). |
| 334 | 493 | 12.99 (br. s., 1 H) 7.95-8.00 (m, 2 H) 7.88 (s, 1 H) 7.06-7.10 (m, 2 H) 5.72 (d, J = 8.70 Hz, 1 H) 4.88-4.97 (m, 1 H) 3.25-3.30 (m, 4 H) 2.89-2.95 (m, 2 H) 2.73 (t, J = 6.64 Hz, 2 H) 2.62 (t, J = 6.64 Hz, 2 H) 2.55-2.60 (m, 4 H) 2.35 (q, J = 7.17 Hz, 2 H) 1.99-2.06 (m, 2 H) 1.95-2.02 (m, 2 H) 1.64 (dtd, J = 11.83, 11.63, 3.66 Hz, 2 H) 1.02 (t, J = 7.17 Hz, 3 H). |
| 335 | 537 | 13.01 (br. s., 1 H) 7.97 (s, 1 H) 7.96-8.00 (m, 2 H) 7.06-7.10 (m, 2 H) 5.43 (d, J = 8.85 Hz, 1 H) 4.90-4.98 (m, 1 H) 3.25-3.30 (m, 4 H) 2.87-2.94 (m, 2 H) 2.73 (t, J = 6.71 Hz, 2 H) 2.62 (t, J = 6.71 Hz, 2 H) 2.55-2.60 (m, 4 H) 2.35 (q, J = 7.17 Hz, 2 H) 2.02-2.08 (m, 2 H) 1.97-2.04 (m, 2 H) 1.62 (qd, J = 11.50, 3.66 Hz, 2 H) 1.02 (t, J = 7.17 Hz, 3 H). |
| 336 | 585 | 12.98 (br. s., 1 H) 7.95-7.99 (m, 2 H) 7.87 (s, 1 H) 7.21-7.25 (m, 2 H) 7.05-7.10 (m, 2 H) 6.88-6.91 (m, 2 H) 5.73 (d, J = 8.70 Hz, 1 H) 4.91-5.00 (m, 1 H) 3.74 (s, 3 H) 3.44 (s, 2 H) 3.26-3.31 (m, 4 H) 2.74 (t, J = 6.71 Hz, 2 H) 2.63 (t, J = 6.71 Hz, 2 H) 2.56-2.61 (m, 4 H) 2.05-2.13 (m, 2 H) 1.93-2.00 (m, 2 H) 1.64 (qd, J = 11.57, 3.43 Hz, 2 H). |
| 337 | 551 | 13.00 (br. s., 1 H) 7.97 (s, 1 H) 7.95-8.00 (m, 2 H) 7.05-7.10 (m, 2 H) 5.38 (d, J = 9.00 Hz, 1 H) 4.86-4.95 (m, 1 H) 3.25-3.30 (m, 4 H) 2.80-2.86 (m, 2 H) 2.73 (t, J = 6.71 Hz, 2 H) 2.67-2.76 (m, 1 H) 2.62 (t, J = 6.71 Hz, 2 H) 2.54-2.60 (m, 4 |

TABLE 2-continued

| Ex | m/z | ¹H NMR (600 MHz, DMSO-$d_6$) δ ppm |
|---|---|---|
| | | H) 2.28 (td, J = 11.32, 2.14 Hz, 2 H) 1.98-2.05 (m, 2 H) 1.58 (qd, J = 11.32, 3.59 Hz, 2 H) 1.00 (d, J = 6.56 Hz, 6 H). |
| 338 | 598 | 13.01 (br. s., 1 H) 7.97-8.01 (m, 2 H) 7.97 (s, 1 H) 7.00-7.05 (m, 2 H) 5.54-5.62 (m, 1 H) 5.29 (d, J = 9.16 Hz, 1 H) 3.33-3.36 (m, 2 H) 3.23-3.27 (m, 4 H) 3.22 (s, 3 H) 2.46-2.49 (m, 4 H) 2.33-2.38 (m, 2 H) 2.22 (s, 3 H) 1.85 (dd, J = 11.98, 3.43 Hz, 2 H) 1.66-1.72 (m, 2 H) 1.48 (t, J = 11.98 Hz, 2 H) 1.18 (s, 6 H) 1.10 (s, 6 H). |
| 339 | 584 | 13.01 (br. s., 1 H) 7.97-8.00 (m, 2 H) 7.97 (s, 1 H) 7.00-7.05 (m, 2 H) 5.54-5.63 (m, 1 H) 5.29 (d, J = 9.31 Hz, 1 H) 3.47 (t, J = 5.80 Hz, 2 H) 3.25 (s, 3 H) 3.22-3.27 (m, 4 H) 2.53-2.56 (m, 4 H) 2.51 (t, J = 5.80 Hz, 2 H) 2.22 (s, 3 H) 1.85 (dd, J = 11.90, 3.51 Hz, 2 H) 1.48 (t, J = 11.90 Hz, 2 H) 1.18 (s, 6 H) 1.10 (s, 6 H). |
| 340 | 631 | 13.05 (br. s., 1 H) 8.68 (dd, J = 4.90, 1.71 Hz, 1 H) 8.67 (dd, J = 2.25, 0.93 Hz, 1 H) 7.99-8.04 (m, 2 H) 7.98 (s, 1 H) 7.90 (ddd, J = 7.79, 2.25, 1.71 Hz, 1 H) 7.51 (ddd, J = 7.79, 4.90, 0.93 Hz, 1 H) 7.04-7.09 (m, 2 H) 5.54-5.63 (m, 1 H) 5.31 (d, J = 9.31 Hz, 1 H) 3.72-3.84 (m, 2 H) 3.44-3.53 (m, 2 H) 3.37-3.45 (m, 2 H) 3.28-3.36 (m, 2 H) 2.22 (s, 3 H) 1.85 (dd, J = 11.90, 3.51 Hz, 2 H) 1.49 (t, J = 11.90 Hz, 2 H) 1.18 (s, 6 H) 1.10 (s, 6 H). |
| 341 | 649 | 13.03 (br. s., 1 H) 7.98-8.01 (m, 2 H) 7.97 (s, 1 H) 7.07 (d, J = 1.87 Hz, 1 H) 7.01-7.06 (m, 2 H) 5.54-5.62 (m, 1 H) 5.37 (d, J = 1.87 Hz, 1 H) 5.30 (d, J = 9.46 Hz, 1 H) 5.28 (t, J = 5.87 Hz, 1 H) 3.50 (s, 3 H) 3.25-3.30 (m, 4 H) 3.09-3.14 (m, 2 H) 2.55-2.59 (m, 4 H) 2.53-2.57 (m, 2 H) 2.22 (s, 3 H) 1.86 (dd, J = 11.83, 3.59 Hz, 2 H) 1.48 (t, J = 11.83 Hz, 2 H) 1.18 (s, 6 H) 1.10 (s, 6 H). |
| 342 | 611 | 13.03 (br. s., 1 H) 8.00-8.04 (m, 2 H) 7.97 (s, 1 H) 7.01-7.05 (m, 2 H) 5.54-5.63 (m, 1 H) 5.30 (d, J = 9.31 Hz, 1 H) 3.91 (s, 2 H) 3.56-3.61 (m, 2 H) 3.48-3.55 (m, 6 H) 3.42 (q, J = 6.98 Hz, 2 H) 2.22 (s, 3 H) 1.86 (dd, J = 11.98, 3.36 Hz, 2 H) 1.48 (t, J = 11.98 Hz, 2 H) 1.18 (s, 6 H) 1.10 (s, 6 H) 1.08 (t, J = 6.98 Hz, 3 H). |
| 343 | 512 | 12.98 (br. s., 1 H) 7.98 (d, J = 9.2 Hz, 2 H) 7.87 (s, 1 H) 7.06 (d, J = 9.2 Hz, 2 H) 5.73 (d, J = 8.9 Hz, 1 H) 4.86-4.98 (m, 1 H) 3.33 (t, J = 6.3 Hz, 2 H) 3.25 (t, J = 5.2 Hz, 4 H) 3.22 (s, 3 H) 2.81 (d, J = 11.3 Hz, 2 H) 2.48 (t, J = 4.9 Hz, 4 H) 2.31 (t, J = 7.0 Hz, 2 H) 2.20 (s, 3 H) 2.04 (t, J = 10.9 Hz, 2 H) 1.96 (d, J = 9.8 Hz, 2 H) 1.66 (qd, J = 11.7, 3.8 Hz, 2 H) 1.43-1.58 (m, 4 H). |
| 344 | 556 | 12.99 (br. s., 1 H) 7.98 (d, J = 9.2 Hz, 2 H) 7.97 (s, 1 H) 7.06 (d, J = 9.2 Hz, 2 H) 5.40 (d, J = 8.9 Hz, 1 H) 4.87-4.98 (m, 1 H) 3.33 (t, J = 6.1 Hz, 2 H) 3.26 (t, J = 4.9 Hz, 4 H) 3.22 (s, 3 H) 2.79 (d, J = 11.0 Hz, 2 H) 2.48 (t, J = 5.2 Hz, 4 H) 2.32 (t, J = 7.0 Hz, 2 H) 2.21 (s, 3 H) 2.07 (t, J = 10.8 Hz, 2 H) 1.99 (d, J = 10.7 Hz, 2 H) 1.64 (qd, J = 11.5, 3.5 Hz, 2 H) 1.44-1.57 (m, 4 H). |
| 345 | 526 | 12.97 (br. s., 1 H) 7.97 (d, J = 8.9 Hz, 2 H) 7.87 (s, 1 H) 7.06 (d, J = 9.2 Hz, 2 H) 5.71 (d, J = 8.9 Hz, 1 H) 4.85-5.00 (m, 1 H) 3.33 (t, J = 6.3 Hz, 2 H) 3.25 (t, J = 5.2 Hz, 4 H) 3.22 (s, 3 H) 2.92 (d, J = 11.0 Hz, 2 H) 2.48 (t, J = 4.9 Hz, 4 H) 2.35 (q, J = 7.3 Hz, 2 H) 2.31 (t, J = 7.0 Hz, 2 H) 2.02 (t, J = 11.6 Hz, 2 H) 1.99 (d, J = 11.0 Hz, 2 H) 1.63 (qd, J = 11.6, 3.7 Hz, 2 H) 1.43-1.56 (m, 4 H) 1.02 (t, J = 7.2 Hz, 3 H). |
| 346 | 570 | 13.01 (br. s., 1 H) 7.98 (d, J = 8.5 Hz, 2 H) 7.97 (s, 1 H) 7.06 (d, J = 9.2 Hz, 2 H) 5.42 (d, J = 8.5 Hz, 1 H) 4.87-5.00 (m, 1 H) 3.33 (t, J = 6.4 Hz, 2 H) 3.25 (t, J = 5.2 Hz, 4 H) 3.22 (s, 3 H) 2.90 (d, J = 11.0 Hz, 2 H) 2.48 (t, J = 4.9 Hz, 4 H) 2.35 (q, J = 7.2 Hz, 2 H) 2.31 (t, J = 7.0 Hz, 2 H) 2.05 (t, J = 12.1 Hz, 2 H) 2.01 (d, J = 11.3 Hz, 2 H) 1.62 (qd, J = 11.4, 3.7 Hz, 2 H) 1.45-1.56 (m, 4 H) 1.02 (t, J = 7.2 Hz, 3 H). |
| 347 | 618 | 12.98 (s, 1 H) 7.96 (d, J = 8.9 Hz, 2 H) 7.87 (s, 1 H) 7.23 (d, J = 8.5 Hz, 2 H) 7.06 (d, J = 9.2 Hz, 2 H) 6.89 (d, J = 8.5 Hz, 2 H) 5.73 (d, J = 8.9 Hz, 1 H) 4.92-5.00 (m, 1 H) 3.74 (s, 3 H) 3.43 (s, 2 H) 3.33 (t, J = 6.4 Hz, 2 H) 3.26 (t, J = 5.2 Hz, 4 H) 3.22 (s, 3 H) 2.85 (d, J = 11.3 Hz, 2 H) 2.49 (t, J = 5.2 Hz, 4 H) 2.32 (t, J = 7.0 Hz, 2 H) 2.09 (t, J = 10.8 Hz, 2 H) 1.97 (d, J = 10.1 Hz, 2 H) 1.65 (qd, J = 11.7, 3.7 Hz, 2 H) 1.45-1.56 (m, 4 H). |
| 348 | 554 | 13.00 (br. s., 1 H) 7.96-8.00 (m, 2 H) 7.88 (s, 1 H) 7.00-7.05 (m, 2 H) 5.54-5.63 (m, 2 H) 3.35-3.36 (m, 2 H) 3.23-3.27 (m, 4 H) 3.22 (s, 3 H) 2.45-2.50 (m, 4 H) 2.33-2.38 (m, 2 H) 2.22 (s, 3 H) 1.79-1.85 (m, 2 H) 1.66-1.73 (m, 2 H) 1.52 (t, J = 11.67 Hz, 2 H) 1.18 (s, 6 H) 1.10 (s, 6 H). |
| 349 | 540 | 12.99 (br. s., 1 H) 7.96-8.00 (m, 2 H) 7.87 (s, 1 H) 7.00-7.04 (m, 2 H) 5.55-5.64 (m, 2 H) 3.47 (t, J = 5.80 Hz, 2 H) 3.25 (s, 3 H) 3.22-3.26 (m, 4 H) 2.53-2.56 (m, 4 H) 2.52 (t, J = 5.80 Hz, 2 H) 2.22 (s, 3 H) 1.83 (dd, J = 11.67, 2.37 Hz, 2 H) 1.51 (t, J = 11.67 Hz, 2 H) 1.18 (s, 6 H) 1.10 (s, 6 H). |
| 350 | 589 | 13.02 (br. s., 1 H) 8.68 (dd, J = 4.86, 1.70 Hz, 1 H) 8.67 (dd, J = 2.22, 0.92 Hz, 1 H) 7.99-8.03 (m, 2 H) 7.90 (ddd, J = 7.80, 2.22, 1.70 Hz, 1 H) 7.88 (s, 1 H) 7.51 (ddd, J = 7.80, 4.86, 0.92 Hz, 1 H) 7.05-7.09 (m, 2 H) 5.54-5.65 (m, 2 H) 3.73-3.83 (m, 2 H) 3.44-3.52 (m, 2 H) 3.38-3.45 (m, 2 H) 3.27-3.36 (m, 2 H) 2.22 (s, 3 H) 1.80-1.85 (m, 2 H) 1.52 (t, J = 11.67 Hz, 2 H) 1.18 (s, 6 H) 1.10 (s, 6 H). |
| 351 | 605 | 12.99 (br. s., 1 H) 7.97-8.01 (m, 2 H) 7.88 (s, 1 H) 7.07 (dd, J = 1.88, 0.54 Hz, 1 H) 7.01-7.06 (m, 2 H) 5.55-5.64 (m, 2 H) 5.37 (dd, J = 1.88, 0.34 Hz, 1 H) 5.28 (t, J = 5.88 Hz, 1 H) 3.50 (s, 3 H) 3.25-3.31 (m, 4 H) 3.11 (dt, J = 7.59, 5.88 Hz, 2 H) 2.55-2.59 (m, 4 H) 2.53-2.57 (m, 2 H) 2.22 (s, 3 H) 1.79-1.86 (m, 2 H) 1.52 (t, J = 11.60 Hz, 2 H) 1.18 (s, 6 H) 1.10 (s, 6 H). |
| 352 | 568 | 13.02 (br. s., 1 H) 7.99-8.03 (m, 2 H) 7.88 (s, 1 H) 7.00-7.05 (m, 2 H) 5.55-5.64 (m, 2 H) 3.90 (s, 2 H) 3.56-3.61 (m, 2 H) 3.48-3.55 (m, 6 H) 3.42 (q, J = 7.02 Hz, 2 H) 2.22 (s, 3 H) 1.80-1.86 (m, 2 H) 1.52 (t, J = 11.52 Hz, 2 H) 1.18 (s, 6 H) 1.10 (s, 6 H) 1.08 (t, J = 7.02 Hz, 3 H). |
| 353 | 589 | 12.99 (br. s., 1 H) 7.98 (d, J = 9.2 Hz, 2 H) 7.88 (s, 1 H) 7.07 (d, J = 1.5 Hz, 1 H) 7.07 (d, J = 8.9 Hz, 2 H) 5.72 (d, J = 8.9 Hz, 1 H) 5.37 (d, J = 1.8 Hz, 1 H) 5.27 (t, J = 5.8 Hz, 1 H) 4.89-4.99 (m, 1 H) 3.51 (s, 3 H) 3.28 (t, J = 5.2 Hz, 4 H) 3.12 (q, J = 6.5 Hz, 2 H) 3.03 (d, J = 11.0 Hz, 2 H) 2.58 (t, J = 4.9 Hz, 4 H) 2.56 (t, J = 6.7 Hz, 2 |

TABLE 2-continued

| Ex | m/z | $^1$H NMR (600 MHz, DMSO-$d_6$) δ ppm |
|---|---|---|
| | | H) 2.21 (d, J = 6.7 Hz, 2 H) 2.08 (t, J = 10.8 Hz, 2 H) 1.99 (d, J = 10.1 Hz, 2 H) 1.66 (qd, J = 11.6, 3.7 Hz, 2 H) 0.81-0.91 (m, 1 H) 0.45-0.50 (m, 2 H) 0.08-0.11 (m, 2H). |
| 354 | 524 | 12.98 (br. s., 1 H) 7.97 (d, J = 8.9 Hz, 2 H) 7.88 (s, 1 H) 7.06 (d, J = 8.9 Hz, 2 H) 5.72 (d, J = 8.9 Hz, 1 H) 4.88-4.98 (m, 1 H) 4.46 (br. s., 1 H) 3.41-3.49 (m, 2 H) 3.25 (t, J = 5.2 Hz, 4 H) 3.03 (d, J = 11.6 Hz, 2 H) 2.49 (t, J = 5.2 Hz, 4 H) 2.38 (t, J = 7.3 Hz, 2 H) 2.21 (d, J = 6.7 Hz, 2 H) 2.08 (t, J = 10.8 Hz, 2 H) 1.98 (d, J = 10.4 Hz, 2 H) 1.66 (qd, J = 11.6, 3.4 Hz, 2 H) 1.61 (dt, J = 14.3, 6.4 Hz, 2 H) 0.81-0.91 (m, 1 H) 0.45-0.50 (m, 2H) 0.07-0.11 (m, 2 H). |
| 355 | 538 | 13.00 (br. s., 1 H) 8.00 (d, J = 8.9 Hz, 2 H) 7.88 (s, 1 H) 7.05 (d, J = 9.2 Hz, 2 H) 5.72 (d, J = 8.5 Hz, 1 H) 4.88-4.99 (m, 1 H) 3.91 (s, 2 H) 3.56-3.60 (m, 2 H) 3.51-3.56 (m, 4 H) 3.47-3.50 (m, 2 H) 3.25 (s, 3 H) 3.03 (d, J = 11.3 Hz, 2 H) 2.21 (d, J = 6.4 Hz, 2 H) 2.09 (t, J = 10.8 Hz, 2 H) 1.99 (d, J = 10.7 Hz, 2 H) 1.66 (qd, J = 11.6, 3.4 Hz, 2 H) 0.81-0.91 (m, 1 H) 0.45-0.51 (m, 2 H) 0.07-0.13 (m, 2 H). |
| 356 | 538 | 12.97 (br. s., 1 H) 7.97 (d, J = 9.2 Hz, 2 H) 7.87 (s, 1 H) 7.05 (d, J = 9.2 Hz, 2 H) 5.70 (d, J = 8.9 Hz, 1 H) 4.88-5.00 (m, 1 H) 3.36 (t, J = 6.4 Hz, 2 H) 3.25 (t, J = 5.2 Hz, 4 H) 3.22 (s, 3 H) 3.02 (d, J = 11.3 Hz, 2 H) 2.49 (t, J = 5.2 Hz, 4 H) 2.36 (t, J = 7.6 Hz, 2 H) 2.21 (d, J = 6.7 Hz, 2 H) 2.08 (t, J = 10.8 Hz, 2 H) 1.98 (d, J = 10.7 Hz, 2 H) 1.69 (dt, J = 14.6, 6.4 Hz, 2 H) 1.65 (qd, J = 12.2, 3.4 Hz, 2 H) 0.80-0.90 (m, 1 H) 0.45-0.50 (m, 2H) 0.07-0.11 (m, 2H). |
| 357 | 524 | 12.98 (br. s., 1 H) 7.97 (d, J = 8.9 Hz, 2 H) 7.88 (s, 1 H) 7.05 (d, J = 8.9 Hz, 2 H) 5.72 (d, J = 8.9 Hz, 1 H) 4.88-5.00 (m, 1 H) 3.47 (t, J = 5.8 Hz, 2 H) 3.25 (s, 3 H) 3.25 (t, J = 4.9 Hz, 4 H) 3.03 (d, J = 11.3 Hz, 2 H) 2.55 (t, J = 4.9 Hz, 4 H) 2.52 (t, J = 5.8 Hz, 2 H) 2.21 (d, J = 6.4 Hz, 2 H) 2.08 (t, J = 11.9 Hz, 2 H) 1.98 (d, J = 9.8 Hz, 2 H) 1.66 (qd, J = 11.7, 3.7 Hz, 2 H) 0.81-0.89 (m, 1 H) 0.45-0.50 (m, 2 H) 0.07-0.12 (m, 2 H). |
| 358 | 538 | 12.97 (br. s., 1 H) 7.97 (d, J = 8.9 Hz, 2 H) 7.87 (s, 1 H) 7.05 (d, J = 9.2 Hz, 2 H) 5.71 (d, J = 8.5 Hz, 1 H) 4.88-4.99 (m, 1 H) 3.51 (t, J = 6.0 Hz, 2 H) 3.43 (q, J = 7.0 Hz, 2 H) 3.25 (t, J = 5.2 Hz, 4 H) 3.02 (d, J = 11.0 Hz, 2 H) 2.56 (t, J = 4.9 Hz, 4 H) 2.52 (t, J = 6.1 Hz, 2 H) 2.21 (d, J = 6.7 Hz, 2 H) 2.08 (t, J = 11.4 Hz, 2 H) 1.98 (d, J = 11.3 Hz, 2 H) 1.66 (qd, J = 11.6, 3.5 Hz, 2 H) 1.11 (t, J = 7.0 Hz, 3 H) 0.80-0.91 (m, 1 H) 0.45-0.50 (m, 2H) 0.07-0.11 (m, 2 H). |
| 359 | 557 | 12.98 (br. s., 1 H) 8.53 (d, J = 1.5 Hz, 1 H) 8.49 (dd, J = 4.9, 1.8 Hz, 1 H) 7.97 (d, J = 9.2 Hz, 2 H) 7.87 (s, 1 H) 7.75 (dt, J = 7.9, 1.9 Hz, 1 H) 7.38 (ddd, J = 7.6, 4.9, 0.6 Hz, 1 H) 7.05 (d, J = 8.9 Hz, 2 H) 5.71 (d, J = 8.9 Hz, 1 H) 4.88-4.98 (m, 1 H) 3.57 (s, 2 H) 3.27 (t, J = 5.2 Hz, 4 H) 3.02 (d, J = 11.3 Hz, 2 H) 2.52 (t, J = 5.2 Hz, 4 H) 2.20 (d, J = 6.4 Hz, 2 H) 2.08 (t, J = 11.0 Hz, 2 H) 1.98 (d, J = 10.1 Hz, 2 H) 1.65 (qd, J = 11.7, 3.7 Hz, 2 H) 0.80-0.89 (m, 1 H) 0.45-0.49 (m, 2 H) 0.07-0.11 (m, 2 H). |
| 360 | 563 | 12.99 (br. s., 1 H) 7.98 (d, J = 8.9 Hz, 2 H) 7.88 (s, 1 H) 7.74 (d, J = 3.1 Hz, 1 H) 7.69 (d, J = 3.4 Hz, 1 H) 7.07 (d, J = 9.2 Hz, 2 H) 5.71 (d, J = 8.2 Hz, 1 H) 4.87-4.99 (m, 1 H) 3.91 (s, 2 H) 3.30 (t, J = 5.2 Hz, 4 H) 3.02 (d, J = 11.6 Hz, 2 H) 2.65 (t, J = 4.9 Hz, 4 H) 2.20 (d, J = 6.4 Hz, 2 H) 2.08 (t, J = 11.0 Hz, 2 H) 1.98 (d, J = 10.1 Hz, 2 H) 1.66 (qd, J = 11.8, 3.7 Hz, 2 H) 0.80-0.90 (m, 1 H) 0.45-0.50 (m, 2 H) 0.07-0.12 (m, 2 H). |
| 361 | 510 | 13.01 (br. s., 1 H) 7.98-8.02 (m, 2 H) 7.88 (s, 1 H) 7.06-7.11 (m, 2 H) 5.75 (d, J = 9.00 Hz, 1 H) 4.87-4.96 (m, 1 H) 3.67-3.74 (m, 4 H) 3.23-3.29 (m, 4 H) 2.78-2.85 (m, 2 H) 2.21 (s, 3 H) 2.05 (td, J = 11.64, 1.68 Hz, 2 H) 1.93-2.00 (m, 2 H) 1.57 (dtd, J = 11.75, 11.64, 3.59 Hz, 2 H) 1.23 (s, 9 H). |
| 362 | 554 | 13.03 (br. s., 1 H) 7.98-8.03 (m, 2 H) 7.97 (s, 1 H) 7.06-7.11 (m, 2 H) 5.44 (d, J = 7.93 Hz, 1 H) 4.88-4.97 (m, 1 H) 3.67-3.74 (m, 4 H) 3.24-3.29 (m, 4 H) 2.75-2.83 (m, 2 H) 2.21 (s, 3 H) 2.03-2.11 (m, 2H) 1.95-2.02 (m, 2 H) 1.65 (qd, J = 11.60, 3.51 Hz, 2 H) 1.23 (s, 9 H). |
| 363 | 568 | 13.03 (br. s., 1 H) 7.98-8.02 (m, 2 H) 7.97 (s, 1 H) 7.05-7.12 (m, 2 H) 5.43 (d, J = 8.70 Hz, 1 H) 4.90-4.98 (m, 1 H) 3.67-3.74 (m, 4 H) 3.22-3.29 (m, 4 H) 2.86-2.94 (m, 2 H) 2.36 (q, J = 7.17 Hz, 2 H) 2.02-2.09 (m, 2 H) 1.98-2.03 (m, 2 H) 1.62 (dtd, J = 11.52, 11.37, 3.28 Hz, 2 H) 1.23 (s, 9 H) 1.03 (t, J = 7.17 Hz, 3 H). |
| 364 | 633 | 13.01 (br. s., 1 H) 7.97 (s, 1 H) 7.98 (d, J = 9.1 Hz, 2 H) 7.08 (s, 1 H) 7.07 (d, J = 9.2 Hz, 2 H) 5.43 (d, J = 8.9 Hz, 1 H) 5.37 (d, J = 1.8 Hz, 1 H) 5.28 (t, J = 5.8 Hz, 1 H) 4.90-5.00 (m, 1 H) 3.51 (s, 3 H) 3.28 (t, J = 5.2 Hz, 4 H) 3.12 (td, J = 7.3, 6.1 Hz, 2 H) 3.01 (d, J = 11.0 Hz, 2 H) 2.58 (t, J = 4.9 Hz, 4 H) 2.56 (t, J = 6.7 Hz, 2 H) 2.21 (d, J = 6.7 Hz, 2 H) 2.11 (t, J = 11.0 Hz, 2 H) 2.00 (d, J = 10.4 Hz, 2 H) 1.64 (qd, J = 11.5, 3.5 Hz, 2 H) 0.81-0.91 (m, 1 H) 0.45-0.51 (m, 2 H) 0.07-0.12 (m, 2 H). |
| 365 | 568 | 13.00 (br. s., 1 H) 7.97 (s, 1 H) 7.97 (d, J = 8.8 Hz, 2 H) 7.06 (d, J = 8.9 Hz, 2 H) 5.42 (d, J = 8.9 Hz, 1 H) 4.90-5.00 (m, 1 H) 4.47 (t, J = 4.7 Hz, 1 H) 3.43-3.49 (m, 2 H) 3.25 (t, J = 4.9 Hz, 4 H) 3.00 (d, J = 11.0 Hz, 2 H) 2.49 (t, J = 4.9 Hz, 4 H) 2.38 (t, J = 7.2 Hz, 2 H) 2.21 (d, J = 6.7 Hz, 2 H) 2.11 (t, J = 11.1 Hz, 2 H) 2.00 (d, J = 10.1 Hz, 2 H) 1.64 (qd, J = 11.3, 2.8 Hz, 2 H) 1.61 (quin, J = 6.9 Hz, 2 H) 0.81-0.90 (m, 1 H) 0.45-0.50 (m, 2 H) 0.06-0.12 (m, 2 H). |
| 366 | 582 | 13.03 (br. s., 1 H) 8.00 (d, J = 9.2 Hz, 2 H) 7.98 (s, 1 H) 7.05 (d, J = 9.2 Hz, 2 H) 5.44 (d, J = 8.9 Hz, 1 H) 4.90-5.00 (m, 1 H) 3.91 (s, 2 H) 3.56-3.60 (m, 2 H) 3.51-3.56 (m, 4 H) 3.46-3.51 (m, 2 H) 3.25 (s, 3 H) 3.01 (d, J = 11.3 Hz, 2 H) 2.21 (d, J = 6.7 Hz, 2 H) 2.11 (t, J = 10.8 Hz, 2 H) 2.01 (d, J = 10.4 Hz, 2 H) 1.64 (qd, J = 11.4, 3.4 Hz, 2 H) 0.81-0.90 (m, 1 H) 0.46-0.51 (m, 2 H) 0.07-0.12 (m, 2 H). |
| 367 | 582 | 13.01 (br. s., 1 H) 7.97 (s, 1 H) 7.97 (d, J = 8.9 Hz, 2 H) 7.05 (d, J = 9.2 Hz, 2 H) 5.43 (d, J = 8.9 Hz, 1 H) 4.89-5.00 (m, 1 H) 3.36 (t, J = 6.4 Hz, 2 H) 3.25 (t, J = 5.2 Hz, 4 H) 3.22 (s, 3 H) 3.00 (d, J = 11.0 Hz, 2 H) 2.49 (t, J = 5.2 Hz, 4 H) 2.36 (t, J = 7.6 Hz, 2 H) 2.21 (d, J = 6.7 Hz, 2 H) 2.11 (t, J = 11.0 Hz, 2 H) 2.00 (d, J = 10.1 Hz, |

TABLE 2-continued

| Ex | m/z | ¹H NMR (600 MHz, DMSO-d₆) δ ppm |
|---|---|---|
| | | 2 H) 1.69 (quin, J = 6.9 Hz, 2 H) 1.64 (qd, J = 11.4, 3.2 Hz, 2 H) 0.81-0.90 (m, 1 H) 0.44-0.51 (m, 2 H) 0.06-0.13 (m, 2 H). |
| 368 | 568 | 13.01 (br. s., 1 H) 7.97 (s, 1 H) 7.97 (d, J = 8.9 Hz, 2 H) 7.06 (d, J = 9.2 Hz, 2 H) 5.44 (d, J = 8.9 Hz, 1 H) 4.89-5.00 (m, 1 H) 3.47 (t, J = 5.6 Hz, 2 H) 3.25 (s, 3 H) 3.25 (t, J = 4.9 Hz, 4 H) 3.01 (d, J = 11.0 Hz, 2 H) 2.55 (t, J = 4.9 Hz, 4 H) 2.52 (t, J = 5.8 Hz, 2 H) 2.21 (d, J = 6.4 Hz, 2 H) 2.11 (t, J = 11.0 Hz, 2 H) 2.00 (d, J = 10.1 Hz, 2 H) 1.64 (qd, J = 11.5, 3.8 Hz, 2 H) 0.80-0.90 (m, 1 H) 0.45-0.50 (m, 2 H) 0.07-0.12 (m, 2 H). |
| 369 | 582 | 13.01 (s, 1 H) 7.97 (s, 1 H) 7.97 (d, J = 9.2 Hz, 2 H) 7.06 (d, J = 8.9 Hz, 2 H) 5.44 (d, J = 8.9 Hz, 1 H) 4.90-4.99 (m, 1 H) 3.51 (t, J = 6.0 Hz, 2 H) 3.43 (q, J = 7.0 Hz, 2 H) 3.25 (t, J = 5.2 Hz, 4 H) 3.00 (d, J = 11.0 Hz, 2 H) 2.56 (t, J = 4.6 Hz, 4 H) 2.52 (t, J = 6.1 Hz, 2 H) 2.21 (d, J = 6.7 Hz, 2 H) 2.11 (t, J = 10.8 Hz, 2 H) 2.00 (d, J = 10.1 Hz, 2 H) 1.64 (qd, J = 11.4, 3.5 Hz, 2 H) 1.11 (t, J = 7.0 Hz, 3 H) 0.81-0.89 (m, 1 H) 0.45-0.50 (m, 2 H) 0.07-0.12 (m, 2 H). |
| 370 | 601 | 13.00 (br. s., 1 H) 8.53 (d, J = 1.5 Hz, 1 H) 8.49 (dd, J = 4.7, 1.7 Hz, 1 H) 7.97 (s, 1 H) 7.97 (d, J = 8.9 Hz, 2 H) 7.75 (dt, J = 7.9, 1.9 Hz, 1 H) 7.38 (ddd, J = 7.8, 4.7, 0.9 Hz, 1 H) 7.05 (d, J = 9.2 Hz, 2 H) 5.42 (d, J = 8.9 Hz, 1 H) 4.87-5.01 (m, 1 H) 3.57 (s, 2 H) 3.27 (t, J = 5.2 Hz, 4 H) 3.00 (d, J = 10.7 Hz, 2 H) 2.52 (t, J = 5.2 Hz, 4 H) 2.20 (d, J = 6.7 Hz, 2 H) 2.10 (t, J = 10.8 Hz, 2 H) 2.00 (d, J = 11.3 Hz, 2 H) 1.63 (qd, J = 11.4, 3.5 Hz, 2 H) 0.80-0.90 (m, 1 H) 0.44-0.50 (m, 2 H) 0.07-0.11 (m, 2 H). |
| 371 | 607 | 13.01 (br. s., 1 H) 7.98 (d, J = 8.9 Hz, 2 H) 7.97 (s, 1 H) 7.74 (d, J = 3.4 Hz, 1 H) 7.69 (d, J = 3.4 Hz, 1 H) 7.07 (d, J = 8.9 Hz, 2 H) 5.42 (d, J = 8.2 Hz, 1 H) 4.90-5.00 (m, 1 H) 3.91 (s, 2 H) 3.30 (t, J = 4.6 Hz, 4 H) 3.00 (d, J = 11.0 Hz, 2 H) 2.65 (t, J = 4.9 Hz, 4 H) 2.21 (d, J = 6.7 Hz, 2 H) 2.11 (t, J = 11.0 Hz, 2 H) 2.00 (d, J = 10.1 Hz, 2 H) 1.64 (qd, J = 11.5, 3.7 Hz, 2 H) 0.81-0.90 (m, 1 H) 0.44-0.49 (m, 2 H) 0.07-0.11 (m, 2 H). |
| 372 | 502 | 13.17 (br. s., 1 H) 7.91 (s, 1 H) 7.88 (dd, J = 8.4, 2.0 Hz, 1 H) 7.83 (dd, J = 14.2, 2.0 Hz, 1 H) 7.17 (t, J = 8.9 Hz, 1 H) 5.83 (d, J = 8.5 Hz, 1 H) 4.83-4.94 (m, 1 H) 3.47 (t, J = 5.6 Hz, 2 H) 3.25 (s, 3 H) 3.10 (t, J = 4.9 Hz, 4 H) 2.82 (d, J = 11.6 Hz, 2 H) 2.59 (br. s., 4 H) 2.53 (t, J = 5.8 Hz, 2 H) 2.20 (s, 3 H) 2.04 (td, J = 11.6, 1.5 Hz, 2 H) 1.96 (d, J = 9.5 Hz, 2 H) 1.68 (qd, J = 11.7, 3.7 Hz, 2 H). |
| 373 | 546 | 13.20 (br. s., 1 H) 8.01 (s, 1 H) 7.89 (dd, J = 8.4, 2.0 Hz, 1 H) 7.83 (dd, J = 14.2, 2.0 Hz, 1 H) 7.17 (t, J = 8.9 Hz, 1 H) 5.54 (d, J = 8.9 Hz, 1 H) 4.84-4.95 (m, 1 H) 3.47 (t, J = 5.8 Hz, 2 H) 3.25 (s, 3 H) 3.10 (t, J = 4.9 Hz, 4 H) 2.80 (d, J = 11.0 Hz, 2 H) 2.59 (br. s., 4 H) 2.53 (t, J = 5.8 Hz, 2 H) 2.21 (s, 3 H) 2.06 (t, J = 10.8 Hz, 2 H) 1.98 (d, J = 9.8 Hz, 2 H) 1.66 (qd, J = 11.5, 3.7 Hz, 2 H). |
| 374 | 516 | 13.18 (br. s., 1 H) 7.92 (s, 1 H) 7.88 (dd, J = 8.4, 2.0 Hz, 1 H) 7.83 (dd, J = 14.2, 2.0 Hz, 1 H) 7.17 (t, J = 8.9 Hz, 1 H) 5.84 (d, J = 8.9 Hz, 1 H) 4.85-4.95 (m, 1 H) 3.47 (t, J = 5.8 Hz, 2 H) 3.25 (s, 3 H) 3.10 (t, J = 4.6 Hz, 4 H) 2.93 (d, J = 11.3 Hz, 2 H) 2.58 (br. s., 4 H) 2.53 (t, J = 5.8 Hz, 2 H) 2.35 (q, J = 7.3 Hz, 2 H) 2.02 (t, J = 12.1 Hz, 2 H) 1.98 (d, J = 11.3 Hz, 2 H) 1.65 (qd, J = 11.7, 3.7 Hz, 2 H) 1.02 (t, J = 7.2 Hz, 3 H). |
| 375 | 560 | 13.21 (br. s., 1 H) 8.01 (s, 1 H) 7.88 (dd, J = 8.2, 1.8 Hz, 1 H) 7.83 (dd, J = 14.2, 2.0 Hz, 1 H) 7.17 (t, J = 8.9 Hz, 1 H) 5.54 (d, J = 8.5 Hz, 1 H) 4.85-4.97 (m, 1 H) 3.47 (t, J = 5.8 Hz, 2 H) 3.25 (s, 3 H) 3.10 (t, J = 4.6 Hz, 4 H) 2.91 (d, J = 11.3 Hz, 2 H) 2.59 (br. s., 4 H) 2.53 (t, J = 5.8 Hz, 2 H) 2.35 (q, J = 7.3 Hz, 2 H) 2.05 (t, J = 11.4 Hz, 2 H) 2.00 (d, J = 11.6 Hz, 2 H) 1.64 (qd, J = 11.4, 3.5 Hz, 2 H) 1.02 (t, J = 7.2 Hz, 3 H). |
| 376 | 542 | 13.17 (br. s., 1 H) 7.91 (s, 1 H) 7.88 (dd, J = 8.5, 1.8 Hz, 1 H) 7.83 (dd, J = 14.2, 2.0 Hz, 1 H) 7.16 (t, J = 9.0 Hz, 1 H) 5.83 (d, J = 8.5 Hz, 1 H) 4.85-4.97 (m, 1 H) 3.47 (t, J = 5.8 Hz, 2 H) 3.25 (s, 3 H) 3.10 (t, J = 4.6 Hz, 4 H) 3.03 (d, J = 11.9 Hz, 2 H) 2.58 (br. s., 4 H) 2.53 (t, J = 5.8 Hz, 2 H) 2.21 (d, J = 6.4 Hz, 2 H) 2.09 (t, J = 11.0 Hz, 2 H) 1.98 (d, J = 10.4 Hz, 2 H) 1.67 (qd, J = 11.6, 3.5 Hz, 2 H) 0.80-0.92 (m, 1 H) 0.45-0.50 (m, 2 H) 0.07-0.12 (m, 2 H). |
| 377 | 586 | 13.20 (br. s., 1 H) 8.00 (s, 1 H) 7.88 (dd, J = 8.4, 2.0 Hz, 1 H) 7.83 (dd, J = 14.2, 2.0 Hz, 1 H) 7.16 (t, J = 8.9 Hz, 1 H) 5.52 (d, J = 7.9 Hz, 1 H) 4.85-4.98 (m, 1 H) 3.47 (t, J = 5.8 Hz, 2 H) 3.25 (s, 3 H) 3.10 (t, J = 4.6 Hz, 4 H) 3.01 (d, J = 11.3 Hz, 2 H) 2.58 (br. s., 4 H) 2.53 (t, J = 5.8 Hz, 2 H) 2.21 (d, J = 6.7 Hz, 2 H) 2.11 (t, J = 10.8 Hz, 2 H) 2.00 (d, J = 10.4 Hz, 2 H) 1.65 (qd, J = 11.5, 3.4 Hz, 2 H) 0.81-0.89 (m, 1 H) 0.44-0.50 (m, 2 H) 0.07-0.12 (m, 2 H). |
| 378 | 530 | 13.17 (br. s., 1 H) 7.91 (s, 1 H) 7.88 (dd, J = 8.2, 1.8 Hz, 1 H) 7.83 (dd, J = 14.3, 1.8 Hz, 1 H) 7.16 (t, J = 8.9 Hz, 1 H) 5.77 (d, J = 7.0 Hz, 1 H) 4.83-4.94 (m, 1 H) 3.47 (t, J = 5.8 Hz, 2 H) 3.25 (s, 3 H) 3.10 (t, J = 4.6 Hz, 4 H) 2.85 (d, J = 11.6 Hz, 2 H) 2.72 (spt, J = 6.6 Hz, 1 H) 2.58 (br. s., 4 H) 2.53 (t, J = 5.8 Hz, 2 H) 2.27 (td, J = 11.6, 1.8 Hz, 2 H) 1.99 (d, J = 9.5 Hz, 2 H) 1.61 (qd, J = 11.5, 3.5 Hz, 2 H) 1.00 (d, J = 6.7 Hz, 6 H). |
| 379 | 553 | 13.03 (br. s., 1 H) 7.96-8.00 (m, 2 H) 7.96 (s, 1 H) 7.01-7.06 (m, 2 H) 5.47 (br. s., 1 H) 4.90-4.99 (m, 1 H) 3.77 (s, 2 H) 3.47 (t, J = 5.76 Hz, 2 H) 3.25 (s, 3 H) 3.22-3.27 (m, 4 H) 2.83-2.89 (m, 2 H) 2.53-2.58 (m, 4 H) 2.52 (t, J = 5.76 Hz, 2 H) 2.37 (td, J = 11.50, 1.98 Hz, 2 H) 2.02-2.08 (m, 2 H) 1.69 (qd, J = 11.50, 3.74 Hz, 2 H). |
| 380 | 571 | 13.21 (br. s., 1 H) 8.00 (s, 1 H) 7.88 (dd, J = 8.60, 1.95 Hz, 1 H) 7.84 (dd, J = 14.19, 1.95 Hz, 1 H) 7.13 (t, J = 8.60 Hz, 1 H) 5.59 (br. s., 1 H) 4.89-4.97 (m, 1 H) 3.77 (s, 2 H) 3.47 (t, J = 5.80 Hz, 2 H) 3.25 (s, 3 H) 3.07-3.13 (m, 4 H) 2.84-2.90 (m, 2 H) 2.56-2.61 (m, 4 H) 2.53 (t, J = 5.80 Hz, 2 H) 2.37 (td, J = 11.50, 1.98 Hz, 2 H) 2.01-2.07 (m, 2 H) 1.71 (dtd, J = 11.67, 11.50, 3.51 Hz, 2 H). |
| 381 | 514 | 13.13 (br. s., 1 H) 7.90 (s, 1 H) 7.74 (d, J = 1.8 Hz, 1 H) 7.68 (dd, J = 8.2, 1.8 Hz, 1 H) 6.99 (d, J = 8.5 Hz, 1 H) 5.86 (d, J = 8.9 Hz, 1 H) 4.88-5.00 (m, 1 H) 3.89 (s, 3 |

TABLE 2-continued

| Ex | m/z | ¹H NMR (600 MHz, DMSO-d₆) δ ppm |
|---|---|---|
| | | H) 3.47 (t, J = 5.8 Hz, 2 H) 3.25 (s, 3 H) 3.04 (br. s., 4 H) 2.84 (d, J = 11.3 Hz, 2 H) 2.57 (br. s., 4 H) 2.52 (t, J = 5.8 Hz, 2 H) 2.19 (s, 3 H) 2.03 (td, J = 11.6, 1.8 Hz, 2 H) 1.97 (d, J = 11.6 Hz, 2 H) 1.68 (qd, J = 11.7, 3.7 Hz, 2 H). |
| 382 | 558 | 13.15 (br. s., 1 H) 7.99 (s, 1 H) 7.74 (d, J = 2.1 Hz, 1 H) 7.68 (dd, J = 8.2, 1.8 Hz, 1 H) 6.99 (d, J = 8.2 Hz, 1 H) 5.55 (d, J = 8.5 Hz, 1 H) 4.88-5.01 (m, 1 H) 3.89 (s, 3 H) 3.46 (t, J = 5.8 Hz, 2 H) 3.25 (s, 3 H) 3.04 (br. s., 4 H) 2.82 (d, J = 11.6 Hz, 2 H) 2.57 (br. s., 4 H) 2.52 (t, J = 5.8 Hz, 2 H) 2.19 (s, 3 H) 2.05 (t, J = 11.7 Hz, 2 H) 1.99 (d, J = 10.7 Hz, 2 H) 1.67 (qd, J = 11.6, 3.5 Hz, 2 H). |
| 383 | 528 | 13.12 (br. s., 1 H) 7.90 (s, 1 H) 7.74 (d, J = 1.8 Hz, 1 H) 7.68 (dd, J = 8.2, 1.8 Hz, 1 H) 6.99 (d, J = 8.2 Hz, 1 H) 5.84 (d, J = 8.9 Hz, 1 H) 4.89-5.04 (m, 1 H) 3.88 (s, 3 H) 3.46 (t, J = 5.8 Hz, 2 H) 3.25 (s, 3 H) 3.04 (br. s., 4 H) 2.94 (d, J = 11.6 Hz, 2 H) 2.57 (br. s., 4 H) 2.52 (t, J = 5.8 Hz, 2 H) 2.34 (q, J = 7.0 Hz, 2 H) 2.02 (d, J = 11.9 Hz, 2 H) 2.00 (d, J = 11.0 Hz, 2 H) 1.65 (qd, J = 11.9, 3.4 Hz, 2 H) 1.01 (t, J = 7.2 Hz, 3 H). |
| 384 | 572 | 13.15 (br. s., 1 H) 7.99 (s, 1 H) 7.74 (d, J = 1.8 Hz, 1 H) 7.68 (dd, J = 8.1, 2.0 Hz, 1 H) 6.99 (d, J = 8.5 Hz, 1 H) 5.54 (d, J = 8.5 Hz, 1 H) 4.91-5.02 (m, 1 H) 3.88 (s, 3 H) 3.46 (t, J = 5.8 Hz, 2 H) 3.25 (s, 3 H) 3.04 (br. s., 4 H) 2.93 (d, J = 11.3 Hz, 2 H) 2.57 (br. s., 4 H) 2.52 (t, J = 5.8 Hz, 2 H) 2.34 (q, J = 7.0 Hz, 2 H) 2.04 (t, J = 11.9 Hz, 2 H) 2.02 (d, J = 11.0 Hz, 2 H) 1.64 (qd, J = 11.7, 3.8 Hz, 2 H) 1.01 (t, J = 7.2 Hz, 3 H). |
| 385 | 554 | 13.12 (br. s., 1 H) 7.90 (s, 1 H) 7.74 (d, J = 1.8 Hz, 1 H) 7.67 (dd, J = 8.2, 1.8 Hz, 1 H) 6.98 (d, J = 8.2 Hz, 1 H) 5.83 (d, J = 8.5 Hz, 1 H) 4.90-5.00 (m, 1 H) 3.88 (s, 3 H) 3.46 (t, J = 6.0 Hz, 2 H) 3.25 (s, 3 H) 3.04 (br. s., 6 H) 2.56 (br. s., 4 H) 2.52 (t, J = 5.8 Hz, 2 H) 2.19 (d, J = 6.4 Hz, 2 H) 2.08 (t, J = 11.1 Hz, 2 H) 2.00 (d, J = 10.1 Hz, 2 H) 1.67 (qd, J = 11.7, 3.7 Hz, 2 H) 0.79-0.89 (m, 1 H) 0.45-0.49 (m, 2 H) 0.05-0.10 (m, 2 H). |
| 386 | 598 | 13.15 (br. s., 1 H) 7.99 (s, 1 H) 7.74 (d, J = 1.8 Hz, 1 H) 7.67 (dd, J = 8.2, 1.8 Hz, 1 H) 6.99 (d, J = 8.2 Hz, 1 H) 5.53 (d, J = 8.5 Hz, 1 H) 4.90-5.01 (m, 1 H) 3.88 (s, 3 H) 3.46 (t, J = 5.8 Hz, 2 H) 3.25 (s, 3 H) 3.04 (br. s., 6 H) 2.57 (br. s., 4 H) 2.52 (t, J = 5.8 Hz, 2 H) 2.20 (d, J = 6.4 Hz, 2 H) 2.11 (t, J = 11.0 Hz, 2 H) 2.02 (d, J = 10.1 Hz, 2 H) 1.66 (qd, J = 11.5, 3.7 Hz, 2 H) 0.80-0.89 (m, 1 H) 0.44-0.50 (m, 2 H) 0.05-0.10 (m, 2 H). |
| 387 | 542 | 13.12 (br. s., 1 H) 7.90 (s, 1 H) 7.75 (d, J = 1.8 Hz, 1 H) 7.67 (dd, J = 8.2, 1.8 Hz, 1 H) 6.98 (d, J = 8.2 Hz, 1 H) 5.81 (d, J = 8.9 Hz, 1 H) 4.88-4.98 (m, 1 H) 3.88 (s, 3 H) 3.46 (t, J = 5.8 Hz, 2 H) 3.25 (s, 3 H) 3.04 (br. s., 4 H) 2.85 (d, J = 11.3 Hz, 2 H) 2.72 (spt, J = 6.6 Hz, 1 H) 2.56 (br. s., 4 H) 2.52 (t, J = 5.8 Hz, 2 H) 2.28 (td, J = 11.5, 1.5 Hz, 2 H) 2.01 (d, J = 9.8 Hz, 2 H) 1.61 (qd, J = 11.7, 3.8 Hz, 2 H) 0.98 (d, J = 6.4 Hz, 6 H). |
| 388 | 502 | 12.68 (br. s., 1 H) 7.91 (s, 1 H) 7.87 (t, J = 9.0 Hz, 1 H) 6.93 (dd, J = 9.0, 2.3 Hz, 1 H) 6.88 (dd, J = 15.0, 2.4 Hz, 1 H) 5.77 (d, J = 8.5 Hz, 1 H) 4.85-4.96 (m, 1 H) 3.47 (t, J = 5.8 Hz, 2 H) 3.29 (t, J = 5.2 Hz, 4 H) 3.25 (s, 3 H) 2.79 (d, J = 11.3 Hz, 2 H) 2.54 (t, J = 5.2 Hz, 4 H) 2.52 (t, J = 5.8 Hz, 2 H) 2.18 (s, 3 H) 2.01 (t, J = 11.6 Hz, 2 H) 1.95 (d, J = 11.3 Hz, 2 H) 1.66 (qd, J = 11.6, 3.7 Hz, 2 H). |
| 389 | 546 | 12.70 (br. s., 1 H) 8.00 (s, 1 H) 7.88 (t, J = 8.9 Hz, 1 H) 6.93 (dd, J = 9.2, 2.4 Hz, 1 H) 6.88 (dd, J = 15.0, 2.4 Hz, 1 H) 5.47 (d, J = 8.5 Hz, 1 H) 4.84-4.97 (m, 1 H) 3.47 (t, J = 5.8 Hz, 2 H) 3.29 (t, J = 5.2 Hz, 4 H) 3.25 (s, 3 H) 2.78 (d, J = 11.3 Hz, 2 H) 2.54 (t, J = 5.2 Hz, 4 H) 2.52 (t, J = 5.8 Hz, 2 H) 2.19 (s, 3 H) 2.03 (t, J = 11.3 Hz, 2 H) 1.97 (d, J = 10.1 Hz, 2 H) 1.64 (qd, J = 11.5, 3.7 Hz, 2 H). |
| 390 | 516 | 12.68 (br. s., 1 H) 7.90 (s, 1 H) 7.87 (t, J = 9.0 Hz, 1 H) 6.92 (dd, J = 8.9, 2.4 Hz, 1 H) 6.88 (dd, J = 15.0, 2.1 Hz, 1 H) 5.75 (d, J = 8.9 Hz, 1 H) 4.86-4.98 (m, 1 H) 3.47 (t, J = 5.6 Hz, 2 H) 3.28 (t, J = 5.2 Hz, 4 H) 3.25 (s, 3 H) 2.90 (d, J = 11.6 Hz, 2 H) 2.54 (t, J = 5.2 Hz, 4 H) 2.52 (t, J = 5.8 Hz, 2 H) 2.33 (q, J = 7.3 Hz, 2 H) 1.95-2.03 (m, 4 H) 1.63 (qd, J = 11.7, 3.8 Hz, 2 H) 1.01 (t, J = 7.2 Hz, 3 H). |
| 391 | 560 | 12.71 (br. s., 1 H) 8.00 (s, 1 H) 7.87 (t, J = 8.9 Hz, 1 H) 6.92 (dd, J = 8.9, 2.4 Hz, 1 H) 6.88 (dd, J = 15.0, 2.4 Hz, 1 H) 5.45 (d, J = 9.2 Hz, 1 H) 4.86-4.99 (m, 1 H) 3.47 (t, J = 5.5 Hz, 2 H) 3.29 (t, J = 5.2 Hz, 4 H) 3.25 (s, 3 H) 2.88 (d, J = 11.6 Hz, 2 H) 2.54 (t, J = 5.2 Hz, 4 H) 2.52 (t, J = 5.8 Hz, 2 H) 2.33 (q, J = 7.0 Hz, 2 H) 1.97-2.06 (m, 4 H) 1.61 (qd, J = 11.5, 3.2 Hz, 2 H) 1.01 (t, J = 7.2 Hz, 3 H). |
| 392 | 542 | 12.68 (br. s., 1 H) 7.91 (s, 1 H) 7.87 (t, J = 8.9 Hz, 1 H) 6.92 (dd, J = 9.2, 2.4 Hz, 1 H) 6.88 (dd, J = 15.0, 2.1 Hz, 1 H) 5.76 (d, J = 8.5 Hz, 1 H) 4.87-4.97 (m, 1 H) 3.47 (t, J = 5.8 Hz, 2 H) 3.28 (t, J = 5.2 Hz, 4 H) 3.25 (s, 3 H) 3.01 (d, J = 11.6 Hz, 2 H) 2.54 (t, J = 5.2 Hz, 4 H) 2.52 (t, J = 5.8 Hz, 2 H) 2.19 (d, J = 6.4 Hz, 2 H) 2.05 (t, J = 11.3 Hz, 2 H) 1.97 (d, J = 11.0 Hz, 2 H) 1.65 (qd, J = 11.7, 3.7 Hz, 2 H) 0.80-0.89 (m, 1 H) 0.44-0.50 (m, 2 H) 0.06-0.11 (m, 2 H). |
| 393 | 586 | 12.70 (br. s., 1 H) 8.00 (s, 1 H) 7.87 (t, J = 8.9 Hz, 1 H) 6.92 (dd, J = 9.0, 2.3 Hz, 1 H) 6.88 (dd, J = 14.8, 2.3 Hz, 1 H) 5.46 (d, J = 8.2 Hz, 1 H) 4.87-4.99 (m, 1 H) 3.47 (t, J = 5.6 Hz, 2 H) 3.28 (t, J = 5.2 Hz, 4 H) 3.25 (s, 3 H) 2.99 (d, J = 11.0 Hz, 2 H) 2.54 (t, J = 5.2 Hz, 4 H) 2.52 (t, J = 5.8 Hz, 2 H) 2.19 (d, J = 6.7 Hz, 2 H) 2.08 (t, J = 11.0 Hz, 2 H) 1.99 (d, J = 9.8 Hz, 2 H) 1.63 (qd, J = 11.6, 3.5 Hz, 2 H) 0.80-0.88 (m, 1 H) 0.44-0.50 (m, 2 H) 0.06-0.10 (m, 2 H). |
| 394 | 530 | 12.68 (br. s., 1 H) 7.90 (s, 1 H) 7.87 (t, J = 8.9 Hz, 1 H) 6.92 (dd, J = 8.9, 2.4 Hz, 1 H) 6.88 (dd, J = 15.0, 2.1 Hz, 1 H) 5.70 (d, J = 8.2 Hz, 1 H) 4.83-4.95 (m, 1 H) 3.47 (t, J = 5.8 Hz, 2 H) 3.29 (t, J = 5.5 Hz, 4 H) 3.25 (s, 3 H) 2.82 (d, J = 11.6 Hz, 2 H) 2.70 (spt, J = 6.5 Hz, 1 H) 2.54 (t, J = 5.5 Hz, 4 H) 2.52 (t, J = 6.0 Hz, 2 H) 2.24 (td, J = 11.6, 1.8 Hz, 2 H) 1.99 (d, J = 10.7 Hz, 2 H) 1.59 (qd, J = 11.5, 3.4 Hz, 2 H) 0.99 (d, J = 6.4 Hz, 6 H). |
| 395 | 537 | 12.98 (br. s., 1 H) 7.95-8.00 (m, 2 H) 7.88 (s, 1 H) 7.03-7.08 (m, 2 H) 5.79 (d, J = 8.70 Hz, 1 H) 4.89-4.98 (m, 1 H) 3.36 (t, J = 6.41 Hz, 2 H) 3.23-3.28 (m, 4 H) |

TABLE 2-continued

| Ex | m/z | ¹H NMR (600 MHz, DMSO-$d_6$) δ ppm |
|---|---|---|
| | | 3.22 (s, 3 H) 2.93-2.99 (m, 2 H) 2.71 (t, J = 6.70 Hz, 2 H) 2.61 (t, J = 6.70 Hz, 2 H) 2.48-2.51 (m, 4 H) 2.34-2.38 (m, 2 H) 2.16 (td, J = 11.79, 2.06 Hz, 2 H) 1.96-2.03 (m, 2 H) 1.66-1.72 (m, 2 H) 1.63-1.70 (m, 2 H). |
| 396 | 523 | 12.99 (br. s., 1 H) 7.96-8.00 (m, 2 H) 7.87 (s, 1 H) 7.03-7.08 (m, 2 H) 5.78 (d, J = 9.00 Hz, 1 H) 4.90-4.98 (m, 1 H) 3.47 (t, J = 5.80 Hz, 2 H) 3.25 (s, 3 H) 3.23-3.27 (m, 4 H) 2.94-3.00 (m, 2 H) 2.71 (t, J = 6.70 Hz, 2 H) 2.61 (t, J = 6.70 Hz, 2 H) 2.53-2.58 (m, 4 H) 2.52 (t, J = 5.80 Hz, 2 H) 2.16 (td, J = 11.75, 1.98 Hz, 2 H) 1.96-2.03 (m, 2 H) 1.67 (dtd, J = 11.98, 11.75, 3.51 Hz, 2 H). |
| 397 | 551 | 12.99 (br. s., 1 H) 7.95-8.00 (m, 2 H) 7.87 (s, 1 H) 7.03-7.08 (m, 2 H) 5.78 (d, J = 8.70 Hz, 1 H) 4.90-4.99 (m, 1 H) 3.33 (t, J = 6.41 Hz, 2 H) 3.23-3.28 (m, 4 H) 3.22 (s, 3 H) 2.93-3.00 (m, 2 H) 2.71 (t, J = 6.70 Hz, 2 H) 2.61 (t, J = 6.70 Hz, 2 H) 2.46-2.50 (m, 4 H) 2.32 (t, J = 6.94 Hz, 2 H) 2.16 (td, J = 11.80, 1.91 Hz, 2 H) 1.96-2.03 (m, 2 H) 1.67 (qd, J = 11.80, 3.59 Hz, 2 H) 1.45-1.56 (m, 4 H). |
| 398 | 549 | 13.01 (br. s., 1 H) 7.98-8.03 (m, 2 H) 7.88 (s, 1 H) 7.05-7.10 (m, 2 H) 5.80 (d, J = 8.85 Hz, 1 H) 4.90-4.98 (m, 1 H) 3.68-3.73 (m, 4 H) 3.23-3.29 (m, 4 H) 2.93-3.00 (m, 2 H) 2.71 (t, J = 6.70 Hz, 2 H) 2.61 (t, J = 6.70 Hz, 2 H) 2.17 (td, J = 11.60, 1.75 Hz, 2 H) 1.96-2.03 (m, 2 H) 1.67 (dtd, J = 12.05, 11.60, 3.28 Hz, 2 H) 1.23 (s, 9 H). |
| 399 | 523 | 12.97 (br. s., 1 H) 7.96-8.00 (m, 2 H) 7.87 (s, 1 H) 7.03-7.08 (m, 2 H) 5.77 (d, J = 8.55 Hz, 1 H) 4.90-4.99 (m, 1 H) 4.46 (t, J = 4.84 Hz, 1 H) 3.46 (td, J = 6.26, 4.84 Hz, 2 H) 3.22-3.28 (m, 4 H) 2.93-2.99 (m, 2 H) 2.71 (t, J = 6.70 Hz, 2 H) 2.61 (t, J = 6.70 Hz, 2 H) 2.48-2.50 (m, 4 H) 2.36-2.40 (m, 2 H) 2.16 (td, J = 11.80, 1.60 Hz, 2 H) 1.96-2.03 (m, 2 H) 1.67 (qd, J = 11.80, 3.66 Hz, 2 H) 1.58-1.65 (m, 2 H). |
| 400 | 551 | 13.00 (br. s., 1 H) 7.99-8.03 (m, 2 H) 7.88 (s, 1 H) 7.02-7.08 (m, 2 H) 5.80 (d, J = 8.39 Hz, 1 H) 4.90-4.99 (m, 1 H) 3.91 (s, 2 H) 3.57-3.61 (m, 2 H) 3.49-3.56 (m, 6 H) 3.43 (q, J = 7.02 Hz, 2 H) 2.94-3.00 (m, 2 H) 2.71 (t, J = 6.70 Hz, 2 H) 2.61 (t, J = 6.70 Hz, 2 H) 2.16 (td, J = 11.80, 1.83 Hz, 2 H) 1.97-2.03 (m, 2 H) 1.67 (qd, J = 11.80, 3.66 Hz, 2 H) 1.09 (t, J = 7.02 Hz, 3 H). |
| 401 | 541 | 13.18 (br. s., 1 H) 7.92 (s, 1 H) 7.89 (dd, J = 8.32, 1.75 Hz, 1 H) 7.83 (dd, J = 14.19, 1.98 Hz, 1 H) 7.16 (t, J = 8.77 Hz, 1 H) 5.89 (d, J = 8.85 Hz, 1 H) 4.87-4.96 (m, 1 H) 3.47 (t, J = 5.80 Hz, 2 H) 3.25 (s, 3 H) 3.07-3.13 (m, 4 H) 2.94-3.00 (m, 2 H) 2.71 (t, J = 6.70 Hz, 2 H) 2.61 (t, J = 6.70 Hz, 2 H) 2.56-2.61 (m, 4 H) 2.53 (t, J = 5.80 Hz, 2 H) 2.16 (td, J = 11.71, 1.83 Hz, 2 H) 1.96-2.02 (m, 2 H) 1.68 (dtd, J = 11.90, 11.71, 3.59 Hz, 2 H). |
| 402 | 567 | 13.02 (br. s., 1 H) 7.97 (s, 1 H) 7.96-8.00 (m, 2 H) 7.03-7.08 (m, 2 H) 5.50 (d, J = 8.55 Hz, 1 H) 4.91-4.99 (m, 1 H) 3.47 (t, J = 5.80 Hz, 2 H) 3.25 (s, 3 H) 3.22-3.27 (m, 4 H) 2.91-2.99 (m, 2 H) 2.71 (t, J = 6.70 Hz, 2 H) 2.61 (t, J = 6.70 Hz, 2 H) 2.53-2.58 (m, 4 H) 2.52 (t, J = 5.80 Hz, 2 H) 2.18 (td, J = 11.60, 1.60 Hz, 2 H) 1.97-2.05 (m, 2 H) 1.65 (dtd, J = 11.79, 11.60, 3.59 Hz, 2 H). |
| 403 | 595 | 13.01 (br. s., 1 H) 7.97 (s, 1 H) 7.96-8.00 (m, 2 H) 7.03-7.08 (m, 2 H) 5.50 (d, J = 8.70 Hz, 1 H) 4.90-4.99 (m, 1 H) 3.33 (t, J = 6.26 Hz, 2 H) 3.23-3.28 (m, 4 H) 3.22 (s, 3 H) 2.92-2.99 (m, 2 H) 2.71 (t, J = 6.70 Hz, 2 H) 2.61 (t, J = 6.70 Hz, 2 H) 2.46-2.50 (m, 4 H) 2.32 (t, J = 7.02 Hz, 2 H) 2.18 (td, J = 11.60, 1.83 Hz, 2 H) 1.98-2.05 (m, 2 H) 1.65 (qd, J = 11.65, 3.81 Hz, 2 H) 1.45-1.56 (m, 4 H). |
| 404 | 593 | 13.04 (br. s., 1 H) 7.98-8.03 (m, 2 H) 7.98 (s, 1 H) 7.06-7.10 (m, 2 H) 5.51 (d, J = 8.55 Hz, 1 H) 4.91-4.99 (m, 1 H) 3.68-3.74 (m, 4 H) 3.23-3.29 (m, 4 H) 2.91-2.98 (m, 2 H) 2.71 (t, J = 6.70 Hz, 2 H) 2.61 (t, J = 6.70 Hz, 2 H) 2.18 (td, J = 11.60, 1.83 Hz, 2 H) 1.98-2.05 (m, 2 H) 1.66 (dtd, J = 11.83, 11.60, 3.74 Hz, 2 H) 1.23 (s, 9 H). |
| 405 | 567 | 13.01 (br. s., 1 H) 7.97-8.00 (m, 2 H) 7.96 (s, 1 H) 7.02-7.08 (m, 2 H) 5.47 (br. s., 1 H) 4.91-5.00 (m, 1 H) 4.46 (t, J = 5.10 Hz, 1 H) 3.46 (td, J = 6.26, 5.10 Hz, 2 H) 3.21-3.29 (m, 4 H) 2.92-2.98 (m, 2 H) 2.71 (t, J = 6.70 Hz, 2 H) 2.61 (t, J = 6.70 Hz, 2 H) 2.48-2.51 (m, 4 H) 2.38 (t, J = 7.25 Hz, 2 H) 2.18 (td, J = 11.64, 2.06 Hz, 2 H) 1.98-2.05 (m, 2 H) 1.61-1.69 (m, 2 H) 1.57-1.65 (m, 2 H). |
| 406 | 595 | 13.03 (br. s., 1 H) 7.99-8.03 (m, 2 H) 7.98 (s, 1 H) 7.03-7.07 (m, 2 H) 5.51 (d, J = 8.85 Hz, 1 H) 4.91-5.00 (m, 1 H) 3.91 (s, 2 H) 3.57-3.61 (m, 2 H) 3.49-3.56 (m, 4 H) 3.43 (q, J = 7.02 Hz, 2 H) 2.92-2.99 (m, 2 H) 2.71 (t, J = 6.70 Hz, 2 H) 2.61 (t, J = 6.70 Hz, 2 H) 2.18 (td, J = 11.70, 1.91 Hz, 2 H) 1.98-2.05 (m, 2 H) 1.66 (qd, J = 11.70, 3.74 Hz, 2 H) 1.09 (t, J = 7.02 Hz, 3 H). |
| 407 | 585 | 13.20 (br. s., 1 H) 8.01 (s, 1 H) 7.89 (dd, J = 8.39, 1.98 Hz, 1 H) 7.83 (dd, J = 14.19, 1.98 Hz, 1 H) 7.16 (t, J = 8.85 Hz, 1 H) 5.60 (d, J = 8.70 Hz, 1 H) 4.88-4.96 (m, 1 H) 3.47 (t, J = 5.80 Hz, 2 H) 3.25 (s, 3 H) 3.07-3.13 (m, 4 H) 2.92-2.98 (m, 2 H) 2.71 (t, J = 6.70 Hz, 2 H) 2.61 (t, J = 6.70 Hz, 2 H) 2.56-2.61 (m, 4 H) 2.53 (t, J = 5.80 Hz, 2 H) 2.18 (td, J = 11.60, 1.83 Hz, 2 H) 1.97-2.04 (m, 2 H) 1.67 (dtd, J = 11.79, 11.60, 3.51 Hz, 2 H). |
| 408 | 558 | 12.98 (br. s., 1 H) 8.73 (d, J = 1.5 Hz, 1 H) 8.61 (dd, J = 2.4, 1.5 Hz, 1 H) 8.56 (d, J = 2.7 Hz, 1 H) 7.97 (d, J = 8.9 Hz, 2 H) 7.87 (s, 1 H) 7.06 (d, J = 9.2 Hz, 2 H) 5.72 (d, J = 8.5 Hz, 1 H) 4.87-4.99 (m, 1 H) 3.74 (s, 2 H) 3.29 (t, J = 5.2 Hz, 4 H) 3.02 (d, J = 11.3 Hz, 2 H) 2.60 (t, J = 4.9 Hz, 4 H) 2.20 (d, J = 6.7 Hz, 2 H) 2.08 (t, J = 11.0 Hz, 2 H) 1.98 (d, J = 10.1 Hz, 2 H) 1.65 (qd, J = 11.6, 3.5 Hz, 2 H) 0.81-0.89 (m, 1 H) 0.44-0.50 (m, 2 H) 0.06-0.11 (m, 2 H). |
| 409 | 558 | 12.99 (br. s., 1 H) 9.12 (s, 1 H) 8.78 (s, 2 H) 7.97 (d, J = 8.9 Hz, 2 H) 7.88 (s, 1 H) 7.06 (d, J = 9.2 Hz, 2 H) 5.73 (d, J = 8.9 Hz, 1 H) 4.86-5.01 (m, 1 H) 3.60 (s, 2 H) 3.28 (t, J = 5.2 Hz, 4 H) 3.02 (d, J = 11.9 Hz, 2 H) 2.54 (t, J = 4.6 Hz, 4 H) 2.20 (d, J = 6.7 Hz, 2 H) 2.08 (t, J = 11.1 Hz, 2 H) 1.98 (d, J = 11.1 Hz, 2 H) 1.66 (qd, J = 11.7, 3.7 Hz, 2 H) 0.79-0.93 (m, 1 H) 0.44-0.52 (m, 2 H) 0.06-0.11 (m, 2 H). |

TABLE 2-continued

| Ex | m/z | $^1$H NMR (600 MHz, DMSO-$d_6$) δ ppm |
|---|---|---|
| 410 | 557 | 12.99 (br. s., 1 H) 8.53 (d, J = 6.1 Hz, 2 H) 7.97 (d, J = 9.2 Hz, 2 H) 7.87 (s, 1 H) 7.37 (d, J = 5.8 Hz, 2 H) 7.06 (d, J = 9.2 Hz, 2 H) 5.72 (d, J = 8.5 Hz, 1 H) 4.88-4.99 (m, 1 H) 3.58 (s, 2 H) 3.29 (t, J = 4.9 Hz, 4 H) 3.02 (d, J = 11.3 Hz, 2 H) 2.53 (t, J = 4.6 Hz, 4 H) 2.20 (d, J = 6.4 Hz, 2 H) 2.08 (t, J = 10.8 Hz, 2 H) 1.98 (d, J = 11.1 Hz, 2 H) 1.65 (qd, J = 11.7, 3.7 Hz, 2 H) 0.80-0.91 (m, 1 H) 0.44-0.50 (m, 2 H) 0.06-0.12 (m, 2 H). |

BIOLOGICAL EXAMPLES

Method for Measurement of Cell Toxicity

The CellTiter-Blue® Cell Viability Assay provides a homogeneous, fluorometric method for estimating the number of viable cells present in multi-well plates. The assay uses the indicator dye resazurin to measure the metabolic capacity of cells. Viable cells retain the ability to reduce resazurin into resorufin, which is highly fluorescent. Non-viable cells rapidly lose metabolic capacity and do not reduce the indicator dye, and thus do not generate a fluorescent signal.

Stock solutions (10 or 100 mM in DMSO) of compounds were serially diluted 1:2 in 11 concentrations and 25 nL/well (100 mM stock) or 50 nL/well (10 mM stock) were acoustically dispensed in assay plates with an EDC acoustic dispenser. Final starting concentration in the assay was 20 μM (0.2% DMSO) or 100 μM (0.1% DMSO) for test compounds.

Peripheral blood mononuclear cells (PBMC) from CLL patients or healthy volunteers were seeded in assay plates (384-well black/clear, Greiner #781091) pre-dispensed with compounds, 25 μL/well, and cultured for 24, 48 and 72 h. The cell concentration was 50 000 cells/well for PBMC from CLL patients or healthy volunteers. After 24, 48 and 72 h culture, Celltiter Blue reagent was added (5 μL/well) and the plates were incubated for 2 h. The plates were read in an Envision fluorescence reader (PerkinElmer) with Ex544 nm/Em590 nm. Results were calculated as % cytotoxicity compared to background (cells treated with 0.2% DMSO).

Examples demonstrating effects on cell toxicity in PBMC from CLL patients and healthy volunteers are illustrated in Table 3. Thus, IC$_{50}$ values for cell toxicity in PBMC from CLL patients as well as healthy volunteers for some compounds of the invention are shown in Table 3.

TABLE 3

| Ex. | PBMC CLL patients IC$_{50}$ (μM) | PBMC healthy volunteers IC$_{50}$ (μM) |
|---|---|---|
| 2 | 0.16 | >20 |
| 10 | 0.11 | >20 |
| 14 | 0.42 | 15.6 |
| 16 | 0.08 | 17.2 |
| 22 | 0.17 | 18.6 |
| 27 | 0.09 | 17.7 |
| 35 | 0.43 | >20 |
| 37 | 0.29 | >20 |
| 44 | 0.44 | >20 |
| 53 | 0.48 | >20 |
| 63 | 0.96 | >20 |
| 70 | 0.16 | >20 |
| 83 | 1.00 | >20 |
| 90 | 0.87 | >20 |
| 98 | 0.06 | >20 |
| 103 | 0.35 | >20 |
| 115 | 0.04 | 16.2 |
| 119 | 0.04 | 17.0 |
| 126 | 0.13 | >20 |

TABLE 3-continued

| Ex. | PBMC CLL patients IC$_{50}$ (μM) | PBMC healthy volunteers IC$_{50}$ (μM) |
|---|---|---|
| 142 | 0.24 | 14.8 |
| 151 | 0.39 | 13.7 |
| 157 | 0.29 | >20 |
| 168 | 0.23 | 17.2 |
| 174 | 0.01 | >20 |
| 230 | 0.07 | >20 |
| 239 | 0.10 | >20 |
| 246 | 0.11 | >20 |
| 254 | 0.05 | 16.3 |
| 260 | 0.22 | >20 |
| 268 | 0.01 | >20 |
| 276 | 0.05 | >20 |
| 281 | 0.06 | 8.4 |
| 291 | 0.04 | 6.5 |
| 299 | 0.09 | >20 |
| 304 | 0.06 | >20 |
| 308 | 0.65 | >20 |
| 320 | 0.10 | >20 |
| 326 | 0.26 | >20 |
| 331 | 0.19 | >20 |
| 337 | 0.25 | >20 |
| 342 | 0.04 | >20 |
| 355 | 0.11 | >20 |
| 363 | 0.14 | 3.1 |
| 372 | 0.31 | >20 |
| 381 | 0.40 | >20 |
| 387 | 1.30 | >20 |
| 396 | 0.19 | >20 |
| 406 | 0.23 | >20 |

The invention claimed is:

1. A compound of formula (I') or (I")

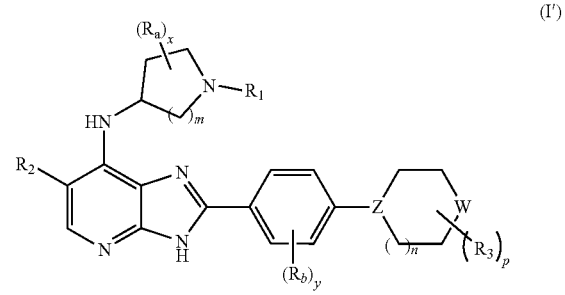

-continued

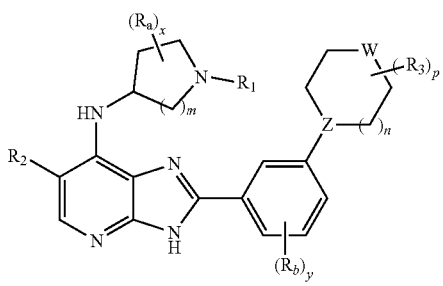

(I″)

or a pharmaceutically acceptable salt thereof, wherein
x is an integer of from 0 to 4;
each $R_a$ is independently selected from C1-C3 alkyl;
m is 1 or 2;
$R_1$ is C1-C6 alkyl, C3-C6 cycloalkyl, C3-C6 cycloalkyl-C1-C6 alkyl, C1-C6 alkyl-C3-C6 cycloalkyl, C1-C6 alkoxy-C1-C6 alkyl, cyano-C1-C6 alkyl, or a moiety of formula (II)

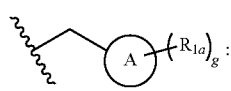

(II)

ring A is phenyl or 5- or 6-membered heteroaryl;
g is an integer of from 0 to 3;
each $R_{1a}$ is independently selected from C1-C6 alkyl, $R_{1b}O$, and $R_{1c}R_{1d}N$;
each $R_{1b}$ is independently selected from H and C1-C6 alkyl;
each $R_{1c}$ is independently selected from H and C1-C6 alkyl;
each $R_{1d}$ is independently selected from H and C1-C6 alkyl;
or two $R_{1a}$, attached to adjacent atoms of ring A form, together with the atoms to which they are attached, a 5- or 6-membered ring optionally containing one or more heteroatoms;
$R_2$ is Cl or Br;
p is an integer of from 0 to 3;
each $R_3$ is independently selected from C1-C6 alkyl;
y is an integer of from 0 to 3;
$R_b$ is selected from halogen, C1-C3 alkyl, and C1-C3 alkoxy;
Z is N or CH;
W is $>Q-R_4$, —O— or —N($R_5$)C(O)—;
Q is N or CH;
n is 1 or 2 when W is $>Q-R_4$ or —O—;
n is 0 or 1 when W is —N($R_5$)C(O)—;
$R_4$ is C1-C6 alkyl, $R_{4a}[O(CH_2)_q]_r$—Y, $R_{4b}S(O)_2$, $R_{4b}C(O)$, cyano-C1-C6 alkyl, or a moiety of formula (III)

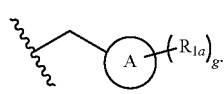

(III)

each q is independently selected from 1, 2, 3 and 4;
r is 1 or 2;
h is an integer of from 0 to 3;

Y is a direct bond or C(O);
L is a direct bond, C1-C4 alkylene, or -$L_1$-$L_2$-;
$L_1$ is a direct bond or C1-C4 alkylene;
$L_2$ is C(O) or NH;
$R_{4a}$ is H or C1-C6 alkyl;
$R_{4b}$ is C1-C6 alkyl;
$R_{4c}$ is C1-C6 alkyl;
$R_{4d}$ is C1-C6 alkyl;
ring B is selected from phenyl and 5- or 6-membered heteroaryl;
$R_5$ is H, C1-C6 alkyl, $R_{5a}[O(CH_2)_u]_v$, or a moiety of formula (IV)

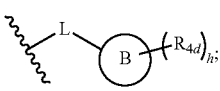

(IV)

$R_{5a}$ is H or C1-C6 alkyl;
each u is independently selected from 1, 2, 3 and 4;
is 1 or 2;
M is a direct bond or C1-C4 alkylene;
ring C is selected from phenyl and 5- or 6-membered heteroaryl;
$R_{5b}$ is C1-C6 alkyl; and
j is an integer of from 0 to 3.

2. The compound or the pharmaceutically acceptable salt according to claim 1, wherein m is 2.

3. The compound or the pharmaceutically acceptable salt according to claim 1, wherein n is 1 when W is $>Q-R_4$ or —O—; and n is 0 when W is —N($R_5$)C(O)—.

4. The compound or the pharmaceutically acceptable salt according to claim 1, wherein $R_1$ is C1-C6 alkyl, C3-C6 cycloalkyl, C3-C6 cycloalkyl-C1-C6 alkyl, C1-C6 alkyl-C3-C6 cycloalkyl, or a moiety of formula (II)

(II)

5. The compound or the pharmaceutically acceptable salt according to claim 1, wherein W is $>Q-R_4$ or —N($R_5$)C(O)—.

6. The compound or the pharmaceutically acceptable salt according to claim 5, wherein
W is $>Q-R_4$.

7. The compound or the pharmaceutically acceptable salt according to claim 1, wherein $R_4$ is $R_{4a}[O(CH_2)_q]_r$—Y.

8. The compound or the pharmaceutically acceptable salt according to claim 1, wherein r is 1.

9. The compound or the pharmaceutically acceptable salt according to claim 1, wherein Y is a direct bond.

10. The compound or the pharmaceutically acceptable salt according to claim 1, wherein Z is N.

11. The compound or the pharmaceutically acceptable salt according to claim 1, wherein
x is 0;
m is 2;
$R_1$ is C1-C6 alkyl, C3-C6 cycloalkyl, C3-C6 cycloalkyl-C1-C6 alkyl, or a moiety of formula (II)

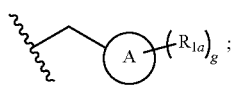 (II)

p is 0;
y is 0;
Z is N;
W is >N—R$_4$ or —N(R$_5$)C(O)—;
n is 1 when W is >N—R$_4$;
n is 0 when W is —N(R$_5$)C(O)—;
R$_4$ is R$_{4a}$O(CH$_2$)$_q$—, or a moiety of formula (III)

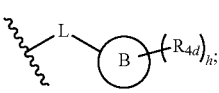 (III)

L is C1-C4 alkylene;
R$_{4a}$ is H or C1-C6 alkyl;
R$_{4d}$ is C1-C6 alkyl;
ring B is 5- or 6-membered heteroaryl;
R$_5$ is R$_{5a}$O(CH$_2$)$_u$—;
R$_{5a}$ is H or C1-C6 alkyl; and
u is 2 or 3.

12. The compound or the pharmaceutically acceptable salt according to claim 1, of formula (I").

13. A compound according to claim 1, selected from
6-Bromo-2-[4-(4-methylpiperazin-1-yl)phenyl]-N-(1-methylpiperidin-4-yl)-3H-imidazo[4,5-b]pyridin-7-amine,
6-Chloro-2-[4-(4-methylpiperazin-1-yl)phenyl]-N-(1-methylpiperidin-4-yl)-3H-imidazo[4,5-b]pyridin-7-amine,
6-Chloro-N-[1-(4-methoxybenzyl)piperidin-4-yl]-2-[4-(4-methylpiperazin-1-yl)phenyl]-3H-imidazo[4,5-b]pyridin-7-amine,
2-[4-(4-{6-Bromo-7-[(1-methylpiperidin-4-yl)amino]-3H-imidazo[4,5-b]pyridin-2-yl}phenyl)piperazin-1-yl]ethanol,
2-[4-(4-{6-Chloro-7-[(1-methylpiperidin-4-yl)amino]-3H-imidazo[4,5-b]pyridin-2-yl}phenyl)piperazin-1-yl]ethanol,
2-[4-(4-{6-Chloro-7-[(1-ethylpiperidin-4-yl)amino]-3H-imidazo[4,5-b]pyridin-2-yl}phenyl)piperazin-1-yl]ethanol,
6-Bromo-2-{4-[4-(2-methoxyethyl)piperazin-1-yl]phenyl}-N-(1-methylpiperidin-4-yl)-3H-imidazo[4,5-b]pyridin-7-amine,
6-Chloro-2-{4-[4-(2-methoxyethyl)piperazin-1-yl]phenyl}-N-(1-methylpiperidin-4-yl)-3H-imidazo[4,5-b]pyridin-7-amine,
6-Chloro-N-(1-ethylpiperidin-4-yl)-2-{4-[4-(2-methoxyethyl)piperazin-1-yl]phenyl}-3H-imidazo[4,5-b]pyridin-7-amine,
6-Bromo-2-[4-(4-ethylpiperazin-1-yl)phenyl]-N-(1-methylpiperidin-4-yl)-3H-imidazo[4,5-b]pyridin-7-amine,
6-Chloro-2-[4-(4-ethylpiperazin-1-yl)phenyl]-N-(1-methylpiperidin-4-yl)-3H-imidazo[4,5-b]pyridin-7-amine,
6-Chloro-2-[4-(4-ethylpiperazin-1-yl)phenyl]-N-(1-ethylpiperidin-4-yl)-3H-imidazo[4,5-b]pyridin-7-amine,
2-{4-[4-(6-Chloro-7-{[1-(4-methoxybenzyl)piperidin-4-yl]amino}-3H-imidazo[4,5-b]pyridin-2-yl)phenyl]piperazin-1-yl}ethanol,
6-Chloro-N-[1-(4-methoxybenzyl)piperidin-4-yl]-2-{4-[4-(2-methoxyethyl)piperazin-1-yl]phenyl}-3H-imidazo[4,5-b]pyridin-7-amine,
6-Chloro-2-[4-(4-ethylpiperazin-1-yl)phenyl]-N-[1-(4-methoxybenzyl)piperidin-4-yl]-3H-imidazo[4,5-b]pyridin-7-amine,
6-Bromo-N-(1-methylpiperidin-4-yl)-2-[4-(4-pyridin-4-ylpiperazin-1-yl)phenyl]-3H-imidazo[4,5-b]pyridin-7-amine,
6-Chloro-N-(1-methylpiperidin-4-yl)-2-[4-(4-pyridin-4-ylpiperazin-1-yl)phenyl]-3H-imidazo[4,5-b]pyridin-7-amine,
6-Chloro-N-[1-(1-methylethyl)piperidin-4-yl]-2-[4-(4-pyridin-4-ylpiperazin-1-yl)phenyl]-3H-imidazo[4,5-b]pyridin-7-amine,
6-Chloro-N-[1-(4-methoxybenzyl)piperidin-4-yl]-2-[4-(4-pyridin-4-ylpiperazin-1-yl)phenyl]-3H-imidazo[4,5-b]pyridin-7-amine,
6-Bromo-N-[1-(1-methylethyl)piperidin-4-yl]-2-[4-(4-pyridin-4-ylpiperazin-1-yl)phenyl]-3H-imidazo[4,5-b]pyridin-7-amine,
6-Bromo-2-[4-(4-methyl-1,4-diazepan-1-yl)phenyl]-N-(1-methylpiperidin-4-yl)-3H-imidazo[4,5-b]pyridin-7-amine,
6-Chloro-2-[4-(4-methyl-1,4-diazepan-1-yl)phenyl]-N-(1-methylpiperidin-4-yl)-3H-imidazo[4,5-b]pyridin-7-amine,
6-Chloro-2-[4-(4-methyl-1,4-diazepan-1-yl)phenyl]-N-[1-(1-methylethyl)piperidin-4-yl]-3H-imidazo[4,5-b]pyridin-7-amine,
6-Bromo-2-[4-(4-methyl-1,4-diazepan-1-yl)phenyl]-N-[1-(1-methylethyl)piperidin-4-yl]-3H-imidazo[4,5-b]pyridin-7-amine,
6-Chloro-N-[1-(4-methoxybenzyl)piperidin-4-yl]-2-[4-(4-methyl-1,4-diazepan-1-yl)phenyl]-3H-imidazo[4,5-b]pyridin-7-amine,
6-Bromo-N-(1-methylpiperidin-4-yl)-2-(4-morpholin-4-ylphenyl)-3H-imidazo[4,5-b]pyridin-7-amine,
6-Chloro-N-(1-methylpiperidin-4-yl)-2-(4-morpholin-4-ylphenyl)-3H-imidazo[4,5-b]pyridin-7-amine,
6-Chloro-N-[1-(1-methylethyl)piperidin-4-yl]-2-(4-morpholin-4-ylphenyl)-3H-imidazo[4,5-b]pyridin-7-amine,
6-Bromo-N-[1-(1-methylethyl)piperidin-4-yl]-2-(4-morpholin-4-ylphenyl)-3H-imidazo[4,5-b]pyridin-7-amine,
6-Chloro-N-[1-(4-methoxybenzyl)piperidin-4-yl]-2-(4-morpholin-4-ylphenyl)-3H-imidazo[4,5-b]pyridin-7-amine,
2-[4-(4-Acetylpiperazin-1-yl)phenyl]-6-bromo-N-(1-methylpiperidin-4-yl)-3H-imidazo[4,5-b]pyridin-7-amine,
2-[4-(4-Acetylpiperazin-1-yl)phenyl]-6-chloro-N-(1-methylpiperidin-4-yl)-3H-imidazo[4,5-b]pyridin-7-amine,
2-[4-(4-Acetylpiperazin-1-yl)phenyl]-6-chloro-N-[1-(1-methylethyl)piperidin-4-yl]-3H-imidazo[4,5-b]pyridin-7-amine,
2-[4-(4-Acetylpiperazin-1-yl)phenyl]-6-bromo-N-[1-(1-methylethyl)piperidin-4-yl]-3H-imidazo[4,5-b]pyridin-7-amine,
2-[4-(4-Acetylpiperazin-1-yl)phenyl]-6-chloro-N-[1-(4-methoxybenzyl)piperidin-4-yl]-3H-imidazo[4,5-b]pyridin-7-amine, 4-(4-{6-Bromo-7-[(1-methylpiperidin-4-yl)amino]-3H-imidazo[4,5-b]pyridin-2-yl}phenyl)piperazin-2-one,
4-(4-{6-Chloro-7-[(1-methylpiperidin-4-yl)amino]-3H-imidazo[4,5-b]pyridin-2-yl}phenyl)piperazin-2-one,
4-[4-(6-Chloro-7-{[1-(1-methylethyl)piperidin-4-yl]amino}-3H-imidazo[4,5-b]pyridin-2-yl}phenyl]piperazin-2-one,
4-[4-(6-Chloro-7-{[1-(4-methoxybenzyl)piperidin-4-yl]amino}-3H-imidazo[4,5-b]pyridin-2-yl}phenyl]piperazin-2-one,
6-Bromo-N-(1-methylpiperidin-4-yl)-2-{4-[4-(methylsulfonyl)piperazin-1-yl]phenyl}-3H-imidazo[4,5-b]pyridin-7-amine,
6-Chloro-N-(1-methylpiperidin-4-yl)-2-{4-[4-(methylsulfonyl)piperazin-1-yl]phenyl}-3H-imidazo[4,5-b]pyridin-7-amine,
6-Chloro-N-[1-(1-methylethyl)piperidin-4-yl]-2-{4-[4-(methylsulfonyl)piperazin-1-yl]phenyl}-3H-imidazo[4,5-b]pyridin-7-amine,
6-Bromo-N-(1-(1-methylethyl)piperidin-4-yl]-2-{4-[4-(methylsulfonyl)piperazin-1-yl]phenyl}-3H-imidazo[4,5-b]pyridin-7-amine,
6-Chloro-N-[1-(4-methoxybenzyl)piperidin-4-yl]-2-{4-[4-(methylsulfonyl)piperazin-1-yl]phenyl}-3H-imidazo[4,5-b]pyridin-7-amine,
6-Chloro-N-(1-ethylpiperidin-4-yl)-2-{4-[4-(methylsulfonyl)piperazin-1-yl]phenyl}-3H-imidazo[4,5-b]pyridin-7-amine,
6-Bromo-N-(1-ethylpiperidin-4-yl)-2-{4-[4-(methylsulfonyl)piperazin-1-yl]phenyl}-3H-imidazo[4,5-b]pyridin-7-amine,
1-(4-{6-Bromo-7-[(1-methylpiperidin-4-yl)amino]-3H-imidazo[4,5-b]pyridin-2-yl}phenyl)-1,4-diazepan-5-one,
1-(4-{6-Chloro-7-[(1-methylpiperidin-4-yl)amino]-3H-imidazo[4,5-b]pyridin-2-yl}phenyl)-1,4-diazepan-5-one,
1-[4-(6-Chloro-7-{[1-(1-methylethyl)piperidin-4-yl]amino}-3H-imidazo[4,5-b]pyridin-2-yl}phenyl]-1,4-diazepan-5-one,
1-[4-(6-Bromo-7-{[1-(1-methylethyl)piperidin-4-yl]amino}-3H-imidazo[4,5-b]pyridin-2-yl}phenyl]-1,4-diazepan-5-one,
1-[4-(6-Chloro-7-{[1-(4-methoxybenzyl)piperidin-4-yl]amino}-3H-imidazo[4,5-b]pyridin-2-yl}phenyl]-1,4-diazepan-5-one,
1-(4-{6-Chloro-7-[(1-ethylpiperidin-4-yl)amino]-3H-imidazo[4,5-b]pyridin-2-yl}phenyl)-1,4-diazepan-5-one,
1-(4-{6-Bromo-7-[(1-ethylpiperidin-4-yl)amino]-3H-imidazo[4,5-b]pyridin-2-yl}phenyl)-1,4-diazepan-5-one,
1-{4-[6-Chloro-7-({1-[(1,3,5-trimethyl-1H-pyrazol-4-yl)methyl]piperidin-4-yl}amino)-3H-imidazo[4,5-b]pyridin-2-yl]phenyl}-1,4-diazepan-5-one,
6-Chloro-2-[4-(4-methylpiperazin-1-yl)phenyl]-N-{1-[(1,3,5-trimethyl-1H-pyrazol-4-yl)methyl]piperidin-4-yl}-3H-imidazo[4,5-b]pyridin-7-amine,
2-(4-{4-[6-Chloro-7-({1-[(1,3,5-trimethyl-1H-pyrazol-4-yl)methyl]piperidin-4-yl}amino)-3H-imidazo[4,5-b]pyridin-2-yl]phenyl}piperazin-1-yl)ethanol,
6-Chloro-2-{4-[4-(2-methoxyethyl)piperazin-1-yl]phenyl}-N-{1-[(1,3,5-trimethyl-1H-pyrazol-4-yl)methyl]piperidin-4-yl}-3H-imidazo[4,5-b]pyridin-7-amine,
6-Chloro-2-(4-morpholin-4-ylphenyl)-N-{1-[(1,3,5-trimethyl-1H-pyrazol-4-yl)methyl]piperidin-4-yl}-3H-imidazo[4,5-b]pyridin-7-amine,
2-[4-(4-Acetylpiperazin-1-yl)phenyl]-6-chloro-N-{1-[(1,3,5-trimethyl-1H-pyrazol-4-yl)methyl]piperidin-4-yl}-3H-imidazo[4,5-b]pyridin-7-amine,
6-Chloro-2-{4-[4-(methylsulfonyl)piperazin-1-yl]phenyl}-N-{1-[(1,3,5-trimethyl-1H-pyrazol-4-yl)methyl]piperidin-4-yl}-3H-imidazo[4,5-b]pyridin-7-amine,
6-Bromo-2-{4-[4-(2-methoxyethyl)-1,4-diazepan-1-yl]phenyl}-N-(1-methylpiperidin-4-yl)-3H-imidazo[4,5-b]pyridin-7-amine,
6-Chloro-2-{4-[4-(2-methoxyethyl)-1,4-diazepan-1-yl]phenyl}-N-(1-methylpiperidin-4-yl)-3H-imidazo[4,5-b]pyridin-7-amine,
6-Chloro-2-{4-[4-(2-methoxyethyl)-1,4-diazepan-1-yl]phenyl}-N-[1-(1-methylethyl)piperidin-4-yl]-3H-imidazo[4,5-b]pyridin-7-amine,
6-Chloro-N-[1-(4-methoxybenzyl)piperidin-4-yl]-2-{4-[4-(2-methoxyethyl)-1,4-diazepan-1-yl]phenyl}-3H-imidazo[4,5-b]pyridin-7-amine,
6-Chloro-N-(1-(ethylpiperidin-4-yl)-2-{4-[4-(2-methoxyethyl)-1,4-diazepan-1-yl]phenyl}-3H-imidazo[4,5-b]pyridin-7-amine,
6-Bromo-2-{4-[4-(2-ethoxyethyl)piperazin-1-yl]phenyl}-N-(1-methylpiperidin-4-yl)-3H-imidazo[4,5-b]pyridin-7-amine,
6-Chloro-2-{4-[4-(2-ethoxyethyl)piperazin-1-yl]phenyl}-N-(1-methylpiperidin-4-yl)-3H-imidazo[4,5-b]pyridin-7-amine,
6-Chloro-2-{4-[4-(2-ethoxyethyl)piperazin-1-yl]phenyl}-N-[1-(1-methylethyl)pipendin-4-yl]-3H-imidazo[4,5-b]pyridin-7-amine,
6-Chloro-2-{4-[4-(2-ethoxyethyl)piperazin-1-yl]phenyl}-N-[1-(4-methoxybenzyl)piperidin-4-yl]-3H-imidazo[4,5-b]pyridin-7-amine,
6-Chloro-2-{4-[4-(2-ethoxyethyl)piperazin-1-yl]phenyl}-N-(1-ethylpiperidin-4-yl)-3H-imidazo[4,5-b]pyridin-7-amine,
6-Bromo-2-{4-[4-(2-ethoxyethyl)-1,4-diazepan-1-yl]phenyl}-N-(1-methylpiperidin-4-yl)-3H-imidazo[4,5-b]pyridin-7-amine,
6-Chloro-2-{4-[4-(2-ethoxyethyl)-1,4-diazepan-1-yl]phenyl}-N-(1-methylpiperidin-4-yl)-3H-imidazo[4,5-b]pyridin-7-amine,
6-Chloro-2-{4-[4-(2-ethoxyethyl)-1,4-diazepan-1-yl]phenyl}-N-[1-(1-methylethyl)piperidin-4-yl]-3H-imidazo[4,5-b]pyridin-7-amine,
6-Chloro-2-{4-[4-(2-ethoxyethyl)-1,4-diazepan-1-yl]phenyl}-N-[1-(4-methoxybenzyl)piperidin-4-yl]-3H-imidazo[4,5-b]pyridin-7-amine,
6-Chloro-2-{4-[4-(2-ethoxyethyl)-1,4-diazepan-1-yl]phenyl}-N-(1-ethylpiperidin-4-yl)-3H-imidazo[4,5-b]pyridin-7-amine,
6-Bromo-2-(4-{4-[2-(1-methylethoxy)ethyl]piperazin-1-yl}phenyl)-N-(1-methylpiperidin-4-yl)-3H-imidazo[4,5-b]pyridin-7-amine,
6-Chloro-2-(4-{4-[2-(1-methylethoxy)ethyl]piperazin-1-yl}phenyl)-N-(1-methylpiperidin-4-yl)-3H-imidazo[4,5-b]pyridin-7-amine,
6-Chloro-2-(4-{4-[2-(1-methylethoxy)ethyl]piperazin-1-yl}phenyl)-N-[1-(1-methylethyl)piperidin-4-yl]-3H-imidazo[4,5-b]pyridin-7-amine,
6-Chloro-N-[1-(4-methoxybenzyl)piperidin-4-yl]-2-(4-{4-[2-(1-methylethoxy)ethyl]piperazin-1-yl}phenyl)-3H-imidazo[4,5-b]pyridin-7-amine,
6-Chloro-N-(1-ethylpiperidin-4-yl)-2-(4-{4-[2-(1-methylethoxy)ethyl]piperazin-1-yl}phenyl)-3H-imidazo[4,5-b]pyridin-7-amine, 2-{4-[4-(6-Chloro-7-{[1-(thiophen-2-ylmethyl)piperidin-4-yl]amino}-3H-imidazo[4,5-b]pyridin-2-yl)phenyl]piperazin-1-yl}ethanol, 6-Chloro-2-{4-[4-(2-methoxyethyl)piperazin-1-yl]phenyl}-N-[1-(thiophen-2-ylmethyl)piperidin-4-yl]-3H-imidazo[4,5-b]pyridin-7-amine, 6-Chloro-2-(4-morpholin-4-ylphenyl)-N-[1-(thiophen-2-ylmethyl)piperidin-4-yl]-3H-imidazo[4,5-b]pyridin-7-amine, 6-Chloro-2-[4-(4-pyridin-4-ylpiperazin-1-yl)phenyl]-N-[1-(thiophen-2-ylmethyl)piperidin-4-yl]-3H-imidazo[4,5-b]pyridin-7-amine, 6-Chloro-2-{4-[4-(2-ethoxyethyl)piperazin-1-yl]phenyl}-N-[1-(thiophen-2-ylmethyl)piperidin-4-yl]-3H-imidazo[4,5-b]pyridin-7-amine, 6-Chloro-2-(4-{4-[2-(1-methylethoxy)ethyl]piperazin-1-yl}phenyl)-N-[1-(thiophen-2-ylmethyl)piperidin-4-yl]-3H-imidazo[4,5-b]pyridin-7-amine, 2-(4-{4-[6-Chloro-7-({1-[4-(dimethylamino)benzyl]piperidin-4-yl}amino)-3H-imidazo[4,5-b]pyridin-2-yl]phenyl}piperazin-1-yl)ethanol, 6-Chloro-N-{1-[4-(dimethylamino)benzyl]piperidin-4-yl}-2-{4-[4-(2-methoxyethyl)piperazin-1-yl]phenyl}-3H-imidazo[4,5-b]pyridin-7-amine, 6-Chloro-N-{1-[4-(dimethylamino)benzyl]piperidin-4-yl}-2-{4-[4-(2-methoxyethyl)piperazin-1-yl]phenyl}-3H-imidazo[4,5-b]pyridin-7-amine, 6-Chloro-N-{1-[4-(dimethylamino)benzyl]piperidin-4-yl}-2-(4-{4-[2-(1-methylethoxy)ethyl]piperazin-1-yl}phenyl)-3H-imidazo[4,5-b]pyridin-7-amine, 6-Bromo-2-(4-{4-[2-(1-methylethoxy)ethyl]-1,4-diazepan-1-yl}phenyl)-N-(1-methylpiperidin-4-yl)-3H-imidazo[4,5-b]pyridin-7-amine, 6-Chloro-2-(4-{4-[2-(1-methylethoxy)ethyl]-1,4-diazepan-1-yl}phenyl)-N-(1-methylpiperidin-4-yl)-3H-imidazo[4,5-b]pyridin-7-amine, 6-Chloro-2-(4-{4-[2-(1-methylethoxy)ethyl]-1,4-diazepan-1-yl}phenyl)-N-[1-(1-methylethyl)piperidin-4-yl]-3H-imidazo[4,5-b]pyridin-7-amine, 6-Chloro-N-[1-(4-methoxybenzyl)piperidin-4-yl]-2-(4-{4-[2-(1-methylethoxy)ethyl]-1,4-diazepan-1-yl}phenyl)-3H-imidazo[4,5-b]pyridin-7-amine, 6-Bromo-N-(1-ethylpiperidin-4-yl)-2-(4-{4-[2-(1-methylethoxy)ethyl]-1,4-diazepan-1-yl}phenyl)-3H-imidazo[4,5-b]pyridin-7-amine, 6-Chloro-N-(1-ethylpiperidin-4-yl)-2-(4-{4-[2-(1-methylethoxy)ethyl]-1,4-diazepan-1-yl}phenyl)-3H-imidazo[4,5-b]pyridin-7-amine, 6-Chloro-N-(1-methylpiperidin-4-yl)-2-[4-(4-pyrazin-2-ylpiperazin-1-yl)phenyl]-3H-imidazo[4,5-b]pyridin-7-amine, 6-Chloro-N-(1-methylpiperidin-4-yl)-2-{4-[4-(pyridin-2-ylmethyl)piperazin-1-yl]phenyl}-3H-imidazo[4,5-b]pyridin-7-amine, 6-Chloro-N-(1-methylpiperidin-4-yl)-2-{4-[4-(pyridin-3-ylmethyl)piperazin-1-yl]phenyl}-3H-imidazo[4,5-b]pyridin-7-amine, 6-Chloro-N-(1-methylpiperidin-4-yl)-2-{4-[4-(pyridin-4-ylmethyl)piperazin-1-yl]phenyl}-3H-imidazo[4,5-b]pyridin-7-amine, 6-Chloro-N-(1-methylpiperidin-4-yl)-2-[4-(4-pyridin-3-ylpiperazin-1-yl)phenyl]-3H-imidazo[4,5-b]pyridin-7-amine, 4-({4-[(6-Chloro-2-{4-[4-(2-hydroxyethyl)piperazin-1-yl]phenyl}-3H-imidazo[4,5-b]pyridin-7-yl)amino]piperidin-1-yl}methyl)-2-methoxyphenol, 4-({4-[(6-Chloro-2-{4-[4-(2-methoxyethyl)piperazin-1-yl]phenyl}-3H-imidazo[4,5-b]pyridin-7-yl)amino]piperidin-1-yl}methyl)-2-methoxyphenol, 2-{4-[4-(6-Chloro-7-{[1-(2,3-dihydro-1-benzofuran-5-ylmethyl)piperidin-4-yl]amino}-3H-imidazo[4,5-b]pyridin-2-yl)phenyl]piperazin-1-yl}ethanol, 6-Chloro-N-[1-(2,3-dihydro-1-benzofuran-5-ylmethyl)piperidin-4-yl]-2-{4-[4-(2-methoxyethyl)piperazin-1-yl]phenyl}-3H-imidazo[4,5-b]pyridin-7-amine, 6-Chloro-N-[1-(2,3-dihydro-1-benzofuran-5-ylmethyl)piperidin-4-yl]-2-{4-[4-(methylsulfonyl)piperazin-1-yl]phenyl}-3H-imidazo[4,5-b]pyridin-7-amine, 6-Chloro-N-[1-(2,3-dihydro-1-benzofuran-5-ylmethyl)piperidin-4-yl]-2-{4-[4-(2-ethoxyethyl)piperazin-1-yl]phenyl}-3H-imidazo[4,5-b]pyridin-7-amine, 6-Chloro-N-(1-methylpiperidin-4-yl)-2-{4-[4-(1,3-thiazol-2-ylmethyl)piperazin-1-yl]phenyl}-3H-imidazo[4,5-b]pyridin-7-amine, 6-Chloro-2-{4-[4-(1H-imidazol-4-ylmethyl)piperazin-1-yl]phenyl}-N-(1-methylpiperidin-4-yl)-3H-imidazo[4,5-b]pyridin-7-amine, 6-Chloro-N-(1-methylpiperidin-4-yl)-2-(4-{4-[(6-methylpyridin-2-yl)methyl]piperazin-1-yl}phenyl)-3H-imidazo[4,5-b]pyridin-7-amine, 6-Bromo-N-(1-methylpiperidin-4-yl)-2-{4-[4-(pyridin-4-ylmethyl)piperazin-1-yl]phenyl}-3H-imidazo[4,5-b]pyridin-7-amine, 6-Bromo-N-(1-methylpiperidin-4-yl)-2-{4-[4-(1,3-thiazol-2-ylmethyl)piperazin-1-yl]phenyl}-3H-imidazo[4,5-b]pyridin-7-amine, 6-Bromo-2-{4-[4-(1H-imidazol-4-ylmethyl)piperazin-1-yl]phenyl}-N-(1-methylpiperidin-4-yl)-3H-imidazo[4,5-b]pyridin-7-amine, 6-Bromo-N-(1-methylpiperidin-4-yl)-2-(4-{4-[(6-methylpyridin-2-yl)methyl]piperazin-1-yl}phenyl)-3H-imidazo[4,5-b]pyridin-7-amine, 6-Bromo-N-(1-methylpiperidin-4-yl)-2-{4-[4-(pyridin-2-ylmethyl)piperazin-1-yl]phenyl}-3H-imidazo[4,5-b]pyridin-7-amine, 6-Bromo-N-(1-methylpiperidin-4-yl)-2-{4-[4-(pyridin-3-ylmethyl)piperazin-1-yl]phenyl}-3H-imidazo[4,5-b]pyridin-7-amine, 6-Bromo-2-(4-{4-[(3,5-dimethylisoxazol-4-yl)methyl]piperazin-1-yl}phenyl)-N-(1-methylpiperidin-4-yl)-3H-imidazo[4,5-b]pyridin-7-amine, 6-Bromo-2-{4-[4-(furan-2-ylmethyl)piperazin-1-yl]phenyl}-N-(1-methylpiperidin-4-yl)-3H-imidazo[4,5-b]pyridin-7-amine, 6-Chloro-2-(4-{4-[(3,5-dimethylisoxazol-4-yl)methyl]piperazin-1-yl}phenyl)-N-(1-methylpiperidin-4-yl)-3H-imidazo[4,5-b]pyridin-7-amine, 6-Chloro-2-{4-[4-(furan-2-ylmethyl)piperazin-1-yl]phenyl}-N-(1-methylpiperidin-4-yl)-3H-imidazo[4,5-b]pyridin-7-amine, 2-{4-[4-(6-Chloro-7-{[(3S)-1-methylpyrrolidin-3-yl]amino}-3H-imidazo[4,5-b]pyridin-2-yl)phenyl]piperazin-1-yl}ethanol, 6-Chloro-2-{4-[4-(2-methoxyethyl)piperazin-1-yl]phenyl}-N-[(3S)-1-methylpyrrolidin-3-yl]-3H-imidazo[4,5-b]pyridin-7-amine, 6-Chloro-2-{4-[4-(2-ethoxyethyl)piperazin-1-yl]phenyl}-N-[(3S)-1-methylpyrrolidin-3-yl]-3H-imidazo[4,5-b]pyridin-7-amine, 6-Chloro-N-[(3S)-1-methylpyrrolidin-3-yl]-2-{4-[4-(pyridin-2-ylmethyl)piperazin-1-yl]phenyl}-3H-imidazo[4,5-b]pyridin-7-amine, 6-Chloro-N-[(3S)-1-methylpyrrolidin-3-yl]-2-{4-[4-(pyridin-3-ylmethyl)piperazin-1-yl]phenyl}-3H-imidazo[4,5-b]pyridin-7-amine, 6-Chloro-N-[(3S)-1-methylpyrrolidin-3-yl]-2-{4-[4-(pyridin-4-ylmethyl)piperazin-1-yl]phenyl}-3H-imidazo[4,5-b]pyridin-7-amine, 2-{4-[4-(6-Chloro-7-{[(3S)-1-propylpyrrolidin-3-yl]amino}-3H-imidazo[4,5-b]pyridin-2-yl)phenyl]piperazin-1-yl}ethanol, 6-Chloro-2-{4-[4-(2-methoxyethyl)piperazin-1-yl]phenyl}-N-[(3S)-1-propylpyrrolidin-3-yl]-3H-imidazo[4,5-b]pyridin-7-amine, 6-Chloro-N-[(3S)-1-propylpyrrolidin-3-yl]-2-{4-[4-(pyridin-2-ylmethyl)piperazin-1-yl]phenyl}-3H-imidazo[4,5-b]pyridin-7-amine, 6-Chloro-N-[(3S)-1-propylpyrrolidin-3-yl]-2-{4-[4-(pyridin-3-ylmethyl)piperazin-1-yl]phenyl}-3H-imidazo[4,5-b]pyridin-7-amine, 6-Chloro-N-[(3S)-1-propylpyrrolidin-3-yl]-2-{4-[4-(pyridin-4-ylmethyl)piperazin-1-yl]phenyl}-3H-imidazo[4,5-b]pyridin-7-amine, 6-Chloro-N-(1-methylpiperidin-4-yl)-2-{4-[4-(pyrimidin-5-ylmethyl)piperazin-1-yl]phenyl}-3H-imidazo[4,5-b]pyridin-7-amine, 6-Bromo-N-(1-methylpiperidin-4-yl)-2-{4-[4-(pyrimidin-5-ylmethyl)piperazin-1-yl]phenyl}-3H-imidazo[4,5-b]pyridin-7-amine, 6-Chloro-N-(1-methylpiperidin-4-yl)-2-(4-{4-[(6-methylpyridin-3-yl)methyl]piperazin-1-yl}phenyl)-3H-imidazo[4,5-b]pyridin-7-amine, 6-Bromo-N-(1-methylpiperidin-4-yl)-2-(4-{4-[(6-methylpyridin-3-yl)methyl]piperazin-1-yl}phenyl)-3H-imidazo[4,5-b]pyridin-7-amine, 6-Chloro-N-(1-ethylpiperidin-4-yl)-2-{4-[4-(pyridin-2-ylmethyl)piperazin-1-yl]phenyl}-3H-imidazo[4,5-b]pyridin-7-amine, 6-Chloro-N-(1-ethylpiperidin-4-yl)-2-{4-[4-(pyridin-3-ylmethyl)piperazin-1-yl]phenyl}-3H-imidazo[4,5-b]pyridin-7-amine, 6-Chloro-N-(1-ethylpiperidin-4-yl)-2-{4-[4-(pyridin-4-ylmethyl)piperazin-1-yl]phenyl}-3H-imidazo[4,5-b]pyridin-7-amine, 6-Chloro-N-(1-ethylpiperidin-4-yl)-2-[4-(4-pyridin-3-ylpiperazin-1-yl)phenyl]-3H-imidazo[4,5-b]pyridin-7-amine, 6-Chloro-N-(1-ethylpiperidin-4-yl)-2-{4-[4-(1,3-thiazol-2-ylmethyl)piperazin-1-yl]phenyl}-3H-imidazo[4,5-b]pyridin-7-amine, 6-Chloro-N-(1-ethylpiperidin-4-yl)-2-{4-[4-(1H-imidazol-4-ylmethyl)piperazin-1-yl]phenyl}-3H-imidazo[4,5-b]pyridin-7-amine, 6-Chloro-N-(1-ethylpiperidin-4-yl)-2-(4-{4-[(6-methylpyridin-2-yl)methyl]piperazin-1-yl}phenyl)-3H-imidazo[4,5-b]pyridin-7-amine, 6-Chloro-N-(1-methylpiperidin-4-yl)-2-{4-[4-(pyrazin-2-ylmethyl)piperazin-1-yl]phenyl}-3H-imidazo[4,5-b]pyridin-7-amine, 6-Bromo-N-(1-methylpiperidin-4-yl)-2-{4-[4-(pyrazin-2-ylmethyl)piperazin-1-yl]phenyl}-3H-imidazo[4,5-b]pyridin-7-amine, 2-{4-[4-(6-Chloro-7-{[(3S)-1-(4-methoxybenzyl)pyrrolidin-3-yl]amino}-3H-imidazo[4,5-b]pyridin-2-yl)phenyl]piperazin-1-yl}ethanol, 6-Chloro-N-[(3S)-1-(4-methoxybenzyl)pyrrolidin-3-yl]-2-{4-[4-(2-methoxyethyl)piperazin-1-yl]phenyl}-3H-imidazo[4,5-b]pyridin-7-amine, 6-Chloro-N-[(3S)-1-(4-methoxybenzyl)pyrrolidin-3-yl]-2-{4-[4-(pyridin-3-ylmethyl)piperazin-1-yl]phenyl}-3H-imidazo[4,5-b]pyridin-7-amine, 6-Chloro-2-{4-[4-(3-methoxypropyl)piperazin-1-yl]phenyl}-N-(1-methylpiperidin-4-yl)-3H-imidazo[4,5-b]pyridin-7-amine, 6-Bromo-2-{4-[4-(3-methoxypropyl)piperazin-1-yl]phenyl}-N-(1-methylpiperidin-4-yl)-3H-imidazo[4,5-b]pyridin-7-amine, 6-Bromo-N-[1-(1-methylethyl)piperidin-4-yl]-2-{4-[4-(pyridin-3-ylmethyl)piperazin-1-yl]phenyl}-3H-imidazo[4,5-b]pyridin-7-amine, 6-Bromo-N-[1-(1-methylethyl)piperidin-4-yl]-2-{4-[4-(pyridin-4-ylmethyl)piperazin-1-yl]phenyl}-3H-imidazo[4,5-b]pyridin-7-amine, 6-Bromo-N-(1-(1-methylethyl)piperidin-4-yl]-2-[4-(4-pyridin-3-ylpiperazin-1-yl)phenyl]-3H-imidazo[4,5-b]pyridin-7-amine, 6-Bromo-2-(4-{4-[(3,5-dimethylisoxazol-4-yl)methyl]piperazin-1-yl}phenyl)-N-[1-(1-methylethyl)piperidin-4-yl]-3H-imidazo[4,5-b]pyridin-7-amine, 6-Bromo-2-{4-[4-(furan-2-ylmethyl)piperazin-1-yl]phenyl}-N-[1-(1-methylethyl)piperidin-4-yl]-3H-imidazo[4,5-b]pyridin-7-amine, 6-Bromo-N-[1-(1-methylethyl)piperidin-4-yl]-2-{4-[4-(pyrimidin-5-ylmethyl)piperazin-1-yl]phenyl}-3H-imidazo[4,5-b]pyridin-7-amine, 6-Bromo-2-{4-[4-(2-methoxyethyl)piperazin-1-yl]phenyl}-N-[(3S)-1-methylpyrrolidin-3-yl]-3H-imidazo[4,5-b]pyridin-7-amine, 6-Bromo-N-[(3S)-1-methylpyrrolidin-3-yl]-2-{4-[4-(pyrimidin-5-ylmethyl)piperazin-1-yl]phenyl}-3H-imidazo[4,5-b]pyridin-7-amine, 6-Bromo-N-[(3S)-1-methylpyrrolidin-3-yl]-2-{4-[4-(pyridin-2-ylmethyl)piperazin-1-yl]phenyl}-3H-imidazo[4,5-b]pyridin-7-amine, 6-Bromo-N-[(3S)-1-methylpyrrolidin-3-yl]-2-{4-[4-(pyridin-3-ylmethyl)piperazin-1-yl]phenyl}-3H-imidazo[4,5-b]pyridin-7-amine, 6-Bromo-N-[(3S)-1-methylpyrrolidin-3-yl]-2-{4-[4-(pyridin-4-ylmethyl)piperazin-1-yl]phenyl}-3H-imidazo[4,5-b]pyridin-7-amine, 6-Bromo-N-[(3S)-1-methylpyrrolidin-3-yl]-2-[4-(4-pyridin-3-ylpiperazin-1-yl)phenyl]-3H-imidazo[4,5-b]pyridin-7-amine, 6-Bromo-N-[(3S)-1-methylpyrrolidin-3-yl]-2-[4-(4-pyrazin-2-ylpiperazin-1-yl)phenyl]-3H-imidazo[4,5-b]pyridin-7-amine, 6-Chloro-2-(4-{4-[(3,5-dimethylisoxazol-4-yl)methyl]piperazin-1-yl}phenyl)-N-[1-(1-methylethyl)piperidin-4-yl]-3H-imidazo[4,5-b]pyridin-7-amine, 6-Chloro-2-{4-[4-(furan-2-ylmethyl)piperazin-1-yl]phenyl}-N-[1-(1-methylethyl)piperidin-4-yl]-3H-imidazo[4,5-b]pyridin-7-amine, 6-Chloro-N-[1-(1-methylethyl)piperidin-4-yl]-2-{4-[4-(pyrimidin-5-ylmethyl)piperazin-1-yl]phenyl}-3H-imidazo[4,5-b]pyridin-7-amine, 6-Chloro-N-[1-(1-methylethyl)piperidin-4-yl]-2-(4-{4-[(6-methylpyridin-3-yl)methyl]piperazin-1-yl}phenyl)-3H-imidazo[4,5-b]pyridin-7-amine, 6-Chloro-N-[1-(1-methylethyl)piperidin-4-yl]-2-{4-[4-(pyrazin-2-ylmethyl)piperazin-1-yl]phenyl}-3H-imidazo[4,5-b]pyridin-7-amine, 6-Chloro-N-[1-(1-methylethyl)piperidin-4-yl]-2-{4-[4-(pyridin-3-ylmethyl)piperazin-1-yl]phenyl}-3H-imidazo[4,5-b]pyridin-7-amine, 6-Bromo-N-(1-ethylpiperidin-4-yl)-2-{4-[4-(pyridin-2-ylmethyl)piperazin-1-yl]phenyl}-3H-imidazo[4,5-b]pyridin-7-amine,
6-Bromo-N-(1-ethylpiperidin-4-yl)-2-(4-{4-[(6-methylpyridin-3-yl)methyl]piperazin-1-yl}phenyl)-3H-imidazo[4,5-b]pyridin-7-amine,
6-Bromo-N-(1-ethylpiperidin-4-yl)-2-{4-[4-(1,3-thiazol-2-ylmethyl)piperazin-1-yl]phenyl}-3H-imidazo[4,5-b]pyridin-7-amine,
6-Bromo-2-{4-[4-(2-ethoxyethyl)piperazin-1-yl]phenyl}-N-(1-ethylpiperidin-4-yl)-3H-imidazo[4,5-b]pyridin-7-amine,
6-Bromo-N-(1-ethylpiperidin-4-yl)-2-{4-[4-(1H-imidazol-4-ylmethyl)piperazin-1-yl]phenyl}-3H-imidazo[4,5-b]pyridin-7-amine,
6-Bromo-N-(1-ethylpiperidin-4-yl)-2-{4-[4-(pyridin-3-ylmethyl)piperazin-1-yl]phenyl}-3H-imidazo[4,5-b]pyridin-7-amine,
2-{4-[4-(6-Bromo-7-{[(3S)-1-methylpyrrolidin-3-yl]amino}-3H-imidazo[4,5-b]pyridin-2-yl)phenyl]piperazin-1-yl}ethanol,
6-Bromo-N-[(3S)-1-methylpyrrolidin-3-yl]-2-{4-[4-(pyrazin-2-ylmethyl)piperazin-1-yl]phenyl}-3H-imidazo[4,5-b]pyridin-7-amine,
6-Bromo-2-{4-[4-(furan-2-ylmethyl)piperazin-1-yl]phenyl}-N-[(3S)-1-methylpyrrolidin-3-yl]-3H-imidazo[4,5-b]pyridin-7-amine,
6-Bromo-N-[(3S)-1-methylpyrrolidin-3-yl]-2-{4-[4-(1,3-thiazol-2-ylmethyl)piperazin-1-yl]phenyl}-3H-imidazo[4,5-b]pyridin-7-amine,
6-Bromo-2-{4-[4-(1H-imidazol-4-ylmethyl)piperazin-1-yl]phenyl}-N-[(3S)-1-methylpyrrolidin-3-yl]-3H-imidazo[4,5-b]pyridin-7-amine,
6-Bromo-2-(4-{4-[(6-methylpyridin-3-yl)methyl]piperazin-1-yl}phenyl)-N-[(3S)-1-methylpyrrolidin-3-yl]-3H-imidazo[4,5-b]pyridin-7-amine,
6-Bromo-2-(4-{4-[(6-methylpyridin-2-yl)methyl]piperazin-1-yl}phenyl)-N-[(3S)-1-methylpyrrolidin-3-yl]-3H-imidazo[4,5-b]pyridin-7-amine,
6-Chloro-2-(4-{4-[(5-methylfuran-2-yl)methyl]piperazin-1-yl}phenyl)-N-(1-methylpiperidin-4-yl)-3H-imidazo[4,5-b]pyridin-7-amine,
6-Bromo-2-(4-{4-[(5-methylfuran-2-yl)methyl]piperazin-1-yl}phenyl)-N-(1-methylpiperidin-4-yl)-3H-imidazo[4,5-b]pyridin-7-amine,
6-Chloro-2-{4-[4-(furan-3-ylmethyl)piperazin-1-yl]phenyl}-N-(1-methylpiperidin-4-yl)-3H-imidazo[4,5-b]pyridin-7-amine,
6-Bromo-2-{4-[4-(furan-3-ylmethyl)piperazin-1-yl]phenyl}-N-(1-methylpiperidin-4-yl)-3H-imidazo[4,5-b]pyridin-7-amine,
6-Chloro-2-(4-{4-[2-(2-methoxyethoxy)ethyl]piperazin-1-yl}phenyl)-N-(1-methylpiperidin-4-yl)-3H-imidazo[4,5-b]pyridin-7-amine,
6-Bromo-2-(4-{4-[2-(2-methoxyethoxy)ethyl]piperazin-1-yl}phenyl)-N-(1-methylpiperidin-4-yl)-3H-imidazo[4,5-b]pyridin-7-amine,
6-Chloro-N-(1-ethylpiperidin-4-yl)-2-(4-{4-[2-(2-methoxyethoxy)ethyl]piperazin-1-yl}phenyl)-3H-imidazo[4,5-b]pyridin-7-amine,
6-Chloro-2-(4-{4-[2-(2-methoxyethoxy)ethyl]piperazin-1-yl}phenyl)-N-[1-(1-methylethyl)piperidin-4-yl]-3H-imidazo[4,5-b]pyridin-7-amine,
6-Chloro-2-(4-{4-[2-(2-methoxyethoxy)ethyl]piperazin-1-yl}phenyl)-N-[(3S)-1-methylpyrrolidin-3-yl]-3H-imidazo[4,5-b]pyridin-7-amine,
6-Chloro-2-(4-{4-[2-(2-methoxyethoxy)ethyl]piperazin-1-yl}phenyl)-N-[1-(thiophen-3-ylmethyl)piperidin-4-yl]-3H-imidazo[4,5-b]pyridin-7-amine,
6-Chloro-2-(4-{4-[2-(2-methoxyethoxy)ethyl]piperazin-1-yl}phenyl)-N-[1-(thiophen-2-ylmethyl)piperidin-4-yl]-3H-imidazo[4,5-b]pyridin-7-amine,
6-Chloro-N-(1-methylpiperidin-4-yl)-2-{4-[4-(1,3-thiazol-4-ylmethyl)piperazin-1-yl]phenyl}-3H-imidazo[4,5-b]pyridin-7-amine,
6-Bromo-N-(1-methylpiperidin-4-yl)-2-{4-[4-(1,3-thiazol-4-ylmethyl)piperazin-1-yl]phenyl}-3H-imidazo[4,5-b]pyridin-7-amine,
6-Chloro-N-(1-methylpiperidin-4-yl)-2-{4-[4-(1,3-thiazol-5-ylmethyl)piperazin-1-yl]phenyl}-3H-imidazo[4,5-b]pyridin-7-amine,
6-Bromo-N-(1-methylpiperidin-4-yl)-2-{4-[4-(1,3-thiazol-5-ylmethyl)piperazin-1-yl]phenyl}-3H-imidazo[4,5-b]pyridin-7-amine,
6-Chloro-N-(1-ethylpiperidin-4-yl)-2-{4-[4-(3-methoxypropyl)piperazin-1-yl]phenyl}-3H-imidazo[4,5-b]pyridin-7-amine,
6-Bromo-N-(1-ethylpiperidin-4-yl)-2-{4-[4-(3-methoxypropyl)piperazin-1-yl]phenyl}-3H-imidazo[4,5-b]pyridin-7-amine,
6-Chloro-2-{4-[4-(3-methoxypropyl)piperazin-1-yl]phenyl}-N-[1-(1-methylethyl)piperidin-4-yl]-3H-imidazo[4,5-b]pyridin-7-amine,
6-Bromo-2-{4-[4-(3-methoxypropyl)piperazin-1-yl]phenyl}-N-[1-(1-methylethyl)piperidin-4-yl]-3H-imidazo[4,5-b]pyridin-7-amine,
6-Chloro-2-{4-[4-(2-methoxyethyl)-3-methylpiperazin-1-yl]phenyl}-N-(1-methylpiperidin-4-yl)-3H-imidazo[4,5-b]pyridin-7-amine,
6-Bromo-2-{4-[4-(2-methoxyethyl)-3-methylpiperazin-1-yl]phenyl}-N-(1-methylpiperidin-4-yl)-3H-imidazo[4,5-b]pyridin-7-amine,
6-Chloro-N-(1-ethylpiperidin-4-yl)-2-{4-[4-(2-methoxyethyl)-3-methylpiperazin-1-yl]phenyl}-3H-imidazo[4,5-b]pyridin-7-amine,
6-Chloro-N-(1-methylpiperidin-4-yl)-2-{4-[3-methyl-4-(pyridin-3-ylmethyl)piperazin-1-yl]phenyl}-3H-imidazo[4,5-b]pyridin-7-amine,
6-Bromo-N-(1-methylpiperidin-4-yl)-2-{4-[3-methyl-4-(pyridin-3-ylmethyl)piperazin-1-yl]phenyl}-3H-imidazo[4,5-b]pyridin-7-amine,
6-Bromo-N-(1-ethylpiperidin-4-yl)-2-{4-[3-methyl-4-(pyridin-3-ylmethyl)piperazin-1-yl]phenyl}-3H-imidazo[4,5-b]pyridin-7-amine,
6-Chloro-2-(4-{4-[(1-methyl-1H-imidazol-2-yl)methyl]piperazin-1-yl}phenyl)-N-(1-methylpiperidin-4-yl)-3H-imidazo[4,5-b]pyridin-7-amine,
6-Bromo-2-(4-{4-[(1-methyl-1H-imidazol-2-yl)methyl]piperazin-1-yl}phenyl)-N-(1-methylpiperidin-4-yl)-3H-imidazo[4,5-b]pyridin-7-amine,
6-Chloro-N-(1-ethylpiperidin-4-yl)-2-(4-{4-[(1-methyl-1H-imidazol-2-yl)methyl]piperazin-1-yl}phenyl)-3H-imidazo[4,5-b]pyridin-7-amine,
6-Chloro-N-(1-methylpiperidin-4-yl)-2-(4-{4-[(5-methylpyridin-2-yl)methyl]piperazin-1-yl}phenyl)-3H-imidazo[4,5-b]pyridin-7-amine,
6-Bromo-N-(1-methylpiperidin-4-yl)-2-(4-{4-[(5-methylpyridin-2-yl)methyl]piperazin-1-yl}phenyl)-3H-imidazo[4,5-b]pyridin-7-amine,
6-Chloro-N-(1-ethylpiperidin-4-yl)-2-(4-{4-[(5-methylpyridin-2-yl)methyl]piperazin-1-yl}phenyl)-3H-imidazo[4,5-b]pyridin-7-amine, 6-Bromo-N-(1-ethylpiperidin-4-yl)-2-(4-{4-[(5-methylpyridin-2-yl)methyl]piperazin-1-yl}phenyl)-3H-imidazo[4,5-b]pyridin-7-amine, 6-Chloro-2-{4-[4-(3-methoxypropyl)-3-methylpiperazin-1-yl]phenyl}-N-(1-methylpiperidin-4-yl)-3H-imidazo[4,5-b]pyridin-7-amine, 6-Bromo-2-{4-[4-(3-methoxypropyl)-3-methylpiperazin-1-yl]phenyl}-N-(1-methylpiperidin-4-yl)-3H-imidazo[4,5-b]pyridin-7-amine, 6-Bromo-N-(1-ethylpiperidin-4-yl)-2-{4-[4-(3-methoxypropyl)-3-methylpiperazin-1-yl]phenyl}-3H-imidazo[4,5-b]pyridin-7-amine, 6-Chloro-N-(1-methylpiperidin-4-yl)-2-{4-[3-methyl-4-(1,3-thiazol-2-ylmethyl)piperazin-1-yl]phenyl}-3H-imidazo[4,5-b]pyridin-7-amine, 6-Bromo-N-(1-methylpiperidin-4-yl)-2-{4-[3-methyl-4-(1,3-thiazol-2-ylmethyl)piperazin-1-yl]phenyl}-3H-imidazo[4,5-b]pyridin-7-amine, 6-Chloro-N-(1-ethylpiperidin-4-yl)-2-{4-[3-methyl-4-(1,3-thiazol-2-ylmethyl)piperazin-1-yl]phenyl}-3H-imidazo[4,5-b]pyridin-7-amine, 6-Chloro-N-(1-methylpiperidin-4-yl)-2-{4-[2-methyl-4-(1,3-thiazol-2-ylmethyl)piperazin-1-yl]phenyl}-3H-imidazo[4,5-b]pyridin-7-amine, 6-Bromo-N-(1-methylpiperidin-4-yl)-2-{4-[2-methyl-4-(1,3-thiazol-2-ylmethyl)piperazin-1-yl]phenyl}-3H-imidazo[4,5-b]pyridin-7-amine, 6-Chloro-2-{4-[4-(2-methoxyethyl)-2-methylpiperazin-1-yl]phenyl}-N-(1-methylpiperidin-4-yl)-3H-imidazo[4,5-b]pyridin-7-amine, 6-Bromo-2-{4-[4-(2-methoxyethyl)-2-methylpiperazin-1-yl]phenyl}-N-(1-methylpiperidin-4-yl)-3H-imidazo[4,5-b]pyridin-7-amine, 2-[4-(4-Benzylpiperazin-1-yl)phenyl]-6-chloro-N-(1-methylpiperidin-4-yl)-3H-imidazo[4,5-b]pyridin-7-amine, 2-[4-(4-Benzylpiperazin-1-yl)phenyl]-6-bromo-N-(1-methylpiperidin-4-yl)-3H-imidazo[4,5-b]pyridin-7-amine, 2-[4-(4-Benzylpiperazin-1-yl)phenyl]-6-chloro-N-(1-ethylpiperidin-4-yl)-3H-imidazo[4,5-b]pyridin-7-amine, 6-Chloro-2-{4-[4-(3-methoxypropyl)-2-methylpiperazin-1-yl]phenyl}-N-(1-methylpiperidin-4-yl)-3H-imidazo[4,5-b]pyridin-7-amine, 6-Bromo-2-{4-[4-(3-methoxypropyl)-2-methylpiperazin-1-yl]phenyl}-N-(1-methylpiperidin-4-yl)-3H-imidazo[4,5-b]pyridin-7-amine, 6-Chloro-N-(1-ethylpiperidin-4-yl)-2-{4-[4-(3-methoxypropyl)-2-methylpiperazin-1-yl]phenyl}-3H-imidazo[4,5-b]pyridin-7-amine, 4-(4-{6-Chloro-7-[(1-methylpiperidin-4-yl)amino]-3H-imidazo[4,5-b]pyridin-2-yl}phenyl)-1-(2-methoxyethyl)piperazin-2-one, 4-(4-{6-Bromo-7-[(1-methylpiperidin-4-yl)amino]-3H-imidazo[4,5-b]pyridin-2-yl}phenyl)-1-(2-methoxyethyl)piperazin-2-one, 4-(4-{6-Chloro-7-[(1-ethylpiperidin-4-yl)amino]-3H-imidazo[4,5-b]pyridin-2-yl}phenyl)-1-(2-methoxyethyl)piperazin-2-one, 4-[4-(6-Chloro-7-{[1-(1-methylethyl)piperidin-4-yl]amino}-3H-imidazo[4,5-b]pyridin-2-yl}phenyl]-1-(2-methoxyethyl)piperazin-2-one, 4-[4-(6-Bromo-7-{[1-(1-methylethyl)piperidin-4-yl]amino}-3H-imidazo[4,5-b]pyridin-2-yl)phenyl]-1-(2-methoxyethyl)piperazin-2-one, 4-(4-{6-Bromo-7-[(1-ethylpiperidin-4-yl)amino]-3H-imidazo[4,5-b]pyridin-2-yl}phenyl)-1-(2-methoxyethyl)piperazin-2-one, 6-Chloro-2-{4-[4-(methoxyacetyl)piperazin-1-yl]phenyl}-N-(1-methylpiperidin-4-yl)-3H-imidazo[4,5-b]pyridin-7-amine, 6-Bromo-2-{4-[4-(methoxyacetyl)piperazin-1-yl]phenyl}-N-(1-methylpiperidin-4-yl)-3H-imidazo[4,5-b]pyridin-7-amine, 6-Chloro-N-(1-ethylpiperidin-4-yl)-2-{4-[4-(methoxyacetyl)piperazin-1-yl]phenyl}-3H-imidazo[4,5-b]pyridin-7-amine, 6-Bromo-N-(1-ethylpiperidin-4-yl)-2-{4-[4-(methoxyacetyl)piperazin-1-yl]phenyl}-3H-imidazo[4,5-b]pyridin-7-amine, 6-Chloro-2-{4-[4-(methoxyacetyl)piperazin-1-yl]phenyl}-N-[1-(1-methylethyl)piperidin-4-yl]-3H-imidazo[4,5-b]pyridin-7-amine, 6-Bromo-2-{4-[4-(methoxyacetyl)piperazin-1-yl]phenyl}-N-[1-(1-methylethyl)piperidin-4-yl]-3H-imidazo[4,5-b]pyridin-7-amine, 4-(4-{6-Chloro-7-[(1-methylpiperidin-4-yl)amino]-3H-imidazo[4,5-b]pyridin-2-yl}phenyl)-1-(3-methoxypropyl)piperazin-2-one, 4-(4-{6-Bromo-7-[(1-methylpiperidin-4-yl)amino]-3H-imidazo[4,5-b]pyridin-2-yl}phenyl)-1-(3-methoxypropyl)piperazin-2-one, 4-(4-{6-Chloro-7-[(1-ethylpiperidin-4-yl)amino]-3H-imidazo[4,5-b]pyridin-2-yl}phenyl)-1-(3-methoxypropyl)piperazin-2-one, 4-(4-{6-Bromo-7-[(1-ethylpiperidin-4-yl)amino]-3H-imidazo[4,5-b]pyridin-2-yl}phenyl)-1-(3-methoxypropyl)piperazin-2-one, 4-[4-(6-Chloro-7-{[1-(1-methylethyl)piperidin-4-yl]amino}-3H-imidazo[4,5-b]pyridin-2-yl)phenyl]-1-(3-methoxypropyl)piperazin-2-one, 4-[4-(6-Bromo-7-{[1-(1-methylethyl)piperidin-4-yl]amino}-3H-imidazo[4,5-b]pyridin-2-yl)phenyl]-1-(3-methoxypropyl)piperazin-2-one, 4-(4-{6-Chloro-7-[(1-methylpiperidin-4-yl)amino]-3H-imidazo[4,5-b]pyridin-2-yl}phenyl)-1-(2-ethoxyethyl)piperazin-2-one, 4-(4-{6-Bromo-7-[(1-methylpiperidin-4-yl)amino]-3H-imidazo[4,5-b]pyridin-2-yl}phenyl)-1-(2-ethoxyethyl)piperazin-2-one, 4-(4-{6-Chloro-7-[(1-ethylpiperidin-4-yl)amino]-3H-imidazo[4,5-b]pyridin-2-yl}phenyl)-1-(2-ethoxyethyl)piperazin-2-one, 4-(4-{6-Bromo-7-[(1-ethylpiperidin-4-yl)amino]-3H-imidazo[4,5-b]pyridin-2-yl}phenyl)-1-(2-ethoxyethyl)piperazin-2-one, 4-[4-(6-Chloro-7-{[1-(1-methylethyl)piperidin-4-yl]amino}-3H-imidazo[4,5-b]pyridin-2-yl}phenyl]-1-(2-ethoxyethyl)piperazin-2-one, 4-[4-(6-Bromo-7-{[1-(1-methylethyl)piperidin-4-yl]amino}-3H-imidazo[4,5-b]pyridin-2-yl}phenyl]-1-(2-ethoxyethyl)piperazin-2-one, 2-[1-(4-{6-Chloro-7-[(1-methylpiperidin-4-yl)amino]-3H-imidazo[4,5-b]pyridin-2-yl}phenyl)piperidin-4-yl]ethanol, 2-[1-(4-{6-Bromo-7-[(1-methylpiperidin-4-yl)amino]-3H-imidazo[4,5-b]pyridin-2-yl}phenyl)piperidin-4-yl]ethanol, 2-[1-(4-{6-Chloro-7-[(1-ethylpiperidin-4-yl)amino]-3H-imidazo[4,5-b]pyridin-2-yl}phenyl)piperidin-4-yl]ethanol, 2-[1-(4-{6-Bromo-7-[(1-ethylpiperidin-4-yl)amino]-3H-imidazo[4,5-b]pyridin-2-yl}phenyl)piperidin-4-yl]ethanol,
2-{1-[4-(6-Chloro-7-{[1-(1-methylethyl)piperidin-4-yl]amino}-3H-imidazo[4,5-b]pyridin-2-yl)phenyl]piperidin-4-yl}ethanol,
2-{1-[4-(6-Bromo-7-{[1-(1-methylethyl)piperidin-4-yl]amino}-3H-imidazo[4,5-b]pyridin-2-yl)phenyl]piperidin-4-yl}ethanol,
4-[4-(6-Chloro-7-{[1-(4-methoxybenzyl)piperidin-4-yl]amino}-3H-imidazo[4,5-b]pyridin-2-yl)phenyl]-1-(2-methoxyethyl)piperazin-2-one,
4-[4-(6-Chloro-7-{[1-(4-methoxybenzyl)piperidin-4-yl]amino}-3H-imidazo[4,5-b]pyridin-2-yl)phenyl]-1-(2-ethoxyethyl)piperazin-2-one,
6-Chloro-2-{4-[4-(methoxyacetyl)piperazin-1-yl]phenyl}-N-[1-(4-methoxybenzyl)piperidin-4-yl]-3H-imidazo[4,5-b]pyridin-7-amine,
4-[4-(6-Chloro-7-{[1-(4-methoxybenzyl)piperidin-4-yl]amino}-3H-imidazo[4,5-b]pyridin-2-yl)phenyl]-1-(3-methoxypropyl)piperazin-2-one,
2-{1-[4-(6-Chloro-7-{[1-(4-methoxybenzyl)piperidin-4-yl]amino}-3H-imidazo[4,5-b]pyridin-2-yl)phenyl]piperidin-4-yl}ethanol,
6-Chloro-2-{4-[4-(methoxyacetyl)piperazin-1-yl]phenyl}-N-[1-(thiophen-2-ylmethyl)piperidin-4-yl]-3H-imidazo[4,5-b]pyridin-7-amine,
4-[4-(6-Chloro-7-{[1-(thiophen-2-ylmethyl)piperidin-4-yl]amino}-3H-imidazo[4,5-b]pyridin-2-yl)phenyl]-1-(3-methoxypropyl)piperazin-2-one,
3-[4-(4-{6-Chloro-7-[(1-methylpiperidin-4-yl)amino]-3H-imidazo[4,5-b]pyridin-2-yl}phenyl)piperazin-1-yl]propan-1-ol,
3-[4-(4-{6-Bromo-7-[(1-methylpiperidin-4-yl)amino]-3H-imidazo[4,5-b]pyridin-2-yl}phenyl)piperazin-1-yl]propan-1-ol,
3-[4-(4-{6-Chloro-7-[(1-ethylpiperidin-4-yl)amino]-3H-imidazo[4,5-b]pyridin-2-yl}phenyl)piperazin-1-yl]propan-1-ol,
4-(4-{6-Chloro-7-[(1-methylpiperidin-4-yl)amino]-3H-imidazo[4,5-b]pyridin-2-yl}phenyl)-1-[2-(1-methylethoxy)ethyl]piperazin-2-one,
4-(4-{6-Bromo-7-[(1-methylpiperidin-4-yl)amino]-3H-imidazo[4,5-b]pyridin-2-yl}phenyl)-1-[2-(1-methylethoxy)ethyl]piperazin-2-one,
4-(4-{6-Chloro-7-[(1-ethylpiperidin-4-yl)amino]-3H-imidazo[4,5-b]pyridin-2-yl}phenyl)-1-[2-(1-methylethoxy)ethyl]piperazin-2-one,
4-(4-{6-Bromo-7-[(1-ethylpiperidin-4-yl)amino]-3H-imidazo[4,5-b]pyridin-2-yl}phenyl)-1-[2-(1-methylethoxy)ethyl]piperazin-2-one,
4-[4-(6-Chloro-7-{[1-(1-methylethyl)piperidin-4-yl]amino}-3H-imidazo[4,5-b]pyridin-2-yl)phenyl]-1-[2-(1-methylethoxy)ethyl]piperazin-2-one,
4-[4-(6-Chloro-7-{[1-(4-methoxybenzyl)piperidin-4-yl]amino}-3H-imidazo[4,5-b]pyridin-2-yl)phenyl]-1-[2-(1-methylethoxy)ethyl]piperazin-2-one,
6-Chloro-2-{4-[4-(3-methoxypropanoyl)piperazin-1-yl]phenyl}-N-(1-methylpiperidin-4-yl)-3H-imidazo[4,5-b]pyridin-7-amine,
6-Bromo-2-{4-[4-(3-methoxypropanoyl)piperazin-1-yl]phenyl}-N-(1-methylpiperidin-4-yl)-3H-imidazo[4,5-b]pyridin-7-amine,
6-Chloro-N-(1-ethylpiperidin-4-yl)-2-{4-[4-(3-methoxypropanoyl)piperazin-1-yl]phenyl}-3H-imidazo[4,5-b]pyridin-7-amine,
6-Bromo-N-(1-ethylpiperidin-4-yl)-2-{4-[4-(3-methoxypropanoyl)piperazin-1-yl]phenyl}-3H-imidazo[4,5-b]pyridin-7-amine,
6-Chloro-N-[1-(4-methoxybenzyl)piperidin-4-yl]-2-{4-[4-(3-methoxypropanoyl)piperazin-1-yl]phenyl}-3H-imidazo[4,5-b]pyridin-7-amine,
6-Chloro-2-{4-[4-(2-methoxyethyl)piperidin-1-yl]phenyl}-N-(1-methylpiperidin-4-yl)-3H-imidazo[4,5-b]pyridin-7-amine,
6-Bromo-2-{4-[4-(2-methoxyethyl)piperidin-1-yl]phenyl}-N-(1-methylpiperidin-4-yl)-3H-imidazo[4,5-b]pyridin-7-amine,
6-Chloro-N-(1-ethylpiperidin-4-yl)-2-{4-[4-(2-methoxyethyl)piperidin-1-yl]phenyl}-3H-imidazo[4,5-b]pyridin-7-amine,
6-Bromo-N-(1-ethylpiperidin-4-yl)-2-{4-[4-(2-methoxyethyl)piperidin-1-yl]phenyl}-3H-imidazo[4,5-b]pyridin-7-amine,
6-Chloro-2-{4-[4-(2-methoxyethyl)piperidin-1-yl]phenyl}-N-[1-(1-methylethyl)piperidin-4-yl]-3H-imidazo[4,5-b]pyridin-7-amine,
6-Chloro-2-{4-[4-(2-ethoxyethyl)piperidin-1-yl]phenyl}-N-(1-methylpiperidin-4-yl)-3H-imidazo[4,5-b]pyridin-7-amine,
6-Bromo-2-{4-[4-(2-ethoxyethyl)piperidin-1-yl]phenyl}-N-(1-methylpiperidin-4-yl)-3H-imidazo[4,5-b]pyridin-7-amine,
6-Chloro-N-(1-ethylpiperidin-4-yl)-2-{4-[4-(2-ethoxyethyl)piperidin-1-yl]phenyl}-3H-imidazo[4,5-b]pyridin-7-amine,
6-Bromo-N-(1-ethylpiperidin-4-yl)-2-{4-[4-(2-ethoxyethyl)piperidin-1-yl]phenyl}-3H-imidazo[4,5-b]pyridin-7-amine,
6-Chloro-2-{4-[4-(2-ethoxyethyl)piperidin-1-yl]phenyl}-N-[1-(1-methylethyl)piperidin-4-yl]-3H-imidazo[4,5-b]pyridin-7-amine,
1-Benzyl-4-(4-{6-chloro-7-[(1-methylpiperidin-4-yl)amino]-3H-imidazo[4,5-b]pyridin-2-yl}phenyl)piperazin-2-one,
1-Benzyl-4-(4-{6-bromo-7-[(1-methylpiperidin-4-yl)amino]-3H-imidazo[4,5-b]pyridin-2-yl}phenyl)piperazin-2-one,
1-Benzyl-4-(4-{6-chloro-7-[(1-ethylpiperidin-4-yl)amino]-3H-imidazo[4,5-b]pyridin-2-yl}phenyl)piperazin-2-one,
1-Benzyl-4-(4-{6-bromo-7-[(1-ethylpiperidin-4-yl)amino]-3H-imidazo[4,5-b]pyridin-2-yl}phenyl)piperazin-2-one,
1-Benzyl-4-[4-(6-chloro-7-{[1-(4-methoxybenzyl)piperidin-4-yl]amino}-3H-imidazo[4,5-b]pyridin-2-yl)phenyl]piperazin-2-one,
4-(4-{6-Chloro-7-[(1-methylpiperidin-4-yl)amino]-3H-imidazo[4,5-b]pyridin-2-yl}phenyl)-1-methylpiperazin-2-one,
4-(4-{6-Bromo-7-[(1-methylpiperidin-4-yl)amino]-3H-imidazo[4,5-b]pyridin-2-yl}phenyl)-1-methylpiperazin-2-one,
4-(4-{6-Chloro-7-[(1-ethylpiperidin-4-yl)amino]-3H-imidazo[4,5-b]pyridin-2-yl}phenyl)-1-methylpiperazin-2-one,
4-(4-{6-Bromo-7-[(1-ethylpiperidin-4-yl)amino]-3H-imidazo[4,5-b]pyridin-2-yl}phenyl)-1-methylpiperazin-2-one,
4-[4-(6-Chloro-7-{[1-(4-methoxybenzyl)piperidin-4-yl]amino}-3H-imidazo[4,5-b]pyridin-2-yl)phenyl]-1-methylpiperazin-2-one, 6-Chloro-N-(1-methylpiperidin-4-yl)-2-{4-[4-(pyridin-3-ylcarbonyl)piperazin-1-yl]phenyl}-3H-imidazo[4,5-b]pyridin-7-amine,
6-Bromo-N-(1-methylpiperidin-4-yl)-2-{4-[4-(pyridin-3-ylcarbonyl)piperazin-1-yl]phenyl}-3H-imidazo[4,5-b]pyridin-7-amine,
6-Chloro-N-(1-ethylpiperidin-4-yl)-2-{4-[4-(pyridin-3-ylcarbonyl)piperazin-1-yl]phenyl}-3H-imidazo[4,5-b]pyridin-7-amine,
6-Bromo-N-(1-ethylpiperidin-4-yl)-2-{4-[4-(pyridin-3-ylcarbonyl)piperazin-1-yl]phenyl}-3H-imidazo[4,5-b]pyridin-7-amine,
6-Chloro-N-[1-(4-methoxybenzyl)piperidin-4-yl]-2-{4-[4-(pyridin-3-ylcarbonyl)piperazin-1-yl]phenyl}-3H-imidazo[4,5-b]pyridin-7-amine,
6-Chloro-2-{4-[4-(3-methoxypropyl)piperazin-1-yl]phenyl}-N-(1-propylpiperidin-4-yl)-3H-imidazo[4,5-b]pyridin-7-amine,
6-Bromo-2-{4-[4-(3-methoxypropyl)piperazin-1-yl]phenyl}-N-(1-propylpiperidin-4-yl)-3H-imidazo[4,5-b]pyridin-7-amine,
6-Chloro-N-[1-(2-methoxyethyl)piperidin-4-yl]-2-{4-[4-(3-methoxypropyl)piperazin-1-yl]phenyl}-3H-imidazo[4,5-b]pyridin-7-amine,
4-(4-{6-Chloro-7-[(1-propylpiperidin-4-yl)amino]-3H-imidazo[4,5-b]pyridin-2-yl}phenyl)-1-(2-ethoxyethyl)piperazin-2-one,
4-[4-(6-Chloro-7-{[1-(2-methoxyethyl)piperidin-4-yl]amino}-3H-imidazo[4,5-b]pyridin-2-yl}phenyl]-1-(2-ethoxyethyl)piperazin-2-one,
4-(4-{6-Chloro-7-[(1-cyclohexylpiperidin-4-yl)amino]-3H-imidazo[4,5-b]pyridin-2-yl}phenyl)-1-(2-methoxyethyl)piperazin-2-one,
3-[4-(4-{6-Bromo-7-[(1-ethylpiperidin-4-yl)amino]-3H-imidazo[4,5-b]pyridin-2-yl}phenyl)piperazin-1-yl]propan-1-ol,
6-Chloro-N-(1-ethylpiperidin-4-yl)-2-{4-[4-(pyrazin-2-ylmethyl)piperazin-1-yl]phenyl}-3H-imidazo[4,5-b]pyridin-7-amine,
6-Bromo-N-(1-ethylpiperidin-4-yl)-2-{4-[4-(pyrazin-2-ylmethyl)piperazin-1-yl]phenyl}-3H-imidazo[4,5-b]pyridin-7-amine,
6-Chloro-N-[1-(4-methoxybenzyl)piperidin-4-yl]-2-{4-[4-(pyrazin-2-ylmethyl)piperazin-1-yl]phenyl}-3H-imidazo[4,5-b]pyridin-7-amine,
6-Chloro-N-(1-ethylpiperidin-4-yl)-2-{4-[4-(1,3-thiazol-4-ylmethyl)piperazin-1-yl]phenyl}-3H-imidazo[4,5-b]pyridin-7-amine,
6-Bromo-N-(1-ethylpiperidin-4-yl)-2-{4-[4-(1,3-thiazol-4-ylmethyl)piperazin-1-yl]phenyl}-3H-imidazo[4,5-b]pyridin-7-amine,
6-Chloro-N-[1-(4-methoxybenzyl)piperidin-4-yl]-2-{4-[4-(1,3-thiazol-4-ylmethyl)piperazin-1-yl]phenyl}-3H-imidazo[4,5-b]pyridin-7-amine,
6-Chloro-N-[1-(4-methoxybenzyl)piperidin-4-yl]-2-{4-[4-(1,3-thiazol-5-ylmethyl)piperazin-1-yl]phenyl}-3H-imidazo[4,5-b]pyridin-7-amine,
6-Chloro-N-(1-ethylpiperidin-4-yl)-2-{4-[4-(1,3-thiazol-5-ylmethyl)piperazin-1-yl]phenyl}-3H-imidazo[4,5-b]pyridin-7-amine,
6-Bromo-N-(1-ethylpiperidin-4-yl)-2-{4-[4-(1,3-thiazol-5-ylmethyl)piperazin-1-yl]phenyl}-3H-imidazo[4,5-b]pyridin-7-amine,
6-Chloro-N-(1-methylpiperidin-4-yl)-2-[4-(4-{2-[(1-methyl-1H-pyrazol-5-yl)amino]ethyl}piperazin-1-yl)phenyl]-3H-imidazo[4,5-b]pyridin-7-amine,
6-Bromo-N-(1-methylpiperidin-4-yl)-2-[4-(4-{2-[(1-methyl-1H-pyrazol-5-yl)amino]ethyl}piperazin-1-yl)phenyl]-3H-imidazo[4,5-b]pyridin-7-amine,
6-Chloro-N-(1-ethylpiperidin-4-yl)-2-[4-(4-{2-[(1-methyl-1H-pyrazol-5-yl)amino]ethyl}piperazin-1-yl)phenyl]-3H-imidazo[4,5-b]pyridin-7-amine,
6-Bromo-N-(1-ethylpiperidin-4-yl)-2-[4-(4-{2-[(1-methyl-1H-pyrazol-5-yl)amino]ethyl}piperazin-1-yl)phenyl]-3H-imidazo[4,5-b]pyridin-7-amine,
6-Chloro-N-[1-(1-methylethyl)piperidin-4-yl]-2-[4-(4-{2-[(1-methyl-1H-pyrazol-5-yl)amino]ethyl}piperazin-1-yl)phenyl]-3H-imidazo[4,5-b]pyridin-7-amine,
6-Chloro-N-[1-(4-methoxybenzyl)piperidin-4-yl]-2-[4-(4-{2-[(1-methyl-1H-pyrazol-5-yl)amino]ethyl}piperazin-1-yl)phenyl]-3H-imidazo[4,5-b]pyridin-7-amine,
6-Chloro-N-(1-methylpiperidin-4-yl)-2-{4-[4-(pyridin-4-ylcarbonyl)piperazin-1-yl]phenyl}-3H-imidazo[4,5-b]pyridin-7-amine,
6-Bromo-N-(1-methylpiperidin-4-yl)-2-{4-[4-(pyridin-4-ylcarbonyl)piperazin-1-yl]phenyl}-3H-imidazo[4,5-b]pyridin-7-amine,
6-Chloro-N-(1-ethylpiperidin-4-yl)-2-{4-[4-(pyridin-4-ylcarbonyl)piperazin-1-yl]phenyl}-3H-imidazo[4,5-b]pyridin-7-amine,
6-Bromo-N-(1-ethylpiperidin-4-yl)-2-{4-[4-(pyridin-4-ylcarbonyl)piperazin-1-yl]phenyl}-3H-imidazo[4,5-b]pyridin-7-amine,
3-[4-(4-{6-Chloro-7-[(1-methylpiperidin-4-yl)amino]-3H-imidazo[4,5-b]pyridin-2-yl}phenyl}piperazin-1-yl]propanenitrile,
3-[4-(4-{6-Bromo-7-[(1-methylpiperidin-4-yl)amino]-3H-imidazo[4,5-b]pyridin-2-yl}phenyl)piperazin-1-yl]propanenitrile,
3-[4-(4-{6-Chloro-7-[(1-ethylpiperidin-4-yl)amino]-3H-imidazo[4,5-b]pyridin-2-yl}phenyl)piperazin-1-yl]propanenitrile,
3-[4-(4-{6-Bromo-7-[(1-ethylpiperidin-4-yl)amino]-3H-imidazo[4,5-b]pyridin-2-yl}phenyl)piperazin-1-yl]propanenitrile,
3-{4-[4-(6-Chloro-7-{[1-(4-methoxybenzyl)piperidin-4-yl]amino}-3H-imidazo[4,5-b]pyridin-2-yl)phenyl]piperazin-1-yl}propanenitrile,
3-{4-[4-(6-Bromo-7-{[1-(1-methylethyl)piperidin-4-yl]amino}-3H-imidazo[4,5-b]pyridin-2-yl)phenyl]piperazin-1-yl}propanenitrile,
6-Bromo-2-{4-[4-(3-methoxypropyl)piperazin-1-yl]phenyl}-N-(1,2,2,6,6-pentamethylpiperidin-4-yl)-3H-imidazo[4,5-b]pyridin-7-amine,
6-Bromo-2-{4-[4-(2-methoxyethyl)piperazin-1-yl]phenyl}-N-(1,2,2,6,6-pentamethylpiperidin-4-yl)-3H-imidazo[4,5-b]pyridin-7-amine,
6-Bromo-N-(1,2,2,6,6-pentamethylpiperidin-4-yl)-2-{4-[4-(pyridin-3-ylcarbonyl)piperazin-1-yl]phenyl}-3H-imidazo[4,5-b]pyridin-7-amine,
6-Bromo-2-[4-(4-{2-[(1-methyl-1H-pyrazol-5-yl)amino]ethyl}piperazin-1-yl)phenyl]-N-(1,2,2,6,6-pentamethylpiperidin-4-yl)-3H-imidazo[4,5-b]pyridin-7-amine,
4-(4-{6-Bromo-7-[(1,2,2,6,6-pentamethylpiperidin-4-yl)amino]-3H-imidazo[4,5-b]pyridin-2-yl}phenyl)-1-(2-ethoxyethyl)piperazin-2-one,
6-Chloro-2-{4-[4-(4-methoxybutyl)piperazin-1-yl]phenyl}-N-(1-methylpiperidin-4-yl)-3H-imidazo[4,5-b]pyridin-7-amine, 6-Bromo-2-{4-[4-(4-methoxybutyl)piperazin-1-yl]phenyl}-N-(1-methylpiperidin-4-yl)-3H-imidazo[4,5-b]pyridin-7-amine, 6-Chloro-N-(1-ethylpiperidin-4-yl)-2-{4-[4-(4-methoxybutyl)piperazin-1-yl]phenyl}-3H-imidazo[4,5-b]pyridin-7-amine, 6-Bromo-N-(1-ethylpiperidin-4-yl)-2-{4-[4-(4-methoxybutyl)piperazin-1-yl]phenyl}-3H-imidazo[4,5-b]pyridin-7-amine, 6-Chloro-N-[1-(4-methoxybenzyl)piperidin-4-yl]-2-{4-[4-(4-methoxybutyl)piperazin-1-yl]phenyl}-3H-imidazo[4,5-b]pyridin-7-amine, 6-Chloro-2-{4-[4-(3-methoxypropyl)piperazin-1-yl]phenyl}-N-(1,2,2,6,6-pentamethylpiperidin-4-yl)-3H-imidazo[4,5-b]pyridin-7-amine, 6-Chloro-2-{4-[4-(2-methoxyethyl)piperazin-1-yl]phenyl}-N-(1,2,2,6,6-pentamethylpiperidin-4-yl)-3H-imidazo[4,5-b]pyridin-7-amine, 6-Chloro-N-(1,2,2,6,6-pentamethylpiperidin-4-yl)-2-{4-[4-(pyridin-3-ylcarbonyl)piperazin-1-yl]phenyl}-3H-imidazo[4,5-b]pyridin-7-amine, 6-Chloro-2-[4-(4-{2-[(1-methyl-1H-pyrazol-5-yl)amino]ethyl}piperazin-1-yl)phenyl]-N-(1,2,2,6,6-pentamethylpiperidin-4-yl)-3H-imidazo[4,5-b]pyridin-7-amine, 4-(4-{6-Chloro-7-[(1,2,2,6,6-pentamethylpiperidin-4-yl)amino]-3H-imidazo[4,5-b]pyridin-2-yl}phenyl)-1-(2-ethoxyethyl)piperazin-2-one, 6-Chloro-N-[1-(cyclopropylmethyl)piperidin-4-yl]-2-[4-(4-{2-[(1-methyl-1H-pyrazol-5-yl)amino]ethyl}piperazin-1-yl)phenyl]-3H-imidazo[4,5-b]pyridin-7-amine, 3-{4-[4-(6-Chloro-7-{[1-(cyclopropylmethyl)piperidin-4-yl]amino}-3H-imidazo[4,5-b]pyridin-2-yl)phenyl]piperazin-1-yl}propan-1-ol, 4-[4-(6-Chloro-7-{[1-(cyclopropylmethyl)piperidin-4-yl]amino}-3H-imidazo[4,5-b]pyridin-2-yl)phenyl]-1-(2-methoxyethyl)piperazin-2-one, 6-Chloro-N-[1-(cyclopropylmethyl)piperidin-4-yl]-2-{4-[4-(3-methoxypropyl)piperazin-1-yl]phenyl}-3H-imidazo[4,5-b]pyridin-7-amine, 6-Chloro-N-[1-(cyclopropylmethyl)piperidin-4-yl]-2-{4-[4-(2-methoxyethyl)piperazin-1-yl]phenyl}-3H-imidazo[4,5-b]pyridin-7-amine, 6-Chloro-N-[1-(cyclopropylmethyl)piperidin-4-yl]-2-{4-[4-(2-ethoxyethyl)piperazin-1-yl]phenyl}-3H-imidazo[4,5-b]pyridin-7-amine, 6-Chloro-N-[1-(cyclopropylmethyl)piperidin-4-yl]-2-{4-[4-(pyridin-3-ylmethyl)piperazin-1-yl]phenyl}-3H-imidazo[4,5-b]pyridin-7-amine, 6-Chloro-N-[1-(cyclopropylmethyl)piperidin-4-yl]-2-{4-[4-(1,3-thiazol-2-ylmethyl)piperazin-1-yl]phenyl}-3H-imidazo[4,5-b]pyridin-7-amine, 6-Chloro-2-{4-[4-(2,2-dimethylpropanoyl)piperazin-1-yl]phenyl}-N-(1-methylpiperidin-4-yl)-3H-imidazo[4,5-b]pyridin-7-amine, 6-Bromo-2-{4-[4-(2,2-dimethylpropanoyl)piperazin-1-yl]phenyl}-N-(1-methylpiperidin-4-yl)-3H-imidazo[4,5-b]pyridin-7-amine, 6-Bromo-2-{4-[4-(2,2-dimethylpropanoyl)piperazin-1-yl]phenyl}-N-(1-ethylpiperidin-4-yl)-3H-imidazo[4,5-b]pyridin-7-amine, 6-Bromo-N-[1-(cyclopropylmethyl)piperidin-4-yl]-2-[4-(4-{2-[(1-methyl-1H-pyrazol-5-yl)amino]ethyl}piperazin-1-yl)phenyl]-3H-imidazo[4,5-b]pyridin-7-amine, 3-{4-[4-(6-Bromo-7-{[1-(cyclopropylmethyl)piperidin-4-yl]amino}-3H-imidazo[4,5-b]pyridin-2-yl)phenyl]piperazin-1-yl}propan-1-ol, 4-[4-(6-Bromo-7-{[1-(cyclopropylmethyl)piperidin-4-yl]amino}-3H-imidazo[4,5-b]pyridin-2-yl)phenyl]-1-(2-methoxyethyl)piperazin-2-one, 6-Bromo-N-[1-(cyclopropylmethyl)piperidin-4-yl]-2-{4-[4-(3-methoxypropyl)piperazin-1-yl]phenyl}-3H-imidazo[4,5-b]pyridin-7-amine, 6-Bromo-N-[1-(cyclopropylmethyl)piperidin-4-yl]-2-{4-[4-(2-methoxyethyl)piperazin-1-yl]phenyl}-3H-imidazo[4,5-b]pyridin-7-amine, 6-Bromo-N-[1-(cyclopropylmethyl)piperidin-4-yl]-2-{4-[4-(2-ethoxyethyl)piperazin-1-yl]phenyl}-3H-imidazo[4,5-b]pyridin-7-amine, 6-Bromo-N-[1-(cyclopropylmethyl)piperidin-4-yl]-2-{4-[4-(pyridin-3-ylmethyl)piperazin-1-yl]phenyl}-3H-imidazo[4,5-b]pyridin-7-amine, 6-Bromo-N-[1-(cyclopropylmethyl)piperidin-4-yl]-2-{4-[4-(1,3-thiazol-2-ylmethyl)piperazin-1-yl]phenyl}-3H-imidazo[4,5-b]pyridin-7-amine, 6-Chloro-2-{3-fluoro-4-[4-(2-methoxyethyl)piperazin-1-yl]phenyl}-N-(1-methylpiperidin-4-yl)-3H-imidazo[4,5-b]pyridin-7-amine, 6-Bromo-2-{3-fluoro-4-[4-(2-methoxyethyl)piperazin-1-yl]phenyl}-N-(1-methylpiperidin-4-yl)-3H-imidazo[4,5-b]pyridin-7-amine, 6-Chloro-N-(1-ethylpiperidin-4-yl)-2-{3-fluoro-4-[4-(2-methoxyethyl)piperazin-1-yl]phenyl}-3H-imidazo[4,5-b]pyridin-7-amine, 6-Bromo-N-(1-ethylpiperidin-4-yl)-2-{3-fluoro-4-[4-(2-methoxyethyl)piperazin-1-yl]phenyl}-3H-imidazo[4,5-b]pyridin-7-amine, 6-Chloro-N-[1-(cyclopropylmethyl)piperidin-4-yl]-2-{3-fluoro-4-[4-(2-methoxyethyl)piperazin-1-yl]phenyl}-3H-imidazo[4,5-b]pyridin-7-amine, 6-Bromo-N-[1-(cyclopropylmethyl)piperidin-4-yl]-2-{3-fluoro-4-[4-(2-methoxyethyl)piperazin-1-yl]phenyl}-3H-imidazo[4,5-b]pyridin-7-amine, 6-Chloro-2-{3-fluoro-4-[4-(2-methoxyethyl)piperazin-1-yl]phenyl}-N-[1-(1-methylethyl)piperidin-4-yl]-3H-imidazo[4,5-b]pyridin-7-amine, (4-[(6-Bromo-2-{4-[4-(2-methoxyethyl)piperazin-1-yl]phenyl}-3H-imidazo[4,5-b]pyridin-7-yl)amino]piperidin-1-yl}acetonitrile, (4-[(6-Bromo-2-{3-fluoro-4-[4-(2-methoxyethyl)piperazin-1-yl]phenyl}-3H-imidazo[4,5-b]pyridin-7-yl)amino]piperidin-1-yl}acetonitrile, 6-Chloro-2-{3-methoxy-4-[4-(2-methoxyethyl)piperazin-1-yl]phenyl}-N-(1-methylpiperidin-4-yl)-3H-imidazo[4,5-b]pyridin-7-amine, 6-Bromo-2-{3-methoxy-4-[4-(2-methoxyethyl)piperazin-1-yl]phenyl}-N-(1-methylpiperidin-4-yl)-3H-imidazo[4,5-b]pyridin-7-amine, 6-Chloro-N-(1-ethylpiperidin-4-yl)-2-{3-methoxy-4-[4-(2-methoxyethyl)piperazin-1-yl]phenyl}-3H-imidazo[4,5-b]pyridin-7-amine, 6-Bromo-N-(1-ethylpiperidin-4-yl)-2-{3-methoxy-4-[4-(2-methoxyethyl)piperazin-1-yl]phenyl}-3H-imidazo[4,5-b]pyridin-7-amine, 6-Chloro-N-[1-(cyclopropylmethyl)piperidin-4-yl]-2-{3-methoxy-4-[4-(2-methoxyethyl)piperazin-1-yl]phenyl}-3H-imidazo[4,5-b]pyridin-7-amine, 6-Bromo-N-[1-(cyclopropylmethyl)piperidin-4-yl]-2-{3-methoxy-4-[4-(2-methoxyethyl)piperazin-1-yl]phenyl}-3H-imidazo[4,5-b]pyridin-7-amine, 6-Chloro-2-{3-methoxy-4-[4-(2-methoxyethyl)piperazin-1-yl]phenyl}-N-[1-(1-methylethyl)piperidin-4-yl]-3H-imidazo[4,5-b]pyridin-7-amine, 6-Chloro-2-{2-fluoro-4-[4-(2-methoxyethyl)piperazin-1-yl]phenyl}-N-(1-methylpiperidin-4-yl)-3H-imidazo[4,5-b]pyridin-7-amine, 6-Bromo-2-{2-fluoro-4-[4-(2-methoxyethyl)piperazin-1-yl]phenyl}-N-(1-methylpiperidin-4-yl)-3H-imidazo[4,5-b]pyridin-7-amine, 6-Chloro-N-(1-ethylpiperidin-4-yl)-2-{2-fluoro-4-[4-(2-methoxyethyl)piperazin-1-yl]phenyl}-3H-imidazo[4,5-b]pyridin-7-amine, 6-Bromo-N-(1-ethylpiperidin-4-yl)-2-{2-fluoro-4-[4-(2-methoxyethyl)piperazin-1-yl]phenyl}-3H-imidazo[4,5-b]pyridin-7-amine, 6-Chloro-N-[1-(cyclopropylmethyl)piperidin-4-yl]-2-{2-fluoro-4-[4-(2-methoxyethyl)piperazin-1-yl]phenyl}-3H-imidazo[4,5-b]pyridin-7-amine, 6-Bromo-N-[1-(cyclopropylmethyl)piperidin-4-yl]-2-{2-fluoro-4-[4-(2-methoxyethyl)piperazin-1-yl]phenyl}-3H-imidazo[4,5-b]pyridin-7-amine, 6-Chloro-2-{2-fluoro-4-[4-(2-methoxyethyl)piperazin-1-yl]phenyl}-N-[1-(1-methylethyl)piperidin-4-yl]-3H-imidazo[4,5-b]pyridin-7-amine, 3-{4-[(6-Chloro-2-{4-[4-(3-methoxypropyl)piperazin-1-yl]phenyl}-3H-imidazo[4,5-b]pyridin-7-yl)amino]piperidin-1-yl}propanenitrile, 3-{4-[(6-Chloro-2-{4-[4-(2-methoxyethyl)piperazin-1-yl]phenyl}-3H-imidazo[4,5-b]pyridin-7-yl)amino]piperidin-1-yl}propanenitrile, 3-{4-[(6-Chloro-2-{4-[4-(4-methoxybutyl)piperazin-1-yl]phenyl}-3H-imidazo[4,5-b]pyridin-7-yl)amino]piperidin-1-yl}propanenitrile, 3-{4-[(6-Chloro-2-{4-[4-(2,2-dimethylpropanoyl)piperazin-1-yl]phenyl}-3H-imidazo[4,5-b]pyridin-7-yl)amino]piperidin-1-yl}propanenitrile, 3-{4-[(6-Chloro-2-{4-[4-(3-hydroxypropyl)piperazin-1-yl]phenyl}-3H-imidazo[4,5-b]pyridin-7-yl)amino]piperidin-1-yl}propanenitrile, 3-{4-[(6-Chloro-2-{4-[4-(2-ethoxyethyl)-3-oxopiperazin-1-yl]phenyl}-3H-imidazo[4,5-b]pyridin-7-yl)amino]piperidin-1-yl}propanenitrile, 3-{4-[(6-Chloro-2-{2-fluoro-4-[4-(2-methoxyethyl)piperazin-1-yl]phenyl}-3H-imidazo[4,5-b]pyridin-7-yl)amino]piperidin-1-yl}propanenitrile, 3-{4-[(6-Bromo-2-{4-[4-(2-methoxyethyl)piperazin-1-yl]phenyl}-3H-imidazo[4,5-b]pyridin-7-yl)amino]piperidin-1-yl}propanenitrile, 3-{4-[(6-Bromo-2-{4-[4-(4-methoxybutyl)piperazin-1-yl]phenyl}-3H-imidazo[4,5-b]pyridin-7-yl)amino]piperidin-1-yl}propanenitrile, 3-{4-[(6-Bromo-2-{4-[4-(2,2-dimethylpropanoyl)piperazin-1-yl]phenyl}-3H-imidazo[4,5-b]pyridin-7-yl)amino]piperidin-1-yl}propanenitrile, 3-{4-[(6-Bromo-2-{4-[4-(3-hydroxypropyl)piperazin-1-yl]phenyl}-3H-imidazo[4,5-b]pyridin-7-yl)amino]piperidin-1-yl}propanenitrile, 3-{4-[(6-Bromo-2-{4-[4-(2-ethoxyethyl)-3-oxopiperazin-1-yl]phenyl}-3H-imidazo[4,5-b]pyridin-7-yl)amino]piperidin-1-yl}propanenitrile, 3-{4-[(6-Bromo-2-{2-fluoro-4-[4-(2-methoxyethyl)piperazin-1-yl]phenyl}-3H-imidazo[4,5-b]pyridin-7-yl)amino]piperidin-1-yl}propanenitrile, 6-Chloro-N-[1-(cyclopropylmethyl)piperidin-4-yl]-2-{4-[4-(pyrazin-2-ylmethyl)piperazin-1-yl]phenyl}-3H-imidazo[4,5-b]pyridin-7-amine, 6-Chloro-N-[1-(cyclopropylmethyl)piperidin-4-yl]-2-{4-[4-(pyrimidin-5-ylmethyl)piperazin-1-yl]phenyl}-3H-imidazo[4,5-b]pyridin-7-amine, 6-Chloro-N-[1-(cyclopropylmethyl)piperidin-4-yl]-2-{4-[4-(pyridin-4-ylmethyl)piperazin-1-yl]phenyl}-3H-imidazo[4,5-b]pyridin-7-amine, or a pharmaceutically acceptable salt thereof.

14. The compound or the pharmaceutically acceptable salt according to claim 11, wherein $R_1$ is C1-C6 alkyl;

W is >N—$R_4$; and $R_4$ is $R_{4a}O(CH_2)_q$—.

15. The compound or the pharmaceutically acceptable salt according to claim 14, wherein $R_{4a}$ is C1-C6 alkyl.

16. The compound or the pharmaceutically acceptable salt according to claim 14, of formula (I').

17. A pharmaceutical composition comprising a compound according to claim 1, or a pharmaceutically acceptable salt thereof, and optionally a pharmaceutically acceptable excipient.

18. A method of treatment of a hematologic cancer, by administering a therapeutically effective amount of a compound according to claim 1, to a mammal in need of such treatment.

19. The method according to claim 18, wherein the hematologic cancer is leukemia.

20. The method according to claim 18, wherein the hematologic cancer is chronic lymphocytic leukemia.

* * * * *